(12) United States Patent
Kano et al.

(10) Patent No.: US 6,458,780 B1
(45) Date of Patent: Oct. 1, 2002

(54) CARBAPENEM DERIVATIVES

(75) Inventors: Yuko Kano; Toshiro Sasaki; Yumiko Sambongi; Kiyoshi Tanabe; Yoshihisa Akiyama; Hideo Kitagawa; Takahisa Maruyama; Hiromasa Takizawa; Takashi Ando; Kazuhiro Aihara; Kunio Atsumi; Katsuyoshi Iwamatsu; Takashi Ida, all of Yokohama (JP)

(73) Assignee: Meiji Seika Kaisha, Ltd., Tokyo-to (JP)

( * ) Notice: Subject to any disclaimer, the term of this patent is extended or adjusted under 35 U.S.C. 154(b) by 0 days.

(21) Appl. No.: 09/744,583

(22) PCT Filed: Jul. 27, 1999

(86) PCT No.: PCT/JP99/04025

§ 371 (c)(1),
(2), (4) Date: Jan. 26, 2001

(87) PCT Pub. No.: WO00/06581

PCT Pub. Date: Feb. 10, 2000

(30) Foreign Application Priority Data

Jul. 27, 1999 (JP) .................................... 10-210534/1998

(51) Int. Cl.⁷ ..................... A61L 31/429; C07D 519/06; C07D 513/04; A61P 31/04
(52) U.S. Cl. .................. 514/210.09; 540/302
(58) Field of Search ...................... 540/302; 514/210.09

(56) References Cited

U.S. PATENT DOCUMENTS 6,310,056 B1 * 10/2001 Kano .......................... 540/302

FOREIGN PATENT DOCUMENTS

| EP | 0 760 370 | 3/1997 |
|---|---|---|
| JP | 8-311071 | 11/1996 |
| JP | 9-249667 | 9/1997 |
| JP | 10-507185 | 7/1998 |
| WO | 98/32760 | 7/1998 |
| WO | WO01/55154 A1 * | 8/2001 |

* cited by examiner

Primary Examiner—Mark L. Berch
(74) Attorney, Agent, or Firm—Wenderoth, Lind & Ponack, LLP

(57) ABSTRACT

Disclosed is a novel carbapenem derivative having a substituted imidazo[5,1-b]thiazole group at the 2-position on the carbapenem ring have high anti-microbial activities against β-lactamase producing bacteria, MRSA, resistant-*Pseudomonas aeruginosa*, PRSP, enterococci, and influenza, and high stabilities to DHP-1. According to the present invention, there is provided a compound represented by the formula (I), or a pharmacologically acceptable salt thereof or an ester at the 3-position on the carbapenem ring thereof:

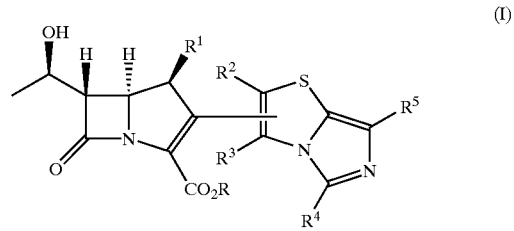

(I)

2 Claims, No Drawings

CARBAPENEM DERIVATIVES

BACKGROUND OF THE INVENTION

1. Field of the Invention

The present invention relates to a carbapenem compound which has excellent antimicrobial activity and wide range of anti-microbial spectrum, and can be administered not only as an injection but also orally. More particularly, the present invention relates to a novel carbapenem derivative which has a substituted imidazo[5,1-b]thiazole group or a salt thereof.

2. Background Art

Carbapenem derivatives, by virtue of potent antibacterial activity against a wide spectrum of bacteria, have been energetically studied as a highly useful β-lactam agent, and Imipenem, Panipenem, and Meropenem have been clinically used.

Both Imipenem and Panipenem, however, are used as a mixture due to instability against renal dehydropeptidase-1 ("DHP-1") in the case of Imipenem and in order to reduce nephrotoxicity in the case of Panipenem. Meropenem which has recently been marketed has a methyl group at the 1β-position, so that it has increased stability to DHP-1 and thus can be used alone.

However, a need still exists for a drug having higher stability to DHP-1. Furthermore, drugs effective for methicillin resistant *Staphylococcus aureus* ("MRSA"), penicillin resistant *Streptococcus pneumoneae* ("PRSP"), resistant *Pseudomonas aeruginosa* and enterococci which have recently become serious problems as well as influenza have been demanded as well.

Some of the present inventors have previously reported the carbapenem derivatives having a novel heteroaromatic ring imidazo[5,1-b]thiazolium-6-ylmethyl group at the 2-position on the carbapenem ring in WO 96/028455 and the carbapenem derivatives having an imidazo[5,1-b]thiazole group through a pyrrolidinylthio group at the 2-position of the carbapenem ring in W98/023623 and, furthermore, the carbapenem derivatives having an imidazo[5,1-b]thiazole group directly at the 2-position of the carbapenem ring in WO98/032760.

Further, WO96/011932 and WO 96/034868 and Japanese Patent Laid-Open Publication No. 273876/1992 disclose the carbapenem derivatives in which a carbon atom on the heteroaromatic ring is bonded to the 2-position of the carbapenem ring. However, there have been described no specific data on the anti-microbial activities or effectiveness for these derivatives. There have been described neither bicyclic heteroaromatic rings nor carbapenem rings having imidazo[5,1-b]thiazole group.

SUMMARY OF THE INVENTION

The present inventors have now found that novel carbapenem derivatives having a substituted imidazo[5,1-b] thiazole group at the 2-position on the carbapenem ring have high anti-microbial activities against β-lactamase producing bacteria, MRSA, a resistant-*Pseudomonas aeruginosa*, PRSP, enterococci, and influenza, and high stabilities to DHP-1. The present invention is based on such findings.

Accordingly, the object of the present invention is to provide novel compounds which have wide range of anti-gram-positive and gram-negative microbial activities, especially high anti-microbial activities against microorganisms including β-lactamase producing bacteria, MRSA, enterococci, PRSP, influenza, and high stabilities to DHP-1.

According to the present invention, there is provided a compound represented by the formula (I), or a pharmacologically acceptable salt thereof or an ester at the 3-position on the carbapenem ring thereof:

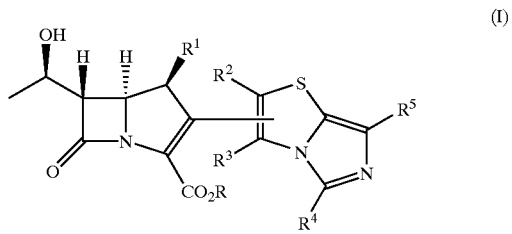

(I)

wherein
$R^1$ represents a hydrogen atom or a methyl group,
$R^2$, $R^3$, $R^4$, and $R^5$, either one of which represents the bonding to the 2-position on the carbapenem ring, and the other three of which may be the same or different, respectively represent
a hydrogen atom,
a halogen atom,
a nitro group,
a cyano group,
a lower alkyl group which may be substituted,
a lower cycloalkyl group which may be substituted,
a lower alkylthio group,
an arylthio group,
a $C_{2-4}$ alkenyl group which may be substituted,
a formyl group,
a lower alkylcarbonyl group which may be substituted,
a lower alkoxycarbonyl group,
a lower alkylsulfonyl group,
an arylsulfonyl group which may be substituted,
an aminosulfonyl group,
an N-loweralkylaminosulfonyl group which may be substituted,
an N,N-di-lower alkylaminosulfonyl group which may be substituted,
an N-lower alkoxy-N-lower alkylaminosulfonyl group,
a lower alkylsufinyl group,
an arylsulfinyl group,
an aminosulfinyl group,
an arylcarbonyl group,
an aryl group which may be substituted,
a carbamoyl group,
an N-lower alkylcarbamoyl group,
an N,N-di-lower alkylaminocarbonyl group,
a lower alkoxyiminomethyl group,
a hydroxyiminomethyl group, or
a five- or six-membered aromatic heterocyclic ring having one or more hetero atoms selected from nitrogen, oxygen and sulfur atoms, and
R represents a hydrogen atom or a group which may be hydrolyzed in organisms.

DETAILED DESCRIPTION OF THE INVENTION

Definition

As used herein, the term "lower alkyl" or "lower alkoxy" as a group or a part of a group means a straight chain or branched chain alkyl or alkyloxy having 1–6 carbon atoms, preferably 1–4 carbon atoms. The examples of the lower alkyl include methyl, ethyl, n-propyl, isopropyl, n-butyl, i-butyl, s-butyl, t-butyl, n-pentyl, n-hexyl, and the like. Further, the lower alkoxy includes by way of example methoxy, ethoxy, n-propoxy, i-propoxy, n-butoxy, i-butoxy, s-butoxy, t-butoxy, and the like.

The term "lower cycloalkyl" means monocyclic alkyl having 3–6 carbon atoms.

Further, the term "aryl" means an aromatic ring and aromatic polycyclic hydrocabon ring, preferably phenyl or naphthyl.

The term "halogen" herein means fluorine, chlorine, bromine, or iodine.

Compound

In the formul(I), any one of $R^2$, $R^3$, $R^4$, and $R^5$ represents the bond to the 2-position on the carbapenem ring. The remaining three groups, which may be the same or different, respectively represent a hydrogen atom, a halogen atom, a nitro group, a cyano group, a lower alkyl group which may be substituted, a lower cycloalkyl group which may be substituted, a lower alkylthio group, an arylthio group, a $C_{2-4}$ alkenyl group which may be substituted, a formyl group, a lower alkylcarbonyl group which may be substituted, a lower alkoxycarbonyl group, a lower alkylsulfonyl group, an arylsulfonyl group which may be substituted, an aminosulfonyl group, an N-loweralkylaminosulfonyl group which may be substituted, an N,N-di-lower alkylaminosulfonyl group which may substituted, an N-lower alkoxy-N-lower alkylaminosulfonyl group, a lower alkylsufinyl group, an arylsulfinyl group, an aminosulfinyl group, an arylcarbonyl group, an aryl group which may be substituted, a carbamoyl group, an N-lower alkylcarbamoyl group, an N,N-di-lower alkylaminocarbonyl group, a lower alkoxyiminomethyl group, a hydroxyiminomethyl group, or a five- or six-membered aromatic heterocyclic ring having one or more hetero atoms selected from nitrogen, oxygen and sulfur atoms.

According to the preferred embodiment of the present invention, the remaining three groups, which may be the same or different, respectively represent a hydrogen atom, a halogen atom, a cyano group, a lower alkyl group which may be substituted, a lower cycloalkyl group which may be substituted, a lower alkylthio group, an arylthio group, a $C_{2-4}$ alkenyl group which may be substituted, a formyl group, a lower alkylcarbonyl group which may be substituted, a lower alkylsulfonyl group, an arylsulfonyl group which may be substituted, an aminosulfonyl group, an N-loweralkylaminosulfonyl group which may be substituted, an N,N-di-lower alkylaminosulfonyl group which may be substituted, a lower alkylsufinyl group, an arylcarbonyl group, an aryl group which be substituted, a lower alkoxyiminomethyl group, a hydroxyiminomethyl group, or a five- or six-membered aromatic heterocyclic ring having one or more hetero atoms selected from nitrogen, oxygen and sulfur atoms. More preferably, the remaining three groups represent a hydrogen atom, a halogen atom, a cyano group, a lower alkyl group (in which one or more hydrogen atoms on the alkyl group may be substituted by groups selected from the group consisting of a halogen atom, a hydroxy group, an amino group, a formylamino group, a lower alkylcarbonylamino group, a carbamoyl group, and a lower alkylsulfonylamino group), a lower cycloalkyl group which may be substituted by carbamoyl, a lower alkylthio group, an arylthio group, a $C_{2-4}$ alkenyl group (in which one or more hydrogen atoms on the alkenyl group may be substituted by a lower alkylcarbonyl group or a lower alkoxycarbonyl group), a formyl group, a lower alkylcarbonyl group (in which one or more hydrogen atoms on the alkyl group may be substituted by groups selected from the group consisting of a halogen atom, a hydroxy group, an amino group, a lower alkylcarbonylamino group, N,N-di-lower alkylaminocarbonyl group, an (N-lower alkylamino) sulfonylamino group, an (N,N-di-lower alkylamino) sulfonylamino group and a lower alkylsulfonylamino group), a lower alkylsulfonyl group, an arylsulfonyl group (in which one or more hydrogen atoms may be substituted by a lower alkyl group), an aminosulfonyl group, an N-loweralkylaminosulfonyl group (in which one or more hydrogen atoms on the alkyl group may be substituted by groups selected from the group consisting of a lower alkoxy group, a hydroxy group, and an aryl group (in which one or more hydrogen atoms on the aryl group may be substituted by an amino group)), an N,N-di-lower alkylaminosulfonyl group, a lower alkylsufinyl group, an arylcarbonyl group, an aryl group which be substituted by a lower alkylcarbonyl group, a lower alkoxyiminomethyl group, a hydroxyiminomethyl group, or a five- or six-membered aromatic heterocyclic ring having one or more hetero atoms (nitrogen, oxygen or sulfur atom).

In $R^2$, $R^3$, $R^4$, $R^5$ and R which represent lower alkyl, one or more hydrogen atoms on the lower alkyl may be substituted by halogen, nitro, cyano, lower cycloalkyl, lower alkylthio, lower alkoxy, hydroxy, amino, N-lower alkylamino, formyl, lower alkylcarbonyl, arylcarbonyl, carboxy, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino)sulfonyl, (N,N-di-lower alkylamino)sulfonyl, (N-lower alkylamino)sulfonylamino, aminosulfonylamino, (N,N-di-lower alkylamino)sulfonylamino, lower alkylsulfonylamino, and aryl. According to the preferred embodiment of the present invention, the substituent includes preferably halogen, hydroxy, amino, formylamino, lower alkylcarbonyl, carbamoyl and lower alkylsulfonyamino. The substituted alkyl includes for example aminomethyl, hydroxymethyl, 2-hydroxyethyl, carbamoylmethyl, 2-carbamoylethyl, 2-fluoroethyl, cyclopropylmethyl, 2-(N-methylcarbamoyl)ethyl, N,N-dimethylcarbamoylmethyl, 2-(N,N-dimethylcarbamoyl)ethyl, 2-aminosulfonylaminoethyl, aminosulfonylaminomethyl, 2-(aminosulfonylamino)ethyl, methoxymethyl, ethoxycarbonylmethyl, formylaminomethyl, methoxyiminomethyl, hydroxyiminomethyl, and benzyl.

In $R^2$, $R^3$, $R^4$, and $R^5$ which represent lower cycloalkyl, one or more hydrogen atoms on the cycloalkyl may be substituted by a group selected from the group consisting of lower alkyl, halogen, nitro, cyano, lower alkylthio, lower alkoxy, hydroxy, amino, N-lower alkylamino, formyl, lower alkylcarbonyl, arylcarbonyl, carboxy, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino) sulfonyl, (N,N-di-lower alkylamino)sulfonyl, (N-lower alkylamino)sulfonylamino, aminosulfonylamino, (N,N-di-lower alkylamino)sulfonylamino, and aryl, more preferably carbamoyl.

Furthermore, in $R^2$, $R^3$, $R^4$, and $R^5$ which represent alkenyl, one or more hydrogen atoms on the alkenyl may be substituted, and the substituent includes for example a group selected from the group consisting of lower alkyl, halogen, nitro, cyano, lower cycloalkyl, lower alkylthio, lower alkoxy, hydroxy, amino, N-lower alkylamino, formyl, lower alkylcarbonyl, arylcarbonyl, carboxyl, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino)

sulfonyl, (N,N-di-lower alkylamino)sulfonyl, (N-lower alkylamino)sulfonylamino, aminosulfonylamino, (N,N-di-lower alkylamino)sulfonylamino, and aryl, more preferably lower alkylcarbonyl and lower alkoxycarbonyl.

In $R^2$, $R^3$, $R^4$, and $R^5$ which represent lower alkylcarbonyl, one or more hydrogen atoms on the group may be substituted, and the substituent includes for example a group selected from the group consisting of halogen, nitro, cyano, lower cycloalkyl, lower alkylthio, lower alkoxy, hydroxy, amino, N-lower alkylamino, formyl, lower alkylcarbonyl, arylcarbonyl, carboxyl, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino)sulfonyl, (N,N-di-lower alkylamino)sulfonyl, (N-lower alkylamino)sulfonylamino, aminosulfonylamino, (N,N-di-lower alkylamino)sulfonylamino, lower alkylsulfonylamino, and aryl, more preferably halogen, hydroxy, amino, lower alkylcarbonylamino, N,N-di-lower alkylaminocarbonyl, (N-lower alkylamino)sulfonyl, aminosulfonylamino, (N,N-di-lower alkylamino)sulfonylamino, and lower alkylsulfonylamino.

In $R^2$, $R^3$, $R^4$, and $R^5$ which represent arylsulfonyl, one or more hydrogen atoms on the group may be substituted, and the substituent includes for example a group selected from the group consisting of lower alkyl, halogen, nitro, cyano, lower cycloalkyl, lower alkylthio, lower alkoxy, hydroxy, amino, N-lower alkylamino, formyl, lower alkylcarbonyl, arylcarbonyl, carboxyl, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino)sulfonyl, (N,N-di-lower alkylamino)sulfonyl, (N-lower alkylamino)sulfonylamino, aminosulfonylamino, and (N,N-di-lower alkylamino)sulfonylamino, more preferably lower alkyl.

Furthermore, in $R^2$, $R^3$, $R^4$, and $R^5$ which represent N-lower alkylaminosulfonyl, one or more hydrogen atoms on the group may be substituted, and the substituent includes for example a group selected from the group consisting of halogen, nitro, cyano, lowercycloalkyl, loweralkylthio, lower alkoxy, hydroxy, amino, N-lower alkylamino, formyl, lower alkylcarbonyl, arylcarbonyl, carboxyl, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino)sulfonyl, (N,N-di-lower alkylamino)sulfonyl, (N-lower alkylamino)sulfonylamino, aminosulfonylamino, and (N,N-di-lower alkylamino)sulfonylamino, and aryl (in which one or more hydrogen atoms on the aryl may be substituted, and the substituent includes for example a group selected from the group consisting of lower alkyl, halogen, nitro, cyano, lower cycloalkyl, lower alkylthio, lower alkoxy, hydroxy, amino, N-lower alkylamino, formyl, lower alkylcarbonyl, arylcarbonyl, carboxy, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino)sulfonyl, (N,N-di-lower alkylamino)sulfonyl, (N-lower alkylamino)sulfonylamino, aminosulfonylamino, and (N,N-di-lower alkylamino)sulfonylamino), more preferably lower alkoxy, hydroxy, and aryl (which may be substituted by amino).

Furthermore, in $R^2$, $R^3$, $R^4$, and $R^5$ which represent N-di-lower alkylaminosulfonyl, one or more hydrogen atoms on the group may be substituted, and the substituent includes for example a group selected from the group consisting of halogen, nitro, cyano, lowercycloalkyl, loweralkylthio, loweralkoxy, hydroxy, amino, N-lower alkylamino, formyl, lower alkylcarbonyl, arylcarbonyl, carboxy, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino)sulfonyl, (N,N-di-lower alkylamino)sulfonyl, (N-lower alkylamino)sulfonylamino, aminosulfonylamino, (N,N-di-lower alkylamino)sulfonylamino, and aryl.

Furthermore, in $R^2$, $R^3$, $R^4$, and $R^5$ which represent aryl, one or more hydrogen atoms on the group may be substituted, and the substituent includes for example a group selected from the group consisting of lower alkyl, halogen, nitro, cyano, lower cycloalkyl, lower alkylthio, lower alkoxy, hydroxy, amino, N-lower alkylamino, formyl, lower alkylcarbonyl, arylcarbonyl, carboxy, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino)sulfonyl, (N,N-di-lower alkylamino)sulfonyl, (N-lower alkylamino)sulfonylamino, aminosulfonylamino, and (N,N-di-lower alkylamino)sulfonylamino, more preferably lower alkylcarbonyl.

Examples of a five- or six-membered aromatic heterocyclic ring having one or more hetero atoms selected from nitrogen, oxygen and sulfur atoms represented by $R^2$, $R^3$, $R^4$, and $R^5$ include thiazolyl, imidazolyl, oxazolyl, pyridyl, pyrrolyl, pyrazinyl, and pyrimidinyl, more preferably thiazolyl. On these groups, one or more hydrogen atoms may be substituted, and the substituent includes for example lower alkyl, halogen, lower alkoxy, hydroxy, and amino.

R represents a group which may be hydrolyzed in organisms, preferably an ester residue. Examples of the group include $C_{1-10}$ alkyl, arylcarbonyloxy-lower alkyl group, aryl lower alkyloxy-lower-alkylcarbonyloxy-lower alkyl group, lower alkylcarbonyloxy-lower-alkyl, lower cycloalkylcarbonyloxy-lower-alkyl, lower cycloalkyl-lower-alkylcarbonyloxy-lower-alkyl, dicyclohexylmethylcarbonyloxy-lower-alkyl, adamantylcarbonyloxy-lower-alkyl, lower alkyloxycarbonyloxy-lower-alkyl, lower cycloalkyloxycarbonyloxy-lower-alkyl, (lower cycloalkyloxycarbonyloxy)(lower-cycloalkyl)methyl, lower cycloalkyl-lower-alkyloxycarbonyloxy-lower-alkyl, adamantyloxlycarbonyloxy-lower-alkyl, 2-indanyloxycarbonyloxy-lower-alkyl, aryl-lower-alkyloxycarbonyloxy-lower-alkyl, aryloxycarbonyloxy-lower-alkyl in which the aromatic ring may be substituted, 5-indanyloxycarbonyloxoy-lower-alkyl in which the aromatic ring may be substituted, 2-oxo-5-lower alkyl-1,3-dioxolen-4-ylmethyl, 3-phthalidyl in which the aromatic ring may be substituted, or 2-(3-phthalidylidene)ethyl in which the aromatic ring may be substituted.

According to another preferred embodiment of the present invention, R preferably represents $C_{1-10}$ alkyl, arylcarbonyloxy-lower alkyl, aryl lower alkyloxy-lower-alkylcarbonyloxy-lower alkyl group, lower cycloalkyl-lower alkylcarbonyloxy-lower-alkyl, dicyclohexylmethylcarbonyloxy-lower-alkyl, adamantylcarbonyloxy-lower-alkyl, (lower cycloalkyloxycarbonyloxy)(lower-cycloalkyl) methyl, lower cycloalkylethoxycarbonyloxy-lower-alkyl, adamantyloxlycarbonyloxy-lower-alkyl, 2-indanyloxycarbonyloxy-lower-alkyl, aryl-lower-alkyloxycarbonyloxy-lower-alkyl,
aryloxycarbonyloxy-lower-alkyl in which the aromatic ring may be substituted, or
5-indanyloxycarbonyloxy-lower-alkyl.

According to another preferred embodiment of the present invention, R represents benzoyloxymethyl,
1-(benzoyloxy)ethyl,
1-(2-methylbenzoyloxy)ethyl,
4-t-butylbenzoyloxymethy,
2,4,6-trimethylbenzoyloxymethyl,
4-(N,N-di-n-propylaminosulfony)benzoyloxymethly,
1-[4-(N,N-di-n-propylaminosulfony)benzoyloxymethly]ethyl,
2-naphtylcarbonyloxymethyl,
1-adamantylcarbonyloxymethyl,
1-(1-adamantylcarbonyloxy)ethyl,
cyclohexyl(cyclohexyloxycarbonyloxy)methyl,
(1R,2S,5R)-(l)-menthyloxycarbonyloxymethyl,
(1S,2R,5S)-(d)-menthyloxycarbonyloxymethyl,
1-[(cyclohexylethoxy)carbonyloxy]ethyl,
2-adamantyloxycarbonyloxymethyl,
1-(2-phenyl-1-ethyloxycarbonyloxy)ethyl,
1-(4-methylphenoxycarbonyloxy)ethyl,
1-(2-methylphenoxycarobonyloxy)ethyl,
1-(2-ethylphenoxycarobonyloxy)ethyl,
1-[2-(2-propyl)phenoxycarobonyloxy]ethyl,
1-(2,4-dimethylphenoxycarobonyloxy)ethyl,
1-(2,5-dimethylphenoxycarobonyloxy)ethyl,
1-(3,5-dimethylphenoxycarobonyloxy)ethyl,
1-(2,3,5-trimethylphenoxycarobonyloxy)ethyl,
1-(2,6-dimethylphenoxycarobonyloxy)methyl,
2-methyl-1-(phenoxycarbonyloxy)-1-propyl,
1-(2-methoxyphenoxycarobonyloxy)ethyl,
1-(1-naphthoxycarbonyloxy)ethyl,
(indan-5-yl)oxycarbonyloxymethyl,
1-((indan-5-yl)oxycarbonyloxy)methyl, and
1-((indan-5-yl)oxycarbonyloxy)-1-propyl.

Examples of the substituents on the 2-indanyloxycarbonyloxy-lower-alkyl, 5-indanyloxycarbonyloxy-lower-alkyl, 3-phthalidyl, and 2-(3-phthalidylidene)ethyl include lower alkyl, halogen, nitro, cyano, lower cycloalkyl, lower alkylthio, lower alkoxy, hydroxy, amino, N-lower alkylamino, formyl, lower alkylcarbonyl, arylcarbonyl, carboxy, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino) sulfonyl, (N,N-di-lower alkylamino)sulfonyl, (N-lower alkylamino)sulfonylamino, aminosulfonylamino, (N,N-di-lower alkylamino)sulfonylamino, and aryl, more preferably lower alkoxy, hydroxy, formylamino, and carbamoyl.

One or more hydrogen atoms on the alkyl group of lower-alklycarbonyloxy-lower-alkyl, lower-alkyloxycarbonyloxy-lower-alkyl, and 2-oxo-5-lower alkyl-1,3-dioxolen-4-ylmethyl represented by R may be substituted, and the substituents include for example halogen, nitro, cyano, lower cycloalkyl, lower alkylthio, lower alkoxy, hydroxy, amino, N-lower alkylamino, formyl, lower alkylcarbonyl, arylcarbonyl, carboxy, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino) sulfonyl, (N,N-di-lower alkylamino)sulfonyl, (N-lower alkylamino)sulfonylamino, aminosulfonylamino, (N,N-di-lower alkylamino)sulfonylamino, lower-alkylsulfonylamino, and aryl, more preferably lower alkoxy, lower-cycloalkyl, and aryl.

One or more hydrogen atoms on the aryl group of arylcarbonyoxy lower alkyl, aryl lower alkyloxy lower alkylcarbonyloxy lower alkyl, aryl lower alkyloxycarbonyloxy lower alkyl, aryloxycarbonyloxy lower alkyl represented by R may be substituted, and the substituents include for example lower alkyl, halogen, nitro, cyano, lowercycloalkyl, lower alkylthio, lower alkoxy, hydroxy, amino, N-lower alkylamino, formyl, lower alkylcarbonyl, arylcarbonyl, carboxy, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino)sulfonyl, (N,N-di-lower alkylamino)sulfonyl, (N-lower alkylamino)sulfonylamino, aminosulfonylamino, (N,N-di-lower alkylamino)sulfonylamino, and aryl, more preferably lower alkyl, lower alkoxy, lower-cycloalkyl, and aryl.

One or more hydrogen atoms on the cycloalkyl group of lower cycloalkylcarbonyloxy-lower-alkyl, lower cycloalkyl-lower-alkylcarbonyloxy-lower-alkyl, lower cycloalkyloxycarbonyloxy-lower-alkyl, (lower cycloalkyloxycarbonyloxy)(lower-cycloalkyl)methyl, and lower cycloalkyl lower alkyloxycarbonyloxy lower alkyl represented by R may be substituted, and the substituents include for example loweralkyl, halogen, nitro, cyano, loweralkylthio, lower alkoxy, hydroxy, amino, N-lower alkylamino, formyl, lower alkylcarbonyl, arylcarbonyl, carboxy, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino)sulfonyl, (N,N-di-lower alkylamino)sulfonyl, (N-lower alkylamino)sulfonylamino, aminosulfonylamino, (N,N-di-lower alkylamino)sulfonylamino, and aryl, more preferably lower alkyl, lower alkoxy, and lower-cycloalkyl.

The preferred compounds of the formula (I) according to the present invention include those in which $R^1$ represents a hydrogen atom or a methyl group, $R^2$, $R^3$, $R^4$, and $R^5$, either one of which represents the bonding to the 2-position on the carbapenem ring, and the other three of which may be the same or different, respectively represent
a hydrogen atom,
a halogen atom,
a cyano group,
a lower alkyl group which may be substituted,
a lower cycloalkyl group which may be substituted,
a lower alkylthio group,
an arylthio group,
a $C_{2-4}$ alkenyl group which may be substituted,
a formyl group,
a lower alkylcarbonyl group which may be substituted,
a lower alkylsulfonyl group,
an arylsulfonyl group which may be substituted,
an aminosulfonyl group,
an N-loweralkylaminosulfonyl group which may be substituted,
an N,N-di-lower alkylaminosulfonyl group which may be substituted,
a lower alkylsufinyl group,
an arylcarbonyl group,
an aryl group which may be substituted,
a lower alkoxyiminomethyl group,
a hydroxyiminomethyl group, or
a five- or six-membered aromatic heterocyclic ring having one or more hetero atoms selected from nitrogen, oxygen and sulfur atoms.

The preferred compounds of the formula (I) according to the present invention include those in which $R^2$ represents the bonding to the 2-position on the carbapenem ring. Among the compounds of formula (I) in which $R^2$ represents the bonding to the 2-position on the carbapenem ring, the preferred compounds include those in which $R^1$ represents hydrogen or methyl, $R^3$, $R^4$, and $R^5$, which may be the same or different, and respectively represent a hydrogen atom, a halogen atom, a cyano group, a lower alkyl group in which one or more hydrogen atoms on the alkyl group may be substituted by groups selected from the group consisting of a halogen atom, a hydroxy group, an amino group, a formylamino group, a lower alkylcarbonylamino group, a carbamoyl group, and a lower alkylsulfonylamino group, a lower-cycloalkyl group which may be substituted by a carbamoyl group, a lower alkylthio group, an arylthio group, a $C_{2-4}$ alkenyl group in which one or more hydrogen atoms on the alkenyl group may be substituted by a lower alkylcarbonyl group or a lower alkoxy carbonyl group, a formyl group, a lower alkylcarbonyl group in which one or more hydrogen atoms on the alkyl group may be substituted by groups selected from the group consisting of a halogen atom, a hydroxy group, an amino group, a lower alkylcarbonylamino group, N,N-di-lower alkylaminocarbonyl group, an (N-lower alkylamino) sulfonylamino group, an (N,N-di-lower alkylamino) sulfonylamino group and a lower alkylsulfonylamino group, a lower alkyl sulfonyl group, an aryl sulfonyl group in which one or more hydrogen atoms on the aryl group may be substituted by a lower alkyl group, an aminosulfonyl group, an N-lower alkylaminosulfonyl group in which one or more hydrogen atoms on the alkyl group may be substituted by groups selected from the group consisting of a lower alkoxy group, a hydroxy group, and an aryl group (in which one or more hydrogen atoms on the aryl group may be substituted by an amino group), an N,N-di-lower alkylaminosulfonyl group a lower alkylsufinyl group, an arylcarbonyl group, an aryl group which may be substituted by a lower alkylcarbonyl group, a lower alkoxyiminomethyl group, a hydroxyiminomethyl group, or a five- or six-membered aromatic heterocyclic ring having one or more hetero atoms selected from nitrogen, oxygen and sulfur atoms.

Among the compounds, more preferred compounds include those in which $R^1$ represents methyl, $R^3$, $R^4$, and $R^5$, which may be the same or different, and respectively represent a hydrogen atom, a lower alkyl group which may be substituted by groups selected from the group consisting of a halogen atom, a hydroxy group, an amino group, a formylamino group, a lower alkylcarbonylamino group, a carbamoyl group, a lower alkylsulfonylamino group, and an aryl group, a lower alkylthio group, an arylthio group, a lower alkylcarbonyl group which may be substituted by groups selected from the group consisting of a halogen atom, a hydroxy group, an amino group, a lower alkylcarbonylamino group, N,N-di-lower alkylaminocarbonyl group, an (N-lower alkylamino) sulfonylamino group, an (N,N-di-lower alkylamino) sulfonylamino group and a lower alkylsulfonylamino group, a lower alkyl sulfonyl group, an aryl sulfonyl group which may be substituted by a lower alkyl group, an aminosulfonyl group, an N-lower alkylaminosulfonyl group which may be substituted by groups selected from the group consisting of a lower alkoxy group, a hydroxy group, and an aryl group (which may be substituted by an amino group), an N,N-di-lower alkylaminosulfonyl group a lower alkylsufinyl group, a hydroxyiminomethyl group, or a five- or six-membered aromatic heterocyclic ring having one or more hetero atoms selected from nitrogen, oxygen and sulfur atoms.

Another preferred compounds include those in which $R^1$ represents methyl, $R^2$ represents the bonding to the 2-position on the carbapenem ring, $R^3$ and $R^4$ represent a hydrogen atom, $R^5$ represents a lower alkylthio group or a lower alkylsulfonyl group, and R represents a hydrogen atom or a group which may be hydrolyzed in organisms. Among these compounds, more preferred compounds include those in which $R^5$ represents methylthio or methylsulfonyl.

Another preferred compounds include those in which $R^1$ represents methyl, $R^2$ represents the bonding to the 2-position on the carbapenem ring, $R^3$ and $R^4$ represent a hydrogen atom, $R^5$ represents a lower alkylcarbonyl group (in which one or more hydrogen atoms on the alkyl group may be substituted by groups selected from the group consisting of a halogen atom, a hydroxy group, an amino group, a lower alkylcarbonylamino group, N,N-di-lower alkylaminocarbonyl group, an (N-lower alkylamino)sulfonylamino group, an (N,N-di-lower alkylamino)sulfonylamino group and a lower alkylsulfonylamino group), a lower alkyl group substituted by a lower alkylcarbonylamino group, an N,N-di-lower alkylaminosulfonyl group, or a lower alkylsulfinyl group. Another preferred compounds include those in which $R^1$ represents methyl, $R^2$ represents the bonding to the 2-position on the carbapenem ring, $R^3$ and $R^4$ represent a hydrogen atom, $R^5$ represents a lower alkyl group substituted by a lower alkylcarbonylamino group, those in which $R^1$ represents methyl,
$R^2$ represents the bonding to the 2-position on the carbapenem ring,
$R^3$ and $R^4$ represent a hydrogen atom,
$R^5$ represents an N,N-di-lower alkylaminosulfonyl group, those in which
$R^1$ represents methyl,
$R^2$ represents the bonding to the 2-position on the carbapenem ring,
$R^3$ and $R^4$ represent a hydrogen atom,
$R^1$ represents an N,N-dimethylaminosulfonyl group, those in which
$R^1$ represents methyl,
$R^2$ represents the bonding to the 2-position on the carbapenem ring,
$R^3$ represents a hydrogen atom,
$R^4$ represents a lower alkyl group,
$R^5$ represents a lower alkylcarbonyl group which may be substituted by a hydroxy group, those in which
$R^1$ represents methyl,
$R^2$ represents the bonding to the 2-position on the carbapenem ring,
$R^3$ represents a hydrogen atom,
$R^4$ represents a lower alkyl group, and
$R^5$ represents a lower alkylsulfonyl group, those in which
$R^1$ represents methyl,
$R^2$ represents the bonding to the 2-position on the carbapenem ring,
$R^3$ represents a hydrogen atom,
$R^4$ represents methyl, and
$R^5$ represents methylsulfonyl. those in which
$R^1$ represents methyl,
$R^2$ represents the bonding to the 2-position on the carbapenem ring,
$R^3$ and $R^4$ represent a hydrogen atom, and
$R^5$ represents a lower alkylsulfinyl group, those in which
$R^1$ represents methyl,
$R^2$ represents the bonding to the 2-position on the carbapenem ring,
$R^3$ and $R^4$ represent a hydrogen atom, and
$R^5$ represents methylsulfinyl group.

Another preferred compounds include those in which
$R^1$ represents a hydrogen atom or a methyl group,
$R^2$, $R^3$, $R^4$, and $R^5$, except the one which represents the bonding to the 2-position on the carbapenem ring, which may be the same or different, and respectively represent a hydrogen atom,
a lower alkyl group which be substituted,
an arylthio group,
a lower alkylcarbonyl group which may be substituted,
an arylsulfonyl group which may be substituted,
an N-loweralkylaminosulfonyl group which may be substituted,
an N,N-di-lower alkylaminosulfonyl group which may be substituted,
an N-lower alkoxy-N-lower alkylaminosulfonyl group,
a lower alkylsufinyl group,
a arylsulfinyl group,
an aminosulfinyl group, or
a five- or six-membered aromatic heterocyclic ring having one or more hetero atoms selected from nitrogen, oxygen and sulfur atoms, those in which $R^1$ represents a hydrogen atom or a methyl group,
$R^2$, $R^3$, $R^4$, and $R^5$, except the one which represents the bonding to the 2-position on the carbapenem ring, which may be the same or different, and respectively represent
a hydrogen atom,
a lower alkyl group in which one or more hydrogen atoms on the alkyl group may be substituted by groups selected from the group consisting of a halogen atom, a hydroxy group, an amino group, an N-lower alkylamino group, a formylamino group, a lower alkylcarbonylamino group, a carbamoyl group, and a lower alkylsulfonylamino group,
an arylthio group,
a lower alkylcarbonyl group, in which one or more hydrogen atoms on the alkyl group may be substituted by groups selected from the group consisting of a halogen atom, a hydroxy group, an amino group, a lower alkylcarbonlyamino group, N,N-di-lower alkylaminocarbonyl group, an (N-lower alkylamino)sulfonylamino group, an (N,N-di-lower alkylamino)sulfonylamino group and a lower alkylsulfonylamino group,
a arylsulfonyl group substituted by a lower alkyl group,
an N-lower alkylaminosulfonyl group in which one or more hydrogen atoms on the alkyl group may be substituted by groups selected from the group consisting of a lower alkoxy group, a hydroxy group, and an aryl group (which may be substituted by an amino group), an N,N-di-lower alkylaminosulfonyl group
a lower alkylsufinyl group, or
a five- or six-membered aromatic heterocyclic ring having one or more hetero atoms selected from nitrogen, oxygen and sulfur atoms, and those in which $R^1$ represents a hydrogen atom or a methyl group,
$R^2$, $R^3$, $R^4$, and $R^5$, except the one which represents the bonding to the 2-position on the carbapenem ring, which may be the same or different, and respectively represent
a hydrogen atom,
a lower alkyl group, in which one or more hydrogen atoms on the alkyl group may be substituted by groups selected from the group consisting of a halogen atom, a nitro group, a cyano group, a lower cycloalkyl group, a lower alkylthio group, a lower alkoxy group, a hydroxy group, an amino group, an N-lower alkylamino group, a formyl group, a lower alkylcarbonyl group, an aryl carbonyl group, a carboxyl group, a lower alkoxycarbonyl group, a formylamino group, a lower alkylcarbonylamino group, a carbamoyl group, an N-lower alkylcarbamoyl group, an N,N-di-lower alkylaminocarbonyl group, an aminosulfonyl group, an (N-lower alkylamino)sulfonyl group, an (N,N-di-lower alkylamino)sulfonyl group, an (N-lower alkylamino)sulfonylamino group, an aminosulfonylamino group, an (N,N-di-lower alkylamino)sulfonylamino group, a lower alkylsulfonylamino group and an aryl group, or an arylthio group.

According to the preferred embodiment of the present invention, R preferably represents
$C_{1-10}$ alkyl which may be substituted,
arylcarbonyloxy-lower-alkyl group which may be substituted, aryl lower alkyloxy-lower-alkylcarbonyloxy-lower alkyl group which may be substituted, lower cycloalkyl-lower-alkylcarbonyloxy-lower-alkyl which may be substituted, dicyclohexylmethylcarbonyloxy-lower-alkyl which may be substituted, adamantylcarbonyloxy-lower-alkyl which may be substituted, (lower cycloalkyloxycarbonyloxy)(lower-cycloalkyl)methyl which may be substituted, lower cycloalkyl-ethoxycarbonyloxy-lower-alkyl which may be substituted, adamantyloxlycarbonyloxy-lower-alkyl which may be substituted, 2-indanyloxycarbonyloxy-lower-alkyl which may be substituted, aryl-lower-alkyloxycarbonyloxy-lower-alkyl which may be substituted, or 5-indanyloxycarbonyloxy-lower-alkyl which may be substituted.

According to another preferred embodiment of the present invention, R preferably represents $C_{1-10}$ alkyl, arylcarbonyloxy-lower alkyl, aryl lower alkyloxy-lower-alkylcarbonyloxy-lower alkyl group, lower cycloalkyl-lower alkylcarbonyloxy-lower-alkyl, dicyclohexylmethylcarbonyloxy-lower-alkyl, adamantylcarbonyloxy-lower-alkyl, (lower cycloalkyloxycarbonyloxy)(lower-cycloalkyl)methyl, lower cycloalkylethoxycarbonyloxy-lower-alkyl, adamantyloxycarbonyloxy-lower-alkyl, 2-indanyloxycarbonyloxy-lower-alkyl, aryl-lower-alkyloxycarbonyloxy-lower-alkyl, aryloxycarbonyloxy-lower-alkyl in which the aromatic ring may be substituted, or 5-indanyloxycarbonyloxy-lower-alkyl.

Among them, R preferably represents $C_{1-10}$ alkyl, arylcarbonyloxy-lower-alkyl, aryl lower alkyloxy-lower-alkylcarbonyloxy-lower-alkyl group, lower cycloalkylcarbonyloxy-lower-alkyl, lower cycloalkyl-lower-alkylcarbonyloxy-lower-alkyl, dicyclohexylmethylcarbonyloxy-lower-alkyl, adamantylcarbonyloxy-lower-alkyl, lower alkyloxycarbonyloxy-lower-alkyl, lower cycloalkyloxycarbonyloxy-lower-alkyl, (lower cycloalkyloxycarbonyloxy)(lower-cycloalkyl)methyl, lower cycloalkyl-lower-alkyloxycarbonyloxy-lower-alkyl, adamantyloxycarbonyloxy-lower-alkyl, 2-indanyloxycarbonyloxy-lower-alkyl in which the aromatic ring may be substituted, aryl-lower-alkyloxycarbonyloxy-lower-alkyl, aryloxycarbonyloxy-lower-alkyl, 5-indanyloxycarbonyloxy-lower-alkyl in which the aromatic ring may be substituted. One or more hydrogen atoms on the alkyl group, the lower cycloalkyl group or the aryl group on the above groups may be substituted.

The compound represented by the formula (I) according to the present invention can exist as a salt, and the preferred salt is a pharmacologically acceptable salt. Such a salt includes for example inorganic salts such as lithium, sodium, potassium, calcium, or magnesium salts, an ammonium salt, salts with organic bases such as triethylamine or diisopropylethylamine, salts with mineral acids such as hydrochloric acid, sulfuric acid, phosphoric acid, or nitric acid, or salts with organic acids such as acetic acid, carbonic acid, citric acid, malic acid, oxalic acid, or methanesulfonic acid, preferably an inner salt, or sodium or potassium salt.

Specific examples of carbapenem derivatives represented by formula (I) according to the present invention include, but are not limited to:

1. Sodium(1S,5R,6S)-6-((1R)-1-hydroxyethyl)-1-methyl-2-(7-propionylimidazo[5,1-b]thiazol-2-yl)-1-carbapen-2-em-3-carboxylate
2. Pivaloyloxymethyl(1S,5R,6S)-6-((1R)-1-hydroxyethyl)-1-methyl-2-(7-propionylimidazo[5,1-b]thiazol-2-yl)-1-carbapen-2-em-3-carboxylate
3. Sodium(1S,5R,6S)-6-((1R)-1-hydroxyethyl)-2-(7-hydroxyiminomethylimidazo[5,1-b]thiazol-2-yl)-1-methyl-1-carbapen-2-em-3-carboxylate (a geometrical isomer derived from a starting compound as a low-polarity oxime isomer)
4. Sodium(5R,6S)-6-((1R)-1-hydroxyethyl)-2-(7-methoxyiminomethylimidazo[5,1-b]thiazol-3-yl)-1-carbapen-2-em-3-carboxylate (a geometrical isomer derived from a starting compound as a low-polarity oxime isomer)
5. Pivaloyloxymethyl(5R,6S)-6-((1R)-1-hydroxyethyl)-2-(7-methoxyiminomethylimidazo[5,1-b]thiazol-3-yl)-1-carbapen-2-em-3-carboxylate (a geometrical isomer derived from a starting compound as a low-polarity oxime isomer)
6. Sodium(1S,5R,6S)-6-((1R)-1-hydroxyethyl)-1-methyl-2-(7-pivaloylimidazo[5,1-b]thiazol-2-yl)-1-carbapen-2-em-3-carboxylate
7. Pivaloyloxymethyl(1S,5R,6S)-6-((1R)-1-hydroxyethyl)-1-methyl-2-(7-pivaloylimidazo[5,1-b]-thiazol-2-yl)-1-carbapen-2-em-3-carboxylate
8. Sodium(5R,6S)-2-(7-acetyl-3-methylimidazo[5,1-b]thiazol-2-yl)-6-((1R)-1-hydroxyethyl)-1-carbapen-2-em-3-carboxylate
9. Pivaloyloxymethyl(5R,6S)-2-(7-acetyl-3-methylimidazo[5,1-b]thiazol-2-yl)-6-((1R)-1-hydroxy-ethyl)-1-carbapen-2-em-3-carboxylate
10. Sodium(1S,5R,6S)-2-[7-(2-formylaminopropionyl)imidazo[5,1-b]thiazol-2-yl]-6-((1R)-1-hydroxyethyl)-1-methyl-1-carbapen-2-em-3-carboxylate (a high-polarity isomer)
11. Sodium(1S,5R,6S)-2-[7-(2-formylaminopropionyl)imidazo[5,1-b]thiazol-2-yl]-6-((1R)-1-hydroxyethyl)-1-methyl-1-carbapen-2-em-3-carboxylate (a low-polarity isomer)
12. Sodium(1S,5R,6S)-6-((1R)-1-hydroxyethyl)-2-(7-isobutyrylimidazo[5,1-b]thiazol-2-yl)-1-methyl-1-carbapen-2-em-3-carboxylate
13. Pivaloyloxymethyl(1S,5R,6S)-6-((1R)-1-hydroxyethyl)-2-(7-isobutyrylimidazo[5,1-b]thiazol-2-yl)-1-methyl-1-carbapen-2-em-3-carboxylate
14. Sodium(5R,6S)-6-((1R)-1-hydroxyethyl)-2-(7-propionylimidazo[5,1-b]thiazol-3-yl)-1-carbapen-2-em-3-carboxylate
15. Sodium(5R,6S)-2-(7-acetylimidazo[5,1-b]thiazol-2-yl)-6-((1R)-1-hydroxyethyl)-1-carbapen-2-em-3-carboxylate 16. Pivaloyloxymethyl(5R,6S)-2-(7-acetylimidazo[5,1-b]thiazol-2-yl)-6-((1R)-1-hydroxyethyl)-1-methyl-1-carbapen-2-em-3-carboxylate
17. Sodium(5R,6S)-6-((1R)-1-hydroxyethyl)-2-(7-isobutyrylimidazo[5,1-b]thiazol-2-yl)-1-carbapen-2-em-3-carboxylate
18. Pivaloyloxymethyl(5R,6S)-6-((1R)-1-hydroxyethyl)-2-(7-isobutyrylimidazo[5,1-b]thiazol-2-yl)-1-carbapen-2-em-3-carboxylate
19. Sodium(1S,5R,6S)-2-(7-acetyl-5-methylimidazo[5,1-b]thiazol-2-yl)-6-((1R)-1-hydroxyethyl)-1-methyl-1-carbapen-2-em-3-carboxylate
20. Pivaloyloxymethyl(1S,5R,6S)-2-(7-acetyl-5-methylimidazo[5,1-b]thiazol-2-yl)-6-((1R)-1-hydroxyethyl)-1-methyl-1-carbapen-2-em-3-carboxylate
21. Sodium(1S,5R,6S)-2-(7-acetyl-3-methylimidazo[5,1-b]thiazol-2-yl)-6-((1R)-1-hydroxyethyl)-1-methyl-1-carbapen-2-em-3-carboxylate
22. Pivaloyloxymethyl(1S,5R,6S)-2-(7-acetyl-3-methylimidazo[5,1-b]thiazol-2-yl)-6-((1R)-1-hydroxyethyl)-1-methyl-1-carbapen-2-em-3-carboxylate
23. Sodium(5R,6S)-6-((1R)-1-hydroxyethyl)-2-(7-methanesulfonylimidazo[5,1-b]thiazol-2-yl)-1-carbapen-2-em-3-carboxylate
24. Sodium(5R,6S)-6-((1R)-1-hydroxyethyl)-2-(7-methanesulfonylimidazo[5,1-b]thiazol-3-yl)-1-carbapen-2-em-3-carboxylate
25. Sodium(1S,5R,6S)-6-((1R)-1-hydroxyethyl)-2-(7-methanesulfonylimidazo[5,1-b]thiazol-3-yl)-1-methyl-1-carbapen-2-em-3-carboxylate
26. Sodium(1S,5R,6S)-6-((1R)-1-hydroxyethyl)-2-(7-methanesulfinylimidazo[5,1-b]thiazol-2-yl)-1-methyl-1-carbapen-2-em-3-carboxylate (a mixture of diastereomers)
27. Sodium(5R,6S)-6-((1R)-1-hydroxyethyl)-2-(7-propionylimidazo[5,1-b]thiazol-2-yl)-1-carbapen-2-em-3-carboxylate
28. Pivaloyloxymethyl(5R,6S)-6-((1R)-1-hydroxyethyl)-2-(7-propionylimidazo[5,1-b]thiazol-2-yl)-1-carbapen-2-em-3-carboxylate
29. Pivaloyloxymethyl(5R,6S)-2-(7-acetylimidazo[5,1-b]thiazol-3-yl)-6-((1R)-1-hydroxyethyl)-1-carbapen-2-em-3-carboxylate
30. Sodium(1S,5R,6S)-2-(7-ethanesulfonylimidazo[5,1-b]thiazol-2-yl)-6-((1R)-1-hydroxyethyl)-1-methyl-1-carbapen-2-em-3-carboxylate
31. Sodium(1S,5R,6S)-6-((1R)-1-hydroxyethyl)-1-methyl-2-(7-N-methylsulfamoylimidazo[5,1-b]thiazol-2-yl)-1-carbapen-2-em-3-carboxylate
32. Sodium(5R,6S)-6-((1R)-1-hydroxyethyl)-2-(7-N-methylsulfamoylimidazo[5,1-b]thiazol-2-yl)-1-carbapen-2-em-3-carboxylate
33. Sodium(5R,6S)-2-(7-acetyl-5-methylimidazo[5,1-b]thiazol-2-yl)-6-((1R)-1-hydroxyethyl)-1-carbapen-2-em-3-carboxylate
34. Sodium(5R,6S)-2-(7-ethanesulfonylimidazo[5,1-b]thiazol-2-yl)-6-((1R)-1-hydroxyethyl)-1-carbapen-2-em-3-carboxylate
35. Sodium(1S,5R,6S)-6-((1R)-1-hydroxyethyl)-1-methyl-2-(7-p-toluenesulfonylimidazo[5,1-b]thiazol-2-yl)-1-carbapen-2-em-3-carboxylate
36. Sodium(5R,6S)-2-(7-hydroxyacetylimidazo[5,1-b]thiazol-2-yl)-6-((1R)-1-hydroxyethyl)-1-carbapen-2-em-3-carboxylate
37. Sodium(1S,5R,6S)-2-(7-benzoylimidazo[5,1-b]thiazol-2-yl)-6-((1R)-1-hydroxyethyl)-1-methyl-1-carbapen-2-em-3-carboxylate
38. Sodium(5R,6S)-2-(7-hydroxyacetylimidazo[5,1-b]thiazol-3-yl)-6-((1R)-1-hydroxyethyl)-1-carbapen-2-em-3-carboxylate
39. Sodium(5R,6S)-2-(7-benzoylimidazo[5,1-b]thiazol-2-yl)-6-((1R)-1-hydroxyethyl)-1-carbapen-2-em-3-carboxylate
40. Sodium(1S,5R,6S)-2-[7-[N-(4-aminobenzyl)sulfamoyl]imidazo[5,1-b]thiazol-2-yl]-6-((1R)-1-hydroxyethyl)-1-methyl-1-carbapen-2-em-3-carboxylate
41. Sodium(1S,5R,6S)-2-(7-fluoroimidazo[5,1-b]thiazol-2-yl)-6-((1R)-1-hydroxyethyl)-1-methyl-1-carbapen-2-em-3-carboxylate
42. Sodium(1S,5R,6S)-6-((1R)-1-hydroxyethyl)-2-[7-[N-(2-hydroxyethyl)-N-methylsulfamoyl]imidazo[5,1-b]thiazol-2-yl]-1-methyl-1-carbapen-2-em-3-carboxylate
43. Sodium(1S,5R,6S)-2-(7-acetylaminoacetylimidazo[5,1-b]thiazol-2-yl)-6-((1R)-1-hydroxyethyl)-1-methyl-1-carbapen-2-em-3-carboxylate
44. Sodium(1S,5R,6S)-6-((1R)-1-hydroxyethyl)-2-(7-methanesulfonyl-5-methylimidazo[5,1-b]thiazol-2-yl)-1-methyl-1-carbapen-2-em-3-carboxylate
45. Sodium(1S,5R,6S)-6-((1R)-1-hydroxyethyl)-2-(7-methanesulfinyl-5-methylimidazo[5,1-b]thiazol-2-yl)-1-methyl-1-carbapen-2-em-3-carboxylate (a mixture of diastereomers)
46. 1-(Ethoxycarbonyloxy)ethyl(1S,5R,6S)-2-(7-acetylimidazo[5,1-b]thiazol-2-yl)-6-((1R)-1-hydroxyethyl)-1-methyl-1-carbapen-2-em-3-carboxylate (a mixture of diastereomers)
47. 1-(Isopropoxycarbonyloxy)ethyl(1S,5R,6S)-2-(7-acetylimidazo[5,1-b]thiazol-2-yl)-6-((1R)-1-hydroxyethyl)-1-methyl-1-carbapen-2-em-3-carboxylate (a mixture of diastereomers)
48. 1-(Cyclohexyloxycarbonyloxy)ethyl(1S,5R,6S)-2-(7-acetylimidazo[5,1-b]thiazol-2-yl)-6-((1R)-1-hydroxyethyl)-1-methyl-1-carbapen-2-em-3-carboxylate (a
49. Cyclohexyloxycarbonyloxymethyl(1S,5R,6S)-2-(7-acetylimidazo[5,1-b]thiazol-2-yl)-6-((1R)-1-hydroxyethyl)-1-methyl-1-carbapen-2-em-3-carboxylate
50. 3-Phthalidyl(1S,5R,6S)-2-(7-acetylimidazo[5,1-b]thiazol-2-yl)-6-((1R)-1-hydroxyethyl)-1-methyl-1-carbapen-2-em-3-carboxylate (a mixture of diastereomers)
51. 1-(Acetoxy)ethyl(1S,5R,6S)-2-(7-acetylimidazo[5,1-b]thiazol-2-yl)-6-((1R)-1-hydroxyethyl)-1-methyl-1-carbapen-2-em-3-carboxylate (a mixture of diastereomers)
52. (5-Methyl-2-oxo-1,3-dioxolen-4-yl)methyl(1S,5R,6S)-2-(7-acetylimidazo[5,1-b]thiazol-2-yl)-6-((1R)-1-hydroxyethyl)-1-methyl-1-carbapen-2-em-3-carboxylate
53. Sodium(1S,5R,6S)-2-(7-N-acetylaminomethylimidazo-[5,1-b]thiazol-2-yl)-6-((1R)-1-hydroxyethyl)-1-methyl-1-carbapen-2-em-3-carboxylate
54. Pivaloyloxymethyl(1S,5R,6S)-2-(7-N-acetylaminomethylimidazo[5,1-b]thiazol-2-yl)-6-((1R)-1-hydroxyethyl)-1-methyl-1-carbapen-2-em-3-carboxylate
55. 1-(Acetoxy)ethyl(1S,5R,6S)-2-(7-N-acetylaminomethylimidazo[5,1-b]thiazol-2-yl)-6-((1R)-1-hydroxyethyl)-1-methyl-1-carbapen-2-em-3-carboxylate (a mixture of diastereomers)
56. 1-(Cyclohexyloxycarbonyloxy)ethyl(1S,5R,6S)-2-(7-N-acetylaminomethylimidazo[5,1-b]thiazol-2-yl)-6-((1R)-1-hydroxyethyl)-1-methyl-1-carbapen-2-em-3-carboxylate (a mixture of diastereomers)
57. 3-Phthalidyl(1S,5R,6S)-2-(7-N-acetylaminomethylimidazo[5,1-b]thiazol-2-yl)-6-((1R)-

1-hydroxyethyl)-1-methyl-1-carbapen-2-em-3-carboxylate (a mixture of diastereomers)
58. (5-Methyl-2-oxo-1,3-dioxolen-4-yl)methyl(1S,5R,6S)-2-(7-N-acetylaminomethylimidazo[5,1-b]thiazol-2-yl)-6-((1R)-1-hydroxyethyl)-1-methyl-1-carbapen-2-em-3-carboxylate
59. 1-[(Cyclohexylmethoxy)carbonyloxy]ethyl(1S,5R,6S)-2-(7-N-acetylaminomethylimidazo[5,1-b]thiazol-2-yl)-6-((1R)-1-hydroxyethyl)-1-methyl-1-carbapen-2-em-3-carboxylate (a mixture of diastereomers)
60. (1R,2S,5R)-(1)-Menthyloxycarbonyloxymethyl(1S,5R,6S)-2-(7-N-acetylaminomethylimidazo[5,1-b]thiazol-2-yl)-6-((1R)-1-hydroxyethyl)-1-methyl-1-carbapen-2-em-3-carboxylate
61. 1-(Cyclohexyloxycarbonyloxy)-n-propyl(1S,5R,6S)-2-(7-N-acetylaminomethylimidazo[5,1-b]thiazol-2-yl)-6-((1R)-1-hydroxyethyl)-1-methyl-1-carbapen-2-em-3-carboxylate (a mixture of diastereomers)
62. Sodium(1S,5R,6S)-6-((1R)-1-hydroxyethyl)-2-(7-methanesulfonylimidazo[5,1-b]thiazol-2-yl)-1-methyl-1-
63. Pivaloyloxymethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate
64. 1-(Acetoxy)ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (a mixture of diastereomers)
65. 1-(Cyclohexyloxycarbonyloxy)ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (a mixture of diastereomers)
66. 3-Phthalidyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (a mixture of diastereomers)
67. (5-Methyl-2-oxo-1,3-dioxolen-4-yl)methyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate
68. 1-[(Cyclohexylmethoxy)carbonyloxy]ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate
69. (1-Methylcyclohexan-1-yl)carbonyloxymethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate
70. 1-(Cyclohexyloxycarbonyloxy)-n-propyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (a mixture of diastereomers)
71. Sodium(1S,5R,6S)-2-(7-hydroxyacetylimidazo[5,1-b]thiazol-2-yl)-6-((1R)-1-hydroxyethyl)-1-methyl-1
72. Pivaloyloxymethyl(1S,5R,6S)-2-(7-hydroxyacetylimidazo[5,1-b]thiazol-2-yl)-6-((1R)-1-hydroxyethyl)-1-methyl-1-carbapen-2-em-3-carboxylate
73. 1-(Acetoxy)ethyl(1S,5R,6S)-2-(7-hydroxyacetylimidazo[5,1-b]thiazol-2-yl)-6-((1R)-1-hydroxyethyl)-1-methyl-1-carbapen-2-em-3-carboxylate (a mixture of diastereomers)
74. 1-(Cyclohexyloxycarbonyloxy)ethyl(1S,5R,6S)-2-(7-hydroxyacetylimidazo[5,1-b]thiazol-2-yl)-6-((1R)-1-hydroxyethyl)-1-methyl-1-carbapen-2-em-3-carboxylate (a mixture of diastereomers)
75. 3-Phthalidyl(1S,5R,6S)-2-(7-hydroxyacetylimidazo[5,1-b]thiazol-2-yl)-6-((1R)-1-hydroxyethyl)-1-methyl-1-carbapen-2-em-3-carboxylate (a mixture of diastereomers)
76. (5-Methyl-2-oxo-1,3-dioxolen-4-yl)methyl(1S,5R,6S)-2-(7-hydroxyacetylimidazo[5,1-b]thiazol-2-yl)-6-((1R)-1-hydroxyethyl)-1-methyl-1-carbapen-2-em-3-carboxylate
77. (1-Methylcyclohexan-1-yl)carbonyloxymethyl(1S,5R,6S)-2-(7-hydroxyacetylimidazo[5,1-b]thiazol-2-yl)-6-((1R)-1-hydroxyethyl)-1-methyl-1-carbapen-2-em-3-carboxylate
78. 1-[(Cyclohexylmethoxy)carbonyloxy]ethyl(1S,5R,6S)-2-(7-hydroxyacetylimidazo[5,1-b]thiazol-2-yl)-6-((1R)-1-hydroxyethyl)-1-methyl-1-carbapen-2-em-3-carboxylate (a mixture of diastereomers)
79. 1-(Cyclohexyloxycarbonyloxy)-n-propyl(1S,5R,6S)-2-(7-hydroxyacetylimidazo[5,1-b]thiazol-2-yl)-6-((1R)-1-hydroxyethyl)-1-methyl-1-carbapen-2-em-3-carboxylate (a mixture of diastereomers)
80. Sodium(1S,5R,6S)-2-[7-(N,N-dimethylcarbamoyl)-acetylimidazo[5,1-b]thiazol-2-yl]-6-((1R)-1-hydroxyethyl)-1-methyl-1-carbapen-2-em-3-carboxylate
81. Pivaloyloxymethyl(1S,5R,6S)-2-[7-(N,N-dimethylcarbamoyl)acetylimidazo[5,1-b]thiazol-2-yl]-6-((1R)-1-hydroxyethyl)-1-methyl-1-carbapen-2-em-3-carboxylate
82. (1-Methylcyclohexan-1-yl)carbonyloxymethyl(1S,5R,6S)-2-[7-(N,N-dimethylcarbamoyl)acetylimidazo[5,1-b]thiazol-2-yl]-6-((1R)-1-hydroxyethyl)-1-methyl-1-carbapen-2-em-3-carboxylate
83. 1-(Cyclohexyloxycarbonyloxy)ethyl(1S,5R,6S)-2-[7-(N,N-dimethylcarbamoyl)acetylimidazo[5,1-b]thiazol-2-yl]-6-((1R)-1-hydroxyethyl)-1-methyl-1-carbapen-2-em-3-carboxylate (a mixture of diastereomers)
84. 3-Phthalidyl(1S,5R,6S)-2-[7-(N,N-dimethylcarbamoyl)acetylimidazo[5,1-b]thiazol-2-yl]-6-((1R)-1-hydroxyethyl)-1-methyl-1-carbapen-2-em-3-carboxylate (a mixture of diastereomers)
85. (5-Methyl-2-oxo-1,3-dioxolen-4-yl)methyl(1S,5R,6S)-2-[7-(N,N-dimethylcarbamoyl)acetylimidazo-[5,1-b]thiazol-2-yl]-6-((1R)-1-hydroxyethyl)-1-methyl-1-carbapen-2-em-3-carboxylate
86. 1-[(Cyclohexylmethoxy)carbonyloxy]ethyl(1S,5R,6S)-2-[7-(N,N-dimethylcarbamoyl)acetylimidazo[5,1-b]thiazol-2-yl]-6-((1R)-1-hydroxyethyl)-1-methyl-1-carbapen-2-em-3-carboxylate (a mixture of diastereomers)
87. 1-(Cyclohexyloxycarbonyloxy)-n-propyl(1S,5R,6S)-2-[7-(N,N-dimethylcarbamoyl)acetylimidazo[5,1-b]thiazol-2-yl]-6-((1R)-1-hydroxyethyl)-1-methyl-1-carbapen-2-em-3-carboxylate (a mixture of diastereomers)
88. Sodium(1S,5R,6S)-2-[7-(N,N-dimethylsulfamoyl)imidazo[5,1-b]thiazol-2-yl]-6-((1R)-1-hydroxyethyl)-1-methyl-1-carbapen-2-em-3-carboxylate
89. (1S,5R,6S)-2-[7-(N,N-dimethylsulfamoyl)imidazo[5,1-b]thiazol-2-yl]-6-((1R)-1-hydroxyethyl)-1-methyl-1-carbapen-2-em-3-carboxylatepivaloyloxymethyl
90. (1-Methylcyclohexan-1-yl)carbonyloxymethyl(1S,5R,6S)-2-[7-(N,N-dimethylsulfamoyl)imidazo[5,1-b]thiazol-2-yl]-6-((1R)-1-hydroxyethyl)-1-methyl-1-carbapen-2-em-3-carboxylate
91. 1-(Cyclohexyloxycarbonyloxy)ethyl(1S,5R,6S)-2-[7-(N,N-dimethylsulfamoyl)imidazo[5,1-b]thiazol-2-yl]-6-((1R)-1-hydroxyethyl)-1-methyl-1-carbapen-2-em-3-carboxylate (a mixture of diastereomers)
92. 3-Phthalidyl(1S,5R,6S)-2-[7-(N,N-dimethylsulfamoyl)imidazo[5,1-b]thiazol-2-yl]-6-((1R)-1-hydroxyethyl)-1-methyl-1-carbapen-2-em-3-carboxylate (a mixture of diastereomers)

93. (5-Methyl-2-oxo-1,3-dioxolen-4-yl)methyl(1S,5R,6S)-2-[7-(N,N-dimethylsulfamoyl)imidazo[5,1-b]thiazol-2-yl]-6-((1R)-1-hydroxyethyl)-1-methyl-1-carbapen-2-em-3-carboxylate
94. 1-[(Cyclohexylmethoxy)carbonyloxy]ethyl(1S,5R,6S)-2-[7-(N,N-dimethylsulfamoyl)imidazo[5,1-b]thiazol-2-yl]-6-((1R)-1-hydroxyethyl)-1-methyl-1-carbapen-2-em-3-carboxylate (a mixture of diastereomers)
95. 1-(Cyclohexyloxycarbonyloxy)-n-propyl(1S,5R,6S)-2-[7-(N,N-dimethylsulfamoyl)imidazo[5,1-b]thiazol-2-yl]-6-((1R)-1-hydroxyethyl)-1-methyl-1-carbapen-2-em-3-carboxylate (a mixture of diastereomers)
96. Sodium(1S,5R,6S)-6-((1R)-1-hydroxyethyl)-2-(7-methoxycarbonylimidazo[5,1-b]thiazol-2-yl)-1-methyl-1-carbapen-2-em-3-carboxylate
97. Sodium(1S,5R,6S)-6-((1R)-1-hydroxyethyl)-2-[7-(N-methoxy-N-methylsulfamoyl)imidazo[5,1-b]thiazol-2-yl]-1-methyl-1-carbapen-2-em-3-carboxylate
98. Sodium(1S,5R,6S)-6-((1R)-1-hydroxyethyl)-1-methyl-2-(7-trifluoroacetylimidazo[5,1-b]thiazol-2-yl)-1-carbapen-2-em-3-carboxylate
99. Sodium(1S,5R,6S)-6-((1R)-1-hydroxyethyl)-1-methyl-2-(7-sulfamoylimidazo[5,1-b]thiazol-2-yl)-1-carbapen-2-em-3-carboxylate
100. Sodium(1S,5R,6S)-6-((1R)-1-hydroxyethyl)-2-[7-(2-(E)-methoxycarbonylvinyl)imidazo[5,1-b]thiazol-2-yl]-1-methyl-1-carbapen-2-em-3-carboxylate
101. Sodium(1S,5R,6S)-6-((1R)-1-hydroxyethyl)-2-[7-(2-(Z)-methoxycarbonylvinyl)imidazo[5,1-b]thiazol-2-yl]-1-methyl-1-carbapen-2-em-3-carboxylate
102. Sodium(1S,5R,6S)-6-((1R)-1-hydroxyethyl)-1-methyl-2-[7-(thiazol-4-yl)imidazo[5,1-b]thiazol-2-yl]-1-carbapen-2-em-3-carboxylate
103. Sodium(1S,5R,6S)-2-(7-hydroxyacetyl-5-methylimidazo[5,1-b]thiazol-2-yl)-6-((1R)-1-hydroxyethyl)-1-methyl-1-carbapen-2-em-3-carboxylate
104. Sodium(5R,6S)-6-((1R)-1-hydroxyethyl)-2-(7-methanesulfonyl-5-methylimidazo[5,1-b]thiazol-2-yl)-1-carbapen-2-em-3-carboxylate
105. Sodium(5R,6S)-6-((1R)-1-hydroxyethyl)-2-(7-methanesulfinyl-5-methylimidazo[5,1-b]thiazol-2-yl)-1-carbapen-2-em-3-carboxylate (a mixture of diastereomers)
106. Sodium(5R,6S)-2-(7-hydroxyacetyl-5-methylimidazo[5,1-b]thiazol-2-yl)-6-((1R)-1-hydroxy-ethyl)-1-carbapen-2-em-3-carboxylate
107. Pivaloyloxymethyl(1S,5R,6S)-6-((1R)-1-hydroxyethyl)-2-(7-methanesulfonyl-5-methylimidazo[5,1-b]thiazol-2-yl)-1-methyl-1-carbapen-2-em-3-carboxylate
108. Sodium(1S,5R,6S)-6-((1R)-1-hydroxyethyl)-2-(7-methanesulfonylaminoacetylimidazo[5,1-b]thiazol-2-yl)-1-methyl-1-carbapen-2-em-3-carboxylate
109. Sodium(1S,5R,6S)-6-((1R)-1-hydroxyethyl)-1-methyl-2-(5-methyl-7-methylthioimidazo[5,1-b]thiazol-2-yl)-1-carbapen-2-em-3-carboxylate
110. Sodium(1S,5R,6S)-6-((1R)-1-hydroxyethyl)-2-[7-(methanesulfonylaminomethyl)imidazo[5,1-b]thiazol-2-yl]-1-methyl-1-carbapen-2-em-3-carboxylate
111. Sodium(1S,5R,6S)-6-((1R)-1-hydroxyethyl)-1-methyl-2-(7-methylthioimidazo[5,1-b]thiazol-2-yl)-1-carbapen-2-em-3-carboxylate
112. Sodium(5R,6S)-2-(7-dimethylaminosulfonyl-imidazo[5,1-b]thiazol-2-yl)-6-((1R)-1-hydroxy-ethyl)-1-carbapen-2-em-3-carboxylate
113. Sodium(5R,6S)-2-(7-aminosulfonylimidazo[5,1-b]thiazol-2-yl)-6-((1R)-1-hydroxyethyl)-1-carbapen-2-em-3-carboxylate
114. Sodium(1S,5R,6S)-6-((1R)-1-hydroxyethyl)-1-methyl-2-[7-((E)-3-oxo-1-buten-1-yl)imidazo[5,1-b]thiazol-2-yl]-1-carbapen-2-em-3-carboxylate
115. Sodium(1S,5R,6S)-2-(7-formyl-5-methylimidazo[5,1-b]thiazol-2-yl)-6-((1R)-1-hydroxyethyl)-1-methyl-1-carbapen-2-em-3-carboxylate
116. Sodium(5R,6S)-6-((1R)-1-hydroxyethyl)-2-(7-methylthioimidazo[5,1-b]thiazol-2-yl)-1-carbapen-2-em-3-carboxylate
117. Sodium(5R,6S)-6-((1R)-1-hydroxyethyl)-2-(7-methanesulfinylimidazo[5,1-b]thiazol-2-yl)-1-carbapen-2-em-3-carboxylate (a mixture of diastereomers)
118. Sodium(5R,6S)-2-[7-(N,N-dimethylaminosulfonylamino)acetylimidazo[5,1-b]thiazol-2-yl]-6-((1R)-1-hydroxyethyl)-1-carbapen-2-em-3-carboxylate
119. Sodium(1S,5R,6S)-2-[7-(N,N-dimethylaminosulfonylamino)acetylimidazo[5,1-b]thiazol-2-yl]-6-((1R)-1-hydroxyethyl)-1-methyl-1-carbapen-2-em-3-carboxylate
120. Sodium(5R,6S)-6-((1R)-1-hydroxyethyl)-2-(5-methyl-7-methylthioimidazo[5,1-b]thiazol-2-yl)-1-carbapen-2-em-3-carboxylate
121. Sodium(1S,5R,6S)-2-(7-aminoacetylimidazo[5,1-b]thiazol-2-yl)-6-((1R)-1-hydroxyethyl)-1-methyl-1-carbapen-2-em-3-carboxylate
122. Sodium(1S,5R,6S)-2-(7-aminomethylimidazo[5,1-b]thiazol-2-yl)-6-((1R)-1-hydroxyethyl)-1-methyl-1-carbapen-2-em-3-carboxylate
123. Sodium(1S,5R,6S)-2-[7-(2-aminoethanesulfonylamino)acetylimidazo[5,1-b]thiazol-2-yl]-6-((1R)-1-hydroxyethyl)-1-methyl-1-carbapen-2-em-3-carboxylate
124. Sodium(5R,6S)-2-[7-(2-aminoethanesulfonyl-amino)acetylimidazo[5,1-b]thiazol-2-yl]-6-((1R)-1-hydroxyethyl)-1-carbapen-2-em-3-carboxylate
125. Sodium(1S,5R,6S)-6-((1R)-1-hydroxyethyl)-2-(5-methanesulfonylimidazo[5,1-b]thiazol-2-yl)-1-methyl-1-carbapen-2-em-3-carboxylate
126. Sodium(1S,5R,6S)-6-((1R)-1-hydroxyethyl)-1-methyl-2-(5-methylthioimidazo[5,1-b]thiazol-2-yl)-1-carbapen-2-em-3-carboxylate
127. Sodium(1S,5R,6S)-2-[5,7-bis(methylthio)imidazo[5,1-b]thiazol-2-yl]-6-((1R)-1-hydroxyethyl)-1-methyl-1-carbapen-2-em-3-carboxylate
128. Sodium(1S,5R,6S)-6-((1R)-1-hydroxyethyl)-1-methyl-2-(7-phenylthioimidazo[5,1-b]thiazol-2-yl)-1-carbapen-2-em-3-carboxylate
129. Sodium(5R,6S)-6-((1R)-1-hydroxyethyl)-2-(7-methylthioimidazo[5,1-b]thiazol-3-yl)-1-carbapen-2-em-3-carboxylate
130. Sodium(5R,6S)-6-((1R)-1-hydroxyethyl)-2-(7-phenylthioimidazo[5,1-b]thiazol-2-yl)-1-carbapen-2-em-3-carboxylate
131. Sodium(1S,5R,6S)-6-((1R)-1-hydroxyethyl)-1-methyl-2-(3-methylthioimidazo[5,1-b]thiazol-2-yl)-1-carbapen-2-em-3-carboxylate
132. Sodium(1S,5R,6S)-2-(7-ethylthioimidazo-[5,1-b]thiazol-2-yl)-6-((1R)-1-hydroxyethyl)-1-methyl-1-carbapen-2-em-3-carboxylate
133. Sodium(5R,6S)-6-((1R)-1-hydroxyethyl)-2-(3-methylthioimidazo[5,1-b]thiazol-2-yl)-1-carbapen-2-em-3-carboxylate
134. Sodium(5R,6S)-2-(7-ethylthioinmidazo[5,1-b]thiazol-2-yl)-6-((1R)-1-hydroxyethyl)-1-carbapen-2-em-3-carboxylate
135. Sodium(5R,6S)-6-((1R)-1-hydroxyethyl)-2-(3-methyl-7-methylthioimidazo[5,1-b]thiazol-2-yl)-1-carbapen-2-em-3-carboxylate 136. Sodium(1S,5R,6S)-6-((1R)-1-hydroxyethyl)-2-(7-methanesulfinyl-5-methylthioimidazo[5,1-b]thiazol-2-yl)-1-methyl-1-carbapen-2-em-3-carboxylate (a mixture of diastereomers)

137. Sodium(5R,6S)-6-((1R)-1-hydroxyethyl)-2-(3-hydroxymethyl-7-methylthioimidazo[5,1-b]thiazol-2-yl)-1-carbapen-2-em-3-carboxylate 138. Sodium(5R,6S)-6-((1R)-1-hydroxyethyl)-2-(3-phenylimidazo[5,1-b]thiazol-2-yl)-1-carbapen-2-em-3-carboxylate 139. Sodium(5R,6S)-2-(7-aminoacetylimidazo[5,1-b]thiazol-2-yl)-6-((1R)-1-hydroxyethyl)-1-carbapen-2-em-3-carboxylate 140. Sodium(1S,5R,6S)-6-((1R)-1-hydroxyethyl)-2-(5-methanesulfinylimidazo[5,1-b]thiazol-2-yl)-1-methyl-1-carbapen-2-em-3-carboxylate (a mixture of diastereomers)

141. Sodium(1S,5R,6S)-2-(5,7-dimethanesulfinyl-imidazo[5,1-b]thiazol-2-yl)-6-((1R)-1-hydroxy-ethyl)-1-methyl-1-carbapen-2-em-3-carboxylate (a mixture of diastereomers)

142. Sodium(1S,5R,6S)-6-((1R)-1-hydroxyethyl)-2-(5-methanesulfinyl-7-methanesulfonylimidazo[5,1-b]thiazol-2-yl)-1-methyl-1-carbapen-2-em-3-carboxylate (a mixture of diastereomers)

143. Sodium(1S,5R,6S)-2-[5,7-bis(methane-sulfonyl)imidazo[5,1-b]thiazol-2-yl]-6-((1R)-1-hydroxyethyl)-1-methyl-1-carbapen-2-em-3-carboxylate 144. Sodium(5R,6S)-2-(3-aminomethylimidazo[5,1-b]thiazol-2-yl)-6-((1R)-1-hydroxyethyl)-1-carbapen-2-em-3-carboxylate 145. Sodium(5R,6S)-6-((1R)-1-hydroxyethyl)-2-(3-hydroxymethylimidazo[5,1-b]thiazol-2-yl)-1-carbapen-2-em-3-carboxylate 146. Sodium(5R,6S)-2-[5,7-bis(methylthio)-imidazo[5,1-b]thiazol-2-yl]-6-((1R)-1-hydroxyethyl)-1-carbapen-2-em-3-carboxylate 147. Sodium(1S,5R,6S)-2-(5-acetyl-7-methylthioimidazo[5,1-b]thiazol-2-yl)-6-((1R)-1-hydroxyethyl)-1-methyl-1-carbapen-2-em-3-carboxylate 148. Sodium(1S,5R,6S)-2-[3,7-bis(methylthio)-imidazo[5,1-b]thiazol-2-yl]-6-((1R)-1-hydroxyethyl)-1-methyl-1-carbapen-2-em-3-carboxylate 149. Sodium(1S,5R,6S)-2-(5-acetyl-7-methanesulfonylimidazo [5,1-b]thiazol-2-yl)-6-((1R)-1-hydroxyethyl)-1-methyl-1-carbapen-2-em-3-carboxylate 150. Sodium(1S,5R,6S)-2-(5-bromo-7-methylthioimidazo[5,1-b]thiazol-2-yl)-6-((1R)-1-hydroxyethyl)-1-methyl-1-carbapen-2-em-3-carboxylate 151. Sodium(5R,6S)-2-(5-acetyl-7-methylthioimidazo[5,1-b]thiazol-2-yl)-6-((1R)-1-hydroxyethyl)-1-carbapen-2-em-3-carboxylate 152. Sodium(1S,5R,6S)-2-(5-cyano-7-methylthioimidazo[5,1-b]thiazol-2-yl)-6-((1R)-1-hydroxyethyl)-1-methyl-1-carbapen-2-em-3-carboxylate 153. Sodium(5R,6S)-2-[3,7-bis(methylthio)imidazo[5,1-b]thiazol-2-yl]-6-((1R)-1-hydroxyethyl)-1-carbapen-2-em-3-carboxylate 154. Sodium(1S,5R,6S)-2-(5-chloro-7-methylthioimidazo[5,1-b]thiazol-2-yl)-6-((1R)-1-hydroxyethyl)-1-methyl-1-carbapen-2-em-3-carboxylate 155. Sodium(5R,6S)-2-(5-cyano-7-methylthioimidazo[5,1-b]thiazol-2-yl)-6-((1R)-1-hydroxyethyl)-1-carbapen-2-em-3-carboxylate 156. Sodium(1S,5R,6S)-6-((1R)-1-hydroxyethyl)-1-methyl-2-[7-(1-propyl)thioimidazo[5,1-b]thiazol-2-yl]-1-carbapen-2-em-3-carboxylate 157. Sodium(5R,6S)-6-((1R)-1-hydroxyethyl)-2-(7-(1-propyl)thioimidazo[5,1-b]thiazol-2-yl)-1-carbapen-2-em-3-carboxylate 158. Sodium(1S,5R,6S)-6-((1R)-1-hydroxyethyl)-2-(7-isopropylthioimidazo[5,1-b]thiazol-2-yl)-1-methyl-1-carbapen-2-em-3-carboxylate 159. Sodium(5R,6S)-6-((1R)-1-hydroxyethyl)-2-(7-isopropylthioimidazo[5,1-b]thiazol-2-yl)-1-carbapen-2-em-3-carboxylate 160. 1-Methylcyclohexylcarbonyloxymethyl(1S,5R,6S)-6-((1R)-1-hydroxyethyl)-2-(7-methanesulfonyl-5-methylimidazo[5,1-b]thiazol-2-yl)-1-methyl-1-carbapen-2-em-3-carboxylate 161. 1-(Cyclohexyloxycarbonyloxy)ethyl(1S,5R,6S)-6-((1R)-1-hydroxyethyl)-2-(7-methanesulfonyl-5-methylimidazo[5,1-b]thiazol-2-yl)-1-methyl-1-carbapen-2-em-3-carboxylate (a mixture of diastereomers)

162. Cyclohexyloxycarbonyloxymethyl(1S,5R,6S)-6-((R)-1-hydroxyethyl)-2-(7-methanesulfonyl-5-methylimidazo[5,1-b]thiazol-2-yl)-1-methyl-1-carbapen-2-em-3-carboxylate 163. 3-Phthalidyl(1S,5R,6S)-6-((1R)-1-hydroxyethyl)-2-(7-methanesulfonyl-5-methyl-imidazo[5,1-b]thiazol-2-yl)-1-methyl-1-carbapen-2-em-3-carboxylate (a mixture of diastereomers)

164. 5-Methyl-2-oxo-1,3-dioxolen-4-ylmethyl(1S,5R,6S)-6-((1R)-1-hydroxyethyl)-2-(7-methanesulfonyl-5-methylimidazo[5,1-b]thiazol-2-yl)-1-methyl-1-carbapen-2-em-3-carboxylate 165. (Z)-2-(3-Phthalidylidene)ethyl(1S,5R,6S)-6-((1R)-1-hydroxyethyl)-2-(7-methanesulfonyl-5-methylimidazo[5,1-b]thiazol-2-yl)-1-methyl-1-carbapen-2-em-3-carboxylate 166. 1-(Ethoxycarbonyloxy)ethyl(1S,5R,6S)-2-(7-acetyl-5-methylimidazo[5,1-b]thiazol-2-yl)-6-((1R)-1-hydroxyethyl)-1-methyl-1-carbapen-2-em-3-carboxylate (a mixture of diastereomers)

167. 1-(Cyclohexyloxycarbonyloxy)ethyl(1S,5R,6S)-2-(7-acetyl-5-methylimidazo[5,1-b]thiazol-2-yl)-6-((1R)-1-hydroxyethyl)-1-methyl-1-carbapen-2-em-3-carboxylate (a mixture of diastereomers)

168. Cyclohexyloxycarbonyloxymethyl(1S,5R,6S)-2-(7-acetyl-5-methylimidazo[5,1-b]thiazol-2-yl)-6-((1R)-1-hydroxyethyl)-1-methyl-1-carbapen-2-em-3-carboxylate 169. 3-Phthalidyl(1S,5R,6S)-2-(7-acetyl-5-methylimidazo[5,1-b]thiazol-2-yl)-6-((1R)-1-hydroxyethyl)-1-methyl-1-carbapen-2-em-3-carboxylate (a mixture of diastereomers)

170. 5-Methyl-2-oxo-1,3-dioxolen-4-ylmethyl(1S,5R,6S)-2-(7-acetyl-5-methylimidazo[5,1-b]thiazol-2-yl)-6-((1R)-1-hydroxyethyl)-1-methyl-1-carbapen-2-em-3-carboxylate 171. Cyclopentyloxycarbonyloxymethyl(1S,5R,6S)-2-(7-acetyl-5-methylimidazo[5,1-b]thiazol-2-yl)-6-((1R)-1-hydroxyethyl)-1-methyl-1-carbapen-2-em-3-carboxylate 172. 1-(Pivaloyloxy)ethyl(1S,5R,6S)-2-(7-acetylimidazo[5,1-b]thiazol-2-yl)-6-((1R)-1-hydroxyethyl)-1-methyl-1-carbapen-2-em-3-carboxylate (a mixture of diastereomers)

173. 1-Methylcyclohexylcarbonyloxymethyl(1S,5R,6S)-2-(7-acetylimidazo[5,1-b]thiazol-2-yl)-6-((1R)-1-hydroxyethyl)-1-methyl-1-carbapen-2-em-3-carboxylate 174. Cyclohexylcarbonyloxymethyl(1S,5R,6S)-2-(7-acetylimidazo[5,1-b]thiazol-2-yl)-6-((1R)-1-hydroxyethyl)-1-methyl-1-carbapen-2-em-3-carboxylate 175. 1-(Cyclohexylcarbonyloxy)ethyl(1S,5R,6S)-2-(7-acetylimidazo[5,1-b]thiazol-2-yl)-6-((1R)-1-

175. ...hydroxyethyl)-1-methyl-1-carbapen-2-em-3-carboxylate (a mixture of diastereomers)
176. Hexanoyloxymethyl(1S,5R,6S)-2-(7-acetylimidazo[5,1-b]thiazol-2-yl)-6-((1R)-1-hydroxyethyl)-1-methyl-1-carbapen-2-em-3-carboxylate
177. 2-Ethylbutyryloxymethyl(1S,5R,6S)-2-(7-acetylimidazo[5,1-b]thiazol-2-yl)-6-((1R)-1-hydroxyethyl)-1-methyl-1-carbapen-2-em-3-carboxylate
178. Cyclopentyloxycarbonyloxymethyl(1S,5R,6S)-2-(7-acetylimidazo[5,1-b]thiazol-2-yl)-6-((1R)-1-hydroxyethyl)-1-methyl-1-carbapen-2-em-3-carboxylate
179. 1-(3-Pentyloxycarbonyloxy)ethyl(1S,5R,6S)-2-(7-acetylimidazo[5,1-b]thiazol-2-yl)-6-((1R)-1-hydroxyethyl)-1-methyl-1-carbapen-2-em-3-carboxylate (a mixture of diastereomers)
180. 3-Pentyloxycarbonyloxymethyl(1S,5R,6S)-2-(7-acetylimidazo[5,1-b]thiazol-2-yl)-6-((1R)-1-hydroxyethyl)-1-methyl-1-carbapen-2-em-3-carboxylate
181. Cyclohexylmethoxycarbonyloxymethyl(1S,5R,6S)-2-(7-acetylimidazo[5,1-b]thiazol-2-yl)-6-((1R)-1-hydroxyethyl)-1-methyl-1-carbapen-2-em-3-carboxylate
182. 1-(Isobutyryloxy)ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (a mixture of diastereomers)
183. 1-(Pivaloyloxy)ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (a mixture of diastereomers)
184. Hexanoyloxymethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate
185. Cyclohexylcarbonyloxymethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate
186. Cyclohexylacetoxymethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate
187. Dicyclohexylacetoxymethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate
188. 1-(1-Methylcyclohexylcarbonyloxy)ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (a mixture of diastereomers)
189. 1-Adamantylcarbonyloxymethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate
190. 1-(1-Adamantylcarbonyloxy)ethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate (a mixture of diastereomers)
191. 1-(Benzoyloxy)ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (a mixture of diastereomers)
192. 4-(2-Propyl)benzoyloxymethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate
193. 4-n-Butylbenzoyloxymethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate
194. 4-Phenylbenzoyloxymethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate
195. 4-t-Butylbenzoyloxymethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate
196. 1-(4-t-Butylbenzoyloxy)ethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate (a mixture of diastereomers)
197. 2,4,6-Trimethylbenzoyloxymethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate
198. 1-(2-Propyloxycarbonyloxy)ethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate (a mixture of diastereomers)
199. 1-(2-Butyloxycarbonyloxy)ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (a mixture of diastereomers)
200. 1-(3-Pentyloxycarbonyloxy)ethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate (a mixture of diastereomers)
201. 1-(1-Butyloxycarbonyloxy)ethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate (a mixture of diastereomers)
202. 4-Heptyloxycarbonyloxymethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate
203. 1-(4-Heptyloxycarbonyloxy)ethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate (a mixture of diastereomers)
204. 1-(1-Pentyloxycarbonyloxy)ethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate (a mixture of diastereomers)
205. 1-(4-Methyl-1-pentyloxycarbonyloxy)ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (a mixture of diastereomers)
206. 5-Nonyloxycarbonyloxymethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate
207. 1-(5-Nonyloxycarbonyloxy)ethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate (a mixture of diastereomers)
208. 1-(2,2-Dimethyl-1-propyloxycarbonyloxy)ethyl (1S,5R,6S)-6-((1R)-1-hydroxyethyl)-2-(7-methanesulfonylimidazo[5,1-b]thiazol-2-yl)-1-methyl-1-carbapen-2-em-3-carboxylate (a mixture of diastereomers)
209. 1-(3,3-Dimethyl-2-butyloxycarbonyloxy)ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (a mixture of diastereomers)
210. Cyclohexylmethoxycarbonyloxymethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate
211. 1-(Cyclohexylmethoxycarbonyloxy)-1-propyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (a mixture of diastereomers)
212. 1-(Dicyclohexylmethoxycarbonyloxy)ethyl(1S,5R,6S)-6-((1R)-1-hydroxyethyl)-2-(7- methanesulfonylimidazo[5,1-b]thiazol-2-yl)-1-methyl-1-carbapen-2-em-3-carboxylate (a mixture of diastereomers)
213. Cyclohexyloxycarbonyloxymethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate
214. 1-(Cyclohexyloxycarbonyloxy)-2-methyl-1-propyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (a mixture of diastereomers)
215. Cyclohexyl(cyclohexyloxycarbonyloxy)methyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (a mixture of diastereomers)
216. (1R,2S,5R)-(1)-menthyloxycarbonyloxymethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate
217. 1-((1R,2S,5R)-(1)-Menthyloxycarbonyloxy)-ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (a mixture of diastereomers)
218. (1S,2R,5S)-(d)-Menthyloxycarbonyloxymethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate
219. (1S,2R,5R)-isomenthyloxycarbonyloxymethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate
220. (1S,2S,5R)-Neomenthyloxycarbonyloxymethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate
221. 3,3,5,5-Tetramethylcyclohexyloxycarbonyloxy-methyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate
222. 2-Adamantyloxycarbonyloxymethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate
223. 1-((Indan-2-yl)oxycarbonyloxy)ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (a mixture of diastereomers)
224. 1-(2-Methylphenoxycarbonyloxy)ethyl(1S,5R,6S)-6-((1R)-1-hydroxyethyl)-1-methyl-2-(7-methanesulfonylimidazo[5,1-b]thiazol-2-yl)-1-carbapen-2-em-3-carboxylate (a mixture of diastereomers)
225. 1-(2-Ethylphenoxycarbonyloxy)ethyl(1S,5R,6S)-6-((1R)-1-hydroxyethyl)-1-methyl-2-(7-methanesulfonylimidazo[5,1-b]thiazol-2-yl)-1-carbapen-2-em-3-carboxylate (a mixture of diastereomers)
226. 1-(3-Methylphenoxycarbonyloxy)ethyl(1S,5R,6S)-6-((1R)-1-hydroxyethyl)-1-methyl-2-(7-methanesulfonylimidazo[5,1-b]thiazol-2-yl)-1-carbapen-2-em-3-carboxylate (a mixture of diastereomers)
227. 1-(4-Methylphenoxycarbonyloxy)ethyl(1S,5R,6S)-6-((1R)-1-hydroxyethyl)-1-methyl-2-(7-methanesulfonylimidazo[5,1-b]thiazol-2-yl)-1-carbapen-2-em-3-carboxylate (a mixture of diastereomers)
228. 1-(2,6-Dimethylphenoxycarbonyloxy)ethyl(1S,5R,6S)-6-((1R)-1-hydroxyethyl)-1-methyl-2-(7-methanesulfonylimidazo[5,1-b]thiazol-2-yl)-1-carbapen-2-em-3-carboxylate (a mixture of diastereomers)
229. 1-(2,4-Dimethylphenoxycarbonyloxy)ethyl(1S,5R,6S)-6-((1R)-(1-hydroxyethyl)-1-methyl-2-(7-methanesulfonylimidazo[5,1-b]thiazol-2-yl)-1-carbapen-2-em-3-carboxylate (a mixture of diastereomers)
230. 1-(3,5-Dimethylphenoxycarbonyloxy)ethyl(1S,5R,6S)-6-((1R)-1-hydroxyethyl)-1-methyl-2-(7-methanesulfonylimidazo[5,1-b]thiazol-2-yl)-1-carbapen-2-em-3-carboxylate (a mixture of diastereomers)
231. 1-(2,4,6-Trimethylphenoxycarbonyloxy)ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (a mixture of diastereomers)
232. 1-(4-t-Butylphenoxycarbonyloxy)ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (a mixture of diastereomers)
233. (Indan-5-yl)oxycarbonyloxymethyl(1S,5R,6S)-6-((1R)-1-hydroxyethyl)-1-methyl-2-(7-methanesulfonylimidazo[5,1-b]thiazol-2-yl)-1-carbapen-2-em-3-carboxylate
234. 1-((Indan-5-yl)oxycarbonyloxy)ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (a mixture of diastereomers)
235. 1-((Indan-5-yl)oxycarbonyloxy)-1-propyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (a mixture of diastereomers)
236. Ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate
237. 2-Propyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate
238. 1-Decyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate
239. (Z)-2-(3-Phthalidylidene)ethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate
240. Acetoxymethyl(1S,5R,6S)-6-((1R)-1-hydroxyethyl)-1-methyl-2-(7-methylthioimidazo-[5,1-b]thiazol-2-yl)-1-carbapen-2-em-3-carboxylate
241. 1-(Acetoxy)ethyl (1S,5R,6S)-6-((1R)-1-hydroxyethyl)-1-methyl-2-(7-methylthioimidazo-[5,1-b]thiazol-2-yl)-1-carbapen-2-em-3-carboxylate (a mixture of diastereomers)
242. 1-(Isobutyryloxy)ethyl(1S,5R,6S)-6-((1R)-1-hydroxyethyl)-1-methyl-2-(7-methylthioimidazo-[5,1-b]thiazol-2-yl)-1-carbapen-2-em-3-carboxylate (a mixture of diastereomers)
243. Pivaloyloxymethyl(1S,5R,6S)-6-((1R)-1-hydroxyethyl)-1-methyl-2-(7-methylthioimidazo-[5,1-b]thiazol-2-yl)-1-carbapen-2-em-3-carboxylate
244. 1-(Pivaloyloxy)ethyl(1S,5R,6S)-6-((1R)-1-hydroxyethyl)-1-methyl-2-(7-methylthioimidazo-[5,1-b]thiazol-2-yl)-1-carbapen-2-em-3-carboxylate (a mixture of diastereomers)
245. 2-Ethylbutyryloxymethyl(1S,5R,6S)-6-((1R)-1-hydroxyethyl)-1-methyl-2-(7-methylthioimidazo-[5,1-b]thiazol-2-yl)-1-carbapen-2-em-3-carboxylate
246. 1-(2-Ethylbutyryloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)

247. Cyclohexylcarbonyloxymethyl(1S,5R,6S)-6-((1R)-1-hydroxyethyl)-1-methyl-2-(7-methylthioimidazo[5,1-b]thiazol-2-yl)-1-carbapen-2-em-3-carboxylate
248. 1-(Cyclohexylcarbonyloxy)ethyl(1S,5R,6S)-6-((1R)-1-hydroxyethyl)-1-methyl-2-(7-methylthio-imidazo[5,1-b]thiazol-2-yl)-1-carbapen-2-em-3-carboxylate (a mixture of diastereomers)
249. Dicyclohexylacetoxymethyl(1S,5R,6S)-6-((1R)-1-hydroxyethyl)-1-methyl-2-(7-methylthio-imidazo[5,1-b]thiazol-2-yl)-1-carbapen-2-em-3-carboxylate
250. 1-Adamantylcarbonyloxymethyl(1S,5R,6S)-6-((1R)-1-hydroxyethyl)-1-methyl-2-(7-methylthio-imidazo[5,1-b]thiazol-2-yl)-1-carbapen-2-em-3-carboxylate
251. 1-(1-Adamantylcarbonyloxy)ethyl(1S,5R,6S)-6-((1R)-1-hydroxyethyl)-1-methyl-2-(7-methylthio-imidazo[5,1-b]thiazol-2-yl)-1-carbapen-2-em-3-carboxylate (a mixture of diastereomers)
252. 3-Phthalidyl(1S,5R,6S)-6-((1R)-1-hydroxyethyl)-1-methyl-2-(7-methylthioimidazo-[5,1-b]thiazol-2-yl)-1-carbapen-2-em-3-carboxylate (a mixture of diastereomers)
253. Benzoyloxymethyl(1S,5R,6S)-6-((1R)-1-hydroxyethyl)-1-methyl-2-(7-methylthioimidazo-[5,1-b]thiazol-2-yl)-1-carbapen-2-em-3-carboxylate
254. 1-(Benzoyloxy)ethyl(1S,5R,6S)-6-((1R)-1-hydroxyethyl)-1-methyl-2-(7-methylthioimidazo-[5,1-b]thiazol-2-yl)-1-carbapen-2-em-3-carboxylate (a mixture of diastereomers)
255. 2-Methylbenzoyloxymethyl(1S,5R,6S)-6-((1R)-1-hydroxyethyl)-1-methyl-2-(7-methylthioimidazo-[5,1-b]thiazol-2-yl)-1-carbapen-2-em-3-carboxylate
256. 1-(2-Methylbenzoyloxy)ethyl(1S,5R,6S)-6-((1R)-1-hydroxyethyl)-1-methyl-2-(7-methylthio-imidazo[5,1-b]thiazol-2-yl)-1-carbapen-2-em-3-carboxylate (a mixture of diastereomers)
257. 4-Methylbenzoyloxymethyl(1S,5R,6S)-6-((1R)-1-hydroxyethyl)-1-methyl-2-(7-methylthioimidazo-[5,1-b]thiazol-2-yl)-1-carbapen-2-em-3-carboxylate
258. 4-(2-Propyl)benzoyloxymethyl(1S,5R,6S)-6-((1R)-1-hydroxyethyl)-1-methyl-2-(7-methylthio-imidazo[5,1-b]thiazol-2-yl)-1-carbapen-2-em-3-carboxylate
259. 2,4-Dimethylbenzoyloxymethyl(1S,5R,6S)-6-((1R)-1-hydroxyethyl)-1-methyl-2-(7-methylthio-imidazo[5,1-b]thiazol-2-yl)-1-carbapen-2-em-3-carboxylate
260. 2,4,6-Trimethylbenzoyloxymethyl(1S,5R,6S)-6-((1R)-1-hydroxyethyl)-1-methyl-2-(7-methylthio-imidazo[5,1-b]thiazol-2-yl)-1-carbapen-2-em-3-carboxylate
261. 1-(Benzyloxyacetoxy)ethyl(1S,5R,6S)-6-((1R)-1-hydroxyethyl)-1-methyl-2-(7-methylthio-imidazo[5,1-b]thiazol-2-yl)-1-carbapen-2-em-3-carboxylate (a mixture of diastereomers)
262. 1-(Ethoxycarbonyloxy)ethyl(1S,5R,6S)-6-((1R)-1-hydroxyethyl)-1-methyl-2-(7-methylthio-imidazo(5,1-b]thiazol-2-yl)-1-carbapen-2-em-3-carboxylate (a mixture of diastereomers)
263. 2-Propyloxycarbonyloxymethyl(1S,5R,6S)-6-((1R)-1-hydroxyethyl)-1-methyl-2-(7-methylthio-imidazo[5,1-b]thiazol-2-yl)-1-carbapen-2-em-3-carboxylate
264. 1-(2-Propyloxycarbonyloxy)ethyl(1S,5R,6S)-6-((1R)-1-hydroxyethyl)-1-methyl-2-(7-methylthio-imidazo[5,1-b]thiazol-2-yl)-1-carbapen-2-em-3-carboxylate (a mixture of diastereomers)
265. 1-(2-Propyloxycarbonyloxy)-1-propyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
266. 2-Methyl-1-(2-propyloxycarbonyloxy)-1-propyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
267. 1-(1-Propyloxycarbonyloxy)ethyl(1S,5R,6S)-6-((1R)-1-hydroxyethyl)-1-methyl-2-(7-methylthio-imidazo[5,1-b]thiazol-2-yl)-1-carbapen-2-em-3-carboxylate (a mixture of diastereomers)
268. 3-Pentyloxycarbonyloxymethyl(1S,5R,6S)-6-((1R)-1-hydroxyethyl)-1-methyl-2-(7-methylthio-imidazo[5,1-b]thiazol-2-yl)-1-carbapen-2-em-3-carboxylate
269. 1-(3-Pentyloxycarbonyloxy)ethyl(1S,5R,6S)-6-((1R)-1-hydroxyethyl)-1-methyl-2-(7-methylthio-imidazo[5,1-b]thiazol-2-yl)-1-carbapen-2-em-3-carboxylate (a mixture of diastereomers)
270. 1-(1-Butyloxycarbonyloxy)ethyl(1S,5R,6S)-6-((1R)-1-hydroxyethyl)-1-methyl-2-(7-methylthio-imidazo[5,1-b]thiazol-2-yl)-1-carbapen-2-em-3-carboxylate (a mixture of diastereomers)
271. 4-Heptyloxycarbonyloxymethyl(1S,5R,6S)-6-((1R)-1-hydroxyethyl)-1-methyl-2-(7-methylthio-imidazo[5,1-b]thiazol-2-yl)-1-carbapen-2-em-3-carboxylate
272. 1-(4-Heptyloxycarbonyloxy)ethyl(1S,5R,6S)-6-((1R)-1-hydroxyethyl)-1-methyl-2-(7-methylthio-imidazo[5,1-b]thiazol-2-yl)-1-carbapen-2-em-3-carboxylate (a mixture of diastereomers)
273. 1-(3-Methyl-1-butyloxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
274. 1-(1-Pentyloxycarbonyloxy)ethyl(1S,5R,6S)-6-((1R)-1-hydroxyethyl)-1-methyl-2-(7-methylthio-imidazo[5,1-b]thiazol-2-yl)-1-carbapen-2-em-3-carboxylate (a mixture of diastereomers)
275. 1-(4-Methyl-1-pentyloxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
276. 5-Nonyloxycarbonyloxymethyl(1S,5R,6S)-6-((1R)-1-hydroxyethyl)-1-methyl-2-(7-methylthio-imidazo[5,1-b]thiazol-2-yl)-1-carbapen-2-em-3-carboxylate
277. 1-[3-(2,4-Dimethyl)pentoxycarbonyloxy]ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
278. 1-(2,2-Dimethyl-1-propyloxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
279. 1-(3,3-Dimethyl-2-butyloxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
280. 1-(2Cyclohexyl-1-ethyloxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
281. 1-(2Phenyl-1-ethyloxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
282. Cyclohexyloxycarbonyloxymethyl(1S,5R,6S)-6-((1R)-1-hydroxyethyl)-1-methyl-2-(7-methylthio-imidazo[5,1-b]thiazol-2-yl)-1-carbapen-2-em-3-carboxylate
283. 1-(Cyclohexyloxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
284. 1-(Cyclohexyloxycarbonyloxy)-1-propyl(1S,5R,6S)-6-((1R)-1-hydroxyethyl)-1-methyl-2-(7-methylthioimidazo 285. 1-(Cyclohexyloxycarbonyloxy)-2-methyl-1-propyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
286. Cyclohexyl(cyclohexyloxycarbonyloxy)methyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
287. 2-Adamantyloxycarbonyloxymethyl(1S,5R,6S)-6-((1R)-1-hydroxyethyl)-1-methyl-2-(7-methylthioimidazo[5,1-b]thiazol-2-yl)-1-carbapen-2-em-3-carboxylate
288. Phenoxycarbonyloxymethyl(1S,5R,6S)-6-((1R)-1-hydroxyethyl)-1-methyl-2-(7-methylthioimidazo-[5,1-b]thiazol-2-yl)-1-carbapen-2-em-3-carboxylate
289. 1-(Phenoxycarbonyloxy)ethyl(1S,5R,6S)-6-((1R)-1-hydroxyethyl)-1-methyl-2-(7-methylthio-imidazo[5,1-b]thiazol-2-yl)-1-carbapen-2-em-3-carboxylate (a mixture of diastereomers)
290. 1-(Phenoxycarbonyloxy)-1-propyl(1S,5R,6S)-6-((1R)-1-hydroxyethyl)-1-methyl-2-(7-methylthio-imidazo[5,1-b]thiazol-2-yl)-1-carbapen-2-em-3-carboxylate (a mixture of diastereomers)
291. 1-(2-Methylphenoxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
292. 1-(2-Ethylphenoxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
293. 1-(2-Methoxyphenoxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
294. 1-(3-Methylphenoxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
295. 1-(3-Methoxyphenoxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
296. 1-(4-Methylphenoxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
297. 1-(4-Ethylphenoxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
298. 1-(4-Methoxyphenoxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
299. 1-(2,6-Dimethylphenoxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
300. 1-(2,4-Dimethylphenoxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
301. 1-(2,5-Dimethylphenoxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
302. 1-[2-Methyl-5-(2-propyl)phenoxycarbonyloxy]-ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
303. 1-(3,5-Dimethylphenoxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
304. 1-(2,4,6-Trimethylphenoxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
305. 1-((Indan-5-yl)oxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers) (a mixture of diastereomers)
306. 1-((Indan-5-yl)oxycarbonyloxy)-1-propyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
307. 1-Heptyl(1S,5R,6S)-6-((1R)-1-hydroxyethyl)-1-methyl-2-(7-methylthioimidazo[5,1-b]thiazol-2-yl)-1-carbapen-2-em-3-carboxylate
308. 5-Methyl-2-oxo-1,3-dioxolen-4-ylmethyl(1S,5R,6S)-6-((1R)-1-hydroxyethyl)-1-methyl-2-(7-methylthioimidazo[5,1-b]thiazol-2-yl)-1-carbapen-2-em-3-carboxylate
309. (Z)-2-(3-Phthalidylidene)ethyl(1S,5R,6S)-6-((1R)-1-hydroxyethyl)-1-methyl-2-(7-methylthio-imidazo[5,1-b]thiazol-2-yl)-1-carbapen-2-em-3-carboxylate
310. 1-(1,1-Dimethyl-1-butyloxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
311. 1-(3,3-Dimethyl-1-butyloxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
312. 1-(2-Methoxybenzoyloxy)ethyl(1S,5R,6S)-6-((1R)-1-hydroxyethyl)-1-methyl-2-(7-methylthio-imidazo[5,1-b]thiazol-2-yl)-1-carbapen-2-em-3-carboxylate (a mixture of diastereomers)
313. 3,5-Dimethylbenzoyloxymethyl(1S,5R,6S)-6-((1R)-1-hydroxyethyl)-1-methyl-2-(7-methylthio-imidazo[5,1-b]thiazol-2-yl)-1-carbapen-2-em-3-carboxylate
314. 1-[2-(2-Propyl)phenoxycarbonyloxy]ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
315. (2,2-Dimethyl-1-propyloxycarbonyloxy)methyl(1S,5R,6S)-6-((1R)-1-hydroxyethyl)-1-methyl-2-(7-methylthioimidazo[5,1-b]thiazol-2-yl)-1-carbapen-2-em-3-carboxylate
316. 1-(2-Ethyl-1-butyloxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
317. 1-(3-Methyl-1-butyloxycarbonyloxy)-1-propyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
318. 1-(2,6-Dimethylphenoxycarbonyloxy)methyl(1S,5R,6S)-6-((1R)-1-hydroxyethyl)-1-methyl-2-(7-methylthioimidazo[5,1-b]thiazol-2-yl)-1-carbapen-2-em-3-carboxylate 319. 1-(2,3,5-Trimethylphenoxycarbonyloxy)ethyl(1S,5R, 6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
320. 2-Naphthylcarbonyloxymethyl(1S,5R,6S)-6-((1R)-1-hydroxyethyl)-1-methyl-2-(7-methylthio-imidazo[5,1-b]thiazol-2-yl)-1-carbapen-2-em-3-carboxylate
321. 2,5-Dimethylbenzoyloxymethyl(1S,5R,6S)-6-((1R)-1-hydroxyethyl)-1-methyl-2-(7-methylthio-imidazo[5,1-b]thiazol-2-yl)-1-carbapen-2-em-3-carboxylate
322. Cyclohexyloxycarbonyloxymethyl(1S,5R,6S)-2-[7-(N,N-dimethylaminosulfonyl)imidazo[5,1-b]thiazol-2-yl]-6-((1R)-1-hydroxyethyl)-1-methyl-1-carbapen-2-em-3-carboxylate
323. 2-Methyl-1-(phenoxycarbonyloxy)-1-propyl(1S,5R, 6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
324. 1-(1-Naphthoxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
325. 1-[2-(1-Propyl)phenoxycarbonyloxy]ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
326. (2-Ethylphenoxycarbonyloxy)ethyl(1S,5R,6S)-2-(7-acetylimidazo[5,1-b]thiazol-2-yl)-6-((1R)-1-hydroxyethyl)-1-methyl-1-carbapen-2-em-3-carboxylate (a mixture of diastereomers)
327. (2-Ethylphenoxycarbonyloxy)ethyl(1S,5R,6S)-2-[7-(N,N-dimethylaminosulfonyl)imidazo[5,1-b]thiazol-2-yl]-6-((1R)-1-hydroxyethyl)-1-methyl-1-carbapen-2-em-3-carboxylate
328. Pivaloyloxymethyl(1S,5R,6S)-6-((1R)-1-hydroxyethyl)-1-methyl-2-(7-methylsulfinyl-imidazo[5,1-b]thiazol-2-yl)-1-carbapen-2-em-3-carboxylate (a mixture of diastereomers)
329. 1-(2-Benzyloxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
330. 1-(2-Methyl-1-propyloxycarbonyloxy)ethyl(1S,5R, 6S)-6-((1R)-1-hydroxyethyl)-1-methyl-2-(7-methylthioimidazo[5,1-b]thiazol-2-yl)-1-carbapen-2-em-3-carboxylate (a mixture of diastereomers)
331. 4-(N,N-di-n-propylaminosulfonyl)benzoyl-oxymethyl (1S,5R,6S)-6-((1R)-1-hydroxyethyl)-1-methyl-2-(7-methylthioimidazo[5,1-b]thiazol-2-yl)-1-carbapen-2-em-3-carboxylate
332. 1-[4-(N,N-Di-n-propylaminosulfonyl)benzoyl-oxy] ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (a mixture of diastereomers).

Preparation of the Compounds

The compounds according to the present invention can be prepared by a variety of methods. The preferred preparation methods are shown below.

Process (1)

The compound of the formula (I) in which R is hydrogen can be prepared according to the following reaction scheme.

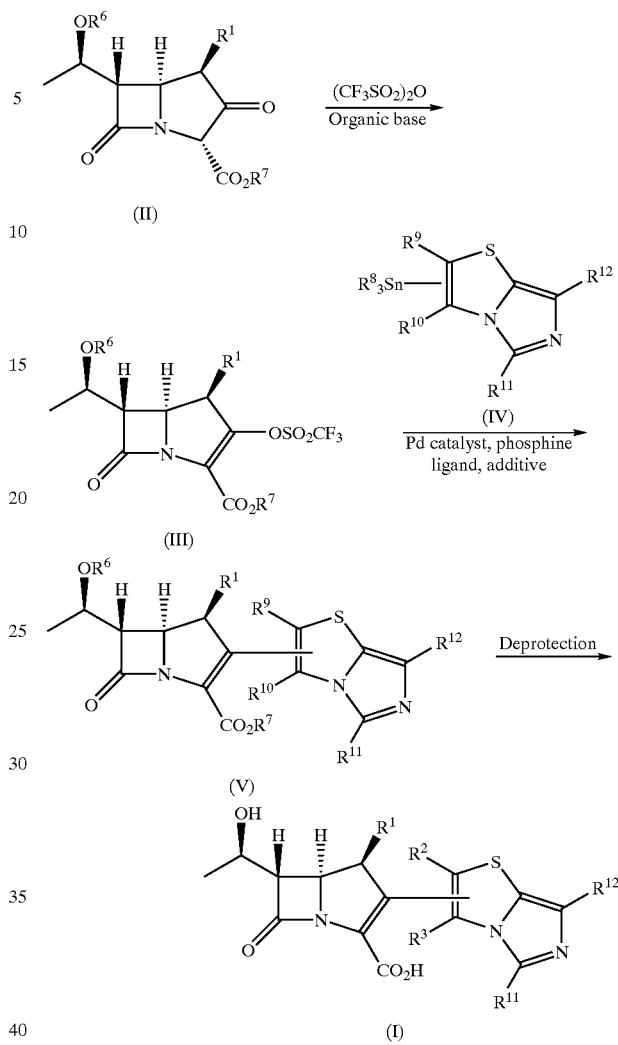

wherein $R^1$, $R^2$, $R^3$, $R^4$ and $R^5$ have the same meaning as defined in the formula (I), $R^6$ represents hydrogen or a hydroxyl protecting group such as t-butyldimethylsilyl, trimethylsilyl, triethylsilyl, 4-nitrobenzyloxycarbonyl, 4-methoxybenzyloxycarbonyl, $R^7$ represents a carboxyl protecting group such as 4-nitrobenzyl, 4-methoxybenzyl, diphenylmethyl, t-butyldimethylsilyl, $R^8$ represents lower alkyl, preferably n-butyl and methyl, $R^9$, $R^{10}$, $R^{11}$, and $R^{12}$ have the same meaning as $R^1$, $R^2$, $R^3$, $R^4$ and $R^5$ or represent a protected group thereof in which a functional group such as hydroxy, amino, carboxy, and hydroxyimino is protected by a conventional protective group.

The compound of the formula (II) can be prepared by the ordinary method, and the tin compound of the formula (IV) can be prepared by a method described below.

In the first step, the compound of the formula (II) can be converted into the compound of the formula (III) by the following method. The compound (III) can be prepared by reacting the compound of the the formula (II) with one (1) equivalent or an excessive amount of anhydrous trifluoromethanesulfonic acid in the presence of an organic base, preferably diisopropylethylamine in an amount of one (1) equivalent or an excessive amount to anhydrous trifluoromethanesulfonic acid in an inert solvent such as acetonitrile, tetrahydrofuran, dichloromethane, and toluene, and the mixed solvent thereof at a temperature of −50° C.−+50° C. for 10 minutes–24 hours, and then subjecting the reaction mixture to the usual purification procedure.

In the second step, the compound of the formula (III) can be converted into the compound of the formula (V) by the following method. The compound of the formula (V) can be prepared by reacting the compound of the formula (III) with one (1) equivalent or an excessive amount of the compound of the formula (V) in the presence of 0.001–1 equivalent of a palladium catalyst such as tetrakis(triphenylphosphine)palladium(0), tris(dibenzylideneacetone)-dipalladium(0), or tris(dibenzylideneacetone)dipalladium(0)-chloroform adduct, 0.01–1 equivalent of a phosphine ligand such as triphenylphosphine, tri-2-furylphosphine, or tri-2-thienylphosphine, tris(2,4,6-trimethoxyphenyl)phosphine, and 1–10 equivalents of an additive such as zinc chloride, lithium chloride, or cesium fluoride alone or in combination thereof in an inert solvent such as tetrahydrofuran, dimethoxyethane, dioxane, acetonitrile, acetone, ethanol, dimethylsulfoxide, sulfolane, N,N-dimethylformamide, N,N-dimethylacetamide, N-methylpyrrolidinone, or hexamethylphosphoric triamide, or a mixed solvent thereof at 0° C.−100° C. for 10 minutes–7 days, and then subjecting the reaction mixture to the ordinary post-treatment.

In the third step, the protective groups $R^6$ and $R^7$ or the protective groups on $R^9$, $R^{10}$, $R^{11}$, and $R^{12}$ in the compound of the formula (V) can be removed by the deprotection reaction in one step or plural steps depending on the kinds of the protective groups to obtain the compound of the formula (I) according to the present invention. The deprotection reactions, which depend on the kinds of the protective groups $R^6$ and $R7^8$ or the protective groups on $R^9$, $R^{10}$, $R^{11}$, and $R^{12}$ used, can be carried out according to the usual methods generally known in the art. When either one or both of the protective groups can be removed under the acidic condition, a mineral acid such as hydrochloric acid, an organic acid such as oxalic acid, acetic acid or citric acid, or a Lewis acid such as aluminium chloride is used. When the protective groups is removed under a reducing condition, catalytic reduction with a variety of catalysts, or a metallic reducing agent such as zinc or iron is used. When $R^6$ is a silyl type protective group such as a t-butyldimethylsilyl group, a trimethylsilyl group or a triethylsilyl group, it can be easily removed with use of a fluorine ion reagent such as tetrabutylammonium fluoride. When $R^6$ is an allyloxycarbonyl group and $R^7$ is an allyl group, the protective groups can be easily removed with use of a variety of palladium complexes such as tetrakis(triphenylphosphine)palladium (0).

Process (2)

The compound of the formula (V) in which at least one of $R^9$, $R^{10}$, $R^{11}$, and $R^{12}$ is lower alkylthio can be converted to the compound of formula (V') in which the lower alkylthio group is converted to lower alkylsulfonyl or lower alkylsulfinyl according to the following reaction.

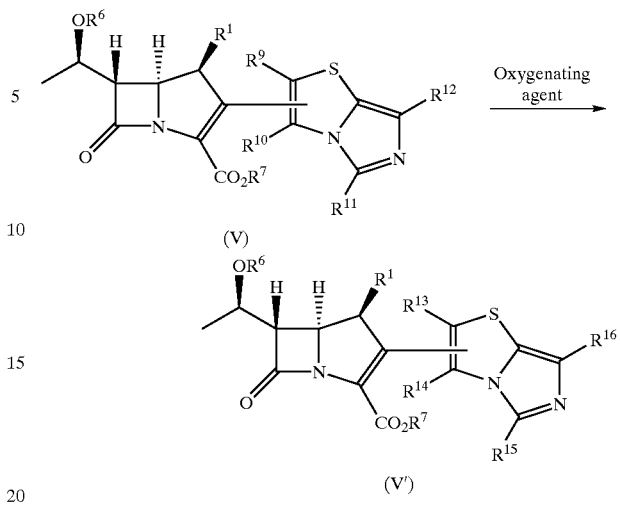

in which $R^1$ has the same meaning as defined in the formula (I), $R^6$, $R^7$, $R^9$, $R^{10}$, $R^{11}$ and $R^{12}$ have the same meaning as defined in the formula (V) in Process (1) above, $R^{13}$, $R^{14}$, $R^{15}$ and $R^{16}$ have the same meaning as $R^9$, $R^{10}$, $R^{11}$ and $R^{12}$, provided that at least one of $R^9$, $R^{10}$, $R^{11}$ and $R^{12}$ represents lower alkylthio and at least one of $R^{13}$, $R^{14}$, $R^{15}$ and $R^{16}$ represents lower alkylsulfonyl or lower alkylsulfinyl.

The compound of the formula (V) can be converted into the compound of the formula (V') by reacting the compound of the the formula (V) with one (1) equivalent or an excessive amount of an oxygenation agent (e.g. OXONE by Du Pont, m-chloroperbenzoic acid) in an inert solvent such as THF, dioxane, dichloromethane, chloroform or water or a mixed solvent thereof at a temperature of −50° C.−+100° C. for 10 minutes–7 days, and then subjecting the reaction mixture to the usual purification procedure.

The compound of the formula (V') can be concerted to the compound of the formula (I) in the same manner as in the third step of Process (1).

The compound of the formula (I) thus obtained can be isolated and purified by crystallization or by chromatography with a nonionic macro-high porous resin, gel filtration with Sephadex or the like, or reverse phase silica gel column chromatography.

Process (3)

The compounds of the formula (I) in which R represents an ester hydrolizable in organisms can be prepared by converting the compounds represented by the formula (I) in which R is hydrogen into the ester derivatives.

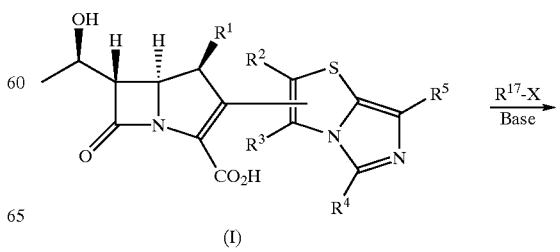

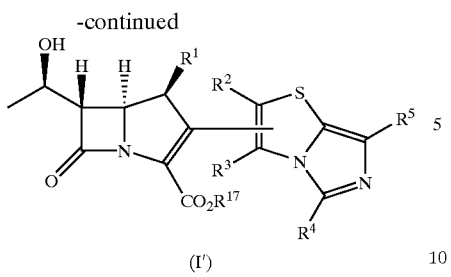

(I')

in which
R$^1$, R$^2$, R$^3$, R$^4$, and R$^5$ have the same meanings as defined in the formula (I),
R$^{17}$ represents C$_{1-10}$ alkyl, arylcarbonyloxy-lower alkyl group, aryl lower alkyloxy-lower-alkylcarbonyloxy-lower alkyl group, lower alkylcarbonyloxy-lower-alkyl, lower cycloalkylcarbonyloxy-lower-alkyl, lower cycloalkyl-lower-alkylcarbonyloxy-lower-alkyl, dicyclohexylmethylcarbonyloxy-lower-alkyl, adamantylcarbonyloxy-lower-alkyl, lower alkyloxycarbonyloxy-lower-alkyl, lower cycloalkyloxycarbonyloxy-lower-alkyl, (lower cycloalkyloxycarbonyloxy)(lower-cycloalkyl)methyl, lower cycloalkyl-lower-alkyloxycarbonyloxy-lower-alkyl, adamantyloxlycarbonyloxy-lower-alkyl, 2-indanyloxycarbonyloxy-lower-alkyl in which the aromatic ring may be substituted, aryl-lower-alkyloxycarbonyloxy-lower-alkyl, aryloxycarbonyloxy-lower-alkyl in which the aromatic ring may be substituted, 5-indanyloxycarbonyloxy-lower-alkyl in which the aromatic ring may be substituted, 2-oxo-5-lower alkyl-1,3-dioxolen-4-ylmethyl, 3-phthalidyl in which the aromatic ring may be substituted, or 2-(3-phthalidylidene)ethyl in which the aromatic ring may be substituted, X represents a leaving group such as Cl, Br, I, —OSO$_2$CF$_3$, —OSO$_2$CH$_3$, or —OSO$_2$PhCH$_3$.

The compound of the formula (I') can be prepared by reacting the compound of the formula (I) with an alkyl halide R$^{17}$—X in the presence of one (1) equivalent or an excessive amount of a base at a temperature of −70–+50° C., preferably −30° C.–+20° C. for 10 minutes–24 hours.

The base usable in the reaction includes for example organic bases such as diisopropylethylamine, diazabicyclo[2,2,2]undecene and 2,6-lutidine, and inorganic bases such as sodium hydroxide, potassium hydroxide, sodium hydrogen carbonate, potassium hydrogen carbonate, sodium carbonate, potassium carbonate and cesium carbonate.

The alkyl halide R$^{17}$—X includes for example pivaloyloxymethyl iodide,
1-(pivaloyloxy)ethyl iodide,
isobutyryloxymethyl iodide,
1-(isobutyryloxy)ethyl iodide,
acetoxymethyl iodide,
1-(acetoxy)ethyl iodide,
(1-methyl cyclohexan-1-yl)carbonyloxymethyl iodide,
benzoyloxymethyl iodide,
1-(benzoyloxy)ethyl iodide,
1-(2-methylbenzoyloxy)ethyl iodide,
4-t-butylbenzoyloxymethy iodide,
2,4,6-trimethylbenzoyloxymethyl iodide,
4-(N,N-di-n-propylaminosulfonyl)benzoyloxymethyl iodide,
1-[4-(N,N-di-n-propylaminosulfonyl)benzoyloxy]ethyl iodide,
2-naphtylcarbonyloxymethyl iodide,
1-adamantylcarbonyloxymethyl iodide,
1-(1-adamantylcarbonyloxy)ethyl iodide,
cyclohexyloxycarbonyloxymethyl iodide,
1-(cyclohexyloxycarbonyloxy)ethyl iodide,
1-(cyclohexyloxycarbonyloxy)-1-propyl iodide,
1-[(cyclohexylmethoxy)carbonyloxy]ethyl iodide,
1-[(cyclohexylethoxy)carbonyloxy]ethyl iodide,
1-(ethoxycarbonyloxy)ethyl iodide,
1-[(2-methylcyclohexan-1-yl)oxycarbonyloxy]ethyl iodide,
cyclopentyloxycarbonyloxymethyl iodide,
1-(isopropyloxycarbonyloxy)ethyl iodide,
(1R,2S,5R)-(l)-menthyloxycarbonyloxymethyl iodide,
(1S,2R,5S)-(d)-menthyloxycarbonyloxymethyl iodide,
2-adamantyloxycarbonyloxymethyl iodide,
1-(2-phenyl-1-ethyloxycarbonyloxy)ethyl iodide,
phenyloxycarbonyloxymethyl iodide,
1-(phenyloxycarbonyloxy)ethyl iodide,
1-(4-methylphenoxycarbonyloxy)ethyl iodide,
1-(2-methylphenoxycarbonyloxy)ethyl iodide,
1-(2-ethylphenoxycarbonyloxy)ethyl iodide,
1-[2-(2-propyl)phenoxycarobonyloxy]ethyl iodide,
1-(2,4-dimethylphenoxycarbonyloxy)ethyl iodide,
1-(2,5-dimethylphenoxycarbonyloxy)ethyl iodide,
1-(3,5-dimethylphenoxycarbonyloxy)ethyl iodide,
1-(2,3,5-trimethylphenoxycarbonyloxy)ethyl iodide,
1-(2,6-dimethylphenoxycarbonyloxy)methyl iodide,
2-methyl-1-(phenoxycarbonyloxy)-1-propyl iodide,
1-(2-methoxyphenoxycarbonyloxy)ethyl iodide,
1-(1-naphthoxycarbonyloxy)ethyl iodide,
(indan-5-yl)oxycarbonyloxymethyl iodide,
1-((indan-5-yl)oxycarbonyloxy)methyl iodide,
1-((indan-5-yl)oxycarbonyloxy)-1-propyl iodide,
(5-methyl-2-oxo-1,3-dioxolen-4-yl)methyl bromide,
3-phthalidyl bromide,
4-(Z)-2-(3-phthalidylidne)ethyl bromide.

The inert solvent usable in the reaction includes N,N-dimethylforamide, N,N-dimethylacetamide, N,N-diethylformamide, N,N-diethylacetamide, N-methylpyrrolidinone, N,N-dimethylimidazolidinoen, dimethylsulfoxide, sulfolane, acetonitrile, acetone, ethyl acetate, tetrahydrofuran, 1,4-dioxane, diethyl ether, anisole, dichloromethane, 1,2-dichloroethane, chloroform, toluene, benzene, hexamethylphosphoric triamide, methanol, and ethanol.

The compoound (I') thus obtained can be isolated and purified by precipitation, crystallization, gel filtration with Sephadex, or silica gel chromatography.

Process (4)
The compound of the formula (IV) used in the above described reaction can be prepared by the following method.

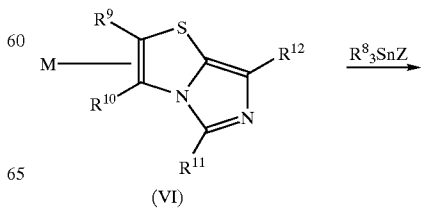

(VI)

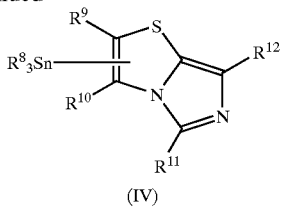

(IV)

in which

R⁹, R¹⁰, R¹¹, and R¹², either one of which is M or R⁸₃SN, and the remaining three, which may be the same or different, have the same meanings as R², R³, R⁴, and R⁵ or represent a protected group thereof in which a functional group such as hydroxyl, amino, carboxy, and hydroxyimino is protected by a conventional protective group, R⁸ represents lower alkyl, preferably n-butyl or methyl, M represents Li, MgCl, MgBr or MgI, and Z represents Cl, Br, I or —OSO₂CF₃.

The compound of the formula (VI) used can be prepared according to the method described in WO98/023623.

The compound of the formula (VI) can be converted into the compound of the formula (IV) by the following method. The compound of the formula (IV) can be prepared by reacting the compound of the formula (VI) in an inert solvent such as tetrahydrofuran, diethyl ether, 1,4-dioxane, anisole, dimethoxyethane, dichloromethane or toluene solely or in combination thereof with R⁸₃SNZ in a proportion of one (1) equivalent or an excessive amount to the compound of the formula (VI) at a temperature of −100° C.−+50° C. for 15 minutes−24 hours, and then subjected to the usual post-treatment.

The compound of the formula (IV) thus obtained can be isolated and purified by crystallization or by chromatography with a nonionic macro-high porous resin, gel filtration with Sephadex or the like, or reverse phase silica gel column chromatography.

Use of the Compound/pharmaceutical Composition

The compound according to the present invention has wide and strong anti-microbial activities against Gram-positive and Gram-negative bacteria, and exhibits strong anti-microbial activities against MRSA, PRSP, enterococci, influenza and β-lactamase producing bacteria as well. Furthermore, it has low toxicity and stable to DHP-1. Thus, the compound according to the present invention can be used for the treatment of infections caused by various pathogenic bacteria in animals including human beings.

The compound of the formula (I) in which R represents a group hydrolyzable in organisms above all can be advantageously administered orally because of its excellent oral absorption property.

The pharmaceutical composition comprising the compound according to the present invention and a pharmacologically acceptable salt and ester thereof as an effective ingredient can be adminitered orally or parenterally by the adminitration routes including intravenous injection, intramuscular injection, or subcutaneous, rectal or percutaneous administration to human beins and the other animals. Thus, the pharmaceutical composition comprising the compound according to the present invention as an effective ingredient can be formed into appropriate dosage forms depending on its administration routes, and specifically prepared primarily into any one of the preparation forms including injections such as intravenous injection and intramuscular injection, preparations for oral administration such as capsules, tablets, granules, powder, pills, particulates, troches, preparations for rectal administration, and fatty suppositories. These preparations can be prepared by the usual methods with ordinarily used excipients, fillers, binding agents, humidifiers, disintegrants, surface active agents, lubricants, dispersants, buffers, storing agents, dissolution aids, preservatives, flavoring agents, analgesic agents, stabilizing agents, and the like. Such non-toxic additives which can be used include for example lactose, fructose, glucose, starch, gelatin, magnesium carbonate, synthetic magnesium silicate, talc, magnesium stearate, methylcellulose or a salt thereof, gum arabic, polyethylene glycol, syrup, petrolatum, glycerol, ethanol, propylene glycol, citric acid, sodium chloride, sodium sulfite, sodium phosphate, and the like. The dosage amount is appropriately determined in consideration of the dosage route, and the age, sex and condition of a patient, and the preparation may be administered for the treatment of infections usually in an amount of about 25 mg–2000 mg, preferably 50 mg–1000 mg per day for adult in one or several portions.

EXAMPLES

The following examples and Preparations further illustrate the present invention but are not intended to limit it.

Preparation 1

7-Propionyl-3-(tri-n-butylstannyl)imidazo[5,1-b]thiazole and 7-propionyl-2-(tri-n-butylstannyl)imidazo-[5,1-b]thiazole a) 7-Propionylimidazo[5,1-b]thiazole Aluminum chloride (16.0 g) was added to a solution of 12.1 ml of propionyl chloride in 100 ml of carbon disulfide. A solution of 2.48 g of imidazo[5,1-b]thiazole in 100 ml of dichloromethane was added dropwise thereto. The mixture was stirred at room temperature for 18 hr. Propionyl chloride (12.1 ml) and 16.0 g of aluminum chloride were further added thereto, followed by stirring for 24 hr. The reaction solution was poured into 100 g of ice. Dichloromethane (200 ml) was added thereto. Sodium carbonate (100 g) and sodium sulfate (100 g) were added in that order to the mixture with stirring. The insolubles were removed by filtration and washed with dichloromethane. The filtrate was concentrated under the reduced pressure. Ethyl acetate (10 ml) was added to the concentrate. The crystals thus formed were collected by filtration. The filtrate was purified by column chromatography on silica gel (dichloromethane: ethyl acetate=1:1), and then combined with the collected crystals to obtain 2.49 g of 7-propionylimidazo[5,1-b]thiazole.

NMR (CDCl₃) δ: 1.26 (3H, t, J=7.4 Hz), 3.07 (2H, q, J=7.4 Hz), 7.10 (1H, d, J=4.2 Hz), 7.54 (1H, d, J=4.2 Hz), 8.00 (1H, s)

b) 7-Propionyl-3-(tri-n-butylstannyl)imidazo[5,1-b]thiazole and 7-propionyl-2-(tri-n-butylstannyl)-imidazo[5,1-b]thiazole A 1.0 N lithiumbis(trimethylsilyl)amide/THF solution (6.17 ml) was added to 60 ml of THF. A solution of 2.12 ml of tri-n-butylstannyl chloride in 24 ml of THF and a solution of 1.11 g of 7-propionylimidazo[5,1-b]thiazole in 24 ml of THF were dropwise added in that order in an argon atmosphere at −73° C. to the mixture. The mixture was stirred at the same temperature for one hr. A 1.0 N lithiumbis (trimethylsilyl)amide/THF solution (6.17 ml) was added dropwise thereto. The mixture was stirred at the same temperature for 2 hr. An ammonium chloride solution (250 ml) was added to the reaction solution, followed by extraction with ethyl acetate. The organic layer was washed with brine, dried over anhydrous magnesium sulfate, and filtered. The solvent was removed by distillation under the reduced pressure. The residue was purified by column chromatography on silica gel (hexane:ethyl acetate=2:1). Of two main components, the fraction, which had been eluted earlier, was collected to give 234 mg of 7-propionyl-3-(tri-n-butylstannyl)imidazo[5,1-b]thiazole.

NMR (CDCl$_3$) δ: 0.91 (9H, m), 1.30 (15H, m), 1.60 (6H, m), 3.07 (2H, q, J=7.4 Hz), 6.88 (1H, s), 7.88 (1H, s)

Of the two main components, the fraction, which had been eluted later, was collected to give 234 mg of 7-propionyl-2-(tri-n-butylstannyl)imidazo[5,1-b]thiazole.

NMR (CDCl$_3$) δ: 0.91 (9H, t, J=7.1 Hz), 1.18 (6H, m), 1.26 (3H, t, J=7.4 Hz), 1.35 (6H, m), 3.05 (2H, q, J=7.4 Hz), 7.27 (1H, s), 7.93 (1H, s)

Preparation 2

7-(4-Nitrobenzyloxyiminomethyl)-2-(tri-n-butylstannyl)imidazo[5,1-b]thiazole (A Geometrical Isomer Derived from a Starting Compound as a Low-polarity Oxime Isomer)

a) 7-Formylimidazo[5,1-b]thiazole

DMF (15.48 ml) was added to 80 ml of dichloromethane. A solution of 18.32 ml of phosphorus oxychloride in 80 ml of dichloromethane was dropwise added thereto under ice cooling. A reaction was allowed to proceed at room temperature for 30 min. A solution of imidazo[5,1-b]thiazole in 40 ml of dichloromethane was added dropwise thereto. The mixture was heated under reflux for 2.5 hr. The reaction solution was poured into ice. The reaction solution was adjusted to pH 9.8 by the addition of a 5 N aqueous sodium hydroxide solution, followed by extraction five times with 200 ml of dichloromethane. The extract was dried over anhydrous magnesium sulfate. The solvent was removed by distillation under the reduced pressure. The residue was purified by column chromatography on silica gel (eluting with dichloromethane:ethyl acetate=5:1, ethyl acetate alone, and then dichloromethane:methanol=10:1) to give 2.37 g of 7-formylimidazo[5,1-b]thiazole.

NMR (CDCl$_3$) δ: 7.17 (1H, d, J=4.1 Hz), 7.60 (1H, d, J=4.1 Hz), 8.07 (1H, s), 9.93 (1H, s)

b) 7-Hydroxyiminomethylimidazo[5,1-b]thiazole (A Low-polarity Geometrical Isomer)

7-Formylimidazo[5,1-b]thiazole (249 mg) was suspended in 10 ml of ethanol. Hydroxylamine hydrochloride (137 mg) and 2.0 ml of a 1 N aqueous sodium hydroxide solution were added under ice cooling to the suspension. The mixture was stirred at the same temperature for 1.5 hr, and then stirred at room temperature for 3 hr. The reaction solution was concentrated under the reduced pressure until the volume of the reaction solution was reduced to approximately the half of the original volume. The concentrate was adjusted to pH 12 by the addition of a potassium carbonate solution, followed by extraction three times with dichloromethane. The extract was dried over anhydrous magnesium sulfate. The solvent was removed by distillation under the reduced pressure. The residue was purified by column chromatography on silica gel (dichloromethane:ethyl acetate=1:2). Of two main components, the fraction, which had been eluted earlier, was collected to give 160 mg of 7-hydroxyiminomethylimidazo [5,1-b]thiazole (a low-polarity geometrical isomer).

NMR (DMSO-d$_6$) δ: 7.40 (1H, d, J=4.1 Hz), 7.98 (1H, d, J=4.1 Hz), 8.09 (1H, s), 8.27 (1H, s)

c) 7-Hydroxyiminomethyl-2-(tri-n-butylstannyl)imidazo[5,1-b]thiazole (A Geometrical Isomer Derived from a Starting Compound as a Low-polarity Oxime Isomer)

7-Hydroxyiminomethylimidazo[5,1-b]thiazole (a low-polarity geometrical isomer) (831 mg) was dissolved in 25 ml of THF and 5 ml of hexamethylphosphoramide (HMPA). A 1.55 N n-butyllithium/n-hexane solution (7.67 ml) was dropwise added in an argon atmosphere at −70° C. to the solution. The mixture was stirred at the same temperature for 40 min. Tri-n-butylstannyl chloride (1.84 ml) was added thereto. The mixture was stirred for 1.5 hr while raising the temperature to −40° C. An ammonium chloride solution was added to the reaction solution, followed by extraction with ethyl acetate. The organic layer was washed with brine, dried over anhydrous magnesium sulfate, and filtered. The solvent was removed by distillation under the reduced pressure. The residue was purified by column chromatography on silica gel (hexane:ethyl acetate=3:1 to 1:1) to give 680 mg of 7hydroxyiminomethyl-2-(tri-n-butylstannyl) imidazo[5,1-b]thiazole (a geometrical isomer derived from a starting compound as a low-polarity oxime isomer).

NMR (CDCl$_3$) δ: 0.91 (9H, t, J=7.4 Hz), 1.17 (6H, m), 1.35 (6H, m), 1.58 (6H, m), 7.23 (1H, s), 7.98 (1H, s), 8.30 (1H, s)

d) 7-(4Nitrobenzyloxyiminomethyl)-2-(tri-n-butylstannyl)imidazo[5,1-b]thiazole (A Geometrical Isomer Derived from a Starting Compound as a Low-polarity Oxime Isomer)

4Nitrobenzyl bromide (671 mg) and 290 mg of t-butoxypotassium were added in an argon atmosphere to a solution of 1.18 g of 7-hydroxyiminomethyl-2-(tri-n-butylstannyl)imidazo[5,1-b]thiazole (a geometrical isomer derived from a starting compound as a low-polarity oxime isomer) in 25 ml of DMF at −40° C. The mixture was stirred at the same temperature for one hr. Ethyl acetate was added to the reaction solution. The mixture was washed three times with brine, and dried over anhydrous magnesium sulfate. The solvent was removed by distillation under the reduced pressure. The residue was purified by column chromatography on silica gel (dichloromethane:ethyl acetate=5:1) to give 169 mg of the title compound.

NMR (CDCl$_3$) δ: 0.92 (9H, m), 1.17 (6H, m), 1.35 (6H, m), 1.59 (6H, m), 5.27 (2H, s), 7.21 (1H, s), 7.60 (2H, d, J=8.9 Hz), 7.96 (1H, s), 8.22 (2H, d, J=8.9 Hz), 8.32 (1H, s)

Preparation 3

7-Methoxyiminomethyl-3-(tri-n-butylstannyl)imidazo-[5,1-b]thiazole (A Stereoisomer Derived from a Starting Compound as a Low-polarity Oxime Isomer)

a) 7-Methoxyiminomethylimidazo[5,1-b]thiazole (A Low-polarity Stereoisomer)

7-Formylimidazo[5,1-b]thiazole (249 mg) was suspended in 10 ml of ethanol. o-Methylhydroxyamine hydrochloride (219 mg) and 2.67 ml of a 1 N aqueous sodium hydroxide solution were added to the suspension. The mixture was stirred at room temperature for 20 hr. The reaction solution was concentrated. Water (50 ml) was added to the concentrate, followed by extraction with dichloromethane. The extract was dried over anhydrous magnesium sulfate. The solvent was removed by distillation under the reduced pressure. The residue was purified by column chromatography on silica gel (dichloromethane:ethyl acetate=1:1). Of two main components, the fraction, which had been eluted earlier, was collected to give 164 mg of 7-methoxyiminomethylimidazo[5,1-b]thiazole (a low-polarity geometrical isomer).

NMR (CDCl$_3$) δ: 3.96 (3H, s), 7.01 (1H, d, J=4.1 Hz), 7.48 (1H, d, J=4.1 Hz), 8.02 (1H, s), 8.24 (1H, s)

b) 7-Methoxyiminomethyl-3-(tri-n-butylstannyl)-imidazo[5,1-b]thiazole (A Stereoisomer Derived from a Starting Compound as a Low-polarity Oxime Isomer)

7-Methoxyiminomethylimidazo[5,1-b]thiazole (a low-polarity geometrical isomer) (1.47 g) was dissolved in 44 ml of THF. A 1.55 N n-butyllithium/n-hexane solution (6.27 ml) was added dropwise in an argon atmosphere at −70° C. The mixture was stirred at the same temperature for one hr. Tri-n-butylstannyl chloride (2.77 ml) was added to the reaction mixture. The mixture was stirred for 2 hr while raising the temperature to −55° C. An ammonium chloride solution was added to the reaction solution. The mixture was extracted with ethyl acetate. The organic layer was washed with brine, dried over anhydrous magnesium sulfate, and filtered. The solvent was removed by distillation under the reduced pressure. The residue was purified by column chromatography on silica gel (hexane:ethyl acetate=5:1 to 3:1). The tile compound (1.68 g) was obtained from the fraction of Rf=0.7 (hexane:ethyl acetate=3:1).

NMR (CDCl$_3$) δ: 0.90 (9H, t, J=7.4 Hz), 1.24 (6H, m), 1.35 (6H, m), 1.55 (6H, m), 3.96 (3H, s), 6.81 (1H, s), 7.92 (1H, s), 8.25 (1H, s)

Preparation 4

7-Pivaloyl-2-(tri-n-butylstannyl)imidazo[5,1-b]thiazole a) 7-Pivaloylimidazo[5,1-b]thiazole

Aluminum chloride (6.0 g) was added to a solution of 6.1 ml of pivaloyl chloride in 50 ml of carbon disulfide. The mixture was stirred. A solution of 1.2 g of imidazo[5,1-b]thiazole in 20 ml of dichloromethane was added thereto, and the mixture was stirred at room temperature for 48 hr. Dichloromethane (200 ml) was added to the reaction mixture. The mixture was washed with water and a saturated aqueous sodium hydrogencarbonate solution in that order, and then dried over anhydrous magnesium sulfate. The solvent was removed by distillation. The residue was purified by column chromatography on silica gel (hexane:ethyl acetate=1:2) to give 0.92 g of 7-pivaloylimidazo[5,1-b]thiazole.

NMR (CDCl$_3$) δ: 1.39 (9H, s), 6.73 (1H, d, J=4.3 Hz), 7.32 (1H, d, J=4.3 Hz), 7.92 (1H, s)

b) 7-Pivaloyl-2-(tri-n-butylstannyl)imidazo[5,1-b]thiazole

A 1.6 N n-butyllithium/n-hexane solution (2.9 ml) was added to a solution of 0.92 g of 7-pivaloylimidazo[5,1-b]thiazole in 20 ml of dry THF in an argon atmosphere at −50° C. The mixture was stirred at the same temperature for 20 min. Tri-n-butylstannyl chloride (1.3 ml) was added thereto, followed by stirring for 20 min. A saturated aqueous ammonium chloride solution was added to the reaction mixture. Ethyl acetate was added thereto. The mixture was washed with water and saturated brine in that order. The organic layer was dried over anhydrous magnesium sulfate. The solvent was removed by distillation. The residue was purified by column chromatography on silica gel (hexane:ethyl acetate=1:3) to give 0.82 g of the title compound.

NMR (CDCl$_3$) δ: 0.92 (9H, t, J=7.2 Hz), 1.13 (6H, t, J=8.4 Hz), 1.30–1.40 (15H, m), 1.52–1.62 (6H, m), 7.08 (1H, s), 7.88 (1H, s)

Preparation 5

7-Acetyl-3-methyl-2-(tri-n-butylstannyl)imidazo-[5,1-b]thiazole a) 7-Acetyl-3-methylimidazo[5,1-b]thiazole

Aluminum chloride (16.0 g) was added to a solution of 10.0 ml of acetyl chloride in 100 ml of carbon disulfide at room temperature. The mixture was stirred for 30 min. A solution of 2.76 g of 3-methylimidazo[5,1-b]thiazole in 40 ml of dichloromethane was added dropwise thereto over a period of 15 min with stirring. The mixture was further stirred for 6 hr. The reaction solution was added to a mixture of 200 ml of dichloromethane with 100 g of ice with thorough stirring. After dissolution of the ice, 40 g of sodium carbonate and 50 g of sodium sulfate were added in that order with thorough stirring. The mixture was stirred under ice cooling for 30 min. After standing, the organic layer was separated by decantation. The gum residue was extracted with dichloromethane (100 ml, five times), and then combined with the organic layer. The combined organic layer was dried over anhydrous magnesium sulfate, and concentrated to dryness under the reduced pressure. Ethyl acetate (10 ml) was added to the concentrate. The resultant solid was triturated with 10 ml of ethyl acetate, collected by filtration, and washed with a minor amount of ethyl acetate. The washed product was dried under the reduced pressure to give 2.92 g of 7-acetyl-3-methylimidazo[5,1-b]thiazole.

NMR (CDCl$_3$) δ: 2.51 (3H, d, J=1.3 Hz), 2.61 (3H, s), 7.66 (1H, q, J=1.3 Hz), 7.88 (1H, s)

b) 7-Acetyl-3-methyl-2-(tri-n-butylstannyl)imidazo-[5,1-b]thiazole

A 1.0 N lithiumbis(trimethylsilyl)amide/n-hexane solution (2.2 ml) was added dropwise to a solution of 0.360 g of 7-acetyl-3-methylimidazo[5,1-b]thiazole in THF (20 ml) at −70° C. The mixture was stirred for 15 min. A 1.6 N n-butyllithium/n-hexane solution (2.8 ml) was added dropwise to the reaction solution at the same temperature. The mixture was stirred for one hr. A solution (4 ml) of 0.846 g of tri-n-butylstannyl chloride in THF was added dropwise to the reaction solution. The mixture was stirred at −40° C. for 30 min. The reaction solution was added under ice cooling to a mixed solution composed of ether (50 ml) and 0.2 N phosphate buffer (pH 7) (50 ml) with thorough stirring. The organic layer was separated, washed with 0.2 N phosphate buffer (pH 7) (30 ml), and dried over anhydrous magnesium sulfate. The solvent was removed by distillation. The residue was subjected to separation and purification by flash column chromatography on silica gel (ethyl acetate) to give 0.752 g of the title compound.

NMR (CDCl$_3$) δ: 0.90 (9H, t, J=7.3 Hz), 1.10 to 1.43 (12H, m), 1.50 to 1.62 (6H, m), 2.46 (3H, s), 2.60 (3H, s), 7.80 (1H, s)

Preparation 6

7-(2-Formylamino)propionyl-2-(tri-n-butylstannyl)-imidazo[5,1-b]thiazole a) 7-Acetylimidazo[5,1-b]thiazole

In the same manner as in Preparation 9-a), 5.09 g of 7-acetylimidazo[5,1-b]thiazole was obtained from 4.97 g of imidazo[5,1-b]thiazole.

NMR (CDCl$_3$) δ: 2.62 (3H, s), 7.10 (1H, d, J=4.1 Hz), 7.55 (1H, d, J=4.1 Hz), 8.00 (1H, s) MS (TS): 167 (M$^+$+H)

b) 7-Azidoacetylimidazo[5,1-b]thiazole

A 1.0 N lithiumbis(trimethylsilyl)amide/n-hexane solution (5.8 ml) was added to a solution of 0.83 g of 7-acetylimidazo[5,1-b]thiazole in 20 ml of dry THF and 5 ml of HMPA in an argon atmosphere at −50° C. The mixture was stirred for 30 min. Trimethylsilyl chloride (0.76 ml) was added thereto at −20° C. The mixture was stirred for 30 min. Further, a solution of 1.07 g of N-bromosuccinimide in 20 ml of dry THF was added thereto at 0° C. The mixture was stirred at room temperature for 2 hr. Ethyl acetate was added to the reaction mixture. The mixture was washed with water and saturated brine in that order, and dried over anhydrous magnesium sulfate. DMF (10 ml) was added thereto. The solvent was concentrated. Sodium azide (0.39 g) was added to a solution of the reaction mixture in 10 ml of DMF. The mixture was stirred at room temperature for 12 hr. Ethyl acetate was added to the reaction mixture. The mixture was washed with water and saturated brine in that order, and dried over anhydrous magnesium sulfate. The solvent was removed by distillation. The residue was purified by column chromatography on silica gel (ethyl acetate) to give 0.44 g of 7-azidoacetylimidazo[5,1-b]thiazole.

NMR (CDCl$_3$) δ: 4.62 (2H, s), 7.17 (1H, d, J=3.6 Hz), 7.60 (1H, d, J=3.6 Hz), 8.03 (1H, s)

c) 7-Formylaminoacetylimidazo[5,1-b]thiazole

A 10% hydrochloric acid/methanol solution (1 ml) and 120 mg of 10%Pd-C were added to a solution of 0.44 g of 7-azidoacetylimidazo[5,1-b]thiazole in 50 ml of methanol and 50 ml of THF. The atmosphere in the reactor was replaced with hydrogen. The system was stirred at room temperature for 2 hr. The reaction mixture was filtered. The solvent was removed by distillation. To the residue were added 10 ml of DMF, 0.39 g of 4-nitrophenyl formate, and 0.66 ml of triethylamine. The mixture was stirred at room temperature for 30 min. Dichloromethane was added to the reaction solution. The mixture was washed with water and saturated brine in that order, and then dried over anhydrous magnesium sulfate. The solvent was removed by distillation. The residue was purified by column chromatography on silica gel (dichloromethane:methanol=10:1) to give 0.24 g of 7-formylaminoacetylimidazo[5,1-b]thiazole.

NMR (DMSO-d$_6$) δ: 4.56 (2H, d, J=5.8 Hz), 7.54 (1H, d, J=5.0 Hz), 8.11 (1H, d, J=5.0 Hz), 8.15 (1H, s), 8.33 (1H, s), 8.37 (1H, s)

d) 7-(2-Formylaminopropionyl)imidazo[5,1-b]thiazole

Sodium hydride (31 mg) was added to a solution of 0.24 g of 7-formylaminoacetylimidazo[5,1-b]thiazole in 4 ml of DMF. The mixture was stirred at 60° C. for 30 min, and cooled to room temperature. Thereafter, 176 mg of methyl iodide was added thereto. The mixture was stirred for one hr. Dichloromethane was added to the reaction mixture. The mixture was washed with water and saturated brine in that order, and dried over anhydrous magnesium sulfate. The solvent was removed by distillation. The residue was purified by column chromatography on silica gel (dichloromethane:methanol=20:1) to give 0.12 g of 7-(2-formylaminopropionyl)imidazo[5,1-b]thiazole.

NMR (CDCl$_3$) δ: 1.61 (3H, d, J=7.0 Hz), 5.60–5.70 (1H, m), 6.85 (1H, s), 7.16 (1H, d, J=4.1 Hz), 7.60 (1H, d, J=4.1 Hz), 8.02 (1H, s), 8.27 (1H, s)

e) 7-(2-Formylamino)propionyl-2-(tri-n-butylstannyl)imidazo[5,1-b]thiazole

In substantially the same manner as in Preparation 4-b), 96 mg of the title compound was obtained from 0.12 g of 7-(2-formylaminopropionyl)imidazo[5,1-b]thiazole.

NMR (CDCl$_3$) δ: 0.85–0.95 (9H, m), 1.15–1.25 (6H, m), 1.25–1.45 (2H, m), 1.50–1.65 (9H, m), 5.60–5.70 (1H, m), 6.95 (1H, s), 7.32 (1H, s), 7.95 (1H, s), 8.26 (1H, s)

Preparation 7

7-Isobutyryl-2-(tri-n-butylstannyl)imidazo[5,1-b]thiazole a) 7-Isobutyrylimidazo[5,1-b]thiazole

Aluminum chloride (16.2 g) was added to a solution of 15.0 ml of isobutyryl chloride in 100 ml of carbon disulfide. A solution of 40 ml of dichloromethane in 2.50 g of imidazo[5,1-b]thiazole was added dropwise to the mixture. The mixture was stirred at room temperature for 20 hr. Dichloromethane (100 ml) was added to the reaction solution. Water (60 ml) was added dropwise thereto with stirring. The organic layer was then separated. Dichloromethane (200 ml) and 100 g of sodium carbonate were added to the aqueous layer. The mixture was stirred. The insolubles were removed by filtration, and washed with dichloromethane. The filtrate was combined with the organic layer. The combined organic layer was dried over anhydrous magnesium sulfate and filtered. The filtrate was concentrated under the reduced pressure. The residue was purified by column chromatography on silica gel (dichloromethane:ethyl acetate=1:1) to give 2.75 g of 7-isobutyrylimidazo[5,1-b]thiazole.

NMR (CDCl$_3$) δ: 1.26 (6H, d, J=6.9 Hz), 3.73 (1H, m), 7.09 (1H, d, J=4.1 Hz), 7.54 (1H, d, J=4.1 Hz), 8.00 (1H, s)

b) 7-Isobutyryl-2-(tri-n-butylstannyl)imidazo[5,1-b]thiazole

A 1.0 N lithiumbis(trimethylsilyl)amide/THF solution (12 ml) was added to 60 ml of THF. Tri-n-butylstannyl chloride (2.36 ml) and a solution of 1.18 g of 7-isobutyrylimidazo [5,1-b]thiazole in 18 ml of THF were added drop wise there to in an argon atmosphere at −68° C. The mixture was stirred at the same temperature for one hr. Ethyl acetate (450 ml) was added to the reaction solution, and the mixture was washed with 200 ml of brine. The organic layer was dried over anhydrous magnesium sulfate, and then filtered. The solvent was removed by distillation under the reduced pressure. The residue was purified by column chromatography on silica gel (hexane:ethyl acetate=3:2) to give 1.55 g of the title compound.

NMR (CDCl$_3$) δ: 0.86 (9H, t, J=7.3 Hz), 1.13 (6H, m), 1.21 (6H, d, J=6.9 Hz), 1.30 (6H, m), 1.53 (6H, m), 3.69 (1H, m), 7.28 (1H, s), 7.92 (1H, s)

Preparation 8

7-Acetyl-3-(tri-n-butylstannyl)imidazo[5,1-b]thiazole and 7-acetyl-2-(tri-n-butylstannyl)imidazo-[5,1-b]thiazole In the same manner as in Example 9-b), a reaction was allowed to proceed using 10.5 g of 7-acetylimidazo[5,1-b]thiazole was used as the starting compound. Purification was carried out by column chromatography on silica gel (hexane:ethyl acetate=1:1). Of two main components, the fraction, which had been eluted earlier, was collected to give 1.36 g of 7-acetyl-3-(tri-n-butylstannyl)imidazo[5,1-b]thiazole.

NMR (CDCl$_3$) δ: 0.90 (9H, t, J=7.4 Hz), 1.31 (12H, m), 1.56 (6H, m), 2.62 (3H, s), 6.90 (1H, s), 7.89 (1H, s) MS (ESI): 457 (M$^+$+H)

Of the two main components, the fraction, which had been eluted later, was collected to give 19.5 g of 7-acetyl-2-(tri-n-butylstannyl)imidazo[5,1-b]thiazole.

NMR (CDCl$_3$) δ: 0.91 (9H, t, J=7.2 Hz), 1.19 (6H, m), 1.35 (6H, m), 1.58 (6H, m), 2.61 (3H, s), 7.28 (1H, s), 7.94 (1H, s) MS (ESI): 457 (M$^+$+H)

Preparation 9

7-Acetyl-5-methyl-2-(tri-n-butylstannyl)imidazo-[5,1-b]thiazole a) 7-Acetyl-5-methylimidazo[5,1-b]thiazole

Aluminum chloride (6.96 g) was added to a solution of 4.33 ml of acetyl chloride in 40 ml of carbon disulfide. A solution of 1.20 g of 5-methylimidazo[5,1-b]thiazole in 40 ml of dichloromethane was added dropwise thereto. The mixture was stirred at room temperature for 24 hr. The reaction solution was poured into 40 g of ice. Dichloromethane (100 ml) was added thereto. Sodium carbonate (32 g) was added to the mixture with stirring. The insolubles were removed by filtration, and washed with dichloromethane. The filtrate was concentrated under the reduced pressure. Ethyl acetate (20 ml) was added thereto. The resultant crystal was collected by filtration. The filtrate was purified by column chromatography on silica gel (dichloromethane:methanol=20:1). The purification product was combined with the above collected crystal to give 1.45 g of 7-acetyl-5-methylimidazo[5,1-b]thiazole.

NMR (CDCl$_3$) δ: 2.58 (3H, s), 2.65 (3H, s), 7.06 (1H, d, J=4.2 Hz), 7.37 (1H, d, J=4.2 Hz)

b) 7-Acetyl-5-methyl-2-(tri-n-butylstannyl)imidazo[5,1-b]thiazole

A 1.0 N lithiumbis(trimethylsilyl)amide/THF solution (3.75 ml) was added dropwise to a solution of 613 mg of 7-acetyl-5-methylimidazo[5,1-b]thiazole in 34 ml of THF in an argon atmosphere at –73° C. The mixture was stirred at the same temperature for 50 min. A 1.59 N n-butyllithium/n-hexane solution (4.71 ml) was added dropwise thereto. The mixture was stirred at the same temperature for 50 min. Tri-n-butylstannyl chloride (1.16 ml) was added dropwise thereto. The mixture was further stirred at the same temperature for 40 min. An ammonium chloride solution was added to the reaction solution, followed by extraction with ethyl acetate and washing with brine. The extract was dried over anhydrous magnesium sulfate and then filtered. The solvent was removed by distillation under the reduced pressure. The residue was purified by column chromatography on silica gel (hexane:ethyl acetate=1:1) to give 1.40 g of the title compound.

NMR (CDCl$_3$) δ: 0.91 (9H, t, J=7.4 Hz), 1.18 (6H, m), 1.35 (6H, m), 1.58 (6H, m), 2.57 (3H, s), 2.64 (3H, s), 7.06 (1H, s)

Preparation 10

7-Methanesulfonyl-2-(tri-n-butylstannyl,)imidazo-[5,1-b]thiazole

A 1.6 N n-butyllithium/n-hexane solution (2.8 ml) was added to a solution of 404 mg of 7-methanesulfonylimidazo[5,1-b]thiazole in 20 ml of dry THF in an argon atmosphere at –40° C. The mixture was stirred at the same temperature for 30 min. Tri-n-butylstannyl chloride (0.6 ml) was added thereto. A saturated aqueous ammonium chloride solution was added to the reaction solution. Ethyl acetate was then added thereto. The mixture was washed with water and saturated brine in that order. The organic layer was dried over anhydrous magnesium sulfate. The solvent was removed by distillation. The residue was purified by column chromatography on silica gel (hexane:ethyl acetate=2:1) to give 251 mg of the title compound.

NMR (CDCl$_3$) δ: 0.85–0.95 (9H, m), 1.25–1.33 (6H, m), 1.25–1.40 (6H, m), 1.52–1.64 (6H, m), 3.20 (3H, s), 7.26 (1H, s), 7.99 (1H, s)

Preparation 11

7-Methanesulfonyl-3-(tri-n-butylstannyl)imidazo-[5,1-b]thiazole a) 7-Methanesulfonylimidazo[5,1-b]thiazole

In substantially the same manner as in Example 12-a), 0.94 g of 7-methanesulfonylimidazo[5,1-b]thiazole was obtained from 2.50 g of 7-iodoimidazo[5,1-b]thiazole and 0.81 ml of methanesulfonyl chloride.

NMR (CDCl$_3$) δ: 3.20 (3H, s), 7.09 (1H, d, J=4.2 Hz), 7.61 (1H, d, J=4.2 Hz), 8.10 (1H, s)

b) 7-Methanesulfonyl-3-(tri-n-butylstannyl)imidazo[5,1-b]thiazole

A 1.6 N n-butyllithium/n-hexane solution (0.7 ml) was added to a solution of 202 mg of 7-methanesulfonylimidazo[5,1-b]thiazole in 20 ml of dry THF in an argon atmosphere at –70° C. The mixture was stirred at the same temperature for 30 min. Tri-n-butylstannyl chloride (0.3 ml) was added thereto. A saturated aqueous ammonium chloride solution was added to the reaction mixture. Ethyl acetate was then added thereto. The mixture was washed with water and saturated brine in that order. The organic layer was dried over anhydrous magnesium sulfate. The solvent was removed by distillation. The residue was purified by column chromatography on silica gel (hexane:ethyl acetate=2:1) to give 110 mg of the title compound.

NMR (CDCl$_3$) δ: 0.85–0.95 (9H, m), 1.25–1.40 (12H, m), 1.50–1.60 (6H, m), 3.20 (3H, s), 6.81 (1H, s), 7.95 (1H, s)

Preparation 12

7-Methylthio-2-(tri-n-butylstannyl)imidazo[5,1-b]thiazole a-1) 7-Methylthioimidazo[5,1-b]thiazole

A 1 M ethylmagnesium bromide/THF solution (1.4 ml) was added under ice cooling to a solution of 0.31 g of 7-iodoimidazo[5,1-b]thiazole in 3 ml of dry THF in an argon atmosphere. The mixture was stirred at the same temperature for one hr. Methyl methanethiolsulfonate (0.15 ml) was added thereto. The mixture was stirred at room temperature for 12 hr. A saturated aqueous ammonium chloride solution was added to the reaction solution. Ethyl acetate was added thereto. The mixture was washed with a dilute aqueous sodium thiosulfate solution and saturated brine in that order. The organic layer was dried over anhydrous magnesium sulfate. The solvent was removed by distillation. The residue was purified by column chromatography on silica gel (ethyl acetate) to give 0.15 g of 7-methylthioimidazo[5,1-b]thiazole.

NMR (CDCl$_3$) δ: 2.41 (3H, s), 6.86 (1H, d, J=4.2 Hz), 7.39 (1H, d, J=4.2 Hz), 8.00 (1H, s)

a-2) 7-Methylthioimidazo[5,1-b]thiazole

To 200 ml of dichloromethane cooled at 0° C., 35 ml of trichlorotitanium and 40 g of methyl metahnethiolsulfonate were added and the mixture was stirred at the same temperature for 20 min. The mixture was added dropwise to 1L of nitorbenzene containing 26 g of imidazo[5,1-b]thiazole at 5 to 10° C. and stirred at the same temperature for five hr. The reaction was stopped by adding 400 ml of 0.5N hydrochloride, followed by filtration to remove insolubles. The mixture was washed with 200 ml of dichloromethane and 200 ml of water. The organic layer was removed and the aqueous layer was washed with 800 ml of dichloromethane twice. After the pH of the aqueous layer was adjusted to 4.0, the extraction three times with dichloromethane. The organic layer was dried and the solvent was removed to give 19.8 g of 7-Methylthioimidazo[5,1-b]thiazole.

b) 7-Methylthio-2-(tri-n-butylstannyl)imidazor[5,1-b[thiazole

In substantially the same manner as in Preparation 4-b), 1.50 g of the title compound was obtained from 0.79 g of 7-methylthioimidazo[5,1-b]thiazole.

NMR (CDCl$_3$) δ: 0.92 (9H, t, J=7.2 Hz), 1.15 (6H, t, J=8.4 Hz), 1.30–1.40 (6H, m), 1.55–1.65 (6H, m), 2.40 (3H, s), 7.13 (1H, s), 7.94 (1H, s)

Preparation 13

7-Ethanesulfonyl-2-(tri-n-butylstannyl)imidazo[5,1-b]thiazole a) 7-Ethanesulfonylimidazo[5,1-b]thiazole

A solution of 725 mg of 7-methanesulfonylimidazo[5,1-b]thiazole in 35 ml of THF was cooled in an argon atmosphere to −70° C. A 1 N-lithiumbis(trimethylsilyl)amide/THF solution (3.9 ml) was added dropwise thereto at the same temperature. The mixture was stirred for 30 min. Thereafter, 0.25 ml of methyl iodide was added thereto. The mixture was stirred at the same temperature for 70 min. A saturated aqueous sodium chloride solution was added thereto, followed by extraction four times with ethyl acetate. The extract was dried over anhydrous magnesium sulfate. The solvent was removed by distillation under the reduced pressure. The residue was purified by column chromatography on silica gel (ethyl acetate:methanol=9:1) to give 0.79 g of 7-ethanesulfonylimidazo[5,1-b]thiazole.

NMR (CDCl$_3$) δ: 1.34 (3H, t, J=7.4 Hz), 3.33 (2H, q, J=7.4 Hz), 7.07 (1H, d, J=4.3 Hz), 7.55 (1H, s), 8.08 (1H, s)

b) 7-Ethanesulfonyl-2-(tri-n-butylstannyl)imidazo[5,1-b]thiazole

A solution of 669 mg of 7-ethanesulfonylimidazo[5,1-b]thiazole in 30 ml of THF was cooled to −40° C. in an argon atmosphere. A 1.6 N n-butyllithium/n-hexane solution (4.3 ml) was added dropwise thereto at the same temperature. The mixture was stirred for 15 min. Tri-n-butylstannyl chloride (0.88 ml) was added thereto, followed by stirring at the same temperature for 10 min. A saturated aqueous ammonium chloride solution was added thereto. The mixture was extracted twice with ethyl acetate. The extract was dried over anhydrous magnesium sulfate. The solvent was removed by distillation under the reduced pressure. The residue was purified by column chromatography on silica gel (hexane:ethyl acetate=1:1). The title compound (1.54 g) was obtained from the fraction of Rf=0.2.

NMR (CDCl$_3$) δ: 0.92 (9H, t, J=7.1 Hz), 1.22 (6H, m), 1.38 (9H, m), 1.58 (6H, m), 3.31 (2H, q, J=7.4 Hz), 7.26 (1H, s), 8.00 (1H, s)

Preparation 14

7-(N-Methylsulfamoyl)-2-(tri-n-butylstannyl)-imidazo[5,1-b]thiazole a) 7-(N-Methylsulfamoyl)imidazo[5,1-b]thiazole

In substantially the same manner as in Example 25-b), 0.34 g of 7-(N-methylsulfamoyl)imidazo[5,1-b]thiazole was obtained from 0.36 g of 7-chlorosulfonylimidazo[5,1-b]thiazole and 10 ml of a 2 M methylamine/THF solution.

NMR (CDCl$_3$) δ: 2.71 (3H, d, J=5.4 Hz), 4.76–4.85 (1H, m), 7.04 (1H, d, J=4.1 Hz), 7.53 (1H, d, J=4.1 Hz), 8.06 (1H, s)

b) 7-(N-Methylsulfamoyl)-2-(tri-n-butylstannyl)imidazo[5,1-b]thiazole

A 1.6 N n-butyllithium/n-hexane solution (1.6 ml) was added to a solution of 0.26 g of 7-(N-methylsulfamoyl)imidazo[5,1-b]thiazole in 8 ml of dry THF and 4 ml of HMPA in an argon atmosphere at −50° C. The mixture was stirred at the same temperature for 30 min. Tri-n-butylstannyl chloride (0.34 ml) was added thereto. The mixture was stirred for 30 min. A 1.6 N n-butyllithium/n-hexane solution (0.8 ml) was further added thereto. The mixture was stirred for 30 min. Tri-n-butylstannyl chloride (0.2 ml) was added thereto, followed by stirring at the same temperature for 30 min. A saturated aqueous ammonium chloride solution was added thereto. Ethyl acetate was then added, followed by washing with water and saturated brine in that order. The organic layer was dried over anhydrous magnesium sulfate. The solvent was removed by distillation. The residue was purified by column chromatography on silica gel (hexane:ethyl acetate=1:2) to give 0.39 g of the title compound.

NMR (CDCl$_3$) δ: 0.92 (9H, t, J=7.2 Hz), 1.18 (6H, t, J=8.5 Hz), 1.30–1.40 (6H, m), 1.53–1.60 (6H, m), 2.71 (3H, d, J=5.4 Hz), 4.65–4.72 (1H, m), 7.24 (1H, s), 7.98 (1H, s)

Preparation 15

7-p-Toluenesulfonyl-2-(tri-n-butylstannyl)imidazo-[5,1-b]thiazole a) 7-p-Toluenesulfonylimidazo[5,1-b]thiazole

A solution of 23.9 g of p-toluenesulfonyl chloride in 100 ml of dichloromethane was cooled to ice temperature in an argon atmosphere. Aluminum chloride (15.3 g) was added thereto. The mixture was stirred for 10 min. A solution of 3.15 g of imidazo[5,1-b]thiazole in 25 ml of dichloromethane was added dropwise thereto. The mixture was stirred for 22 hr. Dichloromethane (200 ml), 70 ml of water, and 75 g of a sodium carbonate powder were added thereto, followed by extraction. The extract was dried over anhydrous magnesium sulfate. The solvent was removed by distillation under the reduced pressure to give 995 mg of 7-p-toluenesulfonylimidazo[5,1-b]thiazole.

NMR (CDCl$_3$) δ: 2.36 (3H, s), 7.40 (2H, d, J=8.3 Hz), 7.46 (1H, d, J=4.1 Hz), 7.76 (2H, d, J=8.3 Hz), 8.03 (1H, d, J=4.1 Hz), 8.34 (1H, s)

b) 7-p-Toluenesulfonyl-2-(tri-n-butylstannyl) imidazo[5,1-b]thiazole

A solution of 669 mg of 7-p-toluenesulfonylimidazo[5,1-b]thiazole in 65 ml of THF was cooled to −60° C. in an argon atmosphere. A 1.6 N n-butyllithium/n-hexane solution (2.5 ml) was added dropwise thereto at the same temperature. The mixture was stirred for 20 min. A solution of 1.25 g of tri-n-butylstannyl chloride in 10 ml of THF was added thereto, and the mixture was stirred at the same temperature for 40 min. A semisaturated aqueous ammonium chloride solution (150 ml) was added thereto, followed by extraction with 250 ml of ethyl acetate. The extract was dried over anhydrous magnesium sulfate. The solvent was removed by distillation under the reduced pressure. The residue was purified by column chromatography on silica gel (hexane:ethyl acetate=1:1). The title compound (590 mg) was obtained from the fraction of Rf=0.4.

NMR (CDCl$_3$) δ: 0.92 (9H, t, J=7.3 Hz), 1.83 (6H, m), 1.35 (6H, m), 1.56 (6H, m), 2.39 (3H, s), 7.20 (1H, s), 7.29 (2H, d, J=8.4 Hz), 7.91 (1H, s), 7.97 (2H, d, J=8.4 Hz)

Preparation 16

7-t-Butyldimethylsilyloxyacetyl-3-(tri-n-butylstannyl)imidazo[5,1-b]thiazole and 7-t-butyldimethylsilyloxyacetyl-2-(tri-n-butylstannyl)-imidazo[5,1-b]-thiazole a) 7-Acetoxyacetylimidazo[5,1-b]thiazole 7-Acetylimidazo[5,1-b]thiazole (2.49 g) was dissolved in a solution of 150 ml of THF and 30 ml of HMPA. A 1.0 N lithiumbis(trimethylsilyl)amide/THF solution (18 ml) was added dropwise to the solution in an argon atmosphere at −70° C. The mixture was stirred at the same temperature for 30 min. Trimethylsilyl chloride (2.28 ml) was added dropwise thereto. The mixture was stirred at the same temperature for 30 min. A solution of 3.21 g of N-bromosuccinimide in 90 ml of THF was added dropwise thereto. The mixture was stirred for 2 hr while raising the temperature to room temperature. Ethyl acetate (400 ml) was added to the reaction solution. The mixture was washed twice with brine, dried over anhydrous magnesium sulfate, and filtered. The solvent was removed by distillation under the reduced pressure. The residue was dissolved in 120 ml of DMF. Sodium acetate (1.48 g) was added to the solution. The mixture was stirred at room temperature for 14 hr and then at 60° C. for 4 hr. The reaction solution was concentrated under the reduced pressure until the amount of the solution became half. Brine (200 ml) was added to the concentrate, followed by extraction twice with 300 ml of ethyl acetate. The organic layers were combined together, washed three times with brine, dried over anhydrous magnesium sulfate, and filtered. The solvent was removed by distillation under the reduced pressure. The residue was purified by column chromatography on silica gel (eluting with dichloromethane:ethyl acetate=1:1 and then with ethyl acetate) to give 2.11 g of 7-acetoxyacetylimidazo[5,1-b]thiazole.

NMR (CDCl$_3$) δ: 2.24 (3H, s), 5.44 (2H, s), 7.13 (1H, d, J=4.1 Hz), 7.57 (1H, d, J=4.1Hz), 8.00 (1H, s)

b) 7-Hydroxyacetylimidazo[5,1-b]thiazole

7-Acetoxyacetylimidazo[5,1-b]thiazole (24.6 mg) was dissolved in 2 ml of methanol and 0.5 ml of water. Potassium carbonate (17.3 mg) was added under ice cooling to the solution. The mixture was stirred for 45 min. Methanol was removed by distillation under the reduced pressure. Water (10 ml) was added to the residue, followed by extraction five times with dichloromethane. The extract was dried over anhydrous magnesium sulfate, and then filtered. The solvent was removed by distillation under the reduced pressure to give 18.8 mg of 7-hydroxyacetylimidazo[5,1-b]thiazole.

NMR (CDCl$_3$) δ: 3.55 (1H, t, J=4.7 Hz), 4.92 (2H, d, J=4.7 Hz), 7.16 (1H, d, J=4.1 Hz), 7.60 (1H, d, J=4.1 Hz), 8.03 (1H, s)

c) 7-t-Butyldimethylsilyloxyacetylimidazo[5,1-b] thiazole

7-Hydroxyacetylimidazo[5,1-b]thiazole (1.42 g) was dissolved in 10 ml of DMF. Imidazole (847 mg) and 1.77 g of t-butyldimethylsilyl chloride were added to the solution in an argon atmosphere. The mixture was stirred at room temperature for 24 hr. Brine was added to the reaction solution, followed by extraction twice with ethyl acetate. The organic layers were combined together, washed with brine, dried over anhydrous magnesium sulfate, and then filtered. The solvent was removed by distillation under the reduced pressure. The residue was purified by column chromatography on silica gel (hexane:ethyl acetate=1:2) to give 2.19 g of 7-t-butyldimethylsilyloxyacetylimidazo[5,1-b]thiazole.

NMR (CDCl$_3$) δ: 0.16 (6H, s), 0.97 (9H, s), 5.10 (2H, s), 7.11 (1H, d, J=4.2 Hz), 7.55 (1H, d, J=4.2 Hz), 7.98 (1H, s)

d) 7-t-Butyldimethylsilyloxyacetyl-3-(tri-n-butylstannyl)imidazo[5,1-b]thiazole and 7-t-butyldimethylsilyloxyacetyl-2-(tri-n-butylstannyl)-imidazo[5,1-b]thiazole Tri-n-butylstannyl chloride (2.97 ml) and 16.0 ml of a 1.0 N lithiumbis(trimethylsilyl)amide/THF solution were added dropwise in that order to a solution of 2.37 g of 7-t-butyldimethylsilyloxyacetylimidazo[5,1-b]thiazole in 80 ml of THF in an argon atmosphere at −73° C. The mixture was stirred at the same temperature for 30 min. An ammonium chloride solution was added to the reaction solution, followed by extraction with ethyl acetate. The extract was dried over anhydrous magnesium sulfate, and then filtered. The solvent was removed by distillation under the reduced pressure. The residue was purified by column chromatography on silica gel (hexane:ethyl acetate=5:1 to 2:1). Of two main components, the fraction, which had been eluted earlier, was collected to give 484 mg of 7-t-butyldimethylsilyloxyacetyl-3-(tri-n-butylstannyl)-imidazo[5,1-b]thiazole.

NMR (CDCl$_3$) δ: 0.16 (6H, s), 0.92 (9H, t, J=7.1 Hz), 0.97 (9H, s), 1.31 (12H, m), 1.60 (6H, m), 5.10 (2H, s), 6.88 (1H, s), 7.85 (1H, s)

Of the two main components, the fraction, which had been eluted later, was collected to give 3.51 g of 7-t-butyldimethylsilyloxyacetyl-2-(tri-n-butylstannyl)-imidazo[5,1-b]thiazole.

NMR (CDCl$_3$) δ: 0.15 (6H, s), 0.91 (9H, t, J=7.2 Hz), 0.96 (9H, s), 1.18 (6H, m), 1.35 (6H, m), 1.56 (6H, m), 5.08 (2H, s), 7.27 (1H, s), 7.91 (1H, s)

Preparation 17

7-Benzoyl-2-(tri-n-butylstannyl)imidazo[5,1-b]-thiazole a) 7-Benzoylimidazo[5,1-b]thiazole

Aluminum chloride (5.33 g) was added to a solution of 4.64 ml of benzoyl chloride in 50 ml of carbon disulfide. A solution of 1.24 g of imidazo[5,1-b]thiazole in 50 ml of dichloromethane was added dropwise thereto. The mixture was stirred at room temperature for 2 hr. The reaction solution was poured into 50 g of ice. Dichloromethane (100 ml) was added thereto. Sodium carbonate (16.7 g) and 16.7 g of sodium sulfate were added in that order to the mixture with stirring. The insolubles were removed by filtration through Celite, and then washed with dichloromethane. Filtrate was concentrated under the reduced pressure. The residue was purified by column chromatography on silica gel (hexane:ethyl acetate=5:1 to dichloromethane:ethyl acetate=2:1) to give 1.39 g of 7-benzoylimidazo[5,1-b]thiazole.

NMR (CDCl$_3$) δ: 7.16 (1H, d, J=4.1 Hz), 7.54 (3H, m), 7.60 (1H, d, J=4.1 Hz), 8.09 (1H, s), 8.54 (2H, m)

b) 7-Benzoyl-2-(tri-n-butylstannyl)imidazo[5,1-b]thiazole

In the same manner as in Preparation 16-d), 2.59 g of the title compound was obtained from 1.39 g of 7-benzoylimidazo[5,1-b]thiazole.

NMR (CDCl$_3$) δ: 0.92 (9H, t, J=7.2 Hz), 1.21 (6H, m), 1.36 (6H, m), 1.60 (6H, m), 7.34 (1H, s), 7.53 (3H, m), 8.03 (1H, s), 8.51 (2H, m)

Preparation 18

7-(4-Nitrobenzylsulfamoyl)-2-(tri-n-butylstannyl)-imidazo[5,1-b]thiazole a) 7-(4-Nitrobenzylsulfamoyl)imidazo[5,1-b]thiazole

4-Nitrobenzylamine (1.24 g) and 2 ml of diisopropylethylamine were added to a solution of 0.95 g of 7-chlorosulfonylimidazo[5,1-b]thiazole in 20 ml of DMF. The mixture was stirred at room temperature for 12 hr. Ethyl acetate was added to the reaction mixture. The mixture was washed with water and saturated brine in that order. The organic layer was dried over anhydrous magnesium sulfate. The solvent was evaporated, and the resultant powder was collected by filtration to give 1.07 g of 7-(4-nitrobenzylsulfamoyl)imidazo[5,1-b]thiazole.

NMR (DMSO-d$_6$) δ: 4.18 (2H, s), 7.36 (1H, d, J=4.2 Hz), 7.47 (2H, d, J=12.0 Hz), 7.95 (1H, d, J=4.2 Hz), 8.07 (2H, d, J=12.0 Hz), 8.30 (1H, s), 8.44 (1H, s)

b) 7-(4-Nitrobenzylsulfamoyl)-2-(tri-n-butylstannyl)imidazor5,1-b]thiazole

A 1.0 N lithiumbis(trimethylsilyl)amide/n-hexane solution (4.8 ml) was added to a solution of 0.68 g of 7-(4-nitrobenzylsulfamoyl)imidazo[5,1-b]thiazole in 20 ml of THF and 4 ml of HMPA in an argon atmosphere at −40° C. The mixture was stirred at the same temperature for 30 min. Tri-n-butylstannyl chloride (0.57 ml) was added thereto. The mixture was stirred at the same temperature for 30 min. A saturated aqueous ammonium chloride solution was added thereto. Ethyl acetate was then added thereto. The mixture was then washed with water and saturated brine in that order. The organic layer was dried over anhydrous magnesium sulfate. The solvent was removed by distillation. The residue was purified by column chromatography on silica gel (hexane:ethyl acetate=1:1) to give 0.78 g of the tile compound.

NMR (CDCl$_3$) δ: 0.92 (9H, t, J=7.2 Hz), 1.19 (6H, t, J=8.4 Hz), 1.30–1.40 (6H, m), 1.55–1.65 (6H, m), 4.33 (2H, d, J=6.4 Hz), 6.25 (2H, d, J=6.4 Hz), 7.17 (1H, s), 7.49 (2H, d, J=11.0 Hz), 7.90 (1H, s), 8.07 (2H, d, J=11.0 Hz)

Preparation 19

7-Fluoro-2-(tri-n-butylstannyl)imidazo[5,1-b]-thiazole a) 7-Fluoroimidazo[5,1-b]thiazole

N-Fluoro-N'-(chloromethyl)triethylenediaminebis(tetrafluoroborane) (11 g) was added to a solution of 2.0 g of imidazo[5,1-b]thiazole in 90 ml of a 1,2-dichloroethane in an argon atmosphere. The mixture was stirred at room temperature for 6 hr. A saturated aqueous sodium hydrogencarbonate solution was added thereto, followed by extraction with dichloromethane and washing with saturated brine. The extract was dried over anhydrous magnesium sulfate and then filtered. The solvent was removed by distillation under the reduced pressure. The residue was purified by column chromatography on silica gel (dichloromethane:ethyl acetate=40:1) to give 457 mg of 7-fluoroimidazo[5,1-b]thiazole.

NMR (CDCl$_3$) δ: 6.80 (1H, d, J=4.2 Hz), 7.32 (1H, dd, J$_1$=4.2 Hz, J$_2$=1.7 Hz), 7.59 (1H, s)

b) 7-Fluoro-2-(tri-n-butylstannyl)imidazo[5,1-b]thiazole

A 1.0 N lithiumbis(trimethylsilyl)amide/THF solution (3.2 ml) and 0.75 ml of tri-n-butylstannyl chloride were added in that order to a solution of 7-fluoroimidazo[5,1-b]thiazole in dry THF in an argon atmosphere at −78° C. The mixture was stirred at the same temperature for 10 min. Water was added thereto, followed by extraction with ethyl acetate and washing with saturated brine. The extract was dried over anhydrous magnesium sulfate and then filtered. The solvent was removed by distillation under the reduced pressure. The residue was purified by column chromatography on silica gel (hexane:ethyl acetate=7:1) to give 820 mg of the title compound.

NMR (CDCl$_3$) δ: 0.94 (9H, t, J=7.4 Hz), 1.15 (6H, m)1.35 (6H, m), 1.57 (6H, m), 7.04 (1H, d, J=1.7 Hz), 7.51 (1H, s)

Preparation 20

7-[N-(2-Hydroxyethyl)-N-methyl]sulfamoyl-2-(tri-n-butylstannyl)imidazo[5,1-b]thiazole a) 7-[N-(2-Hydroxyethyl)-N-methyl]sulfamoylimidazo-[5,1-b]thiazole

In substantially the same manner as in Example 27-a), 1.11 g of 7-[N-(2-hydroxyethyl)-N-methyl]sulfamoylimidazo[5,1-b]thiazole was obtained from 1.05 g of 7-chlorosulfonylimidazo[5,1-b]thiazole and 0.46 g of N-methylethanolamine.

NMR (CDCl$_3$) δ: 2.88 (3H, s), 3.57 (2H, t, J=4.5 Hz), 3.80–3.90 (2H, m), 4.35 (1H, m), 4.30–4.40 (1H, m), 7.07 (1H, d, J=4.2 Hz), 7.55 (1H, d, J=4.2 Hz), 8.05 (1H, s)

b) 7-[N-(2-t-Butyldimethylsilyloxyethyl)-N-methyl]sulfamoylimidazo[5,1-b]thiazole t-Butyldimethylsilyl chloride (0.33 g) and 0.16 g of imidazole were added to a solution of 0.52 g of 7-[N-(2- hydroxyethyl)-N-methyl]sulfamoylimidazo[5,1-b]thiazole in 20 ml of dichloromethane. The mixture was stirred at room temperature for 30 min. Ethyl acetate was added to the reaction mixture. The mixture was washed with water and saturated brine in that order. The organic layer was dried over anhydrous magnesium sulfate. The solvent was removed by distillation. The residue was purified by column chromatography on silica gel (hexane:ethyl acetate=1:1) to give 0.87 g of 7-[N-(2-t-butyldimethylsilyloxyethyl)-N-methyl]sulfamoylimidazo-[5,1-b]thiazole.

NMR (CDCl$_3$) δ: 0.05 (3H, s), 0.06 (3H, s), 0.88 (9H, s), 2.99 (3H, s), 3.33 (2H, t, J=5.8 Hz), 3.84 (2H, t, J=5.8 Hz), 7.02 (1H, d, J=4.1 Hz), 7.53 (1H, d, J=4.1 Hz), 8.03 (1H, s)

c) 7-[N-(2-t-Butyldimethylsilyloxyethyl)-N-methyl]
sulfamoyl-2-(tri-n-butylstannyl)imidazo[5,1-b]-
thiazole In substantially the same manner as in Preparation4-b), 0.54 g of the title compound was obtained from 0.45 g of 7-[N-(2-t-butyldimethylsilyloxyethyl)-N-methyl] sulfamoylimidazo[5,1-b]thiazole.

NMR (CDCl$_3$) δ: 0.06 (6H, s), 0.85–0.95 (21H, m), 1.15–1.21 (6H, m), 1.30–1.40 (6H, m), 1.55–1.65 (6H, m), 2.99 (3H, s), 3.32 (2H, t, J=6.0 Hz), 3.83 (2H, t, J=6.0 Hz), 7.24 (1H, s), 7.96 (1H, s)

Preparation 21

7-Acetylaminoacetyl-2-(tri-n-butylstannyl)imidazo-
[5,1-b]thiazole a) 7-Acetylaminoacetylimidazo[5,1-b]thiazole A solution (17 ml) of 10% hydrochloric acid in methanol and 800 mg of 10%Pd-C were added to a solution of 1.78 g of 7-azidoacetylimidazo[5,1-b]thiazole in 85 ml of methanol and 85 ml of THF. The atmosphere in the reactor was replaced with hydrogen. The system was stirred at room temperature for 5 hr. The catalyst was removed by filtration through Celite and washed with methanol. The solvent was removed by distillation. The residue was dissolved in 50 ml of DMF. Pyridine (3.43 ml) and 1.22 ml of acetic anhydride were added to the solution under ice cooling. The mixture was stirred at the same temperature for 2 hr. Dichloromethane and brine were added to the reaction solution. The mixture was adjusted to pH 10 by the addition of potassium carbonate. The organic layer were separated. The aqueous layer was further extracted five times with dichloromethane. The organic layers were combined together, dried over anhydrous magnesium sulfate, and filtered. The filtrate was concentrated under the reduced pressure. The residue was purified by column chromatography on silica gel (dichloromethane:methanol=40:1 to 20:1) to give 397 mg of 7-acetylaminoacetylimidazo[5,1-b]thiazole.

NMR (CDCl$_3$) δ: 2.10 (3H, s), 4.82 (2H, d, J=4.7 Hz), 6.50 (1H, br), 7.14 (1H, d, J=4.1 Hz), 7.58 (1H, d, J=4.1 Hz), 8.01 (1H, s)

b) 7-Acetylaminoacetyl-2-(tri-n-butylstannyl)
imidazo[5,1-b]thiazole

7-Acetylaminoacetylimidazo[5,1-b]thiazole (397 mg) was dissolved in 40 ml of THF and 8 ml of HMPA. Tri-n-butylstannyl chloride (0.76 ml) and 7.1 ml of a 1.0 N lithiumbis(trimethylsilyl)amide/THF solution were added dropwise in that order in an argon atmosphere at −73° C. The mixture was stirred at the same temperature for one hr. An ammonium chloride solution was added to the reaction solution, followed by extraction with ethyl acetate. The organic layer was washed twice with brine, dried over anhydrous magnesium sulfate, and then filtered. The solvent was removed by distillation under the reduced pressure. The residue was purified by column chromatography on silica gel (eluting with ethyl acetate and then with dichloromethane:methanol=20:1) to give 152 mg of the title compound.

NMR (CDCl$_3$) δ: 0.91 (9H, t, J=7.2 Hz), 1.20 (6H, m), 1.35 (6H, m), 1.56 (6H, m), 2.09 (3H, s), 4.79 (2H, d, J=4.5 Hz), 6.58 (1H, br), 7.31 (1H, s), 7.96 (1H, s)

Preparation 22

5-Methyl-7-methylthio-3-(tri-n-butylstannyl)-
imidazo[5,1-b]thiazole and 5-methyl-7-methylthio-
2-(tri-n-butylstannyl)imidazo[5,1-b]thiazole a) 7-Iodo-5-methylimidazo[5,1-b]thiazole 5-Methylimidazo[5,1-b]thiazole (6.90 g) was dissolved in 500 ml of dichloromethane. N-Iodosuccinimide (10.6 g) was added to the solution. The mixture was stirred at room temperature for 24 hr. N-Iodosuccinimide (1.06 g) was added thereto, followed by stirring for additional one hr. The reaction solution was washed with an aqueous sodium thiosulfate solution and brine in that order, dried over anhydrous magnesium sulfate, and then filtered. The solvent was removed by distillation under the reduced pressure. The residue was dissolved in 200 ml of dichloromethane and 100 ml of ethyl acetate. Silica gel (30 g) was added to the solution. The mixture was stirred. The silica gel was removed by filtration. The filtrate was washed with 200 ml of a mixed solution of dichloromethane:ethyl acetate=2:1. The filtrate was concentrated under the reduced pressure to give 13.08 g of 7-iodo-5-methylimidazo[5,1-b]thiazole.

NMR (CDCl$_3$) δ: 2.58 (3H, s), 6.83 (1H, d, J=4.2 Hz), 7.29 (1H, d, J=4.2 Hz)

b) 5-Methyl-7-methylthioimidazo[5,1-b]thiazole

In the same manner as in Preparation 12-a), 3.56 g of 5-methyl-7-methylthioimidazo[5,1-b]thiazole was obtained from 5.28 g of 7-iodo-5-methylimidazo[5,1-b]thiazole.

NMR (CDCl$_3$) δ: 2.40 (3H, s), 2.56 (3H, s), 6.81 (1H, d, J=4.2 Hz), 7.20 (1H, d, J=4.2 Hz)

c) 5-Methyl-7-methylthio-3-(tri-n-butylstannyl)
imidazo[5,1-b]thiazole and 5-methyl-7-methylthio-
2-(tri-n-butylstannyl)imidazo[5,1-b]thiazole 5-Methyl-7-methylthioimidazo[5,1-b]thiazole (3.34 g) was dissolved in 150 ml of THF. A 1.59 N n-butyllithium/n-hexane solution (22.8 ml) was added dropwise to the solution in an argon atmosphere at −73° C. The mixture was stirred at the same temperature for 40 min. Tri-n-butylstannyl chloride (6.39 ml) was added thereto, followed by stirring at the same temperature for one hr. An ammonium chloride solution was added to the reaction solution. The mixture was extracted with ethyl acetate. The extract was dried over anhydrous magnesium sulfate, and then filtered. The solvent was removed by distillation under the reduced pressure. The residue was purified by column chromatography on silica gel (hexane:ethyl acetate=2:1 to 1:1). Of two main components, the fraction, which had been eluted earlier, was collected to give 598 mg of 5-methyl-7-methylthio-3-(tri-n-butylstannyl)imidazo[5,1-b]thiazole.

NMR (CDCl$_3$) δ: 0.90 (9H, t, J=7.3 Hz), 1.19 (6H, m), 1.34 (6H, m), 1.53 (6H, m), 2.40 (3H, s), 2.61 (3H, s), 6.61 (1H, s)

Of the two main components, the fraction, which had been eluted later, was collected to give 6.04 g of 5-methyl-7-methylthio-2-(tri-n-butylstannyl)imidazo[5,1-b]-thiazole.

NMR (CDCl$_3$) δ: 0.92 (9H, t, J=7.3 Hz), 1.15 (6H, m), 1.35 (6H, m), 1.57 (6H, m), 2.39 (3H, s), 2.56 (3H, s), 6.92 (1H, s)

Preparation 23

7-N-Acetylaminomethyl-2-(tri-n-butylstannyl)-imidazo[5,1-b]thiazole a) 7-N-Acetylaminomethylimidazo[5,1-b]thiazole Hydrazine monohydrate (0.34 ml) was added to a solution of 0.63 g of 7-phthalimidomethylimidazo[5,1-b]thiazole in 15 ml of ethanol. The mixture was heated under reflux for one hr. The system was cooled to room temperature. The insolubles were removed by filtration. The solvent was removed by distillation. DMF (10 ml), 2 ml of pyridine and 1 ml of acetic anhydride were added the residue. The mixture was stirred at room temperature for 30 min. Methanol (5 ml) was added thereto. The solvent was removed by distillation. The residue was purified by column chromatography on silica gel (dichloromethane:methanol=20:1) to give 0.41 g of 7-N-acetylaminomethylimidazo[5,1-b]thiazole.

NMR (CDCl$_3$) δ: 2.02 (3H, s), 4.49 (2H, d, J=5.5 Hz), 6.25 (1H, s), 6.83 (2H, d, J=4.2 Hz), 7.37 (2H, d, J=4.2 Hz), 7.93 (1H, s)

b) 7-N-Acetylaminomethyl-2-(tri-n-butylstannyl)imidazo[5,1-b]thiazole

A 1.6 N n-butyllithium/n-hexane solution (2.5 ml) was added to a solution of 0.24 g of 7-N-acetylaminomethylimidazo[5,1-b]thiazole in 10 ml of dry THF and 2 ml of HMPA in an argon atmosphere at −50° C. The mixture was stirred at the same temperature for 30 min. Tri-n-butylstannyl chloride (0.36 ml) was added thereto, followed by stirring for 30 min. A saturated aqueous ammonium chloride solution was added thereto. Ethyl acetate was then added, followed by washing with water and saturated brine in that order. The organic layer was dried over anhydrous magnesium sulfate. The solvent was removed by distillation. The residue was purified by column chromatography on silica gel (dichloromethane:methanol=50:1) to give 0.42 g of the title compound.

NMR (CDCl$_3$) δ: 0.91 (9H, t, J=7.3 Hz), 1.14 (6H, t, J=8.4 Hz), 1.30–1.40 (6H, m), 1.50–1.60 (6H, m), 2.02 (3H, s), 4.48 (2H, d, J=5.3 Hz), 6.10 (1H, s), 7.12 (1H, s), 7.88 (1H, s)

Preparation 24

7-N,N-Dimethylcarbamoylacetyl-2-(tri-n-butylstannyl)imidazo[5,1-b]thiazole a) 7-[(2-N,N-dimethylcarbamoyl-1-hydroxy)ethyl]imidazo[5,1-b]thiazole Dimethylacetamide (0.97 ml) was added to 10 ml of a 1.0 N lithiumbis(trimethylsilyl)amide/THF solution in an argon atmosphere at −70° C. The mixture was stirred at the same temperature for 30 min. A solution of 1.52 g of 7-formylimidazo[5,1-b]thiazole in 40 ml of dry THF was added thereto. The mixture was stirred at the same temperature for 30 min. A saturated aqueous ammonium chloride solution was added thereto. Ethyl acetate was then added, followed by washing with water and saturated brine in that order. The organic layer was dried over anhydrous magnesium sulfate. The solvent was removed by distillation. The residue was purified by column chromatography on silica gel (dichloromethane:methanol=20:1) to give 1.04 g of 7-[(2-N,N-dimethylcarbamoyl-1-hydroxy)ethyl]imidazo[5,1-b]thiazole.

NMR (CDCl$_3$) δ: 2.80 (1H, m), 2.97 (3H, s), 3.03 (3H, s), 3.03–3.10 (1H, m), 5.06 (1H, d, J=3.6 Hz), 5.27–5.35 (1H, m), 6.81 (1H, d, J=4.1 Hz), 7.35 (1H, d, J=4.1 Hz), 7.92 (1H, s)

b) 7-N,N-Dimethylcarbamoylacetylimidazo[5,1-b]thiazole

Manganese dioxide (2.84 g) was added to a solution of 1.04 g of 7-[(2-N,N-dimethylcarbamoyl-1-hydroxy)ethyl]imidazo[5,1-b]thiazole in 30 ml of dichloromethane. The mixture was stirred at room temperature for 12 hr. Manganese dioxide was removed by filtration. The solvent was removed by distillation. The residue was purified by column chromatography on silica gel (dichloromethane:methanol= 20:1) to give 0.98 g of 7-N,N-dimethylcarbamoylacetylimidazo[5,1-b]thiazole.

NMR (CDCl$_3$) δ: 3.01 (3H, s), 3.09 (3H, s), 4.18 (2H, s), 7.11 (1H, d, J=4.1 Hz), 7.56 (1H, d, J=4.1 Hz), 8.00 (1H, s)

c) 7-N,N-Dimethylcarbamoylacetyl-2-(tri-n-butylstannyl)imidazo[5,1-b]thiazole

A 1.0 N lithiumbis(trimethylsilyl)amide/THF solution (2.1 ml) was added to a solution of 0.24 g of 7-N,N-dimethylcarbamoylacetylimidazo[5,1-b]thiazole in 5 ml of dry THF in an argon atmosphere at −50° C. The mixture was stirred at the same temperature for 30 min. Tri-n-butylstannyl chloride (0.29 ml) was added thereto. The mixture was stirred for 30 min. A saturated aqueous ammonium chloride solution was added thereto. Ethyl acetate was then added, followed by washing with water and saturated brine in that order. The organic layer was dried over anhydrous magnesium sulfate. The solvent was removed by distillation. The residue was purified by column chromatography on silica gel (dichloromethane:methanol=20:1) to give 0.29 g of the title compound.

NMR (CDCl$_3$) δ: 0.91 (9H, t, J=7.1 Hz), 1.18 (3H, t, J=8.3 Hz), 1.30–1.40 (6H, m), 1.53–1.65 (6H, m), 3.00 (3H, s), 3.07 (3H, s), 4.18 (2H, s), 7.27 (1H, s), 7.94 (1H, s)

Preparation 25

7-N,N-Dimethylsulfamoyl-2-(tri-n-butylstannyl)-imidazo[5,1-b]thiazole a) 7-Chlorosulfonylimidazo[5,1-b]thiazole A solution of chlorosulfuric acid in 20 ml of carbon tetrachloride was added under ice cooling to a solution of 11.18 g of imidazo[5,1-b]thiazole in 200 ml of carbon tetrachloride. The reaction mixture was heated under reflux for 6 hr. Water was added thereto under ice cooling to terminate the reaction. The mixture was extracted with dichloromethane. The organic layers were combined together. The combined organic layers were washed with a dilute aqueous sodium hydroxide solution and saturated brine in that order and then dried over anhydrous magnesium sulfate. The solvent was removed by distillation. Isopropyl ether was added to the residue. The resultant powder was collected by filtration to give 4.01 g of 7-chlorosulfonylimidazo[5,1-b]thiazole.

NMR (CDCl$_3$) δ: 7.19 (1H, d, J=4.1 Hz), 7.65 (1H, d, J=4.1 Hz), 8.12 (1H, s)

b) 7-N,N-Dimethylsulfamoylimidazo[5,1-b]thiazole

A 2 M THF solution (6 ml) of dimethylamine was added under ice cooling to a solution of 1.11 g of 7-chlorosulfonylimidazo[5,1-b]thiazole in 20 ml of THF. The mixture was stirred at room temperature for 30 min. Dichloromethane was added thereto, followed by washing with water and saturated brine in that order. The organic layer was dried over anhydrous magnesium sulfate. The solvent was removed by distillation. Ethyl acetate was added to the residue. The resultant powder was collected by filtration to give 1.10 g of 7-N,N-dimethylsulfamoylimidazo [5,1-b]thiazole.

NMR (CDCl$_3$) δ: 2.87 (6H, s), 7.03 (1H, d, J=4.2 Hz), 7.54 (1H, d, J=4.2 Hz), 8.05 (1H, s)

c) 7-N,N-Dimethylsulfamoyl-2-(tri-n-butylstannyl) imidazo[5,1-b]thiazole

In substantially the same manner as in Preparation 4-b), 1.11 g of the title compound was obtained from 1.22 g of 7-N,N-dimethylsulfamoylimidazo[5,1-b]thiazole.

NMR (CDCl$_3$) δ: 0.92 (9H, t, J=7.2 Hz), 1.15–1.22 (6H, m), 1.30–1.40 (6H, m), 1.56–1.63 (6H, m), 2.86 (6H, s), 7.26 (1H, S), 7.97 (1H, s)

Preparation 26

Methyl 2-(tri-n-butylstannyl)imidazo[5,1-b]thiazole 7-carboxylate a) Imidazo[5,1-b]thiazole-7-carboxylic acid A 0.95 M ethylmagnesium bromide/THF solution (12.6 ml) was added dropwise to a solution (50 ml) of 2.501 g of 7-iodoimidazo[5,1-b]thiazole in THF at −70° C. The mixture was stirred for 30 min. Carbon dioxide (which had been evolved from about 5 g of dry ice and passed through a calcium chloride tube) was introduced into the reaction solution at the same temperature over a period of 40 min. The reaction solution was allowed to stand at −20° C. overnight, and then added to an ice cold mixed solution composed of an aqueous sodium hydroxide (0.41 g) solution (100 ml) and ether (200 ml) with stirring. The mixture was stirred for one hr. The organic layer was separated and concentrated under the reduced pressure by a minor amount, and the remaining organic solvent was removed by distillation. The residue was adjusted to pH 3.5 by the addition of 2 N hydrochloric acid under ice cooling. The resultant precipitate was washed with a minor amount of cold water, and then dried under the reduced pressure to give 1.407 g of imidazo[5,1-b]thiazole-7-carboxylic acid.

NMR (DMSO-d$_6$) δ: 7.44 (1H, d, J=4.1 Hz), 8.03 (1H, d, J=4.1 Hz), 8.29 (1H, s)

b) Methyl imidazo[5,1-b]thiazole-7-carboxylate

Imidazo[5,1-b]thiazole-7-carboxylic acid (0.680 g) was suspended in 30 ml of water. Potassium carbonate (0.279 g) was added to the suspension. The mixture was stirred to prepare a homogeneous solution which was then lyophilized to give a potassium salt. DMF (25 ml) was added to the potassium salt. The mixture was ice cooled. Methyl iodide (0.633 g) was added thereto, followed by stirring for 18 hr under ice cooling. DMF was removed from the reaction solution by distillation under the reduced pressure. Dichloromethane (100 ml) and 100 ml of a 15% aqueous sodium chloride solution were added to the residue for dissolution. The organic layer was separated. The aqueous layer was extracted with dichloromethane (50 ml, twice). The organic layers were combined together, dried over anhydrous magnesium sulfate, and then concentrated to a volume of 50 ml under the reduced pressure. Ethyl acetate (50 ml) was then added to the concentrate, followed by concentration to a volume of 20 ml. The concentrate was allowed to stand at 0° C. for 3 hr. The resultant crystal was collected by filtration, washed with a minor amount of cold ethyl acetate, and then dried under the reduced pressure to give 0.644 g of methyl imidazo 5,1-b]thiazole-7-carboxylate.

NMR (CDCl$_3$) δ: 3.96 (3H, s), 7.06 (1H, d, J=4.2 Hz), 7.55 (1H, d, J=4.2 Hz), 8.02 (1H, s)

c) Methyl 2-(tri-n-butylstannyl)imidazo[5,1-b] thiazole-7-carboxylate

A solution (5 ml) of 0.716 g of tri-n-butylstannyl chloride in THF was added to a solution (20 ml) of 0.364 g of methyl imidazo[5,1-b]thiazole-7-carboxylate in THF at −70° C. A 1.0 N lithiumbis(trimethylsilyl)amide/n-hexane solution (4.4 ml) was added dropwise thereto at −70° C. The mixture was stirred at −50° C. for 30 min. The reaction solution was added to an ice cold mixed solution composed of 50 ml of 0.2 N phosphate buffer (pH 7) and 50 ml of dichloromethane with stirring. The organic layer was separated, and then dried over anhydrous magnesium sulfate. The solvent was removed by distillation. The residue was subjected to separation and purification by flash column chromatography on silica gel (hexane:ethyl acetate=1:1) to give 0.395 g of the title compound.

NMR (CDCl$_3$) δ: 0.92 (9H, t, J=7.3 Hz), 1.42–1.06 (12H, m), 1.64–1.52 (6H, m), 3.94 (3H, S), 7.26 (1H, s), 7.95 (1H, s)

Preparation 27

7-(N-Methoxy-N-methylsulfamoyl)-2-(tri-n-butylstannyl)imidazo[5,1-b]thiazole a) 7-(N-Methoxy-N-methylsulfamoyl)imidazo[5,1-b]thiazole N,O-Dimethylhydroxylamine hydrochloride (0.23 g) and 0.56 ml of triethylamine were added to a solution of 0.44 g of 7-chlorosulfonylimidazo[5,1-b]thiazole in 5 ml of DMF. The mixture was stirred at room temperature for one hr. Ethyl acetate was added thereto, followed by washing with water and saturated brine in that order. The organic layer was dried over anhydrous magnesium sulfate. The solvent was removed by distillation. The residue was purified by column chromatography on silica gel (hexane:ethyl acetate=1:2) to give 0.44 g of 7-(N-methoxy-N-methylsulfamoyl)imidazo [5,1-b]thiazole.

NMR (CDCl$_3$) δ: 3.05 (H, s), 3.83 (3H, s), 7.07 (1H, d, J=4.2 Hz), 7.58 (1H, d, J=4.2 Hz), 8.09 (1H, s)

b) 7-(N-Methoxy-N-methylsulfamoyl)-2-(tri-n-butylstannyl)imidazo[5,1-b]thiazole

A 1.0 N lithiumbis(trimethylsilyl)amide/THF solution (2.0 ml) was added to a solution of 0.44 g of 7-(N-methoxy-N-methylsulfamoyl)imidazo[5,1-b]thiazole in 9 ml of dry THF in an argon atmosphere at −40° C. The mixture was stirred at the same temperature for 30 min. Tri-n-butylstannyl chloride (0.58 ml) was added thereto. The mixture was stirred for 30 min. Further, a 1.0 N lithiumbis (trimethylsilyl)amide/THF solution (2.5 ml) was then added, followed by stirring for 30 min. Tri-n-butylstannyl chloride (0.1 ml) was added thereto. The mixture was stirred at the same temperature for 30 min. A saturated aqueous ammonium chloride solution was added thereto, and the ethyl acetate was then added, followed by washing with water and saturated brine in that order. The organic layer was dried over anhydrous magnesium sulfate. The solvent was removed by distillation. The residue was purified by column chromatography on silica gel (hexane:ethyl acetate=1:2) to give 0.39 g of the title compound.

NMR (CDCl$_3$) δ: 0.92 (9H, t, J=7.2 Hz), 1.16–1.25 (6H, m), 1.35–1.45 (6H, m), 1.55–1.65 (6H, m), 3.05 (3H, s), 3.84 (3H, s), 7.26 (1H, s), 8.00 (1H, s)

Preparation 28

7-Trifluoroacetyl-2-(tri-n-butylstannyl)imidazo-[5,1-b]thiazole a) 7-Trifluoroacetylimidazo[5,1-b]thiazole A 1 M ethylmagnesium bromide/THF solution (10 ml) was added to a solution of 2.50 g of 7-iodoimidazo[5,1-b]thiazole in 10 ml of dry THF in an argon atmosphere at −50° C. The mixture was stirred at the same temperature for one hr. Trifluoroacetic anhydride (1.53 ml) was added thereto, followed by stirring at the same temperature for 10 min. A saturated aqueous ammonium chloride solution was added to the reaction mixture. Ethyl acetate was then added, followed by washing with a dilute aqueous sodium thiosulfate solution and saturated brine in that order. The organic layer was dried over anhydrous magnesium sulfate. The solvent was removed by distillation. The residue was purified by column chromatography on silica gel (hexane:ethyl acetate=1:1) to give 0.64 g of 7-trifluoroacetylimidazo[5,1-b]thiazole.

NMR (CDCl$_3$) δ: 7.25 (1H, d, J=4.1 Hz), 7.68 (1H, d, J=4.1 Hz), 8.13 (1H, s)

b) 7-Trifluoroacetyl-2-(tri-n-butylstannyl)-imidazo[5,1-b]thiazole

A 1.0 N lithiumbis(trimethylsilyl)amide/THF solution (2.0 ml) was added to a solution of 0.34 g of 7-trifluoroacetylimidazo[5,1-b]thiazole and 0.48 ml of tri-n-butylstannyl chloride in 16 ml of dry THF in an argon atmosphere at −40° C. The mixture was stirred at the same temperature for 30 min. A saturated aqueous ammonium chloride solution was added thereto. Ethyl acetate was then added, followed by washing with water and saturated brine in that order. The organic layer was dried over anhydrous magnesium sulfate. The solvent was removed by distillation. The residue was purified by column chromatography on silica gel (hexane:ethyl acetate=4:1) to give 0.14 g of the title compound.

NMR (CDCl$_3$) δ: 0.92 (9H, t, J=7.4 Hz), 1.20–1.40 (12H, m), 1.55–1.70 (6H, m), 7.38 (1H, s), 8.05 (1H, s)

Preparation 29

7-(t-Butyldimethylsilylsulfamoyl)-2-(tri-n-butylstannyl)imidazo[5,1-b]thiazole a) 7-Sulfamoylimidazo[5,1-b]thiazole A 2 M ammonia/methanol solution (4 ml) was added to a solution of 0.44 g of 7-chlorosulfonylimidazo[5,1-b]thiazole in 10 ml of THF. The mixture was stirred at room temperature for 12 hr. The reaction mixture was concentrated. The residue was purified by column chromatography on silica gel (dichloromethane:methanol=10:1) to give 0.34 g of 7-sulfamoylimidazo[5,1-b]thiazole.

NMR (CDCl$_3$) δ: 7.33 (2H, s), 7.38 (1H, d, J=4.1 Hz), 8.00 (1H, d, J=4.1 Hz), 7.32 (1H, s)

b) 7-(t-Butyldimethylsilylsulfamoyl)imidazo[5,1-b]thiazole t-Butyldimethylsilyl chloride (0.30 g) and 0.33 ml of triethylamine were added to a solution of 0.20 g of 7-sulfamoylimidazo[5,1-b]thiazole in 5ml of DMF. The mixture was stirred at room temperature for one hr. Ethyl acetate was added to the reaction mixture, followed by washing with water and saturated brine in that order. The organic layer was dried over anhydrous magnesium sulfate. The solvent was removed by distillation. The residue was purified by column chromatography on silica gel (hexane:ethyl acetate=1:1) to give 0.34 g of 7-(t-butyldimethylsilylsulfamoyl)imidazo[5,1-b]thiazole.

NMR (CDCl$_3$) δ: 0.24 (6H, s), 0.82 (9H, s), 4.54 (1H, s), 7.00 (1H, d, J=4.2 Hz), 7.50 (1H, d, J=4.2 Hz), 8.02 (1H, s)

c) 7-(t-Butyldimethylsilylsulfamoyl)-2-(tri-n-butylstannyl)imidazo[5,1-b]thiazole In substantially the same manner as in Preparation 28-b), 0.73 g of the title compound was obtained from 0.52 g of 7-(t-butyldimethylsilylsulfamoyl)imidazo[5,1-b]thiazole and 0.53 ml of tri-n-butylstannyl chloride.

NMR (CDCl$_3$) δ: 0.24 (6H, s), 0.88–0.96 (21H, m), 1.18 (6H, t, J=8.4 Hz), 1.30–1.40 (6H, s), 1.55–1.65 (6H, m), 4.52 (1H, s), 7.21 (1H, s), 7.94 (1H, s)

Preparation 30

7-(2-Methoxycarbonylvinyl)-2-(tri-n-butylstannyl)-imidazo[5,1-b]thiazole (A Mixture of Geometrical Isomers)

a) 7-(2-Methoxycarbonylvinyl)imidazo[5,1-b]thiazole (A Mixture of Geometrical Isomers)

Methyl triphenylphosphoranylideneacetate (500 mg) was added to a solution of 150 mg of 7-formylimidazo[5,1-b]thiazole in 15 ml of methanol. The mixture was stirred at room temperature for 15 min. Ethyl acetate was added thereto. The mixture was washed with water, dried over anhydrous magnesium sulfate, and filtered. The solvent was removed by distillation under the reduced pressure. The residue was purified by column chromatography on silica gel (chloroform:methanol=20:1) to give 228 mg of 7-(2-methoxycarbonylvinyl)imidazo[5,1-b]thiazole (a mixture of geometrical isomers).

NMR (CDCl$_3$) δ: 3.80 (3H, s), 6.17 (1H, d, J=15.8 Hz), 7.01 (1H, d, J=4.1 Hz), 7.50 (1H, d, J=4.1 Hz), 7.77 (1H, d, J=15.8 Hz), 8.05 (1H, s)

NMR (CDCl$_3$) δ: 3.81 (3H, s), 5.82 (1H, d, J=12.4 Hz), 7.03 (1H, d, J=4.1 Hz), 7.13 (1H, d, J=12.4 Hz), 7.50 (1H, d, J=4.1 Hz), 8.06 (1H, s)

b) 7-(2-Methoxycarbonylvinyl)-2-(tri-n-butylstannyl)imidazo[5,1-b]thiazole (A Mixture of Geometrical Isomers)

Tri-n-butylstannyl chloride (250 μl) and 2.1 ml of a 1.0 N lithiumbis(trimethylsilyl)amide/THF solution were added in that order to a solution of 7-(2-methoxycarbonylvinyl)

imidazo[5,1-b]thiazole (a mixture of geometrical isomers) in dry THF in an argon atmosphere at −78° C. The mixture was stirred at the same temperature for 15 min. Water was added thereto. The mixture was extracted with ethyl acetate, followed by washing with saturated brine. The extract was dried over anhydrous magnesium sulfate and then filtered. The solvent was removed by distillation under the reduced pressure. The residue was purified by column chromatography on silica gel (hexane:ethyl acetate=4:1) to give 408 mg of the title compound.

NMR (CDCl$_3$) δ: 0.92 (9H, t, J=7.4 Hz), 1.18 (6H, m), 1.36 (6H, m), 1.58 (6H, m), 3.78 (3H, s), 6.13 (1H, d, J=15.8 Hz), 7.23 (1H, s), 7.77 (1H, d, J=15.8 Hz), 7.98 (1H, s)

NMR (CDCl$_3$) δ: 0.92 (9H, t, J=7.4 Hz), 1.18 (6H, m), 1.36 (6H, m), 1.58 (6H, m), 3.82 (3H, s), 5.77 (1H, d, J=12.4 Hz), 7.10 (1H, d, J=12.4 Hz), 7.25 (1H, s), 8.01 (1H, s)

Preparation 31

7-(Thiazol-4-yl)-2-(tri-n-butylstannyl)imidazo[5,1-b]thiazole a) 7-Chloroacetylimidazo[5,1-b]thiazole Chloroacetyl chloride (5.97 ml) was added to a solution of 12.5 g of aluminum chloride in 40 ml of 1,2-dichloroethane. The mixture was stirred at room temperature for 20 min. A solution of 1.93 g of imidazo[5,1-b]thiazole in 20 ml of 1,2-dichloroethane was added thereto. The mixture was heated under reflux for 2 hr. Water was added thereto, followed by extraction with dichloromethane. The organic layers were combined together. The combined organic layers were washed with a dilute aqueous sodium hydroxide solution and saturated brine in that order. The solvent was removed by distillation. Isopropyl ether was added to the residue. The resultant powder was collected by filtration to obtain the title compound.

NMR (CDCl$_3$) δ: 4.83 (2H, s), 7.16 (1H, d, J=4.1 Hz), 7.60 (1H, d, J=4.1 Hz), 8.02 (1H, s)

b) 7-(Thiazol-4-yl)imidazo[5,1-b]thiazole

Diphosphorus pentasulfide (846 mg) was added to 8.4 ml of formamide. The mixture was stirred at room temperature overnight. 7-Chloroacetylimidazo[5,1-b]thiazole (2.32 g) was added to the reaction solution. The mixture was stirred at room temperature for 15 hr. Water (20 ml) and 10 ml of dichloromethane were added thereto. The mixture was adjusted to pH 8.8 by gradually adding a sodium hydrogencarbonate powder. Extraction was carried out six times with 50 ml of dichloromethane. The organic layer was dried over anhydrous magnesium sulfate. The solvent was removed by distillation under the reduced pressure. The residue was purified by column chromatography on silica gel (hexane:ethyl acetate=1:2) to give 1.72 g of 7-(thiazol-4-yl)imidazo[5,1-b]thiazole.

NMR (CDCl$_3$) δ: 6.93 (1H, d, J=4.2 Hz), 7.46 (1H, d, J=4.2 Hz), 7.60 (1H, d, J=2.1 Hz), 8.05 (1H, s)8.87 (1H, d, J=2.1 Hz) MS (EI): 207 (M$^+$)

c) 7-(Thiazol-4-yl)-2-(tri-n-butylstannyl)-imidazo[5,1-b]thiazole

A solution of 1.01 g of 7-(thiazol-4-yl)imidazo[5,1-b]thiazole in 45 ml of THF was cooled to −70° C. in an argon atmosphere. Tri-n-butylstannyl chloride (1.58 ml) was added thereto. A 1 N lithiumbis(trimethylsilyl)amide/THF solution (11.2 ml) was added dropwise at the same temperature. The mixture was stirred for 30 min. The temperature of the mixture was raised to −30° C. over a period of one hr. A saturated aqueous sodium chloride solution was added thereto, followed by extraction twice with ethyl acetate. The extract was dried over anhydrous magnesium sulfate. The solvent was removed by distillation under the reduced pressure. The residue was purified by column chromatography on silica gel (hexane:ethyl acetate=1:1). The title compound (294 mg) was obtained from the fraction of Rf=0.5.

NMR (CDCl$_3$) δ: 0.92 (9H, t, J=7.4 Hz), 1.20 (6H, m), 1.37 (6H, m), 1.58 (6H, m), 7.22 (1H, s), 7.59 (1H, d, J=2.2 Hz), 8.00 (1H, s)8.87 (1H, d, J=2.2 Hz)

Preparation 32

7-t-Butyldimethylsilyloxyacetyl-5-methyl-2-(tri-n-butylstannyl)imidazo[5,1-b]thiazole a) 7-Acetoxyacetyl-5-methylimidazo[5,1-b]thiazole In the same manner as in Preparation 16-a), 734 mg of 7-acetoxyacetyl-5-methylimidazo[5,1-b]thiazole was obtained from 821 mg of 7-acetyl-5-methylimidazo[5,1-b]thiazole.

NMR (CDCl$_3$) δ: 2.23 (3H, s), 2.63 (3H, s), 5.40 (2H, s), 7.08 (1H, d, J=4.1 Hz), 7.39 (1H, d, J=4.1 Hz)

b) 7-Hydroxyacetyl-5-methylimidazo[5,1-b]thiazole

In the same manner as in Preparation 16-b), 704 mg of 7-hydroxyacetyl-5-methylimidazo[5,1-b]thiazole was obtained from 872 mg of 7-acetoxyacetyl-5-methylimidazo[5,1-b]thiazole.

NMR (DMSO-d$_6$) δ: 2.56 (3H, s), 4.63 (2H, s), 7.49 (1H, d, J=3.7 Hz), 8.05 (1H, d, J=3.7 Hz)

c) 7-t-Butyldimethylsilyloxyacetylimidazo[5,1-b]thiazole

In the same manner as in Preparation 16-c), 699 mg of 7-t-butyldimethylsilyloxyacetyl-5-methylimidazo[5,1-b]thiazole was obtained from 508 mg of 7-hydroxyacetyl-5-methylimidazo[5,1-b]thiazole.

NMR (CDCl$_3$) δ: 0.15 (6H, s), 0.96 (9H, s), 2.63 (3H, s), 5.04 (2H, s), 7.05 (1H, d, J=4.1 Hz), 7.36 (1H, d, J=4.1 Hz)

d) 7-t-Butyldimethylsilyloxyacetyl-5-methyl-2-(tri-n-butylstannyl)imidazo[5,1-b]thiazole 7-t-Butyldimethylsilyloxyacetyl-5-methylimidazo-[5,1-b]thiazole (49.5 mg) was dissolved in 2 ml of THF and 0.4 ml of HMPA. Tri-n-butylstannyl chloride (0.059 ml) and 0.319 ml of a 1.0 N lithiumbis(trimethylsilyl)amide/THF solution were added dropwise in that order to the solution in an argon atmosphere at −73° C. The mixture was stirred at the same temperature for one hr. A 1.0 N lithiumbis(trimethylsilyl)amide/THF solution (0.160 ml) was added dropwise thereto. The mixture was stirred at the same temperature for additional 40 min. An ammonium chloride solution was added to the reaction solution, followed by extraction with ethyl acetate and washing three times with brine. The extract was dried over anhydrous magnesium sulfate and then filtered. The solvent was removed by distillation under the reduced pressure. The residue was purified by column chromatography on silica gel (hexane:ethyl acetate=5:1) to give 66.9 mg of the title compound.

NMR (CDCl$_3$) δ: 0.15 (6H, s), 0.91 (9H, t, J=7.4 Hz), 0.96 (9H, s), 1.18 (6H, m), 1.35 (6H, m), 1.58 (6H, m), 2.62 (3H, s), 5.03 (2H, s), 7.06 (1H, s)

Preparation 33

7-Methanesulfonylaminoacetyl-2-(tri-n-butylstannyl)imidazo[5,1-b]thiazole a) 7-Methanesulfonylaminoacetylimidazo[5,1-b]thiazole

2 N hydrochloric acid (4.88 ml) and 336 mg of 10%Pd-C were added to a solution of 673 mg of 7-azidoacetylimidazo[5,1-b]thiazole in 16 ml of water and 20 ml of THF. The atmosphere in the reactor was replaced with hydrogen. The system was stirred at room temperature for 2 hr. The catalyst was removed by filtration through Celite and then washed with water. THF was removed by distillation under the reduced pressure. A 1 N aqueous sodium hydroxide solution (12.8 ml) was added thereto, followed by extraction nine times with dichloromethane. The organic layers were combined together, dried over anhydrous magnesium sulfate, and filtered. The filtrate was concentrated under the reduced pressure. The residue was dissolved in 20 ml of dichloromethane. N,N-diisopropylethylamine (0.849 ml) and 0.377 ml of methanesulfonyl chloride were added to the solution. The mixture was stirred at room temperature for one hr. An aqueous sodium hydrogencarbonate solution was added to the reaction solution, followed by extraction three times with dichloromethane. The organic layers were combined together, dried over anhydrous magnesium sulfate, and filtered. The filtrate was concentrated under the reduced pressure. The residue was purified by column chromatography on silica gel (dichloromethane:methanol=30:1) to give 397 mg of 7-methanesulfonylaminoacetylimidazo[5,1-b]thiazole.

NMR (DMSO-$d_6$) δ: 2.98 (3H, s), 4.51 (2H, d, J=5.7 Hz), 7.36 (1H, t, J=5.7 Hz), 7.55 (1H, d, J=4.2 Hz), 8.12 (1H, d, J=4.2 Hz), 8.37 (1H, s)

b) 7-Methanesulfonylaminoacetyl-2-(tri-n-butylstannyl)imidazo[5,1-b]thiazole 7-Methanesulfonylaminoacetylimidazo[5,1-b]thiazole (46.2 mg) was dissolved in 2 ml of THF and 0.4 ml of HMPA. Tri-n-butylstannyl chloride (0.076 ml) and 0.713 ml of a 1.0 N lithiumbis(trimethylsilyl)amide/THF solution were added dropwise in that order to the solution in an argon atmosphere at −70° C. The mixture was stirred at the same temperature for 1.5 hr. A 1.59 Nn-butyllithium/n-hexane solution (0.146 ml) was added dropwise thereto. The mixture was stirred at the same temperature for one hr. A 1.59 N n-butyllithium/n-hexane solution (0.146 ml) and 0.076 ml of tri-n-butylstannyl chloride were added dropwise thereto. The mixture was stirred at the same temperature for 45 min. An ammonium chloride solution was added to the reaction solution, followed by extraction with ethyl acetate. The organic layer was washed twice with brine, dried over anhydrous magnesium sulfate, and filtered. The solvent was removed by distillation under the reduced pressure. The residue was purified by column chromatography on silica gel (hexane:ethyl acetate=1:1) to give 37.5 mg of the title compound.

NMR (CDCl$_3$) δ: 0.92 (9H, t, J=7.4 Hz), 1.20 (6H, m), 1.35 (6H, m), 1.60 (6H, m), 3.00 (3H, s), 4.69 (2H, d, J=5.0 Hz), 5.44 (1H, br), 7.32 (1H, s), 7.96 (1H, s)

Preparation 34

7-Methanesulfonylaminomethyl-2-(tri-n-but-stannyl)imidazo[5,1-b]thiazole a) 7-(Methanesulfonylaminomethyl)imidazo[5,1-b]thiazole

Triethylamine (0.18 ml) and 0.075 ml of methanesulfonyl chloride were added in that order under ice cooling to a solution of 134 mg of 7-aminomethylimidazo[5,1-b]thiazole in 2.5 ml of dry dichloromethane. In this state, the system was stirred for 2 hr while gradually raising the temperature to room temperature. The reaction solution was diluted with 20 ml of dichloromethane, followed by washing with saturated brine. The aqueous layer was extracted with 10 ml of dichloromethane. The organic layers were combined together, dried over anhydrous magnesium sulfate, and filtered. The solvent was removed by distillation. The oil thus obtained was purified using Sephadex LH-20 (dichloromethane:methanol=1:1) to give 130 mg of 7-(methanesulfonylaminomethyl)imidazo[5,1-b]thiazole as a light yellow solid.

NMR (CDCl$_3$) δ: 2.91 (3H, s), 4.43 (2H, d, J=6.0 Hz), 5.26 (1H, br.t), 6.87 (1H, d, J=4.2 Hz), 7.40 (1H, d, J=4.2 Hz), 7.99 (1H, s) MS (TSP): m/z=232 (M$^+$+H)

b) 7-Methanesulfonylaminomethyl-2-(tri-n-butylstannyl)imidazo[5,1-b]thiazole A solution of 231 mg of 7-(methanesulfonylaminomethyl)imidazo[5,1-b]thiazole dissolved in a mixed solution composed of 10 ml of dry THF and 1 ml of dry HMPA was cooled to −50° C. with stirring. A 1.6 N n-butyllithium/n-hexane solution (2.0 ml) was added dropwise to the mixed solution in an argon atmosphere at −51 to −49° C. over a period of 15 min. The mixture was stirred at the same temperature for 15 min. Further, 0.34 ml of tri-n-butylstannyl chloride was added dropwise thereto at −50 to −48° C. over a period of 10 min. The mixture was stirred at −50 to −40° C. for 140 min. Tri-n-butylstannyl chloride (0.07 ml) was additionally added to the reaction solution at −42° C. The mixture was stirred for 30 min. 0.38 M phosphate buffer (pH 6.0) (15 ml) was added thereto. The mixed solution was extracted with 30 ml of ethyl acetate. The organic layer was washed with 0.38 M phosphate buffer (pH 6.0) and saturated brine in that order, and then dried over anhydrous sodium sulfate. The anhydrous magnesium sulfate was removed by filtration. The solvent was removed by distillation. The brown oil thus obtained was purified by column chromatography on silica gel (eluting with dichloromethane:ethyl acetate 1:1 and then with ethyl acetate only) to give 160 mg of the title compound as a yellow crystal.

NMR (CDCl$_3$) δ: 0.92 (9H, t, J=7.2 Hz), 1.05–1.20 (6H, m), 1.25–1.40 (6H, m), 1.45–1.70 (6H, m), 2.91 (3H, s), 4.41 (2H, d, J=5.8 Hz), 5.03 (1H, br.t), 7.14 (1H, s), 7.92 (1H, s) MS (FAB$^+$): m/z=522 (M$^+$+H), 520 (M$^+$−2+H)

Preparation 35

7-(N,N-Dimethylaminosulfonylamino)acetyl-2-(tri-n-butylstannyl)imidazo[5,1-b]thiazole a) 7-(N,N-Dimethylaminosulfonylamino)acetyl-imidazo[5,1-b]thiazole

7-Azidoacetylimidazo[5,1-b]thiazole (207 mg) was dissolved in 6 ml of THF, 4.5 ml of water, and 3 ml of 1 N aqueous hydrochloric acid. 10%Pd-C (103 mg) was added to the solution. The air in the reactor was replaced by hydrogen. The system was then stirred at room temperature for 17 hr. The catalyst was removed by filtration through Celite, followed by washing with water. The filtrate was concentrated to half the amount thereof. A 1 N aqueous sodium hydroxide solution (4 ml) was added to the filtrate. The mixture was extracted six times with dichloromethane. The organic layer was dried over anhydrous magnesium sulfate. The solvent was removed by distillation under the reduced pressure. The residue was dissolved in 5 ml of dichloromethane. N,N-diisopropylethylamine (0.783 ml) and 0.322 ml of N,N-dimethylaminosulfonyl chloride were added to the solution. The mixture was stirred at room temperature for 7 hr. An aqueous sodium hydrogencarbonate solution was added to the reaction solution. The mixture was extracted with dichloromethane. The organic layer was dried over anhydrous magnesium sulfate. The solvent was removed by distillation under the reduced pressure. The residue was purified by column chromatography on silica gel (dichloromethane:methanol=30:1) to give 167 mg of 7-(N,N-dimethylaminosulfonylamino)acetyl-imidazo[5,1-b]thiazole.

NMR (CDCl$_3$): 2.83 (6H, s), 4.59 (2H, d, J=4.9 Hz), 5.45 (1H, br.s), 7.17 (1H, d, J=4.1 Hz), 7.62 (1H, d, J=4.1 Hz), 8.03 (1H, s)

b) 7-(N,N-Dimethylaminosulfonylamino)acetyl-2-(tri-n-butylstannyl)imidazo[5,1-b]thiazole Tri-n-butylstannyl chloride (0.962 ml) and 8.42 ml of a 1.0 N lithiumbis(trimethylsilyl)amide/THF solution were sequentially added at −73° C. in an argon atmosphere to a solution of 485 mg of 7-(N,N-dimethylaminosulfonylamino)acetyl-imidazo[5,1-b]thiazole in 18 ml of THF. The mixture was stirred at the same temperature for 30 min. An aqueous ammonium chloride solution was added to the reaction solution. The mixture was extracted with ethyl acetate. The extract was dried over anhydrous magnesium sulfate, and then filtered. The solvent was removed by distillation under the reduced pressure. The residue was purified by column chromatography on silica gel (hexane:ethyl acetate=1:1) to give 427 mg of the title compound.

NMR (CDCl$_3$): 0.92 (9H, t, J=7.3 Hz), 1.15–1.25 (6H, m), 1.3–1.45 (6H, m), 1.5–1.7 (6H, m), 2.83 (6H, s), 4.58 (2H, d, J=4.7 Hz), 5.47 (1H, br.s), 7.31 (1H, s), 7.95 (1H, s)

Preparation 36

7-[2-(4-Nitrobenzyloxycarbonyl)aminoethane-sulfonylamino]acetyl-2-(tri-n-butylstannyl)-imidazo[5,1-b]thiazole a) 7-[2-(4-Nitrobenzyloxycarbonyl)-aminoethanesulfonylamino]acetylimidazo[5,1-b]-thiazole 7-Azidoacetylimidazo[5,1-b]thiazole (685 mg) was dissolved in 20 ml of THF, 15 ml of water, and 10 ml of 1 N aqueous hydrochloric acid. 10%Pd-C (341 mg) was added to the solution. The air in the reactor was replaced by hydrogen. The system was stirred at room temperature for 2 hr. The catalyst was removed by filtration through Celite, followed by washing with water. The filtrate was concentrated to half of the amount thereof. A 1 N aqueous sodium hydroxide solution (13 ml) was added to the concentrate. The mixture was extracted six time with dichloromethane. The organic layer was dried over anhydrous magnesium sulfate. The solvent was removed by distillation under the reduced pressure. The residue was dissolved in 10 ml of dichloromethane. N,N-Diisopropylethylamine (0.865 ml) and 1.60 g of 2-(4-nitrobenzyloxycarbonyl)aminoethanesulfonyl chloride were added to the solution under ice cooling. The mixture was stirred at the same temperature for one hr. An aqueous sodium hydrogencarbonate solution was added to the reaction solution. The mixture was extracted with dichloromethane. The organic layer was dried over anhydrous magnesium sulfate. The solvent was removed by distillation under the reduced pressure. The residue was purified by column chromatography on silica gel (dichloromethane:methanol=30:1) to give 808 mg of 7-[2-(4-nitrobenzyloxycarbonyl)aminoethane-sulfonylamino]acetylimidazo[5,1-b]thiazole.

NMR (CDCl$_3$): 3.25–3.35 (2H, m), 3.7–3.8 (2H, m), 4.69 (2H, d, J=5.0 Hz), 5.20 (2H, s), 5.49 (1H, br.s), 5.75 (1H, br.s), 7.17 (1H, d, J=4.2 Hz), 7.50 (2H, d, J=8.7 Hz), 7.60 (1H, d, J=4.2 Hz), 8.02 (1H, s), 8.19 (2H, d, J=8.7 Hz)

b) 7-[2-(4-Nitrobenzyloxycarbonyl)amino-ethanesulfonylamino]acetyl-2-(tri-n-butylstannyl)imidazo[5,1-b]thiazole Tri-n-butylstannyl chloride (0.83 ml) and 7.3 ml of a 1.0 N lithiumbis(trimethylsilyl)amide/THF solution were sequentially added at −73° C. in an argon atmosphere to a solution of 682 mg of 7-[2-(4-Nitrobenzyloxycarbonyl)aminoethane-sulfonylamino]acetylimidazo[5,1-b]thiazole in 16 ml of THF and 3 ml of HMPA. The mixture was stirred at the same temperature for 30 min. An aqueous ammonium chloride solution was added to the reaction solution. The mixture was extracted with ethyl acetate. The extract was dried over anhydrous magnesium sulfate and then filtered. The solvent was removed by distillation under the reduced pressure. The residue was purified by column chromatography on silica gel (hexane:ethyl acetate=1:1–1:2) to give 327 mg of the title compound.

NMR (CDCl$_3$): 0.91 (9H, t, J=7.3 Hz), 1.15–1.25 (6H, m), 1.25–1.4 (6H, m), 1.5–1.65 (6H, m), 3.25–3.35 (2H, m), 3.7–3.8 (2H, m), 4.68 (2H, d, J=5.1 Hz), 5.19 (2H, s), 5.60 (1H, br.s), 5.85 (1H, br.s), 7.32 (1H, s), 7.49 (2H, d, J=8.8 Hz), 7.96 (1H, s), 8.18 (2H, d, J=8.8 Hz)

Preparation 37

7-Phenylthio-2-(tri-n-butylstannyl)imidazo-[5,1-b]thiazole a) 7-Phenylthioimidazo[5,1-b]thiazole A 1 M ethylmagnesium bromide/THF solution (3.46 ml) was added in an argon atmosphere under ice cooling to a solution of 840 mg of 7-iodoimidazo[5,1-b]thiazole in 20 ml of dry THF. The mixture was stirred at the same temperature for one hr. Phenylbenzenethiol sulfonate (939 mg) was added thereto, and the mixture was stirred at the same temperature for one hr. A saturated aqueous ammonium chloride solution was added to the reaction mixture. Ethyl acetate was added thereto. The mixture was washed with a dilute aqueous sodium thiosulfate solution and saturated brine in that order. The organic layer was dried over anhydrous magnesium sulfate. The solvent was removed by distillation. The residue was purified by column chromatography on silica gel (hexane:ethyl acetate=1:1) to give 385 mg of 7-phenylthioimidazo[5,1-b]thiazole.

NMR(CDCl$_3$): 6.90 (1H, d, J=4.3 Hz), 7.1–7.2 (1H, m), 7.2–7.25 (5H, m), 7.45 (1H, d, J=4.3 Hz), 8.09 (1H, s)

b) 7-Phenylthio-2-(tri-n-butylstannyl)-imidazo[5,1-b]thiazole

A 1.59 N n-butyl lithium/n-hexane solution (0.189 ml) was added dropwise at −73° C. in an argon atmosphere to a solution of 66.5 mg of 7-phenylthioimidazo[5,1-b]thiazole in 3 ml of THF. Subsequently, 0.098 ml of tri-n-butylstannyl chloride was added to the mixture. The mixture was stirred at the same temperature for 15 min. The temperature of the system was raised to −40° C. A 1.0 N lithiumbis(trimethylsilyl)amide/THF solution (0.11 ml) was added thereto. The mixture was stirred for one hr. An aqueous ammonium chloride solution was added to the reaction solution. The mixture was extracted with ethyl acetate. The extract was dried over anhydrous magnesium sulfate, and then filtered. The solvent was removed by distillation under the reduced pressure. The residue was purified by column chromatography on silica gel (hexane:ethyl acetate=5:1) to give 115 mg of the title compound.

NMR (CDCl$_3$): 0.91 (9H, t, J=7.2 Hz), 1.1–1.2 (6H, m), 1.3–1.4 (6H, m), 1.5–1.7 (6H, m), 7.05–7.15 (1H, m), 7.15–7.25 (6H, m), 8.03 (1H, s)

Preparation 38

7-Ethylthio-2-(tri-n-butylstannyl)imidazo-[5,1-b]thiazole a) Ethylethanethiol Sulfonate Diethyl disulfide (3.69 ml) was dissolved in 450 ml of dichloromethane. 3-Chloroperbenzoic acid (19.43 g) was added under ice cooling to the soluiton. The mixture was stirred at room temperature for 3 hr. The insolubles were removed by filtration. The filtrate was washed with an aqueous sodium thiosulfate solution, an aqueous sodium hydrogencarbonate solution, and brine in that order, dried over anhydrous magnesium sulfate, and then filtered. The solvent was removed by distillation under the reduced pressure. The residue was purified by column chromatography on silica gel(hexane:ethyl acetate=5:1) to give 2.05 g of ethylethanethiol sulfonate.

NMR (CDCl$_3$): 1.44 (3H, t, J=7.4 Hz), 1.48 (3H, t, J=7.4 Hz), 3.16 (2H, q, J=7.4 Hz), 3.33 (2H, q, J=7.4 Hz)

b) 7-Ethylthioimidazo[5,1-b]thiazole

A 1 M ethylmagnesium bromide/THF solution (8.52 ml) was added in an argon atmosphere under ice cooling to a solution of 2.07 g of 7-iodoimidazo[5,1-b]thiazole in 40 ml of dry THF. The mixture was stirred at the same temperature for one hr. Ethylethanethiol sulfonate (1.527 g) was added thereto, and the mixture was stirred at room temperature for 30 min. A saturated aqueous ammonium chloride solution was added to the reaction mixture. Ethyl acetate was then added thereto, followed by washing with a dilute aqueous sodium thiosulfate solution and saturated brine in that order. The organic layer was dried over anhydrous magnesium sulfate. The solvent was removed by distillation. The residue was purified by column chromatography on silica gel (dichloromethane:ethyl acetate=1:1) to give 1.064 g of 7-ethylthioimidazo[5,1-b]thiazole.

NMR(CDCl$_3$): 1.26 (3H, t, J=7.4 Hz), 2.83 (2H, q, J=7.4 Hz), 6.87 (1H, d, J=4.2 Hz), 7.40 (1H, d, J=4.2 Hz), 8.01 (1H, s)

c) 7-Ethylthio-2-(tri-n-butylstannyl)-imidazo[5,1-b]thiazole

In the same manner as in Preparation 37-b), 2.34 g of the title compound was obtained from 1.10 g of 7-ethylthioimidazo[5,1-b]thiazole.

NMR(CDCl$_3$): 0.92 (9H, t, J=7.4 Hz), 1.1–1.2 (6H, m), 1.27 (3H, t, J=7.3 Hz), 1.3–1.4 (6H, m), 1.5–1.65 (6H, m), 2.82 (2H, q, J=7.3 Hz), 7.14 (1H, s), 7.95 (1H, s)

Preparation 39

3-Methyl-7-methylthio-2-(tri-n-butylstannyl)imidazo[5,1-b]thiazole a) 7-Iodo-3-methylimidazo[5,1-b]thiazole In the same manner as in Preparation 22-a), 525 mg of 7-iodo-3-methylimidazo[5,1-b]thiazole was obtained from 505 mg of 3-methylimidazo[5,1-b]thiazole.

NMR(CDCl$_3$): 2.40 (3H, s), 6.46 (1H, s), 7.84 (1H, s)

b) 3-Methyl-7-methylthioimidazo[5,1-b]-thiazole

In the same manner as in Preparation 12-a), 1.88 g of 3-methyl-7-methylthioimidazo-[5,1-b]thiazole was obtained from 3.0 g of 7-iodo-3-methylimidazo[5,1-b]thiazole.

NMR(CDCl$_3$): 2.40 (3H, s), 2.43 (3H, s), 6.44 (1H, s), 7.89 (1H, s)

c) 3-Methyl-7-methylthio-2-(tri-n-butylstannyl)imidazo[5,1-b]thiazole

In the same manner as in Preparation 4-b), 4.70 g of the title compound was obtained from 2.15 g of 3-methyl-7-methylthioimidazo[5,1-b]thiazole.

NMR(CDCl$_3$): 0.91 (9H, t, J=7.3 Hz), 1.1–1.2 (6H, m), 1.25–1.4 (6H, m), 1.5–1.65 (6H, m), 2.36 (3H, s), 2.42 (3H, s), 7.81 (1H, s)

Preparation 40

3-t-Butyldimethylsilyloxymethyl-7-methyl-thio-2-(tri-n-butylstannyl)imidazo[5,1-b]thiazole a) 3-t-Butyldimethylsilyloxymethyl-7-iodoimidazo-[5,1-b]thiazole In the same manner as in Preparation 22-a), 3.21 g of 3-t-butyldimethylsilyloxymethyl-7-iodoimidazo-[5,1-b]thiazole was obtained from 3.26 g of 3-t-butyldimethylsilyloxymethylimidazo[5,1-b]-thiazole.

NMR(CDCl$_3$): 0.10 (6H, s), 0.90 (9H, s), 4.75 (2H, s), 6.66 (1H, s), 7.98 (1H, s) b) 3-t-Butyldimethylsilyloxymethyl-7-methyl-thioimidazo[5,1-b]thiazole In the same manner as in Preparation 12-a), 1.06 g of 3-t-butyldimethylsilyloxymethyl-7-methylthioimidazo[5,1-b]thiazole was obtained from 1.70 of 3-t-butyldimethylsilyloxymethyl-7-iodoimidazo[5,1-b]thiazole.

NMR(CDCl$_3$): 0.11 (6H, s), 0.91 (9H, s), 2.44 (3H, s), 4.76 (2H, s), 6.64 (1H, s), 8.02 (1H, s)

c) 3-t-Butyldimethylsilyloxymethyl-7-methylthio-2-(tri-n-butylstannyl)imidazo[5,1-b]thiazole In the same manner as in Preparation 4-b), 1.77 g of the title compound was obtained from 1.06 g of 3-t-butyldimethylsilyloxymethyl-7-methylthioimidazo[5,1-b]thiazole.

NMR(CDCl$_3$): 0.14 (6H, s), 0.91 (9H, t, J=7.4 Hz), 0.92 (9H, s), 1.1–1.2 (6H, m), 1.3–1.4 (6H, m), 1.5–1.65 (6H, m), 2.43 (3H, s), 4.66 (2H, s), 7.99 (1H, s)

Preparation 41

3-Azidomethyl-2-(tri-n-butylstannyl)imidazo[5,1-b]thiazole a) 3-Azidomethylimidazo[5,1-b]thiazole Diphenylphosphoryl azide (0.259 ml) and 0.157 ml of 1,8-diazabicyclo[5,4,0]-7-undecene were added to a suspension of 154 mg of 3-hydroxymethylimidazo[5,1-b]thiazole in 2 ml of toluene. The mixture was stirred at room temperature for 30 hr. Brine was added to the reaction mixture, and the mixture was extracted twice with ethyl acetate. The organic layer was dried over anhydrous magnesium sulfate. The solvent was removed by distillation. The residue was purified by column chromatography on silica gel (dichloromethane:methanol=30:1) to give 156 mg of 3-azidomethylimidazo[5,1-b]thiazole.

NMR(CDCl$_3$): 4.49 (2H, s), 6.82 (1H, s), 7.15 (1H, s), 8.02 (1H, s)

b) 3-Azidomethyl-2-(tri-n-butylstannyl)-imidazo[5,1-b]thiazole

In the same manner as in Preparation 16-d), 59.3 mg of the title compound was obtained from 69.3 mg of 3-azidomethylimidazo[5,1-b]thiazole.

NMR(CDCl$_3$): 0.92 (9H, t, J=7.3 Hz), 1.15–1.25 (6H, m), 1.25–1.4 (6H, m), 1.5–1.65 (6H, m), 4.41 (2H, s), 7.07 (1H, s), 7.96 (1H, s)

Preparation 42

3-t-Butyldimethylsilyloxymethyl-2-(tri-n-butylstannyl)imidazo[5,1-b]thiazole

In the same manner as in Preparation 4-b), 3.92 g of the title compound was obtained from 2.68 g of 3-t-butyldimethylsilyloxymethylimidazo[5,1-b]-thiazole.

NMR(CDCl$_3$): 0.15 (6H, s), 0.91 (9H, t, J=7.4 Hz), 0.93 (9H, s), 1.1–1.2 (6H, m), 1.3–1.4 (6H, m), 1.5–1.65 (6H, m), 4.68 (2H, s), 7.02 (1H, s), 8.02 (1H, s)

Preparation 43

3,7-Bis(methylthio)-2-(tri-n-butylstannyl)-imidazo[5,1-b]thiazole a) 7-Methylthio-2-trimethylsilylimidazo-[5,1-b]thiazole A 1.59 N n-butyllithium/n-hexane solution (9.91 ml) was added dropwise in an argon atmosphere at −50° C. to a solution of 2.55 g of 7-methylthioimidazo[5,1-b]thiazole in 100 ml of THF. The mixture was stirred at the same temperature for 25 min. Trimethylsilyl chloride (2.08 ml) was added thereto, and the mixture was stirred for 30 min. The temperature of the system was raised to −30° C. A 1.59 N n-butyllithium/n-hexane solution (5.72 ml) was added dropwise thereto, and the mixture was stirred at the same temperature for 30 min. An aqueous ammonium chloride solution was added to the reaction solution. The mixture was extracted with ethyl acetate. The extract was dried over anhydrous magnesium sulfate and then filtered. The solvent was removed by distillation under the reduced pressure. The residue was purified by column chromatography on silica gel (hexane:ethyl acetate=1:2) to give 2.58 g of 7-methylthio-2-trimethylsilylimidazo[5,1-b]-thiazole.

NMR(CDCl$_3$): 0.34 (9H, s), 2.42 (3H, s), 7.27 (1H, s), 7.93 (1H, s)

b) 3.7-Bis(methylthio)-2-trimethylsilyl-imidazo[5,1-b]thiazole

A 1.59 N n-butyllithium/n-hexane solution (7.38 ml) was added dropwise in an argon atmosphere at −65° C. to a solution of 2.58 g of 7-methylthio-2-trimethylsilylimidazo[5,1-b]-thiazole in 40 ml of THF. The mixture was stirred at the same temperature for 20 min. Methylmethanethiol sulfonate (1.32 ml) was added thereto, and the mixture was stirred at −50° C. for 30 min. An aqueous ammonium chloride solution was added to the reaction solution. The mixture was extracted with ethyl acetate. The extract was dried over anhydrous magnesium sulfate and then filtered. The solvent was removed by distillation under the reduced pressure. The residue was purified by column chromatography on silica gel (hexane:ethyl acetate=1:1) to give 1.88 g of 3,7-bis(methylthio)-2-trimethylsilylimidazo[5,1-b]thiazole.

NMR(CDCl$_3$): 0.42 (9H, s), 2.39 (3H, s), 2.42 (3H, s), 8.02 (1H, s)

c) 3.7-Bis(methylthio)imidazo[5,1-b]thiazole

A solution of 1.88 g of 3,7-bis(methylthio)-2-trimethylsilylimidazo[5,1-b]thiazole in 50 ml of THF was ice cooled. A 1 M tetra-n-butylammonium fluoride/THF solution (8.16 ml) was added in an argon atmosphere to the solution. The mixture was stirred at the same temperature for one hr. Brine was added thereto, and the mixture was extracted twice with ethyl acetate. The organic layer was washed with brine, dried over anhydrous magnesium sulfate, and then filtered. The solvent was removed by distillation under the reduced pressure. The residue was purified by column chromatography on silica gel (hexane:ethyl acetate=1:1) to give 1.30 g of 3,7-bis(methylthio)imidazo[5,1-b]thiazole.

NMR(CDCl$_3$): 2.44 (3H, s), 2.49 (3H, s), 6.82 (1H, s), 8.04 (1H, s)

d) 3,7-Bis(methylthio)-2-(tri-n-butylstannyl)imidazo[5,1-b]thiazole

In the same manner as in Preparation 4-b), 2.10 g of the title compound was obtained from 1.30 g of 3,7-bis(methylthio)imidazo[5,1-b]thiazole.

NMR (CDCl$_3$): 0.92 (9H, t, J=7.3 Hz), 1.2–1.3 (6H, m), 1.3–1.4 (6H, m), 1.5–1.6 (6H, m), 2.37 (3H, s), 2.43 (3H, s), 7.99 (1H, s)

Preparation 44

7-(1-Propyl)thio-2-(tri-n-butylstannyl)-imidazo[5,1-b]thiazole a) 1-Propyl 1-propanethiolsulfonate In the same manner as in Preparation 38-a), 666 mg of 1-propyl 1-propanethiolsulfonate was obtained from 1.57 ml of dipropyl disulfide.

NMR(CDCl$_3$): 1.04 (3H, t, J=7.4 Hz), 1.09 (3H, t, J=7.4 Hz), 1.7–1.85 (2H, m), 1.9–2.05 (2H, m), 3.05–3.15 (2H, m), 3.25–3.35 (2H, m)

b) 7-(1-Propyl)thioimidazo[5,1-b]thiazole

In the same manner as in Preparation 38-b), 1.74 g of 7-(1-propyl)thioimidazo[5,1-b]thiazole was obtained from 3.33 g of 7-iodoimidazo[5,1-b]thiazole and 3.03 g of 1-propyl 1-propanesulfonate.

NMR (CDCl$_3$): 0.99 (3H, t, J=7.4 Hz), 1.55–1.7 (2H, m), 2.75–2.85 (2H, m), 6.86 (1H, d, J=4.2 Hz), 7.39 (1H, d, J=4.2 Hz), 8.00 (1H, s)

c) 7-(1-Propyl)thio-2-(tri-n-butylstannyl)-imidazo[5,1-b]thiazole

In the same manner as in Preparation 37-b), 1.84 g of the title compound was obtained from 882 mg of 7-(1-propyl)thioimidazo[5,1-b]thiazole.

NMR(CDCl$_3$): 0.92 (9H, t, J=7.4 Hz), 0.99 (3H, t, J=7.4 Hz), 1.1–1.2 (6H, m), 1.3–1.4 (6H, m), 1.5–1.7 (8H, m), 2.7–2.8 (2H, m), 7.13 (1H, s), 7.94 (1H, s)

Preparation 45

7-Isopropylthio-2-(tri-n-butylstannyl)-imidazo[5,1-b]thiazole a) 7-Isopropylthioimidazo[5,1-b]thiazole

A 0.69 M isopropylmagnesium bromide/THF solution (9.13 ml) was added in an argon atmosphere under ice cooling to a solution of 1.50 g of 7-iodoimidazo[5,1-b]thiazole in 30 ml of dry THF. The mixture was then stirred at the same temperature for 20 min. Sulfur (211 mg) was added thereto, and the mixture was heated under reflux for one hr. A saturated aqueous ammonium chloride solution was added to the reaction mixture. The mixture was extracted twice with ethyl acetate, followed by washing with an aqueous sodium thiosulfate solution and a saturated brine in that order. The organic layer was dried over anhydrous magnesium sulfate. The solvent was removed by distillation. The residue was purified by column chromatography on silica gel (hexane:ethyl acetate=1:2) to give 833 mg of 7-isopropylthioimidazo[5,1-b]thiazole.

NMR(CDCl$_3$): 1.28 (6H, d, J=6.7 Hz), 3.28 (1H, sept, J=6.7 Hz), 6.87 (1H, d, J=4.2 Hz), 7.40 (1H, d, J=4.2 Hz), 8.02 (1H, s)

b) 7-Isopropylthio-2-(tri-n-butylstannyl)-imidazo[5,1-b]thiazole

In the same manner as in Preparation 4-b), 1.38 g of the title compound was obtained from 1.02 g of 7-isopropylthioimidazo[5,1-b]thiazole.

NMR(CDCl$_3$): 0.92 (9H, t, J=7.3 Hz), 1.1–1.2 (6H, m), 1.28 (6H, d, J=6.8 Hz), 1.3–1.4 (6H, m), 1.5–1.65 (6H, m), 3.26 (1H, sept, J=6.8 Hz), 7.14 (1H, s), 7.95 (1H, s)

Preparation 46

5-Methylthio-2-(tri-n-butylstannyl)-imidazo[5,1-b]thiazole a) 5-Methylthioimidazo[5,1-b]thiazole

In substantially the same manner as in Preparation 12-a), 1.03 g of 5-methylthioimidazo[5,1-b]thiazole was obtained from 2.07 g of 5-iodoimidazo[5,1-b]thiazole.

NMR(CDCl$_3$): 2.52 (3H,s), 6.84 (1H, d, J=4.2 Hz), 7.13 (1H, s), 7.42 (1H, d, J=4.2 Hz)

b) 5-Methylthio-2-(tri-n-butylstannyl)-imidazo[5,1-b]thiazole

In substantially the same manner as in Preparation 4-b), 2.40 g of the title compound was obtained from 1.03 g of 5-methylthioimidazo[5,1-b]thiazole.

NMR(CDCl$_3$): 0.92 (9H, t, J=7.2 Hz), 1.16 (6H, m), 1.30–1.40 (6H, m), 1.55–1.64 (6H, m), 2.51 (3H, s), 7.07 (1H, s), 7.15 (1H, s)

Preparation 47

5,7-Bis(methylthio)-2-(tri-n-butylstannyl)-imidazo[5,1-b]thiazole a) 5,7-Bis(methylthio)imidazo[5,1-b]thiazole

A 1 M ethylmagnesium bromide/THF solution (4.2 ml) was added in an argon atmosphere under ice cooling to a solution of 0.77 g of 5,7-diiodoimidazo[5,1-b]thiazole in 6 ml of dry THF. The mixture was stirred at the same temperature for one hr. Methylmethanethiol sulfonate (0.46 ml) was added thereto. The mixture was stirred at room temperature for 2 hr. A saturated aqueous ammonium chloride solution was added to the reaction mixture. Ethyl acetate was then added thereto, followed by washing with a dilute aqueous sodium thiosulfate solution and a saturated brine in that order. The organic layer was dried over anhydrous magnesium sulfate. The solvent was removed by distillation. The residue was purified by column chromatography on silica gel (ethyl acetate:hexane=1:2) to give 0.27 g of 5,7-bis(methylthio)imidazo[5,1-b]thiazole.

NMR(CDCl$_3$): 2.43 (3H, s), 2.55 (3H, s), 6.86 (1H, d, J=4.4 Hz), 7.38 (1H, d, J=4.4 Hz)

b) 5,7-Bis(methylthio)-2-(tri-n-butylstannyl)imidazo[5,1-b]thiazole

In substantially the same manner as in Preparation 4-b), 2.31 g of the title compound was obtained from 1.66 g of 5,7-bis(methylthio)imidazo[5,1-b]thiazole.

NMR(CDCl$_3$): 0.92 (9H, t, J=7.2 Hz), 1.17 (6H, m), 1.31–1.41 (6H, m), 1.55–1.64 (6H, m), 2.42 (3H, s), 2.54 (3H, s), 7.12 (1H, s)

Preparation 48

3-Methylthio-2-(tri-n-butylstannyl)imidazo-[5,1-b]thiazole a) 2-(Trimethylsilyl)imidazo[5,1-b]thiazole

A 1.6 N n-butyllithium/n-hexane solution (16.7 ml) was added in an argon atmosphere at −50° C. to a solution of 3.17 g of imidazo[5,1-b]thiazole in 120 ml of dry THF. The mixture was stirred at the same temperature for 30 min. Trimethylsilyl chloride (3.54 ml) was added thereto, and the mixture was stirred for 20 min. A 1.6 N n-butyllithium/n-hexane solution (8.0 ml) was added thereto, and the mixture was stirred for 20 min. A saturated aqueous ammonium chloride solution was added to the reaction mixture. Ethyl acetate was then added thereto, followed by washing with water and saturated brine in that order. The organic layer was dried over anhydrous magnesium sulfate. The solvent was removed by distillation. The residue was purified by column chromatography on silica gel (ethyl acetate) to give 4.53 g of 2-(trimethylsilyl)imidazo[5,1-b]thiazole.

NMR(CDCl$_3$): 0.34 (9H, s), 7.04 (1H, s), 7.29 (1H, s), 7.94 (1H, s)

b) 3-Methylthio-2-(trimethylsilyl)imidazo-[5,1-b]thiazole

A 1.6 N n-butyllithium/n-hexane solution (15.3 ml) was added in an argon atmosphere at −55° C. to a solution of 4.40 g of 2-(trimethylsilyl)imidazo[5,1-b]thiazole in 70 ml of dry THF. The mixture was stirred at the same temperature for 30 min. Methylmethanethiol sulfonate (2.75 ml) was then added thereto. The temperature of the system was raised to −5° C. over a period of 2 hr. A saturated aqueous ammonium chloride solution was added to the reaction mixture. Ethyl acetate was then added thereto, followed by washing with water and saturated brine in that order. The organic layer was dried over anhydrous magnesium sulfate. The solvent was removed by distillation. The residue was purified by column chromatography on silica gel (ethyl acetate) to give 3.87 g of 3-methylthio-2-(trimethylsilyl)imidazo[5,1-b]-thiazole.

NMR (CDCl$_3$): 0.41 (9H, s), 2.39 (3H, s), 7.10 (1H, s), 8.04 (1H, s)

c) 3-Methylthioimidazo[5,1-b]thiazole

A 1 M Tetra-n-butylammonium fluoride/THF solution (20.0 ml) was added in an argon atmosphere at room temperature to a solution of 3.87 g of 3-methylthio-2-(trimethylsilyl)imidazo[5,1-b]-thiazole in 70 ml of dry THF. The mixture was stirred at the same temperature for 15 min. Semi-saturated brine was added to the reaction mixture. Ethyl acetate was then added thereto, followed by washing with semi-saturated brine. The organic layer was dried over anhydrous magnesium sulfate. The solvent was removed by distillation. The residue was purified by column chromatography on silica gel (ethyl acetate) to give 2.62 g of 3-methylthioimidazo[5,1-b]thiazole.

NMR (CDCl$_3$): 2.49 (3H, s), 6.80 (1H, s), 7.14 (1H, s), 8.05 (1H, s)

d) 3-Methylthio-2-(tri-n-butylstannyl)-imidazo[5,1-b]thiazole

In substantially the same manner as in Preparation 4-b), 5.44 g of the title compound was obtained from 2.62 g of 3-methylthioimidazo[5,1-b]thiazole.

NMR (CDCl$_3$): 0.92 (9H, t, J=7.3 Hz), 1.24 (6H, m), 1.30–1.40 (6H, m), 1.54–1.63 (6H, m), 2.37 (3H, s), 7.14 (1H, s), 8.01 (1H, s)

Preparation 49

5-Acetyl-7-methylthio-2-(tri-n-butylstannyl)imidazo[5,1-b]thiazole a) 5-Iodo-7-methylthioimidazo[5,1-b]thiazole N-Iodosuccinimide (3.08 g) was added under ice cooling to a solution of 2.28 g of 7-methylthioimidazo[5,1-b]thiazole in dichloromethane. The mixture was stirred at room temperature for 7 hr. Saturated brine was added to the reaction mixture, followed by separation. The organic layer was washed with a dilute aqueous sodium thiosulfate solution and saturated brine in that order, and then dried over anhydrous magnesium sulfate. The solvent was removed by distillation. The residue was purified by column chromatography on silica gel (ethyl acetate:dichloromethane=1:1) to give 3.78 g of 5-iodo-7-methylthioimidazo[5,1-b]thiazole.

NMR (CDCl$_3$): 2.42 (3H, s), 6.93 (1H, d, J=4.4 Hz), 7.25 (1H, d, J=4.4 Hz)

b) 5-Acetyl-7-methylthioimidazo[5,1-b]-thiazole

A 1 M ethylmagnesium bromide/THF solution (4.78 ml) was added in an argon atmosphere at −40° C. to a solution of 963 mg of 5-iodo-7-methylthioimidazo[5,1-b]thiazole in 30 ml of dry THF. The mixture was stirred at the same temperature for 30 min. Acetyl chloride (0.35ml) was added thereto. The temperature of the system was raised to −5° C. over a period of 2 hr. A saturated aqueous ammonium chloride solution was added to the reaction mixture. Ethyl acetate was added thereto, followed by washing with a dilute aqueous sodium thiosulfate solution and saturated brine in that order. The organic layer was dried over anhydrous magnesium sulfate. The solvent was removed by distillation. The residue was purified by column chromatography on silica gel (dichloromethane:ethyl acetate:hexane=2:1:1) to give 384 mg of 5-acetyl-7-methylthioimidazo[5,1-b]thiazole.

NMR(CDCl$_3$): 2.52 (3H, s), 2.67 (3H, s), 7.10 (1H, d, J=4.2 Hz), 8.46 (1H, d, J=4.2 Hz)

c) 5-Acetyl-7-methylthio-2-(tri-n-butylstannyl) imidazo[5,1-b]thiazole

In substantially the same manner as in Preparation 5-b), 283 mg of the title compound was obtained from 378 mg of 5-acetyl-7-methylthioimidazo[5,1-b]thiazole.

NMR(CDCl$_3$): 0.92 (9H, t, J=7.3 Hz), 1.19 (6H, m), 1.33–1.44 (6H, m), 1.55–1.64 (6H, m), 2.52 (3H, s), 2.66 (3H, s), 8.23 (1H, s)

Preparation 50

5-Cyano-7-methylthio-2-(tri-n-butylstannyl)-imidazo[5,1-b]thiazole a) 5-Cyano-7-methylthioimidazo[5,1-b]thiazole A 1 M ethylmagnesium bromide/THF solution (2.0 ml) was added in an argon atmosphere at −40° C. to a solution of 405 mg of 5-iodo-7-methylthioimidazo[5,1-b]thiazole in 12 ml of dry THF. The mixture was stirred at the same temperature for 30 min. p-Toluenesulfonyl cyanide (372 mg) was added thereto. The temperature of the system was raised to −5° C. over a period of one hr. A saturated aqueous ammonium chloride solution was added to the reaction mixture. Ethyl acetate was added thereto, followed by washing with saturated brine. The organic layer was dried over anhydrous magnesium sulfate. The solvent was removed by distillation. The residue was purified by column chromatography on silica gel (dichloromethane:ethyl acetate:hexane=3:1:1) to give 131 mg of 5-cyano-7-methylthioimidazo[5,1-b]thiazole.

NMR(CDCl$_3$): 2.52 (3H, s), 2.67 (3H, s), 7.10 (1H, d, J=4.2 Hz), 8.46 (1H, d, J=4.2 Hz)

b) 5-Cyano-7-methylthio-2-(tri-n-butylstannyl) imidazo[5,1-b]thiazole

In substantially the same manner as in Preparation 4-b), 262 mg of the title compound was obtained from 253 mg of 5-cyano-7-methylthio-imidazo[5,1-b]thiazole.

NMR(CDCl$_3$): 0.93 (9H, t, J=7.3 Hz), 1.23 (6H, m), 1.31–1.41 (6H, m), 1.52–1.62 (6H, m), 2.50 (3H, s), 7.37 (1H, s)

Preparation 51

7-(4-Nitrobenzyloxycarbonylamino)acetyl-2-(tri-n-butylstannyl)imidazo[5,1-b]thiazole a) 7-(4-Nitrobenzyloxycarbonylamino)acetyl-imidazo[5,1-b]thiazole 7-Azidoacetylimidazo[5,1-b]thiazole (1.71 g) was dissolved in 60 ml of THF. Water (30 ml), 24.8 ml of 1 N hydrochloric acid, and 850 mg of 10%Pd-C were added to the solution. A reaction was allowed to proceed in a hydrogen atmosphere at room temperature for one hr. After the completion of the reaction, the catalyst was removed by filtration through Celite, followed by washing with a 50% aqueous THF solution. A 1 N aqueous sodium hydroxide solution (34.7 ml) and 2.14 g of 4-nitrobenzyl chlorocarbonate were added under ice cooling to the filtrate. The mixture was allowed to react at the same temperature for one hr. The resultant precipitate was collected by filtration, washed with a 50% aqueous THF solution (20 ml) and ethyl acetate (20 ml) in that order, and then dried under the reduced pressure to give 2.59 g of 7-(4-nitrobenzyloxycarbonylamino)acetylimidazo-[5,1-b]thiazole.

NMR(DMSO-d$_6$): 4.47 (2H, d), 5.52 (2H, s), 7.53 (1H, d), 7.65 (2H, d), 8.10 (1H, d), 8.26 (2H, d), 8.35 (1H, s)

b) 7-(4-Nitrobenzyloxycarbonylamino)acetyl-2-(tri-n-butylstannyl)imidazo[5,1-b]thiazole 7-(4-Nitrobenzyloxycarbonylamino)acetyl-imidazo[5,1-b]thiazole (2.52 g) was suspended in 50 ml of anhydrous THF. The suspension was cooled in an argon atmosphere to −70° C. Tri-n-butylstannyl chloride (3 ml) was added to the suspension. A solution (31.5 ml) of 1 N lithiumbis(trimethylsilyl)amide in THF was then added dropwise thereto over a period of 20 min. The mixture was allowed to react at the same temperature for one hr. The reaction solution was poured into a mixed solution composed of 250 ml of ethyl acetate and 150 ml of 15% brine. The organic layer was washed with 15% brine, and then dried over anhydrous magnesium sulfate. The solvent was removed by distillation. The residue was purified by column chromatography on silica gel (ethyl acetate:dichloromethane=1:10) to give 1.41 g of the title compound.

NMR(CDCl$_3$): 0.92 (9H, t), 1.21 (6H, m), 1.38 (6H, m), 1.58 (6H, m), 4.77 (2H, d), 5.26 (2H, s), 5.88 (1H, m), 7.30 (1H, s), 7.54 (2H, d), 7.95 (1H, s), 8.22 (2H, d)

Preparation 52

7-(4-Nitrobenzyloxycarbonylamino)methyl-2-(tri-n-butylstannyl)imidazo[5,1-b]thiazole a) 7-(4-Nitrobenzyloxycarbonylamino)methyl-imidazo[5,1-b]thiazole 7-Aminomethylimidazo[5,1-b]thiazole (1.53 g) was dissolved in 50 ml of THF and 30 ml of water. A 1 N aqueous sodium hydroxide solution (12 ml) and 2.59 g of 4-nitrobenzyl chlorocarbonate were added under ice cooling to the solution. The mixture was allowed to react at the same temperature for 30 min. The reaction solution was extracted with 200 ml of ethyl acetate, followed by washing with 15% brine. The organic layer was dried over anhydrous magnesium sulfate, and concentrated under the reduced pressure to about 20 ml. The resultant crystal was collected by filtration, washed with 20 ml of ethyl acetate, and dried under the reduced pressure to give 2.26 g of 7-(4-nitrobenzyloxycarbonylamino)methylimidazo-[5,1-b]thiazole.

NMR (DMSO-d$_6$): 4.23 (2H, d), 5.21 (2H, s), 7.14 (1H, d), 7.62 (2H, d), 7.81 (1H, d), 7.96 (1H, m), 8.10 (1H, s), 8.24 (2H, d)

b) 7-(4-Nitrobenzyloxycarbonylamino)methyl-2-(tri-n-butylstannyl)imidazo[5,1-b]thiazole The title compound (772 mg) was obtained from 1.59 g of 7-(4-nitrobenzyloxycarbonylamino)methyl-imidazo[5,1-b]thiazole in the same manner as in Preparation 51-b), except that a mixed solution of anhydrous THF-HMPA was used as the reaction solvent.

NMR(CDCl$_3$): 0.91 (9H, t), 1.15 (6H, m), 1.35 (6H, m), 1.58 (6H, m), 4.47 (2H, d), 5.22 (2H, s), 5.42 (1H, m), 7.12 (1H, s), 7.52 (2H, d), 7.89 (1H, s), 8.20 (2H, d)

Preparation 53

3-Phenyl-2-(tri-n-butylstannyl)imidazo[5,1-b]thiazole

In the same manner as in Preparation 4-b), 1.09 g of the title compound was obtained from 600 mg of 3-phenylimidazo[5,1-b]thiazole.

NMR(CDCl$_3$): 0.85 (9H, t), 0.92 (6H, m), 1.25 (6H, m), 1.40 (6H, m), 7.06 (1H, s), 7.50 (5H, s), 7.77 (1H, s)

Preparation 54

7-((E)-3-Oxo-1-buten-1-yl)-2-(tri-n-butylstannyl)imidazo[5,1-b]thiazole a) 7-((E)-3-Oxo-1-buten-1-yl)imidazo[5,1-b]-thiazole 7-Formyl-imidazo[5,1-b]thiazole was dissolved in 15 ml of methanol. Methyl(triphenylphosphoranylidene)acetate (500 mg) was added to the solution. The mixture was stirred at room temperature for 15 min. The reaction solution was concentrated under the reduced pressure. The concentrate was purified by chromatography on silica gel to give 208 mg of 7-((E)-3-oxo-1-buten-1-yl)imidazo[5,1-b]thiazole.

NMR (CDCl$_3$): 2.39 (3H, s), 6.43 (1H, dd, J=16.3 Hz), 7.04 (1H, d, J=4.1 Hz), 7.52 (1H, d, J=16.3 Hz), 8.09 (1H, s)

b) 7-((E)-3-Oxo-1-buten-1-yl)-2-(tri-n-butylstannyl)imidazo[5,1-b]thiazole

In the same manner as in Preparation 4-b), 408 mg of the title compound was obtained from 208 mg of 7-((E)-3-oxo-1-buten-1-yl)imidazo[5,1-b]-thiazole.

NMR(CDCl$_3$): 0.94 (9H, t, J=7.3 Hz), 1.15–1.40 (12H, m), 1.55–1.65 (6H, m), 2.37 (3H, s), 6.38 (1H, d, J=16.1 Hz), 7.25 (1H, s), 7.65 (1H, d, J=16.1 Hz), 8.02 (1H, s)

Preparation 55

7-(t-Butyldimethylsilyloxy)methyl-5-methyl-2-(tri-n-butylstannyl)imidazo[5,1-b]thiazole a) 7-formyl-5-methylimidazo[5,1-b]thiazole DMF (8 ml) was added to 40 ml of dichloromethane. The mixture was cooled in an argon atmosphere to 0° C. A solution of 9 ml of phosphorus oxychloride in 40 ml of dichloromethane was added dropwise thereto. Further, a solution of 1.2 g of 5-methylimidazo[5,1-b]thiazole in 20 ml of dichloromethane was added dropwise thereto. The mixture was heated under reflux for 5 hr. The reaction solution was poured into iced water, and then adjusted to pH 10 by the addition of an aqueous sodium hydroxide solution. The mixture was extracted with dichloromethane. The extract was dried over magnesium sulfate. The solvent was then concentrated under the reduced pressure. The residue was purified by chromatography on silica gel to give 1.5 g of 7-formyl-5-methylimidazo[5,1-b]thiazole.

NMR (CDCl$_3$): 2.26 (3H, s), 7.13 (1H, d, J=4.1 Hz), 7.42 (1H, d, J=4.1 Hz), 9.84 (1H, s)

b) 7-(t-Butyldimethylsilyloxy)methyl-5-methylimidazo[5,1-b]thiazole

7-Formyl-5-methylimidazo[5,1-b]thiazole (1.5 g) was dissolved in 20 ml of methanol. Sodium boron hydride (210 mg) was added to the solution. The mixture was stirred at 0° C. for 40 min. A saturated sodium hydrogencarbonate solution was added thereto. The mixture was extracted with dichloromethane. The extract was dried over magnesium sulfate, and then concentrated under the reduced pressure. The residue was dissolved in DMF. Imidazole (900 mg) and 1.8 g of t-butyldimethylsilyl chloride were added in an argon atmosphere to the solution. The mixture was stirred at room temperature for 16 hr. Water was added to the reaction solution, and the mixture was extracted with ethyl acetate, followed by washing with saturated brine. The extract was dried over magnesium sulfate. The solvent was removed under the reduced pressure. The residue was purified by chromatography on silica gel to give 2.18 g of 7-(t-butyldimethylsilyloxy)methyl-5-methylimidazo-[5,1-b]thiazole.

NMR(CDCl$_3$): 0.13 (6H, s), 0.98 (9H, s), 2.54 (3H, s), 4.84 (2H, s), 6.73 (1H, d, J=4.4 Hz), 7.16 (1H, d, J=4.4 Hz), 7.27 (1H, s)

c) 7-(t-Butyldimethylsilyloxy)methyl-5-methyl-2-(tri-n-butylstannyl)imidazo[5,1-b]-thiazole In the same manner as in Preparation 4-b), 1.2 g of the tile compound was obtained from 980 mg of 7-(t-butyldimethylsilyloxy)methyl-5-methyl-imidazo[5,1-b]thiazole.

NMR(CDCl₃): 0.13 (6H, s), 0.93 (9H, t, J=7.3 Hz), 0.97 (9H, s), 1.13 (6H, s), 1.36 (6H, s), 1.58 (6H, s), 2.53 (3H, s), 4.82 (2H, s), 6.88 (1H, s), 7.27 (1H, s)

Example 1

Sodium(1S,5R,6S)-6-((1R)-1-hydroxyethyl)-1-methyl-2-(7-propionylimidazo[5,1-b]thiazol-2-yl)-1-carbapen-2-em-3-carboxylate a) 4-Nitrobenzyl(1S5R,6S)-6-((1R)-1-hydroxyethyl)-1-methyl-2-(7-propionylimidazo[5,1-b]thiazol-2-yl,)-1-carbapen-2-em-3-carboxylate N,N-Diisopropylethylamine (0.392 ml) and 0.252 ml of trifluoromethanesulfonic anhydride were added dropwise in that order to a solution of 543 mg of 4-nitrobenzyl(1R,3R,5R,6S)-6-((1R)-1-hydroxyethyl)-1-methyl-2-oxo-1-carbapenam-3-carboxylate in 15 ml of dry acetonitrile in an argon atmosphere at −30° C. The mixture was stirred at that temperature for 30 min. Ethyl acetate (150 ml) was added thereto. The mixture was then washed with semisaturated brine, a mixed solution (pH 1.1) composed of semisaturated brine and a 1 N aqueous hydrochloric acid solution, a mixed solution (pH 8.9) composed of semisaturated brine and a saturated aqueous sodium hydrogencarbonate solution, and semisaturated brine in that order. The mixture was then dried over anhydrous magnesium sulfate and filtered. The solvent was removed by distillation under the reduced pressure. The residue was dissolved in 8 ml of dry N-methylpyrrolidinone. Tri-2-furylphosphine (42 mg), 409 mg of zinc chloride, 42 mg of tris(dibenzylideneacetone)dipalladium (0), and 844 mg of 7-propionyl-2-(tri-n-butylstannyl)imidazo[5,1-b]thiazole were added to the solution. The mixture was stirred in an argon atmosphere at 50° C. for 1.5 hr. Ethyl acetate (100 ml) and 50 ml of a semisaturated aqueous sodium hydrogencarbonate solution were added to the reaction solution, followed by stirring. The insolubles were removed by filtration. The organic layer was separated from the filtrate, washed three times with 100 ml of semisaturated brine, and dried over anhydrous magnesium sulfate. The solvent was removed by distillation under the reduced pressure. The residue was purified by column chromatography on silica gel (dichloromethane:methanol=30:1 to 20:1) to give 454 mg of 4-nitrobenzyl(1S,5R,6S)-6-((1R)-1-hydroxyethyl)-1-methyl-2-(7-propionylimidazo[5,1-b]thiazol-2-yl)-1-carbapen-2-em-3-carboxylate.

NMR (CDCl₃) δ: 1.26 (3H, t, J=7.4 Hz), 1.30 (3H, d, J=7.4 Hz), 1.60 (3H, d, J=6.3 Hz), 3.06 (2H, q, J=7.4 Hz), 3.39 (1H, dd, J₁=6.4 Hz, J₂=2.8 Hz), 3.52 (1H, m), 4.33 (1H, m), 4.41 (1H, dd, J₁=9.8 Hz, J₂=2.8 Hz), 5.28 (1H, d, J=13.5 Hz), 5.52 (1H, d, J=13.5 Hz), 7.68 (2H, d, J=8.9 Hz), 8.00 (1H, s), 8.24 (2H, d, J=8.9 Hz), 8.51 (1H, s)

b) Sodium(1S,5R,6S)-6-((1R)-1-hydroxyethyl)-1-methyl-2-(7-propionylimidazo[5,1-b]thiazol-2-yl)-1-carbapen-2-em-3-carboxylate 4-Nitrobenzyl(1S,5R,6S)-6-((1R)-1-hydroxyethyl)-1-methyl-2-(7-propionylimidazo[5,1-b]thiazol-2-yl)-1-carbapen-2-em-3-carboxylate (350 mg) was dissolved in 20 ml of THF and 20 ml of 1/15 M sodium phosphate buffer (pH 6.6). 10%Pd-C (350 mg) was added to the solution. The atmosphere in the reactor was replaced by hydrogen, and the system was stirred at room temperature for 1.5 hr. The catalyst was removed by filtration through Celite, followed by washing with water. The filtrate was adjusted to pH 7.0 by the addition of an aqueous sodium hydrogencarbonate solution, and washed with ethyl acetate. The aqueous layer was purified by column chromatography on Diaion HP-20 (10% aqueous methanol) to give 198 mg of the title compound.

NMR (D₂O) δ (HOD=4.80 ppm): 1.18 (3H, t, J=7.5 Hz), 1.25 (3H, d, J=7.1 Hz), 1.33 (3H, d, J=6.3 Hz), 2.93 (2H, q, J=7.5 Hz), 3.53 (1H, m), 3.64 (1H, m), 4.31 (2H, m), 8.04 (1H, s), 8.17 (1H, s)

Example 2

Pivaloyloxymethyl(1S,5R,6S)-6-((1R)-1-hydroxyethyl)-1-methyl-2-(7-propionylimidazo[5,1-b]thiazol-2-yl)-1-carbapen-2-em-3-carboxylate Sodium(1S,5R,6S)-6-((1R)-1-hydroxyethyl)-1-methyl-2-(7-propionylimidazo[5,1-b]thiazol-2-yl)-1-carbapen-2-em-3-carboxylate (75.8 mg) was dissolved in 7 ml of DMF. Sodium hydrogencarbonate (4.9 mg) and 0.038 ml of pivaloyloxymethyl iodide were added to the solution in an argon atmosphere at −30° C. The mixture was stirred for 1.5 hr. Ethyl acetate (50 ml) was added to the reaction solution. The mixture was washed three times with 30 ml of semisaturated brine. The organic layer was dried over anhydrous magnesium sulfate, and filtered. The filtrate was concentrated to 5 ml under the reduced pressure. The residue was purified by column chromatography on silica gel (dichloromethane:methanol=30:1) to give 62.3 mg of the title compound.

NMR (CDCl₃) δ: 1.20 (9H, s), 1.26 (3H, t, J=7.4 Hz), 1.28 (3H, d, J=7.2 Hz), 1.37 (3H, d, J=6.3 Hz), 3.07 (2H, q, J=7.4 Hz), 3.35 (1H, dd, J₁=6.6 Hz, J₂=2.8 Hz), 3.50 (1H, m), 4.30 (1H, m), 4.39 (1H, dd, J₁=9.6 Hz, J₂=2.8 Hz), 5.87 (1H, d, J=5.6 Hz), 5.99 (1H, d, J=5.6 Hz), 8.03 (1H, s), 8.51 (1H, s)

Example 3

Sodium(1S,5R,6S)-6-((1R)-1-hydroxyethyl)-2-(7-hydroxyiminomethylimidazor[5,1-b]thiazol-2-yl)-1-methyl-1-carbapen-2-em-3-carboxylate (A Geometrical Isomer Derived From a Starting Compound as a Low-polarity Oxime Isomer)

a) 4-Nitrobenzyl(1S,5R,6S)-6-((1R)-1-hydroxyethyl)-1-methyl-2-[7-(4-nitrobenzyloxyiminomethyl)imidazo[5,1-b]thiazol-2-yl]-1-carbapen-2-em-3-carboxylate (A Geometrical Isomer Derived From a Starting Compound as a Low-polarity Oxime Isomer)

In the same manner as in Example 1-a), 77.3 mg of 4-nitrobenzyl(1S,5R,6S)-6-((1R)-1-hydroxyethyl)-1-methyl-2-[7-(4-nitrobenzyloxyiminomethyl)imidazo[5,1-b]thiazol-2-yl]-1-carbapen-2-em-3-carboxylate (a geometrical isomer derived from a starting compound as a low-polarity oxime isomer) was obtained from 86 mg of 4-nitrobenzyl (1R,3R,5R,6S)-6-((1R)-1-hydroxyethyl)-1-methyl-2-oxo-1-carbapenam-3-carboxylate and 169 mg of 7-(4-nitrobenzyloxyiminomethyl)-2-(tri-n-butylstannyl)-imidazo[5,1-b]thiazole (a geometrical isomer derived from a starting compound as a low-polarity oxime isomer).

NMR (DMSO-d₆) δ: 1.20 (6H, m), 3.42 (1H, m), 3.70 (1H, m), 4.03 (1H, m), 4.34 (1H, m), 5.26 (2H, s), 5.39 (1H, d, J=13.5 Hz), 5.53 (1H, d, J=13.5 Hz), 7.71 (4H, m), 8.22 (4H, m), 8.32 (2H, s), 8.50 (1H, s)

b) Sodium(1S,5R,6S)-6-((1R)-1-hydroxyethyl)-2-(7-hydroxyiminomethylimidazo[5,1-b]thiazol-2-yl)-1-methyl-1-carbapen-2-em-3-carboxylate (A Geometrical Isomer Derived From a Starting Compound as a Low-polarity Oxime Isomer)

The title compound (2.4 mg) was obtained from 77.3 mg of 4-nitrobenzyl(1S,5R,6S)-6-((1R)-1-hydroxyethyl)-1- methyl-2-[7-(4-nitrobenzyloxyiminomethyl)imidazo[5,1-b]-thiazol-2-yl]-1-carbapen-2-em-3-carboxylate (a geometrical isomer derived from a starting compound as a low-polarity oxime isomer) in the same manner as in Example 1-b), except that the purification was carried out by column chromatography on Diaion HP-20 (10% aqueous methanol) and Cosmosil 40C18-PREP (20% aqueous methanol).

NMR (D$_2$O) δ (HOD=4.80 ppm): 1.22 (3H, d, J=6.6 Hz), 1.31 (3H, d, J=6.3 Hz), 3.50 (2H, m), 4.28 (2H, m), 7.84 (1H, s), 8.04 (1H, s), 8.17 (1H, s)

Example 4

Sodium(5R,6S)-6-((1R)-1-hydroxyethyl)-2-(7-methoxyiminomethylimidazo[5,1-b]thiazol-3-yl)-1-carbapen-2-em-3-carboxylate (A Geometrical Isomer Derived From a Starting Compound as a Low-polarity Oxime Isomer)

a) 4-Nitrobenzyl(5R,6S)-6-((1R)-1-hydroxyethyl)-2-(7-methoxyiminomethylimidazo[5,1-b]thiazol-3-yl)-1-carbapen-2-em-3-carboxylate (A Geometrical Isomer Derived From a Starting Compound as a Low-polarity Oxime Isomer)

In the same manner as in Example 1-a), 357 mg of 4-nitrobenzyl(5R,6S)-6-((1R)-1-hydroxyethyl)-2-(7-methoxyiminomethylimidazo[5,1-b]thiazol-3-yl)-1-carbapen-2-em-3-carboxylate (a geometrical isomer derived from a starting compound as a low-polarity oxime isomer) was obtained from 522 mg of 4-nitrobenzyl(3R,5R,6S)-6-((1R)-1-hydroxyethyl)-2-oxo-1-carbapenam-3-carboxylate and 846 mg of 7-methoxyiminomethyl-3-(tri-n-butylstannyl)imidazo[5,1-b]thiazole (a geometrical isomer derived from a starting compound as a low-polarity oxime isomer).

NMR (CDCl$_3$) δ: 1.40 (3H, d, J=6.3 Hz), 3.39 (3H, m), 3.96 (3H, s), 4.32 (1H, m), 4.45 (1H, m), 5.17 (1H, d, J=13.3 Hz), 5.32 (1H, d, J=13.3 Hz), 7.15 (1H, s), 7.37 (2H, d, J=8.5 Hz), 7.74 (1H, s), 8.15 (1H, s), 8.15 (2H, d, J=8.5 Hz)

b) Sodium(5R,6S)-6-((1R)-1-hydroxyethyl)-2-(7-methoxyiminomethylimidazo[5,1-b]thiazol-3-yl)-1-carbapen-2-em-3-carboxylate (A Geometrical Isomer Derived From a Starting Compound as a Low-polarity Oxime Isomer)

The title compound (93.9 mg) was obtained from 287 mg of 4-nitrobenzyl(5R,6S)-6-((1R)-1-hydroxyethyl)-2-(7-methoxyiminomethylimidazo[5,1-b]thiazol-3-yl)-1-carbapen-2-em-3-carboxylate (a geometrical isomer derived from a starting compound as a low-polarity oxime isomer) in the same manner as in Example 1-b), except that the purification was carried out by column chromatography on Diaion HP-20 (10% aqueous methanol) and Cosmosil 40C18-PREP (10% aqueous methanol).

NMR (D$_2$O) δ (HOD=4.80 ppm): 1.32 (3H, d, J=6.3 Hz), 3.21 (1H, m), 3.48 (1H, m), 3.60 (1H, m), 3.94 (3H, s), 4.28 (1H, m), 4.39 (1H, m), 7.20 (1H, s), 7.94 (1H, s), 8.22 (1H, s)

Example 5

Pivaloyloxymethyl(5R,6S)-6-((1R)-1-hydroxyethyl)-2-(7-methoxyiminomethylimidazo[5,1-b]thiazol-3-yl)-1-carbapen-2-em-3-carboxylate (A Geometrical Isomer Derived From a Starting Compound as a Low-polarity Oxime Isomer)

In the same manner as in Example 2, 22.6 g of the title compound was obtained from 40.0 mg of sodium(5R,6S)-6-((1R)-1-hydroxyethyl)-2-(7-methoxyiminomethylimidazo-[5,1-b]thiazol-3-yl)-1-carbapen-2-em-3-carboxylate (a geometrical isomer derived from a starting compound as a low-polarity oxime isomer).

NMR (CDCl$_3$) δ: 1.19 (9H, s), 1.38 (3H, d, J=6.3 Hz), 3.37 (3H, m), 3.96 (3H, s), 4.30 (1H, m), 4.42 (1H, m), 5.78 (1H, d, J=5.6 Hz), 5.88 (1H, d, J=5.6 Hz), 7.25 (1H, s), 7.79 (1H, s), 8.21 (1H, s)

Example 6

Sodium(1S,5R,6S)-6-((1R)-1-hydroxyethyl)-1-methyl-2-(7-pivaloylimidazo[5,1-b]thiazol-2-yl)-1-carbapen-2-em-3-carboxylate a) 4-Nitrobenzyl(1S,5R,6S)-6-((1R)-1-hydroxyethyl)-1-methyl-2-(7-pivaloylimidazo[5,1-b]-thiazol-2-yl)-1-carbapen-2-em-3-carboxylate In substantially the same manner as in Example 1-a), 487 mg of 4-nitrobenzyl(1S,5R,6S)-6-((1R)-1-hydroxyethyl)-1-methyl-2-(7-pivaloylimidazo[5,1-b]-thiazol-2-yl)-1-carbapen-2-em-3-carboxylate was obtained from 362 mg of 4-nitrobenzyl(1R,3R,5R,6S)-6-((1R)-1-hydroxyethyl)-1-methyl-2-oxo-1-carbapenam-3-carboxylate and 460 mg of 7-pivaloyl-2-(tri-n-butylstannyl)imidazo[5,1-b]thiazole.

NMR (DMSO-d$_6$) δ: 1.22 (3H, t, J=7.4 Hz), 1.30 (12H, m), 3.38–3.43 (1H, m), 3.60–3.70 (1H, m), 3.95–4.05 (1H, m), 4.27–4.32 (1H, m), 5.38 (1H, d, J=13.5 Hz), 5.50 (1H, d, J=13.5 Hz), 7.71 (2H, d, J=8.9 Hz), 8.20–8.30 (3H, m), 8.35 (1H, s)

b) Sodium(1S,5R,6S)-6-((1R)-1-hydroxyethyl)-1-methyl-2-(7-pivaloylimidazo[5,1-b]thiazol-2-yl)-1-carbapen-2-em-3-carboxylate The title compound (99 mg) was obtained from 487 mg of 4-nitrobenzyl(1S,5R,6S)-6-((1R)-1-hydroxyethyl)-1-methyl-2-(7-pivaloylimidazo[5,1-b]thiazol-2-yl)-1-carbapen-2-em-3-carboxylate in substantially the same manner as in Example 1-b), except that the purification was carried out using Cosmosil 40C18-PREP (10% aqueous acetonitrile).

NMR (D$_2$O) δ (HOD=4.80 ppm): 1.24 (3H, d, J=7.1 Hz), 1.28–1.32 (12H, m), 3.46–4.54 (2H, m), 4.23–4.32 (2H, m), 7.81 (1H, s), 8.02 (1H, s)

Example 7

Pivaloyloxymethyl(1S,5R,6S)-6-((1R)-1-hydroxyethyl)-1-methyl-2-(7-pivaloylimidazo[5,1-b]-thiazol-2-yl)-1-carbapen-2-em-3-carboxylate In substantially the same manner as in Example 2, the title compound (31 mg) was obtained from 40 mg of sodium (1S,5R,6S)-6-((1R)-1-hydroxyethyl)-1-methyl-2-(7-pivaloylimidazo[5,1-b]thiazol-2-yl)-1-carbapen-2-em-3-carboxylate.

NMR (CDCl$_3$) δ: 1.22 (9H, s), 1.28 (3H, d, J=7.3 Hz), 1.35–1.40 (12H, m), 3.31 (1H, dd, J$_1$=6.7 Hz, J$_2$=2.8 Hz), 3.40–3.56 (1H, m), 5.88 (1H, d, J=5.6 Hz), 5.98 (1H, d, J=5.6 Hz), 7.89 (1H, s), 8.25 (1H, s)

Example 8

Sodium(5R,6S)-2-(7-acetyl-3-methylimidazo[5,1-b]ithiazol-2-yl)-6-((1R)-1-hydroxyethyl)-1-carbapen-2-em-3-carboxylate a) 4-Nitrobenzyl(5R,6S)-2-(7-acetyl-3-methylimidazo[5,1-b]thiazol-2-yl)-6-((1R)-1-hydroxy-ethyl)-1-carbapen-2-em-3-carboxylate In the same manner as in Example 1-a), 303 mg of 4-nitrobenzyl(5R,6S)-2-(7-acetyl-3-methylimidazo[5,1-b]

thiazol-2-yl)-6-((1R)-1-hydroxyethyl)-1-carbapen-2-em-3-carboxylate was obtained from 453 mg of 4-nitrobenzyl(3R,5R,6S)-6-((1R)-1-hydroxyethyl)-2-oxo-1-carbapenam-3-carboxylate and 745 mg of 7-acetyl-3-methyl-2-(tri-n-butylstannyl)imidazo[5,1-b]thiazole.

NMR (CDCl$_3$) δ: 1.40 (3H, d, J=6.3 Hz), 2.27 (3H, s), 2.61 (3H, s), 3.21 (1H, dd, J$_1$=18.5 Hz, J$_2$=9.4 Hz), 3.23 (1H, dd, J$_1$=18.5 Hz, J$_2$=9.5 Hz), 3.38 (1H, dd, J$_1$=6.4 Hz, J$_2$=3.0 Hz), 4.26–4.41 (1H, m), 4.42 (1H, td, J$_1$=9.5 Hz, J$_2$=3.0 Hz), 5.23 (1H, d, J=13.5 Hz), 5.41 (1H, d, J=13.5 Hz), 7.55 (2H, dm, J=8.8 Hz), 7.82 (1H, s), 8.16 (2H, dm, J=8.8 Hz)

b) Sodium(5R,6S)-2-(7-acetyl-3-methylimidazo[5,1-bithiazol-2-yl)-6-((1R)-1-hydroxyethyl)-1-carbapen-2-em-3-carboxylate In the same manner as in Example 1-b), the title compound (125 mg) was obtained from 303 mg of 4-nitrobenzyl(5R,6S)-2-(7-acetyl-3-methylimidazo[5,1-b]thiazol-2-yl)-6-((1R)-1-hydroxyethyl)-1-carbapen-2-em-3-carboxylate.

NMR (D$_2$O) δ (HOD=4.80 ppm): 1.30 (3H, d, J=6.5 Hz), 2.35 (3H, s), 2.54 (3H, s), 3.14 (1H, dd, J$_1$=17.3 Hz, J$_2$=9.9 Hz), 3.33 (1H, dd, J$_1$=17.3 Hz, J$_2$=8.4 Hz), 3.57 (1H, dd, J$_1$=5.8 Hz, J$_2$=3.1 Hz), 4.27 (1H, qd, J$_1$=6.5 Hz, J$_2$=5.8 Hz), 4.36 (1H, ddd, J$_1$=9.9 Hz, J$_2$=8.4 Hz, J$_3$=3.1 Hz), 8.19 (1H, s)

Example 9

Pivaloyloxymethyl(5R,6S)-2-(7-acetyl-3-methylimidazo[5,1-b]thiazol-2-yl)-6-((1R)-1-hydroxy-ethyl)-1-carbapen-2-em-3-carboxylate In the same manner as in Example 2, the title compound (19 mg) was obtained from 35 mg of sodium(5R,6S)-2-(7-acetyl-3-methylimidazo[5,1-b]thiazol-2-yl)-6-((1R)-1-hydroxyethyl)-1-carbapen-2-em-3-carboxylate.

NMR (CDCl$_3$) δ: 1.10 (9H, s), 1.37 (3H, d, J=6.3 Hz), 1.99 (1H, broad), 2.37 (1H, s), 2.61 (1H, s), 3.20 (1H, dd, J$_1$=18.5 Hz, J$_2$=7.5 Hz), 3.22 (1H, dd, J$_1$=18.5 Hz, J$_2$=7.5 Hz), 3.35 (1H, dd, J$_1$=6.5 Hz, J$_2$=3.0 Hz), 4.33 to 4.35 (1H, m), 4.39 (1H, td, J$_1$=9.5 Hz, J$_2$=3.0 Hz), 5.78 (1H, d, J=5.5 Hz), 5.88 (1H, d, J=5.5 Hz), 7.90 (1H, s)

Example 10

Sodium(1S,5R,6S)-2-[7-(2-formylaminopropionyl)imidazo[5,1-b]thiazol-2-yl]-6-((1R)-1-hydroxyethyl)-1-methyl-1-carbapen-2-em-3-carboxylate (A High-polarity Isomer)

In substantially the same manner as in Example 1-a), 68 mg of a crude product of 4-nitrobenzyl(1S,5R,6S)-2-[7-(2-formylaminopropionyl)imidazo[5,1-b]thiazol-2-yl]-6-((1R)-1-hydroxyethyl)-1-methyl-1-carbapen-2-em-3-carboxylate (a mixture of diastereomers) was obtained from 91 mg of 4-nitrobenzyl(1R,3R,5R,6S)-6-((1R)-1-hydroxyethyl)-1-methyl-2-oxo-1-carbapenam-3-carboxylate and 96 mg of 7-(2-formylaminopropionyl)-2-(tri-n-butylstannyl)imidazo(5,1-b]thiazole. The title compound (3.2 mg) was obtained from this crude product in substantially the same manner as in Example 6-b).

NMR (D$_2$O) δ (HOD=4.80 ppm): 1.23 (3H, d, J=7.1 Hz), 1.32 (3H, d, J=6.3 Hz), 1.50 (3H, d, J=7.4 Hz), 3.52 (1H, dd, J$_1$=6.1 Hz, J$_2$=2.1 Hz), 3.55–3.65 (1H, m), 4.22–4.35 (2H, m), 5.35 (1H, q, J=7.4 Hz), 8.0 (1H, s), 8.12 (2H, m)

Example 11

Sodium(1S,5R,6S)-2-[7-(2-formylaminopropionyl)imidazo[5,1-b]thiazol-2-yl]-6-((1R)-1-hydroxyethyl)-1-methyl-1-carbapen-2-em-3-carboxylate (A Low-polarity Isomer)

In substantially the same manner as in Example 6-b), the title compound (3.4 mg) was obtained from 68 mg of the crude product of 4-nitrobenzyl(1S,5R,6S)-2-[7-(2-formylaminopropionyl)imidazo[5,1-b]thiazol-2-yl]-6-((1R)-1-hydroxyethyl)-1-methyl-1-carbapen-2-em-3-carboxylate (a mixture of diastereomers) prepared in Example 10.

NMR (D$_2$O) δ (HOD=4.80 ppm): 1.23 (3H, d, J=7.1 Hz), 1.32 (3H, d, J=6.3 Hz), 1.47 (3H, d, J=7.4 Hz), 3.50 (1H, dd, J$_1$=6.0 Hz, J$_2$=2.4 Hz), 3.55–3.65 (1H, m), 4.23–4.35 (2H, m), 5.32 (1H, d, J=7.4 Hz), 8.03 (1H, s), 8.13 (1H, s), 8.18 (1H, s)

Example 12

Sodium(1S,5R,6S)-6-((1R)-1-hydroxyethyl)-2-(7-isobutyrylimidazo[5,1-b]thiazol-2-yl)-1-methyl-1-carbapen-2-em-3-carboxylate a) 4-Nitrobenzyl(1S,5R,6S)-6-((1R)-1-hydroxyethyl)-2-(7-isobutyrylimidazo[5,1-b]thiazol-2-yl)-1-methyl-1-carbapen-2-em-3-carboxylate In the same manner as in Example 1-a), 440 mg of 4-nitrobenzyl(1S,5R,6S)-6-((1R)-1-hydroxyethyl)-2-(7-isobutyrylimidazo[5,1-b]thiazol-2-yl)-1-methyl-1-carbapen-2-em-3-carboxylate was obtained from 725 mg of 4-nitrobenzyl(1R,3R,5R,6S)-6-((1R)-1-hydroxyethyl)-1-methyl-2-oxo-1-carbapenam-3-carboxylate and 1.03 g of 7-isobutyryl-2-(tri-n-butylstannyl)imidazo[5,1-b]thiazole.

NMR (CDCl$_3$) δ: 1.13 (6H, d, J=6.6 Hz), 1.20 (3H, d, J=7.4 Hz), 1.29 (3H, d, J=6.0 Hz), 3.30 (1H, m), 3.46 (1H, m), 3.58 (1H, m), 4.19 (1H, m), 4.36 (1H, dd, J$_1$=9.6 Hz, J$_2$=2.7 Hz), 5.15 (1H, d, J=13.7 Hz), 5.39 (1H, d, J=13.7 Hz), 7.54 (2H, d, J=8.6 Hz), 7.98 (1H, s), 8.05 (2H, d, J=8.6 Hz), 8.37 (1H, s)

b) Sodium(1S,5R,6S)-6-((1R)-1-hydroxyethyl)-2-(7-isobutyrylimidazo[5,1-b]thiazol-2-yl)-1-methyl-1-carbapen-2-em-3-carboxylate The title compound (133 mg) was obtained from 440 mg of 4-nitrobenzyl(1S,5R,6S)-6-((1R)-1-hydroxyethyl)-2-(7-isobutyrylimidazo[5,1-b]thiazol-2-yl)-1-methyl-1-carbapen-2-em-3-carboxylate in the same manner as in Example 1-b), except that the purification was carried out by column chromatography on Diaion HP-20 (10% aqueous methanol) and Cosmosil 40C18-PREP (10% aqueous acetonitrile).

NMR (D$_2$O) δ (HOD=4.80 ppm): 1.18 (9H, m), 1.32 (3H, d, J=6.5 Hz), 3.44 (1H, m), 3.49 (1H, dd, J$_1$=6.3 Hz, J$_2$=2.7 Hz), 3.57 (1H, m), 4.27 (1H, m), 4.32 (1H, dd, J$_1$=9.2 Hz, J$_2$=2.7 Hz), 7.94 (1H, s), 8.07 (1H, s)

Example 13

Pivaloyloxymethyl(1S,5R,6S)-6-((1R)-1-hydroxyethyl)-2-(7-isobutyrylimidazo[5,1-b]thiazol-2-yl)-1-methyl-1-carbapen-2-em-3-carboxylate In the same manner as in Example 2, 48 mg of the title compound was obtained from 52 mg of sodium(1S,5R,6S)-6-((1R)-1-hydroxyethyl)-2-(7-isobutyrylimidazo[5,1-b]thiazol-2-yl)-1-methyl-1-carbapen-2-em-3-carboxylate.

NMR (CDCl$_3$) δ: 1.17 (9H, s), 1.26 (9H, m), 1.35 (3H, d, J=6.3 Hz), 3.35 (1H, dd, J$_1$=6.6 Hz, J$_2$=2.8 Hz), 3.49 (1H, m), 3.70 (1H, m), 4.28 (1H, m), 4.39 (1H, dd, J$_1$=9.8 Hz, J$_2$=2.8 Hz), 5.85 (1H, d, J=5.6 Hz), 5.97 (1H, d, J=5.6 Hz), 8.05 (1H, s), 8.49 (1H, s)

Example 14

Sodium(5R,6S)-6-((1R)-1-hydroxyethyl)-2-(7-propionylimidazo[5,1-b]thiazol-3-yl)-1-carbapen-2-em-3-carboxylate a) 4-Nitrobenzyl(5R,6S)-6-((1R)-1-hydroxyethyl)-2-(7-propionylimidazo[5,1-b]thiazol-3-yl)-1-carbapen-2-em-3-carboxylate In the same manner as in Example 1-a), 51.8 mg of 4-nitrobenzyl(5R,6S)-6-((1R)-1-hydroxyethyl)-2-(7- propionylimidazo[5,1-b]thiazol-3-yl)-1-carbapen-2-em-3-carboxylate was obtained from 168 mg of 4-nitrobenzyl(3R,5R,6S)-6-((1R)-1-hydroxyethyl)-2-oxo-1-carbapenam-3-carboxylate and 272 mg of 7-propionyl-3-(tri-n-butylstannyl)imidazo[5,1-b]thiazole.

NMR (CDCl$_3$) δ: 1.24 (3H, t, J=7.4 Hz), 1.41 (3H, d, J=6.3 Hz), 3.03 (2H, q, J=7.4 Hz), 3.39 (3H, m), 4.33 (1H, m), 4.47 (1H, m), 5.22 (1H, d, J=13.6 Hz), 5.38 (1H, d, J=13.6 Hz), 7.22 (1H, s), 7.49 (2H, d, J=8.8 Hz), 7.6 4 (1H, s), 8.18 (2H, d, J=8.8 Hz)

b) Sodium(5R,6S)-6-((1R)-1-hydroxyethyl)-2-(7-propionylimidazo[5,1-b]thiazol-3-yl)-1-carbapen-2-em-3-carboxylate In the same manner as in Example 1-b), the title compound (17.4 mg) was obtained from 51.8 mg of 4-nitrobenzyl(5R,6S)-6-((1R)-1-hydroxyethyl)-2-(7-propionylimidazo-[5,1-b]thiazol-3-yl)-1-carbapen-2-em-3-carboxylate.

NMR (D$_2$O) δ (HOD=4.80 ppm): 1.19 (3H, t, J=7.4 Hz), 1.33 (3H, d, J=6.2 Hz), 2.97 (2H, q, J=7.4 Hz), 3.25 (1H, dd, J$_1$=17.4 Hz, J$_2$=10.0 Hz), 3.50 (1H, dd, J$_1$=17.4 Hz, J$_2$=8.7Hz), 3.62 (1H, dd, J$_1$=5.9 Hz, J$_2$=2.8 Hz), 4.30 (1H, m), 4.42 (1H, m), 7.30 (1H, s), 7.92 (1H, s)

Example 15

Sodium(5R,6S)-2-(7-acetylimidazo[5,1-b]thiazol-2-yl)-6-((1R)-1-hydroxyethyl)-1-carbapen-2-em-3-carboxylate a) 4-Nitrobenzyl(5R,6S)-2-(7-acetylimidazo[5,1-b]thiazol-2-yl)-6-((1R)-1-hydroxyethyl)-1-carbapen-2-em-3-carboxylate In the same manner as in Example 1-a), 0.79 g of 4-nitrobenzyl(5R,6S)-2-(7-acetylimidazo[5,1-b]thiazol-2-yl)-6-((1R)-1-hydroxyethyl)-1-carbapen-2-em-3-carboxylate was obtained from 2.68 g of 4-nitrobenzyl(3R,5R,6S)-6-((1R)-1-hydroxyethyl)-2-oxo-1-carbapenam-3-carboxylate and 3.86 g of 7-acetyl-2-(tri-n-butylstannyl)imidazo[5,1-b]thiazole.

NMR (CDCl$_3$) δ: 1.37 (3H, t, J=6.4 Hz), 2.61 (3H, s), 3.30–3.42 (3H, m), 4.21 (1H, m), 4.35 (1H, m), 5.35 (1H, d, J=13.5 Hz), 5.54 (1H, d, J=14.1 Hz), 7.68 (2H, d, J=14.1 Hz), 7.71 (2H, d, J=8.8 Hz), 8.05 (1H, s), 8.24 (2H, d, J=8.8 Hz), 8.39 (1H, s)MS (TSP): 497 (M$^+$+H)

b) Sodium(5R,6S)-2-(7-acetylimidazo[5,1-b]thiazol-2-yl)-6-((1R)-1-hydroxyethyl)-1-carbapen-2-em-3-carboxylate In the same manner as in Example 1-b), 157 mg of the title compound was obtained from 368 mg of 4-nitrobenzyl(5R,6S)-2-(7-acetylimidazo[5,1-b]thiazol-2-yl)-6-((1R)-1-hydroxyethyl)-1-carbapen-2-em-3-carboxylate.

NMR (D$_2$O) δ (HOD=4.80 ppm): 1.31 (3H, d, J=6.4 Hz), 2.49 (3H, s), 3.30 (2H, m), 3.51 (1H, dd, J$_1$=5.8 Hz, J$_2$=3.0 Hz), 4.25 (2H, m), 7.85 (1H, s), 8.11 (1H, s)

Example 16

Pivaloyloxymethyl(5R,6S)-2-(7-acetylimidazo[5,1-b]thiazol-2-yl)-6-((1R)-1-hydroxyethyl)-1-methyl-1-carbapen-2-em-3-carboxylate In the same manner as in Example 2, 18.6 mg of the title compound was obtained from 22.0 mg of sodium(5R,6S)-2-(7-acetylimidazo[5,1-b]thiazol-2-yl)-6-((1R)-1-hydroxyethyl)-1-carbapen-2-em-3-carboxylate and 0.014 ml of pivaloyloxymethyl iodide.

NMR (CDCl$_3$) δ: 1.17 (9H, s), 1.31 (3H, d, J=6.3 Hz), 2.55 (3H, S), 3.22–3.32 (3H, m), 4.19–4.31 (2H, m), 5.83 (1H, d, J=5.6 Hz), 5.95 (1H, d, J=5.6 Hz), 7.95 (1H, s), 8.46 (1H, s) MS (TSP): 476 (M$^+$+H)

Example 17

Sodium(5R,6S)-6-((1R)-1-hydroxyethyl)-2-(7-isobutyrylimidazo[5,1-b]thiazol-2-yl)-1-carbapen-2-em-3-carboxylate a) 4-Nitrobenzyl(5R,6S)-6-((1R)-1-hydroxyethyl)-2-(7-isobutyrylimidazo[5,1-b]thiazol-2-yl)-1-carbapen-2-em-3-carboxylate In the same manner as in Example 1-a), 360 mg of 4-nitrobenzyl(5R,6S)-6-((1R)-1-hydroxyethyl)-2-(7-isobutyrylimidazo[5,1-b]thiazol-2-yl)-1-carbapen-2-em-3-carboxylate was obtained from 350 mg of 4-nitrobenzyl(3R,5R,6S)-6-((1R)-1-hydroxyethyl)-2-oxo-1-carbapenam-3-carboxylate and 450 mg of 7-isobutyryl-2-(tri-n-butylstannyl)imidazo[5,1-b]thiazole.

NMR (CDCl$_3$) δ: 1.21 (6H, d, J=6.9 Hz), 1.36 (3H, d, J=6.2 Hz), 3.35 (3H, m), 3.64 (1H, m), 4.32 (2H, m), 5.23 (1H, d, J=13.8 Hz), 5.45 (1H, d, J=13.8 Hz), 7.60 (2H, d, J=8.8 Hz), 7.98 (1H, s), 8.11 (2H, d, J=8.8 Hz), 8.2 5 (1H, s)

b) Sodium(5R,6S)-6-((1R)-1-hydroxyethyl)-2-(7-isobutyrylimidazo[5,1-b]thiazol-2-yl)-1-carbapen-2-em-3-carboxylate The title compound (178 mg) was obtained from 350 mg of 4-nitrobenzyl(5R,6S)-6-((1R)-1-hydroxyethyl)-2-(7-isobutyrylimidazo[5,1-b]thiazol-2-yl)-1-carbapen-2-em-3-carboxylate in the same manner as in Example 1-b), except that the purification was carried out by column chromatography on Diaion HP-20 (10% aqueous methanol) and Cosmosil 40C18-PREP (10% aqueous acetonitrile).

NMR (D$_2$O) δ (HOD=4.80 ppm): 1.16 (6H, m), 1.31 (3H, d, J=6.5 Hz), 3.24 (2H, m), 3.42 (2H, m), 4.25 (2H, m), 7.75 (1H, s), 8.01 (1H, s)

Example 18

Pivaloyloxymethyl(5R,6S)-6-((1R)-1-hydroxyethyl) 2-(7-isobutyrylimidazo[5,1-b]thiazol-2-yl)-1-carbapen-2-em-3-carboxylate In the same manner as in Example 2, the title compound (60.8 mg) was obtained from 62 mg of sodium(5R,6S)-6-((1R)-1-hydroxyethyl)-2-(7-isobutyrylimidazo[5,1-b]thiazol-2-yl)-1-carbapen-2-em-3-carboxylate.

NMR (CDCl$_3$) δ: 1.22 (9H, s), 1.26 (6H, d, J=6.9 Hz), 1.37 (3H, d, J=6.3 Hz), 3.34 (3H, m), 3.70 (1H, m), 4.31 (2H, m), 5.89 (1H, d, J=5.6 Hz), 6.01 (1H, d, J=5.6 Hz), 8.04 (1H, s), 8.54 (1H, s)

Example 19

Sodium(1S,5R,6S)-2-(7-acetyl-5-methylimidazo[5,1-b]thiazol-2-yl)-6-((1R)-1-hydroxyethyl)-1-methyl-1-carbapen-2-em-3-carboxylate a) 4-Nitrobenzyl(1S,5R,6S)-2-(7-acetyl-5-methylimidazo[5,1-b]thiazol-2-yl)-6-((1R)-1-hydroxyethyl)-1-methyl-1-carbapen-2-em-3-carboxylate In the same manner as in Example 1-a), 301 mg of 4-nitrobenzyl(1S,5R,6S)-2-(7-acetyl-5-methylimidazo[5,1- b]thiazol-2-yl)-6-((1R)-1-hydroxyethyl)-1-methyl-1-carbapen-2-em-3-carboxylate was obtained from 455 mg of 4-nitrobenzyl(1R,3R,5R,6S)-6-((1R)-1-hydroxyethyl)-1-methyl-2-oxo-1-carbapenam-3-carboxylate and 707 mg of 7-acetyl-5-methyl-2-(tri-n-butylstannyl)imidazo[5,1-b]thiazole.

NMR (CDCl$_3$) δ: 1.30 (3H, d, J=7.4 Hz), 1.40 (3H, d, J=6.2 Hz), 2.58 (3H, s), 2.66 (3H, s), 3.38 (1H, dd, J$_1$=6.5 Hz, J$_2$=2.9 Hz), 3.51 (1H, m), 4.32 (1H, m), 4.40 (1H, dd, J$_1$=9.5 Hz, J$_2$=2.9 Hz), 5.28 (1H, d, J=13.5 Hz), 5.54 (1H, d, J=13.5 Hz), 7.68 (2H, d, J=8.8 Hz), 8.24 (2H, d, J=8.8 Hz), 8.38 (1H, s)

b) Sodium(1S,5R,6S)-2-(7-acetyl-5-methylimidazo[5,1-b]thiazol-2-yl)-6-((1R)-1-hydroxyethyl)-1-methyl-1-carbapen-2-em-3-carboxylate In the same manner as in Example 1-b), the title compound (109 mg) was obtained from 155 mg of 4-nitrobenzyl (1S,5R,6S)-2-(7-acetyl-5-methylimidazo[5,1-b]thiazol-2-yl)-6-((1R)-1-hydroxyethyl)-1-methyl-1-carbapen-2-em-3-carboxylate.

NMR (D$_2$O) δ (HOD=4.80 ppm): 1.17 (3H, d, J=7.1 Hz), 1.33 (3H, d, J=6.3 Hz), 2.38 (3H, s), 2.46 (3H, s), 3.46 (1H, m), 3.54 (1H, m), 4.29 (2H, m), 7.69 (1H, s)

Example 20

Pivaloyloxymethyl(1S,5R,6S)-2-(7-acetyl-5-methylimidazo[5,1-b]thiazol-2-yl)-6-((1R)-1-hydroxyethyl)-1-methyl-1-carbapen-2-em-3-carboxylate In the same manner as in Example 2, the title compound (37.2 mg) was obtained from 49.1 mg of sodium (1S,5R,6S)-2-(7-acetyl-5-methylimidazo[5,1-b]thiazol-2-yl)-6-((1R)-1-hydroxyethyl)-1-methyl-1-carbapen-2-em-3-carboxylate.

NMR (CDCl$_3$) δ: 1.20 (9H, s), 1.28 (3H, d, J=7.1 Hz), 1.37 (3H, d, J=6.3 Hz), 2.58 (3H, s), 2.70 (3H, s), 3.35 (1H, dd, J$_1$=6.6 Hz, J$_2$=2.8 Hz), 3.49 (1H, m), 4.29 (1H, m), 4.38 (1H, dd, J$_1$=9.8 Hz, J$_2$=2.8 Hz), 5.86 (1H, d, J=5.6 Hz), 6.00 (1H, d, J=5.6 Hz), 8.35 (1H, s)

Example 21

Sodium(1S,5R,6S)-2-(7-acetyl-3-methylimidazo[5,1-b]thiazol-2-yl)-6-((1R)-1-hydroxyethyl)-1-methyl-1-carbapen-2-em-3-carboxylate a) 4-Nitrobenzyl(1S,5R,6S)-2-(7-acetyl-3-methylimidazo[5,1-b]thiazol-2-yl)-6-((1R)-1-hydroxy-ethyl)-1-methyl-1-carbapen-2-em-3-carboxylate In the same manner as in Example 1-a), 237 mg of 4-nitrobenzyl(1S,5R,6S)-2-(7-acetyl-3-methylimidazo[5,1-b]thiazol-2-yl)-6-((1R)-1-hydroxyethyl)-1-methyl-1-carbapen-2-em-3-carboxylate was obtained from 343 mg of 4-nitrobenzyl(1R,3R,5R,6S)-6-((1R)-1-hydroxyethyl)-1-methyl-2-oxo-1-carbapenam-3-carboxylate and 533 mg of 7-acetyl-3-methyl-2-(tri-n-butylstannyl)imidazo[5,1-b]thiazole.

NMR (CDCl$_3$) δ: 1.19 (3H, d, J=7.2 Hz), 1.39 (3H, d, J=6.3 Hz), 2.28 (3H, s), 2.62 (3H, s), 3.44 (2H, m), 4.33 (1H, m), 4.48 (1H, dd, J$_1$=10.2 Hz, J$_2$=3.2 Hz), 5.20 (1H, d, J=13.5 Hz), 5.40 (1H, d, J=13.5 Hz), 7.53 (2H, d, J=8.9 Hz), 7.82 (1H, s), 8.16 (2H, d, J=8.9 Hz)

b) Sodium(1S,5R,6S)-2-(7-acetyl-3-methylimidazo[5,1-b]thiazol-2-yl)-6-((1R)-1-hydroxyethyl)-1-methyl-1-carbapen-2-em-3-carboxylate In the same manner as in Example 1-b), 130 mg of the title compound was obtained from 237 mg of 4-nitrobenzyl(1S,5R,6S)-2-(7-acetyl-3-methylimidazo[5,1-b]thiazol-2-yl)-6-((1R)-1-hydroxyethyl)-1-methyl-1-carbapen-2-em-3-carboxylate.

NMR (D$_2$O) δ (HOD=4.80 ppm): 1.16 (3H, d, J=7.1 Hz), 1.30 (3H, d, J=6.3 Hz), 2.37 (3H, s), 2.53 (3H, s), 3.37 (1H, m), 3.56 (1H, dd, J$_1$=5.8 Hz, J$_2$=2.9 Hz), 4.28 (1H, m), 4.37 (1H, dd, J$_1$=9.4 Hz, J$_2$=2.9 Hz), 8.20 (1H, s)

Example 22

Pivaloyloxymethyl(1S,5R,6S)-2-(7-acetyl-3-methylimidazo[5,1-b]thiazol-2-yl)-6-((1R)-1-hydroxy-ethyl)-1-methyl-1-carbapen-2-em-3-carboxylate In the same manner as in Example 2, the title compound (41.2 mg) was obtained from 48.4 mg of sodium (1S,5R,6S)-2-(7-acetyl-3-methylimidazo[5,1-b]thiazol-2-yl)-6-((1R)-1-hydroxyethyl)-1-methyl-1-carbapen-2-em-3-carboxylate.

NMR (CDCl$_3$) δ: 1.08 (9H, s), 1.18 (3H, d, J=7.4 Hz), 1.37 (3H, d, J=6.3 Hz), 2.39 (3H, s), 2.61 (3H, s), 3.42 (2H, m), 4.30 (1H, m), 4.46 (1H, dd, J$_1$=10.1 Hz, J$_2$=3.0 Hz), 5.73 (1H, d, J=5.5 Hz), 5.88 (1H, d, J=5.5 Hz), 7.93 (1H, s)

Example 23

Sodium(5R,6S)-6-((1R)-1-hydroxyethyl)-2-(7-methanesulfonylimidazo[5,1-b]thiazol-2-yl)-1-carbapen-2-em-3-carboxylate a) 4-Nitrobenzyl(5R,6S)-6-((1R)-1-hydroxyethyl)-2-(7-methanesulfonylimidazo[5,1-b]thiazol-2-yl)-1-carbapen-2-em-3-carboxylate In substantially the same manner as in Example 1-a), 453 mg of 4-nitrobenzyl(5R,6S)-6-((1R)-1-hydroxyethyl)-2-(7-methanesulfonylimidazo[5,1-b]thiazol-2-yl)-1-carbapen-2-em-3-carboxylate was obtained from 209 mg of 4-nitrobenzyl(3R,5R,6S)-6-((1R)-1-hydroxyethyl)-2-oxo-1-carbapenam-3-carboxylate and 251 mg of 7-methanesulfonyl-2-(tri-n-butylstannyl)imidazo[5,1-b]thiazole.

NMR (CDCl$_3$) δ: 1.36 (3H, d, J=6.3 Hz), 3.22 (3H, s), 3.32 (2H, dd, J$_1$=7.0 Hz, J$_2$=3.1 Hz), 3.36–3.40 (1H, m), 4.20–4.28 (1H, m), 4.30–4.38 (1H, m), 5.34 (1H, d, J=13.5 Hz), 5.52 (1H, d, J=13.5 Hz), 7.70 (2H, d, J=8.9 Hz), 8.13 (1H, s), 8.26 (2H, d, J=8.9 Hz), 8.30 (1H, s)

b) Sodium(5R,6S)-6-((1R)-1-hydroxyethyl)-2-(7-methanesulfonylimidazo[5,1-b]thiazol-2-yl)-1-carbapen-2-em-3-carboxylate The title compound (69.7 mg) was obtained from 282 mg of 4-nitrobenzyl(5R,6S)-6-((1R)-1-hydroxyethyl)-2-(7-methanesulfonylimidazo[5,1-b]thiazol-2-yl)-1-carbapen-2-em-3-carboxylate in substantially the same manner as in Example 1-b), except that the purification was carried out using Cosmosil 40C18-PREP (5% aqueous methanol).

NMR (D$_2$O) δ (HOD=4.80 ppm): 1.30 (3H, d, J=6.3 Hz), 3.29 (3H, s), 3.29–3.36 (2H, m), 3.50–3.55 (1H, m), 4.25–4.35 (2H, m), 7.90 (1H, s), 8.25 (1H, s)

Example 24

Sodium(5R,6S)-6-((1R)-1-hydroxyethyl)-2-(7-methanesulfonylimidazo[5,1-b]thiazol-3-yl)-1-carbapen-2-em-3-carboxylate a) 4-Nitrobenzyl(5R,6S)-6-((1R)-1-hydroxyethyl)-2-(7-methanesulfonylimidazo[5,1-b]thiazol-3-yl)-1-carbapen-2-em-3-carboxylate In substantially the same manner as in Example 1-a), 84 mg of 4-nitrobenzyl(5R,6S)-6-((1R)-1-hydroxyethyl)-2-(7- methanesulfonylimidazo[5,1-b]thiazol-3-yl)-1-carbapen-2-em-3-carboxylate was obtained from 87 mg of 4-nitrobenzyl (3R,5R,6S)-6-((1R)-1-hydroxyethyl)-2-oxo-1-carbapenam-3-carboxylate and 110 mg of 7-methanesulfonyl-3-(tri-n-butylstannyl)imidazo[5,1-b]thiazole.

NMR (CDCl$_3$) δ: 1.40 (3H, d, J=6.3 Hz), 3.20 (3H, s), 3.35–3.45 (3H, m), 4.25–4.33 (1H, m), 4.45–4.52 (1H, m), 5.22 (1H, d, J=13.5 Hz), 5.38 (1H, d, J=13.5 Hz), 7.20 (1H, s), 7.54 (2H, d, J=8.8 Hz), 7.80 (1H, s), 8.20 (2H, d, J=8.8 Hz)

b) Sodium(5R,6S)-6-((1R)-1-hydroxyethyl)-2-(7-methanesulfonylimidazo[5,1-b]thiazol-3-yl)-1-carbapen-2-em-3-carboxylate The title compound (30.1 mg) was obtained in substantially the same manner as in Example 1-b) from 84 mg of 4-nitrobenzyl(5R,6S)-6-((1R)-1-hydroxyethyl)-2-(7-methanesulfonylimidazo[5,1-b]thiazol-3-yl)-1-carbapen-2-em-3-carboxylate, except that the purification was carried out using Cosmosil 40C18-PREP (5% aqueous methanol).

NMR (D$_2$O) δ (HOD=4.80 ppm): 1.30 (3H, d, J=6.3 Hz), 3.22 (1H, dd, J$_1$=17.3 Hz, J$_2$=9.7 Hz), 3.30 (3H, s), 3.48 (1H, dd, J$_1$=17.3 Hz, J$_2$=8.2 Hz), 3.59–3.62 (1H, m), 4.23–4.30 (1H, m), 4.35–4.43 (1H, m), 7.25 (1H, s), 8.05 (1H, s)

Example 25

Sodium(1S,5R,6S)-6-((1R)-1-hydroxyethyl)-2-(7-methanesulfonylimidazo[5,1-b]thiazol-3-yl)-1-methyl-1-carbapen-2-em-3-carboxylate a) 4-Nitrobenzyl(1S,5R,6S)-6-((1R)-1-hydroxyethyl)-1-methyl-2-(7-methylthioimidazo[5,1-b]-thiazol-3-yl)-1-carbapen-2-em-3-carboxylate In substantially the same manner as in Example 1-a), 817 mg of 4-nitrobenzyl(1S,5R,6S)-6-((1R)-1-hydroxyethyl)-1-methyl-2-(7-methylthioimidazo[5,1-b]-thiazol-3-yl)-1-carbapen-2-em-3-carboxylate was obtained from 797 mg of 4-nitrobenzyl(1R,3R,5R,6S)-6-((1R)-1-hydroxyethyl)-1-methyl-2-oxo-1-carbapenam-3-carboxylate and 919 mg of 7-methylthio-3-(tri-n-butylstannyl)imidazo[5,1-b]thiazole.

NMR (DMSO-d$_6$) δ: 1.06 (3H, d, J=7.2 Hz), 1.17 (3H, d, J=6.3 Hz), 3.32 (3H, s), 3.53–3.57 (1H, m), 3.63–3.70 (1H, m), 4.00–4.08 (1H, m), 4.41 (1H, dd, J$_1$=10.3 Hz, J$_2$=3.1 Hz), 5.20 (1H, d, J=13.5 Hz), 5.30 (1H, d, J=13.5 Hz), 7.40 (1H, s), 7.45 (2H, d, J=8.3 Hz), 8.15 (2H, d, J=8.3 Hz), 8.19 (1H, s)

b) 4-Nitrobenzyl(1S,5R,6S)-6-((1R)-1-hydroxyethyl)-2-(7-methanesulfonylimidazo[5,1-b]thiazol-3-yl)-1-methyl-1-carbapen-2-em-3-carboxylate OXONE (manufactured by Du Pont (E.I.) de Nemours & Co.) (123 mg) was added under ice cooling to a solution of 51.4 mg of 4-nitrobenzyl(1S,5R,6S)-6-((1R)-1-hydroxyethyl)-1-methyl-2-(7-methylthioimidazo[5,1-b]thiazol-2-yl)-1-carbapen-2-em-3-carboxylate in a mixture of 0.5 ml of THF with 0.5 ml of water, followed by stirring at the same temperature for 40 min. Thereafter, a saturated aqueous sodium hydrogencarbonate solution was added thereto, and the mixture was extracted with dichloromethane. The organic layer was dried over anhydrous magnesium sulfate. The solvent was removed by distillation. The residue was purified by column chromatography on silica gel (dichloromethane:methanol=20:1) to give 23.5 mg of 4-nitrobenzyl(1S,5R,6S)-6-((1R)-1-hydroxyethyl)-2-(7-methanesulfonylimidazo[5,1-b]thiazol-3-yl)-1-methyl-1-carbapen-2-em-3-carboxylate.

NMR (CDCl$_3$) δ: 1.20 (3H, d, J=7.3 Hz), 1.39 (3H, d, J=6.3 Hz), 3.20 (3H, s), 3.50 (1H, dd, J$_1$=6.0 Hz, J$_2$=3.2 Hz), 3.58–3.68 (1H, m), 4.30–4.40 (1H, m), 4.56 (1H, dd, J$_1$=10.7 Hz, J$_2$=3.2 Hz), 5.18 (1H, d, J=13.5 Hz), 5.37 (1H, d, J=13.5 HZ), 7.13 (1H, s), 7.49 (2H, d, J=8.6 Hz), 7.82 (1H, s), 8.20 (2H, d, J=8.6 Hz)

c) Sodium(1S,5R,6S)-6-((1R)-1-hydroxyethyl)-2-(7-methanesulfonylimidazo[5,1-b]thiazol-3-yl)-1-methyl-1-carbapen-2-em-3-carboxylate The title compound (29.8 mg) was obtained from 62.4 mg of 4-nitrobenzyl(1S,5R,6S)-6-((1R)-1-hydroxyethyl)-2-(7-methanesulfonylimidazo[5,1-b]thiazol-3-yl)-1-methyl-1-carbapen-2-em-3-carboxylate in substantially the same manner as in Example 1-b), except that the purification was carried out using Cosmosil 40C18-PREP (5% aqueous methanol).

NMR (D$_2$O) δ (HOD=4.80 ppm): 1.15 (3H, d, J=7.0 Hz), 1.31 (3H, d, J=6.3 Hz), 3.31 (3H, s), 3.51–3.65 (2H, m), 4.25–4.35 (1H, m), 4.43 (1H, d, J=10.4 Hz), 7.30 (1H, s), 8.16 (1H, s)

Example 26

Sodium(1S,5R,6S)-6-((1R)-1-hydroxyethyl)-2-(7-methanesulfinylimidazo[5,1-b]thiazol-2-yl)-1-methyl-1-carbapen-2-em-3-carboxylate (A Mixture of Diastereomers)

a) 4-Nitrobenzyl(1S,5R,6S)-6-((1R)-1-hydroxyethyl)-1-methyl-2-(7-methylthioimidazo[5,1-b]-thiazol-2-yl)-1-carbapen-2-em-3-carboxylate In substantially the same manner as in Example 1-a), 453 mg of 4-nitrobenzyl(1S,5R,6S)-6-((1R)-1-hydroxyethyl)-1-methyl-2-(7-methylthioimidazo[5,1-b]-thiazol-2-yl)-1-carbapen-2-em-3-carboxylate was obtained from 399 mg of 4-nitrobenzyl(1R,3R,5R,6S)-6-((1R)-1-hydroxyethyl)-1-methyl-2-oxo-1-carbapenam-3-carboxylate and 442 mg of 7-methylthio-2-(tri-n-butylstannyl)imidazo[5,1-b]thiazole.

NMR (CDCl$_3$) δ: 1.30 (3H, d, J=7.4 Hz), 1.40 (3H, d, J=6.3 Hz), 2.42 (3H, s), 3.36 (1H, dd, J$_1$=6.3 Hz, J$_2$=2.5 Hz), 3.40–3.50 (1H, m), 4.29–4.35 (1H, m), 4.38 (1H, dd, J$_1$=9.4 Hz, J$_2$=2.8 Hz), 5.27 (1H, d, J=13.5 Hz), 5.52 (1H, d, J=13.5 Hz), 7.68 (2H, d, J=8.5 Hz), 8.07 (1H, s), 8.23 (2H, d, J=8.5 Hz), 8.44 (1H, s)

b) 4-Nitrobenzyl(1S,5R,6S)-6-((1R)-1-hydroxyethyl)-2-(7-methanesulfinylimidazo[5,1-b]thiazol-2-yl)-1-methyl-1-carbapen-2-em-3-carboxylate (A Mixture of Diastereomers)

In the same manner as in Example 25-b), 61 mg of 4-nitrobenzyl(1S,5R,6S)-6-((1R)-1-hydroxyethyl)-2-(7-methanesulfinylimidazo[5,1-b]thiazol-2-yl)-1-methyl-1-carbapen-2-em-3-carboxylate (a mixture of diastereomers) was obtained using 190 mg of 4-nitrobenzyl(1S,5R,6S)-6-((1R)-1-hydroxyethyl)-1-methyl-2-(7-methylthioimidazo-[5,1-b]thiazol-2-yl)-1-carbapen-2-em-3-carboxylate and 227 mg of OXONE (manufactured by Du Pont (E.I.) de Nemours & Co.)

NMR (CDCl$_3$) δ: 1.28, 1.29 (3H, d, J=7.4 Hz), 1.39 (3H, d, J=6.3 Hz), 3.35–3.39 (1H, m), 3.40–3.50 (1H, m), 4.25–4.35 (1H, m), 4.38–4.40 (1H, m), 5.27 (1H, d, J=13.5 Hz), 5.52 (1H, d, J=13.5 Hz), 7.68 (2H, d, J=8.5 Hz), 8.07 (1H, s), 8.23 (2H, d, J=8.5 Hz), 8.44 (1H, s)

c) Sodium(1S,5R,6S)-6-((1R)-1-hydroxyethyl)-2-(7-methanesulfinylimidazo[5,1-b]thiazol-2-yl)-1-methyl-1-carbapen-2-em-3-carboxylate (A Mixture of Diastereomers))

The title compound (23.8 mg) was obtained from 61 mg of 4-nitrobenzyl(1S,5R,6S)-6-((1R)-1-hydroxyethyl)-2-(7-methanesulfonylimidazo[5,1-b]thiazol-3-yl)-1-methyl-1-carbapen-2-em-3-carboxylate in substantially the same manner as in Example 1-b), except that the purification was carried out using Cosmosil40Cl8-PREP (5% aqueous methanol).

NMR ($D_2O$) δ (HOD=4.80 ppm): 1.21 (3H, d, J=7.2 Hz), 1.31 (3H, d, J=6.3 Hz), 3.06 (3H, d), 3.45–3.60 (2H, m), 7.94, 7.96 (1H, s), 8.21, 8.22 (1H, s)

Example 27

Sodium(5R,6S)-6-((1R)-1-hydroxyethyl)-2-(7-propionylimidazo[5,1-b]thiazol-2-yl)-1-carbapen-2-em-3-carboxylate a) 4-Nitrobenzyl(5R,6S)-6-((1R)-1-hydroxyethyl)-2-(7-propionylimidazo[5,1-b]thiazol-2-yl)-1-carbapen-2-em-3-carboxylate In the same manner as in Example 1-a), 362 mg of 4-nitrobenzyl(5R,6S)-6-((1R)-1-hydroxyethyl)-2-(7-propionylimidazo[5,1-b]thiazol-2-yl)-1-carbapen-2-em-3-carboxylate was obtained from 522 mg of 4-nitrobenzyl(3R,5R,6S)-6-((1R)-1-hydroxyethyl)-2-oxo-1-carbapenam-3-carboxylate and 844 mg of 7-propionyl-2-(tri-n-butylstannyl)imidazo[5,1-b]thiazole.

NMR (DMSO-$d_6$) δ: 1.10 (3H, t, J=7.5 Hz), 1.17 (3H, d, J=6.2 Hz), 2.91 (2H, q, J=7.5 Hz), 3.49 (3H, m), 4.01 (1H, m), 4.26 (1H, m), 5.43 (1H, d, J=13.9 Hz), 5.56 (1H, d, J=13.9 Hz), 7.77 (2H, d, J=8.8 Hz), 8.24 (2H, d, J=8.8 Hz), 8.32 (1H, s), 8.47 (1H, s)

b) Sodium(5R,6S)-6-((1R)-1-hydroxyethyl)-2-(7-propionylimidazo[5,1-b]thiazol-2-yl)-1-carbapen-2-em-3-carboxylate In the same manner as in Example 1-b), 91.2 mg of the title compound was obtained from 162 mg of 4-nitrobenzyl(5R,6S)-6-((1R)-1-hydroxyethyl)-2-(7-propionylimidazo[5,1-b]thiazol-2-yl)-1-carbapen-2-em-3-carboxylate.

NMR ($D_2O$) δ (HOD=4.80 ppm): 1.11 (3H, t, J=6.9 Hz), 1.32 (3H, d, J=6.3 Hz), 2.77 (2H, q, J=6.9 Hz), 3.20 (2H, m), 3.48 (1H, dd, $J_1$=5.7 Hz, $J_2$=2.5 Hz), 4.25 (2H, m), 7.65 (1H, s), 7.93 (1H, s)

Example 28

Pivaloyloxymethyl(5R,6S)-6-((1R)-1-hydroxyethyl)-2-(7-propionylimidazo[5,1-b]thiazol-2-yl)-1-carbapen-2-em-3-carboxylate In the same manner as in Example 2, 28.6 mg of the title compound was obtained from 50.2 mg of sodium(5R,6S)-6-((1R)-1-hydroxyethyl)-2-(7-propionylimidazo[5,1-b]-thiazol-2-yl)-1-carbapen-2-em-3-carboxylate.

NMR (CDCl$_3$) δ: 1.22 (9H, s), 1.26 (3H, t, J=7.4 Hz), 1.38 (3H, d, J=6.3 Hz), 3.06 (2H, q, J=7.4 Hz), 3.32 (3H, m), 4.31 (2H, m), 5.90 (1H, d, J=5.6 Hz), 6.02 (1H, d, J=5.6 Hz), 8.02 (1H, s), 8.55 (1H, s)

Example 29

Pivaloyloxymethyl(5R,6S)-2-(7-acetylimidazo[5,1-b]thiazol-3-yl)-6-((1R)-1-hydroxyethyl)-1-carbapen-2-em-3-carboxylate a) 4-Nitrobenzyl(5R,6S)-2-(7-acetylimidazo[5,1-b]thiazol-3-yl)-6-((1R)-1-hydroxyethyl)-1-carbapen-2-em-3-carboxylate In the same manner as in Example 1-a), 312 mg of 4-nitrobenzyl(5R,6S)-2-(7-acetylimidazo[5,1-b]thiazol-3-yl)-6-((1R)-1-hydroxyethyl)-1-carbapen-2-em-3-carboxylate was obtained from 396 mg of 4-nitrobenzyl(3R,5R,6S)-6-((1R)-1-hydroxyethyl)-2-oxo-1-carbapenam-3-carboxylate and 621 mg of 7-acetyl-3-(tri-n-butylstannyl)imidazo[5,1-b]thiazole.

NMR (CDCl$_3$) δ: 1.40 (3H, d, J=6.3 Hz), 2.58 (3H, s), 3.42 (3H, m), 4.33 (1H, m), 4.48 (1H, m), 5.20 (1H, d, J=13.5 Hz), 5.37 (1H, d, J=13.5 Hz), 7.22 (1H, s), 7.47 (2H, d, J=8.6 Hz), 7.67 (1H, s), 8.17 (2H, d, J=8.6 Hz)

b) Sodium(5R,6S)-2-(7-acetylimidazo[5,1-b]thiazol-3-yl)-6-((1R)-1-hydroxyethyl)-1-carbapen-2-em-3-carboxylate In the same manner as in Example 1-b), 109 mg of sodium (5R,6S)-2-(7-acetylimidazo[5,1-b]thiazol-3-yl)-6-((1R)-1-hydroxyethyl)-1-carbapen-2-em-3-carboxylate was obtained from 216 mg of 4-nitrobenzyl(5R,6S)-2-(7-acetylimidazo[5,1-b]thiazol-3-yl)-6-((1R)-1-hydroxyethyl)-1-carbapen-2-em-3-carboxylate.

NMR ($D_2O$) δ (HOD=4.80 ppm): 1.32 (3H, t, J=6.3 Hz), 2.50 (3H, s), 3.23 (1H, dd, $J_1$=17.1 Hz, $J_2$=9.9 Hz), 3.48 (1H, dd, $J_1$=17.1 Hz, $J_2$=8.5 Hz), 3.60 (1H, dd, $J_1$=5.8 Hz, $J_2$=2.7 Hz), 4.28 (1H, m), 4.41 (1H, m), 7.27 (1H, s), 7.83 (1H, s)

c) Pivaloyloxymethyl(5R,6S)-2-(7-acetylimidazo[5,1-b]thiazol-3-yl)-6-((1R)-1-hydroxyethyl)-1-carbapen-2-em-3-carboxylate In the same manner as in Example 2, 61.3 mg of the title compound was obtained from 69.4 mg of sodium((5R,6S)-2-(7-acetylimidazo[5,1-b]thiazol-3-yl)-6-((1R)-1-hydroxyethyl)-1-carbapen-2-em-3-carboxylate.

NMR (CDCl$_3$) δ: 1.19 (9H, s), 1.39 (3H, d, J=6.2 Hz), 2.61 (3H, s), 3.37 (3H, m), 4.30 (1H, m), 4.44 (1H, m), 5.77 (1H, d, J=5.6 Hz), 5.89 (1H, d, J=5.6 Hz), 7.26 (1H, s), 7.73 (1H, s)

Example 30

Sodium(1S,5R,6S)-2-(7-ethanesulfonylimidazo[5,1-b]thiazol-2-yl)-6-((1R)-1-hydroxyethyl)-1-methyl-1-carbapen-2-em-3-carboxylate a) 4-Nitrobenzyl(1S,5R,6S)-2-(7-ethanesulfonylimidazo[5,1-b]thiazol-2-yl)-6-((1R)-1-hydroxyethyl)-1-methyl-1-carbapen-2-em-3-carboxylate In the same manner as in Example 1-a), 765 mg of 4-nitrobenzyl(1S,5R,6S)-2-(7-ethanesulfonylimidazo[5,1-b]thiazol-2-yl)-6-((1R)-1-hydroxyethyl)-1-methyl-1-carbapen-2-em-3-carboxylate was obtained from 262 mg of 4-nitrobenzyl(1R,3R,5R,6S)-6-((1R)-1-hydroxyethyl)-1-methyl-2-oxo-1-carbapenam-3-carboxylate and 413 mg of 7-ethanesulfonyl-2-(tri-n-butylstannyl)imidazo[5,1-b]-thiazole.

NMR (CDCl$_3$) δ: 1.31 (3H, t, J=7.4 Hz), 1.34 (3H, d, J=7.4 Hz), 1.39 (3H, d, J=6.3 Hz), 3.31 (2H, q, J=7.4 Hz), 3.38 (1H, dd, $J_1$=6.6 Hz, $J_2$=2.7 Hz), 3.50 (1H, m), 4.31 (1H, m), 4.40 (1H, dd, $J_1$=9.6 Hz, $J_2$=2.7 Hz), 5.27 (1H, d, J=13.7 Hz), 5.51 (1H, d, J=13.7 Hz), 7.67 (2H, d, J=8.8 Hz), 8.08 (1H, s), 8.22 (2H, d, J=8.8 Hz), 8.42 (1H, s)

b) Sodium(1S,5R,6S)-2-(7-ethanesulfonylimidazo[5,1-b]thiazol-2-yl)-6-((1R)-1-hydroxyethyl)-1-methyl-1-carbapen-2-em-3-carboxylate In the same manner as in Example 1-b), 139 mg of the title compound was obtained from 232 mg of 4-nitrobenzyl(1S, 5R,6S)-2-(7-ethanesulfonylimidazo[5,1-b]thiazol-2-yl)-6-((1R)-1-hydroxyethyl)-1-methyl-1-carbapen-2-em-3-carboxylate.

NMR (D$_2$O) δ (HOD=4.80 ppm): 1.22 (3H, t, J=7.4 Hz), 1.25 (3H, d, J=7.4 Hz), 1.31 (3H, d, J=6.3 Hz), 3.37 (2H, q, J=7.4 Hz), 3.48 (1H, m), 3.56 (1H, m), 4.23–4.30 (2H, m), 7.97 (1H, s), 8.19 (1H, s)

Example 31

Sodium(1S,5R,6S)-6-((1R)-1-hydroxyethyl)-1-methyl-2-(7-N-methylsulfamoylimidazo[5,1-b]thiazol-2-yl)-1-carbapen-2-em-3-carboxylate a) 4-Nitrobenzyl(1S,5R,6S)-6-((1R)-1-hydroxyethyl)-1-methyl-2-(7-N-methylsulfamoylimidazo[5,1-b]thiazol-2-yl)-1-carbapen-2-em-3-carboxylate In substantially the same manner as in Example 1-a), 307 mg of 4-nitrobenzyl(1S,5R,6S)-6-((1R)-1-hydroxyethyl)-1-methyl-2-(7-N-methylsulfamoylimidazo[5,1-b]thiazol-2-yl)-1-carbapen-2-em-3-carboxylate was obtained from 362 mg of 4-nitrobenzyl(1R,3R,5R,6S)-6-((1R)-1-hydroxyethyl)-1-methyl-2-oxo-1-carbapenam-3-carboxylate and 327 mg of 7-N-methylsulfamoyl-2-(tri-n-butylstannyl)imidazo[5,1-b]thiazole.

NMR (DMSO-d$_6$) δ: 1.18 (3H, d, J=6.1 Hz), 1.22 (3H, d, J=7.2 Hz), 2.43 (3H, d, J=5.1 Hz), 3.42 (1H, dd, J$_1$=5.7 Hz, J$_2$=2.8 Hz), 3.70–3.76 (1H, m), 4.00–4.06 (1H, m), 4.43 (1H, dd, J$_1$=9.9 Hz, J$_2$=2.8 Hz), 5.16 (1H, d, J=5.0 Hz), 5.39 (1H, d, J=13.6 Hz), 5.53 (1H, d, J=13.6 Hz), 7.50 (1H, q, J=5.1 Hz), 7.73 (2H, d, J=8.5 Hz), 8.22 (2H, d, J=8.5 Hz), 8.38 (1H, s), 8.53 (1H, s)

b) Sodium(1S,5R,6S)-6-((1R)-1-hydroxyethyl)-1-methyl-2-(7-N-methylsulfamoylimidazo[5,1-b]thiazol-2-yl,)-1-carbapen-2-em-3-carboxylate In substantially the same manner as in Example 1-b), the title compound (182 mg) was obtained from 307 mg of 4-nitrobenzyl(1S,5R,6S)-6-((1R)-1-hydroxyethyl)-1-methyl-2-(7-N-methylsulfamoylimidazo[5,1-b]thiazol-2-yl)-1-carbapen-2-em-3-carboxylate, except that the purification was carried out using Cosmosil 40C18-PREP (5% aqueous methanol).

NMR (D$_2$O) δ (HOD=4.80 Hz): 1.26 (3H, d, J=7.4 Hz), 1.32 (3H, d, J=6.3 Hz), 2.60 (3H, s), 3.52–3.56 (1H, m), 3.60–3.70 (1H, m), 4.25–4.35 (2H, m), 8.05 (1H, s), 8.26 (1H, s)

Example 32

Sodium(5R,6S)-6-((1R)-1-hydroxyethyl)-2-(7-N-methylsulfamoylimidazo[5,1-b]thiazol-2-yl)-1-carbapen-2-em-3-carboxylate a) 4-Nitrobenzyl(5R,6S)-6-((1R)-1-hydroxyethyl)-2-(7-N-methylsulfamoylimidazo[5,1-b]thiazol-2-yl)-1-carbapen-2-em-3-carboxylate In substantially the same manner as in Example 1-a), 104 mg of 4-nitrobenzyl(5R,6S)-6-((1R)-1-hydroxyethyl)-2-(7-N-methylsulfamoylimidazo[5,1-b]thiazol-2-yl)-1-carbapen-2-em-3-carboxylate was obtained from 139 mg of 4-nitrobenzyl(3R,5R,6S)-6-((1R)-1-hydroxyethyl)-2-oxo-1-carbapenam-3-carboxylate and 164 mg of 7-N-methylsulfamoyl-2-(tri-n-butylstannyl)imidazo[5,1-b]-thiazole.

NMR (DMSO-d$_6$) δ: 1.16 (3H, d, J=6.3 Hz), 2.41 (3H, d, J=4.9 Hz), 3.43–3.55(3H, m), 3.96–4.05 (1H, m), 4.20–4.30 (1H, m), 5.18 (1H, d, J=13.8 Hz), 5.56 (1H, d, J=13.8 Hz), 7.51 (1H, q, J=4.9 Hz), 7.76 (2H, d, J=8.4 Hz), 8.25 (2H, d, J=8.4 Hz), 8.39 (1H, s), 8.44 (1H, s)

b) Sodium(5R,6S)-6-((1R)-1-hydroxyethyl)-2-(7-N-methylsulfamoylimidazo[5,1-b]thiazol-2-yl)-1-carbapen-2-em-3-carboxylate The title compound (54.3 mg) was obtained from 100 mg of 4-nitrobenzyl(5R,6S)-6-((1R)-1-hydroxyethyl)-2-(7-N-methylsulfamoylimidazo[5,1-b]thiazol-2-yl)-1-carbapen-2-em-3-carboxylate in substantially the same manner as in Example 1-b), except that the purification was carried out using Cosmosil 40C18-PREP (5% aqueous methanol).

NMR (D$_2$O) δ (HOD=4.80 ppm): 1.30 (3H, d, J=6.3 Hz), 2.50 (3H, s), 3.30–3.40 (2H, m), 3.51–3.55 (1H, m), 4.23–4.35 (2H, m), 7.90 (1H, s), 8.24 (1H, s)

Example 33

Sodium(5R,6S)-2-(7-acetyl-5-methylimidazo[5,1-b]thiazol-2-yl)-6-((1R)-1-hydroxyethyl)-1-carbapen-2-em-3-carboxylate a) 4-Nitrobenzyl(5R,6S)-2-(7-acetyl-5-methylimidazo[5,1-b]thiazol-2-yl)-6-((1R)-1-hydroxy-ethyl)-1-carbapen-2-em-3-carboxylate In the same manner as in Example 1-a), 380 mg of 4-nitrobenzyl(5R,6S)-2-(7-acetyl-5-methylimidazo[5,1-b]thiazol-2-yl)-6-((1R)-1-hydroxyethyl)-1-carbapen-2-em-3-carboxylate was obtained from 480 mg of 4-nitrobenzyl(3R,5R,6S)-6-((1R)-1-hydroxyethyl)-2-oxo-1-carbapenam-3-carboxylate and 776 mg of 7-acetyl-5-methyl-2-(tri-n-butylstannyl)imidazo[5,1-b]thiazole.

NMR (CDCl$_3$) δ: 1.40 (3H, d, J=6.3 Hz), 2.58 (3H, s), 2.66 (3H, m), 3.36 (3H, m), 4.35 (2H, m), 5.32 (1H, d, J=13.3 Hz), 5.56 (1H, d, J=13.3 Hz), 7.70 (2H, d, J=8.9 Hz), 8.25 (2H, d, J=8.9 Hz), 8.30 (1H, s)

b) Sodium(5R,6S)-2-(7-acetyl-5-methylimidazo[5,1-b]thiazol-2-yl)-6-((1R)-1-hydroxyethyl)-1-carbapen-2-em-3-carboxylate In the same manner as in Example 1-b), 110 mg of the title compound was obtained from 173 mg of 4-nitrobenzyl(5R,6S)-2-(7-acetyl-5-methylimidazo[5,1-b]thiazol-2-yl)-6-((1R)-1-hydroxyethyl)-1-carbapen-2-em-3-carboxylate.

NMR (D$_2$O) δ (HOD=4.80 ppm): 1.32 (3H, t, J=6.3 Hz), 2.35 (3H, s), 2.36 (3H, s), 3.11 (2H, m), 3.48 (1H, dd, J$_1$=5.3 Hz, J$_2$=2.6 Hz), 4.23 (2H, m), 7.40 (1H, s)

Example 34

Sodium(5R,6S)-2-(7-ethanesulfonylimidazo[5,1-b]thiazol-2-yl)-6-((1R)-1-hydroxyethyl)-1-carbapen-2-em-3-carboxylate a) 4-Nitrobenzyl(5R,6S)-2-(7-ethanesulfonylimidazo[5,1-b]thiazol-2-yl)-6-((1R)-1-hydroxyethyl)-1-carbapen-2-em-3-carboxylate In the same manner as in Example 1-a), 74.2 mg of 4-nitrobenzyl(5R,6S)-2-(7-ethanesulfonylimidazo[5,1-b]thiazol-2-yl)-6-((1R)-1-hydroxyethyl)-1-carbapen-2-em-3-carboxylate was obtained from 253 mg of 4-nitrobenzyl(3R,5R,6S)-6-((1R)-1-hydroxyethyl)-2-oxo-1-carbapenam- 3-carboxylate and 396 mg of 7-ethanesulfonyl-2-(tri-n-butylstannyl)imidazo[5,1-b]thiazole.

NMR (CDCl$_3$) δ: 1.20 (3H, t, J=7.0 Hz), 1.39 (3H, d, J=6.2 Hz), 3.26–3.40 (4H, m), 3.48 (2H, q, J=7.0 Hz), 4.32 (1H, m), 5.29 (1H, d, J=13.7 Hz), 5.52 (1H, d, J=13.7 Hz), 7.68 (2H, d, J=8.8 Hz), 7.85 (1H, s), 8.15 (1H, s), 8.21 (2H, d, J=8.9 Hz)

b) Sodium(5R,6S)-2-(7-ethanesulfonylimidazo[5,1-b]thiazol-2-yl)-6-((1R)-1-hydroxyethyl)-1-carbapen-2-em-3-carboxylate In the same manner as in Example 1-b), 10.5 mg of the title compound was obtained from 74.2 mg of 4-nitrobenzyl (1S,5R,6S)-2-(7-ethanesulfonylimidazo[5,1-b]thiazol-2-yl)-6-((1R)-1-hydroxyethyl)-1-methyl-1-carbapen-2-em-3-carboxylate.

NMR (D$_2$O) δ (HOD=4.80 ppm): 1.24 (3H, t, J=7.4 Hz), 1.30 (3H, d, J=6.6 Hz), 3.27 (2H, m), 3.39 (2H, q, J=7.4 Hz), 3.50 (1H, m), 4.25 (2H, m), 7.84 (1H, s), 8.20 (1H, s)

Example 35

Sodium(1S,5R,6S)-6-((1R)-1-hydroxyethyl)-1-methyl-2-(7-p-toluenesulfonylimidazo[5,1-b]thiazol-2-yl)-1-carbapen-2-em-3-carboxylate a) 4-Nitrobenzyl(1S,5R,6S)-6-((1R)-1-hydroxyethyl)-1-methyl-2-(7-p-toluenesulfonylimidazo-[5,1-b]thiazol-2-yl)-1-carbapen-2-em-3-carboxylate In the same manner as in Example 1-a), 176 mg of 4-nitrobenzyl(1S,5R,6S)-6-((1R)-1-hydroxyethyl)-1-methyl-2-(7-p-toluenesulfonylimidazo[5,1-b]thiazol-2-yl)-1-carbapen-2-em-3-carboxylate was obtained from 350 mg of 4-nitrobenzyl(1R,3R,5R,6S)-6-((1R)-1-hydroxyethyl)-1-methyl-2-oxo-1-carbapenam-3-carboxylate and 590 mg of 7-p-toluenesulfonyl-2-(tri-n-butylstannyl)imidazo[5,1-b]-thiazole.

NMR (CDCl$_3$) δ: 1.29 (3H, t, J=7.1 Hz), 1.39 (3H, d, J=6.3 Hz), 2.40 (3H, s), 3.37 (1H, dd, J$_1$=6.6 Hz, J$_2$=2.8 Hz), 3.52 (1H, m), 4.30 (1H, m), 4.40 (1H, dd, J$_1$=9.6 Hz, J$_2$=2.8 Hz), 5.26 (1H, d, J=13.7 Hz), 5.50 (1H, d, J=13.7 Hz), 7.29 (2H, d, J=8.4 Hz), 7.29 (2H, d, J=8.4 Hz), 7.66 (2H, d, J=8.9 Hz), 7.91 (2H, d, J=8.4 Hz), 7.99 (1H, s), 8.20 (2H, d, J=8.9 Hz), 8.35 (1H, s) MS (TSP): 623 (M$^+$+H)

b) Sodium(1S,5R,6S)-6-((1R)-1-hydroxyethyl)-1-methyl-2-(7-p-toluenesulfonylimidazo[5,1-b]thiazol-2-yl)-1-carbapen-2-em-3-carboxylate In the same manner as in Example 1-b), 53.0 mg of the title compound was obtained from 176 mg of 4-nitrobenzyl (1S,5R,6S)-6-((1R)-1-hydroxyethyl)-1-methyl-2-(7-p-toluenesulfonylimidazo[5,1-b]thiazol-2-yl)-1-carbapen-2-em-3-carboxylate.

NMR (D$_2$O) δ (HOD=4.80 ppm): 1.17 (3H, t, J=7.1 Hz), 1.31 (3H, d, J=6.3 Hz), 2.34 (3H, s), 3.47 (2H, m), 4.25 (2H, m), 7.35 (2H, d, J=8.3 Hz), 7.77 (2H, d, J=8.3 Hz), 7.94 (1H, s), 8.12 (1H, s)

Example 36

Sodium(5R,6S)-2-(7-hydroxyacetylimidazo[5,1-b]thiazol-2-yl)-6-((1R)-1-hydroxyethyl)-1-carbapen-2-em-3-carboxylate a) 4-Nitrobenzyl(5R,6S)-2-(7-t-butyldimethylsilyloxyacetylimidazo[5,1-b]thiazol-2-yl)-6-((1R)-1-hydroxyethyl)-1-carbapen-2-em-3-carboxylate In the same manner as in Example 1-a), 255 mg of 4-nitrobenzyl(5R,6S)-2-(7-t-butyldimethylsilyloxyacetylimidazo[5,1-b]thiazol-2-yl)-6-((1R)-1-hydroxyethyl)-1-carbapen-2-em-3-carboxylate was obtained from 325 mg of 4-nitrobenzyl(3R,5R,6S)-6-((1R)-1-hydroxyethyl)-2-oxo-1-carbapenam-3-carboxylate and 655 mg of 7-t-butyldimethylsilyloxyacetyl-2-(tri-n-butylstannyl)-imidazo[5,1b]thiazole.

NMR (CDCl$_3$) δ: 0.15 (6H, s), 0.96 (9H, s), 1.41 (3H, d, J=6.3 Hz), 3.35 (3H, m), 4.34 (2H, m), 5.08 (2H, s), 5.31 (1H, d, J=13.4 Hz), 5.53 (1H, d, J=13.4 Hz), 7.69 (2H, d, J=8.9 Hz), 7.97 (1H, s), 8.23 (2H, d, J=8.9 Hz), 8.42 (1H, s)

b) 4-Nitrobenzyl(5R,6S)-2-(7-hydroxyacetylimidazo[5,1-b]thiazol-2-yl)-6-((1R)-1-hydroxyethyl)-1-carbapen-2-em-3-carboxylate Acetic acid (0.345 ml) and 2.04 ml of a 1 M tetra-n-butylammonium fluoride/THF solution were added to a solution of 255 mg of 4-nitrobenzyl(5R,6S)-2-(7-t-butyldimethylsilyloxyacetylimidazo[5,1-b]thiazol-2-yl)-6-((1R)-1-hydroxyethyl)-1-carbapen-2-em-3-carboxylate in 8 ml of THF. The mixture was stirred at room temperature for 3 hr. Brine was added to the reaction solution. The mixture was adjusted to pH 8.1 by the addition of a saturated sodium hydrogencarbonate solution, and extracted twice with ethyl acetate. The organic layers were combined, washed twice with brine, and dried over anhydrous magnesium sulfate. The solvent was removed by distillation under the reduced pressure. Diethylether(5 ml) was added to the residue. The insoluble was collected by filtration to give 196 mg of 4-nitrobenzyl(5R,6S)-2-(7-hydroxyacetylimidazo[5,1-b] thiazol-2-yl)-6-((1R)-1-hydroxyethyl)-1-carbapen-2-em-3-carboxylate.

NMR (CDCl$_3$) δ: 1.17 (3H, d, J=6.5 Hz), 3.50 (3H, m), 4.01 (1H, m), 4.27 (1H, m), 4.69 (2H, s), 5.44 (1H, d, J=13.8 Hz), 5.58 (1H, d, J=13.8 Hz), 7.77 (2H, d, J=8.9 Hz), 8.25 (2H, d, J=8.9 Hz), 8.34 (1H, s), 8.50 (1H, s)

c) Sodium(5R,6S)-2-(7-hydroxyacetylimidazo[5,1-b]thiazol-2-yl)-6-((1R)-1-hydroxyethyl)-1-carbapen-2-em-3-carboxylate In the same manner as in Example 1-b), 95.9 mg of the title compound was obtained from 196 mg of 4-nitrobenzyl (5R,6S)-2-(7-hydroxyacetylimidazo[5,1-b]thiazol-2-yl)-6-((1R)-1-hydroxyethyl)-1-carbapen-2-em-3-carboxylate.

NMR (D$_2$O) δ (HOD=4.80 ppm): 1.33 (3H, d, J=6.1 Hz), 3.24 (2H, m), 3.50 (1H, m), 4.27 (2H, m), 4.77 (2H, s), 7.75 (1H, s), 8.02 (1H, s)

Example 37

Sodium(1S,5R,6S)-2-(7-benzoylimidazo[5,1-b]thiazol-2-yl)-6-((1R)-1-hydroxyethyl)-1-methyl-1-carbapen-2-em-3-carboxylate a) 4-Nitrobenzyl(1S,5R,6S)-2-(7-benzoylimidazo[5,1-b]thiazol-2-yl)-6-((1R)-1-hydroxy-ethyl)-1-methyl-1-carbapen-2-em-3-carboxylate In the same manner as in Example 1-a), 288 mg of 4-nitrobenzyl(1S,5R,6S)-2-(7-benzoylimidazo[5,1-b] thiazol-2-yl)-6-((1R)-1-hydroxyethyl)-1-methyl-1-carbapen-2-em-3-carboxylate was obtained from 543 mg of 4-nitrobenzyl(1R,3R,5R,6S)-6-((1R)-1-hydroxyethyl)-1-methyl-2-oxo-1-carbapenam-3-carboxylate and 931 mg of 7-benzoyl-2-(tri-n-butylstannyl)imidazo[5,1-b]thiazole.

NMR (DMSO-d$_6$) δ: 1.19 (3H, d, J=6.2 Hz), 1.25 (3H, d, J=7.1 Hz), 3.45 (1H, dd, J$_1$=5.7 Hz, J$_2$=2.7 Hz), 3.77 (1H, m), 4.04 (1H, m), 4.37 (1H, dd, $J_1$=10.1 Hz, $J_2$=2.7 Hz), 5.41 (1H, d, J=14.0 Hz), 5.55 (1H, d, J=14.0 Hz), 7.58 (3H, m), 7.75 (2H, d, J=8.8 Hz), 8.22 (2H, d, J=8.8 Hz), 8.44 (1H, s), 8.49 (2H, m), 8.62 (1H, s)

b) Sodium(1S,5R,6S)-2-(7-benzoylimidazo[5,1-b]thiazol-2-yl)-6-((1R)-1-hydroxyethyl)-1-methyl-1-carbapen-2-em-3-carboxylate The title compound (120 mg) was obtained from 440 mg of 4-nitrobenzyl(1S,5R,6S)-2-(7-benzoylimidazo[5,1-b]thiazol-2-yl)-6-((1R)-1-hydroxyethyl)-1-methyl-1-carbapen-2-em-3-carboxylate in the same manner as in Example 1-b), except that the purification was carried out by column chromatography on Diaion HP-20 (30% aqueous methanol) and Cosmosil 40C18-PREP (30% aqueous methanol).

NMR ($D_2O$) δ (HOD=4.80 ppm): 1.10 (3H, d, J=7.1 Hz), 1.32 (3H, d, J=6.3 Hz), 3.44 (2H, m), 4.23 (2H, m), 7.42 (2H, m), 7.57 (1H, m), 7.87 (3H, m), 8.01 (1H, s)

Example 38

Sodium(5R,6S)-2-(7-hydroxyacetylimidazo[5,1-b]thiazol-3-yl)-6-((1R)-1-hydroxyethyl)-1-carbapen-2-em-3-carboxylate a) 4-Nitrobenzyl(5R,6S)-2-(7-t-butyldimethylsilyloxyacetylimidazo[5,1-b]thiazol-3-yl)-6-((1R)-1-hydroxyethyl)-1-carbapen-2-em-3-carboxylate In the same manner as in Example 1-a), 167 mg of 4-nitrobenzyl(5R,6S)-2-(7-t-butyldimethylsilyloxyacetylimidazo[5,1-b]thiazol-3-yl)-6-((1R)-1-hydroxyethyl)-1-carbapen-2-em-3-carboxylate was obtained from 293 mg of 4-nitrobenzyl(3R,5R,6S)-6-((1R)-1-hydroxyethyl)-2-oxo-1-carbapenam-3-carboxylate and 591 mg of 7-t-butyldimethylsilyloxyacetyl-3-(tri-n-butylstannyl)-imidazo[5,1-b]thiazole.

NMR ($CDCl_3$) δ: 0.15 (6H, s), 0.96 (9H, s), 1.40 (3H, d, J=6.3 Hz), 3.41 (3H, m), 4.31 (1H, m), 4.48 (1H, m), 5.05 (2H, s), 5.21 (1H, d, J=13.5 Hz), 5.38 (1H, d, J=13.5 Hz), 7.24 (1H, s), 7.50 (2H, d, J=8.9 Hz), 7.66 (1H, s), 8.18 (2H, d, J=8.9 Hz)

b) 4-Nitrobenzyl(5R,6S)-2-(7-hydroxyacetylimidazo[5,1-b]thiazol-3-yl)-6-((1R)-1-hydroxyethyl)-1-carbapen-2-em-3-carboxylate In the same manner as in Example 36-b), 56.5 mg of 4-nitrobenzyl(5R,6S)-2-(7-hydroxyacetylimidazo[5,1-b]thiazol-3-yl)-6-((1R)-1-hydroxyethyl)-1-carbapen-2-em-3-carboxylate was obtained from 167 mg of 4-nitrobenzyl(5R,6S)-2-(7-t-butyldimethylsilyloxyacetylimidazo[5,1-b]thiazol-3-yl)-6-((1R)-1-hydroxyethyl)-1-carbapen-2-em-3-carboxylate.

NMR ($CDCl_3$) δ: 1.41 (3H, d, J=6.3 Hz), 3.40 (3H, m), 4.34 (1H, m), 4.48 (1H, m), 4.88 (2H, s), 5.22 (1H, d, J=13.4 Hz), 5.39 (1H, d, J=13.4 Hz), 7.52 (2H, d, J=8.6 Hz), 7.67 (1H, s), 8.20 (3H, m)

c) Sodium(5R,6S)-2-(7-hydroxyacetylimidazo[5,1-b]thiazol-3yl)-6-((1R)-1-hydroxyethyl)-1-carbapen-2-em-3-carboxylate The title compound (27.7 mg) was obtained from 56.5 mg of 4-nitrobenzyl(5R,6S)-2-(7-hydroxyacetylimidazo[5,1-b]thiazol-3-yl)-6-((1R)-1-hydroxyethyl)-1-carbapen-2-em-3-carboxylate in the same manner as in Example 1-b), except that the purification was carried out by column chromatography on Diaion HP-20 (10% aqueous methanol) and Cosmosil 40C18-PREP (5% aqueous methanol).

NMR ($D_2O$) δ (HOD=4.80 ppm): 1.31 (3H, d, J=6.5 Hz), 3.23 (1H, dd, $J_1$=17.5 Hz, $J_2$=10.1 Hz), 3.48 (1H, dd, $J_1$=17.5 Hz, $J_2$=8.8 Hz), 3.60 (1H, dd, $J_1$=5.8 Hz, $J_2$=2.9 Hz), 4.28 (1H, m), 4.40 (1H, m), 4.89 (2H, s), 7.31 (1H, s), 7.93 (1H, s)

Example 39

Sodium(5R,6S)-2-(7-benzoylimidazo[5,1-b]thiazol-2-yl)-6-((1R)-1-hydroxyethyl)-1-carbapen-2-em-3-carboxylate a) 4-Nitrobenzyl(5R,6S)-2-(7-benzoylimidazo[5,1-b]thiazol-2-yl)-6-((1R)-1-hydroxyethyl)-1-carbapen-2-em-3-carboxylate In the same manner as in Example 1-a), 574 mg of 4-nitrobenzyl(5R,6S)-2-(7-benzoylimidazo[5,1-b]thiazol-2-yl)-6-((1R)-1-hydroxyethyl)-1-carbapen-2-em-3-carboxylate was obtained from 522 mg of 4-nitrobenzyl(3R,5R,6S)-6-((1R)-1-hydroxyethyl)-2-oxo-1-carbapenam-3-carboxylate and 931 mg of 7-benzoyl-2-(tri-n-butylstannyl)imidazo[5,1-b]thiazole.

NMR ($CDCl_3$) δ: 1.41 (3H, d, J=6.4 Hz), 3.37 (3H, m), 4.25 (2H, m), 5.33 (1H, d, J=13.5 Hz), 5.56 (1H, d, J=13.5 Hz), 7.54 (3H, m), 7.71 (2H, d, J=8.8 Hz), 8.08 (1H, s), 8.25 (2H, d, J=8.8 Hz), 8.52 (1H, s), 8.54 (2H, m)

b) Sodium(5R,6S)-2-(7-benzoylimidazo[5,1-b]thiazol-2-yl)-6-((1R)-1-hydroxyethyl)-1-carbapen-2-em-3-carboxylate The title compound (178 mg) was obtained from 504 mg of 4-nitrobenzyl(5R,6S)-2-(7-benzoylimidazo[5,1-b]thiazol-2-yl)-6-((1R)-1-hydroxyethyl)-1-carbapen-2-em-3-carboxylate in the same manner as in Example 1-b), except that the purification was carried out by column chromatography on Diaion HP-20 (30% aqueous methanol) and Cosmosil 40C18-PREP (20% aqueous methanol).

NMR ($D_2O$) δ (HOD=4.80 ppm): 1.26 (3H, d, J=6.3 Hz), 2.90 (2H, m), 3.25 (1H, dd, $J_1$=5.8 Hz, $J_2$=2.8 Hz), 4.00 (1H, m), 4.17 (1H, m), 7.38 (2H, m), 7.53 (2H, m), 7.83 (3H, m)

Example 40

Sodium(1S,5R,6S)-2-[7-[N-(4-aminobenzyl)sulfamoyl]imidazo[5,1-b]thiazol-2-yl]-6-((1R)-1-hydroxyethyl)-1-methyl-1-carbapen-2-em-3-carboxylate a) 4-Nitrobenzyl(1S,5R,6S)-6-((1R)-1-hydroxyethyl)-1-methyl-2-[7-[N-(4-nitrobenzyl)-sulfamoyl]imidazo[5,1-b]thiazol-2-yl]-1-carbapen-2-em-3-carboxylate In substantially the same manner as in Example 1-a), 337 mg of 4-nitrobenzyl(1S,5R,6S)-6-((1R)-1-hydroxyethyl)-1-methyl-2-[7-[N-(4-nitrobenzyl)-sulfamoyl]imidazo[5,1-b]thiazol-2-yl]-1-carbapen-2-em-3-carboxylate was obtained from 507 mg of 4-nitrobenzyl(1R,3R,5R,6S)-6-((1R)-1-hydroxyethyl)-1-methyl-2-oxo-1-carbapenam-3-carboxylate and 392 mg of 7-N-(4-nitrobenzyl)sulfamoyl-2-(tri-n-butylstannyl)imidazo[5,1-b]thiazole.

NMR (DMSO-$d_6$) δ: 1.15–1.22 (6H, m), 3.41–3.44 (1H, m), 3.65–3.74 (1H, m), 4.00–4.05 (1H, m), 4.17 (2H, d,

J=6.3 Hz), 4.30–4.36 (1H, m), 5.17 (1H, d, J=5.1 HZ), 5.40 (1H, d, J=13.5 Hz), 5.53 (1H, d, J=13.5 Hz), 7.45 (2H, d, J=8.6 Hz), 7.74 (2H, d, J=8.6 Hz), 8.03 (2H, d, J=8.8 Hz), 8.22 (2H, d, J=8.8 Hz), 8.29 (1H, s), 8.43 (1H, s), 8.50 (1H, t, J=6.3 Hz)

b) Sodium(1S,5R,6S)-2-[7-[N-(4-aminobenzyl) sulfamoyl]imidazo[5,1-b]thiazol-2-yl]-6-((1R)-1-hydroxyethyl)-1-methyl-1-carbapen-2-em-3-carboxylate In substantially the same manner as in Example 1-b), 165 mg of the title compound was obtained from 337 mg of 4-nitrobenzyl(1S,5R,6S)-6-((1R)-1-hydroxyethyl)-1-methyl-2-[7-[N-(4-nitrobenzyl)sulfamoyl]imidazo[5,1-b]thiazol-2-yl]-1-carbapen-2-em-3-carboxylate, except that the purification was carried out using Cosmosil 40C18-PREP (5% aqueous methanol).

NMR (D$_2$O) δ (HOD=4.80 ppm): 1.26 (3H, d, J=7.3 Hz), 1.32 (3H, d, J=6.4 HZ), 3.52–3.64 (2H, m), 4.10 (2H, s), 4.25–4.35 (2H, m), 6.46 (2H, d, J=8.5 Hz), 6.86 (2H, d, J=8.6 HZ), 7.90 (1H, s), 7.96 (1H, s)

Example 41

Sodium(1S,5R,6S)-2-(7-fluoroimidazo[5,1-b]thiazol-2-yl)-6-((1R)-1-hydroxyethyl)-1-methyl-1-carbapen-2-em-3-carboxylate a) 4-nitrobenzyl(1S,5R,6S)-2-(7-fluoroimidazo[5,1-b]thiazol-2-yl)-6-((1R)-1-hydroxyethyl)-1-methyl-1-carbapen-2-em-3-carboxylate In the same manner as in Example 1-a), 40 mg of 4-nitrobenzyl(1S,5R,6S)-2-(7-fluoroimidazo[5,1-b]thiazol-2-yl)-6-((1R)-1-hydroxyethyl)-1-methyl-1-carbapen-2-em-3-carboxylate was obtained from 320 mg of 4-nitrobenzyl (1R,3R,5R,6S)-6-((1R)-1-hydroxyethyl)-1-methyl-2-oxo-1-carbapenam-3-carboxylate and 400 mg of 7-fluoro-2-(tri-n-butylstannyl)imidazo[5,1-b]thiazole.

NMR (CDCl$_3$) δ: 1.31 (3H, d, J=7.4 Hz), 1.39 (3H, d, J=6.3 Hz), 3.39 (1H, dd, J$_1$=6.4 Hz, J$_2$=2.8 Hz), 3.46 (1H, m), 4.27 (1H, m), 4.40 (1H, dd, J$_1$=9.7 Hz, J$_2$=2.8 Hz), 5.27 (1H, d, J=13.6 Hz), 5.51 (1H, d, J=13.6 Hz), 7.62 (1H, s), 7.68 (2H, d, J=8.9 Hz), 8.21 (1H, s), 8.26 (2H, d, J=8.9 Hz)

b) Sodium(1S,5R,6S)-2-(7-fluoroimidazo[5,1-b]thiazol-2-yl)-6-((1R)-1-hydroxyethyl)-1-methyl-1-carbapen-2-em-3-carboxylate In the same manner as in Example 1-b), 3.8 mg of the title compound was obtained from 40 mg of 4-nitrobenzyl (1S,5R,6S)-2-(7-fluoroimidazo[5,1-b]thiazol-2-yl)-6-((1R)-1-hydroxyethyl)-1-methyl-1-carbapen-2-em-3-carboxylate.

NMR (D$_2$O) δ (HOD=4.80 ppm): 1.24 (3H, d, J=7.4 Hz), 1.32 (3H, d, J=6.3 Hz), 3.51 (1H, dd, J$_1$=6.3 Hz, J$_2$=2.7 Hz), 3.53 (1H, m), 4.27 (1H, m), 4.30 (1H, dd, J$_1$=9.2 Hz, J$_2$=2.7 Hz), 7.72 (1H, s), 7.79 (1H, d, J=1.9 Hz)

Example 42

Sodium(1S,5R,6S)-6-((1R)-1-hydroxyethyl)-2-[7-[N-(2-hydroxyethyl)-N-methylsulfamoyl]imidazo[5,1-b]thiazol-2-yl]-1-methyl-1-carbapen-2-em-3-carboxylate a) 4-Nitrobenzyl(1S,5R,6S)-2-[7-[N-(2-t-butyldimethylsilyloxyethyl)-N-methylsulfamoyl]imidazo-[5,1-b]thiazol-2-yl]-6-((1R)-1-hydroxyethyl)-1-methyl-1-carbapen-2-em-3-carboxylate In substantially the same manner as in Example 1-a), 273 mg of 4-nitrobenzyl(1S,5R,6S)-2-[7-[N-(2-t-butyldimethylsilyloxyethyl)-N-methylsulfamoyl[imidazo-[5,1-b]thiazol-2-yl]-6-((1R)-1-hydroxyethyl)-1-methyl-1-carbapen-2-em-3-carboxylate was obtained from 217 mg of 4-nitrobenzyl(1R,3R,5R,6S)-6-((1R)-1-hydroxyethyl)-1-methyl-2-oxo-1-carbapenam-3-carboxylate and 362 mg of 7-[N-(1-t-butyldimethylsilyloxyethyl)-N-methylsulfamoyl]-2-(tri-n-butylstannyl)imidazo[5,1-b]thiazole.

NMR (CDCl$_3$) δ: 0.07 (6H, s), 0.89 (9H, s), 1.32 (3H, d, J=7.2 Hz), 1.41 (3H, d, J=6.2 Hz), 2.99 (3H, s), 3.33 (2H, t, J=6.1 Hz), 3.38 (1H, dd, J$_1$=6.4 Hz, J$_2$=3.3 Hz), 3.45–3.53 (1H, m), 3.84 (1H, t, J=6.1 Hz), 4.30–4.37 (1H, m), 4.40 (1H, dd, J$_1$=9.6 Hz, J$_2$=3.3 Hz), 5.30 (1H, d, J=8.5 Hz), 5.54 (1H, d, J=8.5 Hz), 7.69 (2H, d, J=8.5 Hz), 8.05 (1H, s), 8.26 (2H, d, J=8.5 Hz), 8.46 (1H, s)

b) 4-Nitrobenzyl(1S,5R,6S)-6-((1R)-1-hydroxyethyl)-2-[7-[N-(2-hydroxyethyl)-N-methyl-sulfamoyl]imidazo[5,1-b]thiazol-2-yl]-1-methyl-1-carbapen-2-em-3-carboxylate Acetic acid (0.36 ml) and 2.0 ml of a 1 M-tetra-n-butylammonium fluoride/THF solution were added under ice cooling to a solution of 273 mg of 4-nitrobenzyl(1S,5R,6S)-2-[7-[N-(2-t-butyldimethylsilyloxyethyl)-N-methylsulfamoyl]imidazo[5,1-b]thiazol-2-yl]-6-((1R)-1-hydroxyethyl)-1-methyl-1-carbapen-2-em-3-carboxylate in 8 ml of THF. The mixture was stirred at room temperature for 6 hr. The reaction mixture was added to a dilute aqueous sodium hydrogencarbonate solution, and the mixture was extracted with dichloromethane. The organic layer was dried over anhydrous magnesium sulfate. The solvent was removed by distillation. The residue was purified by column chromatography on silica gel (dichloromethane:methanol= 10:1) to give 175 mg of 4-nitrobenzyl(1S,5R,6S)-6-((1R)-1-hydroxyethyl)-2-[7-[N-(2-hydroxyethyl)-N-methylsulfamoyl]imidazo[5,1-b]thiazol-2-yl]-1-methyl-1-carbapen-2-em-3-carboxylate.

NMR (CDCl$_3$) δ: 1.30 (3H, d, J=7.2 Hz), 1.39 (3H, d, J=6.3 Hz), 2.87 (3H, s), 3.38 (1H, dd, J$_1$=6.6 Hz, J$_2$=2.7 Hz), 3.48–3.53 (1H, m), 3.54 (2H, t, J=4.8 Hz), 3.82 (2H, t, J=4.8 Hz), 4.27–4.37 (1H, m), 4.40 (1H, dd, J$_1$=9.7 Hz, J$_2$=2.7 Hz), 5.28 (1H, d, J=13.7 Hz), 5.52 (1H, d, J=13.7 Hz), 7.67 (2H, d, J=8.8 Hz), 8.05 (1H, s), 8.23 (2H, d, J=8.8 Hz), 8.42 (1H, s)

c) Sodium(1S,5R,6S)-6-((1R)-1-hydroxyethyl)-2-[7-[N-(2-hydroxyethyl)-N-methylsulfamoyl]imidazo[5,1-b]thiazol-2-yl]-1-methyl-1-carbapen-2-em-3-carboxylate The title compound (90.9 mg) was obtained from 175 mg of 4-nitrobenzyl(1S,5R,6S)-6-((1R)-1-hydroxyethyl)-2-[7-[N-(2-hydroxyethyl)-N-methylsulfamoyl]imidazo[5,1-b]thiazol-2-yl]-1-methyl-1-carbapen-2-em-3-carboxylate in substantially the same manner as in Example 1-b), except that the purification was carried out using Cosmosil 40C18-PREP (2.5% aqueous methanol).

NMR (D$_2$O) δ (HOD=4.80 ppm): 1.24 (3H, d, J=7.2 Hz), 1.31 (3H, d, J=6.3 Hz), 2.83 (3H, s), 3.27 (2H, t, J=4.9 Hz), 3.51 (1H, m), 3.56–3.67 (1H, m), 3.72 (2H, t, J=4.9 Hz), 4.23–4.35 (2H, m), 8.04 (1H, s), 8.22 (1H, s)

Example 43

Sodium(1S,5R,6S)-2-(7-acetylaminoacetylimidazo[5,1-b]thiazol-2-yl)-6-((1R)-1-hydroxyethyl)-1-methyl-1-carbapen-2-em-3-carboxylate a) 4-Nitrobenzyl(1S,5R,6S)-2-(7-acetylaminoacetylimidazo[5,1-b]thiazol-2-yl)-6-((1R)-1-hydroxyethyl)-1-methyl-1-carbapen-2-em-3-carboxylate In the same manner as in Example 1-a), 23.8 mg of 4-nitrobenzyl(1S,5R,6S)-2-(7-acetylaminoacetylimidazo[5, 1-b]thiazol-2-yl)-6-((1R)-1-hydroxyethyl)-1-methyl-1-carbapen-2-em-3-carboxylate was obtained from 123 mg of 4-nitrobenzyl(1R,3R,5R,6S)-6-((1R)-1-hydroxyethyl)-1-methyl-2-oxo-1-carbapenam-3-carboxylate and 207 mg of 7-acetylaminoacetyl-2-(tri-n-butylstannyl)imidazo[5,1-b]thiazole.

NMR (CDCl$_3$) δ: 1.30 (3H, d, J=7.1 Hz), 1.40 (3H, d, J=6.2 Hz), 2.10 (3H, s), 3.39 (1H, dd, J$_1$=6.7 Hz, J$_2$=2.9 Hz), 3.52 (1H, m), 4.32 (1H, m), 4.42 (1H, dd, J$_1$=9.8 Hz, J$_2$=2.9 Hz), 4.79 (2H, d, J=4.7 Hz), 5.28 (1H, d, J=13.4 Hz), 5.52 (1H, d, J=13.4 Hz), 6.51 (1H, br), 7.68 (2H, d, J=8.5 Hz), 8.01 (1H, s), 8.24 (2H, d, J=8.5 Hz), 8.46 (1H, s)

b) Sodium(1S,5R,6S)-2-(7-acetylaminoacetylimidazo[5,1-b]thiazol-2-yl)-6-((1R)-1-hydroxyethyl)-1-methyl-1-carbapen-2-em-3-carboxylate The title compound (9.0 mg) was obtained from 23.8 mg of 4-nitrobenzyl(1S,5R,6S)-2-(7-acetylaminoacetylimidazo[5,1-b]thiazol-2-yl)-6-((1R)-1-hydroxyethyl)-1-methyl-1-carbapen-2-em-3-carboxylate in the same manner as in Example 1-b), except that the purification was carried out by column chromatography on Diaion HP-20 (10% aqueous methanol) and Cosmosil 40C18-PREP (5% aqueous methanol).

NMR (D$_2$O) δ (HOD=4.80 ppm): 1.23 (3H, d, J=6.9 Hz), 1.33 (3H, d, J=6.3 Hz), 2.14 (3H, s), 3.52 (2H, m), 4.29 (2H, m), 4.49 (1H, d, J=18.9 Hz), 4.63 (1H, d, J=18.9 Hz), 7.92 (1H, s), 8.07 (1H, s)

Example 44

Sodium(1S,5R,6S)-6-((1R)-1-hydroxyethyl)-2-(7-methanesulfonyl-5-methylimidazo[5,1-b]thiazol-2-yl)-1-methyl-1-carbapen-2-em-3-carboxylate a) 4-Nitrobenzyl(1S,5R,6S)-6-((1R)-1-hydroxyethyl)-1-methyl-2-(5-methyl-7-methylthioimidazo-[5,1-b]thiazol-2-yl)-1-carbapen-2-em-3-carboxylate In the same manner as in Example 1-a), 1.41 g of 4-nitrobenzyl(1S,5R,6S)-6-((1R)-1-hydroxyethyl)-1-methyl-2-(5-methyl-7-methylthioimidazo[5,1-b]thiazol-2-yl)-1-carbapen-2-em-3-carboxylate was obtained from 1.81 g of 4-nitrobenzyl(1R,3R,5R,6S)-6-((1R)-1-hydroxyethyl)-1-methyl-2-oxo-1-carbapenam-3-carboxylate and 2.84 g of 5-methyl-7-methylthio-2-(tri-n-butylstannyl)imidazo[5,1-b]thiazole.

NMR (CDCl$_3$) δ: 1.31 (3H, d, J=7.3 Hz), 1.40 (3H, d, J=6.3 Hz), 2.40 (3H, s), 2.58 (3H, s), 3.36 (1H, dd, J$_1$=6.6 Hz, J$_2$=3.0 Hz), 3.46 (1H, m), 4.34 (2H, m), 5.27 (1H, d, J=13.7 Hz), 5.54 (1H, d, J=13.7 Hz), 7.68 (2H, d, J=8.9 Hz), 8.16 (1H, s), 8.25 (2H, d, J=8.9 Hz)

b) 4-Nitrobenzyl(1S,5R,6S)-6-((1R)-1-hydroxyethyl)-2-(7-methanesulfonyl-5-methylimidazo [5,1-b]thiazol-2-yl)-1-methyl-1-carbapen-2-em-3-carboxylate 4-Nitrobenzyl(1S,5R,6S)-6-((1R)-1-hydroxyethyl)-1-methyl-2-(5-methyl-7-methylthioimidazo[5,1-b]thiazol-2-yl)-1-carbapen-2-em-3-carboxylate (315 mg) was dissolved in 6 ml of THF and 6 ml of water. To the solution was added 368 mg of OXONE (manufactured by Du Pont (E.I.) de Nemours & Co.) under ice cooling. The mixture was stirred at the same temperature for 1.5 hr. An aqueous sodium hydrogencarbonate solution was added thereto, followed by extraction with dichloromethane. The extract was dried over anhydrous magnesium sulfate. The solvent was removed by distillation under the reduced pressure. The residue was purified by column chromatography on silica gel (dichloromethane:methanol=20:1 to 10:1). Of two main components, the fraction, which had been eluted earlier, was concentrated under the reduced pressure to give 145 mg of 4-nitrobenzyl(1S,5R,6S)-6-((1R)-1-hydroxyethyl)-2-(7-methanesulfonyl-5-methylimidazo[5,1-b]thiazol-2-yl)-1-methyl-1-carbapen-2-em-3-carboxylate.

NMR (CDCl$_3$) δ: 1.30 (3H, d, J=7.4 Hz), 1.40 (3H, d, J=6.4 Hz), 2.64 (3H, s), 3.19 (3H, s), 3.38 (1H, dd, J$_1$=6.7 Hz, J$_2$=2.9 Hz), 3.48 (1H, m), 4.32 (1H, m), 4.40 (1H, dd, J$_1$=9.7 Hz, J$_2$=2.9 Hz), 5.28 (1H, d, J=14.0 Hz), 5.54 (1H, d, J=14.0 Hz), 7.69 (2H, d, J=8.5 Hz), 8.25 (2H, d, J=8.5 Hz), 8.32 (1H, s)

c) Sodium(1S,5R,6S)-6-((1R)-1-hydroxyethyl)-2-(7-methanesulfonyl-5-methylimidazo[5,1-b]thiazol-2-yl)-1-methyl-1-carbapen-2-em-3-carboxylate In the same manner as in Example 1-b), 104 mg of the title compound was obtained from 172 mg of 4-nitrobenzyl(1S,5R,6S)-6-((1R)-1-hydroxyethyl)-2-(7-methanesulfonyl-5-methylimidazo[5,1-b]thiazol-2-yl)-1-methyl-1-carbapen-2-em-3-carboxylate.

NMR (D$_2$O) δ (HOD=4.80 ppm): 1.22 (3H, d, J=7.2 Hz), 1.32 (3H, d, J=6.2 Hz), 2.57 (3H, s), 3.25 (3H, s), 3.50 (1H, m), 3.61 (1H, m), 4.29 (2H, m), 7.84 (1H, s)

Example 45

Sodium(1S,5R,6S)-6-((1R)-1-hydroxyethyl)-2-(7-methanesulfinyl-5-methylimidazo[5,1-b]thiazol-2-yl)-1-methyl-1-carbapen-2-em-3-carboxylate (A Mixture of Diastereomers)

a) 4-Nitrobenzyl(1S,5R,6S)-6-((1R)-1-hydroxyethyl)-2-(7-methanesulfinyl-5-methylimidazo[5,1-b]thiazol-2-yl)-1-methyl-1-carbapen-2-em-3-carboxylate (A Mixture of Diastereomers)

Of the two main components, the fraction, which had been eluted later in the column chromatography on silica gel in Example 44-b), was concentrated under the reduced pressure to give 139 mg of 4-nitrobenzyl(1S,5R,6S)-6-((1R)-1-hydroxyethyl)-2-(7-methanesulfinyl-5-methylimidazo[5,1-b]thiazol-2-yl)-1-methyl-1-carbapen-2-em-3-carboxylate (a mixture of diastereomers).

NMR (CDCl$_3$) δ: 1.29 (3H, m), 1.39 (3H, d, J=6.4 Hz), 2.62 (3H, s), 2.92, 2.94 (total 3H, s each), 3.36 (1H, m), 3.45 (1H, m), 4.32 (2H, m), 5.27 (1H, d, J=13.4 Hz), 5.54 (1H, d, J=13.4 Hz), 7.68 (2H, d, J=8.8 Hz), 8.25 (2H, d, J=8.8 Hz), 8.31 (1H, s)

b) Sodium(1S,5R,6S)-6-((1R)-1-hydroxyethyl)-2-(7-methanesulfinyl-5-methylimidazo[5,1-b]thiazol-2-yl)-1-methyl-1-carbapen-2-em-3-carboxylate (A Mixture of Diastereomers)

In the same manner as in Example 1-b), 127 mg of the title compound was obtained from 204 mg of 4-nitrobenzyl(1S,5R,6S)-6-((1R)-1-hydroxyethyl)-2-(7-methanesulfinyl-5-methylimidazo[5,1-b]thiazol-2-yl)-1-methyl-1-carbapen-2-em-3-carboxylate (a mixture of diastereomers).

NMR (D$_2$O) δ (HOD=4.80 ppm): 1.23 (3H, d, J=6.9 Hz), 1.32 (3H, d, J=6.3 Hz), 2.56 (3H, s), 3.03 (3H, s), 3.50 (1H, m), 3.59 (1H, m), 4.29 (2H, m), 7.82, 7.85 (total 1H, s each)

Example 46

1-(Ethoxycarbonyloxy)ethyl(1S,5R,6S)-2-(7-acetylimidazo[5,1-b]thiazol-2-yl)-6-((1R)-1-hydroxy-ethyl)-1-methyl-1-carbapen-2-em-3-carboxylate (A Mixture of Diastereomers)

a) 4-Nitrobenzyl(1S,5R,6S)-2-(7-acetylimidazo[5,1-b]thiazol-2-yl)-6-((1R)-1-hydroxyethyl)-1-methyl1-carbapen-2-em-3-carboxylate In the same manner as in Example 1-a), 5.93 g of 4-nitrobenzyl(1S,5R,6S)-2-(7-acetylimidazo[5,1-b]thiazol-2-yl)-6-((1R)-1-hydroxyethyl)-1-methyl-1-carbapen-2-em-3-carboxylate was obtained from 5.80 g of 4-nitrobenzyl (1R,3R,5R,6s)-6-((1R)-1-hydroxyethyl)-1-methyl-2-oxo-1-carbapenam-3-carboxylate and 8.80 g of 7-acetyl-2-(tri-n-butylstannyl)imidazo[5,1-b]thiazole.

NMR (CDCl$_3$) δ: 1.31 (3H, d, J=7.4 Hz), 1.40 (3H, d, J=6.2 Hz), 2.61 (3H, s), 3.40 (1H, dd, J$_1$=6.6 Hz, J$_2$=2.9 Hz), 3.52 (1H, m), 4.32 (1H, m), 4.42 (1H, dd, J$_1$=9.7 Hz, J$_2$=2.9 Hz), 5.27 (1H, d, J=13.5 Hz), 5.52 (1H, d, J=13.5 Hz), 7.67 (2H, d, J=8.5 Hz), 8.01 (1H, s), 8.22 (2H, d, J=8.5 Hz), 8.50 (1H, s)

b) Sodium(1S,5R,6S)-2-(7-acetylimidazo[5,1-b]thiazol-2-yl)-6-((1R)-1-hydroxyethyl)-1-methyl-1-carbapen-2-em-3-carboxylate In the same manner as in Example 1-b), 954 mg of sodium(1S,5R,6S)-2-(7-acetylimidazo[5,1-b]thiazol-2-yl)-6-((1R)-1-hydroxyethyl)-1-methyl-1-carbapen-2-em-3-carboxylate was obtained from 1.53 g of 4-nitrobenzyl(1S,5R,6S)-2-(7-acetylimidazo[5,1-b]thiazol-2-yl)-6-((1R)-1-hydroxyethyl)-1-methyl-1-carbapen-2-em-3-carboxylate.

NMR (D$_2$O) δ (HOD=4.80 ppm): 1.20 (3H, d, J=7.2 Hz), 1.33 (3H, d, J=6.4 Hz), 2.45 (3H, s), 3.50 (1H, dd, J$_1$=6.1 Hz, J$_2$=2.5 Hz), 3.57 (1H, m), 4.28 (1H, m), 4.33 (1H, dd, J$_1$=9.3 Hz, J$_2$=2.5 Hz), 7.92 (1H, s), 8.05 (1H, s)

c) 1-(Ethoxycarbonyloxy)ethyl(1S,5R,6S)-2-(7-acetylimidazo[5,1-b]thiazol-2-yl)-6-((1R)-1-hydroxyethyl)-1-methyl-1-carbapen-2-em-3-carboxylate (A Mixture of Diastereomers)

Sodium(1S,5R,6S)-2-(7-acetylimidazo[5,1-b]thiazol-2-yl)-6-((1R)-1-hydroxyethyl)-1-methyl-1-carbapen-2-em-3-carboxylate (71.9 mg) was dissolved in 2.0 ml of DMF. 1-(Ethoxycarbonyloxy)ethyl iodide (66.3 mg) was added to the solution in an argon atmosphere at −20° C. The mixture was stirred for 2 hr while raising the temperature to −10° C. Ethyl acetate (20 ml) was added to the reaction solution. The mixture was extracted twice, followed by washing twice with 10 ml of semisaturated brine. The organic layer was dried over anhydrous magnesium sulfate and filtered. The filtrate was concentrated under the reduced pressure to a volume of 2 ml. The residue was purified by column chromatography on silica gel (chloroform:methanol=15:1) and Sephadex LH-20 (dichloromethane:methanol=1:1) in that order to give 57.4 mg of the title compound.

NMR (CDCl$_3$) δ: 1.28 (3H, d, J=7.2 Hz), 1.32–1.41 (6H, m), 1.60, 1.65 (total 3H, d each, J=5.4 Hz), 2.62 (3H, s), 3.34 (1H, m), 3.49 (1H, m), 4.21 (1H, m), 4.29 (2H, m), 4.39 (1H, m), 6.94 (1H, m), 8.02 (1H, s), 8.61, 8.63 (total 1H, s each) MS (TSP): 492 (M$^+$+H)

Example 47

1-(Isopropoxycarbonyloxy)ethyl(1S,5R,6S)-2-(7-acetylimidazo[5,1-b]thiazol-2-yl)-6-((1R)-1-hydroxyethyl)-1-methyl-1-carbapen-2-em-3-carboxylate (A Mixture of Diastereomers)

In the same manner as in Example 46, 41.7 mg of the title compound was obtained from 54.8 mg of sodium(1S,5R,6S)-2-(7-acetylimidazo[5,1-b]thiazol-2-yl)-6-((1R)-1-hydroxyethyl)-1-methyl-1-carbapen-2-em-3-carboxylate and 100.0 mg of 1-(isopropoxycarbonyloxy)ethyl iodide.

NMR (CDCl$_3$) δ: 1.25–1.40 (12H, m), 1.59, 1.66 (total 3H, d each, J=5.5 Hz), 2.62 (3H, s), 3.34 (1H, m), 3.49 (1H, m), 4.29 (1H, m), 4.38 (1H, m), 4.90 (1H, m), 6.93 (1H, m), 8.03 (1H, m), 8.03 (1H, s), 8.43 (1H, s), 8.63, 8.64 (total 1H, s each) MS (TSP): 506 (M$^+$+H)

Example 48

1-(Cyclohexyloxycarbonyloxy)ethyl(1S,5R,6S)-2-(7-acetylimidazo[5,1-b]thiazol-2-yl)-6-((1R)-1-hydroxyethyl)-1-methyl-1-carbapen-2-em-3-carboxylate (A Mixture of Diastereomers)

In the same manner as in Example 46, 59.4 mg of the title compound was obtained from 58.1 mg of (1S,5R,6S)-2-(7-acetylimidazo[5,1-b]thiazol-2-yl)-6-((1R)-1-hydroxy-ethyl-1-methyl-1-carbapen-2-em-3-carboxylate sodium and 65.2 mg of 1-(cyclohexyloxycarbonyloxy)ethyl iodide.

NMR (CDCl$_3$) δ: 1.28 (3H, m), 1.38 (3H, m), 1.25–1.82 (8H, m), 1.59, 1.65 (total 3H, d each, J=5.4 Hz), 1.85–2.02 (2H, m), 2.62 (3H, s), 3.32 (1H, m), 3.48 (1H, m), 4.29 (1H, m), 4.38 (1H, m), 4.65 (1H, m), 6.95 (1H, m), 8.01, 8.02 (total 1H, s each), 8.61, 8.63 (total 1H, s each) MS (TSP): 546 (M$^+$+H)

Example 49

Cyclohexyloxycarbonyloxymethyl(1S,5R,6S)-2-(7-acetylimidazo[5,1-b]thiazol-2-yl)-6-((1R)-1-hydroxyethyl)-1-methyl-1-carbapen-2-em-3-carboxylate In the same manner as in Example 46, 68.7 mg of the title compound was obtained from 56.4 mg of sodium(1S,5R,6S)-2-(7-acetylimidazo[5,1-b]thiazol-2-yl)-6-((1R)-1-hydroxyethyl)-1-methyl-1-carbapen-2-em-3-carboxylate and 60.5 mg of cyclohexyloxycarbonyloxymethyl iodide.

NMR (CDCl$_3$) δ: 1.28 (3H, d, J=7.1 Hz), 1.37, (3H, d, J=6.2Hz), 1.25–1.55 (6H,m), 1.68–1.78 (2H,m), 1.83–1.96 (2H, m), 2.62 (3H, s), 3.35 (1H, dd, J$_1$=6.6 Hz, J$_2$=2.7 Hz), 3.50 (1H, m), 4.30 (1H, m), 4.39 (1H, dd, J$_1$=9.7 Hz, J$_2$=2.7 Hz), 4.64 (1H, m), 5.87, 5.96 (2H, ABq, J=5.8 Hz), 8.04 (1H, s), 8.57 (1H, s) MS (TSP): 532 (M$^+$+H)

Example 50

3-Phthalidyl(1S,5g,6S)-2-(7-acetylimidazo[5,1-b]thiazol-2-yl)-6-((1R)-1-hydroxyethyl)-1-methyl-1-carbapen-2-em-3-carboxylate (A Mixture of Diastereomers)

In the same manner as in Example 46, 39.7 mg of the title compound was obtained from 56.2 mg of sodium of (1S,5R,6S)-2-(7-acetylimidazo[5,1-b]thiazol-2-yl)-6-((1R)-1-hydroxyethyl)-1-methyl-1-carbapen-2-em-3-carboxylate and 60.3 mg of 3-phthalidyl bromide.

NMR (CDCl$_3$) δ: 1.12 (3H, m), 1.22 (3H, m), 2.46 (3H, s), 3.42 (1H, m), 3.75 (1H, m), 3.97 (1H, m), 4.30, (1H, m), 5.10, 5.12 (total 1H, s each), 7.65 (1H, s), 7.74 (1H, m), 7.83 (1H, m), 7.93 (1H, m), 8.33, 8.56 (total 1H, s each), 8.39, 8.60 (total 1H, s each) MS (TSP): 508 (M$^+$+H)

Example 51

1-(Acetoxy)ethyl(1S,5R,6S)-2-(7-acetylimidazo[5,1-b]thiazol-2-yl)-6-((1R)-1-hydroxyethyl)-1-methyl-1-carbapen-2-em-3-carboxylate (a mixture of diastereomers)

In the same manner as in Example 46, 79.3 mg of the title compound was obtained from 93.1 mg of sodium(1S,5R, 6S)-2-(7-acetylimidazo[5,1-b]thiazol-2-yl)-6-((1R)-1-hydroxyethyl)-1-methyl-1-carbapen-2-em-3-carboxylate and 118.0 mg of 1-(acetoxy)ethyl iodide.

NMR (CDCl$_3$) δ: 1.20 (3H, d, J=7.2 Hz), 1.31 (3H, m), 1.49, 1.54 (total 3H, d each, J=5.5 Hz), 1.99, 2.07 (total 3H, s each), 2.55 (3H, s), 3.28 (1H, m), 3.42 (1H, m), 4.22 (1H, m), 4.31 (1H, m), 6.98 (1H, m), 7.95, 7.96 (total 1H, s each), 8.53, 8.54 (total 1H, s each) MS (TSP): 462 (M$^+$+H)

Example 52

(5-Methyl-2-oxo-1,3-dioxolen-4-yl)methyl(1S5R, 6s)-2-(7-acetylimidazo[5,1-b]thiazol-2-yl)-6-((1R)-1-hydroxyethyl)-1-methyl-1-carbapen-2-em-3-carboxylate In the same manner as in Example 46, 94.1 mg of the title compound was obtained from 84.6 mg of sodium(1S,5R,6S)-2-(7-acetylimidazo[5,1-b]thiazol-2-yl)-6-((1R)-1-hydroxyethyl)-1-methyl-1-carbapen-2-em-3-carboxylate and 81.3 mg of (5-methyl-2-oxo-1,3-dioxolen-4-yl)methyl bromide.

NMR (CDCl$_3$) δ: 1.28 (3H, d, J=7.2 Hz), 1.37 (3H, d, J=6.3 Hz), 2.22 (3H, s), 2.61 (3H, s), 3.45 (1H, dd, J$_1$=6.5 Hz, J$_2$=2.8 Hz), 3.54 (1H, m), 4.29 (1H, m), 4.39 (1H, dd, J$_1$=9.8 Hz, J$_2$=2.8 Hz), 5.01, 5.09 (2H, ABq, J=13.8 Hz), 8.05 (1H, s), 8.40 (1H, s) MS (TSP): 488 (M$^+$+H)

Example 53

Sodium(1S,5R,6S)-2-(7-N-acetylaminomethylimidazo-[5,1-b]thiazol-2-yl)-6-((1R)-1-hydroxyethyl)-1-methyl-1-carbapen-2-em-3-carboxylate a) 4-Nitrobenzyl(1S,5R,6S)-2-(7-N-acetyl-aminomethylimidazo[5,1-b]thiazol-2-yl)-6-((1 g)-1-hydroxyethyl)-1-methyl-1-carbapen-2-em-3-carboxylate In substantially the same manner as in Example 1-a), 1.11 g of 4-nitrobenzyl(1S,5R,6S)-2-(7-N-acetylaminomethylimidazo[5,1-b]thiazol-2-yl)-6-((1R)-1-hydroxyethyl)-1-methyl-1-carbapen-2-em-3-carboxylate was obtained from 0.91 g of 4-nitrobenzyl(1R,3R,5R,6S)-6-((1R)-1-hydroxyethyl)-1-methyl-2-oxo-1-carbapenam-3-carboxylate and 1.09 g of 7-N-acetylaminomethyl-2-(tri-n-butylstannyl)imidazo[5,1-b]thiazole.

NMR (DMSO-d$_6$) δ: 1.15–1.20 (6H, m), 1.86 (3H, s), 3.41 (1H, dd, J$_1$=6.0 Hz, J$_2$=2.7 Hz), 3.07–3.17 (1H, m), 3.62 (1H, dd, J$_1$=8.8 Hz, J$_2$=2.7 Hz), 4.00–4.05 (1H, m), 4.16 (2H, d, J=5.8 Hz), 5.13 (1H, d, J=4.9 Hz), 5.39 (1H, d, J=13.8 Hz), 5.48 (1H, d, J=13.8 Hz), 7.71 (2H, d, J=8.5 Hz), 8.22 (2H, d, J=8.5 Hz), 8.21 (1H, s), 8.36 (1H, s), 8.43 (1H, t, J=5.8 Hz)

b) Sodium(1S,5R,6S)-2-(7-N-acetylaminomethylimidazo[5,1-b]thiazol-2-yl)-6-((1R)-1-hydroxyethyl))-1methyl-1-carbapen-2-em-3-carboxylate The title compound (0.52 g) was obtained from 175 mg of 4-nitrobenzyl(1S,5R,6S)-2-(7-N-acetylaminomethylimidazo[5,1-b]thiazol-2-yl)-6-((1R)-1-hydroxyethyl)-1-methyl-1-carbapen-2-em-3-carboxylate in substantially the same manner as in Example 1-b), except that the purification was carried out using Cosmosil 40C18-PREP (5% aqueous methanol).

NMR (D$_2$O) δ (HOD=4.80 ppm): 1.22 (3H, d, J=7.1 Hz), 1.31 (3H, d, J=6.3 Hz), 2.08 (3H, s), 4.37 (2H, S), 7.82 (1H, s), 8.04 (1H, s)

Example 54

Pivaloyloxymethyl(1S,5R,6S)-2-(7-N-acetylaminomethylimidazo[5,1-b]thiazol-2-yl)-6-((1R)-1-hydroxyethyl)-1-methyl-1-carbapen-2-em-3-carboxylate In substantially the same manner as in Example 2, 75 mg of the title compound was obtained from 81 mg of sodium (1S,5R,6S)-2-(7-N-acetylaminomethylimidazo[5,1-b]thiazol-2-yl)-6-((1R)-1-hydroxyethyl)-1-methyl-1-carbapen-2-em-3-carboxylate.

NMR (CDCl$_3$) δ: 1.21 (9H, s), 1.26 (3H, d, J=7.4 Hz), 1.36 (3H, d, J=6.3 Hz), 3.02 (3H, s), 3.32 (1H, d, J$_1$=6.6 Hz, J$_2$=2.8 Hz), 3.40–3.50 (1H, m), 4.25–4.35 (2H, m), 4.39–4.56 (2H, m), 5.87 (1H, d, J=5.6 Hz), 5.98 (1H, d, J=5.6 Hz), 6.30 (1H, s), 7.98 (1H, s), 8.35 (1H, s)

Example 55

1-(Acetoxy)ethyl(1S,5R,6S)-2-(7-N-acetylaminomethylimidazo[5,1-b]thiazol-2-yl)-6-((1R)-1-hydroxyethyl)-1-methyl-1-carbapen-2-em-3-carboxylate (A Mixture of Diastereomers)

In the same manner as in Example 46, 14.4 mg of the title compound was obtained from 45.2 mg of sodium(1S,5R,6S)-2-(7-N-acetylaminomethylimidazo[5,1-b]thiazol-2-yl)-6-((1R)-1-hydroxyethyl)-1-methyl-1-carbapen-2-em-3-carboxylate and 90.8 mg of 1-(acetoxy)ethyl iodide.

NMR (CDCl$_3$) δ: 1.26 (3H, m), 1.37 (3H, m), 1.56, 1.61 (total 3H, d each, J=5.5 Hz), 2.02 (3H, s), 2.06,2.14 (total 3H, s each), 2.10 (1H, s), 3.32 (1H, m), 3.42 (1H, m), 4.26–4.35 (2H, m), 4.40–4.55 (2H, m), 6.25 (1H, m), 7.03 (1H, m), 7.96, 7.97 (total 1H, s each), 8.43, 8.44 (total 1H, s each) MS (TSP): 491 (M$^+$+H)

Example 56

1-(Cyclohexyloxycarbonyloxy)ethyl(1S,5R,6S)-2-(7-N-acetylaminomethylimidazo[5,1-b]thiazol-2-yl)-6-((1R)-1-hydroxyethyl)-1-methyl-1-carbapen-2-em-3-carboxylate (A Mixture of Diastereomers)

In the same manner as in Example 46, 46.5 mg of the title compound was obtained from 45.1 mg of sodium(1S,5R,6S)-2-(7-N-acetylaminomethylimidazo[5,1-b]thiazol-2-yl)-6-((1R)-1-hydroxyethyl)-1-methyl-1-carbapen-2-em-3-carboxylate and 63.0 mg of 1-(cyclohexyloxycarbonyloxy) ethyl iodide.

NMR (CDCl$_3$) δ: 1.26 (3H, m), 1.37 (3H, m), 1.38–2.00 (11H, m), 1.59, 1.65 (total 3H, d each, J=5.5 Hz), 2.03 (3H, s), 3.33 (1H, m), 3.42 (1H, m), 4.26–4.38 (2H, m), 4.40–4.55 (2H, m), 4.65 (1H, m), 6.22 (1H, br.s), 6.94 (1H, m), 7.95 (1H, s), 8.43, 8.44 (total 1H, s each) MS (TSP): 575 (M$^+$+H)

Example 57

3-Phthalidyl(1S,5R,6S)-2-(7-N-acetylaminomethylimidazo[5,1-b]thiazol-2-yl)-6-((1R)-1-hydroxyethyl)-1-methyl-1-carbapen-2-em-3-carboxylate (A Mixture of Diastereomers)

In the same manner as in Example 46, 27.7 mg of the title compound was obtained from 33.2 mg of sodium(1S,5R,6S)-2-(7-N-acetylaminomethylimidazo[5,1-b]thiazol-2-yl)-6-((1R)-1-hydroxyethyl)-1-methyl-1-carbapen-2-em-3-carboxylate and 33.8 mg of 3-phthalidyl bromide.

NMR (CDCl$_3$) δ: 1.26–1.46 (6H, m), 1.70 (1H, m), 2.03, (3H, s), 3.33 (1H, m), 3.48 (1H, m), 4.15–4.35 (2H, m), 4.38–4.68 (2H, m), 6.22 (1H, m), 7.45, 7.46 (total 1H, s each), 7.64–7.81 (3H, m), 7.91–7.98 (1H, m), 8.16, 8.49 (total 1H, s each) MS (TSP): 537 (M$^+$+H)

Example 58

(5-Methyl-2-oxo-1,3-dioxolen-4-yl)methyl(1S,5R, 6S)-2-(7-N-acetylaminomethylimidazo[5,1-b] thiazol-2-yl)-6-((1R)-1-hydroxyethyl)-1-methyl-1-carbapen-2-em-3-carboxylate In the same manner as in Example 46, 25.0 mg of the title compound was obtained from 41.7 mg of sodium(1S,5R, 6S)-2-(7-N-acetylaminomethylimidazo[5,1-b]thiazol-2-yl)-6-((1R)-1-hydroxyethyl)-1-methyl-1-carbapen-2-em-3-carboxylate and 40.0 mg of (5-methyl-2-oxo-1,3-dioxolen-4-yl)methyl bromide.

NMR (CDCl$_3$) δ: 1.27 (3H, d, J=7.1 Hz), 1.36 (3H, d, J=6.2 Hz), 1.80 (1H, br.s), 2.03 (3H, s), 2.21 (3H, s), 3.33 (1H, dd, J$_1$=6.5 Hz, J$_2$=2.9 Hz), 3.47 (1H, m), 4.25–4.55 (2H, m), 5.01, 5.07 (2H, ABq, J=14.0 Hz), 6.32 (1H, m), 7.98 (1H, s), 8.20 (1H, s) MS (TSP): 517 (M$^+$+H)

Example 59

1-[(Cyclohexylmethoxy)carbonyloxy]ethyl(1S,5R, 6S)-2-(7-N-acetylaminomethylimidazo[5,1-b] thiazol-2-yl)-6-((1R)-1-hydroxyethyl)-1-methyl-1-carbapen-2-em-3-carboxylate (a mixture of diastereomers)

In the same manner as in Example 46, 12.8 mg of the title compound was obtained from 24.3 mg of sodium(1S,5R, 6S)-2-(7-N-acetylaminomethylimidazo[5,1-b]thiazol-2-yl)-6-((1R)-1-hydroxyethyl)-1-methyl-1-carbapen-2-em-3-carboxylate and 71.0 mg of 1-[(cyclohexylmethoxy) carbonyloxy]ethyl iodide.

NMR (CDCl$_3$) δ: 0.92–1.05 (3H, m), 1.16–1.25 (2H, m), 1.26 (3H, m), 1.37 (3H, m), 1.60–1.78 (9H, m), 2.03 (3H, s), 3.31 (1H, m), 3.43 (1H, m), 3.93–4.05 (2H, m), 4.25–4.35 (2H, m), 4.40–4.56 (2H, m), 6.20 (1H, m), 6.92 (1H, m), 7.96 (1H, s), 8.44, 8.45 (total 1H, s each) MS (TSP): 589 (M$^+$+H)

Example 60

(1R,2S,5R)-(1)-Menthyloxycarbonyloxymethyl(1S, 5R,6S)-2-(7-N-acetylaminomethylimidazo[5,1-b] thiazol-2-yl)-6-((1R)-1-hydroxyethyl)-1-methyl-1-carbapen-2-em-3-carboxylate In the same manner as in Example 46, 38.1 mg of the title compound was obtained from 33.3 mg of sodium(1S,5R, 6S)-2-(7-N-acetylaminomethylimidazo[5,1-b]thiazol-2-yl)-6-((1R)-1-hydroxyethyl)-1-methyl-1-carbapen-2-em-3-carboxylate and 39.8 mg of (1R,2S,5R)-(1)-menthyloxycarbonyloxymethyl iodide.

NMR (CDCl$_3$) δ: 0.77 (3H, d, J=7.6 Hz), 0.89 (3H, d, J=7.1 Hz), 0.95–1.15 (2H, m), 1.26 (3H, d, J=7.2 Hz), 1.36 (3H, d, J=6.1 Hz), 1.37–1.52 (2H, m), 1.64–1.72 (2H, m), 1.80–2.10 (3H, m), 2.03 (3H, s), 3.32 (1H, dd, J$_1$=6.6 Hz, J$_2$=2.8 Hz), 3.44 (1H, m), 4.25–4.35 (2H, m), 4.45–4.60 (3H, m), 5.91, 5.94 (2H, ABq, J=5.5 Hz), 6.41 (1H, m), 7.97 (1H, S), 8.40 (1H, s) MS (TSP): 617 (M$^+$+H)

Example 61

1-(Cyclohexyloxycarbonyloxy)-n-propyl(1S,5R,6S)-2-(7-N-acetylaminomethylimidazo[5,1-b]thiazol-2-yl)-6-((1R)-1-hydroxyethyl)-1-methyl-1-carbapen-2-em-3-carboxylate (a mixture of diastereomers)

In the same manner as in Example 46, 15.9 mg of the title compound was obtained from 30.4 mg of sodium(1S,5R, 6S)-2-(7-N-acetylaminomethylimidazo[5,1-b]thiazol-2-yl)-6-((1R)-1-hydroxyethyl)-1-methyl-1-carbapen-2-em-3-carboxylate and 33.3 mg of 1-(cyclohexyloxycarbonyloxy)-n-propyl iodide.

NMR (CDCl$_3$) δ: 0.99, 1.07 (total 3H, t each, J=7.7 Hz), 1.25 (3H, m), 1.36 (3H, m), 1.30–1.80 (8H, m), 1.85–2.05 (4H, m), 2.03 (3H, s), 3.31 (1H, m), 3.43 (1H, m), 4.26–4.35 (1H, m), 4.45–4.50 (1H, m), 4.56–4.72 (1H, m), 6.27 (1H, m), 6.80 (1H, m), 7.94, 7.95 (total 1H, s each), 8.45, 8.47 (total 1H, s each) MS (TSP): 589 (M$^+$+H)

Example 62

Sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate a) 4-Nitrobenzyl(1S,5R,6S)-6-((1R)-1-hydroxyethyl)-2-(7-methanesulfonylimidazo[5,1-b] thiazol-2-yl)-1-methyl-1-carbapen-2-em-3-carboxylate In substantially the same manner as in Example 1-a), 123 mg of 4-nitrobenzyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate was obtained from 109 mg of 4-nitrobenzyl(1R,3R,5R,6S)-6-((1R)-1-hydroxyethyl)-1-methyl-2-oxo-1-carbapenam-3-carboxylate and 141 mg of 7-methanesulfonyl-2-(tri-n-butylstannyl)imidazo[5,1-b] thiazole.

NMR (CDCl$_3$) δ: 1.30 (3H, d, J=7.2 Hz), 1.37 (3H, d, J=6.3 Hz), 3.21 (3H, s), 3.36 (1H, dd, J$_1$=6.9 Hz, J$_2$=2.8 Hz), 3.45–3.55 (1H, m), 4.20–4.30 (1H, m), 4.39 (1H, dd, J$_1$=9.6 Hz, J$_2$=2.8 Hz), 5.30 (1H, d, J=13.5 Hz), 5.52 (1H, d, J=13.5 Hz), 7.69 (2H, d, J=8.9 Hz), 8.10 (1H, s), 8.24 (2H, d, J=8.9 Hz), 8.43 (1H, s)

b) Sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate The title compound (83.4 mg) was obtained from 123 mg of 4-nitrobenzyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate, except that the purification was carried out using Cosmosil40C18-PREP (5% aqueous methanol).

NMR (D$_2$O) δ (HOD=4.80 ppm): 1.25 (3H, d, J=7.0 Hz), 1.32 (3H, d, J=6.3 Hz), 3.30 (3H, s), 3.52–3.55 (1H, m), 3.55–3.66 (1H, m), 4.24–4.35 (2H, m), 8.03 (1H, s), 8.28 (1H, s)

Example 63

Pivaloyloxymethyl(1S,5R,6S)-6-((1R)-1-hydroxyethyl)-2-(7-methanesulfonylimidazo[5,1-b] thiazol-2-yl)-1-methyl-1-carbapen-2-em-3-carboxylate In substantially the same manner as in Example 2, 68.5 mg of the title compound was obtained from 54.7 mg of sodium(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate.

NMR (CDCl$_3$) δ: 1.21 (9H, s), 1.28 (3H, d, J=7.3 Hz), 1.34 (3H, d, J=6.3 Hz), 3.23 (3H, s), 3.40 (1H, dd, J$_1$=5.8 Hz, J$_2$=2.7 Hz), 3.50–3.61 (1H, m), 4.23–4.31 (1H, m), 4.40 (1H, dd, J$_1$=9.7 Hz, J$_2$=2.7 Hz), 5.87 (1H, d, J=5.7 Hz), 5.98 (1H, d, J=5.7 Hz), 8.25 (1H, s), 8.51 (1H, s)

Example 64

1-(Acetoxy)ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (A Mixture of Diastereomers)

In the same manner as in Example 46, 22.2 mg of the title compound was obtained from 55.8 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 50.0 mg of 1-(acetoxy)ethyl iodide.

NMR (CDCl$_3$) δ: 1.21 (3H, d, J=7.4 Hz), 1.30 (3H, m), 1.50, 1.54 (total 3H, d each, J=5.5 Hz), 2.02, 2.10 (total 3H, s each), 3.28 (1H, m), 3.40 (1H, m), 4.22 (1H, m), 4.30 (1H, m), 6.95 (1H, m), 8.03, 8.04 (total 1H, s each), 8.48 (1H, s) MS (TSP): 498 (M$^+$+H)

Example 65

1-(Cyclohexyloxycarbonyloxy)ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (A Mixture of Diastereomers)

In the same manner as in Example 46, 19.0 mg of the title compound was obtained from 24.8 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 52.9 mg of 1-(cyclohexyloxycarbonyloxy)ethyl iodide.

NMR (CDCl$_3$) δ: 1.20 (3H, d, J=7.2 Hz), 1.30 (3H, m), 1.35–1.70 (8H, m), 1.52, 1.58 (total 3H, d each, J=5.4 Hz), 1.80–2.00 (2H, m), 3.15 (3H, s), 3.27 (1H, m), 3.38 (1H, m), 4.20 (1H, m), 4.28 (1H, m), 4.58 (1H, m), 6.87 (1H, m), 8.01 (1H, s), 8.49, 8.50 (total 1H, s each) MS (TSP): 582 (M$^+$+H)

Example 66

3-Phthalidyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (a Mixture of Diastereomers)

In the same manner as in Example 46, 23.5 mg of the title compound was obtained from 27.6 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 30.0 mg of 3-phthalidyl bromide.

NMR (CDCl$_3$) δ: 1.29 (3H, m), 1.32 (3H, m), 2.10 (1H, br.s), 3.21, 3.22 (total 1H, s each), 3.36 (1H, m), 3.50 (1H, m), 4.24 (1H, m), 4.38 (1H, m), 7.44, 7.45 (total 1H, s each), 7.63–7.80 .(3H, m), 7.81, 7.91 (total 1H, s each), 8.07, 8.12 (total 1H, s each), 8.32, 8.60 (total 1H, s each) MS (TSP): 544 (M$^+$+H)

Example 67

(5-Methyl-2-oxo-1,3-dioxolen-4-yl)methyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate In the same manner as in Example 46, 17.9 mg of the title compound was obtained from 23.6 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 34.0 mg of (5-methyl-2-oxo-1,3-dioxolen-4-yl)methyl bromide.

NMR (CDCl$_3$) δ: 1.29 (3H, d, J=7.4 Hz), 1.37 (3H, d, J=6.3 Hz), 2.22 (3H, s), 3.23 (3H, s), 3.36 (1H, dd, J$_1$=6.5 Hz, J$_2$=2.8 Hz), 3.49 (1H, m), 4.29 (1H, m), 4.38 (1H, dd, J$_1$=9.6 Hz, J$_2$=2.8 Hz), 5.02, 5.09 (2H, ABq, J=14.0 Hz), 8.12 (1H, s), 8.34 (1H, s) MS (TSP): 524 (M$^+$+H)

Example 68

1-[(Cyclohexylmethoxy)carbonyloxy]ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (A Mixture of Diastereomers)

In the same manner as in Example 46, 28.6 mg of the title compound was obtained from 32.2 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 52.5 mg of 1-[(cyclohexylmethoxy)carbonyloxy]ethyl iodide.

NMR (CDCl$_3$) δ: 0.86–1.06 (3H, m), 1.10–1.55 (3H, m), 1.27 (3H, d, J=7.1 Hz), 1.37 (3H, m), 1.60 (3H, d, J=5.5 Hz), 1.58 (3H, d, J=5.5 Hz), 1.60–1.81 (8H, m), 3.21 (3H, s), 3.45 (1H, m), 3.92–4.05 (2H, m), 4.28 (1H, m), 4.35 (1H, m), 6.93 (1H, m), 8.08, 8.09 (total 3H, s each), 8.56, 8.57 (total 3H, s each) MS (TSP): 596 (M$^+$+H)

Example 69

(1-Methylcyclohexan-1-yl)carbonyloxymethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate In the same manner as in Example 46, 28.6 mg of the title compound was obtained from 26.3 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 45.0 mg of (1-methylcyclohexan-1-yl)carbonyloxymethyl iodide.

NMR (CDCl$_3$) δ: 1.15 (3H, s), 1.27 (3H, d, J=7.2 Hz), 1.37 (3H, d, J=6.3 Hz), 1.28–1.70 (8H, m), 1.96–2.05 (1H, m), 3.22 (3H, s), 3.35 (1H, dd, J$_1$=6.6 Hz, J$_2$=2.8 Hz), 3.46 (1H, m), 4.29 (1H, m), 4.36 (1H, dd, J$_1$=9.8 Hz, J$_2$=2.8 Hz), 5.91, 5.97 (2H, ABq, J=5.6 Hz), 8.11 (1H, s), 8.46 (1H, s) MS (TSP): 566 (M$^+$+H)

Example 70

1-(Cyclohexyloxycarbonyloxy)-n-propyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (A Mixture of Diastereomers)

In the same manner as in Example 46, 17.2 mg of the title compound was obtained from 25.0 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 36.0 mg of 1-(cyclohexyloxycarbonyloxy)-n-propyl iodide.

NMR (CDCl$_3$) δ: 1.02, 1.09 (total 3H, t each, J=7.4 Hz), 1.20–2.05 (11H, m), 1.27 (3H, m), 1.36 (3H, m), 3.22 (3H, s), 3.34 (1H, m), 3.48 (1H, m), 4.29 (1H, m), 4.36 (1H, m), 4.65 (1H, m), 6.80 (1H, m), 8.07 (1H, s), 8.59, 8.60 (total 1H, s each) MS (TSP): 596 (M$^+$+H)

Example 71

Sodium(1S,5R,6S)-2-(7-hydroxyacetylimidazo[5,1-b]thiazol-2-yl)-6-((1R)-1-hydroxyethyl)-1-methyl-1-carbapen-2-em-3-carboxylate a) 4-Nitrobenzyl(1S,5R,6S)-2-(7-t-butyldimethylsilyloxyacetylimidazo[5,1-b]thiazol-2-yl)-6-((1R)-1-hydroxyethyl)-1-methyl-1-carbapen-2-em-3-carboxylate In the same manner as in Example 1-a), 397 mg of 4-nitrobenzyl(1S,5R,6S)-2-(7-t- butyldimethylsilyloxyacetylimidazo[5,1-b]thiazol-2-yl)-6-((1R)-1-hydroxyethyl)-1-methyl-1-carbapen-2-em-3-carboxylate was obtained from 567 mg of 4-nitrobenzyl(1R,3R,5R,6S)-6-((1R)-1-hydroxyethyl)-1-methyl-2-oxo-1-carbapenam-3-carboxylate and 1.10 g of 7-t-butyldimethylsilyloxyacetyl-2-(tri-n-butylstannyl)-imidazo[5,1-b]thiazole.

NMR (CDCl$_3$) δ: 0.15 (6H, s), 0.96 (9H, s), 1.30 (3H, d, J=7.4 Hz), 1.40 (3H, d, J=6.3 Hz), 3.38 (1H, m), 3.50 (1H, m), 4.32 (1H, m), 4.40 (1H, dd, J$_1$=9.5 Hz, J$_2$=2.9 Hz), 5.08 (2H, s), 5.28 (1H, d, J=14.1 Hz), 5.52 (1H, d, J=14.1 Hz), 7.68 (2H, d, J=8.8 Hz), 7.98 (1H, s), 8.25 (2H, d, J=8.8 Hz), 8.51 (1H, s)

b) 4-Nitrobenzyl(1S,5R,6S)-2-(7-hydroxyacetylimidazo[5,1-b]thiazol-2-yl)-6-((1R)-1-hydroxyethyl)-1-methyl-1-carbapen-2-em-3-carboxylate In the same manner as in Example 36-b), 193 mg of 4-nitrobenzyl(1S,5R,6S)-2-(7-hydroxyacetylimidazo[5,1-b]thiazol-2-yl)-6-((1R)-1-hydroxyethyl)-1-methyl-1-carbapen-2-em-3-carboxylate was obtained from 397 mg of 4-nitrobenzyl(1S,5R,6S)-2-(7-t-butyldimethylsilyloxyacetylimidazo[5,1-b]thiazol-2-yl)-6-((1R)-1-hydroxyethyl)-1-methyl-1-carbapen-2-em-3-carboxylate.

NMR (CDCl$_3$) δ: 1.32 (3H, d, J=7.2 Hz), 1.40 (3H, d, J=6.3 Hz), 3.40 (1H, dd, J$_1$=6.3 Hz, J$_2$=2.8 Hz), 3.51 (2H, m), 4.33 (1H, m), 4.42 (1H, dd, J$_1$=9.6 Hz, J$_2$=2.8 Hz), 4.91 (2H, d, J=4.4 Hz), 5.28 (1H, d, J=13.7 Hz), 5.53 (1H, d, J=13.7 Hz), 7.68 (2H, d, J=8.8 Hz), 8.02 (1H, s), 8.24 (2H, d, J=8.8 Hz), 8.51 (1H, s)

c) Sodium(1S,5R,6S)-2-(7-hydroxyacetylimidazo[5,1-b]thiazol-2-yl)-6-((1R)-1-hydroxyethyl)-1-methyl-1-carbapen-2-em-3-carboxylate In the same manner as in Example 1-b), 259 mg of the title compound was obtained from 407 mg of 4-nitrobenzyl(1S,5R,6S)-2-(7-hydroxyacetylimidazo[5,1-b]thiazol-2-yl)-6-((1R)-1-hydroxyethyl)-1-methyl-1-carbapen-2-em-3-carboxylate.

NMR (D$_2$O) δ (HOD=4.80 ppm): 1.20 (3H, d, J=6.7 Hz), 1.33 (3H, d, J=6.3 Hz), 3.50 (2H, m), 4.30 (2H, m), 4.75 (2H, m), 7.88 (1H, s), 8.02 (1H, s)

Example 72

Pivaloyloxymethyl(1S,5R,6S)-2-(7-hydroxyacetylimidazo[5,1-b]thiazol-2-yl)-6-((1R)-1-hydroxyethyl)-1-methyl-1-carbapen-2-em-3-carboxylate In the same manner as in Example 2, 56.2 mg of the title compound was obtained from 60.4 mg of sodium(1S,5R,6S)-2-(7-hydroxyacetylimidazo[5,1-b]thiazol-2-yl)-6-((1R)-1-hydroxyethyl)-1-methyl-1-carbapen-2-em-3-carboxylate.

NMR (CDCl$_3$) δ: 1.20 (9H, s), 1.30 (3H, d, J=7.4 Hz), 1.38 (3H, d, J=6.2 Hz), 3.36 (1H, dd, J$_1$=6.7 Hz, J$_2$=2.9 Hz), 3.50 (2H, m), 4.30 (1H, m), 4.40 (1H, dd, J$_1$=9.9 Hz, J$_2$=2.9 Hz), 4.92 (2H, d, J=3.8 Hz), 5.87 (1H, d, J=5.5 Hz), 6.00 (1H, d, J=5.5 Hz), 8.06 (1H, s), 8.51 (1H, s)

Example 73

1-(Acetoxy)ethyl(1S,5R,6S)-2-(7-hydroxyacetylimidazo[5,1-b]thiazol-2-yl)-6-((1R)-1-hydroxyethyl)-1-methyl-1-carbapen-2-em-3-carboxylate (A Mixture of Diastereomers)

In the same manner as in . . . , the title compound (16.6 mg) was obtained from 25.0 mg of sodium(1S,5R,6S)-2-(7-hydroxyacetylimidazo[5,1-b]thiazol-2-yl)-6-((1R)-1-hydroxyethyl)-1-methyl-1-carbapen-2-em-3-carboxylate and 30.0 mg of 1-(acetoxy)ethyl iodide.

NMR (CDCl$_3$) δ: 1.21 (3H, d, J=7.4 Hz), 1.31 (total 3H, d each, J=6.2 Hz), 1.49, 1.54 (total 3H, d each, J=5.5 Hz), 1.65 (1H, br.s), 2.00, 2.07 (total 3H, s each), 3.28 (1H, m), 3.37–3.50 (2H, mn), 4.22 (1H, m), 4.32 (1H, m), 4.84 (1H, s), 4.85 (1H, s), 6.97 (1H, m), 7.97, 7.98 (total 1H, s each), 8.53 (1H, s) MS (FAB$^+$): 478 (M$^+$+H)

Example 74

1-(Cyclohexyloxycarbonyloxy)ethyl(1S,5R,6S)-2-(7-hydroxyacetylimidazo[5,1-b]thiazol-2-yl)-6-((1R)-1-hydroxyethyl)-1-methyl-1-carbapen-2-em-3-carboxylate (A Mixture of Diastereomers)

In the same manner as in Example 46, 22.7 mg of the title compound was obtained from 22.0 mg of sodium(1S,5R,6S)-6-((1R)-1-hydroxyethyl)-2-(7-hydroxyacetylimidazo[5,1-b]thiazol-2-yl)-1-methyl-1-carbapen-2-em-3-carboxylate and 45.0 mg of 1-(cyclohexyloxycarbonyloxy)ethyl iodide.

NMR (CDCl$_3$) δ: 1.10–1.40 (7H, m), 1.53, 1.58 (total 3H, d each, J=5.5 Hz), 1.42–1.75 (4H, m), 1.78–2.00 (6H, m), 2.12 (1H, br.s), 3.28 (1H, m), 3.38–3.50 (2H, m), 4.23 (1H, m), 4.31 (1H, m), 4.59 (1H, m), 4.84 (1H, s), 4.85 (1H, s), 6.87 (1H, m), 7.97 (1H, s), 8.53, 8.54 (total 1H, s each) MS (FAB$^+$): 562 (M$^+$+H)

Example 75

3-Phthalidyl(1S,5R,6S)-2-(7-hydroxyacetylimidazo[5,1-b]thiazol-2-yl)-6-((1R)-1-hydroxyethyl)-1-methyl-1-carbapen-2-em-3-carboxylate (A Mixture of Diastereomers)

In the same manner as in example 46, 24.8 mg of the title compound was obtained from 29.0 mg of sodium(1S,5R,6S)-2-(7-hydroxyacetylimidazo[5,1-b]thiazol-2-yl)-6-((1R)-1-hydroxyethyl)-1-methyl-1-carbapen-2-em-3-carboxylate and 29.9 mg of 3-phthalidyl bromide.

NMR (CDCl$_3$) δ: 1.25–1.38 (6H, m), 1.68–1.75 (2H, m), 3.38 (1H, m), 3.52 (1H, m), 4.25 (1H, m), 4.38 (1H, m), 4.91 (1H, s), 4.93 (1H, s), 7.45,7.46 (total 1H, s each), 7.65–7.82 (3H, m), 7.92–7.95 (1H, m), 8.04, 8.08 (total 1H, s each), 8.41, 8.70 (total 1H, s each) MS (FAB$^+$): 524 (M$^+$+H)

Example 76

(5-Methyl-2-oxo-1,3-dioxolen-4-yl)methyl(1S,5R,6S)-2-(7-hydroxyacetylimidazo[5,1-b]thiazol-2-yl)-6-((1R)-1-hydroxyethyl)-1-methyl-1-carbapen-2-em-3-carboxylate In the same manner as in Example 46, 23.0 mg of the title compound was obtained from 27.2 mg of sodium(1S,5R,6S)-2-(7-hydroxyacetylimidazo[5,1-b]thiazol-2-yl)-6-((1R)-1-hydroxyethyl)-1-methyl-1-carbapen-2-em-3-carboxylate and 30.0 mg of (5-methyl-2-oxo-1,3-dioxolen-4-yl)methylbromide.

NMR (CDCl$_3$) δ: 1.31 (3H, d, J=7.2 Hz), 1.38 (3H, d, J=6.2 Hz), 1.92 (1H, br.s), 2.23 (3H, s), 3.38 (1H, dd, J$_1$=6.6 Hz, J$_2$=2.9 Hz), 3.49 (1H, br, s), 4.31 (1H, m), 4.40 (1H, dd, J$_1$=9.8 Hz, J$_2$=2.9 HZ), 4.91 (1H, s), 4.93 (1H, s), 5.00, 5.06 (2H, ABq, J=14.0 Hz), 8.07 (1H, s), 8.41 (1H, s) MS (FAB$^+$): 504 (M$^+$+H)

Example 77

(1-Methylcyclohexan-1-yl)carbonyloxymethyl(1S,5R,6S)-2-(7-hydroxyacetylimidazo[5,1-b]thiazol-2-yl)-6-((1R)-1-hydroxyethyl)-1-methyl-1-carbapen-2-em-3-carboxylate In the same manner as in Example 46, 26.4 mg of the title compound was obtained from 20.7 mg of sodium(1S,5R, 6S)-2-(7-hydroxyacetylimidazo[5,1-b]thiazol-2-yl)-6-((1R)-1-hydroxyethyl)-1-methyl-1-carbapen-2-em-3-carboxylate and 30.0 mg of (1-methylcyclohexan-1-yl)carbonyloxymethyl iodide.

NMR (CDCl$_3$) δ: 1.14 (3H, s), 1.20–1.60 (9H, m), 1.30 (3H, d, J=7.4 Hz), 1.37 (3H, d, J=6.3 Hz), 1.95–2.05 (2H, m), 3.36 (1H, dd, J$_1$=6.5 Hz, J$_2$=2.8 Hz), 4.30 (1H, m), 4.40 (1H, dd, J$_1$=9.7 Hz, J$_2$=2.8 Hz), 4.92 (2H, s), 5.92, 5.98 (2H, ABq, J=5.6 Hz), 8.07 (1H, s), 8.50 (1H, s) MS (TSP): 546 (M$^+$+H)

Example 78

1-[(Cyclohexylmethoxy)carbonyloxy]ethyl(1S,5R,6S)-2-(7-hydroxyacetylimidazo[5,1-b]thiazol-2-yl)-6-((1R)-1-hydroxyethyl)-1-methyl-1-carbapen-2-em-3-carboxylate (A Mixture of Diastereomers)

In the same manner as in Example 46, 6.12 mg of the title compound was obtained from 21.2 mg of sodium(1S,5R,6S)-2-(7-hydroxyacetylimidazo[5,1-b]thiazol-2-yl)-6-((1R)-1-hydroxyethyl)-1-methyl-1-carbapen-2-em-3-carboxylate and 33.0 mg of 1-[(cyclohexylmethoxy)carbonyloxy]ethyl iodide.

NMR (CDCl$_3$) δ: 0.88–1.10 (2H, m), 1.15–1.30 (1H, m), 1.29 (3H, m), 1.38 (3H, m), 1.60, 1.66 (total 3H, d each, J=5.5 Hz), 1.65–1.90 (9H, m), 3.35 (1H, m), 3.50 (1H, m), 3.92–4.05 (2H, m), 4.29 (1H, m), 4.38 (1H, m), 4.91 (1H, s), 4.92 (1H, s), 6.94 (1H, m), 8.03 (1H, s), 8.60, 8.62 (total 1H, s each) MS (TSP): 576 (M$^+$+H)

Example 79

1-(Cyclohexyloxycarbonyloxy)-n-propyl(1S,5R,6S)-2-(7-hydroxyacetylimidazo[5,1-b]thiazol-2-yl)-6-((1R)-1-hydroxyethyl)-1-methyl-1-carbapen-2-em-3-carboxylate (A Mixture of Diastereomers)

In the same manner as in Example 46, 18.3 mg of the title compound was obtained from 21.7 mg of sodium(1S,5R,6S)-2-(7-hydroxyacetylimidazo[5,1-b]thiazol-2-yl)-6-((1R)-1-hydroxyethyl)-1-methyl-1-carbapen-2-em-3-carboxylate and 22.0 mg of 1-(cyclohexyloxycarbonyloxy)-n-propyl iodide.

NMR (CDCl$_3$) δ: 1.00, 1.08 (total 3H, t each, J=7.6 Hz), 1.26–1.80 (13H, m), 1.85–2.05 (6H, m), 3.35 (1H, m), 3.50 (2H, m), 4.30 (1H, br.m), 4.39 (1H, m), 4.65 (1H, m), 4.91 (1H, s), 4.92 (1H, s), 6.80, 6.82 (total 1H, d each, J=6.0 Hz), 8.02, 8.03 (total 1H, s each), 8.62, 8.64 (total 1H, s each) MS (TSP): 576 (M$^+$+H)

Example 80

Sodium(1S,5R,6S)-2-[7-(N,N-dimethylcarbamoyl)acetylimidazo[5,1-b]thiazol-2-yl]-6-((1R)-1-hydroxyethyl)-1-methyl-1-carbapen-2-em-3-carboxylate a) 4-Nitrobenzyl(1S,5R,6S)-2-[7-(N,N-dimethylcarbamoyl)acetylimidazo[5,1-b]thiazol-2-yl]-6-((1R)-1-hydroxyethyl)-1-methyl-1-carbapen-2-em-3-carboxylate In substantially the same manner as in Example 1-a), 245 mg of 4-nitrobenzyl(1S,5R,6S)-2-[7-(N,N-dimethylcarbamoyl)acetylimidazo[5,1-b]thiazol-2-yl]-6-((1R)-1-hydroxyethyl)-1-methyl-1-carbapen-2-em-3-carboxylate was obtained from 254 mg of 4-nitrobenzyl(1R,3R,5R,6S)-6-((1R)-1-hydroxyethyl)-1-methyl-2-oxo-1-carbapenam-3-carboxylate and 290 mg of 7-(N,N-dimethylcarbamoylacetyl)-2-(tri-n-butylstannyl)imidazo[5,1-b]thiazole.

NMR (CDCl$_3$) δ: 1.30 (3H, d, J=7.2 Hz), 1.37 (3H, d, J=6.2 Hz), 3.07 (3H, s), 3.25 (3H, s), 3.35–3.41 (1H, m), 3.43 (2H, s), 4.18–4.25 (1H, m), 4.35–4.42 (1H, m), 5.31 (1H, d, J=13.5 Hz), 5.52 (1H, d, J=13.5 Hz), 7.30 (1H, s), 7.70 (2H, d, J=8.8 Hz), 8.55 (1H, s)

b) Sodium(1S,5R,6S)-2-[7-(N,N-dimethylcarbamoyl)acetylimidazo[5,1-b]thiazol-2-yl]-6-((1R)-1-hydroxyethyl)-1-methyl-1-carbapen-2-em-3-carboxylate The title compound (143.2 mg) was obtained from 245 mg of 4-nitrobenzyl(1S,5R,6S)-2-[7-(N,N-dimethylcarbamoyl)acetylimidazo[5,1-b]thiazol-2-yl]-6-((1R)-1-hydroxyethyl)-1-methyl-1-carbapen-2-em-3-carboxylate in substantially the same manner as in Example 1-b), except that the purification was carried out using Cosmosil 40C18-PREP (5% aqueous methanol).

NMR (D$_2$O) δ (HOD=4.80 ppm): 1.24 (3H, d, J=7.1 Hz), 1.32 (3H, d, J=6.3 Hz), 2.98 (3H, s), 3.10 (3H, s), 3.52 (1H, dd, J$_1$=6.1 Hz, J$_2$=2.4 Hz), 3.55–3.66 (1H, m), 4.07 (1H, d, J=16.5 Hz), 4.20 (1H, d, J=16.5 Hz), 4.24–4.35 (2H, m), 8.05 (1H, s), 8.17 (1H, s)

Example 81

Pivaloyloxymethyl(1S,5R,6S)-2-[7-(N,N-dimethylcarbamoyl)acetylimidazo[5,1-b]thiazol-2-yl-6-((1R)-1-hydroxyethyl)-1-methyl-1-carbapen-2-em-3-carboxylate In substantially the same manner as in Example 2, 34.1 mg of the title compound was obtained from 48.5 mg of sodium(1S,5R,6S)-2-[7-(N,N-dimethylcarbamoyl)acetylimidazo-[5,1-b]thiazol-2-yl]-6-((1R)-1-hydroxyethyl)-1-methyl-1-carbapen-2-em-3-carboxylate.

NMR (CDCl$_3$) δ: 1.21 (9H, s), 1.27 (3H, d, J=7.1 Hz), 1.35 (3H, d, J=6.3 Hz), 3.01 (3H, s), 3.10 (3H, s), 3.27 (1H, dd, J$_1$=7.5 Hz, J$_2$=2.5 Hz), 3.42–3.53 (1H, m), 4.16 (2H, s), 4.16–4.25 (1H, m), 4.27–4.33 (1H, m), 5.89 (1H, d, J=5.5 Hz), 5.98 (1H, d, J=5.5 Hz), 8.04 (1H, s), 8.55 (1H, S)

Example 82

(1-Methylcyclohexan-1-yl)carbonyloxymethyl(1S,5R,6S)-2-[7-(N,N-dimethylcarbamoyl)acetylimidazo[5,1-b]thiazol-2-yl]-6-((1R)-1-hydroxyethyl)-1-methyl-1-carbapen-2-em-3-carboxylate In the same manner as in Example 46, 25.5 mg of the title compound was obtained from 25.7 mg of sodium(1S,5R,6S)-2-[7-(N,N-dimethylcarbamoyl)acetylimidazo[5,1-b]thiazol-2-yl]-6-((1R)-1-hydroxyethyl)-1-methyl-1-carbapen-2-em-3-carboxylate and 31.5 mg of (1-methylcyclohexan-1-yl)carbonyloxymethyl iodide.

NMR (CDCl$_3$) δ: 1.15 (3H, s), 1.22–1.30 (2H, m), 1.25 (3H, d, J=7.4 Hz), 1.36 (3H, d, J=6.2 Hz), 1.42–1.75 (4H, m), 1.97–2.08 (2H, m), 3.01 (3H, s), 3.09 (3H, s), 3.31 (1H, dd, J$_1$=7.2 Hz, J$_2$=2.8 Hz), 3.48 (1H, m), 4.17 (1H, s), 4.18 (1H, s), 4.23 (1H, m), 4.33 (1H, dd, J.=9.7 Hz, J$_2$=2.8 Hz), 5.92, 5.97 (2H, ABq, J=5.5 Hz), 8.05 (1H, s), 8.53 (1H, s) MS (TSP): 601 (M$^+$+H)

Example 83

1-(Cyclohexyloxycarbonyloxy)ethyl(1S,5R,6S)-2-[7-(N,N-dimethylcarbamoyl)acetylimidazo[5,1-b]thiazol-2-yl]-6-((1R)-1-hydroxyethyl)-1-methyl-1-carbapen-2-em-3-carboxylate (A Mixture of Diastereomers)

In the same manner as in Example 46, 12.8 mg of the title compound was obtained from 28.2 mg of sodium(1S,5R, 6S)-2-[7-(N,N-dimethylcarbamoyl)acetylimidazo[5,1-b]thiazol-2-yl]-6-((1R)-1-hydroxyethyl)-1-methyl-1-carbapen-2-em-3-carboxylate and 30.0 mg of 1-(cyclohexyloxycarbonyloxy)ethyl iodide.

NMR (CDCl$_3$) δ: 1.22 (3H, d, J=7.4 Hz), 1.35 (3H, m), 1.25–1.80 (9H, m), 1.60, 1.65 (total 3H, d each, J=5.5 Hz), 1.95–2.04 (2H,m), 3.01 (3H, s), 3.09, 3.10 (total 3H, s each), 3.30 (1H, m), 3.47 (1H, m), 4.16, 4.18 (total 2H, s each), 4.25 (1H, m), 4.35 (1H, m), 4.68 (1H, m), 6.94 (1H, m), 8.01, 8.02 (total 1H, s each), 8.63, 8.65 (total 1H, s each) MS (TSP): 617 (M$^+$+H)

Example 84

3-Phthalidyl(1S,5R,6S)-2-[7-(N,N-dimethylcarbamoyl)acetylimidazo[5,1-b]thiazol-2-yl]-6-((1R)-1-hydroxyethyl)-1-methyl-1-carbapen-2-em-3-carboxylate (A Mixture of Diastereomers)

In the same manner as in Example 46, 21.6 mg of the title compound was obtained from 26.0 mg of sodium(1S,5R,6S)-2-[7-(N,N-dimethylcarbamoyl)acetylimidazo[5,1-b]thiazol-2-yl]-6-((1R)-1-hydroxyethyl)-1-methyl-1-carbapen-2-em-3-carboxylate and 24.4 mg of 3-phthalidyl bromide.

NMR (CDCl$_3$) δ: 1.24 (3H, m), 1.32 (3H, d, J=6.2 Hz), 3.01 (3H, s), 3.10 (3H, s), 3.31 (1H, m), 3.41 (1H, m), 4.14–4.24 (3H, m), 4.36 (1H, m), 7.44, 7.46 (total 1H, s each), 7.65–7.80 (3H, m), 7.92 (1H, m), 7.99, 8.03 (total 1H, s each), 8.40, 8.67 (total 1H, s each) MS (TSP): 579 (M$^+$+H)

Example 85

(5-Methyl-2-oxo-1,3-dioxolen-4-yl)methyl(1S,5R,6S)-2-[7-(N,N-dimethylcarbamoyl)acetylimidazo-[5x1-b]thiazol-2-yl]-6-((1R)-1-hydroxyethyl)-1-methyl-1-carbapen-2-em-3-carboxylate In the same manner as in Example 46, 26.1 mg of the title compound was obtained from 36.1 mg of sodium(1S,5R,6S)-2-[7-(N,N-dimethylcarbamoyl)acetylimidazo[5,1-b]thiazol-2-yl]-6-((1R)-1-hydroxyethyl)-1-methyl-1-carbapen-2-em-3-carboxylate and 24.0 mg of (5-methyl-2-oxo-1,3-dioxolen-4-yl)methyl bromide.

NMR (CDCl$_3$) δ: 1.27 (3H, d, J=7.1 Hz), 1.37 (3H, d, J=6.2 Hz), 2.22 (3H, s), 2.70 (1H, br.s), 3.01 (3H, s), 3.10 (3H, s), 3.32 (1H, dd, J$_1$=7.1 Hz, J$_2$=2.8 Hz), 3.50 (1H, m), 4.17 (2H, m), 4.26 (1H, m), 4.38 (1H, dd, J. =9.8 Hz, J$_2$=2.8 Hz), 5.00, 5.10 (2H, ABq, J=14.2 Hz), 8.04 (1H, s), 8.40 (1H, s) MS (TSP): 559 (M$^+$+H)

Example 86

1-[(Cyclohexylmethoxy)carbonyloxy]ethyl(1S,5R,6S)-2-[7-(N,N-dimethylcarbamoyl)acetylimidazo[5,1-b]thiazol-2-yl-6-((1R)-1-hydroxyethyl)-1-methyl-1-carbapen-2-em-3-carboxylate (A Mixture of Diastereomers)

In the same manner as in Example 46, 22.3 mg of the title compound was obtained from 30.2 mg of sodium(1S,5R,6S)-2-[7-(N,N-dimethylcarbamoyl)acetylimidazo[5,1-b]thiazol-2-yl]-6-((1R)-1-hydroxyethyl)-1-methyl-1-carbapen-2-em-3-carboxylate and 45.0 mg of 1[(cyclohexylmethoxy)carbonyloxy]ethyl iodide.

NMR (CDCl$_3$) δ: 0.92–1.02 (2H, m), 1.10–1.30 (2H, m), 1.23 (3H, m), 1.37 (3H, m), 1.60–1.80 (7H, m), 1.60, 1.66 (total 3H, d each, J=5.5 Hz), 3.01(3H, s), 3.09,3.10 (total 3H, s each), 3.30 (1H, m), 3.47 (1H, m), 3.47 (1H, m), 3.95–4.04 (2H, m), 4.16–4.35 (4H, m), 6.94 (1H, m), 8.01, 8.02 (total 1H, s each), 8.63, 8.65 (total 1H, s each) MS (TSP): 631 (M$^+$+H)

Example 87

1-(Cyclohexyloxycarbonyloxy)-n-propyl(1S,5R,6S)-2-[7-(N,N-dimethylcarbamoyl)acetylimidazo[5,1-b1thiazol-2-yl-6-((1R)-1-hydroxyethyl)-1-methyl-1-carbapen-2-em-3-carboxylate (A Mixture of Diastereomers)

In the same manner as in Example 46, 17.9 mg of the title compound was obtained from 25.1 mg of sodium(1S,5R,6S)-2-[7-(N,N-dimethylcarbamoyl)acetylcarbonylimidazo[5,1-b]thiazol-2-yl]-6-((1R)-1-hydroxyethyl)-1-methyl-1-carbapen-2-em-3-carboxylate and 45.0 mg of 1-(cyclohexyloxycarbonyloxy)-n-propyl iodide.

NMR (CDCl$_3$) δ: 0.90–1.40 (3H, m), 1.21 (3H, m), 1.36 (3H, m), 1.45–1.60 (4H, m), 1.85–2.01 (5H, m), 3.01 (1H, s), 3.09 (1H, s), 3.31 (1H, m), 3.49 (1H, m), 3.62 (1H, m), 4.15–4.38 (3H, m), 4.66 (1H, m), 6.80 (1H, m), 8.01, 8.02 (total 1H, s each), 8.64, 8.66 (total 1H, s each) MS (TSP): 631 (M$^+$+H)

Example 88

Sodium(1S,5R,6S)-2-[7-(N,N-dimethylsulfamoyl)imidazo[5,1-b]thiazol-2-yl]-6-((1R)-1-hydroxyethyl)-1-methyl-1-carbapen-2-em-3-carboxylate a) 4-Nitrobenzyl(1S,5R,6S)-2-[7-(N,N-dimethylsulfamoyl)imidazo[5,1-b]thiazol-2-yl-6-((1R)-1-hydroxyethyl)-1-methyl1-carbapen-2-em-3-carboxylate In substantially the same manner as in Example 1-a), 115 mg of 4-nitrobenzyl(1S,5R,6S)-2-[7-(N,N-dimethylsulfamoyl)imidazo[5,1-b]thiazol-2-yl]-6-((1R)-1-hydroxyethyl)-1-methyl-1-carbapen-2-em-3-carboxylate was obtained from 109 mg of 4-nitrobenzyl(1R,3R,5R,6S)-6-((1R)-1-hydroxyethyl)-1-methyl-2-oxo-1-carbapenam-3-carboxylate and 143 mg of 7-(N,N-dimethylsulfamoyl)-2-(tri-n-butylstannyl)imidazo[5,1-b]thiazole.

NMR (CDCl$_3$) δ: 1.30 (3H, d, J=7.2 Hz), 1.37 (3H, d, J=6.1 Hz), 2.84 (6H, m), 3.36 (1H, dd, J$_1$=6.9 Hz, J$_2$=2.5 Hz), 3.50–3.60 (1H, m), 4.20–4.30 (1H, m), 4.38 (1H, dd, J$_1$=9.6 Hz, J$_2$=2.5 Hz), 5.29 (1H, d, J=13.7 Hz), 5.51 (1H, d, J=13.7 Hz), 7.68 (2H, d, J=8.5 Hz), 8.23 (1H, s), 8.23 (2H, d, J=8.5 Hz), 8.40 (1H, s)

b) Sodium(1S,5R,6S)-2-[7-(N,N-dimethylsulfamoyl)imidazo[5,1-b]thiazol-2-yl]-6-((1R)-1-hydroxyethyl)-1-methyl-1-carbapen-2-em-3-carboxylate The title compound (51.7 mg) was obtained from 115 mg of 4-nitrobenzyl(1S,5R,6S)-2-[7-(N,N-dimethylsulfamoyl)imidazo[5,1-b]thiazol-2-yl]-6-((1R)-1-hydroxyethyl)-1-methyl-1-carbapen-2-em-3-carboxylate in substantially the same manner as in Example 1-b), except that the purification was carried out using Cosmosil 40C18-PREP (10% aqueous methanol).

NMR (D$_2$O) δ (HOD=4.80 ppm): 1.25 (3H, d, J=7.1 Hz), 1.31 (3H, d, J=6.0 Hz), 2.77 (6H, s), 3.50–3.55 (1H, m), 3.58–3.66 (1H, m), 4.23–4.36 (2H, m), 8.06 (1H, s), 8.26 (1H, s)

Example 89

(1S,5R,6S)-2-[7-(N,N-dimethylsulfamoyl)imidazo[5,1-b]thiazol-2-yl-6-((1R)-1-hydroxyethyl)-1-methyl-1-carbapen-2-em-3-carboxylatepivaloyloxymethyl In the same manner as in Example 46, 33.7 mg of the title compound was obtained from 52.2 mg of sodium(1S,5R,6S)-2-[7-(N,N-dimethylsulfamoyl)imidazo[5,1-b]thiazol-2-yl]-6-((1R)-1-hydroxyethyl)-1-methyl-1-carbapen-2-em-3-carboxylate and 45 mg of pivaloyloxymethyl iodide.

NMR (CDCl$_3$) δ: 1.21 (9H, s), 1.29 (3H, d, J=7.4 Hz), 1.37 (3H, d, J=6.3 Hz), 2.88 (6H, s), 3.35 (1H, dd, J$_1$=6.5 Hz, J$_2$=2.8 Hz), 3.45 (1H, m), 4.29 (1H, m), 4.37 (1H, dd, J$_1$=9.8 Hz, J$_2$=2.8 Hz), 5.87, 5.99 (2H, ABq, J=5.2 Hz), 8.08 (1H, s), 8.46 (1H, s) MS (TSP): 555 (M$^+$+H)

Example 90

(1-Methylcyclohexan-1-yl)carbonyloxymethyl(1S,5R,6S)-2-[7-(N,N-dimethylsulfamoyl)imidazo[5,1-b]thiazol-2-yl]-6-((1R)-1-hydroxyethyl)-1-methyl-1-carbapen-2-em-3-carboxylate In the same manner as in Example 46, 34.1 mg of the title compound was obtained from 32.6 mg of sodium(1S,5R,6S)-2-[7-(N,N-dimethylsulfamoyl)imidazo[5,1-b]thiazol-2-yl]-6-((1R)-1-hydroxyethyl)-1-methyl-1-carbapen-2-em-3-carboxylate and 39.8 mg of (1-methylcyclohexan-1-yl)carbonyloxymethyl iodide.

NMR (CDCl$_3$) δ: 1.15 (3H, s), 1.20–1.30 (4H, m), 1.27 (3H, d, J=7.2 Hz), 1.36 (3H, d, J=6.3 Hz), 1.41–1.58 (3H, m), 1.97–2.06 (3H, m), 2.87 (6H, s), 3.34 (1H, dd, J$_1$=6.8 Hz, J$_2$=2.7 Hz), 3.48 (1H, m), 4.27 (1H, m), 4.36 (1H, dd, J$_1$=7.4 Hz, J$_2$=2.7 Hz), 5.92, 5.97 (2H, ABq, J=5.6 Hz), 8.11 (1H, s), 8.43 (1H, s) MS (TSP): 595 (M$^+$+H)

Example 91

1-(Cyclohexyloxycarbonyloxy)ethyl(1S,5R,6S)-2-[7-(N,N-dimethylsulfamoyl)imidazo[5,1-b]thiazol-2-yl]-6-((1R)-1-hydroxyethyl)-1-methyl-1-carbapen-2-em-3-carboxylate (A Mixture of Diastereomers)

In the same manner as in Example 46, 17.1 mg of the title compound was obtained from 19.9 mg of sodium(1S,5R,6S)-2-[7-(N,N-dimethylsulfamoyl)imidazo[5,1-b]thiazol-2-yl]-6-((1R)-1-hydroxyethyl)-1-methyl-1-carbapen-2-em-3-carboxylate and 30 mg of 1-(cyclohexyloxycarbonyloxy)ethyl iodide.

NMR (CDCl$_3$) δ: 1.28–1.45 (8H, m), 1.48–1.98 (9H, m), 1.58, 1.65 (total 3H, d each, J=5.5 Hz), 2.87 (6H, s), 3.34 (1H, m), 3.44 (1H, m), 3.62 (1H, m), 4.29 (1H, m), 4.36 (1H, m), 4.66 (1H, m), 6.95 (1H, m), 8.05, 8.06 (total 1H, s each), 8.55, 8.56 (total 1H, s each) MS (TSP): 611 (M$^+$+H)

Example 92

3-Phthalidyl(1S,5R,6S)-2-[7-(N,N-dimethylsulfamoyl)imidazo[5,1-b]thiazol-2-yl]-6-((1R)-1-hydroxyethyl)-1-methyl-1-carbapen-2-em-3-carboxylate (A Mixture of Diastereomers)

In the same manner as in Example 46, 30.7 mg of the title compound was obtained from 32.1 mg of sodium(1S,5R,6S)-2-[7-(N,N-dimethylsulfamoyl)imidazo[5,1-b]thiazol-2-yl]-6-((1R)-1-hydroxyethyl)-1-methyl-1-carbapen-2-em-3-carboxylate and 30.9 mg of 3-phthalidyl bromide.

NMR (CDCl$_3$) δ: 1.25–1.36 (6H, m), 2.20–2.40 (1H, br.s), 2.85 (3H, s), 2.87 (3H, s), 3.36 (1H, m), 3.54 (1H, m), 4.23 (1H, m), 4.38 (1H, m), 7.45, 7.46 (total 1H, s each), 7.65–7.82 (3H, m), 7.90, 7.93 (total 1H, s each), 8.05, 8.09 (total 1H, s each), 8.30, 8.55 (total 1H, s each) MS (TSP): 573 (M$^+$+H)

Example 93

(5-Methyl-2-oxo-1,3-dioxolen-4-yl)methyl(1S,5R,6S)-2-[7-(N,N-dimethylsulfamoyl)imidazo[5,1-b]thiazol-2-yl]-6-((1R)-1-hydroxyethyl)-1-methyl-1-carbapen-2-em-3-carboxylate In the same manner as in Example 46, 38.1 mg of the title compound was obtained from 32.0 mg of sodium(1S,5R,6S)-2-[7-(N,N-dimethylsulfamoyl)imidazo[5,1-b]thiazol-2-yl]-6-((1R)-1-hydroxyethyl)-1-methyl-1-carbapen-2-em-3-carboxylate and 26.0 mg of (5-methyl-2-oxo-1,3-dioxolen-4-yl)methyl bromide.

NMR (CDCl$_3$) δ: 1.29 (3H, d, J=7.1 Hz), 1.37 (3H, d, J=6.1 Hz), 2.22 (3H, s), 2.30 (1H, br.s), 2.07 (6H, s), 3.35 (1H, dd, J$_1$=6.6 Hz, J$_2$=2.8 Hz), 3.50 (1H, m), 4.26–4.33 (1H, m), 4.37 (1H, dd, J$_1$=9.6 Hz, J$_2$=2.8 Hz), 5.02, 5.10 (2H, ABq, J=14.0 Hz), 8.10 (1H, s), 8.34 (1H, s) MS (TSP): 553 (M$^+$+H)

Example 94

1-[(Cyclohexylmethoxy)carbonyloxy]ethyl(1S,5R,6S)-2-[7-(N,N-dimethylsulfamoyl)imidazo[5,1-b]thiazol-2-yl]-6-((1R)-1-hydroxyethyl)-1-methyl-1-carbapen-2-em-3-carboxylate (A Mixture of Diastereomers)

In the same manner as in Example 46, 14.5 mg of the title compound was obtained from 32.0 mg of sodium(1S,5R,6S)-2-[7-(N,N-dimethylsulfamoyl)imidazo[5,1-b]thiazol-2-yl]-6-((1R)-1-hydroxyethyl)-1-methyl-1-carbapen-2-em-3-carboxylate and 45.0 mg of 1-[(cyclohexylmethoxy)carbonyloxy]ethyl iodide.

NMR (CDCl$_3$) δ: 0.95–1.08 (2H, m), 1.15–1.30 (2H, m), 1.27 (3H, d, J=7.4 Hz), 1.37, 1.39 (total 3H, d each, J=6.1 Hz), 1.60, 1.66 (total 3H, d each, J=5, 5 Hz), 1.60–1.80 (9H, m), 2.87 (6H, s), 3.33 (1H, m), 3.45 (1H, m), 3.96 (1H, m), 4.02 (1H, d, J=2.1 Hz), 4.28 (1H, m), 4.36 (1H, m), 6.93 (1H, m), 8.05, 8.06 (total 1H, s each), 8.54, 8.57 (total 1H, s each) MS (TSP): 625 (M$^+$+H)

Example 95

1-(Cyclohexyloxycarbonyloxy)-n-propyl(1S,5R,6S)-2-[7-(N,N-dimethylsulfamoyl)imidazo[5,1-b]thiazol-2-yl]-6-((1R)-1-hydroxyethyl)-1-methyl-1-carbapen-2-em-3-carboxylate (A Mixture of Diastereomers)

In the same manner as in Example 46, 32.8 mg of the title compound was obtained from 31.5 mg of sodium(1S,5R,6S)-2-[7-(N,N-dimethylsulfamoyl)imidazo[5,1-b]thiazol-2-yl]-6-((1R)-1-hydroxyethyl)-1-methyl-1-carbapen-2-em-3-carboxylate and 45.0 mg of 1-(cyclohexyloxycarbonyloxy)-n-propyl iodide.

NMR (CDCl$_3$) δ: 1.00, 1.08 (total 3H, t each, J=7.4 Hz), 1.26–1.40 (7H, m), 1.45–1.65 (3H, m), 1.70–1.82 (3H, m), 1.85–2.05 (6H, m), 2.88 (6H, s), 3.33 (1H, m), 3.45 (1H, m), 3.61 (1H, m), 4.27 (1H, m), 4.36 (1H, m), 4.65 (1H, m), 6.79, 6.81 (total 1H, t each, J=5.7 Hz), 8.05, 8.06 (total 1H, S each), 8.55, 8.57 (total 1H, s each) MS (TSP): 625 (M$^+$+H)

Example 96

Sodium(1S,5R,6S)-6-((1R)-1-hydroxyethyl)-2-(7-methoxycarbonylimidazo[5,1-b]thiazol-2-yl)-1-methyl-1-carbapen-2-em-3-carboxylate a) 4-Nitrobenzyl(1S,5R,6S)-6-((1R)-1-hydroxyethyl)-2-(7-methoxycarbonylimidazo[5,1-b]thiazol-2-yl)-1-methyl-1-carbapen-2-em-3-carboxylate In the same manner as in Example 1-a), 303 mg of 4-nitrobenzyl(1S,5R,6S)-6-((1R)-1-hydroxyethyl)-2-(7- methoxycarbonylimidazo[5,1-b]thiazol-2-yl)-1-methyl-1-carbapen-2-em-3-carboxylate was obtained from 467 mg of 4-nitrobenzyl(1R,3R,5R,6S)-6-((1R)-1-hydroxyethyl)-1-methyl-2-oxo-1-carbapenam-3-carboxylate and 729 mg of methyl 2-(tri-n-butylstannyl)imidazo[5,1-b]thiazole-7-carboxylate.

NMR (CDCl$_3$) δ: 1.32 (3H, d, J=7.3 Hz), 1.40 (3H, d, J=7.6 Hz), 2.00–2.12 (1H, broad), 3.39 (1H, dd, J$_1$=6.6 Hz, J$_2$=2.9 Hz), 3.51 (1H, dq, J$_1$=9.5 Hz, J$_2$=7.3 Hz), 3.96 (3H, s), 4.29–4.37 (1H, m), 4.41 (1H, dd, J$_1$=9.7 Hz, J$_2$=2.9 Hz), 5.28 (1H, d, J=13.7 Hz), 5.52 (1H, d, J=13.7 Hz), 7.68 (2H, dm, J=8.8 Hz), 8.02 (1H, s), 8.24 (2H, dm, J=8.8 Hz), 8.44 (1H, s)

b) Sodium(1S,5R,6S)-6-((1R)-1-hydroxyethyl)-2-(7-methoxycarbonylimidazo[5,1-b]thiazol-2-yl)-1-methyl-1-carbapen-2-em-3-carboxylate In the same manner as in Example 1-b), 188 mg of the title compound was obtained from 303 mg of 4-nitrobenzyl (1S,5R,6S)-6-((1R)-1-hydroxyethyl)-2-(7-methoxycarbonyl-imidazo[5,1-b]thiazol-2-yl)-1-methyl-1-carbapen-2-em-3-carboxylate.

NMR (D$_2$O) δ (HOD=4.80 ppm): 1.21 (3H, d, J=7.1 Hz), 1.32 (3H, d, J=6.2 Hz), 3.50 (1H, dd, J$_1$=6.0 Hz, J$_2$=2.6 Hz), 3.58 (1H, qd, J$_1$=7.1 Hz, J$_2$=6.0 Hz), 4.28 (1H, p, J=6.2 Hz), 4.34 (1H, dd, J$_1$=9.2 Hz, J$_2$=2.6 Hz), 7.87 (1H, s), 8.07 (1H, s)

Example 97

Sodium(1S,5R,6S)-6-((1R)-1-hydroxyethyl)-2-[7-(N-methoxy-N-methylsulfamoyl)imidazo[5,1-b]thiazol-2-yl]-1-methyl-1-carbapen-2-em-3-carboxylate a) 4-Nitrobenzyl(1S,5R,6S)-6-((1R)-1-hydroxyethyl)-2-[7-(N-methoxy-N-methylsulfamoyl)imidazo-[5,1-b]thiazol-2-yl]-1-methyl-1-carbapen-2-em-3-carboxylate In substantially the same manner as in Example 1-a), 160 mg of 4-nitrobenzyl(1S,5R,6S)-6-((1R)-1-hydroxyethyl)-2-[7-(N-methoxy-N-methylsulfamoyl)imidazo-[5,1-b]thiazol-2-yl]-1-methyl-1-carbapen-2-em-3-carboxylate was obtained from 217 mg of 4-nitrobenzyl(1R,3R,5R,6S)-6-((1R)-1-hydroxyethyl)-1-methyl-2-oxo-1-carbapenam-3-carboxylate and 292 mg of 7-(N-methoxy-N-methylsulfamoyl)-2-(tri-n-butylstannyl)imidazo[5,1-b]thiazole.

NMR (CDCl$_3$) δ: 1.31 (3H, d, J=7.2 Hz), 1.39 (3H, d, J=6.2 Hz), 3.05 (3H, s), 3.35–3.45 (1H, m), 3.37–3.44 (1H, m), 3.82 (1H, s), 4.25–4.35 (1H, m), 4.42 (1H, dd, J$_1$=9.8 Hz, J$_2$=2.9 Hz), 5.30 (1H, d, J=13.7 Hz), 5.52 (1H, d, J=13.7 Hz), 7.68 (2H, d, J=8.9 Hz), 8.09 (1H, s), 8.24 (2H, d, J=8.9 Hz), 8.43 (1H, s)

b) Sodium(1S,5R,6S)-6-((1R)-1-hydroxyethyl)-2-[7-(N-methoxy-N-methylsulfamoyl)imidazo[5,1-b]thiazol-2-yl]-1-methyl-1-carbapen-2-em-3-carboxylate The title compound (98 mg) was obtained from 160 mg of 4-nitrobenzyl(1S,5R,6S)-6-((1R)-1-hydroxyethyl)-2-[7-(N-methoxy-N-methylsulfamoyl)imidazo[5,1-b]thiazol-2-yl]-1-methyl-1-carbapen-2-em-3-carboxylate in substantially the same manner as in Example 1-b), except that the purification was carried out using Cosmosil 40C18-PREP (10% aqueous methanol).

NMR (D$_2$O) δ (HOD=4.80 ppm): 1.25 (3H, d, J=7.3 Hz), 1.31 (3H, d, J=6.4 Hz), 2.95 (3H, s), 3.52 (1H, dd, J$_1$=6.8 Hz, J$_2$=2.4 Hz), 3.58–3.68 (1H, s), 3.78 (3H, s), 4.24–4.33 (2H, m), 8.10 (1H, s), 8.28 (1H, s)

Example 98

Sodium(1S,5R,6S)-6-((1R)-1-hydroxyethyl)-1-methyl-2-(7-trifluoroacetylimidazo[5,1-b]thiazol-2-yl)-1-carbapen-2-em-3-carboxylate a) 4-Nitrobenzyl(1S,5R,6S)-6-((1R)-1-hydroxyethyl)-1-methyl-2-(7-trifluoroacetylimidazo[5,1-b]thiazol-2-yl)-1-carbapen-2-em-3-carboxylate In substantially the same manner as in Example 1-a), 68 mg of 4-nitrobenzyl(1S,5R,6S)-6-((1R)-1-hydroxyethyl)-1-methyl-2-(7-trifluoroacetylimidazo[5,1b]thiazol-2-yl)-1-carbapen-2-em-3-carboxylate was obtained from 109 mg of 4-nitrobenzyl(1R,3R,5R,6S)-6-((1R)-1-hydroxyethyl)-1-methyl-2-oxo-1-carbapenam-3-carboxylate and 136 mg of 7-trifluoroacetyl-2-(tri-n-butylstannyl)imidazo[5,1-b]thiazole.

NMR (CDCl$_3$) δ: 1.32 (3H, d, J=7.3 Hz), 1.40 (3H, d, J=6.2 Hz), 3.38–3.42 (1H, m), 3.50–3.60 (1H, m), 4.30–4.40 (1H, m), 4.43 (1H, dd, J$_1$=9.7 Hz, J$_2$=2.8 Hz), 5.23–5.38 (1H, m), 5.53 (1H, d, J=13.5 Hz), 7.70 (2H, d, J=8.9 Hz), 8.13 (1H, s), 8.25 (2H, d, J=8.9 Hz), 8.53 (1H, s)

b) Sodium(1S,5R,6S)-6-((1R)-1-hydroxyethyl)-1-methyl-2-(7-trifluoroacetylimidazo[5,1-b]thiazol-2-yl)-1-carbapen-2-em-3-carboxylate The title compound (20.6 mg) was obtained from 68 mg of 4-nitrobenzyl(1S,5R,6S)-6-((1R)-1-hydroxyethyl)-1-methyl-2-(7-trifluoroacetylimidazo[5,1-b]thiazol-2-yl)-1-carbapen-2-em-3-carboxylate in substantially the same manner as in Example 1-b), except that the purification was carried out using Cosmosil 40C18-PREP (15% aqueous methanol).

NMR (D$_2$O) δ (HOD=4.80 ppm): 1.23 (3H, d, J=7.1 Hz), 1.32 (3H, d, J=6.4 Hz), 3.53 (1H, dd, J$_1$=6.1 Hz, J$_2$=2.8 Hz), 3.60–3.70 (1H, m), 4.25–4.40 (2H, m), 8.12 (1H, s), 8.26 (1H, s)

Example 99

Sodium(1S,5R,6S)-6-((1R)-1-hydroxyethyl)-1-methyl-2-(7-sulfamoylimidazo[5,1-b]thiazol-2-yl)-1-carbapen-2-em-3-carboxylate a) 4-Nitrobenzyl(1S,5R,6S)-2-(7-t-butyldimethylsilylsulfamoylimidazo[5,1-b]thiazol-2-yl)-6-((1R)-1-hydroxyethyl)-1-methyl-1-carbapen-2-em-3-carboxylate In substantially the same manner as in Example 1-a), 197 mg of 4-nitrobenzyl(1S,5R,6S)-2-(7-t-butyldimethylsilylsulfamoylimidazo[5,1-b]thiazol-2-yl)-6-((1R)-1-hydroxyethyl)-1-methyl-1-carbapen-2-em-3-carboxylate was obtained from 217 mg of 4-nitrobenzyl(1R,3R,5R,6S)-6-((1R)-1-hydroxyethyl)-1-methyl-2-oxo-1-carbapenam-3-carboxylate and 303 mg of 7-(t-butyldimethylsilylsulfamoyl)-2-(tri-n-butylstannyl)-imidazo[5,1-b]thiazole.

NMR (CDCl$_3$) δ: 0.24 (3H, s), 0.26 (3H, s), 0.93 (9H, s), 1.31 (3H, d, J=7.1 Hz), 1.41 (3H, d, J=6.3 Hz), 3.40 (1H, dd, J=6.3 Hz, J$_2$=2.7 Hz), 3.45–3.52 (1H, m), 4.30–4.36 (1H, m), 4.40 (1H, dd, J$_1$=9.7 Hz, J$_2$=2.7 Hz), 4.57 (1H, s), 5.30

(1H, d, J=13.7 Hz), 5.55 (1H, d, J=13.7 Hz), 7.70 (2H, d, J=8.3 Hz), 8.03 (1H, s), 8.26 (2H, d, J=8.3 Hz), 8.47 (1H, s)

b) Sodium(1S,5R,6S)-6-((1R)-1-hydroxyethyl)-1-methyl-2-(7-sulfamoylimidazo[5,1-b]thiazol-2-yl)-1-carbapen-2-em-3-carboxylate Acetic acid (0.26 ml) and 1.5 ml of a 1 M-tetra-n-butylammonium fluoride/THF solution were added under ice cooling to a solution of 197 mg of 4-nitrobenzyl(1S,5R,6S)-2-(7-t-butyldimethylsilylsulfamoylimidazo-[5,1-b]thiazol-2-yl)-6-((1R)-1-hydroxyethyl)-1-methyl-1-carbapen-2-em-3-carboxylate in 6 ml of THF. The solution was stirred at room temperature for 3 hr. The reaction mixture was added to an aqueous sodium hydrogencarbonate solution, followed by extraction with dichloromethane. The organic layer was dried over anhydrous magnesium sulfate. The solvent was removed by distillation. The residue was purified by column chromatography on silica gel (dichloromethane:methanol=10:1) to give a crude product of 4-nitrobenzyl(1S,5R,6S)-6-((1R)-1-hydroxyethyl)-1-methyl-2-(7-sulfamoylimidazo[5,1-b]thiazol-2-yl)-1-carbapen-2-em-3-carboxylate. The crude product was dissolved in 5 ml of THF and 5 ml of 1/15 M sodium phosphate buffer (pH 6.6). 10%Pd—C (50 mg) was added thereto. The atmosphere in the reactor was replaced with hydrogen. The system was stirred at room temperature for 30 min. The catalyst was removed by filtration through Celite, followed by washing with water. The filtrate was adjusted to pH 7.0 by the addition of an aqueous sodium hydrogencarbonate solution, and washed with ethyl acetate. Purification was then carried out using Cosmosil 40C18-PREP (30% aqueous methanol) and Dowex 50 (sodium form) in that order to give 40.7 mg of the title compound.

NMR (D$_2$O) δ (HOD=4.80 ppm): 1.26 (3H, d, J=7.4 Hz), 1.32 (3H, d, J=6.3 Hz), 3.53 (1H, dd, J$_1$=6.0 Hz, J$_2$=2.7 Hz), 3.56–3.68 (1H, m), 4.25–4.35 (2H, m), 8.04 (1H, s), 8.23 (1H, s)

Example 100

Sodium(1S,5R,6S)-6-((1R)-1-hydroxyethyl)-2-[7-(2-(E)-methoxycarbonylvinyl)imidazo[5,1-b]thiazol-2-yl]-1-methyl-1-carbapen-2-em-3-carboxylate a) 4-Nitrobenzyl(1S,5R,6S)-6-((1R)-1-hydroxyethyl)-2-[7-(2-(E)-methoxycarbonylvinyl)imidazo-[5,1-b]thiazol-2-yl]-1-methyl-1-carbapen-2-em-3-carboxylate and 4-nitrobenzyl(1S,5R,6S)-6-((1R)-1-hydroxyethyl)-2-[7-(2-Z)-methoxycarbonylvinyl)imidazo-[5,1-b]thiazol-2-yl]-1-methyl-1-carbapen-2-em-3-carboxylate In the same manner as in Example 1-a), 88 mg of 4-nitrobenzyl(1S,5R,6S)-6-((1R)-1-hydroxyethyl)-2-[7-(2-(E)-methoxycarbonylvinyl)imidazo[5,1-b]thiazol-2-yl]-1-methyl-1-carbapen-2-em-3-carboxylate and 28 mg of 4-nitrobenzyl(1S,5R,6S)-6-((1R)-1-hydroxyethyl)-2-[7-(2-(Z)-methoxycarbonylvinyl)imidazo[5,1-b]thiazol-2-yl]-1-methyl-1-carbapen-2-em-3-carboxylate were obtained from 320 mg of 4-nitrobenzyl(1R,3R,5R,6S)-6-((1R)-1-hydroxyethyl)-1-methyl-2-oxo-1-carbapenam-3-carboxylate and 400 mg of 7-(2-methoxycarbonylvinyl)2-(tri-n-butylstannyl)imidazo[5,1-b]thiazole (a mixture of geometrical isomers).

4-Nitrobenzyl(1S,5R,6S)-6-((1R)-1-hydroxyethyl)-2-[7-(2-(E)-methoxycarbonylvinyl)imidazo[5,1-b]thiazol-2-yl]-1-methyl-1-carbapen-2-em-3-carboxylate NMR (CDCl$_3$) δ: 1.32 (3H, d, J=7.3 Hz), 1.41 (3H, d, J=6.3 Hz), 3.39 (1H, dd, J$_1$=6.3 Hz, J$_2$=2.7 Hz), 3.51 (1H, m), 3.81 (3H, s), 4.33 (1H, m), 4.40 (1H, dd, J$_1$=9.7 Hz, J$_2$=2.9 Hz), 5.29 (1H, d, J=13.6 Hz), 5.53 (1H, d, J=13.6 Hz), 6.18 (1H, d, J=15.9 Hz), 7.69 (2H, d, J=8.7 Hz), 7.73 (1H, d, J=15.9 Hz), 8.06 (1H, s), 8.25 (2H, d, J=8.7 Hz), 8.36 (1H, s)

4-Nitrobenzyl(1S,5R,6S)-6-((1R)-1-hydroxyethyl)-2-[7-(2-(Z)-methoxycarbonylvinyl)imidazo[5,1-b]thiazol-2-yl]-1-methyl-1-carbapen-2-em-3-carboxylate NMR (CDCl$_3$) δ: 1.31 (3H, d, J=7.3 Hz), 1.40 (3H, d, J=6.3 Hz), 3.37 (1H, dd, J$_1$=6.3 Hz, J$_2$=2.7 Hz), 3.58 (1H, m), 3.81 (3H, s), 4.32 (1H, m), 4.38 (1H, dd, J$_1$=9.7 Hz, J$_2$=2.9 Hz), 5.27 (1H, d, J=13.6 Hz), 5.52 (1H, d, J=13.6 Hz), 5.84 (1H, d, J=12.4 Hz), 7.12 (1H, d, J=12.4 Hz), 7.67 (2H, d, J=8.8 Hz), 8.07 (1H, s), 8.24 (2H, d, J=8.8 Hz), 8.42 (1H, s)

b) Sodium(1S,5R,6S)-6-((1R)-1-hydroxyethyl)-2-[7-(2-(E)-methoxycarbonylvinyl)imidazo[5,1-b]thiazol-2-yl]-1-methyl-1-carbapen-2-em-3-carboxylate In the same manner as in Example 1-b), 37 mg of the title compound was obtained from 4-nitrobenzyl (1S,5R,6S)-6-((1R)-1-hydroxyethyl)-1-methyl-2-[7-(2-(E)-methoxycarbonylvinyl)imidazo[5,1-b]thiazol-2-yl]-1-carbapen-2-em-3-carboxylate.

NMR (D$_2$O) δ (HOD=4.80 ppm): 1.25 (3H, d, J=7.3 Hz), 1.35 (3H, d, J=6.3 Hz), 3.52 (1H, dd, J$_1$=6.3 Hz, J$_2$=2.4 Hz), 3.60 (1H, m), 3.81 (3H, s), 4.30 (1H, m), 4.33 (1H, dd, J$_1$=9.5 Hz, J$_2$=2.4 Hz), 5.85 (1H, d, J=15.8 Hz), 7.51 (1H, d, J=15.8 Hz), 7.92 (1H, s), 8.11 (1H, s)

Example 101

Sodium(1S,5R,6S)-6-((1R)-1-hydroxyethyl)-2-[7-(2-(Z)-methoxycarbonylvinyl)imidazo[5,1-b]thiazol-2-yl]-1-methyl-1-carbapen-2-em-3-carboxylate In the same manner as in Example 1-b), 9.8 mg of the title compound was obtained from 4-nitrobenzyl(1S,5R,6S)-6-((1R)-1-hydroxyethyl)-2-[7-(2-(Z)-methoxycarbonylvinyl)imidazo[5,1-b]thiazol-2-yl]-1-methyl-1-carbapen-2-em-3-carboxylate.

NMR (D$_2$O) δ (HOD=4.80 ppm): 1.25 (3H, d, J=7.3 Hz), 1.33 (3H, d, J=6.3 Hz), 3.52 (1H, dd, J$_1$=6.3 Hz, J$_2$=2.4 Hz), 3.57 (1H, m), 3.87 (3H, s), 4.29 (1H, m), 4.32 (1H, dd, J$_1$=9.3 Hz, J$_2$=2.4 Hz), 5.88 (1H, d, J=12.5 Hz), 7.02 (1H, d, J=12.5 Hz), 7.97 (1H, s), 8.18 (1H, s)

Example 102

Sodium(1S,5R,6S)-6-((1R)-1-hydroxyethyl)-1-methyl-2-[7-(thiazol-4-yl)imidazo[5,1-b]thiazol-2-yl]-1-carbapen-2-em-3-carboxylate a) 4-Nitrobenzyl(1S,5R,6S)-6-((1R)-1-hydroxyethyl)-1-methyl-2-[7-(thiazol-4-yl)imidazo[5,1-b]thiazol-2-yl]-1-carbapen-2-em-3-carboxylate In the same manner as in Example 1-a), 17 mg of 4-nitrobenzyl(1S,5R,6S)-6-((1R)-1-hydroxyethyl)-1-methyl-2-[7-(thiazol-4-yl)imidazo[5,1-b]thiazol-2-yl]-1-carbapen-2-em-3-carboxylate was obtained from 224 mg of 4-nitrobenzyl(1R,3R,5R,6S)-6-((1R)-1-hydroxyethyl)-1-methyl-2-oxo-1-carbapenam-3-carboxylate and 289 mg of 7-(thiazol-4-yl)-2-(tri-n-butylstannyl)imidazo[5,1-b]thiazole.

NMR (CDCl$_3$) δ: 1.33 (3H, d, J=7.4 Hz), 1.41 (3H, d, J=6.1 Hz), 3.38 (1H, dd, J$_1$=6.5 Hz, J$_2$=2.8 Hz), 3.50 (1H, m), 4.32 (1H, m), 4.36 (1H, dd, J$_1$=9.4 Hz, J$_2$=2.8 Hz), 5.28 (1H, d, J=13.5 Hz), 5.53 (1H, d, J=13.5 Hz), 7.65 (2H, d, J=2.1 Hz), 7.68 (2H, d, J=8.8 Hz), 8.07 (1H, s)8.24 (2H, d, J=8.8 Hz), 8.48 (1H, s), 8.88 (2H, d, J=2.1 Hz) MS (FAB$^+$): 552 (M$^+$+H)

b) Sodium(1S5R,6S)-6-((1R)-1-hydroxyethyl)-1-methyl-2-[7-(thiazol-4-yl)imidazo[5,1-b]thiazol-2-yl]-1carbapen-2-em-3-carboxylate In the same manner as in Example 1-b), 7.0 mg of the title compound was obtained from 16.5 mg of 4-nitrobenzyl(1S,5R,6S)-6-((1R)-1-hydroxyethyl)-1-methyl-2-[7-(thiazol-4-yl)imidazo[5,1-b]thiazol-2-yl]-1-carbapen-2-em-3-carboxylate.

NMR (D$_2$O) δ (HOD=4.80 ppm): 1.20 (3H, t, J=6.9 Hz), 1.34 (3H, d, J=6.4 Hz), 3.45 (1H, m), 3.48 (1H, m), 4.26 (1H, m), 4.30 (1H, m), 7.35 (1H, s), 7.76 (1H, s), 7.91 (1H, s), 8.91 (1H, s)

Example 103

Sodium(1S,5R,6S)-2-(7-hydroxyacetyl-5-methylimidazo[5,1-b]thiazol-2-yl)-6-((1R)-1-hydroxyethyl)-1-methyl-1-carbapen-2-em-3-carboxylate a) 4-Nitrobenzyl(1S,5R,6S)-2-(7-t-butyldimethylsilyloxyacetyl-5-methylimidazo[5,1-b]thiazol-2-yl)-6-((1R)-1-hydroxyethyl)-1-methyl-1-carbapen-2-em-3-carboxylate In the same manner as in Example 1-a), 193 mg of 4-nitrobenzyl(1S,5R,6S)-2-(7-t-butyldimethylsilyloxyacetyl-5-methylimidazo[5,1b]thiazol-2-yl)-6-((1R)-1-hydroxyethyl)-1-methyl-1-carbapen-2-em-3-carboxylate was obtained from 204 mg of 4-nitrobenzyl (1R,3R,5R,6S)-6-((1R)-1-hydroxyethyl)-1-methyl-2-oxo-1-carbapenam-3-carboxylate and 405 mg of 7-t-butyldimethylsilyloxyacetyl-5-methyl-2-(tri-n-butylstannyl)imidazo[5,1-b]thiazole.

NMR (CDCl$_3$) δ: 0.15 (6H, s), 0.96 (9H, s), 1.30 (3H, d, J=7.4 Hz), 1.40 (3H, d, J=6.2 Hz), 2.64 (3H, s), 3.38 (1H, dd, J$_1$=6.5 Hz, J$_2$=2.8 Hz), 3.49 (1H, m), 4.31 (1H, m), 4.40 (1H, dd, J$_1$=9.5 Hz, J$_2$=2.8 Hz), 5.03 (2H, s), 5.27 (1H, d, J=13.7 Hz), 5.53 (1H, d, J=13.7 Hz), 7.68 (2H, d, J=8.5 Hz), 8.24 (2H, d, J=8.5 Hz), 8.37 (1H, s)

b) 4-Nitrobenzyl(1S,5R,6S)-2-(7-hydroxyacetyl-5-methylimidazo[5,1-b]thiazol-2-yl)-6-((1R)-1-hydroxyethyl)-1-methyl-1-carbapen-2-em-3-carboxylate In the same manner as in Example 36-b), 122 mg of 4-nitrobenzyl(1S,5R,6S)-2-(7-hydroxyacetyl-5-methylimidazo[5,1-b]thiazol-2-yl)-6-((1R)-1-hydroxyethyl)-1-methyl-1-carbapen-2-em-3-carboxylate was obtained from 193 mg of 4-nitrobenzyl(1S,5R,6S)-2-(7-t-butyldimethylsilyloxyacetyl-5-methylimidazo[5,1-b]thiazol-2-yl)-6-((1R)-1-hydroxyethyl)-1-methyl-1-carbapen-2-em-3-carboxylate.

NMR (CDCl$_3$) δ: 1.31 (3H, d, J=7.2 Hz), 1.40 (3H, d, J=6.3 Hz), 2.65 (3H, s), 3.39 (1H, dd, J$_1$=6.4 Hz, J$_2$=2.7 Hz), 3.52 (2H, m), 4.33 (1H, m), 4.42 (1H, dd, J$_1$=9.6 Hz, J$_2$=2.7 Hz), 4.85 (2H, s), 5.28 (1H, d, J=13.7 Hz), 5.54 (1H, d, J=13.7 Hz), 7.68 (2H, d, J=8.5 Hz), 8.24 (2H, d, J=8.5 Hz), 8.36 (1H, s)

c) Sodium(1S,5R,6S)-2-(7-hydroxyacetyl-5-methylimidazo[5,1-b]thiazol-2-yl)-6-((1R)-1-hydroxyethyl)-1-methyl-1-carbapen-2-em-3-carboxylate In the same manner as in Example 1-b), 75.9 mg of the title compound was obtained from 122 mg of 4-nitrobenzyl (1S,5R,6S)-2-(7-hydroxyacetyl-5-methylimidazo[5,1-b]thiazol-2-yl)-6-((1R)-1-hydroxyethyl)-1-methyl-1-carbapen-2-em-3-carboxylate.

NMR (D$_2$O) δ (HOD=4.80 ppm): 1.19 (3H, d, J=7.2 Hz), 1.33 (3H, d, J=6.3 Hz), 2.48 (3H, s), 3.48 (1H, dd, J$_1$=6.1 Hz, J$_2$=2.5 Hz), 3.55 (1H, m), 4.30 (2H, m), 4.70 (2H, s), 7.73 (1H, s)

Example 104

Sodium(5R,6S)-6-((1R)-1-hydroxyethyl)-2-(7-methanesulfonyl-5-methylimidazo[5,1-b]thiazol-2-yl)-1-carbapen-2-em-3-carboxylate a) 4-Nitrobenzyl(5R,6S)-6-((1R)-1-hydroxyethyl)-2-(5-methyl-7-methylthioimidazo[5,1-b]thiazol-2-yl)-1-carbapen-2-em-3-carboxylate In the same manner as in Example 1-a), 866 mg of 4-nitrobenzyl(5R,6S)-6-((1R)-1-hydroxyethyl)-2-(5-methyl-7-methylthioimidazo[5,1-b]thiazol-2-yl)-1-carbapen-2-em-3-carboxylate was obtained from 1.04 g of 4-nitrobenzyl(3R,5R,6S)-6-((1R)-1-hydroxyethyl)-2-oxo-1-carbapenam-3-carboxylate and 1.70 g of 5-methyl-7-methylthio-2-(tri-n-butylstannyl)imidazo[5,1-b]thiazole.

NMR (CDCl$_3$) δ: 1.40 (3H, d, J=6.3 Hz), 2.40 (3H, s), 2.58 (3H, s), 3.33 (3H, m), 4.31 (2H, m), 5.31 (1H, d, J=14.0 Hz), 5.56 (1H, d, J=14.0 Hz), 7.70 (2H, d, J=8.9 Hz), 8.04 (1H, s), 8.25 (2H, d, J=8.9 Hz)

b) 4-Nitrobenzyl(5R,6S)-6-((1R)-1-hydroxyethyl)-2-(7-methanesulfonyl-5-methylimidazo[5,1-b]thiazol-2-yl)-1-carbapen-2-em-3-carboxylate A reaction was carried out in the same manner as in Example 44-b), except that 279 mg of 4-nitrobenzyl(5R,6S)-6-((1R)-1-hydroxyethyl)-2-(5-methyl-7-methylthioimidazo[5,1-b]thiazol-2-yl)-1-carbapen-2-em-3-carboxylate was used as the starting compound. The reaction product was purified by column chromatography on silica gel (dichloromethane:methanol=20:1 to 10:1). Of two main components, the fraction, which had been eluted earlier, was concentrated under the reduced pressure to give 91 mg of 4-nitrobenzyl(5R,6S)-6-((1R)-1-hydroxyethyl)-2-(7-methanesulfonyl-5-methylimidazo[5,1-b]thiazol-2-yl)-1-carbapen-2-em-3-carboxylate.

NMR (CDCl$_3$) δ: 1.40 (3H, d, J=6.4 Hz), 2.63 (3H, s), 3.18 (3H, s), 3.35 (3H, m), 4.34 (2H, m), 5.32 (1H, d, J=13.6 Hz), 5.56 (1H, d, J=13.6 Hz), 7.70 (2H, d, J=9.1 Hz), 8.17 (1H, s), 8.25 (2H, d, J=9.1 Hz)

c) Sodium(5R,6S)-6-((1R)-1-hydroxyethyl)-2-(7-methanesulfonyl-5-methylimidazo[5,1-b]thiazol-2-yl)-1-carbapen-2-em-3-carboxylate In the same manner as in Example 1-b), 45.6 mg of the title compound was obtained from 91 mg of 4-nitrobenzyl (5R,6S)-6-((1R)-1-hydroxyethyl)-2-(7-methanesulfonyl-5-methylimidazo[5,1-b]thiazol-2-yl)-1-carbapen-2-em-3-carboxylate.

NMR (D$_2$O) δ (HOD=4.80 ppm): 1.31 (3H, d, J=6.3 Hz), 2.54 (3H, s), 3.24 (3H, s), 3.26 (2H, m), 3.51 (2H, m), 4.26 (2H, m), 7.66 (1H, s)

Example 105

Sodium(5R,6S)-6-((1R)-1-hydroxyethyl)-2-(7-methanesulfinyl-5-methylimidazo[5,1-b]thiazol-2-yl)-1-carbapen-2-em-3-carboxylate (A Mixture of Diastereomers)

a) 4-Nitrobenzyl(5R, 6S)-6-((1R)-1-hydroxyethyl)-2-(7-methanesulfinyl-5-methylimidazo[5,1-b]thiazol-2-yl)-1-carbapen-2-em-3-carboxylate (A Mixture of Diastereomers)

Of the two main components, the fraction, which had been eluted later in the column chromatography on silica gel in Example 104-b), was concentrated under the reduced pressure to give 136 mg of 4-nitrobenzyl(5R,6S)-6-((1R)-1-hydroxyethyl)-2-(7-methanesulfinyl-5-methylimidazo[5,1-b]thiazol-2-yl)-1-carbapen-2-em-3-carboxylate (a mixture of diastereomers).

NMR (CDCl$_3$) δ: 1.39 (3H, d, J=6.2 Hz), 2.60 (3H, s), 2.94 (3H, s), 3.31 (3H, m), 4.30 (2H, m), 5.29 (1H, d, J=13.7 Hz), 5.53 (1H, d, J=13.7 Hz), 7.68 (2H, d, J=8.6 Hz), 8.10 (1H, m), 8.23 (2H, d, J=8.6 Hz)

b) Sodium(5R,6S)-6-((1R)-1-hydroxyethyl)-2-(7-methanesulfinyl-5-methylimidazo[5,1-b]thiazol-2-yl)-1-carbapen-2-em-3-carboxylate (A Mixture of Diastereomers)

In the same manner as in Example 1-b), 71.8 mg of the title compound was obtained from 136 mg of 4-nitrobenzyl(5R,6S)-6-((1R)-1-hydroxyethyl)-2-(7-methanesulfinyl-5-methylimidazo[5,1-b]thiazol-2-yl)-1-carbapen-2-em-3-carboxylate (a mixture of diastereomers).

NMR (D$_2$O) δ (HOD=4.80 ppm): 1.31 (3H, d, J=6.5 Hz), 2.57 (3H, s), 3.05 (3H, s), 3.31 (2H, m), 3.52 (1H, m), 4.26 (2H, m), 7.74 (1H, s)

Example 106

Sodium(5R,6S)-2-(7-hydroxyacetyl-5-methylimidazo[5,1-b]thiazol-2-yl)-6-((1R)-1-hydroxy-ethyl)-1-carbapen-2-em-3-carboxylate a) 4-Nitrobenzyl(5R,6S)-2-(7-t-butyldimethylsilyloxyacetyl-5-methylimidazo[5,1b]thiazol-2-yl)-6-((1R)-1-hydroxyethyl)-1-carbapen-2-em-3-carboxylate In the same manner as in Example 1-a), 190 mg of 4-nitrobenzyl(5R,6S)-2-(7-t-butyldimethylsilyloxyacetyl-5-methylimidazo[5,1-b]thiazol-2-yl)-6-((1R)-1-hydroxy-ethyl)-1-carbapen-2-em-3-carboxylate was obtained from 196 mg of 4-nitrobenzyl(3R,5R,6S)-6-((1R)-1-hydroxyethyl)-2-oxo-1-carbapenam-3-carboxylate and 405 mg of 7-t-butyldimethylsilyloxyacetyl-5-methyl-2-(tri-n-butylstannyl)imidazo[5,1-b]thiazole.

NMR (CDCl$_3$) δ: 0.15 (6H, s), 0.96 (9H, s), 1.40 (3H, d, J=6.1 Hz), 2.63 (3H, s), 3.35 (3H, m), 4.34 (2H, m), 5.03 (2H, s), 5.31 (1H, d, J=13.5 Hz), 5.55 (1H, d, J=13.5 Hz), 7.69 (2H, d, J=8.3 Hz), 8.24 (2H, d, J=8.3 Hz), 8.28 (1H, s)

b) 4-Nitrobenzyl(5R,6S)-2-(7-hydroxyacetyl-5-methylimidazo[5,1-b]thiazol-2-yl)-6-((1R)-1-hydroxy-ethyl)-1-carbapen-2-em-3-carboxylate In the same manner as in Example 36-b), 75.9 mg of 4-nitrobenzyl(5R,6S)-2-(7-hydroxyacetyl-5-methyl-imidazo[5,1-b]thiazol-2-yl)-6-((1R)-1-hydroxyethyl)-1-carbapen-2-em-3-carboxylate was obtained from 190 mg of 4-nitrobenzyl(5R,6S)-2-(7-t-butyldimethylsilyloxy-acetyl-5-methylimidazo[5,1-b]thiazol-2-yl)-6-((1R)-1-hydroxyethyl)-1-carbapen-2-em-3-carboxylate.

NMR (CDCl$_3$) δ: 1.40 (3H, d, J=6.3 Hz), 2.65 (3H, s), 3.35 (3H, m), 3.57 (1H, t, J=5.0 Hz), 4.35 (2H, m), 4.85 (2H, d, J=5.0 Hz), 5.33 (1H, d, J=13.7 Hz), 5.56 (1H, d, J=13.7 Hz), 7.70 (2H, d, J=8.5 Hz), 8.25 (1H, s), 8.25 (2H, d, J=8.5. Hz)

c) Sodium(5R,6S)-2-(7-hydroxyacetyl-5-methylimidazo[5,1-b]thiazol-2-yl)-6-((1R)-1-hydroxyethyl)-1-carbapen-2-em-3-carboxylate In the same manner as in Example 1-b), 34.0 mg of the title compound was obtained from 75.9 mg of 4-nitrobenzyl (5R,6S)-2-(7-hydroxyacetyl-5-methylimidazo[5,1-b]thiazol-2-yl)-6-((1R)-1-hydroxyethyl)-1-carbapen-2-em-3-carboxylate.

NMR (D$_2$O) δ (HOD=4.80 ppm): 1.33 (3H, d, J=6.3 Hz), 2.41 (3H, s), 3.16 (2H, m), 3.49 (1H, dd, J$_1$=5.6 Hz, J$_2$=2.5 Hz), 4.23 (2H, m), 4.68 (2H, s), 7.52 (1H, s)

Example 107

Pivaloyloxymethyl(1S,5R,6S)-6-((1R)-1-hydroxyethyl)-2-(7-methanesulfonyl-5-methylimidazo[5,1-b]thiazol-2-yl)-1-methyl-1-carbapen-2-em-3-carboxylate In the same manner as in Example 2, 26.5 mg of the title compound was obtained from 30.2 mg of sodium(1S,5R, 6S)-6-((1R)-1-hydroxyethyl)-2-(7-methanesulfonyl-5-methylimidazo[5,1-b]thiazol-2-yl)-1-methyl-1-carbapen-2-em-3-carboxylate.

NMR (CDCl$_3$) δ: 1.21 (9H, s), 1.27 (3H, t, J=7.1 Hz), 1.37 (3H, d, J=6.3 Hz), 2.68 (3H, s), 3.20 (3H, s), 3.34 (1H, dd, J$_1$=6.6 Hz, J$_2$=2.8 Hz), 3.45 (1H, m), 4.28 (1H, m), 4.36 (1H, dd, J$_1$=9.9 Hz, J$_2$=2.8 Hz), 5.86 (1H, d, J=5.5 Hz), 6.00 (1H, d, J=5.5 Hz), 8.29 (1H, s)

Example 108

Sodium(1S,5R,6S)-6-((1R)-1-hydroxyethyl)-2-(7-methanesulfonylaminoacetylimidazo[5,1-b]thiazol-2-yl)-1-methyl-1-carbapen-2-em-3-carboxylate a) 4-Nitrobenzyl(1S,5R,6S)-6-((1R)-1-hydroxyethyl)-2-(7-methanesulfonylaminoacetylimidazo-[5,1-b]thiazol-2-yl)-1-methyl-1-carbapen-2-em-3-carboxylate In the same manner as in Example 1-a), 106 mg of 4-nitrobenzyl(1S,5R,6S)-6-((1R)-1-hydroxyethyl)-2-(7-methanesulfonylaminoacetylimidazo[5,1-b]thiazol-2-yl)-1-methyl-1-carbapen-2-em-3-carboxylate was obtained from 159 mg of 4-nitrobenzyl(1R,3R,5R,6S)-6-((1R)-1-hydroxyethyl)-1-methyl-2-oxo-1-carbapenam-3-carboxylate and 264 mg of 7-methanesulfonylaminoacetyl-2-(tri-n-butylstannyl)imidazo[5,1-b]thiazole.

NMR (CDCl$_3$) δ: 1.31 (3H, d, J=7.1 Hz), 1.40 (3H, d, J=6.3 Hz), 3.01 (3H, s), 3.40 (1H, dd, J$_1$=6.5 Hz, J$_2$=2.9 Hz), 3.52 (1H, m), 4.33 (1H, m), 4.43 (1H, dd, J$_1$=9.7 Hz, J$_2$=2.9 Hz), 4.69 (2H, d, J=5.2 Hz), 5.29 (1H, d, J=13.6 Hz), 5.38 (1H, br), 5.53 (1H, d, J=13.6 Hz), 7.68 (2H, d, J=8.8 Hz), 8.01 (1H, s), 8.25 (2H, d, J=8.8 Hz), 8.49 (1H, s)

b) Sodium(1S,5R,6S)-6-((1R)-1-hydroxyethyl)-2-(7-methanesulfonylaminoacetylimidazo[5,1-b]thiazol-2-yl)-1-methyl-1-carbapen-2-em-3-carboxylate In the same manner as in Example 1-b), 65.0 mg of the title compound was obtained from 106 mg of 4-nitrobenzyl (1S,5R,6S)-6-((1R)-1-hydroxyethyl)-2-(7-methanesulfonylaminoacetylimidazo[5,1-b]thiazol-2-yl)-1-methyl-1-carbapen-2-em-3-carboxylate.

NMR (D$_2$O) δ (HOD=4.80 ppm): 1.24 (3H, d, J=6.9 Hz), 1.35 (3H, d, J=6.3 Hz), 3.19 (3H, s), 3.55 (2H, m), 4.32 (2H, m), 4.59 (2H, s), 7.96 (1H, s), 8.11 (1H, s)

Example 109

Sodium(1S,5R,6S)-6-((1R)-1-hydroxyethyl)-1-methyl-2-(5-methyl-7-methylthioimidazo[5,1-b]thiazol-2-yl)-1-carbapen-2-em-3-carboxylate In the same manner as in Example 1-b), 24.3 mg of the title compound was obtained from 42.9 mg of 4-nitrobenzyl (1S,5R,6S)-6-((1R)-1-hydroxyethyl)-1-methyl-2-(5-methyl-7-methylthioimidazo[5,1-b]thiazol-2-yl)-1-carbapen-2-em-3-carboxylate.

NMR (D$_2$O), δ (HOD=4.80 ppm): 1.24 (3H, d, J=6.9 Hz), 1.33 (3H, d, J=5.9 Hz), 2.33 (3H, s), 2.49 (3H, s), 3.54 (2H, m), 4.29 (2H, m), 7.70 (1H, s)

Example 110

Sodium(1S,5R,6S)-6-((1R)-1-hydroxyethyl)-2-[7-(methanesulfonylaminomethyl)imidazo[5,1-b]thiazol-2-yl]-1-methyl-1-carbapen-2-em-3-carboxylate a) 4-Nitrobenzyl(1S,5R,6S)-6-((1R)-1-hydroxyethyl)-2-[7-(methanesulfonylaminomethyl)-imidazo[5,1-b]thiazol-2-yl]-1-methyl-1-carbapen-2-em-3-carboxylate In the same manner as in Example 1-a), 69.4 mg of 4-nitrobenzyl(1S,5R,6S)-6-((1R)-1-hydroxyethyl)-2-[7-(methanesulfonylaminomethyl)imidazo[5,1-b]thiazol-2-yl]-1-methyl-1-carbapen-2-em-3-carboxylate was obtained as an yellowish orange oil from 124 mg of 4-nitrobenzyl(1R,3R,5R,6S)-6-((1R)-1-hydroxyethyl)-1-methyl-2-oxo-1-carbapenam-3-carboxylate and 196 mg of 7-methanesulfonylaminomethyl-2-(tri-n-butylstannyl)-imidazo[5,1-b]thiazole.

NMR (CDCl$_3$) δ: 1.30 (3H, d, J=7.3 Hz), 1.39 (3H, d, J=6.3 Hz), 2.91, 2.94 (total 3H, s each), 3.35–3.40 (2H, m), 4.25–4.45 (4H, m), 5.15 (1H, br.t), 5.27 (1H, d, J=13.5 Hz), 5.52 (1H, d, J=13.5 Hz), 6.87 (⅓H, d, J=4.2 Hz), 7.40 (⅓H, d, J=4.2 Hz), 7.68 (2H, d, J=8.8 Hz), 7.98 (⅓H, s), 8.24 (2H, d, J=8.8 Hz), 8.32 (⅓H, s) MS (TSP): 576 (M$^+$+H)

b) Sodium(1S,5R,6S)-6-((1R)-1-hydroxyethyl)-2-[7-(methanesulfonylaminomethyl)imidazo[5,1-b]thiazol-2-yl]-1-methyl-1-carbapen-2-em-3-carboxylate The title compound (18.2 mg) was obtained as a light yellow flocculate in the same manner as in Example 1-b), except that 68 mg 4-nitrobenzyl(1S,5R,6S)-6-((1R)-1-hydroxyethyl)-2-[7-(methanesulfonylaminomethyl)imidazo-[5,1-b]thiazol-2-yl]-1-methyl-1-carbapen-2-em-3-carboxylate was used as a starting compound and the purification was carried out by column chromatography on Cosmosil 40C18-PREP.

NMR (D$_2$O) δ (HOD=4.80 ppm): 1.25 (3H, d, J=7.4 Hz), 1.32 (3H, d, J=6.3 Hz), 2.99 (3H, s), 3.49–3.62 (2H, m), 4.24–4.35 (2H, m), 4.34 (2H, s), 7.88 (1H, s), 8.09 (1H, s) MS (TSP): 485 (M$^+$+2Na), 463 (M$^+$+Na), 441 (M$^+$+H)

Example 111

Sodium(1S,5R,6S)-6-((1R)-1-hydroxyethyl)-1-methyl-2-(7-methylthioimidazo[5,1-b]thiazol-2-yl)-1-carbapen-2-em-3-carboxylate a) 4-Nitrobenzyl(1S,5R,6S)-6-((1R)-1-hydroxyethyl)-1-methyl-2-(7-methylthioimidazo[5,1-b]thiazol-2-yl)-1-carbapen-2-em-3-carboxylate In the same manner as in Example 1-a), 14.0 g of 4-nitrobenzyl(1S,5R,6S)-6-((1R)-1-hydroxyethyl)-1-methyl-2-(7-methylthioimidazo-[5,1-b]thiazol-2-yl)-1-carbapen-2-em-3-carboxylate was obtained from 11.7 g of 4-nitrobenzyl(1R,3R,5R,6S)-6-((1R)-1-hydroxyethyl)-1-methyl-2-oxo-1-carbapenam-3-carboxylate and 14.0 g of 7-methylthio-2-(tri-n-butylstannyl)imidazo[5,1-b]thiazole.

NMR (CDCl$_3$) δ: 1.31 (3H, d, J=7.3 Hz), 1.40 (3H, d, J=6.3 Hz), 2.43 (3H, s), 3.35–3.40 (1H, s), 3.41–3.52 (1H, m), 4.30–4.42 (2H, m), 5.29 (1H, d, J=13.7 Hz), 5.53 (1H, d, J=13.7 Hz), 7.67 (2H, d, J=8.9 Hz), 8.02 (1H, s), 8.23 (2H, d, J=8.9 Hz), 8.29 (1H, s)

b) Sodium (1S,5R,6S)-6-((1R)-1-hydroxyethyl)-1-methyl-2-(7-methylthioimidazo[5,1-b]thiazol-2-yl)-1-carbapen-2-em-3-carboxylate The title compound (51 mg) was obtained from 103 mg of 4-nitrobenzyl(1S,5R,6S)-6-((1R)-1-hydroxyethyl)-1-methyl-2-(7-methylthioimidazo-[5,1-b]thiazol-2-yl)-1-carbapen-2-em-3-carboxylate in the same manner as in Example 1-b), except that the purification was carried out using Cosmosil 40C18-PREP (10% aqueous methanol).

NMR (D$_2$O) δ (HOD=4.80 ppm): 1.25 (3H, d, J=7.2 Hz), 1.32 (3H, d, J=6.4 Hz), 2.37 (3H, s), 3.50–3.60 (2H, m), 4.25–4.35 (2H, m), 7.90 (1H, s), 8.12 (1H, s)

Example 112

Sodium(5R,6S)-2-(7-dimethylaminosulfonyl-imidazo[5,1-b]thiazol-2-yl)-6-((1R)-1-hydroxy-ethyl)-1-carbapen-2-em-3-carboxylate a) 4-Nitrobenzyl(5R,6S)-2-(7-dimethyl-aminosulfonylimidazo[5,1-b]thiazol-2-yl)-6-((1R)-1-hydroxyethyl)-1-carbapen-2-em-3-carboxylate In the same manner as in Example 1-a), 0.29 g of 4-nitrobenzyl(5R,6S)-2-(7-dimethylamino-sulfonylimidazo [5,1-b]thiazol-2-yl)-6-((1R)-1-hydroxyethyl)-1-carbapen-2-em-3-carboxylate was obtained from 0.35 g of 4-nitrobenzyl (3R,5R,6S)-6-((1R)-1-hydroxyethyl)-2-oxo-1-carbapenam-3-carboxylate and 0.52 g of 7-dimethylamino-sulfonyl-2-(tri-n-butylstannyl)imidazo[5,1-b]-thiazole.

NMR (DMSO-d$_6$) δ: 1.17 (3H, d, J=6.0 Hz), 2.67 (6H, s), 3.40–3.55 (3H, m), 3.95–4.05 (1H, m), 4.20–4.30 (1H, m), 5.18 (1H, d, J=4.9 Hz), 5.42 (1H, d, J=14.0 Hz), 5.57 (1H, d, J=14.0 Hz), 7.75 (2H, d, J=8.5 Hz), 8.24 (2H, d, J=8.5 Hz), 8.42 (1H, s), 8.23 (1H, s)

b) Sodium(5R,6S)-2-(7-dimethylaminosulfonylimidazo[5,1-b]thiazol-2-yl)-6-((1R)-1-hydroxyethyl)-1-carbapen-2-em-3-carboxylate The title compound (84 mg) was obtained from 150 mg of 4-nitrobenzyl(5R,6S)-2-(7-dimethylaminosulfonylimidazo [5,1-b]thiazol-2-yl)-6-((1R)-1-hydroxyethyl)-1-carbapen-2-em-3-carboxylate in the same manner as in Example 1-b), except that the purification was carried out using Cosmosil 40C18-PREP (5% aqueous methanol).

NMR (D$_2$O) δ (HOD=4.80 ppm): 1.32 (3H, d, J=6.2 Hz), 3.30–3.40 (2H, s), 3.50–3.55 (1H, m), 4.25–4.35 (2H, m), 7.90 (1H, s), 8.23 (1H, s)

Example 113

Sodium(5R,6S)-2-(7-aminosulfonylimidazo[5,1-b]thiazol-2-yl)-6-((1R)-1-hydroxyethyl)-1-carbapen-2-em-3-carboxylate a) 4-Nitrobenzyl(5R,6S)-2-(7-t-butyldimethylsilylaminosulfonylimidazo[5,1-b]thiazol-2-yl)-6-((1R)-1-hydroxyethyl)-1-carbapen-2-em-3-carboxylate In the same manner as in Example 1-a), 0.36 g of 4-nitrobenzyl(5R,6S)-2-(7-t- butyldimethylsilylaminosulfonylimidazo[5,1-b]thiazol-2-yl)-6-((1R)-1-hydroxyethyl)-1-carbapen-2-em-3carboxylate was obtained from 0.28 g of 4-nitrobenzyl(3R,5R,6S)-6-((1R)-1-hydroxyethyl)-2-oxo-1-carbapenam-3-carboxylate and 0.44 g of 7-t-butyldimethylsilylaminosulfonyl-2-(tri-n-butylstannyl)imidazo[5,1-b]thiazole.

NMR (DMSO-$d_6$) δ: 0.11 (6H, s), 0.86 (9H, s), 1.17 (3H, d, J=6.0 Hz), 3.40–3.55 (3H, m), 3.95–4.05 (1H, m), 4.20–4.30 (1H, m), 5.42 (1H, d, J=14.0 Hz), 5.57 (1H, d, J=14.0 Hz), 7.65 (1H, s), 7.76 (2H, d, J=8.5 Hz), 8.23 (2H, d, J=8.5 Hz), 8.35 (1H, s), 8.42 (1H, s)

b) Sodium(5R,6S)-2-(7-aminosulfonylimidazo[5,1-b]thiazol-2-yl)-6-((1R)-1-hydroxyethyl)-1-carbapen-2-em-3-carboxylate In the same manner as in Example 99-b), 29 mg of the title compound was obtained from 83 mg of 4-nitrobenzyl(5R,6S)-2-(7-t-butyldimethylsilylaminosulfonylimidazo[5,1-b]thiazol-2-yl)-6-((1R)-1-hydroxyethyl)-1-carbapen-2-em-3-carboxylate.

NMR ($D_2O$) δ (HOD=4.80 ppm): 1.32 (3H, d, J=6.3 Hz), 3.25–3.40 (2H, m), 3.50–3.55 (1H, m), 4.20–4.35 (2H, m), 7.84 (1H, s), 8.19 (1H, s)

Example 114

Sodium(1S,5R,6S)-6-((1R)-1-hydroxyethyl)-1-methyl-2-[7-((E)-3-oxo-1-buten-1-yl)imidazo[5,1-b]thiazol-2-yl]-1-carbapen-2-em-3-carboxylate a) 4-Nitrobenzyl(1S,5R,6S)-6-((1R)-1-hydroxyethyl)-1-methyl-2-[7-((E)-3-oxo-1-buten-1-yl)imidazo[5,1-b]thiazol-2-yl]-1-carbapen-2-em-3-carboxylate In the same manner as in Example 1-a), 89 mg of 4-nitrobenzyl(1S,5R,6S)-6-((1R)-1-hydroxyethyl)-1-methyl-2-[7-((E)-3-oxo-1-buten-1-yl)imidazo[5,1-b]thiazol-2-yl]-1-carbapen-2-em-3-carboxylate was obtained from 320 mg of 4-nitrobenzyl(1R,3R,5R,6S)-6-((1R)-1-hydroxyethyl)-1-methyl-2-oxo-1-carbapenam-3-carboxylate and 208 mg of 7-((E)-3-oxo-1-buten-1-yl)-2-(tri-n-butylstannyl)imidazo[5,1-b]thiazole.

NMR ($CDCl_3$) δ: 1.33 (3H, d, J=7.3 Hz), 1.41 (3H, d, J=6.4 Hz), 2.38 (3H, s), 3.38 (1H, dd, $J_1$=6.4 Hz, $J_2$=2.7 Hz), 3.50 (1H, m), 4.33 (1H, m), 4.41 (1H, dd, $J_1$=9.6 Hz, $J_2$=2.7 Hz), 5.29 (1H, d, J=13.6 Hz), 5.53 (1H, d, J=13.6 Hz), 6.42 (1H, d, J=16.1 Hz), 7.63 (1H, d, J=16.1 Hz), 7.69 (2H, d, J=9.0 Hz), 8.09 (1H, s), 8.25 (2H, d, J=9.0 Hz), 8.39 (1H, s)

b) Sodium(1S,5R,6S)-6-((1R)-1-hydroxyethyl)-1-methyl-2-[7-((E)-3-oxo-1-buten-1-yl)imidazo[5,1-b]thiazol-2-yl]-1-carbapen-2-em-3-carboxylate In the same manner as in Example 1-b), 37 mg of the title compound was obtained from 85 mg of 4-nitrobenzyl (1S,5R,6S)-6-((1R)-1-hydroxyethyl)-1-methyl-2-[7-((E)-3-oxo-1-buten-1-yl)imidazo[5,1-b]thiazol-2-yl]-1-carbapen-2-em-3-carboxylate.

NMR ($D_2O$) δ (HOD=4.80 ppm): 1.08 (3H, d, J=7.0 Hz), 1.20 (3H, d, J=6.4 Hz), 2.21 (3H, s), 3.35 (1H, dd, $J_1$=6.4 Hz, $J_2$=2.7 Hz), 3.42 (1H, m), 4.15 (1H, m), 4.17 (1H, dd, $J_1$=8.6 Hz, $J_2$=2.2 Hz), 5.87 (1H, d, J=15.8 Hz), 7.32 (1H, d, J=15.8 Hz), 7.74 (1H, s), 7.96 (1H, s)

Example 115

Sodium(1S,5R,6S)-2-(7-formyl-5-methylimidazo[5,1-b]thiazol-2-yl)-6-((1R)-1-hydroxyethyl)-1-methyl-1-carbapen-2-em-3-carboxylate a) 4-Nitrobenzyl(1S,5R,6S)-2-[7-(t-butyldimethylsilyloxy)methyl-5-methylimidazo[5,1-b]thiazol-2-yl]-6-((1R)-1-hydroxyethyl)-1-methyl-1-carbapen-2-em-3-carboxylate In the same manner as in Example 1-a), 313 mg of 4-nitrobenzyl(1S,5R,6S)-2-[7-(t-butyldimethylsilyloxy)methyl-5-methylimidazo[5,1-b]thiazol-2-yl]-6-((1R)-1-hydroxyethyl)-1-methyl-1-carbapen-2-em-3-carboxylate was obtained from 730 mg of 4-nitrobenzyl(1R,3R,5R,6S)-6-((1R)-1-hydroxyethyl)-1-methyl-2-oxo-1-carbapenam-3-carboxylate and 1.2 g of 7-(t-butyldimethylsilyloxy)methyl-5-methyl-2-(tri-n-butylstannyl)imidazo[5,1-b]thiazole.

NMR ($CDCl_3$) δ: 0.13 (6H, s×2), 0.96 (9H, s), 1.31 (3H, d, J=7.3 Hz), 1.39 (3H, d, J=6.3 Hz), 2.55 (3H, s), 3.35 (1H, dd, $J_1$=6.6 Hz, $J_2$=2.7 Hz), 3.45 (1H, m), 4.30 (1H, m), 4.35 (1H, dd, $J_1$=9.5 Hz, $J_2$=2.7 Hz), 4.81 (2H, s), 5.26 (1H, d, J=13.6 Hz), 5.53 (1H, d, J=13.6 Hz), 7.67 (2H, d, J=8.7 Hz), 8.18 (1H, s), 8.23 (2H, d, J=8.7 Hz)

b) 4-Nitrobenzyl(1S,5R,6S)-6-((1R)-1-hydroxyethyl)-2-(7-hydroxymethyl-5-methylimidazo-[5,1-b]thiazol-2-yl)-1-methyl-1-carbapen-2-em-3-carboxylate Acetic acid (0.28 ml) and 1.6 ml of a 1 M tetrabutylammonium fluoride/THF solution were added to 313 mg of 4-nitrobenzyl(1S,5R,6S)-2-[7-(t-butyldimethylsilyloxy)methyl-5-methylimidazo[5,1-b]thiazol-2-yl]-6-((1R)-1-hydroxyethyl)-1-methyl-1-carbapen-2-em-3-carboxylate. The mixture was stirred at room temperature for 3.5 hr. The reaction solution was adjusted to pH 7 by the addition of a saturated aqueous sodium hydrogencarbonate solution. The reaction solution was then extracted with ethyl acetate, washed with saturated brine, and dried over magnesium sulfate. The reaction solution was then concentrated under the reduced pressure. The residue was purified by column chromatography to give 279 mg of 4-nitrobenzyl(1S,5R,6S)-6-((1R)-1-hydroxyethyl)-2-(7-hydroxymethyl-5-methylimidazo[5,1-b]thiazol-2-yl)-1-methyl-1-carbapen-2-em-3-carboxylate.

NMR ($CDCl_3$) δ: 1.28 (3H, d, J=7.3 Hz), 1.37 (3H, d, J=6.3 Hz), 2.56 (3H, s), 3.33 (1H, dd, $J_1$=6.3 Hz, $J_2$=2.7 Hz), 3.44 (1H, s), 4.23 (1H, m), 4.32 (1H, dd, $J_1$=9.5 Hz, $J_2$=2.7 Hz), 4.64 (2H, s), 5.28 (1H, d, J=13.8 Hz), 5.52 (1H, d, J=13.7 Hz), 7.67 (2H, d, J=9.0 Hz), 8.15 (1H, s), 8.23 (2H, d, J=9.0 Hz)

c) 4-Nitrobenzyl(1S,5R,6S)-2-(7-formyl-5-methylimidazo[5,1-b]thiazol-2-yl)-6-((1R)-1-hydroxyethyl)-1-methyl-1-carbapen-2-em-3-carboxylate 4-Nitrobenzyl(1S,5R,6S)-6-((1R)-1-hydroxyethyl)-2-(7-hydroxymethyl-5-methylimidazo-[5,1-b]thiazol-2-yl)-1-methyl-1-carbapen-2-em-3-carboxylate (279 mg) was dissolved in 30 ml of dichloromethane. Manganese dioxide (500 mg) was added to the solution. The mixture was stirred at room temperature for 14 hr. The reaction solution was filtered. The filtrate was concentrated under the reduced pressure. The residue was purified by column chromatography on silica gel to give 89 mg of 4-nitrobenzyl(1S,5R,6S)-2-(7-formyl-5-methylimidazo[5,1-b]thiazol-2-yl)-6-((1R)-1-hydroxyethyl)-1-methyl-1-carbapen-2-em-3-carboxylate.

NMR ($CDCl_3$) δ: 1.32 (3H, d, J=7.3 Hz), 1.40 (3H, d, J=6.3 Hz), 2.67 (3H, s), 3.38 (1H, dd, $J_1$=6.3 Hz, $J_2$=2.9 Hz), 3.52 (1H, s), 4.33 (1H, m), 4.42 (1H, dd, $J_1$=9.7 Hz, $J_2$=2.9 Hz), 5.27 (1H, d, J=13.6 Hz), 5.55 (1H, d, J=13.6 Hz), 7.68 (2H, d, J=9.0 Hz), 8.25 (2H, d, J=9.0 Hz), 8.37 (1H, s), 9.85 (1H, s)

d) Sodium(1S,5R,6S)-2-(7-formyl-5-methylimidazo[5,1-b]thiazol-2-yl)-6-((1R)-1-hydroxyethyl)-1-methyl-1-carbapen-2-em-3-carboxylate In the same manner as in Example 1-b), 29 mg of the title compound was obtained from 89 mg of 4-nitrobenzyl(1S, 5R,6S)-2-(7-formyl-5-methylimidazo[5,1-b]thiazol-2-yl)-6-((1R)-1-hydroxyethyl)-1-methyl-1-carbapen-2-em-3-carboxylate.

NMR (D$_2$O) δ (HOD=4.80 ppm): 1.09 (3H, d, J=7.1 Hz), 1.20 (3H, d, J=6.3 Hz), 2.43 (3H, s), 3.37 (1H, dd, J$_1$=6.3 Hz, J$_2$=2.7 Hz), 3.49 (1H, m), 4.14 (1H, q, J=6.3 Hz), 4.20 (1H, dd, J$_1$=9.3 Hz, J$_2$=2.7 Hz), 7.75 (1H, s), 9.25 (1H, s)

Example 116

Sodium(5R,6S)-6-((1R)-1-hydroxyethyl)-2-(7-methylthioimidazo[5,1-b]thiazol-2-yl)-1-carbapen-2-em-3-carboxylate a) 4-Nitrobenzyl(5R,6S)-6-((1R)-1-hydroxyethyl)-2-(7-methylthioimidazo[5,1-b]thiazol-2-yl)-1-carbapen-2-em-3-carboxylate In the same manner as in Example 1-a), 1.79 g of 4-nitrobenzyl(5R,6S)-6-((1R)-1-hydroxyethyl)-2-(7-methylthioimidazo[5,1-b]thiazol-2-yl)-1-carbapen-2-em-3-carboxylate was obtained from 2.30 g of 4-nitrobenzyl(3R,5R,6S)-6-((1R)-1-hydroxyethyl)-2-oxo-1-carbapenam-3-carboxylate and 3.48 g of 7-methylthio-2-(tri-n-butylstannyl)imidazo[5,1-b]thiazole.

NMR (CDCl$_3$) δ: 1.40 (3H, d, J=6.3 Hz), 2.42 (3H, s), 3.32 (3H, m), 4.32 (2H, m), 5.32 (1H, d, J=13.2 Hz), 5.55 (1H, d, J=13.2 Hz), 7.69 (2H, d, J=9.1 Hz), 8.01 (1H, s), 8.18 (1H, s), 8.25 (2H, d, J=9.1 Hz)

b) Sodium(5R,6S)-6-((1R)-1-hydroxyethyl)-2-(7-methylthioimidazo[5,1-b]thiazol-2-yl)-1-carbapen-2-em-3-carboxylate In the same manner as in Example 1-b), 54 mg of the title compound was obtained from 98 mg of 4-nitrobenzyl (5R,6S)-6-((1R)-1-hydroxyethyl)-2-(7-methylthioimidazo[5,1-b]thiazol-2-yl)-1-carbapen-2-em-3-carboxylate.

NMR (D$_2$O) δ (HOD=4.65 ppm): 1.19 (3H, d, J=6.3 Hz), 2.24 (3H, s), 3.16 (2H, m), 3.39 (1H, dd, J$_1$=6.0 Hz, J$_2$=2.9 Hz), 4.14 (2H, m), 7.60 (1H, s), 7.98 (1H, s)

Example 117

Sodium(5R,6S)-6-((1R)-1-hydroxyethyl)-2-(7-methanesulfinylimidazo[5,1-b]thiazol-2-yl)-1-carbapen-2-em-3-carboxylate (A Mixture of Diastereomers)

a) 4-Nitrobenzyl(5R,6S)-6-((1R)-1-hydroxyethyl)-2-(7-methanesulfinylimidazo[5,1-b]thiazol-2-yl)-1-carbapen-2-em-3-carboxylate (A Mixture of Diastereomers)

A reaction was carried out in the same manner as in Example 44-b), except that 639 mg of 4-nitrobenzyl(5R,6S)-6-((1R)-1-hydroxyethyl)-2-(7-methylthioimidazo[5,1-b]thiazol-2-yl)-1-carbapen-2-em-3-carboxylate and 1.57 g of oxone were used as the starting compounds. The reaction product was purified by column chromatography on silica gel (dichloromethane:methanol=20:1 to 10:1) to give 267 mg of 4-nitrobenzyl (5R,6S)-6-((1R)-1-hydroxyethyl)-2-(7-methanesulfinylimidazo[5,1-b]thiazol-2-yl)-1-carbapen-2-em-3-carboxylate (a mixture of diastereomers).

NMR (CDCl$_3$) δ: 1.40 (3H, d, J=6.1 Hz), 2.95, 2.95 (total 3H, s each), 3.33 (3H, m), 4.32 (2H, m), 5.31 (1H, d, J=13.6 Hz), 5.53 (1H, d, J=13.6 Hz), 7.68 (2H, d, J=8.8 Hz), 8.06 (1H, s), 8.24 (2H, d, J=8.8 Hz), 8.38 (1H, s)

b) Sodium(5R,6S)-6-((1R)-1-hydroxyethyl)-2-(7-methanesulfinylimidazo[5,1-b]thiazol-2-yl)-1-carbapen-2-em-3-carboxylate (A Mixture of Diastereomers)

In the same manner as in Example 1-b), 16 mg of the title compound was obtained from 74 mg of 4-nitrobenzyl (5R,6S)-6-((1R)-1-hydroxyethyl)-2-(7-methanesulfinylimidazo[5,1-b]thiazol-2-yl)-1-carbapen-2-em-3-carboxylate (a mixture of diastereomers).

NMR (DMSO-d$_6$) δ: 1.15 (3H, d, J=6.4 Hz), 2.83 (3H, s), 3.12 (2H, m), 3.21 (1H, m), 3.91 (1H, m), 4.01 (1H, m), 5.05 (1H, s), 7.95 (1H, s), 8.23 (1H, s)

Example 118

Sodium(5R,6S)-2-[7-(N,N-dimethylaminosulfonylamino)acetylimidazo[5,1-b]thiazol-2-yl]-6-((1R)-1-hydroxyethyl)-1-carbapen-2-em-3-carboxylate a) 4-Nitrobenzyl(5R,6S)-2-[7-(N,N-dimethylaminosulfonylamino)acetylimidazo[5,1-b]thiazol-2-yl]-6-((1R)-1-hydroxyethyl)-1-carbapen-2-em-3-carboxylate In the same manner as in Example 1-a), 162 mg of 4-nitrobenzyl(5R,6S)-2-[7-(N,N-dimethylaminosulfonylamino)acetylimidazo[5,1-b]thiazol-2-yl]-6-((1R)-1-hydroxyethyl)-1-carbapen-2-em-3-carboxylate was obtained from 244 mg of 4-nitrobenzyl(3R,5R,6S)-6-((1R)-1-hydroxyethyl)-2-oxo-1-carbapenam-3-carboxylate and 222 mg of 7-(N,N-dimethylaminosulfonylamino)acetyl-2-(tri-n-butylstannyl)imidazo[5,1-b]thiazole.

NMR (DMSO-d$_6$) δ: 1.18 (3H, d, J=6.1 Hz), 2.67 (6H, s), 3.4–3.6 (3H, m), 4.0–4.1 (1H, m), 4.2–4.35 (1H, m), 4.43 (2H, s), 5.44 (1H, d, J=13.7 Hz), 5.58 (1H, d, J=13.7 Hz), 7.77 (2H, d, J=8.5 Hz), 8.25 (2H, d, J=8.5 Hz), 8.37 (1H, s), 8.51 (1H, s)

b) Sodium(5R,6S)-2-[7-(N,N-dimethylaminosulfonylamino)acetylimidazo[5,1-b]thiazol-2-yl]-6-((1R)-1-hydroxyethyl)-1-carbapen-2-em-3-carboxylate The title compound (49.5 mg) was obtained from 160 mg of 4-nitrobenzyl(5R,6S)-2-[7-(N,N-dimethylaminosulfonylamino)acetylimidazo[5,1-b]thiazol-2-yl]-6-((1R)-1-hydroxyethyl)-1-carbapen-2-em-3-carboxylate in the same manner as in Example 1-b), except that the purification was carried out by column chromatography on Cosmosil 40C18-PREP (10% aqueous methanol).

NMR (D$_2$O) δ (HOD=4.80 ppm): 1.33 (3H, d, J=6.3 Hz), 2.83 (6H, s), 3.2–3.4 (2H, m), 3.52 (1H, dd, J$_1$=5.7 Hz, J$_2$=2.3 Hz), 4.2–4.35 (2H, m), 4.4–4.6 (2H, m), 7.81 (1H, s), 8.08 (1H, s)

Example 119

Sodium(1S,5R,6S)-2-[7-(N,N-dimethylaminosulfonylamino)acetylimidazo[5,1-b]thiazol-2-yl]-6-((1R)-1-hydroxyethyl)-1-methyl-1-carbapen-2-em-3-carboxylate a) 4-Nitrobenzyl(1S,5R,6S)-2-[7-(N,N-dimethylaminosulfonylamino)acetylimidazo[5,1-b]thiazol-2-yl]-6-((1R)-1-hydroxyethyl)-1-methyl-1-carbapen-2-em- 3-carboxylate In the same manner as in Example 1-a), 65.0 mg of 4-nitrobenzyl(1S,5R,6S)-2-[7-(N,N-dimethylaminosulfonylamino)acetylimidazo[5,1-b]thiazol-2-yl]-6-((1R)-1-hydroxyethyl)-1-methyl-1-carbapen-2-em-3-carboxylate was obtained from 127 mg of 4-nitrobenzyl (1R,3R,5R,6S)-6-((1R)-1-hydroxyethyl)-1-methyl-2-oxo-1- carbapenam-3-carboxylate and 222 mg of 7-(N,N-dimethylaminosulfonylamino)acetyl-2-(tri-n-butylstannyl)imidazo[5,1-b]thiazole.

NMR (CDCl$_3$) δ: 1.31 (3H, d, J=7.1 Hz), 1.40 (3H, d, J=6.3 Hz), 2.83 (6H, s), 3.39 (1H, dd, J$_1$=6.6 Hz, J$_2$=2.7 Hz), 3.45–3.6 (1H, m), 4.3–4.4 (1H, m), 4.43 (1H, dd, J$_1$=9.5 Hz, J$_2$=2.7 Hz), 4.57 (2H, d, J=5.0 Hz), 5.28 (1H, d, J=13.5 Hz), 5.42 (1H, br.s), 5.53 (1H, d, J=13.5 Hz), 7.68 (2H, d, J=8.5 Hz), 8.01 (1H, s), 8.24 (2H, d, J=8.5 Hz), 8.48 (1H, s)

b) Sodium(1S,5R,6S)-2-[7-(N,N-dimethylaminosulfonylamino)acetylimidazo[5,1-b]thiazol-2-yl]-6-((1R)-1-hydroxyethyl)-1-methyl-1-carbapen-2-em-3-carboxylate The title compound (34.4 mg) was obtained from 65.0 mg of 4-nitrobenzyl(1S,5R,6S)-2-[7-(N,N-dimethylaminosulfonylamino)acetylimidazo[5,1-b]thiazol-2-yl]-6-((1R)-1-hydroxyethyl)-1-methyl-1-carbapen-2-em-3-carboxylate in same manner as in Example 1-b), except that the purification was carried out by column chromatography on Cosmosil 40C18-PREP (10% aqueous methanol).

NMR (D$_2$O) δ (HOD=4.80 ppm): 1.22 (3H, d, J=6.9 Hz), 1.33 (3H, d, J=6.3 Hz), 2.83 (6H, s), 3.45–3.6 (2H, m), 4.2–4.35 (2H, m), 4.43 (1H, d, J=18.5 Hz), 4.54 (1H, d, J=18.5 Hz), 7.90 (1H, s), 8.06 (1H, s)

Example 120

Sodium(5R,6S)-6-((1R)-1-hydroxyethyl)-2-(5-methyl-7-methylthioimidazo[5,1-b]thiazol-2-yl)-1-carbapen-2-em-3-carboxylate In the same manner as in Example 1-b), 43 mg of the title compound was obtained from 72 mg of 4-nitrobenzyl(5R,6S)-6-((1R)-1-hydroxyethyl)-2-(5-methyl-7-methylthioimidazo[5,1-b]thiazol-2-yl)-1-carbapen-2-em-3-carboxylate.

NMR (D$_2$O) δ (HOD=4.65 ppm): 1.18 (3H, d, J=5.9 Hz), 2.20 (3H, s), 2.36 (3H, s), 3.12 (2H, m), 3.37 (1H, m), 4.13 (2H, m), 7.44 (1H, s)

Example 121

Sodium(1S,5R,6S)-2-(7-aminoacetylimidazo[5,1-b]thiazol-2-yl)-6-((1R)-1-hydroxyethyl)-1-methyl-1-carbapen-2-em-3-carboxylate a) 4-Nitrobenzyl(1S,5R,6S)-6-((1R)-1-hydroxyethyl)-1-methyl-2-[7-(4-nitrobenzyloxy-carbonylamino)acetylimidazo[5,1-b]thiazol-2-yl]-1-carbapen-2-em-3-carboxylate In the same manner as in Example 1-a), 468 mg of 4-nitrobenzyl(1S,5R,6S)-6-((1R)-1-hydroxyethyl)-1-methyl-2-[7-(4-nitrobenzyloxy-carbonylamino)acetylimidazo[5,1-b]thiazol-2-yl]-1-carbapen-2-em-3-carboxylate was obtained from 362 mg of 4-nitrobenzyl(1R,3R,5R,6S)-6-((1R)-1-hydroxyethyl)-1-methyl-2-oxo-1-carbapenam-3-carboxylate and 714 mg of 7-(4-nitrobenzyloxycarbonylamino)acetyl-2-(tri-n-butylstannyl)imidazo[5,1-b]thiazole.

NMR (DMSO-d$_6$) δ: 1.21 (3H, d), 1.24 (3H, d), 3.42 (1H, dd), 3.74 (1H, m), 4.06 (1H, m), 4.36 (1H, dd), 4.47, (2H, d), 5.16 (1H, d), 5.21 (2H, s), 5.48 (1H, d), 5.54 (1H, d), 7.65 (2H, d), 7.75 (2H, d), 8.21 (2H, d), 8.26 (2H, d), 8.34 (1H, s), 8.60 (1H, s)

b) Sodium(1S,5R,6S)-2-(7-aminoacetylimidazo[5,1-b]thiazol-2-yl)-6-((1R)-1-hydroxyethyl)-1-methyl-1-carbapen-2-em-3-carboxylate The title compound (25 mg) was obtained from 140 mg of 4-nitrobenzyl(1S,5R,6S)-6-((1R)-1-hydroxyethyl)-1-methyl-2-[7-(4-nitrobenzyloxy-carbonylamino)acetylimidazo[5,1-b]thiazol-2-yl]-1-carbapen-2-em-3-carboxylate in the same manner as in Example 1-b), except that the purification was carried out by column chromatography on Cosmosil 40C18-PREP (20% aqueous methanol).

NMR (D$_2$O) δ (HOD=4.80 ppm): 1.21 (3H, d), 1.33 (3H, d), 3.50 (2H, m), 4.30 (2H, m), 4.42 (2H, ABq), 7.91 (1H, s), 8.12 (1H, s)

Example 122

Sodium(1S,5R,6S)-2-(7-aminomethylimidazo[5,1-b]thiazol-2-yl)-6-((1R)-1-hydroxyethyl)-1-methyl-1-carbapen-2-em-3-carboxylate a) 4-Nitrobenzyl(1S,5R,6S)-6-((1R)-1-hydroxyethyl)-1-methyl-2-[7-(4-nitrobenzyloxy-carbonylaminomethyl)imidazo[5,1-b]thiazol-2-yl]-1-carbapen-2-em-3-carboxylate In the same manner as in Example 1-a), 228 mg of 4-nitrobenzyl(1S,5R,6S)-6-((1R)-1-hydroxyethyl)-1-methyl-2-[7-(4-nitrobenzyloxy-carbonylaminomethyl)imidazo[5,1-b]thiazol-2-yl]-1-carbapen-2-em-3-carboxylate was obtained from 181 mg of 4-nitrobenzyl(1R,3R,5R,6S)-6-((1R)-1-hydroxyethyl)-1-methyl-2-oxo-1-carbapenam-3-carboxylate and 373 mg of 7-(4-nitrobenzyloxycarbonylamino)methyl-2-(tri-n-butylstannyl)imidazo[5,1-b]thiazole.

NMR (DMSO-d$_6$) δ: 1.20 (6H, d), 3.39 (1H, dd), 3.62 (1H, m), 4.05 (1H, m), 4.24 (2H, d), 4.32, (1H, dd), 5.12 (1H, d), 5.20 (2H, s), 5.34 (1H, d), 5.48 (1H, d), 7.61 (2H, d), 7.71 (2H, d), 8.00 (1H, m), 8.12 (1H, s), 8.18 (4H, d), 8.35 (1H, s)

b) Sodium(1S,5R,6S)-2-(7-aminomethylimidazo[5,1-b]thiazol-2-yl)-6-((1R)-1-hydroxyethyl)-1-methyl-1-carbapen-2-em-3-carboxylate The title compound (24 mg) was obtained from 81 mg of 4-nitrobenzyl(1S,5R,6S)-6-((1R)-1-hydroxyethyl)-1-methyl-2-[7-(4-nitrobenzyloxy-carbonylaminomethyl)imidazo[5,1-b]thiazol-2-yl]-1-carbapen-2-em-3-carboxylate in the same manner as in Example 1-b), except that the purification was carried out by column chromatography on Cosmosil 40C18-PREP (30% aqueous methanol).

NMR (D$_2$O) δ (HOD=4.80 ppm): 1.20 (3H, d), 1.31 (3H, d), 3.49 (2H, m), 4.13 (1H, dd), 4.22 (2H, s), 4.27 (1H, m), 7.85 (1H, s), 8.13 (1H, s)

Example 123

Sodium(1S,5R,6S)-2-[7-(2-aminoethanesulfonylamino)acetylimidazo[5,1-b]thiazol-2-yl]-6-((1R)-1-hydroxyethyl)-1-methyl-1-carbapen-2-em-3-carboxylate a) 4-Nitrobenzyl(1S,5R,6S)-6-((1R)-1-hydroxyethyl)-1-methyl-2-[7-[2-(4-nitrobenzyloxy-carbonyl)aminoethanesulfonylamino]acetylimidazo[5,1-b]thiazol-2-yl]-1-carbapen-2-em-3-carboxylate In the same manner as in Example 1-a), 57.2 mg of 4-nitrobenzyl(1S,5R,6S)-6-((1R)-1-hydroxyethyl)-1-methyl-2-[7-[2-(4-nitrobenzyloxy-carbonyl)aminoethanesulfonylamino]acetylimidazo[5,1-b]thiazol-2-yl]-1-carbapen-2-em-3-carboxylate was obtained from 120 mg of 4-nitrobenzyl(1R,3R,5R,6S)-6-((1R)-1-hydroxyethyl)-1-methyl-2-oxo-1-carbapenam-3- carboxylate and 192 mg of 7-[2-(4-nitrobenzyloxycarbonyl) aminoethane-sulfonylamino]acetyl-2-(tri-n-butylstannyl)-imidazo[5,1-b]thiazole.

NMR (DMSO-$d_6$) δ: 1.19 (3H, d, J=6.5 Hz), 1.22 (3H, d, J=7.3 Hz), 3.2–3.3 (2H, m), 3.4–3.5 (3H, m), 3.7–3.8 (1H, m), 4.0–4.1 (1H, m), 4.3–4.4 (1H, m), 4.49 (2H, s), 5.17 (2H, s), 5.39 (1H, d, J=14.3 Hz), 5.53 (1H, d, J=14.3 Hz), 7.58 (2H, d, J=8.6 Hz), 7.74 (2H, d, J=8.6 Hz), 8.18 (2H, d, J=8.6 Hz), 8.21 (2H, d, J=8.6 Hz), 8.36 (1H, s), 8.59 (1H, s)

b) Sodium(1S,5R,6S)-2-[7-(2-aminoethanesulfonylamino)acetylimidazo[5,1-b]thiazol-2-yl]-6-((1R)-1-hydroxyethyl)-1-methyl-1-carbapen-2-em-3-carboxylate The title compound (20.1 mg) was obtained from 55.4 mg of 4-nitrobenzyl(1S,5R,6S)-6-((1R)-1-hydroxyethyl)-1-methyl-2-[7-[2-(4-nitrobenzyloxy-carbonyl)aminoethanesulfonylamino]acetylimidazo[5,1-b]thiazol-2-yl]-1-carbapen-2-em-3-carboxylate in the same manner as in Example 1-b), except that the purification was carried out by column chromatography on Cosmosil 40C18-PREP (10% aqueous methanol).

NMR ($D_2O$) δ (HOD=4.80 ppm): 1.20 (3H, d, J=7.1 Hz), 1.33 (3H, d, J=6.4 Hz), 3.4–3.55 (4H, m), 3.55–3.7 (2H, m), 4.2–4.35 (2H, m), 4.78 (2H, s), 7.83 (1H, s), 7.99 (1H, s)

Example 124

Sodium(5R,6S)-2-[7-(2-aminoethanesulfonyl amino)acetylimidazo[5,1-b]thiazol-2-yl]-6-((1R)-1-hydroxyethyl)-1-carbapen-2-em-3-carboxylate a) 4-Nitrobenzyl(5R,6S)-6-((1R)-1-hydroxyethyl)-2-[7-[2-(4-nitrobenzyloxycarbonyl)-aminoethanesulfonylamino]acetylimidazo[5,1-b]thiazol-2-yl]-1-carbapen-2-em-3-carboxylate In the same manner as in Example 1-a), 80.6 mg of 4-nitrobenzyl(5R,6S)-6-((1R)-1-hydroxyethyl)-2-[7-[2-(4-nitrobenzyloxycarbonyl)aminoethane-sulfonylamino]acetylimidazo[5,1-b]thiazol-2-yl]-1-carbapen-2-em-3-carboxylate was obtained from 99 mg of 4-nitrobenzyl(3R,5R,6S)-6-((1R)-1-hydroxyethyl)-2-oxo-1-carbapenam-3-carboxylate and 215 mg of 7-[2-(4-nitrobenzyloxycarbonyl) aminoethanesulfonylamino]-acetyl-2-(tri-n-butylstannyl) imidazo[5,1-b]-thiazole.

NMR (CDCl$_3$) δ: 1.41 (3H, d, J=6.3 Hz), 3.25–3.4 (5H, m), 3.7–3.8 (2H, m), 4.3–4.45 (2H, m), 4.68 (2H, d, J=5.0 Hz), 5.19 (2H, s), 5.33 (1H, d, J=13.3 Hz), 5.55 (1H, d, J=13.3 Hz), 7.49 (2H, d, J=8.8 Hz), 7.70 (2H, d, J=8.8 Hz), 7.99 (1H, s), 8.17 (2H, d, J=8.8 Hz), 8.25 (2H, d, J=8.8 Hz), 8.33 (1H, s)

b) Sodium(5R,6S)-2-[7-(2-aminoethanesulfonylamino)acetylimidazo[5,1-b]thiazol-2-yl]-6-((1R)-1-hydroxyethyl)-1-carbapen-2-em-3-carboxylate The title compound (21.4 mg) was obtained from 80.6 mg of 4-nitrobenzyl(5R,6S)-6-((1R)-1-hydroxyethyl)-2-[7-[2-(4-nitrobenzyloxycarbonyl)-aminoethanesulfonylamino]acetylimidazo[5,1-b]thiazol-2-yl]-1-carbapen-2-em-3-carboxylate in the same manner as in Example 1-b), except that the purification was carried out by column chromatography on Cosmosil 40C18-PREP (20% aqueous methanol).

NMR ($D_2O$) δ (HOD=4.80 ppm): 1.33 (3H, d, J=6.6 Hz), 3.0–3.25 (2H, m), 3.5–3.75 (5H, m), 4.2–4.35 (2H, m), 4.51 (2H, s), 7.59 (1H, s), 7.94 (1H, s)

Example 125

Sodium(1S,5R,6S)-6-((1R)-1-hydroxyethyl)-2-(5-methanesulfonylimidazo[5,1-b]thiazol-2-yl)-1-methyl-1-carbapen-2-em-3-carboxylate a) 4-Nitrobenzyl(1S,5R,6S)-6-((1R)-1-hydroxyethyl)-1-methyl-2-(5-methylthioimidazo-[5,1-b]thiazol-2-yl)-1-carbapen-2-em-3-carboxylate In the same manner as in Example 1-a), 643 mg of 4-nitrobenzyl(1S,5R,6S)-6-((1R)-1-hydroxyethyl)-1-methyl-2-(5-methylthioimidazo-[5,1-b]thiazol-2-yl)-1-carbapen-2-em-3-carboxylate was obtained from 847 mg of 4-nitrobenzyl(1R,3R,5R,6S)-6-((1R)-1-hydroxyethyl)-1-methyl-2-oxo-1-carbapenam-3-carboxylate and 1.13 g of 5-methylthio-2-(tri-n-butylstannyl)imidazo[5,1-b]thiazole.

NMR (CDCl$_3$) δ: 1.32 (3H, d, J=7.3 Hz), 1.39 (3H, d, J=6.3 Hz), 2.55 (3H, s), 3.36 (1H, m), 3.49 (1H, m), 4.31 (1H, m), 4.36, (1H, dd, J$_1$=9.5 Hz, J$_2$=2.7 Hz), 5.28 (1H, d, J=13.6 Hz), 5.53 (1H, d, J=13.6 Hz), 7.11 (1H, s), 7.67 (2H, d, J=8.7 Hz), 8.18 (1H, s), 8.23 (2H, d, J=8.7 Hz)

b) 4-Nitrobenzyl(1S,5R,6S)-6-((1R)-1-hydroxyethyl)-2-(5-methanesulfonylimidazo[5,1-b]thiazol-2-yl)-1-methyl-1-carbapen-2-em-3-carboxylate A reaction was carried in the same manner as in Example 44-b), except that 112 mg of 4-nitrobenzyl(1S,5R,6S)-6-((1R)-1-hydroxyethyl)-1-methyl-2-(5-methylthioimidazo[5,1-b]thiazol-2-yl)-1-carbapen-2-em-3-carboxylate and 268 mg of oxone were used as the starting compounds. The reaction product was purified by column chromatography on silica gel (dichloromethane:methanol=20:1 to 10:1) to give 75 mg of 4-nitrobenzyl (1S,5R,6S)-6-((1R)-1-hydroxyethyl)-2-(5-methanesulfonylimidazo[5,1-b]thiazol-2-yl)-1-methyl-1-carbapen-2-em-3-carboxylate.

NMR (CDCl$_3$) δ: 1.34 (3H, d, J=7.3 Hz), 1.39 (3H, d, J=6.3 Hz), 3.33 (3H, s), 3.38 (1H, m), 3.59 (1H, m), 4.31 (1H, m), 4.38, (1H, dd, J$_1$=9.6 Hz, J$_2$=2.8 Hz), 5.30 (1H, d, J=13.7 Hz), 5.53 (1H, d, J=13.7 Hz), 7.29 (1H, s), 7.66 (2H, d, J=8.8 Hz), 8.23 (2H, d, J=8.8 Hz), 8.54 (1H, s)

c) Sodium(1S,5R,6S)-6-((1R)-1-hydroxyethyl)-2-(5-methanesulfonylimidazo[5,1-b]thiazol-2-yl)-1-methyl-1-carbapen-2-em-3-carboxylate In the same manner as in Example 1-b), 32 mg of the title compound was obtained from 75 mg of 4-nitrobenzyl (1S,5R,6S)-6-((1R)-1-hydroxyethyl)-2-(5-methanesulfonylimidazo[5,1-b]thiazol-2-yl)-1-methyl-1-carbapen-2-em-3-carboxylate.

NMR ($D_2O$) δ (HOD=4.65 ppm): 1.11 (3H, d, J=7.3 Hz), 1.18 (3H, d, J=6.5 Hz), 3.23 (3H, s), 3.40, (1H, dd, J$_1$=6.1 Hz, J$_2$=2.6 Hz), 3.50 (1H, m), 4.13 (1H, m), 4.19, (1H, dd, J$_1$=9.3 Hz, J$_2$=2.5 Hz), 7.21 (1H, s), 8.02 (1H, s)

Example 126

Sodium(1S,5R,6S)-6-((1R)-1-hydroxyethyl)-1-methyl-2-(5-methylthioimidazo[5,1-b]thiazol-2-yl)-1-carbapen-2-em-3-carboxylate In the same manner as in Example 1-b), the title compound (44 mg) was obtained from 107 mg of 4-nitrobenzyl (1S,5R,6S)-6-((1R)-1-hydroxyethyl)-1-methyl-2-(5-methylthioimidazo[5,1-b]thiazol-2-yl)-1-carbapen-2-em-3-carboxylate.

NMR (D₂O) δ (HOD=4.65 ppm): 1.12 (3H, d, J=7.1 Hz), 1.19 (3H, d, J=6.6 Hz), 2.32 (3H, s), 3.38, (1H, dd, J₁=5.4 Hz, J₂=2.1 Hz), 3.46 (1H, m), 4.15 (2H, m), 6.89 (1H, s), 7.01 (1H, s)

Example 127

Sodium(1S,5R,6S)-2-[5,7-bis(methylthio)imidazo[5,1-b]thiazol-2-yl]-6-((1R)-1-hydroxyethyl)-1-methyl-1-carbapen-2-em-3-carboxylate a) 4-Nitrobenzyl(1S,5R,6S)-2-[5,7-bis(methylthio)imidazo[5,1-b]thiazol-2-yl]-6-((1R)-1-hydroxyethyl)-1-methyl-1-carbapen-2-em-3-carboxylate In the same manner as in Example 1-a), 720 mg of 4-nitrobenzyl(1S,5R,6S)-2-[5,7-bis(methylthio)imidazo[5,1-b]thiazol-2-yl]-6-((1R)-1-hydroxyethyl)-1-methyl-1-carbapen-2-em-3-carboxylate was obtained from 762 mg of 4-nitrobenzyl(1R,3R,5R,6S)-6-((1R)-1-hydroxyethyl)-1-methyl-2-oxo-1-carbapenam-3-carboxylate and 1.10 g of 5,7-bis(methylthio)-2-(tri-n-butylstannyl)imidazo[5,1-b]thiazole.

NMR (CDCl₃) δ: 1.31 (3H, d, J=7.3 Hz), 1.39 (3H, d, J=6.3 Hz), 2.43 (3H, s), 2.58 (3H, s), 3.36 (1H, m), 3.49 (1H, m), 4.33 (2H, m), 5.28 (1H, d, J=13.7 Hz), 5.53 (1H, d, J=13.4 Hz), 7.67 (2H, d, J=9.0 Hz), 8.13 (1H, s), 8.23 (2H, d, J=9.0 Hz)

b) Sodium(1S,5R,6S)-2-[5,7-bis(methylthio)imidazo[5,1-b]thiazol-2-yl]-6-((1R)-1-hydroxyethyl)-1-methyl-1-carbapen-2-em-3-carboxylate In the same manner as in Example 1-b), 42 mg of the title compound was obtained from 89 mg of 4-nitrobenzyl(1S,5R,6S)-2-[5,7-bis(methylthio)-imidazo[5,1-b]thiazol-2-yl]-6-((1R)-1-hydroxy-ethyl)-1-methyl-1-carbapen-2-em-3-carboxylate.

NMR (D₂O) δ (HOD=4.65 ppm): 1.09 (3H, d, J=7.3 Hz), 1.18 (3H, d, J=6.3 Hz), 2.20 (3H, s), 2.34 (3H, s), 3.36, (1H, dd, J₁=6.0 Hz, J₂=2.6 Hz), 3.45 (1H, m), 4.15 (2H, m), 7.66 (1H, s)

Example 128

Sodium(1S,5R,6S)-6-((1R)-1-hydroxyethyl)-1-methyl-2-(7-phenylthioimidazo[5,1-b]thiazol-2-yl)-1-carbapen-2-em-3-carboxylate a) 4-Nitrobenzyl(1S,5R,6S)-6-((1R)-1-hydroxyethyl)-1-methyl-2-(7-phenylthioimidazo-[5,1-b]thiazol-2-yl)-1-carbapen-2-em-3-carboxylate In the same manner as in Example 1-a), 92.5 mg of 4-nitrobenzyl(1S,5R,6S)-6-((1R)-1-hydroxyethyl)-1-methyl-2-(7-phenylthioimidazo-[5,1-b]thiazol-2-yl)-1-carbapen-2-em-3-carboxylate was obtained from 146 mg of 4-nitrobenzyl(1R,3R,5R,6S)-6-((1R)-1-hydroxyethyl)-1-methyl-2-oxo-1-carbapenam-3-carboxylate and 231 mg of 7-phenylthio-2-(tri-n-butylstannyl)imidazo[5,1-b]thiazole.

NMR (CDCl₃) δ: 1.30 (3H, d, J=7.3 Hz), 1.39 (3H, d, J=6.2 Hz), 3.36 (1H, dd, J₁=6.5 Hz, J₂=2.8 Hz), 3.4–3.5 (1H, m), 4.25–4.35 (1H, m), 4.36 (1H, dd, J₁=9.7 Hz, J₂=2.8 Hz), 5.27 (1H, d, J=13.5 Hz), 5.52 (1H, d, J=13.5 Hz), 7.1–7.25 (5H, m), 7.67 (2H, d, J=8.7 Hz), 8.10 (1H, s), 8.24 (2H, d, J=8.7 Hz), 8.35 (1H, s)

b) Sodium(1S,5R,6S)-6-((1R)-1-hydroxyethyl)-1-methyl-2-(7-phenylthioimidazo[5,1-b]thiazol-2-yl)-1-carbapen-2-em-3-carboxylate The title compound (23.9 mg) was obtained from 42.8 mg of 4-nitrobenzyl(1S,5R,6S)-6-((1R)-1-hydroxyethyl)-1-methyl-2-(7-phenylthioimidazo[5,1-b]thiazol-2-yl)-1-carbapen-2-em-3-carboxylate in the same manner as in Example 1-b), except that the purification was carried out by column chromatography on Cosmosil 40C18-PREP (20% aqueous methanol).

NMR (D₂O) δ (HOD=4.80 ppm): 1.17 (3H, d, J=6.9 Hz), 1.31 (3H, d, J=6.3 Hz), 3.35–3.5 (2H, m), 4.2–4.3 (2H, m), 7.1–7.3 (5H, m), 7.87 (1H, s), 8.15 (1H, s)

Example 129

Sodium(5R,6S)-6-((1R)-1-hydroxyethyl)-2-(7-methylthioimidazo[5,1-b]thiazol-3-yl)-1-carbapen-2-em-3-carboxylate a) 4-Nitrobenzyl(5R,6S)-6-((1R)-1-hydroxyethyl)-2-(7-methylthioimidazo[5,1-b]-thiazol-3-yl)-1-carbapen-2-em-3-carboxylate In the same manner as in Example 1-a), 230 mg of 4-nitrobenzyl(5R,6S)-6-((1R)-1-hydroxyethyl)-2-(7-methylthioimidazo[5,1-b]thiazol-3-yl)-1-carbapen-2-em-3-carboxylate was obtained from 348 mg of 4-nitrobenzyl(3R,5R,6S)-6-((1R)-1-hydroxyethyl)-2-oxo-1-carbapenam-3-carboxylate and 535 mg of 7-methylthio-3-(tri-n-butylstannyl)imidazo[5,1-b]thiazole.

NMR (DMSO-d₆) δ: 1.18 (3H, d), 2.31 (3H, s), 3.27 (1H, m), 3.56 (2H, m), 4.02 (1H, m), 4.42 (1H, m), 5.27 (1H, d), 5.31 (2H, ABq), 7.43 (1H, s), 7.50 (2H, d), 8.16 (2H, d), 8.30 (1H, s)

b) Sodium(5R,6S)-6-((1R)-1-hydroxyethyl)-2-(7-methylthioimidazo[5,1-b]thiazol-3-yl)-1-carbapen-2-em-3-carboxylate The title compound (28 mg) was obtained from 100 mg of 4-nitrobenzyl(5R,6S)-6-((1R)-1-hydroxyethyl)-2-(7-methylthioimidazo[5,1-b]thiazol-3-yl)-1-carbapen-2-em-3-carboxylate in the same manner as in Example 1-b), except that the purification was carried out by column chromatography on Cosmosil 40C18-PREP (10–20% aqueous methanol).

NMR (D₂O) δ (HOD=4.80 ppm): 1.21 (3H, d), 2.37 (3H, s), 3.18 (1H, dd), 3.44 (1H, dd), 3.58 (1H, dd), 4.28 (1H, m), 4.87 (1H, m), 7.08 (1H, s), 7.92 (1H, s)

Example 130

Sodium(5R,6S)-6-((1R)-1-hydroxyethyl)-2-(7-phenylthioimidazo[5,1-b]thiazol-2-yl)-1-carbapen-2-em-3-carboxylate a) 4-Nitrobenzyl(5R,6S)-6-((1R)-1-hydroxyethyl)-2-(7-phenylthioimidazo[5,1-b]-thiazol-2-yl)-1-carbapen-2-em-3-carboxylate In the same manner as in Example 1-a), 105.3 mg of 4-nitrobenzyl(5R,6S)-6-((1R)-1-hydroxyethyl)-2-(7-phenylthioimidazo[5,1-b]thiazol-2-yl)-1-carbapen-2-em-3-carboxylate was obtained from 140 mg of 4-nitrobenzyl(3R,5R,6S)-6-((1R)-1-hydroxyethyl)-2-oxo-1-carbapenam-3-carboxylate and 232 mg of 7-phenylthio-2-(tri-n-butylstannyl)imidazo[5,1-b]thiazole.

NMR (DMSO-d₆) δ: 1.17 (3H, d, J=6.2 Hz), 3.35–3.55 (3H, m), 3.95–4.05 (1H, m), 4.2–4.3 (1H, m), 5.39 (1H, d, J=13.8 Hz), 5.51 (1H, d, J=13.8 Hz), 7.0–7.3 (5H, m), 7.74 (2H, d, J=8.7 Hz), 8.22 (2H, d, J=8.7 Hz), 8.40 (1H, s), 8.43 (1H, s)

b) Sodium(5R,6S)-6-((1R)-1-hydroxyethyl)-2-(7-phenylthioimidazo[5,1-b]thiazol-2-yl)-1-carbapen-2-em-3-carboxylate The title compound (21.9 mg) was obtained from 47.1 mg of 4-nitrobenzyl(5R,6S)-6-((1R)-1-hydroxyethyl)-2-(7- phenylthioimidazo[5,1-b]-thiazol-2-yl)-1-carbapen-2-em-3-carboxylate in the same manner as in Example 1-b), except that the purification was carried out by column chromatography on Cosmosil 40C18-PREP (10% aqueous methanol).

NMR (D$_2$O) δ (HOD=4.80 ppm): 1.31 (3H, d, J=6.3 Hz), 3.05–3.25 (2H, m), 3.47 (1H, dd, J$_1$=5.8 Hz, J$_2$=2.8 Hz), 4.2–4.3 (2H, m), 7.1–7.3 (5H, m), 7.62 (1H, s), 8.08 (1H, s)

Example 131

Sodium(1S,5R,6S)-6-((1R)-1-hydroxyethyl)-1-methyl-2-(3-methylthioimidazo[5,1-b]thiazol-2-yl)-1-carbapen-2-em-3-carboxylate a) 4-Nitrobenzyl(1S,5R,6S)-6-((1R)-1-hydroxyethyl)-1-methyl-2-(3-methylthioimidazo-[5,1-b]thiazol-2-yl)-1-carbapen-2-em-3-carboxylate In the same manner as in Example 1-a), 287 mg of 4-nitrobenzyl(1S,5R,6S)-6-((1R)-1-hydroxyethyl)-1-methyl-2-(3-methylthioimidazo-[5,1-b]thiazol-2-yl)-1-carbapen-2-em-3-carboxylate was obtained from 1.56 g of 4-nitrobenzyl(1R,3R,5R,6S)-6-((1R)-1-hydroxyethyl)-1-methyl-2-oxo-1-carbapenam-3-carboxylate and 2.05 g of 3-methylthio-2-(tri-n-butylstannyl)imidazo[5,1-b]thiazole.

NMR (CDCl$_3$) δ: 1.21(3H, d, J=7.3 Hz), 1.38 (3H, d, J=6.3 Hz), 2.27 (3H, s), 3.38 (1H, m), 3.46 (1H, m), 4.43 (1H, m), 4.47, (1H, dd, J$_1$=10.5 Hz, J$_2$=3.1 Hz), 5.19 (1H, d, J=13.7 Hz), 5.39 (1H, d, J=13.7 Hz), 7.14 (1H, s), 7.50 (2H, d, J=9.0 Hz), 8.05 (1H, s), 8.14 (2H, d, J=9.0 Hz)

b) Sodium(1S,5R,6S)-6-((1R)-1-hydroxyethyl)-1-methyl-2-(3-methylthioimidazo-[5,1-b]thiazol-2-yl)-1-carbapen-2-em-3-carboxylate In the same manner as in Example 1-b), 37 mg of the title compound was obtained from 83 mg of 4-nitrobenzyl(1S, 5R,6S)-6-((1R)-1-hydroxyethyl)-1-methyl-2-(3-methylthioimidazo[5,1-b]thiazol-2-yl)-1-carbapen-2-em-3-carboxylate.

NMR (D$_2$O) δ (HOD=4.65 ppm): 1.02 (3H, d, J=7.3 Hz), 1.15 (3H, d, J=6.3 Hz), 2.21 (3H, s), 3.31, (1H, m), 3.40 (1H, m), 4.13 (1H, m), 4.22 (1H, dd, J$_1$=10.0 Hz, J$_2$=3.0 Hz), 6.96 (1H, s), 8.15 (1H, s)

Example 132

Sodium(1S,5R,6S)-2-(7-ethylthioimidazo-[5,1-b]thiazol-2-yl)-6-((1R)-1-hydroxyethyl)-1-methyl-1-carbapen-2-em-3-carboxylate a) 4-Nitrobenzyl(1S,5R,6S)-2-(7-ethylthioimidazo[5,1-b]thiazol-2-yl)-6-((1R)-1-hydroxyethyl)-1-methyl-1-carbapen-2-em-3-carboxylate In the same manner as in Example 1-a), 731 mg of 4-nitrobenzyl(1S,5R,6S)-2-(7-ethylthioimidazo[5,1-b]thiazol-2-yl)-6-((1R)-1-hydroxyethyl)-1-methyl-1-carbapen-2-em-3-carboxylate was obtained from 724 mg of 4-nitrobenzyl(1R,3R,5R,6S)-6-((1R)-1-hydroxyethyl)-1-methyl-2-oxo-1-carbapenam-3-carboxylate and 1.04 g of 7-ethylthio-2-(tri-n-butylstannyl)imidazo[5,1-b]thiazole.

NMR (CDCl$_3$) δ: 1.26 (3H, t, J=7.3 Hz), 1.31 (3H, d, J=7.2 Hz), 1.40 (3H, d, J=6.1 Hz), 2.84 (2H, q, J=7.3 Hz), 3.37 (1H, dd, J$_1$=6.5 Hz, J$_2$=2.8 Hz), 3.4–3.5 (1H, m), 4.25–4.35 (1H, m), 4.38 (1H, dd, J$_1$=9.4 Hz, J$_2$=2.8 Hz), 5.28 (1H, d, J=13.7 Hz), 5.53 (1H, d, J=13.7 Hz), 7.68 (2H, d, J=8.4 Hz), 8.03 (1H, s), 8.24 (2H, d, J=8.4 Hz), 8.30 (1H, s)

b) Sodium(1S,5R,6S)-2-(7-ethylthioimidazo[51-b]thiazol-2-yl)-6-((1R)-1-hydroxyethyl)-1-methyl-1-carbapen-2-em-3-carboxylate The title compound (87.5 mg) was obtained from 174 mg of 4-nitrobenzyl(1S,5R,6S)-2-(7-ethylthioimidazo[5,1-b]thiazol-2-yl)-6-((1R)-1-hydroxyethyl)-1-methyl-1-carbapen-2-em-3-carboxylate in the same manner as in Example 1-b), except that the purification was carried out by column chromatography on Cosmosil 40C18-PREP (5% aqueous methanol).

NMR (D$_2$O) δ (HOD=4.80 ppm): 1.15 (3H, t, J=7.3 Hz), 1.24 (3H, d, J=7.4 Hz), 1.32 (3H, d, J=6.2 Hz), 2.76 (2H, q, J=7.3 Hz), 3.45–3.6 (2H, m), 4.2–4.35 (2H, m), 7.88 (1H, s), 8.12 (1H, s)

Example 133

Sodium(5R,6S)-6-((1R)-1-hydroxyethyl)-2-(3-methylthioimidazo[5,1-b]thiazol-2-yl)-1-carbapen-2-em-3-carboxylate a) 4-Nitrobenzyl(5R,6S)-6-((1R)-1-hydroxyethyl)-2-(3-methylthioimidazo[5,1-b]thiazol-2-yl)-1-carbapen-2-em-3-carboxylate In the same manner as in Example 1-a), 37 mg of 4-nitrobenzyl(5R,6S)-6-((1R)-1-hydroxyethyl)-2-(3-methylthioimidazo[5,1-b]thiazol-2-yl)-1-carbapen-2-em-3-carboxylate was obtained from 743 mg of 4-nitrobenzyl(3R, 5R,6S)-6-((1R)-1-hydroxyethyl)-2-oxo-1-carbapenam-3-carboxylate and 1.02 g of 3-methylthio-2-(tri-n-butylstannyl)imidazo[5,1-b]thiazole.

NMR (CDCl$_3$) δ: 1.39 (3H, d, J=6.3 Hz), 2.31 (3H, s), 3.28 (2H, m), 3.39 (1H, m), 4.30 (1H, m), 4.42 (1H, m), 5.24 (1H, d, J=13.7 Hz), 5.38 (1H, d, J=13.7 Hz), 7.13 (1H, s), 7.50 (2H, d, J=9.1 Hz), 8.04 (1H, s), 8.14 (2H, d, J=9.1 Hz)

b) Sodium(5R,6S)-6-((1R)-1-hydroxyethyl)-2-(3-methylthioimidazo[5,1-b]thiazol-2-yl)-1-carbapen-2-em-3-carboxylate In the same manner as in Example 1-b), 15 mg of the title compound was obtained from 35 mg of 4-nitrobenzyl(5R, 6S)-6-((1R)-1-hydroxyethyl)-2-(3-methylthioimidazo[5,1-b]thiazol-2-yl)-1-carbapen-2-em-3-carboxylate.

NMR (D$_2$O) δ (HOD =4.65 ppm): 1.15 (3H, d, J=6.3 Hz), 2.22 (3H, s), 3.03 (1H, m), 3.26 (1H, m), 3.42 (1H, m), 4.12 (1H, m), 4.22 (1H, m), 6.96 (1H, s), 8.16 (1H, s)

Example 134

Sodium(5R,6S)-2-(7-ethylthioimidazo[5,1-b]thiazol-2-yl)-6-((1R)-1-hydroxyethyl)-1-carbapen-2-em-3-carboxylate a) 4-Nitrobenzyl(5R,6S)-2-(7-ethylthioimidazo[5,1-b]thiazol-2-yl)-6-((1R)-1-hydroxyethyl)-1-carbapen-2-em-3-carboxylate In the same manner as in Example 1-a), 691 mg of 4-nitrobenzyl(5R,6S)-2-(7-ethylthioimidazo[5,1-b]thiazol-2-yl)-6-((1R)-1-hydroxyethyl)-1-carbapen-2-em-3-carboxylate was obtained from 869 mg of 4-nitrobenzyl(3R, 5R,6S)-6-((1R)-1-hydroxyethyl)-2-oxo-1-carbapenam-3-carboxylate and 1.30 g of 7-ethylthio-2-(tri-n-butylstannyl) imidazo[5,1-b]thiazole.

NMR (CDCl$_3$) δ: 1.25 (3H, t, J=7.3 Hz), 1.40 (3H, d, J=6.4 Hz), 2.83 (2H, q, J=7.3 Hz), 3.3–3.4 (3H, m), 4.25–4.4

(2H, m), 5.32 (1H, d, J=13.6 Hz), 5.55 (1H, d, J=13.6 Hz), 7.69 (2H, d, J=9.0 Hz), 8.02 (1H, s), 8.20 (1H, s), 8.25 (2H, d, J=9.0 Hz)

b) Sodium(5R,6S)-2-(7-ethylthioimidazo[5,1-b]thiazol-2-yl)-6-((1R)-1-hydroxyethyl)-1-carbapen-2-em-3-carboxylate The title compound (60.7 mg) was obtained from 115 mg of 4-nitrobenzyl(5R,6S)-2-(7-ethylthioimidazo[5,1-b]thiazol-2-yl)-6-((1R)-1-hydroxyethyl)-1-carbapen-2-em-3-carboxylate in the same manner as in Example 1-b), except that the purification was carried out by column chromatography on Cosmosil 40C18-PREP (5% aqueous methanol).

NMR (D$_2$O) δ (HOD=4.80 ppm): 1.16 (3H, t, J=7.4 Hz), 1.32 (3H, d, J=6.4 Hz), 2.77 (2H, q, J=7.4 Hz), 3.2–3.4 (2H, m), 3.45–3.55 (1H, m), 4.2–4.35 (2H, m), 7.72 (1H, s), 8.10 (1H, s)

Example 135

Sodium(5R,6S)-6-((1R)-1-hydroxyethyl)-2-(3-methyl-7-methylthioimidazo[5,1-b]thiazol-2-yl)-1-carbapen-2-em-3-carboxylate a) 4-Nitrobenzyl(5R,6S)-6-((1R)-1-hydroxyethyl)-2-(3-methyl-7-methylthioimidazo[5,1-b]thiazol-2-yl)-1-carbapen-2-em-3-carboxylate In the same manner as in Example 1-a), 927 mg of 4-nitrobenzyl(5R,6S)-6-((1R)-1-hydroxyethyl)-2-(3-methyl-7-methylthioimidazo[5,1-b]thiazol-2-yl)-1-carbapen-2-em-3-carboxylate was obtained from 1.044 g of 4-nitrobenzyl(3R,5R,6S)-6-((1R)-1-hydroxyethyl)-2-oxo-1-carbapenam-3-carboxylate and 1.56 g of 3-methyl-7-methylthio-2-(tri-n-butylstannyl)imidazo[5,1-b]thiazole.

NMR (CDCl$_3$) δ: 1.40 (3H, d, J=6.3 Hz), 2.19 (3H, s), 2.43 (3H, s), 3.1–3.3 (2H, m), 3.36 (1H, dd, J$_1$=6.4 Hz, J$_2$=3.1 Hz), 4.25–4.45 (2H, m), 5.24 (1H, d, J=13.7 Hz), 5.43 (1H, d, J=13.7 Hz), 7.57 (2H, d, J=8.7 Hz), 7.85 (1H, s), 8.18 (2H, d, J=8.7 Hz)

b) Sodium(5R,6S)-6-((1R)-1-hydroxyethyl)-2-(3-methyl-7-methylthioimidazo[5,1-b]thiazol-2-yl)-1-carbapen-2-em-3-carboxylate The title compound (43.6 mg) was obtained from 89.8 mg of 4-nitrobenzyl(5R,6S)-6-((1R)-1-hydroxyethyl)-2-(3-methyl-7-methylthioimidazo[5,1-b]thiazol-2-yl)-1-carbapen-2-em-3-carboxylate in the same manner as in Example 1-b), except that the purification was carried out by column chromatography on Cosmosil 40C18-PREP (5% aqueous methanol).

NMR (D$_2$O) δ (HOD=4.80 ppm): 1.31 (3H, d, J=6.3 Hz), 2.26 (3H, s), 2.36 (3H, s), 3.05–3.35 (2H, m), 3.55 (1H, dd, J$_1$=5.7 Hz, J$_2$=3.0 Hz), 4.2–4.4 (2H, m), 8.11 (1H, s)

Example 136

Sodium(1S,5R,6S)-6-((1R)-1-hydroxyethyl)-2-(7-methanesulfinyl-5-methylthioimidazo[5,1-b]thiazol-2-yl)-1-methyl-1-carbapen-2-em-3-carboxylate (A Mixture of Diastereomers)

a) 4-Nitrobenzyl(1S,5R,6S)-6-((1R)-1-hydroxyethyl)-2-(7-methanesulfinyl-5-methylthioimidazo[5,1-b]thiazol-2-yl)-1-methyl-1-carbapen-2-em-3-carboxylate (A Mixture of Diastereomers)

4-Nitrobenzyl(1S,5R,6S)-2-[5,7-bis(methylthio)imidazo[5,1-b]thiazol-2-yl]-6-((1R)-1-hydroxyethyl)-1-methyl-1-carbapen-2-em-3-carboxylate (140 mg) was dissolved in 2.5 ml of dichloromethane. m-Chloroperbenzoic acid (56 mg) was added to the solution. The mixture was stirred at room temperature for 15 min. An aqueous sodium thiosulfate solution (5 ml) was added thereto, followed by separation. The organic layer was washed with 10 ml of a semisaturated aqueous sodium hydrogencarbonate solution and 10 ml of semisaturated brine and then dried over anhydrous magnesium sulfate. The solvent was removed by distillation under the reduced pressure. The residue was purified by column chromatography on silica gel (dichloromethane:methanol= 20:1) to give 97 mg of 4-nitrobenzyl(1S,5R,6S)-6-((1R)-1-hydroxyethyl)-2-(7-methanesulfinyl-5-methylthioimidazo[5,1-b]thiazol-2-yl)-1-methyl-1-carbapen-2-em-3-carboxylate (a mixture of diastereomers).

NMR (CDCl$_3$) δ: 1.30, 1.31 (total 3H, d each, J=7.3 Hz each), 1.39 (3H, d, J=6.3 Hz), 2.62, 2.63 (total 3H, s each), 2.95, 2.96 (total 3H, s each), 3.36 (1H, m), 3.47 (1H, m), 4.30 (1H, m), 4.36 (1H, m), 5.27 (1H, d, J=13.7 Hz), 5.53 (1H, d, J=13.7 Hz), 7.66 (2H, d, J=8.5 Hz), 8.23 (total 3H, m)

b) 4-Sodium(1S,5R,6S)-6-((1R)-1-hydroxyethyl)-2-(7-methanesulfinyl-5-methylthio-imidazo[5,1-b]thiazol-2-yl)-1-methyl-1-carbapen-2-em-3-carboxylate (A Mixture of Diastereomers)

In the same manner as in Example 1-b), 37 mg of the title compound was obtained from 97 mg of 4-nitrobenzyl(1S, 5R,6S)-6-((1R)-1-hydroxyethyl)-2-(7-methanesulfinyl-5-methylthioimidazo[5,1-b]thiazol-2-yl)-1-methyl-1-carbapen-2-em-3-carboxylate.

NMR (D$_2$O) δ (HOD=4.65 ppm): 1.11 (3H, d, J=7.0 Hz), 1.17 (3H, d, J=6.3 Hz), 2.37, 2.38 (total 3H, s each), 2.92, 2.93 (total 3H, s each), 3.37 (1H, m), 3.50 (1H, m), 4.16 (2H, m), 7.82, 7.84 (total 1H, s each)

Example 137

Sodium(5R,6S)-6-((1R)-1-hydroxyethyl)-2-(3-hydroxymethyl-7-methylthioimidazo[5,1-b]thiazol-2-yl)-1-carbapen-2-em-3-carboxylate a) 4-Nitrobenzyl(5R,6S)-2-(3-t-butyldimethylsilyloxymethyl-7-methylthioimidazo[5,1-b]thiazol-2-yl)-6-((1R)-1-hydroxyethyl)-1-carbapen-2-em-3-carboxylate In the same manner as in Example 1-a), 561 mg of 4-nitrobenzyl(5R,6S)-2-(3-t-butyldimethylsilyloxymethyl-7-methylthioimidazo-[5,1-b]thiazol-2-yl)-6-((1R)-1-hydroxyethyl)-1-carbapen-2-em-3-carboxylate was obtained from 522 mg of 4-nitrobenzyl(3R,5R,6S)-6-((1R)-1-hydroxyethyl)-2-oxo-1-carbapenam-3-carboxylate and 995 mg of 3-t-butyldimethylsilyloxymethyl-7-methylthio-2-(tri-n-butylstannyl)imidazo[5,1-b]thiazole.

NMR (CDCl$_3$) δ: 0.01 (6H, s), 0.83 (9H, s), 1.39 (3H, d, J=6.3 Hz), 2.43 (3H, s), 3.1–3.2 (2H, m), 3.34 (1H, dd, J$_1$=6.5 Hz, J$_2$=3.0 Hz), 4.25–4.45 (2H, m), 4.49 (2H, s), 5.21 (1H, d, J=13.7 Hz), 5.41 (1H, d, J=13.7 Hz), 7.56 (2H, d, J=8.8 Hz), 8.07 (1H, s), 8.17 (2H, d, J=8.8 Hz)

b) 4-Nitrobenzyl(5R,6S)-6-((1R)-1-hydroxyethyl)-2-(3-hydroxymethyl-7-methylthio-imidazo[5,1-b]thiazol-2-yl)-1-carbapen-2-em-3-carboxylate 4-Nitrobenzyl(5R,6S)-6-((1R)-1-hydroxyethyl)-2-(3-hydroxymethyl-7-methylthio-imidazo[5,1-b]thiazol-2-yl)-1-carbapen-2-em-3-carboxylate (315 mg) was obtained from 561 mg of 4-nitrobenzyl(5R,6S)-2-(3-t-butyldimethylsilyloxymethyl-7-methylthioimidazo[5,1-b]thiazol-2-yl)-6-((1R)-1-hydroxyethyl)-1-carbapen-2-em-3-carboxylate in the same manner as in Example 36-b), except that the purification was carried out by column chromatography on silica gel (dichloromethane:methanol=20:1).

NMR (CDCl$_3$) δ: 1.39 (3H, d, J=6.3 Hz), 2.43 (3H, s), 3.1–3.25 (2H, m), 3.36 (1H, dd, J$_1$=6.4 Hz, J$_2$=3.1 Hz), 4.25–4.45 (2H, m), 4.45–4.6 (2H, m), 5.26 (1H, d, J=13.6 Hz), 5.47 (1H, d, J=13.6 Hz), 7.63 (2H, d, J=8.9 Hz), 8.18 (1H, s), 8.23 (2H, d, J=8.9 Hz)

c) Sodium(5R,6S)-6-((1R)-1-hydroxyethyl)-2-(3-hydroxymethyl-7-methylthioimidazo[5,1-b]thiazol-2-yl)-1-carbapen-2-em-3-carboxylate The title compound (59.4 mg) was obtained from 113 mg of 4-nitrobenzyl(5R,6S)-6-((1R)-1-hydroxyethyl)-2-(3-hydroxymethyl-7-methylthio-imidazo[5,1-b]thiazol-2-yl)-1-carbapen-2-em-3-carboxylate in the same manner as in Example 1-b), except that the purification was carried out by column chromatography on Cosmosil 40C18-PREP (5% aqueous methanol).

NMR (D$_2$O) δ (HOD=4.80 ppm): 1.35 (3H, d, J=6.4 Hz), 2.41 (3H, s), 3.1–3.35 (2H, m), 3.60 (1H, dd, J$_1$=5.8 Hz, J$_2$=3.0 Hz), 4.25–4.45 (2H, m), 4.69 (2H, s), 8.29 (1H, s)

Example 138

Sodium(5R,6S)-6-((1R)-1-hydroxyethyl)-2-(3-phenylimidazo[5,1-b]thiazol-2-yl)-1-carbapen-2-em-3-carboxylate a) 4-Nitrobenzyl(5R,6S)-6-((1R)-1-hydroxyethyl)-2-(3-phenylimidazo[5,1-b]thiazol-2-yl)-1-carbapen-2-em-3-carboxylate In the same manner as in Example 1-a), 110 mg of 4-nitrobenzyl(5R,6S)-6-((1R)-1-hydroxyethyl)-2-(3-phenylimidazo[5,1-b]thiazol-2-yl)-1-carbapen-2-em-3-carboxylate was obtained from 348 mg of 4-nitrobenzyl(3R,5R,6S)-6-((1R)-1-hydroxyethyl)-2-oxo-1-carbapenam-3-carboxylate and 513 mg of 3-phenyl-2-(tri-n-butylstannyl)imidazo[5,1-b]thiazole.

NMR (CDCl$_3$) δ: 1.21 (3H, d), 2.90 (2H, m), 3.18 (1H, dd), 4.22 (2H, m), 5.16 (1H, d), 5.32 (1H, d), 7.12 (1H, s), 7.50 (7H, m), 7.92 (1H, s), 8.15 (2H, d)

b) Sodium(5R,6S)-6-((1R)-1-hydroxyethyl)-2-(3-phenylimidazo[5,1-b]thiazol-2-yl)-1-carbapen-2-em-3-carboxylate The title compound (11 mg) was obtained from 100 mg of 4-nitrobenzyl(5R,6S)-6-((1R)-1-hydroxyethyl)-2-(3-phenylimidazo[5,1-b]thiazol-2-yl)-1-carbapen-2-em-3-carboxylate in the same manner as in Example 1-b), except that the purification was carried out by column chromatography on Cosmosil 40C18-PREP (30% aqueous methanol).

NMR (D$_2$O) δ (HOD=4.80 ppm): 1.23 (3H, d), 2.85 (2H, m), 3.37 (1H, m), 4.18 (2H, m), 7.12 (1H, s), 7.56 (5H, s), 8.11 (1H, s)

Example 139

Sodium(5R,6S)-2-(7-aminoacetylimidazo[5,1-b]thiazol-2-yl)-6-((1R)-1-hydroxyethyl)-1-carbapen-2-em-3-carboxylate a) 4-Nitrobenzyl(5R,6S)-6-((1R)-1-hydroxyethyl)-2-[7-(4-nitrobenzyloxycarbonyl-amino)acetylimidazo[5,1-b]thiazol-2-yl]-1-carbapen-2-em-3-carboxylate In the same manner as in Example 1-a), 195 mg of 4-nitrobenzyl(5R,6S)-6-((1R)-1-hydroxyethyl)-2-[7-(4-nitrobenzyloxycarbonylamino)acetyl-imidazo[5,1-b]thiazol-2-yl]-1-carbapen-2-em-3-carboxylate was obtained from 348 mg of 4-nitrobenzyl(3R,5R,6S)-6-((1R)-1-hydroxyethyl)-2-oxo-1-carbapenam-3-carboxylate and 650 mg of 7-(4-nitrobenzyloxycarbonylamino)acetyl-2-(tri-n-butylstannyl)imidazo[5,1-b]thiazole.

NMR (DMSO-d$_6$) δ: 1.18 (3H, d), 3.51 (3H, m), 4.28 (1H, m), 4.47 (3H, m), 5.17 (1H, d), 5.21 (2H, s), 5.51 (2H, ABq), 7.65 (2H, d), 7.77 (2H, d), 8.24 (2H, d), 8.26 (2H, d), 8.37 (1H, s), 8.52 (1H, s)

b) Sodium(5R,6S)-2-(7-aminoacetylimidazo-[5,1-b]thiazol-2-yl)-6-((1R)-1-hydroxyethyl)-1-carbapen-2-em-3-carboxylate The title compound (34 mg) was obtained from 140 mg of 4-nitrobenzyl(5R,6S)-6-((1R)-1-hydroxyethyl)-2-[7-(4-nitrobenzyloxycarbonyl-amino)acetylimidazo[5,1-b]thiazol-2-yl]-1-carbapen-2-em-3-carboxylate in the same manner as in Example 1-b), except that the purification was carried out by column chromatography on Cosmosil 40C18-PREP (10% aqueous methanol).

NMR (D$_2$O) δ (HOD=4.80 ppm): 1.31 (3H, d), 3.08 (2H, m), 3.50 (1H, dd), 4.23 (2H, m), 4.39 (2H, s), 7.57 (1H, s), 7.99 (1H, s)

Example 140

Sodium(1S,5R,6S)-6-((1R)-1-hydroxyethyl)-2-(5-methanesulfinylimidazo[5,1-b]thiazol-2-yl)-1-methyl-1-carbapen-2-em-3-carboxylate (A Mixture of Diastereomers)

a) 4-Nitrobenzyl(1S,5R,6S)-6-((1R)-1-hydroxyethyl)-2-(5-methanesulfinylimidazo[5,1-b]thiazol-2-yl)-1-methyl-1-carbapen-2-em-3-carboxylate (A Mixture of Diastereomers)

4-Nitrobenzyl(1S,5R,6S)-6-((1R)-1-hydroxyethyl)-2-(5-methanesulfinylimidazo[5,1-b]thiazol-2-yl)-1-methyl-1-carbapen-2-em-3-carboxylate (a mixture of diastereomers) (95 mg) was obtained in the same manner as in Example 136-a), except that the reaction was carried out using 112 mg of 4-nitrobenzyl(1S,5R,6S)-6-((1R)-1-hydroxyethyl)-1-methyl-2-(5-methylthioimidazo-[5,1-b]thiazol-2-yl)-1-carbapen-2-em-3-carboxylate and 49 mg of m-chloroperbenzoic acid as the starting compounds.

NMR (CDCl$_3$) δ: 1.32 (3H, d, J=7.3 Hz), 1.39 (3H, d, J=6.3 Hz), 3.12 (3H, s), 3.38 (1H, m), 3.56 (1H, m), 4.36 (2H, m), 5.29 (1H, d, J=13.6 Hz), 5.53 (1H, d, J=13.6 Hz), 7.67 (2H, d, J=8.8 Hz), 8.23 (2H, d, J=8.8 Hz), 8.58, 8.59 (total 1H, s each)

b) Sodium(1S,5R.6S)-6-((1R)-1-hydroxyethyl)-2-(5-methanesulfinylimidazo[5,1-b]thiazol-2-yl)-1-methyl-1-carbapen-2-em-3-carboxylate (A Mixture of Diastereomers)

In the same manner as in Example 1-b), 44 mg of the title compound was obtained from 95 mg of 4-nitrobenzyl(1S,5R,6S)-6-((1R)-1-hydroxyethyl)-2-(5-methanesulfinylimidazo[5,1-b]thiazol-2-yl)-1-methyl-1-carbapen-2-em-3-carboxylate.

NMR (D$_2$O) δ (HOD=4.65 ppm): 1.16 (3H, m), 1.22 (3H, d, J=6.5 Hz), 3.11 (3H, s), 3.44 (1H, m), 3.54 (1H, m), 4.20 (2H, m), 7.20, 7.21 (total 1H, s each), 8.08 (1H, s)

Example 141

Sodium(1S,5R,6S)-2-(5,7-dimethanesulfinyl-
imidazo[5,1-b]thiazol-2-yl)-6-((1R)-1-hydroxy-
ethyl)-1-methyl-1-carbapen-2-em-3-carboxylate (A
Mixture of Diastereomers)

a) 4-Nitrobenzyl(1S,5R,6S)-2-(5,7-
dimethanesulfinylimidazo[5,1-b]thiazol-2-yl)-6-
((1R)-1-hydroxyethyl)-1-methyl-1-carbapen-2-em-3-
carboxylate (A Mixture of Diastereomers)

4-Nitrobenzyl(1S,5R,6S)-2-(5,7-dimethane-sulfinylimidazo[5,1-b]thiazol-2-yl)-6-((1R)-1-hydroxyethyl)-1-methyl-1-carbapen-2-em-3-carboxylate (a mixture of diastereomers) (95 mg) was obtained in the same manner as in Example 136-a), except that the reaction was carried out using 129 mg of 4-nitrobenzyl(1S,5R,6S)-2-[5,7-bis(methylthio)imidazo[5,1-b]thiazol-2-yl]-6-((1R)-1-hydroxyethyl)-1-methyl-1-carbapen-2-em-3-carboxylate and 99 mg of m-chloroperbenzoic acid as the starting compounds.

NMR (CDCl$_3$) δ: 1.31 (3H, d, J=7.3 Hz), 1.38 (3H, d, J=6.4 Hz), 2.96 (3H, m), 3.15 (3H, m), 3.38 (1 H, m), 3.54 (1H, m), 4.31 (1H, m), 4.39 (1H, dd, J$_1$=9.7 Hz, J$_2$=2.7 Hz), 5.29 (1H, d, J=13.4 Hz), 5.43 (1H, d, J=13.4 Hz), 7.67 (2H, d, J=9.1 Hz), 8.23 (2H, d, J=9.1 Hz), 8.66 (1H, m)

b) Sodium(1S,5R,6S)-2-(5,7-
dimethanesulfinylimidazo[5,1-b]thiazol-2-yl)-6-
((1R)-1hydroxyethyl)-1-methyl-1-carbapen-2-em-3-
carboxylate (A Mixture of Diastereomers)

In the same manner as in Example 1-b), 30 mg of the title compound was obtained from 59 mg of 4-nitrobenzyl(1S,5R,6S)-2-(5,7-dimethanesulfinylimidazo[5,1-b]thiazol-2-yl)-6-((1R)-1-hydroxyethyl)-1-methyl-1-carbapen-2-em-3-carboxylate.

NMR (D$_2$O) δ (HOD=4.65 ppm): 1.16 (3H, m), 1.21 (3H, d, J=6.3 Hz), 3.01 (3H, m), 3.14 (3H, s), 3.44 (1H, m), 3.58 (1H, m), 4.19 (2H, m), 8.20 (1H, m)

Example 142

Sodium(1S,5R,6S)-6-((1R)-1-hydroxyethyl)-2-(5-
methanesulfinyl-7-methanesulfonylimidazo[5,1-b]
thiazol-2-yl)-1-methyl-1-carbapen-2-em-3-
carboxylate (A Mixture of Diastereomers)

a) 4-Nitrobenzyl(1S,5R,6S)-6-((1R)-1-
hydroxyethyl)-2-(5-methanesulfinyl-7-methane-
sulfonylimidazo[5,1-b]thiazol-2-yl)-1-methyl-1-
carbapen-2-em-3-carboxylate (A Mixture of
Diastereomers)

4-Nitrobenzyl(1S,5R,6S)-6-((1R)-1-hydroxyethyl)-2-(5-methanesulfinyl-7-methanesulfonylimidazo[5,1-b]thiazol-2-yl)-1-methyl-1-carbapen-2-em-3-carboxylate (a mixture of diastereomers) (53 mg) was obtained in the same manner as in Example 136-a), except that the reaction was carried out using 130 mg of 4-nitrobenzyl(1S,5R,6S)-2-[5,7-bis(methylthio)imidazo[5,1-b]thiazol-2-yl]-6-((1R)-1-hydroxyethyl)-1-methyl-1-carbapen-2-em-3-carboxylate and 135 mg of m-chloroperbenzoic acid as the starting compounds.

NMR (CDCl$_3$) δ: 1.32 (3H, d, J=7.4 Hz), 1.39 (3H, d, J=6.3 Hz), 3.18, 3.19 (total 3H, s each), 3.21, 3.21 (total 3H, s each), 3.39 (1H, dd, J$_1$=6.3 Hz, J$_2$=2.9 Hz), 3.56 (1H, m), 4.32 (1H, m), 4.40 (1H, dd, J$_1$=9.3 Hz, J$_2$=2.7 Hz), 5.29 (1H, d, J=13.6 Hz), 5.53 (1H, d, J=13.6 Hz), 7.67 (2H, d, J=8.5 Hz), 8.24 (2H, d, J=8.5 Hz), 8.65, 8.67 (total 1H, s each)

b) Sodium(1S,5R,6S)-6-((1R)-1-hydroxyethyl)-2-(5-
methanesulfinyl-7-methanesulfonylimidazo[5,1-b]
thiazol-2-yl)-1-methyl-1-carbapen-2-em-3-
carboxylate (A Mixture of Diastereomers)

In the same manner as in Example 1-b), 23 mg of the title compound was obtained from 53 mg of 4-nitrobenzyl(1S,5R,6S)-6-((1R)-1-hydroxyethyl)-2-(5-methanesulfinyl-7-methanesulfonylimidazo[5,1-b]thiazol-2-yl)-1-methyl-1-carbapen-2-em-3-carboxylate.

NMR (D$_2$O) δ (HOD=4.65 ppm): 1.15, 1.16 (total 3H, d each, J=7.2 Hz), 1.21 (3H, d, J=6.3 Hz), 3.14 (3H, s), 3.23, 3.24 (total 3H, s each), 3.44 (1H, dd, J$_1$=5.8 Hz, J$_2$=2.0 Hz), 3.57 (1H, m), 4.16 (1H, m), 4.23 (1H, m), 8.20, 8.21 (total 1H, s each)

Example 143

Sodium(1S,5R,6S)-2-[5,7-bis (methanesulfonyl)
imidazo[5,1-b]thiazol-2-yl]-6-((1R)-1-
hydroxyethyl)-1-methyl-1-carbapen-2-em-3-
carboxylate a) 4-Nitrobenzyl(1S,5R,6S)-2-[5,7-bis
(methanesulfonyl)imidazo[5,1-b]thiazol-2-yl1–6-
((1R)-1-hydroxyethyl)-1-methyl-1-carbapen-2-em-3-
carboxylate 4-Nitrobenzyl(1S,5R,6S)-2-[5,7-bis(methanesulfonyl)imidazo[5,1-b]thiazol-2-yl]-6-((1R)-1-hydroxyethyl)-1-methyl-1-carbapen-2-em-3-carboxylate (107 mg) was obtained in the same manner as in Example 44-b), the reaction was carried out using 102 mg of 4-nitrobenzyl(1S,5R,6S)-2-[5,7-bis(methylthio)imidazo[5,1-b]thiazol-2-yl]-6-((1R)-1-hydroxyethyl)-1-methyl-1-carbapen-2-em-3-carboxylate and 448 mg of oxone as the starting compounds. The reaction product was purified by column chromatography on silica gel (dichloromethane:methanol=20:1 to 10:1).

NMR (CDCl$_3$) δ: 1.33 (3H, d, J=7.3 Hz), 1.35 (3H, d, J=6.3 Hz), 3.25 (3H, s), 3.38 (1H, m), 3.41 (3H, s), 3.59 (1H, m), 4.35 (1H, m), 4.43 (1H, dd, J$_1$=9.7 Hz, J$_2$=2.9 Hz), 5.30 (1H, d, J=13.8 Hz), 5.54 (1H, d, J=13.8 Hz), 7.69 (2H, d, J=9.3 Hz), 8.22 (2H, d, J=9.3 Hz), 8.56 (1H, s)

b) Sodium(1S,5R,6S)-2-[5,7-bis(methanesulfonyl)
imidazo[5,1-b]thiazol-2-yl]-6-((1R)-1-
hydroxyethyl)-1-methyl-1-carbapen-2-em-
3carboxylate In the same manner as in Example 1-b), 20 mg of the title compound was obtained from 67 mg of 4-nitrobenzyl(1S,5R,6S)-2-[5,7-bis(methane-sulfonyl)imidazo[5,1-b]thiazol-2-yl]-6-((1R)-1-hydroxyethyl)-1-methyl-1-carbapen-2-em-3-carboxylate.

NMR (D$_2$O) δ (HOD=4.65 ppm): 1.14 (3H, d, J=7.3 Hz), 1.20 (3H, d, J=6.6 Hz), 3.25 (3H, s), 3.35 (3H, s), 3.44 (1H, dd, J$_1$=6.1 Hz, J$_2$=2.7 Hz), 3.59 (1H, m), 4.16 (1H, m), 4.23 (1H, dd, J$_1$=9.5 Hz, J$_2$=2.7 Hz), 818 (1H, s)

Example 144

Sodium(5R,6S)-2-(3-aminomethylimidazo[5,1b]
thiazol-2-yl)-6-((1R)-1-hydroxyethyl)-1-carbapen-2-
em-3carboxylate a) 4-Nitrobenzyl(5R,6S -2-(3-azidomethylimidazo
[5,1-b]thiazol-2-yl)-6-((1R)-1-hydroxyethyl)-
1carbapen-2-em-3-carboxylate In the same manner as in Example 1-a), 268.2 mg of 4-nitrobenzyl(5R,6S)-2-(3-azidomethylimidazo[5,1-b]

thiazol-2-yl)-6-((1R)-1-hydroxyethyl)-1-carbapen-2-em-3-carboxylate was obtained from 348 mg of 4-nitrobenzyl(3R,5R,6S)-6-((1R)-1-hydroxyethyl)-2-oxo-1-carbapenam-3-carboxylate and 515 mg of 3-azidomethyl-2-(tri-n-butylstannyl)imidazo[5,1-b]thiazole.

NMR (CDCl$_3$) δ: 1.38 (3H, d, J=6.3 Hz), 3.1–3.3 (2H, m), 3.40 (1H, dd, J$_1$=6.1 Hz, J$_2$=3.0 Hz), 4.25–4.35 (1H, m), 4.36 (2H, s), 4.4–4.5 (1H, m), 5.21 (1H, d, J=13.5 Hz), 5.41 (1H, d, J=13.5 Hz), 7.12 (1H, s), 7.53 (2H, d, J=8.5 Hz), 8.03 (1H, s), 8.15 (2H, d, J=8.5 Hz)

b) Sodium(5R,6S)-2-(3-aminomethylimidazo[51-b]thiazol-2-yl)-6-((1R)-1-hydroxyethyl)-1-carbapen-2-em-3-carboxylate The title compound (22.1 mg) was obtained from 97.4 mg of 4-nitrobenzyl(5R,6S)-2-(3-azidomethylimidazo[5,1-b]thiazol-2-yl)-6-((1R)-1-hydroxyethyl)-1-carbapen-2-em-3-carboxylate in the same manner as in Example 1-b), except that the purification was carried out by column chromatography on Cosmosil 40C18-PREP (10% aqueous methanol).

NMR (D$_2$O) δ (HOD=4.80 ppm): 1.29 (3H, d, J=6.1 Hz), 3.1–3.4 (2H, m), 3.5–3.6 (1H, m), 4.2–4.4 (2H, m), 4.34 (2H, s), 7.12 (1H, s), 8.32 (1H, s)

Example 145

Sodium(5R,6S)-6-((1R)-1-hydroxyethyl)-2-(3-hydroxymethylimidazo[5,1-b]thiazol-2-yl)-1-carbapen-2-em-3-carboxylate a) 4-Nitrobenzyl(5R,6S)-2-(3-t-butyldimethylsilyloxymethylimidazo[5,1-b]thiazol-2-yl)-6-((1R)-1-hydroxyethyl)-1-carbapen-2-em-3-carboxylate In the same manner as in Example 1-a), 1.396 g of 4-nitrobenzyl(5R,6S)-2-(3-t-butyldimethylsilyloxymethylimidazo[5,1-b]thiazol-2-yl)-6-((1R)-1-hydroxyethyl)-1-carbapen-2-em-3-carboxylate was obtained from 1.42 g of 4-nitrobenzyl(3R,5R,6S)-6-((1R)-1-hydroxyethyl)-2-oxo-1-carbapenam-3-carboxylate and 2.28 g of 3-t-butyldimethylsilyloxymethyl-2-(tri-n-butylstannyl)imidazo[5,1-b]thiazole.

NMR (CDCl$_3$) δ: 0.00 (6H, s), 0.84 (9H, s), 1.40 (3H, d, J=6.3 Hz), 3.1–3.3 (2H, m), 3.33 (1H, dd, J$_1$=6.3 Hz, J$_2$=2.9 Hz), 4.25–4.45 (2H, m), 4.52 (2H, s), 5.23 (1H, d, J=13.4 Hz), 5.42 (1H, d, J=13.4 Hz), 7.08 (1H, s), 7.55 (2H, d, J=8.9 Hz), 8.10 (1H, s), 8.17 (2H, d, J=8.9 Hz)

b) 4-Nitrobenzyl(5R,6S)-6-((1R)-1-hydroxyethyl)-2-(3-hydroxymethylimidazo[5,1-b]thiazol-2-yl)-1-carbapen-2-em-3-carboxylate 4-Nitrobenzyl(5R,6S)-6-((1R)-1-hydroxyethyl)-2-(3-hydroxymethylimidazo[5,1-b]thiazol-2-yl)-1-carbapen-2-em-3-carboxylate (507 mg) was obtained from 1.396 g of 4-nitrobenzyl(5R,6S)-2-(3-t-butyldimethylsilyloxymethyl-imidazo[5,1-b]thiazol-2-yl)-6-((1R)-1-hydroxyethyl)-1-carbapen-2-em-3-carboxylate in the same manner as in Example 36-b), except that the purification was carried out using Sephadex LH-20 (chloroform:methanol=1:1).

NMR (CDCl$_3$) δ: 1.39 (3H, d, J=6.3 Hz), 3.1–3.3 (2H, m), 3.36 (1H, dd, J$_1$=6.5 Hz, J$_2$=2.9 Hz), 4.25–4.45 (2H, m), 4.5–4.65 (2H, m), 5.27 (1H, d, J=13.4 Hz), 5.47 (1H, d, J=13.4 Hz), 7.10 (1H, s), 7.63 (2H, d, J=8.8 Hz), 8.20 (1H, s), 8.23 (2H, d, J=8.8 Hz)

c) Sodium(5R,6S)-6-((1R)-1-hydroxyethyl)-2-(3-hydroxymethylimidazo[5,1-b]thiazol-2-yl)-1-carbapen-2-em-3-carboxylate The title compound (58.4 mg) was obtained from 145.5 mg of 4-nitrobenzyl(5R,6S)-6-((1R)-1-hydroxyethyl)-2-(3-hydroxymethylimidazo[5,1-b]thiazol-2-yl)-1-carbapen-2-em-3-carboxylate in the same manner as in Example 1-b), except that the purification was carried out by column chromatography on Cosmosil 40C18-PREP (5% aqueous methanol).

NMR (D$_2$O) δ (HOD=4.80 ppm): 1.29 (3H, d, J=6.4 Hz), 3.13 (1H, dd, J$_1$=17.4 Hz, J$_2$=10.1 Hz), 3.28 (1H, dd, J$_1$=17.4 Hz, J$_2$=8.5 Hz), 3.55 (1H, dd, J$_1$=5.8 Hz, J$_2$=2.9 Hz), 4.2–4.4 (2H, m), 4.66 (2H, s), 7.08 (1H, s), 8.25 (1H, s)

Example 146

Sodium(5R,6S)-2-[5,7-bis(methylthio)-imidazo[5,1-b]thiazol-2-yl]-6-((1R)-1-hydroxyethyl)-1-carbapen-2-em-3-carboxylate a) 4-Nitrobenzyl(5R,6S)-2-[5,7-bis(methylthio)imidazo[5,1-b]thiazol-2-yl]-6-((1R)-1-hydroxyethyl)-1-carbapen-2-em-3-carboxylate In the same manner as in Example 1-a), 810 mg of 4-nitrobenzyl(5R,6S)-2-[5,7-bis(methylthio)imidazo[5,1-b]thiazol-2-yl]-6-((1R)-1-hydroxyethyl)-1-carbapen-2-em-3-carboxylate was obtained from 803 mg of 4-nitrobenzyl(3R,5R,6S)-6-((1R)-1-hydroxyethyl)-2-oxo-1-carbapenam-3-carboxylate and 1.18 g of 5,7-bis(methylthio)-2-(tri-n-butylstannyl)imidazo-[5,1-b]thiazole.

NMR (CDCl$_3$) δ: 1.39 (3H, d, J=6.3 Hz), 2.42 (3H, s), 2.58 (3H, s), 3.30–3.40 (total 3H, m), 4.29–4.37 (total 2H, m), 5.33 (1H, d, J=13.6 Hz), 5.56 (1H, d, J=13.6 Hz), 7.69 (2H, d, J=9.0 Hz), 7.96 (1H, s), 8.25 (2H, d, J=9.0 Hz)

b) Sodium(5R,6S)-2-[5.7-bis(methylthio)imidazo[5,1-b]thiazol-2-yl]-6-((1R)-1-hydroxyethyl)-1-carbapen-2-em-3-carboxylate In the same manner as in Example 1-b), 33 mg of the title compound was obtained from 78 mg of 4-nitrobenzyl(5R,6S)-2-[5,7-bis(methylthio)-imidazo[5,1-b]thiazol-2-yl]-6-((1R)-1-hydroxyethyl)-1-carbapen-2-em-3-carboxylate.

NMR (D$_2$O) δ (HOD=4.65 ppm): 1.20 (3H, d, J=6.3 Hz), 2.24 (3H, s), 2.35 (3H, s), 3.18 (2H, m), 3.42 (1H, dd, J$_1$=6.1 Hz, J$_2$=1.9 Hz), 4.14–4.21 (2H, m), 7.55 (1H, s)

Example 147

Sodium(1S,5R,6S)-2-(5-acetyl-7methylthioimidazo[5,1-b]thiazol-2-yl)-6-((1R)-1-hydroxyethyl)-1-methyl-1-carbapen-2-em-3-carboxylate a) 4Nitrobenzyl(1S,5R,6S)-(5-acetyl-7-methylthioimidazo[5,1-b]thiazol-2-yl)-6-((1R)-1-hydroxyethyl)-1methyl-1-carbapen-2-em-3-carboxylate In the same manner as in Example 1-a), 168 mg of 4-nitrobenzyl(1S,5R,6S)-2-(5-acetyl-7-methylthioimidazo-[5,1-b]thiazol-2-yl)-6-((1R)-1-hydroxyethyl)-1-methyl-1-carbapen-2-em-3-carboxylate was obtained from 211 mg of 4-nitrobenzyl(1R,3R,5R,6S)-6-((1R)-1-hydroxyethyl)-1-methyl-2-oxo-1-carbapenam-3-carboxylate and 280 mg of 5-acetyl-7-methylthio-2-(tri-n-butylstannyl)-imidazo[5,1-b]thiazole.

NMR (CDCl$_3$) δ: 1.34 (3H, d, J=7.3 Hz), 1.40 (3H, d, J=6.1 Hz), 2.51 (3H, s), 2.66 (3H, s), 3.39 (1H, m), 3.66 (1H, m), 4.33 (1H, m), 4.39 (1H, dd, J$_1$=9.5 Hz, J$_2$=2.7 Hz), 5.31 (1H, d, J=13.6 Hz), 5.55 (1H, d, J=13.6 Hz), 7.68 (2H, d, J=8.7 Hz), 8.24 (2H, d, J=8.7 Hz), 8.81 (1H, s)

b) Sodium(1S,5R,6S)-2-(5-acetyl-7-methylthioimidazo[5,1-b]thiazol-2-yl)-6-((1R)-1-hydroxyethyl)-1-methyl-1-carbapen-2-em-3-carboxylate In the same manner as in Example 1-b), 29 mg of the title compound was obtained from 54 mg of 4-nitrobenzyl(1S,5R,6S)-2-(5-acetyl-7-methylthio-imidazo[5,1-b]thiazol-2-yl)-6-((1R)-1-hydroxyethyl)-1-methyl-1-carbapen-2-em-3-carboxylate.

NMR (D$_2$O) δ (HOD=4.65 ppm): 1.14 (3H, d, J=7.3 Hz), 1.23 (3H, d, J=6.3 Hz), 2.35 (3H, s), 2.47 (3H, s), 3.42 (1H, m), 3.55 (1H, m), 4.18 (1H, m), 4.25 (1H, m), 8.30 (1H, s)

Example 148

Sodium(1S,5R,6S)-2-[3,7-bis (methylthio)-imidazo[5,1-b]thiazol-2-yl]-6-((1R)-1-hydroxyethyl)-1-methyl-1-carbapen-2-em-3-carboxylate a) 4-Nitrobenzyl(1S,5R,6S)-2-[3,7-bis(methylthio)imidazo[5,1-b]thiazol-2-yl]-6-((1R)-1-hydroxyethyl)-1-methyl-1-carbapen-2-em-3-carboxylate In the same manner as in Example 1-a), 489 mg of 4-nitrobenzyl(1S,5R,6S)-2-[3,7-bis(methylthio)imidazo[5,1-b]thiazol-2-yl]-6-((1R)-1-hydroxyethyl)-1-methyl-1-carbapen-2-em-3-carboxylate was obtained from 724 mg of 4-nitrobenzyl(1R,3R,5R,6S)-6-((1R)-1-hydroxyethyl)-1-methyl-2-oxo-1-carbapenam-3-carboxylate and 1.11 g of 3,7-bis(methylthio)-2-(tri-n-butylstannyl)-imidazo[5,1-b]thiazole.

NMR (CDCl$_3$) δ: 1.22 (3H, d, J=7.4 Hz), 1.39 (3H, d, J=6.2 Hz), 2.28 (3H, s), 2.46 (3H, s), 3.4–3.5 (2H, m), 4.3–4.4 (1H, m), 4.48 (1H, dd, J$_1$=10.4 Hz, J$_2$=3.3 Hz), 5.21 (1H, d, J=13.4 Hz), 5.41 (1H, d, J=13.4 Hz), 7.53 (2H, d, J=8.8 Hz), 8.03 (1H, s), 8.16 (2H, d, J=8.8 Hz)

b) Sodium(1S,5R,6S)-2-[3,7-bis(methylthio)imidazo[5,1-b]thiazol-2-yl]-6-((1R)-1-hydroxyethyl)-1-methyl-1-carbapen-2-em-3-carboxylate The title compound (70.6 mg) was obtained from 157 mg of 4-nitrobenzyl(1S,5R,6S)-2-[3,7-bis(methylthio)imidazo[5,1-b]thiazol-2-yl]-6-((1R)-1-hydroxyethyl)-1-methyl-1-carbapen-2-em-3-carboxylate in the same manner as in Example 1-b), except that the purification was carried out by column chromatography on Cosmosil 40C18-PREP (10% aqueous methanol).

NMR (D$_2$O) δ (HOD=4.80 ppm): 1.13 (3H, d, J=7.2 Hz), 1.31 (3H, d, J=6.4 Hz), 2.34 (3H, s), 2.36 (3H, s), 3.35–3.5 (1H, m), 3.54 (1H, dd, J$_1$=5.9 Hz, J$_2$=3.0 Hz), 4.2–4.35 (1H, m), 4.37 (1H, dd, J$_1$=9.9 Hz, J$_2$=2.9 Hz), 8.30 (1H, s)

Example 149

Sodium(1S,5R,6S)-2-(5-acetyl-7-methanesulfonylimidazo[5,1-b]thiazol-2-yl)-6-((1R)-1-hydroxyethyl)-1-methyl-1-carbapen-2-em-3-carboxylate a) 4-Nitrobenzyl(1S,5R,6s)-2-(5-acetyl-7-methanesulfonylimidazo[5,1-b]thiazol-2-yl)-6-((1R)-1-hydroxyethyl)-1-methyl-1-carbapen-2-em-3-carboxylate 4-Nitrobenzyl(1S,5R,6S)-2-(5-acetyl-7-methanesulfonylimidazo[5,1-b]thiazol-2-yl)-6-((1R)-1-hydroxyethyl)-1-methyl-1-carbapen-2-em-3-carboxylate (54 mg) was obtained in the same manner as in Example 44-b), except that 52 mg of 4-nitrobenzyl(1S,5R,6S)-2-(5-acetyl-7-methylthioimidazo[5,1-b]thiazol-2-yl)-6-((1R)-1-hydroxyethyl)-1-methyl-1-carbapen-2-em-3-carboxylate and 115 mg of oxone were used as the starting compounds. The reaction product was purified by column chromatography on silica gel (dichloromethane:methanol=20:1 to 10:1).

NMR (CDCl$_3$) δ: 1.34 (3H, d, J=7.3 Hz), 1.40 (3H, d, J=6.1 Hz), 2.71 (3H, s), 3.26 (3H, s), 3.40 (1H, m), 3.64 (1H, m), 4.33 (1H, m), 4.43 (1H, dd, J$_1$=9.7 Hz, J$_2$=1.9 Hz), 5.31 (1H, d, J=13.4 Hz), 5.54 (1H, d, J=13.4 Hz), 7.68 (2H, d, J=9.1 Hz), 8.24 (2H, d, J=9.1 Hz), 8.80 (1H, s)

b) Sodium(1S,5R,46S)-2-(5-acetyl-7-methanesulfonylimidazo[5,1-b]thiazol-2-yl)-6-((1R)-1-hydroxyethyl)-1-methyl-1-carbapen-2-em-3-carboxylate In the same manner as in Example 1-b), 15 mg of the title compound was obtained from 53 mg of 4-nitrobenzyl(1S,5R,6S)-2-(5-acetyl-7-methanesulfonylimidazo[5,1-b]thiazol-2-yl)-6-((1R)-1-hydroxyethyl)-1-methyl-1-carbapen-2-em-3-carboxylate.

NMR (D$_2$O) δ (HOD=4.65 ppm): 1.12 (3H, d, J=7.3 Hz), 1.20 (3H, d, J=6.4 Hz), 2.54 (3H, s), 3.24 (3H, s), 3.42 (1H, dd, J$_1$=6.2 Hz, J$_2$=2.8 Hz), 3.60 (1H, m), 4.15 (1H, m), 4.22 (1H, dd, J$_1$=9.3 Hz, J$_2$=2.7 Hz), 8.43 (1H, s)

Example 150

Sodium(1S,5R,6S)-2-(5-bromo-7-methylthioimidazo[5,1-b]thiazol-2-yl)-6-((1R)-1-hydroxyethyl)-1-methyl-1-carbapen-2-em-3-carboxylate a) 4-Nitrobenzyl(1S,5R,6S)-2-(5-bromo-7-methylthioimidazo[5,1-b]thiazol-2-yl)-6-((1R)-1-hydroxyethyl)-1-methyl-1-carbapen-2-em-3-carboxylate 4-Nitrobenzyl(1S,5R,6S)-6-((1R)-1-hydroxyethyl)-1-methyl-2-(7-methylthioimidazo-[5,1-b]thiazol-2-yl)-1-carbapen-2-em-3-carboxylate (77 mg) was dissolved in 5 ml of benzene at room temperature. N-bromosuccinimide (33 mg) and 5 mg of 2,2'-azobis(isobutyronitrile) were added to the solution. The mixture was stirred for 10 min. Dichloromethane (10 ml) and 10 ml of semisaturated brine were added thereto, followed by separation. The organic layer was dried over anhydrous magnesium sulfate. The solvent was removed by distillation under the reduced pressure. The residue was purified by column chromatography on silica gel (dichloromethane:methanol=20:1) to give 70 mg of 4-nitrobenzyl(1S,5R,6S)-2-(5-bromo-7-methylthioimidazo[5,1-b]thiazol-2-yl)-6-((1R)-1-hydroxyethyl)-1-methyl-1-carbapen-2-em-3-carboxylate.

NMR (CDCl$_3$) δ: 1.31 (3H, d, J=7.3 Hz), 1.40 (3H, d, J=6.3 Hz), 2.43 (3H, s), 3.38 (1H, m), 3.48 (1H, m), 4.32 (1H, m), 4.38 (1H, dd, J$_1$=9.8 Hz, J$_2$=2.7 Hz), 5.29 (1H, d, J=13.4 Hz), 5.55 (1H, d, J=13.4 Hz), 7.68 (2H, d, J=8.5 Hz), 8.03 (1H, s), 8.25 (2H, d, J=8.5 Hz)

b) Sodium(1S,5R,6S)-2-(5-bromo-7-methylthioimidazo[5,1-b]thiazol-2-yl)-6-((1R)-1-hydroxyethyl)-1-methyl-1-carbapen-2-em-3-carboxylate In the same manner as in Example 1-b), 14 mg of the title compound was obtained from 68 mg of 4-nitrobenzyl(1S,5R,6S)-2-(5-bromo-7-methylthioimidazo[5,1-b]thiazol-2-yl)-6-((1R)-1-hydroxyethyl)-1-methyl-1-carbapen-2-em-3-carboxylate.

NMR (D$_2$O) δ (HOD=4.65 ppm): 1.12 (3H, d, J=7.3 Hz), 1.19 (3H, d, J=6.4 Hz), 2.23 (3H, s), 3.40 (1H, dd, J$_1$=9.8 Hz, J$_2$=2.7 Hz), 3.48 (1H, m), 4.13–4.22 (1H, m), 7.60 (1H, s)

Example 151

Sodium(5R,6S)-2-(5-acetyl-7-methylthioimidazo[5,1-b]thiazol-2-yl)-6-((1R)-1-hydroxyethyl)-1-carbapen-2-em-3-carboxylate a) 4-Nitrobenzyl(5R,6S)-2-(5-acetyl-7-methylthioimidazo[5,1-b]thiazol-2-yl)-6-((1R)-1-hydroxyethyl)-1-carbapen-2-em-3-carboxylate In the same manner as in Example 1-a), 147 mg of 4-nitrobenzyl(5R,6S)-2-(5-acetyl-7-methylthioimidazo[5,1-b]thiazol-2-yl)-6-((1R)-1-hydroxyethyl)-1-carbapen-2-em-3-carboxylate was obtained from 174 mg of 4-nitrobenzyl (3R,5R,6S)-6-((1R)-1-hydroxyethyl)-2-oxo-1-carbapenam-3-carboxylate and 250 mg of 5-acetyl-7-methylthio-2-(tri-n-butylstannyl)imidazo[5,1-b]thiazole.

NMR (CDCl$_3$) δ: 1.40 (3H, d, J=6.3 Hz), 2.51 (3H, s), 2.66 (3H, s), 3.33–3.52 (total 3H, m), 4.29–4.40 (total 2H, m), 5.34 (1H, d, J=13.4 Hz), 5.57 (1H, d, J=13.4 Hz), 7.70 (2H, d, J=8.7 Hz), 8.25 (2H, d, J=8.7 Hz), 8.67 (1H, s)

b) Sodium(5R,6S)-2-(5-acetyl-7-methylthioimidazo[5,1-b]thiazol-2-yl)-6-((1R)-1-hydroxyethyl)-1-carbapen-2-em-3-carboxylate In the same manner as in Example 1-b), 21 mg of the title compound was obtained from 80 mg of 4-nitrobenzyl(5R,6S)-2-(5-acetyl-7-methylthioimidazo[5,1-b]thiazol-2-yl)-6-((1R)-1-hydroxyethyl)-1-carbapen-2-em-3-carboxylate.

NMR (D$_2$O) δ (HOD=4.65 ppm): 1.21 (3H, d, J=6.4 Hz), 2.29 (3H, s), 2.35 (3H, s), 2.95–3.14 (2H, m), 3.46 (1H, dd, J$_1$=6.1 Hz, J$_2$=2.9 Hz), 4.10–4.18 (2H, m), 7.52 (1H, s)

Example 152

Sodium(1S,5R,6S)-2-(5-cyano-7-methylthioimidazo[5,1-b]thiazol-2-yl)-6-((1R)-1-hydroxyethyl)-1-methyl-1-carbapen-2-em-3-carboxylate a) 4-Nitrobenzyl(1S,5R,6S)-2-(5-cyano-7-methylthioimidazo[5,1-b]thiazol-2-yl)-6-((1R)-1-hydroxyethyl)-1-methyl-1-carbapen-2-em-3-carboxylate In the same manner as in Example 1-a), 91 mg of 4-nitrobenzyl(1S,5R,6S)-2-(5-cyano-7-methylthioimidazo[5,1-b]thiazol-2-yl)-6-((1R)-1-hydroxyethyl)-1-methyl-1-carbapen-2-em-3-carboxylate was obtained from 181 mg of 4-nitrobenzyl(1R,3R,5R,6S)-6-((1R)-1-hydroxyethyl)-1-methyl-2-oxo-1-carbapenam-3-carboxylate and 238 mg of 5-cyano-7-methylthio-2-(tri-n-butylstannyl)-imidazo[5,1-b]thiazole.

NMR (CDCl$_3$) δ: 1.34 (3H, d, J=7.3 Hz), 1.40 (3H, d, J=6.1 Hz), 2.51 (3H, s), 3.40 (1H, m), 3.54 (1H, m), 4.32 (1H, m), 4.42 (1H, dd, J$_1$=9.5 Hz, J$_2$=2.8 Hz), 5.31 (1H, d, J=13.7 Hz), 5.54 (1H, d, J=13.7 Hz), 7.69 (2H, d, J=8.2 Hz), 8.26 (total 3H, m)

b) Sodium(1S,5R,6S)-2-(5-cyano-7-methylthioimidazo[5.1-b]thiazol-2-yl)-6-((1R)-1-hydroxyethyl)-1-methyl-1-carbapen-2-em-3-carboxylate In the same manner as in Example 1-b), 19 mg of the title compound was obtained from 61 mg of 4-nitrobenzyl(1S, 5R,6S)-2-(5-cyano-7-methylthioimidazo[5,1-b]thiazol-2-yl)-6-((1R)-1-hydroxyethyl)-1-methyl-1-carbapen-2-em-3-carboxylate.

NMR (DMSO-d$_6$) δ: 1.10 (3H, d, J=7.1 Hz), 1.16 (3H, d, J=6.4 Hz), 2.41 (3H, s), 3.11, (1H, dd, J$_1$=6.8 Hz, J$_2$=2.6 Hz), 3.56 (1H, m), 3.92 (1H, m), 4.03 (1H, dd, J$_1$=9.2 Hz, J$_2$=2.7 Hz), 5.01 (1H, d, J=5.1 Hz), 8.31 (1H, s)

Example 153

Sodium(5R,6S)-2-[3,7-bis(methylthio)imidazo[5,1-b]thiazol-2-yl]-6-((1R)-1-hydroxyethyl)-1-carbapen-2-em-3-carboxylate a) 4-Nitrobenzyl(5R,6S)-2-[3,7-bis(methylthio)imidazo[5,1-b]thiazol-2-yl]6-((1R)-1-hydroxyethyl)-1-carbapen-2-em-3-carboxylate In the same manner as in Example 1-a), 360 mg of 4-nitrobenzyl(5R,6S)-2-[3,7-bis(methylthio)imidazo[5,1-b]thiazol-2-yl]-6-((1R)-1-hydroxyethyl)-1-carbapen-2-em-3-carboxylate was obtained from 645 mg of 4-nitrobenzyl(3R,5R,6S)-6-((1R)-1-hydroxyethyl)-2-oxo-1-carbapenam-3-carboxylate and 990 mg of 3,7-bis(methylthio)-2-(tri-n-butylstannyl)imidazo-[5,1-b]thiazole.

NMR (CDCl$_3$) δ: 1.40 (3H, d, J=6.3 Hz), 2.31 (3H, s), 2.44 (3H, s), 3.2–3.4 (2H, m), 3.41 (1H, dd, J$_1$=6.5 Hz, J$_2$=3.1 Hz), 4.25–4.4 (1H, m), 4.4–4.5 (1H, m), 5.25 (1H, d, J=13.3 Hz), 5.40 (1H, d, J=13.3 Hz), 7.53 (2H, d, J=8.8 Hz), 8.02 (1H, s), 8.15 (2H, d, J=8.8 Hz)

b) Sodium(5R,6S)-2-[3,7-bis(methylthio)imidazo[5,1-b]thiazol-2-yl]-6-((1R)-1-hydroxyethyl)-1-carbapen-2-em-3-carboxylate The title compound (74.1 mg) was obtained from 145.7 mg of 4-nitrobenzyl(5R,6S)-2-[3,7-bis(methylthio)imidazo[5,1-b]thiazol-2-yl]-6-((1R)-1-hydroxyethyl)-1-carbapen-2-em-3-carboxylate in the same manner as in Example 1-b), except that the purification was carried out by column chromatography on Cosmosil 40C18-PREP (5% aqueous methanol).

NMR (D$_2$O) δ (HOD=4.80 ppm): 1.30 (3H, d, J=6.5 Hz), 2.35 (6H, 2s), 3.16 (1H, dd, J$_1$=17.1 Hz, J$_2$=10.2 Hz), 3.41 (1H, dd, J$_1$=17.1 Hz, J$_2$=8.3 Hz), 3.57 (1H, dd, J$_1$=5.8 Hz, J$_2$=2.8 Hz), 4.2–4.4 (2H, m), 8.28 (1H, s)

Example 154

Sodium(1S,5R,6S)-2-(5-chloro-7-methylthioimidazo[5,1-b]thiazol-2-yl)-6-((1R)-1-hydroxyethyl)-1-methyl-1-carbapen-2-em-3-carboxylate a) 4-Nitrobenzyl(1S,5R,6S)-2-(5-chloro-7-methylthioimidazo[5,1-b]thiazol-2-yl)-6-((1R)-1-hydroxyethyl)-1-methyl-1-carbapen-2-em-3-carboxylate 4-Nitrobenzyl(1S,5R,6S)-6-((1R)-1-hydroxyethyl)-1-methyl-2-(7-methylthioimidazo-[5,1-b]thiazol-2-yl)-1-carbapen-2-em-3-carboxylate (109 mg) was dissolved in 10 ml of benzene at room temperature. N-Chlorosuccinimide (30 mg) and 5 mg of 2,2'-azobis(isobutyronitrile) were added to the solution. The mixture was stirred for 10 min. Dichloromethane (10 ml) and 10 ml of semisaturated brine were added thereto, followed by separation. The organic layer was dried over anhydrous magnesium sulfate. The solvent was removed by distillation under the reduced pressure. The residue was purified by column chromatography on silica gel (dichloromethane:methanol=20:1) to give 32 mg of 4-nitrobenzyl(1S,5R,6S)-2-(5-chloro-7-methylthioimidazo[5,1-b]thiazol-2-yl)-6-((1R)-1-hydroxyethyl)-1-methyl-1-carbapen-2-em-3-carboxylate.

NMR (CDCl$_3$) δ: 1.34 (3H, d, J=7.3 Hz), 1.40 (3H, d, J=6.1 Hz), 2.51 (3H, s), 3.40 (1H, m), 3.54 (1H, m), 4.32 (1H, m), 4.42 (1H, dd, J$_1$=9.5 Hz, J$_2$=2.8 Hz), 5.31 (1H, d, J=13.7 Hz), 5.54 (1H, d, J=13.7 Hz), 7.69 (2H, d, J=8.2 Hz), 8.26 (3H, m)

b) Sodium(1S,5R,6S)-2-(5-chloro-7-methylthioimidazo[5,1-b]thiazol-2-yl)-6-((1R)-1-hydroxyethyl)-1-methyl-1-carbapen-2-em-3-carboxylate In the same manner as in Example 1-b), 2 mg of the title compound was obtained from 30 mg of 4-nitrobenzyl(1S, 5R,6S)-2-(5-chloro-7-methylthioimidazo[5,1-b]thiazol-2-yl)-6-((1R)-1-hydroxyethyl)-1-methyl-1-carbapen-2-em-3-carboxylate.

NMR (D$_2$O) δ (HOD=4.65 ppm): 1.10 (3H, d, J=7.3 Hz), 1.18 (3H, d, J=6.3 Hz), 2.21 (3H, s), 3.36–3.48 (2H, m), 4.10–4.20 (2H, m), 7.60 (1H, s)

Example 155

Sodium(5R,6S)-2-(5-cyano-7-methylthioimidazo[5,1-b]thiazol-2-yl)-6-((1R)-1-hydroxyethyl)-1-carbapen-2-em-3-carboxylate a) 4-Nitrobenzyl(5R,6S)-2-(5-cyano-7-methylthioimidazo[5,1-b]thiazol-2-yl)-6-((1R)-1-hydroxyethyl)-1-carbapen-2-em-3-carboxylate In the same manner as in Example 1-a), 189 mg of 4-nitrobenzyl(5R,6S)-2-(5-cyano-7-methylthioimidazo[5,1-b]thiazol-2-yl)-6-((1R)-1-hydroxyethyl)-1-carbapen-2-em-3-carboxylate was obtained from 188 mg of 4-nitrobenzyl (3R,5R,6S)-6-((1R)-1-hydroxyethyl)-2-oxo-1-carbapenam-3-carboxylate and 262 mg of 5-cyano-7-methylthio-2-(tri-n-butylstannyl)imidazo[5,1-b]thiazole.

NMR (CDCl$_3$) δ: 1.40 (3H, d, J=6.3 Hz), 2.51 (3H, s), 3.34–3.42 (3H, m), 4.29–4.42 (2H, m), 5.34 (1H, d, J=13.5 Hz), 5.56 (1H, d, J=13.5 Hz), 7.71 (2H, d, J=8.0 Hz), 8.10 (1H, s), 8.26 (2H, d, J=8.0 Hz)

b) Sodium(5R,6S)-2-(5-cyano-7-methylthioimidazo[5,1-b]thiazol-2-yl)-6-((1R)-1-hydroxyethyl)-1-carbapen-2-em-3-carboxylate In the same manner as in Example 1-b), 36 mg of the title compound was obtained from 94 mg of 4-nitrobenzyl(5R, 6S)-2-(5-cyano-7-methylthioimidazo[5,1-b]thiazol-2-yl)-6-((1R)-1-hydroxyethyl)-1-carbapen-2-em-3-carboxylate.

NMR (D$_2$O) δ (HOD=4.65 ppm): 1.18 (3H1, d, J=6.6 Hz), 2.31 (3H, s), 3.17 (2H, m), 3.41 (1H, dd, J$_1$=6.0 Hz, J$_2$=3.0 Hz), 4.10–4.20 (2H, m), 7.77 (1H, s)

Example 156

Sodium(1S,5R,6S)-6-((1R)-1-hydroxyethyl)-1-methyl-2-[7-(1-propyl)thioimidazo[5,1-b]thiazol-2-yl]-1-carbapen-2-em-3-carboxylate a) 4-Nitrobenzyl(1S,5R,6S)-6-((1R)-1-hydroxyethyl)-1-methyl-2-[7-(1-propyl)thio-imidazo[5,1-b]thiazol-2-yl]-1-carbapen-2-em-3-carboxylate In the same manner as in Example 1-a), 369 mg of 4-nitrobenzyl(1S,5R,6S)-6-((1R)-1-hydroxyethyl)-1-methyl-2-[7-(1-propyl)thio-imidazo[5,1-b]thiazol-2-yl]-1-carbapen-2-em-3-carboxylate was obtained from 724 mg of 4-nitrobenzyl(1R,3R,5R,6S)-6-((1R)-1-hydroxyethyl)-1-methyl-2-oxo-1-carbapenam-3-carboxylate and 1.07 g of 7-(1-propyl)thio-2-(tri-n-butylstannyl)imidazo-[5,1-b]thiazole.

NMR (CDCl$_3$) δ: 0.99 (3H, t, J=7.4 Hz), 1.31 (3H, d, J=7.1 Hz), 1.40 (3H,d, J=6.3Hz), 1.5–1.7 (2H, m),2.75–2.85 (2H, m), 3.37 (1H, dd, J$_1$=6.3 Hz, J$_2$=2.7 Hz), 3.4–3.55 (1H, m), 4.3–4.4 (2H, m), 5.28 (1H, d, J=13.7 Hz), 5.53 (1H, d, J=13.7 Hz), 7.68 (2H, d, J=8.5 Hz), 8.02 (1H, s), 8.25 (2H, d, J=8.5 Hz), 8.31 (1H, s)

b) Sodium(1S,5R,6S)-6-((1R)-1-hydroxyethyl)-1-methyl-2-[7-(1-propyl)thio-imidazo[5,1-b]thiazol-2-yl]-1-carbapen-2-em-3-carboxylate The title compound (58.2 mg) was obtained from 132 mg of 4-nitrobenzyl(1S,5R,6S)-6-((1R)-1-hydroxyethyl)-1-methyl-2-[7-(1-propyl)thio-imidazo[5,1-b]thiazol-2-yl]-1-carbapen-2-em-3-carboxylate in the same manner as in Example 1-b), except that the purification was carried out by column chromatography on Cosmosil 40C18-PREP (10% aqueous methanol).

NMR (D$_2$O) δ (HOD=4.80 ppm): 0.93 (3H, t, J=7.2 Hz), 1.23 (3H, d, J=7.3 Hz), 1.21 (3H, d, J=6.3 Hz), 1.4–1.6 (2H, m), 2.65–2.75 (2H, m), 3.45–3.6 (2H, m), 4.2–4.35 (2H, m), 7.86 (1H, s), 8.09 (1H, s)

Example 157

Sodium(5R,6S)-6-((1R)-1-hydroxyethyl)-2-(7-(1-propyl)thioimidazo[5,1-b]thiazol-2-yl)-1-carbapen-2-em-3-carboxylate a) 4-Nitrobenzyl(5R,6S)-6-((1R)-1-hydroxyethyl)-2-(7-(1-propyl)thioimidazo[5,1-b]thiazol-2-yl)-1-carbapen-2-em-3-carboxylate In the same manner as in Example 1-a), 396 mg of 4-nitrobenzyl(5R,6S)-6-((1R)-1-hydroxyethyl)-2-(7-(1-propyl)thioimidazo[5,1-b]thiazol-2-yl)-1-carbapen-2-em-3-carboxylate was obtained from 524 mg of 4-nitrobenzyl(3R, 5R,6S)-6-((1R)-1-hydroxyethyl)-2-oxo-1-carbapenam-3-carboxylate and 770 mg of 7-(1-propyl)thio-2-(tri-n-butylstannyl)imidazo[5,1-b]thiazole.

NMR (CDCl$_3$) δ: 0.98 (3H, t, J=7.4 Hz), 1.40 (3H, d, J=6.2 Hz), 1.55–1.7 (2H, m), 2.75–2.85 (2H, m), 3.3–3.4 (3H, m), 4.25–4.4 (2H, m), 5.32 (1H, d, J=13.5 Hz), 5.55 (1H, d, J=13.5 Hz), 7.70 (2H, d, J=8.9 Hz), 8.01 (1H, s), 8.21 (1H, s), 8.25 (2H, d, J=8.5 Hz)

b) Sodium(5R,6s)-6-((1R)-1-hydroxyethyl)-2-(7-(1-propyl)thioimidazo[5,1-b]thiazol-2-yl)-1-carbapen-2-em-3-carboxylate The title compound (72.3 mg) was obtained from 161 mg of 4-nitrobenzyl(5R,6S)-6-((1R)-1-hydroxyethyl)-2-(7-(1-propyl)thioimidazo[5,1-b]thiazol-2-yl)-1-carbapen-2-em-3-carboxylate in the same manner as in Example 1-b), except that the purification was carried out by column chromatography on Cosmosil 40C18-PREP (10% aqueous methanol).

NMR (D$_2$O) δ (HOD=4.80 ppm): 0.92 (3H, t, J=7.4 Hz), 1.31 (3H, d, J=6.3 Hz), 1.4–1.55 (2H, m), 2.72 (2H, t, J=7.2 Hz), 3.15–3.3 (2H, m), 3.49 (1H, dd, J$_1$=6.1 Hz, J$_2$=3.0 Hz), 4.2–4.3 (2H, m), 7.66 (1H, s), 8.04 (1H, s)

Example 158

Sodium(1S,5R,6S)-6-((1R)-1-hydroxyethyl)-2-(7-isopropylthioimidazo[5,1-b]thiazol-2-yl)-1-methyl-1-carbapen-2-em-3-carboxylate a) 4-Nitrobenzyl(1S,5R,6S)-6-((1R)-1-hydroxyethyl)-2-(7-isopropylthioimidazo[5,1-b] thiazol-2-yl)-1-methyl-1-carbapen-2-em-3-carboxylate In the same manner as in Example 1-a), 557 mg of 4-nitrobenzyl(1S,5R,6S)-6-((1R)-1-hydroxyethyl)-2-(7- isopropylthioimidazo[5,1-b]thiazol-2-yl)-1-methyl-1-carbapen-2-em-3-carboxylate was obtained from 629 mg of 4-nitrobenzyl(1R,3R,5R,6S)-6-((1R)-1-hydroxyethyl)-1-methyl-2-oxo-1-carbapenam-3-carboxylate and 890 mg of 7-isopropylthio-2-(tri-n-butylstannyl)imidazo-[5,1-b]thiazole.

NMR (CDCl$_3$) δ: 1.28 (6H, d, J=6.7 Hz), 1.31 (3H, d, J=7.2 Hz), 1.40 (3H, d, J=6.3 Hz), 3.28 (1H, sept, J=6.7 Hz), 3.37 (1H, dd, J$_1$=6.6 Hz, J$_2$=2.9 Hz), 3.4–3.5 (1H, m), 4.3–4.4 (2H, m), 5.28 (1H, d, J=13.7 Hz), 5.53 (1H, d, J=13.7 Hz), 7.68 (2H, d, J=8.8 Hz), 8.03 (1H, s), 8.25 (2H, d, J=8.8 Hz), 8.31 (1H, s)

b) Sodium(1S,5R,6S)-6-((1R)-1-hydroxyethyl)-2-(7-isopropylthioimidazo[5,1-b]thiazol-2-yl)-1-methyl-1-carbapen-2-em-3-carboxylate The title compound (85.1 mg) was obtained from 163 mg of 4-nitrobenzyl(1S,5R,6S)-6-((1R)-1-hydroxyethyl)-2-(7-isopropylthioimidazo[5,1-b]thiazol-2-yl)-1-methyl-1-carbapen-2-em-3-carboxylate in the same manner as in Example 1-b), except that the purification was carried out by column chromatography on Cosmosil 40C18-PREP (5% aqueous methanol).

NMR (D$_2$O) δ (HOD=4.80 ppm): 1.18 (6H, d, J=6.8 Hz), 1.22 (3H, d, J=7.2 Hz), 1.31 (3H, d, J=6.3 Hz), 3.21 (1H, sept, J=6.8 Hz), 3.45–3.6 (2H, m), 4.2–4.35 (2H, m), 7.86 (1H, s), 8.10 (1H, s)

Example 159

Sodium(5R,6S)-6-((1R)-1-hydroxyethyl)-2-(7-isopropylthioimidazo[5,1-b]thiazol-2-yl)-1-carbapen-2-em-3-carboxylate a) 4-Nitrobenzyl(5R,6S)-6-((1R)-1-hydroxyethyl)-2-(7-isopropylthioimidazo[5,1-b]thiazol-2-yl)-1-carbapen-2-em-3-carboxylate In the same manner as in Example 1-a), 261 mg of 4-nitrobenzyl(5R,6S)-6-((1R)-1-hydroxyethyl)-2-(7-isopropylthioimidazo[5,1-b]thiazol-2-yl)-1-carbapen-2-em-3-carboxylate was obtained from 348 mg of 4-nitrobenzyl (3R,5R,6S)-6-((1R)-1-hydroxyethyl)-2-oxo-1-carbapenam-3-carboxylate and 506 mg of 7-isopropylthio-2-(tri-n-butylstannyl)imidazo[5,1-b]thiazole.

NMR (CDCl$_3$) δ: 1.27 (6H, d, J=6.7 Hz), 1.40 (3H, d, J=6.3 Hz), 3.2–3.4 (4H, m), 4.25–4.4 (2H, m), 5.32 (1H, d, J=13.7 Hz), 5.55 (1H, d, J=13.7 Hz), 7.69 (2H, d, J=8.8 Hz), 8.02 (1H, s), 8.21 (1H, s), 8.25 (2H, d, J=8.8 Hz)

b) Sodium(5R,6S)-6-((1R)-1-hydroxyethyl)-2-(7-isopropylthioimidazo[5,1-b]thiazol-2-yl)-1-carbapen-2-em-3-carboxylate The title compound (55.1 mg) was obtained from 110 mg of 4-nitrobenzyl(5R,6S)-6-((1R)-1-hydroxyethyl)-2-(7-isopropylthioimidazo[5,1-b]thiazol-2-yl)-1-carbapen-2-em-3-carboxylate in the same manner as in Example 1-b), except that the purification was carried out by column chromatography on Cosmosil 40C18-PREP (5% aqueous methanol).

NMR (D$_2$O) δ (HOD=4.80 ppm): 1.18 (6H, d, J=6.8 Hz), 1.31 (3H, d, J=6.5 Hz), 3.15–3.35 (3H, m), 3.49 (1H, dd, J$_1$=6.0 Hz, J$_2$=3.0 Hz), 4.2–4.3 (2H, m), 7.66 (1H, s), 8.06 (1H, s)

Example 160

1-Methylcyclohexylcarbonyloxymethyl(1S,5R,6S)-6-((1R)-1-hydroxyethyl)-2-(7-methanesulfonyl-5-methylimidazo[5,1-b]thiazol-2-yl)-1-methyl-1-carbapen-2-em-3-carboxylate In the same manner as in Example 2, 24 mg of the title compound was obtained from 21 mg of sodium(1S,5R,6S)-6-((1R)-1-hydroxyethyl)-2-(7-methanesulfonyl-5-methylimidazo[5,1-b]thiazol-2-yl)-1-methyl-1-carbapen-2-em-3-carboxylate and 27 mg of 1-methylcyclohexylcarbonyloxymethyl iodide.

NMR (CDCl$_3$) δ: 1.15 (3H, s), 1.27 (3H, d, J=7.2 Hz), 1.37 (3H, d, J=6.2 Hz), 1.25–1.70 (8H, m), 1.95–2.03 (2H, m), 2.69 (3H, s), 3.19 (3H, s), 3.34 (1H, dd, J$_1$=7.5 Hz, J$_2$=2.8 Hz), 3.44 (1H, m), 4.29 (1H, m), 4.36 (1H, dd, J$_1$=9.8 Hz, J$_2$=2.8 Hz), 5.90, 5.98 (2H, ABq, J=5.6 Hz), 8.27 (1H, s) MS (TSP): 580 (M$^+$+H)

Example 161

1-(Cyclohexyloxycarbonyloxy)ethyl(1S,5R,6S)-6-((1R)-1-hydroxyethyl)-2-(7-methanesulfonyl-5-methylimidazo[5,1-b]thiazol-2-yl)-1-methyl-1-carbapen-2-em-3-carboxylate (A Mixture of Diastereomers)

In the same manner as in Example 2, 21 mg of the title compound was obtained from 23 mg of sodium(1S,5R,6S)-6-((1R)-1-hydroxyethyl)-2-(7-methanesulfonyl-5-methylimidazo[5,1-b]thiazol-2-yl)-1-methyl-1-carbapen-2-em-3-carboxylate and 0.025 ml of 1-(cyclohexyloxycarbonyloxy)ethyl iodide.

NMR (CDCl$_3$) δ: 1.25–1.40 (8H, s), 1.50–1.95 (8H, m), 1.60, 1.65 (total 3H, d each, J=5.5 Hz), 2.65 (3H, s), 3.20 (3H, s), 3.34 (1H, m), 3.44 (1H, m), 3.62 (1H, m), 4.27 (1H, m), 4.35 (1H, m), 4.65 (1H, m), 6.94 (1H, m), 8.38, 8.43 (total 1H, s each) MS (TSP): 596 (M$^+$+H)

Example 162

Cyclohexyloxycarbonyloxymethyl(1S,5R,6S)-6-((1R)-1-hydroxyethyl)-2-(7-methanesulfonyl-5-methylimidazo[5,1-b]thiazol-2-yl)-1-methyl-1-carbapen-2-em-3-carboxylate In the same manner as in Example 2, 24 mg of the title compound was obtained from 20 mg of sodium(1S,5R,6S)-6-((1R)-1-hydroxyethyl)-2-(7-methanesulfonyl-5-methylimidazo[5,1-b]thiazol-2-yl)-1-methyl-1-carbapen-2-em-3-carboxylate and 0.026 ml of cyclohexyloxycarbonyloxymethyl iodide.

NMR (CDCl$_3$) δ: 1.26 (3H, d, J=7.2 Hz), 1.36 (3H, d, J=6.2 Hz), 1.42–1.48 (4H, m), 1.68–1.98 (6H, m), 2.67 (3H, s), 3.20 (3H, s), 3.34 (1H, dd, J$_1$=6.8 Hz, J$_2$=2.9 Hz), 3.45 (1H, m), 4.30 (1H, m), 4.35 (1H, dd, J$_1$=9.7 Hz, J$_2$=2.9 Hz), 4.66 (1H, m), 5.88, 5.97 (2H, ABq, J=5.8 Hz), 8.37 (1H, s) MS (TSP): 582 (M$^+$+H)

Example 163

3-Phthalidyl(1S,5R,6S)-6-((1R)-1-hydroxyethyl)-2-(7-methanesulfonyl-5-methyl-imidazo[5,1-b]thiazol-2-yl)-1-methyl-1-carbapen-2-em-3-carboxylate (A Mixture of Diastereomers)

In the same manner as in Example 2, 17 mg of the title compound was obtained from 22 of sodium(1S,5R,6S)-6-((1R)-1-hydroxyethyl)-2-(7-methanesulfonyl-5-methylimidazo[5,1-b]thiazol-2-yl)-1-methyl-1-carbapen-2-em-3-carboxylate and 22 mg of 3-phthalidyl bromide.

NMR (CDCl$_3$) δ: 1.26 (3H, m), 1.35 (3H, m), 2.60, 2.67 (total 3H, s each), 3.18, 3.20 (total 3H, s each), 3.35 (1H, m), 3.49 (1H, m), 4.23 (1H, m), 4.37 (1H, m), 7.45, 7.47 (total 1H, s each), 7.65–7.80 (3H, m), 7.92 (1H, m), 8.14, 8.43 (total 1H, s each) MS (TSP): 558 (M$^+$+H)

Example 164

5-Methyl-2-oxo-1,3-dioxolen-4-ylmethyl(1S,5R,6S)-6-((1R)-1-hydroxyethyl)-2-(7-methanesulfonyl-5-methylimidazo[5,1-b]thiazol-2-yl)-1-methyl-1-carbapen-2-em-3-carboxylate In the same manner as in Example 2, 18 mg of the title compound was obtained from 22 mg of sodium(1S,5R,6S)-6-((1R)-1-hydroxyethyl)-2-(7-methanesulfonyl-5-methylimidazo[5,1-b]thiazol-2-yl)-1-methyl-1-carbapen-2-em-3-carboxylate and 19 mg of 5-methyl-2-oxo-1,3-dioxolen-4-ylmethyl bromide.

NMR (CDCl$_3$) δ: 1.29 (3H, d, J=7.2 Hz), 1.37 (3H, d, J=6.3 Hz), 2.22 (3H, s), 2.66 (3H, s), 3.20 (3H, s), 3.35 (1H, dd, J$_1$=6.6 Hz, J$_2$=2.8 Hz), 3.48 (1H, m), 4.29 (1H, m), 4.37 (1H, dd, J$_1$=9.7 Hz, J$_2$=2.8 Hz), 5.02, 5.10 (2H, ABq, J=14.0 Hz), 8.18 (1H, s) MS (TSP): 538 (M$^+$+H)

Example 165

(Z)-2-(3-Phthalidylidene)ethyl(1S,5R,6S)-6-((1R)-1-hydroxyethyl)-2-(7-methanesulfonyl-5-methylimidazo[5,1-b]thiazol-2-yl)-1-methyl-1-carbapen-2-em-3-carboxylate In the same manner as in Example 2, 25 mg of the title compound was obtained from 24 mg of sodium(1S,5R,6S)-6-((1R)-1-hydroxyethyl)-2-(7-methanesulfonyl-5-methylimidazo[5,1-b]thiazol-2-yl)-1-methyl-1-carbapen-2-em-3-carboxylate and 26 mg of (Z)-2-(3-phthalidylidene)ethyl bromide.

NMR (CDCl$_3$) δ: 1.28 (3H, d, J=7.4 Hz), 1.37 (3H, d, J=6.2 Hz), 2.65 (3H, s), 3.19 (3H, s), 3.34 (1H, dd, J$_1$=6.5 Hz, J$_2$=2.7 Hz), 3.45 (1H, m), 4.30 (1H, m), 4.36 (1H, dd, J$_1$=9.6 Hz, J$_2$=2.7 Hz), 5.23 (2H, m), 5.84 (1H, m), 7.60 (1H, m), 7.72 (2H, m), 7.90 (1H, m), 8.33 (1H, s) MS (TSP): 584 (M$^+$+H)

Example 166

1-(Ethoxycarbonyloxy)ethyl(1S,5R,6S)-2-(7-acetyl-5-methylimidazo[5,1-b]thiazol-2-yl)-6-((1R)-1-hydroxyethyl)-1-methyl-1-carbapen-2-em-3-carboxylate (A Mixture of Diastereomers)

In the same manner as in Example 2, 24 mg of the title compound was obtained from 23 mg of sodium(1S,5R,6S)-2-(7-acetyl-5-methylimidazo[5,1-b]thiazol-2-yl)-6-((1R)-1-hydroxyethyl)-1-methyl-1-carbapen-2-em-3-carboxylate and 0.030 ml of 1-(ethoxycarbonyloxy)ethyl iodide.

NMR (CDCl$_3$) δ: 1.27 (3H, m), 1.37 (6H, m), 1.60 (3H, m), 2.58 (3H, s), 2.67 (3H, s), 3.33 (1H, m), 3.48 (1H, m), 4.20–4.30 (4H, m), 4.37 (1H, m), 6.94 (1H, m), 8.44, 8.48 (total 1H, s each) MS (TSP): 506 (M$^+$+H)

Example 167

1-(Cyclohexyloxycarbonyloxy)ethyl(1S,5R,6S)-2-(7-acetyl-5-methylimidazo[5,1-b]thiazol-2-yl)-6-((1R)-1-hydroxyethyl)-1-methyl-1-carbapen-2-em-3-carboxylate (A Mixture of Diastereomers)

In the same manner as in Example 2, 19 mg of the title compound was obtained from 23 mg of sodium(1S,5R,6S)-2-(7-acetyl-5-methylimidazo[5,1-b]thiazol-2-yl)-6((1R)-1-hydroxyethyl)-1-methyl-1-carbapen-2-em-3-carboxylate and 0.034 ml of 1-(cyclohexyloxycarbonyloxy)ethyl iodide.

NMR (CDCl$_3$) δ: 1.27 (3H, m), 1.30–1.95 (10H, m), 1.37 (3H, m), 1.65 (3H, m), 2.58 (3H, s), 2.67 (3H, s), 3.34 (1H, m), 3.50 (1H, m), 4.28 (1H, m), 4.35 (1H, m), 4.64 (1H, m), 6.94 (1H, m), 8.45, 8.48 (total 1H, s each) MS (TSP): 560 (M$^+$+H)

Example 168

Cyclohexyloxycarbonyloxymethyl(1S,5R,6S)-2-(7-acetyl-5-methylimidazo[5,1-b]thiazol-2-yl)-6-((1R)-1-hydroxyethyl)-1-methyl-1-carbapen-2-em-3-carboxylate In the same manner as in Example 2, 25 mg of the title compound was obtained from 21 mg of sodium(1S,5R,6S)-2-(7-acetyl-5-methylimidazo[5,1-b]thiazol-2-yl)-6-((1R)-1-hydroxyethyl)-1-methyl-1-carbapen-2-em-3-carboxylate and 29 mg of cyclohexyloxycarbonyloxymethyl iodide.

NMR (CDCl$_3$) δ: 1.27 (3H, d, J=7.2 Hz), 1.37 (3H, d, J=6.3 Hz), 1.35–2.00 (10H, m), 2.58 (3H, s), 2.68 (3H, s), 3.34 (1H, dd, J$_1$=6.5 Hz, J$_2$=2.7 Hz), 3.47 (1H, m), 4.30 (1H, m), 4.37 (1H, dd, J$_1$=9.8 Hz, J$_2$=2.7 Hz), 4.65 (1H, m), 5.88, 5.97 (2H, ABq, J=5.9 Hz), 8.42 (1H, s) MS (TSP): 546 (M$^+$+H)

Example 169

3-Phthalidyl(1S,5R,6S)-2-(7-acetyl-5-methylimidazo[5,1-b]thiazol-2-yl)-6-((1R)-1-hydroxyethyl)-1-methyl-1-carbapen-2-em-3-carboxylate (A Mixture of Diastereomers)

In the same manner as in Example 2, 22 mg of the title compound was obtained from 20 mg of sodium(1S,5R,6S)-2-(7-acetyl-5-methylimidazo[5,1-b]thiazol-2-yl)-6-((1R)-1-hydroxyethyl)-1-methyl-1-carbapen-2-em-3-carboxylate and 22 mg of 3-phthalidyl bromide.

NMR (CDCl$_3$) δ: 1.28 (3H, m), 1.33 (3H, m), 2.12 (1H, m), 2.57, 2.59 (total 3H, s each), 2.64, 2.69 (total 3H, s each), 3.36 (1H, m), 3.51 (1H, m), 4.24 (1H, m), 4.37 (1H, m), 7.46, 7.48 (total 1H, s each), 7.23–7.70 (3H, m), 7.93 (1H, m), 8.25, 8.54 (total 1H, s each) MS (TSP): 522 (M$^+$+H)

Example 170

5-Methyl-2-oxo-1,3-dioxolen-4-ylmethyl(1S,5R,6S)-2-(7-acetyl-5-methylimidazo[5,1-b]thiazol-2-yl)-6-((1R)-1-hydroxyethyl)-1-methyl-1-carbapen-2-em-3-carboxylate In the same manner as in Example 2, 26 mg of the title compound was obtained from 22 mg of sodium(1S,5R,6S)-2-(7-acetyl-5-methylimidazo[5,1-b]thiazol-2-yl)-6-((1R)-1-hydroxyethyl)-1-methyl-1-carbapen-2-em-3-carboxylate and 20 mg of 5-methyl-2-oxo-1,3-dioxolen-4-ylmethyl bromide.

NMR (CDCl$_3$) δ: 1.29 (3H, d, J=7.1 Hz), 1.38 (3H, d, J=6.3 Hz), 1.91 (1H, br.m), 2.22 (3H, s), 2.58 (3H, s), 2.68 (3H, s), 3.35 (1H, dd, J$_1$=6.5 Hz, J$_2$=2.7 Hz), 3.50 (1H, m), 4.30 (1H, m), 4.37 (1H, dd, J$_1$=9.5 Hz, J$_2$=2.7 Hz), 4.99, 5.09 (2H, ABq, J=13.7 Hz), 8.26 (1H, s) MS (TSP): 502 (M$^+$+H)

Example 171

Cyclopentyloxycarbonyloxymethyl(1S,5R,6S)-2-(7-acetyl-5-methylimidazo[5,1-b]thiazol-2-yl)-6-((1R)-1-hydroxyethyl)-1-methyl-1-carbapen-2-em-3-carboxylate In the same manner as in Example 2, 28 mg of the title compound was obtained from 23 mg of sodium(1S,5R,6S)-

2-(7-acetyl-5-methylimidazo[5,1-b]thiazol-2-yl)-6-((1R)-1-hydroxyethyl)-1-methyl-1-carbapen-2-em-3-carboxylate and 30 mg of cyclopentyloxycarbonyloxymethyl iodide.

NMR (CDCl$_3$) δ: 1.28 (3H, d, J=7.2 Hz), 1.37 (3H, d, J=6.3 Hz), 1.60–1.95 (8H, m), 2.58 (3H, s), 2.68 (3H, s), 3.40 (1H, dd, J$_1$=6.6 Hz, J$_2$=2.8 Hz), 3.49 (1H, m), 4.30 (1H, m), 4.39 (1H, dd, J$_1$=9.9 Hz, J$_2$=2.8 Hz), 5.12 (1H, m), 5.87, 5.96 (2H, ABq, J=5.8 Hz), 8.43 (1H, s) MS (TSP): 532 (M$^+$+H)

Example 172

1-(Pivaloyloxy)ethyl(1S,5R,6S)-2-(7-acetylimidazo[5,1-b]thiazol-2-yl)-6-((1R)-1-hydroxyethyl)-1-methyl-1-carbapen-2-em-3-carboxylate (A Mixture of Diastereomers)

In the same manner as in Example 2, 331 mg of the title compound was obtained from 396 mg of sodium(1S,5R,6S)-2-(7-acetylimidazo[5,1-b]thiazol-2-yl)-6-((1R)-1-hydroxyethyl)-1-methyl-1-carbapen-2-em-3-carboxylate and 495 mg of 1-(pivaloyloxy)ethyl iodide.

NMR (CDCl$_3$) δ: 1.11, 1.17 (total 9H, s each), 1.22 (3H, m), 1.34 (3H, m), 1.50, 1.55 (total 3H, d each, J=5.5 Hz), 2.56 (3H, s), 3.32 (1H, m), 3.45 (1H, m), 4.24 (1H, m), 4.37 (1H, m), 6.98 (1H, m), 8.01 (1H, s), 8.49, 8.51 (total 1H, s each) MS (TSP): 504 (M$^+$+H)

Example 173

1-Methylcyclohexylcarbonyloxymethyl(1S,5R,6S)-2-(7-acetylimidazo[5,1-b]thiazol-2-yl)-6-((1R)-1-hydroxyethyl)-1-methyl-1-carbapen-2-em-3-carboxylate In the same manner as in Example 2,301 mg of the title compound was obtained from 229 mg of sodium(1S,5R,6S)-2-(7-acetylimidazo[5,1-b]thiazol-2-yl)-6-((1R)-1-hydroxyethyl)-1-methyl-1-carbapen-2-em-3-carboxylate and 253 mg of 1-methylcyclohexylcarbonyloxymethyl iodide.

NMR(CDCl$_3$) δ: 0.90–1.54 (8H,m), 1.20 (3H, s), 1.27 (3H, d, J=7.4 Hz), 1.35 (3H, d, J=6.1 Hz), 1.95–2.01 (2H, m), 2.60 (3H, s), 3.35 (1H, dd, J$_1$=6.5 Hz, J$_2$=2.7 Hz), 3.49 (1H, m), 4.28 (1H, m), 4.39 (1H, dd, J$_1$=9.7 Hz, J$_2$=2.7 Hz), 5.89, 5.96 (2H, ABq, J=5.5 Hz), 8.05 (1H, s), 8.48 (1H, s) MS (TSP): 530 (M$^+$+H)

Example 174

Cyclohexylcarbonyloxymethyl(1S,5R,6S)-2-(7-acetylimidazo[5,1-b]thiazol-2-yl)-6-((1R)-1-hydroxyethyl)-1-methyl-1-carbapen-2-em-3-carboxylate In the same manner as in Example 2, 288 mg of the title compound was obtained from 228 mg of sodium(1S,5R,6S)-2-(7-acetylimidazo[5,1-b]thiazol-2-yl)-6-((1R)-1-hydroxyethyl)-1-methyl-1-carbapen-2-em-3-carboxylate and 236 mg of cyclohexylcarbonyloxymethyl iodide.

NMR (CDCl$_3$) δ: 1.15–1.75 (8H, m), 1.28 (3H, d, J=7.1 Hz), 1.37 (3H, d, J=6.0 Hz), 1.80–1.95 (2H, m), 2.35 (1H, m), 2.62 (3H, s), 3.35 (1H, dd, J$_1$=6.5 Hz, J$_2$=2.8 Hz), 3.49 (1H, m), 4.30 (1H, m), 4.39 (1H, dd, J$_1$=9.6 Hz, J$_2$=2.8 Hz), 5.88, 5.96 (2H, ABq, J=5.8 Hz), 8.05 (1H, s), 8.51 (1H, s) MS (TSP): 516 (M$^+$+H)

Example 175

1-(Cyclohexylcarbonyloxy)ethyl(1S,5R,6S)-2-(7-acetylimidazo[5,1-b]thiazol-2-yl)-6-((1R)-1-hydroxyethyl)-1-methyl-1-carbapen-2-em-3-carboxylate (A Mixture of Diastereomers)

In the same manner as in Example 2, 286 mg of the title compound was obtained from 290 mg of sodium(1S,5R,6S)-2-(7-acetylimidazo[5,1-b]thiazol-2-yl)-6-((1R)-1-hydroxyethyl)-1-methyl-1-carbapen-2-em-3-carboxylate and 338 mg of 1-(cyclohexylcarbonyloxy)ethyl iodide.

NMR(CDCl$_3$) δ: 1.25 (3H, m), 1.20–1.95 (8H, m), 1.36 (3H, m), 1.53, 1.58 (total 3H, d each, J=5.5 Hz), 2.25–2.38 (3H, s), 3.10 (3H, s), 3.34 (1H, m), 3.46 (1H, m), 4.27 (1H, m), 4.39 (1H, m), 7.01 (1H, m), 8.05 (1H, s), 8.30, 8.57 (total 1H, s each) MS (TSP): 530 (M$^+$+H)

Example 176

Hexanoyloxymethyl(1S,5R,6S)-2-(7-acetylimidazo[5,1-b]thiazol-2-yl)-6-((1R)-1-hydroxyethyl)-1-methyl-1-carbapen-2-em-3-carboxylate In the same manner as in Example 2, 95.3 mg of the title compound was obtained from 94 mg of sodium(1S,5R,6S)-2-(7-acetylimidazo[5,1-b]thiazol-2-yl)-6-((1R)-1-hydroxyethyl)-1-methyl-1-carbapen-2-em-3-carboxylate and 109 mg of hexanoyloxymethyl iodide.

NMR (CDCl$_3$) δ: 0.87 (3H, t, J=6.7 Hz), 1.2–1.35 (7H, m), 1.38 (3H, d, J=6.3 Hz), 1.55–1.7 (2H, m), 2.37 (2H, t, J=7.7 Hz), 2.62 (3H, s), 3.36 (1H, dd, J$_1$=6.6 Hz, J$_2$=2.8 Hz), 3.45–3.6 (1H, m), 4.25–4.35 (1H, m), 4.39 (1H, dd, J$_1$=9.8 Hz, J$_2$=2.8 Hz), 5.90 (1H, d, J=5.7 Hz), 5.97 (1H, d, J=5.7 Hz), 8.04 (1H, s), 8.54 (1H, s) MS (TSP): 504 (M$^+$+H)

Example 177

2-Ethylbutyryloxymethyl(1S,5R,6S)-2-(7-acetylimidazo[5,1-b]thiazol-2-yl)-6-((1R)-1-hydroxyethyl)-1-methyl-1-carbapen-2-em-3-carboxylate In the same manner as in Example 2, 229 mg of the title compound was obtained from 265 mg of sodium(1S,5R,6S)-2-(7-acetylimidazo[5,1-b]thiazol-2-yl)-6-((1R)-1-hydroxyethyl)-1-methyl-1-carbapen-2-em-3-carboxylate and 390 mg of 2-ethylbutyryloxymethyl iodide.

NMR (CDCl$_3$) δ: 0.8–0.9 (6H, m), 1.28 (3H, d, J=7.4 Hz), 1.36 (3H, d, J=6.3 Hz), 1.45–1.7 (4H, m), 2.2–2.3 (1H, m), 2.62 (3H, s), 3.36 (1H, dd, J$_1$=6.8 Hz, J$_2$=2.9 Hz), 3.45–3.55 (1H, m), 4.25–4.35 (1H, m), 4.39 (1H, dd, J$_1$=9.8 Hz, J$_2$=2.9 Hz), 5.95 (2H, s), 8.05 (1H, s), 8.52 (1H, s) MS (TSP): 504 (M$^+$+H)

Example 178

Cyclopentyloxycarbonyloxymethyl(1S,5R,6S)-2-(7-acetylimidazo[5,1-b]thiazol-2-yl)-6-((1R)-1-hydroxyethyl)-1-methyl-1-carbapen-2-em-3-carboxylate In the same manner as in Example 2, 297 mg of the title compound was obtained from 235 mg of sodium (1S,5R,6S)-2-(7-acetylimidazo[5,1-b]thiazol-2-yl)-6-((1R)-1-hydroxyethyl)-1-methyl-1-carbapen-2-em-3-carboxylate and 249 mg of cyclopentyloxycarbonyloxymethyl iodide.

NMR (CDCl$_3$) δ: 1.27 (3H, d, J=7.1 Hz), 1.35 (3H, d, J=6.1 Hz), 1.55–1.85 (8H, m), 2.60 (3H, s), 3.35 (1H, dd, J$_1$=6.3 Hz, J$_2$=2.5 Hz), 3.49 (1H, m), 4.29 (1H, m), 4.39 (1H, dd, J$_1$=9.7 Hz, J$_2$=2.5 Hz), 5.10 (1H, m), 5.87, 5.94 (2H, ABq, J=5.8 Hz), 8.04 (1H, s), 8.55 (1H, s) MS (TSP): 518 (M$^+$+H)

Example 179

1-(3-Pentyloxycarbonyloxy)ethyl(1S,5R,6S)-2-(7-acetylimidazo[5,1-b]thiazol-2-yl)-6-((1R)-1-hydroxyethyl)-1-methyl-1-carbapen-2-em-3-carboxylate (A Mixture of Diastereomers)

In the same manner as in Example 2, 243 mg of the title compound was obtained from 246 mg of sodium(1S,5R,6S)-

2-(7-acetylimidazo[5,1-b]thiazol-2-yl)-6-((1R)-1-hydroxyethyl)-1-methyl-1-carbapen-2-em-3-carboxylate and 300 mg of 1-(3-pentyloxycarbonyloxy)ethyl iodide.

NMR(CDCl$_3$) δ: 0.82–0.95 (6H, m), 1.26 (3H,m), 1.36 (3H, m), 1.55–1.66 (7H, m), 2.61 (3H, s), 3.34 (1H, m), 3.48 (1H, m), 4.31 (1H, m), 4.35 (1H, m), 4.58 (1H, m), 6.93 (1H, m), 8.01 (1H, s), 8.58, 8.62 (total 1H, s each) MS (TSP): 534 (M$^+$+H)

Example 180

3-Pentyloxycarbonyloxymethyl(1S,5R,6S)-2-(7-acetylimidazo[5,1-b]thiazol-2-yl)-6-((1R)-1-hydroxyethyl)-1-methyl-1-carbapen-2-em-3-carboxylate In the same manner as in Example 2, 265 mg of the title compound was obtained from 218 mg of sodium(1S,5R,6S)-2-(7-acetylimidazo[5,1-b]thiazol-2-yl)-6-((1R)-1-hydroxyethyl)-1-methyl-1-carbapen-2-em-3-carboxylate and 309 mg of 3-pentyloxycarbonyloxymethyl iodide.

NMR (CDCl$_3$) δ: 0.84 (6H, m), 1.25 (3H, d, J=7.4 Hz), 1.33 (3H, d, J=6.3 Hz), 1.56 (4H, m), 2.57 (3H, s), 3.33 (1H, dd, J$_1$=6.8 Hz, J$_2$=2.7 Hz), 3.47 (1H, m), 4.25 (1H, m), 4.37 (1H, dd, J$_1$=9.6 Hz, J$_2$=2.7 Hz), 4, 56 (1H, m), 5.87, 5.93 (2H, ABq, J=5.8 Hz), 8.03 (1H, s), 8.52 (1H, s) MS (TSP): 520 (M$^+$+H)

Example 181

Cyclohexylmethoxycarbonyloxymethyl(1S,5R,6S)-2-(7-acetylimidazo[5,1-b]thiazol-2-yl)-6-((1R)-1-hydroxyethyl)-1-methyl-1-carbapen-2-em-3-carboxylate In the same manner as in Example 2, 317 mg of the title compound was obtained from 237 mg of sodium(1S,5R,6S)-2-(7-acetylimidazo[5,1-b]thiazol-2-yl)-6-((1R)-1-hydroxyethyl)-1-methyl-1-carbapen-2-em-3-carboxylate and 369 mg of cyclohexylmethoxycarbonyloxymethyl iodide.

NMR (CDCl$_3$) δ: 0.90–1.30 (4H, m), 1.28 (3H, d, J=7.1 Hz), 1.37 (3H, d, J=6.2 Hz), 1.65–1.75 (6H, m), 2.15 (1H, br.s), 2.62 (3H, s), 3.36 (1H, dd, J$_1$=6.4 Hz, J$_2$=2.8 Hz), 3.50 (1H, m), 3.98 (2H, d, J=6.3 Hz), 4.30 (1H, m), 4.39 (1H, dd, J$_1$=9.6 Hz, J$_2$=2.8 Hz), 5.90, 5.96 (2H, ABq, J=5.8 Hz), 8.03 (1H, s), 8.57 (1H, s) MS (TSP): 546 (M$^+$+H)

Example 182

1-(Isobutyryloxy)ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (A Mixture of Diastereomers)

In the same manner as in Example 2, 198 mg of the title compound was obtained from 289 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 323 mg of 1-(isobutyryloxy)ethyl iodide.

NMR (CDCl$_3$) δ: 1.14 (3H, m), 1.19 (3H, m), 1.26 (3H, m), 1.36 (3H, m), 1.55, 1.60 (total 3H, d each, J=5.5 Hz), 2.32 (1H, br.s), 2.68 (1H, m), 3.21 (3H, s), 3.33 (1H, m), 3.46 (1H, m), 4.27 (1H, m), 4.35 (1H, m), 7.03 (1H, m), 8.09 (1H, s), 8.51, 8.53 (total 1H, s each) MS (TSP): 526 (M$^+$+H)

Example 183

1-(Pivaloyloxy)ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (A Mixture of Diastereomers)

In the same manner as in Example 2, 234 mg of the title compound was obtained from 361 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 430 mg of 1-(pivaloyloxy)ethyl iodide.

NMR (CDCl$_3$) δ: 1.52, 1.21 (total 9H, s each), 1.25 (3H, m), 1.35 (3H, m), 1.53, 1.58 (total 3H, d each, J=3.6 Hz), 3.19 (3H, s), 3.33 (1H, m), 3.46 (1H, m), 4.25 (1H, m), 4.34 (1H, m), 7.00 (1H, m), 8.10 (1H, s), 8.46, 8.49 (total 1H, s each) MS (TSP): 540 (M$^+$+H)

Example 184

Hexanoyloxymethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate In the same manner as in Example 2, 217 mg of the title compound was obtained from 214 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 265 mg of hexanoyloxymethyl iodide.

NMR (CDCl$_3$) δ: 0.87 (3H, t, J=7.0 Hz), 1.2–1.3 (7H, m), 1.37 (3H, d, J=6.3 Hz), 1.55–1.7 (2H, m), 2.38 (2H, t, J=7.7 Hz), 3.24 (3H, s), 3.35 (1H, dd, J$_1$=6.6 Hz, J$_2$=2.7 Hz), 3.4–3.55 (1H, m), 4.25–4.35 (2H, m), 4.37 (1H, dd, J$_1$=9.8 Hz, J$_2$=2.7 Hz), 5.89 (1H, d, J=5.6 Hz), 5.96 (1H, d, J=5.6 Hz), 8.19 (1H, s), 8.49 (1H, s) MS (TSP): 540 (M$^+$+H)

Example 185

Cyclohexylcarbonyloxymethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate In the same manner as in Example 2, 267 mg of the title compound was obtained from 219 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 200 mg of cyclohexylcarbonyloxymethyl iodide.

NMR (CDCl$_3$) δ: 1.18–1.50 (4H, m), 1.27 (3H, d, J=7.2 Hz), 1.35 (3H, d, J=6.3 Hz), 1.60–1.98 (6H, m), 2.35 (1H, m), 3.22 (3H, s), 3.34 (1H, dd, J$_1$=6.6 Hz, J$_2$=2.8 Hz), 3.47 (1H, m), 4.28 (1H, m), 4.36 (1H, dd, J$_1$=9.7 Hz, J$_2$=2.8 Hz), 5.88, 5.95 (2H, ABq, J=5.7 Hz), 8.12 (1H, s), 8.45 (1H, s) MS (TSP): 552 (M$^+$+H)

Example 186

Cyclohexylacetoxymethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate In the same manner as in Example 2, 272 mg of the title compound was obtained from 212 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 276 mg of cyclohexylacetoxymethyl iodide.

NMR (CDCl$_3$) δ: 0.87–1.25 (6H, m), 1.25 (3H, d, J=7.2 Hz), 1.34 (3H, d, J=6.3 Hz), 1.60–1.80 (5H, m), 2.2 4 (2H, d, J 6.9 Hz), 3.21 (3H, s), 3.33 (1H, dd, J$_1$=6.7 Hz, J$_2$=2.8 Hz), 3.47 (1H, m), 4.26 (1H, m), 4.34 (1H, dd, J$_1$=9.6 Hz, J$_2$=2.8 Hz), 5.88, 5.93 (2H, ABq, J=4.3 Hz), 8.12 (1H, s), 8.44 (1H, s) MS (TSP): 566 (M$^+$+H)

Example 187

Dicyclohexylacetoxymethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate In the same manner as in Example 2, 292 mg of the title compound was obtained from 217 mg of sodium(1S,5R,6S)-

6-((1R)-1-hydroxyethyl)-2-(7-methanesulfonylimidazo[5,1-b]thiazol-2-yl)-1-methyl-1-carbapen-2-em-3-carboxylate and 274 mg of dicyclohexylacetoxymethyl iodide.

NMR (CDCl$_3$) δ: 0.79–1.22 (10H, m), 1.26 (3H, d, J=7.1 Hz), 1.37 (3H, d, J=6.3 Hz), 1.60 (12H, m), 2.11 (1H, t, J=7.5 Hz), 2.57 (1H, br s), 3.22 (3H, s), 3.34 (1H, dd, J$_1$=7.0 Hz, J$_2$=2.9 Hz), 3.47 (1H, m), 4.25 (1H, br t), 4.33 (1H, dd, J$_1$=9.8 Hz, J$_2$=3.0 Hz), 5.89 (1H, d, J=5.6 Hz), 5.96 (1H, d, J=5.6 Hz), 8.15 (1H, s), 8.47 (1H, s) MS (TSP): 648 (M$^+$+H)

Example 188

1-(l-Methylcyclohexylcarbonyloxy)ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (A Mixture of Diastereomers)

In the same manner as in Example 2, 287 mg of the title compound was obtained from 747 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 3.2 g of 1-[(1-methylcyclohexan-1-yl)carbonyloxy] ethyl iodide.

NMR (CDCl$_3$) δ: 1.12, 1.21 (total 3H, s each), 1.56, 1.62 (total 3H, d each, J=5.5 Hz), 1.1–2.1 (16H, m), 3.22 (3H, s), 3.3–3.4 (1H, m), 3.35–3.5 (1H, m), 4.2–4.35 (1H, m), 4.37 (1H, dd, J$_1$=9.6 Hz, J$_2$=2.7 Hz), 7.0–7.1 (1H, m), 8.09 (1H, s), 8.51, 8.57 (total 1H, s each) MS (TSP): 580 (M$^+$+H)

Example 189

1-Adamantylcarbonyloxymethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate In the same manner as in Example 2, 258 mg of the title compound was obtained from 217 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 260 mg of 1-adamantylcarbonyloxymethyl iodide.

NMR (CDCl$_3$) δ: 1.28 (3H, d, J=7.3 Hz), 1.37 (3H, d, J=6.1 Hz), 1.69 (6H, m), 1.86 (6H, m), 2.00 (3H, m), 3.22 (3H, s), 3.35 (1H, dd, J$_1$=6.6 Hz, J$_2$=3.0 Hz), 3.46 (1H, m), 4.29 (1H, m), 4.37 (1H, dd, J$_1$=9.7 Hz, J$_2$=2.9 Hz), 5.88 (1H, d, J=5.6 Hz), 5.96 (1H, d, J=5.6 Hz), 8.11 (1H, s), 8.44 (1H, s) MS (TSP): 604 (M$^+$+H)

Example 190

1-(1-Adamantylcarbonyloxy)ethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate (A Mixture of Diastereomers)

In the same manner as in Example 2, 71 mg of the title compound was obtained from 184 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 500 mg of 1-(1-adamantylcarbonyloxy)ethyl iodide.

NMR (CDCl$_3$) δ: 1.27 (3H, m), 1.38 (3H, m), 1.55, 1.60 (total 3H, d each, J=5.5 Hz), 1.62–2.07 (15H, m), 3.22 (3H, s), 3.34 (1H, m), 3.44 (1H, m), 4.29 (1H, m), 4.37 (1H, m), 7.02 (1H, m), 8.08 (1H, s), 8.53, 8.56 (total 1H, s each) MS (TSP): 618 (M$^+$+H)

Example 191

1-(Benzoyloxy)ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (A Mixture of Diastereomers)

In the same manner as in Example 2, 147 mg of the title compound was obtained from 197 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 250 mg of 1-(benzoyloxy)ethyl iodide.

NMR (CDCl$_3$) δ: 1.28 (3H, m), 1.33, 1.38 (total3H, d each, J=6.2 Hz), 1.71, 1.76 (total 3H, d each, J=5.5 Hz), 3.21 (3H, s), 3.35 (3H, m), 3.44 (1H, m), 4.28 (1H, m), 4.37 (1H, m), 7.30 (1H, m), 7.45 (2H, m), 7.60 (1H, m), 8.00, 8.02 (total 1H, s each), 8.07 (2H, m), 8.51, 8.57 (total 1H, s each) MS (TSP): 560 (M$^+$+H)

Example 192

4-(2-Propyl)benzoyloxymethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate In the same manner as in Example 2, 102 mg of the title compound was obtained from 92 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 120 mg of 4-(2-propyl)benzoyloxymethyl iodide.

NMR (CDCl$_3$) δ: 1.24 (3H, s), 1.25 (3H, d, J=7.1 Hz), 1.26 (3H, s), 1.35 (3H, d, J=6.2 Hz), 2.96 (1H, m), 3.21 (3H, s), 3.34 (1H, dd, J$_1$=6.7 Hz, J$_2$=2.8 Hz), 3.45 (1H, m), 4.28 (1H, m), 4.36 (1H, dd, J$_1$=9.6 Hz, J$_2$=2.8 Hz), 6.14, 6.18 (2H, ABq, J=5.6 Hz), 7.30 (2H, d, J=8.3 Hz), 7.98 (2H, d, J=8.3 Hz), 8.09 (1H, s), 8.47 (1H, s) MS (TSP): 588 (M$^+$+H)

Example 193

4-n-Butylbenzoyloxymethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate In the same manner as in Example 2, 140 mg of the title compound was obtained from 112 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 180 mg of 4-n-butylbenzoyloxymethyl iodide.

NMR (CDCl$_3$) δ: 0.92 (3H, t, J=7.3 Hz), 1.26 (3H, d, J=7.4 Hz), 1.34 (2H, m), 1.35 (3H, d, J=6.3 Hz), 1.60 (2H, m), 2.66 (2H, t, J=8.0 Hz), 3.21 (3H, s), 3.34 (1H, dd, J$_1$=6.5 Hz, J$_2$=2.9 Hz), 3.45 (1H, m), 4.28 (1H, m), 4.36 (1H, dd, J$_1$=9.8 Hz, J$_2$=2.9 Hz), 6.14, 6.17 (2H, ABq, J=5.6 Hz), 7.25 (2H, d, J=8.3 Hz), 7.97 (2H, d, J=8.3 Hz), 8.09 (1H, s), 8.47 (1H, s) MS (TSP): 602 (M$^+$+H)

Example 194

4-Phenylbenzoyloxymethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate In the same manner as in Example 2, 169 mg of the title compound was obtained from 110 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 170 mg of 4-phenylbenzoyloxymethyl iodide.

NMR (CDCl$_3$) δ: 1.27 (3H, d, J=7.3 Hz), 1.36 (3H, d, J=6.3 Hz), 2.17 (1H, br.s), 3.21 (3H, s), 3.35 (1H, dd, J$_1$=6.6 Hz, J$_2$=2.8 Hz), 3.46 (1H, m), 4.29 (1H, m), 4.37 (1H, dd, J$_1$=9.8 Hz, J$_2$=2.8 Hz), 6.20 (2H, s), 7.45 (3H, m), 7.65 (4H, m), 8.10 (1H, s), 8.13 (2H, m), 8.49 (1H, s) MS (TSP): 622 (M$^+$+H)

Example 195

4-t-Butylbenzoyloxymethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate In the same manner as in Example 2, 262 mg of the title compound was obtained from 217 mg of sodium(1S,5R,6S)-

6-((1R)-1-hydroxyethyl)-2-(7-methanesulfonylimidazo[5,1-b]thiazol-2-yl)-1-methyl-1-carbapen-2-em-3-carboxylate and 318 mg of 4-t-butylbenzoyloxymethyl iodide.

NMR (CDCl$_3$) δ: 1.25 (3H, d, J=7.3 Hz), 1.31 (9H, s), 1.34 (3H, d, J=6.4 Hz), 3.20 (3H, s), 3.34 (1H, dd, J$_1$=6.7 Hz, J$_2$=2.8 Hz), 3.48 (1H, dq, J$_1$=9.8 Hz, J$_2$=7.3 Hz), 4.26 (1H, dq, J=6.3 Hz), 4.35 (1H, dd, J$_1$=9.7 Hz, J$_2$=2.9 Hz), 6.14 (1H, d, J=5.6 Hz), 6.17 (1H, d, J=5.6 Hz), 7.45 (2H, m), 7.97 (2H, m), 8.12 (1H, s), 8.44 (1H, s) MS (TSP): 619 (M$^+$+H)

Example 196

1-(4-t-Butylbenzoyloxy)ethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate (A Mixture of Diastereomers)

In the same manner as in Example 2, 154 mg of the title compound was obtained from 192 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 300 mg of 1-(4-t-butylbenzoyloxy)ethyl iodide.

NMR (CDCl$_3$) δ: 1.26 (3H, m), 1.32, 1.34 (total9H, s each), 1.37 (3H, m), 1.70, 1.74 (total 3H, d each, J=5.4 Hz), 3.20 (3H, s), 3.34 (1H, m), 3.44 (1H, m), 4.28 (1H, m), 4.36 (1H, m), 7.29 (1H, m), 7.46 (2H, m), 7.98 (2H, m), 8.01 (1H, s), 8.51, 8.57 (total 1H, s each) MS (TSP): 616 (M$^+$+H)

Example 197

2,4,6-Trimethylbenzoyloxymethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate In the same manner as in Example 2, 214 mg of the title compound was obtained from 178 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 254 mg of 2,4,6-trimethylbenzoyloxymethyl iodide.

NMR (CDCl$_3$) δ: 1.26 (3H, d, J=7.1 Hz), 1.36 (3H, d, J=6.0 Hz), 2.27 (9H, s), 3.21 (3H, s), 3.34 (1H, dd, J$_1$=6.6 Hz, J$_2$=2.2 Hz), 3.47 (1H, m), 4.27 (1H, m), 4.34 (1H, dd, J$_1$=9.8 Hz, J$_2$=2.2 Hz), 6.11, 6.15 (2H, ABq, J=5.6 Hz), 6.83 (2H, s), 8.10 (1H, s), 8.49 (1H, s) MS (TSP): 588 (M$^+$+H)

Example 198

1-(2-Propyloxycarbonyloxy)ethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate (A Mixture of Diastereomers)

In the same manner as in Example 2, 257 mg of the title compound was obtained from 267 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 300 mg of 1-(2-propyloxycarbonyloxy)ethyl iodide.

NMR (CDCl$_3$) δ: 1.28 (6H, m), 1.36 (6H, m), 1.58, 1.64 (total 3H, d each, J=5.4 Hz), 3.22 (3H, s), 3.33 (1H, m), 3.45 (1H, m), 4.28 (1H, m), 4.35 (1H, m), 4.91 (1H, m), 6.93 (1H, m), 8.09 (1H, s), 8.54 (1H, s) MS (TSP): 542 (M$^+$+H)

Example 199

1-(2-Butyloxycarbonyloxy)ethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate (A Mixture of Diastereomers)

In the same manner as in Example 2, 164 mg of the title compound was obtained from 220 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 320 mg of 1-(2-butyloxycarbonyloxy)ethyl iodide.

NMR (CDCl$_3$) δ: 0.85–1.00 (3H, m), 1.25–1.40 (9H, m), 1.55–1.75 (6H, m), 3.22 (3H, s×2), 3.34 (1H, dd, J$_1$=6.8 Hz, J$_2$=2.9 Hz), 3.46 (1H, m), 4.27 (1H, m), 4.35 (1H, m), 4.65–4.85 (1H, m), 6.94 (1H, m), 8.09 (1H, s×2), 8.55 (1H, m)

Example 200

1-(3-Pentyloxycarbonyloxy)ethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate (A Mixture of Diastereomers)

In the same manner as in Example 2, 276 mg of the title compound was obtained from 151 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 199 mg of 1-(3-pentyloxycarbonyloxy)ethyl iodide.

NMR (CDCl$_3$) δ: 0.83–0.95 (6H, m), 1.23 (3H, m), 1.55, 1.70 (7H, m), 3.18 (3H, s), 3.30 (1H, m), 3.46 (1H, m), 4.22 (1H, m), 4.32 (1H, m), 4.58 (1H, m), 6.89 (1H, m), 8.10 (1H, s), 8.45, 8.47 (total 1H, s each) MS (TSP): 570 (M$^+$+H)

Example 201

1-(1-Butyloxycarbonyloxy)ethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate (A Mixture of Diastereomers)

In the same manner as in Example 2, 51.0 mg of the title compound was obtained from 200.0 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 236.2 mg of 1-(1-butyloxycarbonyloxy)ethyl iodide.

NMR (CDCl$_3$) δ: 0.93 (3H, td, J$_1$=7.3 Hz, J$_2$=12.6 Hz), 1.26 (3H, dd, J$_1$=7.3 Hz, J$_2$=2.9 Hz), 1.33 (3H, dd, J$_1$=6.1 Hz, J$_2$=2.5 Hz), 1.55 (2H, m), 1.60 (3H, m), 1.65 (2H, m), 3.22 (3H, s), 3.35 (1H, m), 3.45 (1H, m), 4.15, 4.22 (total 2H, t each, J=6.5), 4.29 (1H, m), 4.38 (1H, td, J$_1$=2.6 Hz, J$_2$=9.8 Hz), 6.94 (1H, m), 8.06, 8.08 (total 1H, s each), 8.58, 8.59 (total 1H, s each) MS (TSP): 556 (M$^+$+H)

Example 202

4-Heptyloxycarbonyloxymethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate In the same manner as in Example 2, 229 mg of the title compound was obtained from 168 mg of sodium(1S,5R,6S)-6-((1R)-1-hydroxyethyl)-2-(7-methane-7 sulfonylimidazo[5,1-b]thiazol-2-yl)-1-methyl-1-carbapen-2-em-3-carboxylate and 200 mg of 4-heptyloxycarbonyloxymethyl iodide.

NMR (CDCl$_3$) δ: 0.89 (6H, m), 1.26 (3H, d, J=7.2 Hz), 1.30–1.40 (4H, m), 1.35 (3H, d, J=6.3 Hz), 1.56 (4H, m), 3.21 (3H, s), 3.33 (1H, dd, J$_1$=6.9 Hz, J$_2$=2.9 Hz), 3.47 (1H, m), 4.26 (1H, m), 4.35 (1H, dd, J$_1$=9.8 Hz, J$_2$=2.9 Hz), 4.74 (1H, m), 5.89, 5.95 (2H, ABq, J=5.8 Hz), 8.11 (1H, s), 8.50 (1H, s) MS (TSP): 584 (M$^+$+H)

Example 203

1-(4-Heptyloxycarbonyloxy)ethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate (A Mixture of Diastereomers)

In the same manner as in Example 2, 171 mg of the title compound was obtained from 178 mg of sodium(1S,5R,6S)-

6-((1R)-1-hydroxyethyl)-2-(7-methane-sulfonylimidazo[5,1-b]thiazol-2-yl)-1-methyl-1-carbapen-2-em-3-carboxylate and 300 mg of 1-(4-heptyloxycarbonyloxy)ethyl iodide.

NMR (CDCl$_3$) δ: 0.90 (6H, m), 1.28 (3H, m), 1.38 (3H, m), 1.30–1.65 (8H, m), 1.60, 1.66 (total 3H, d each, J=5.3 Hz), 3.22 (3H, s), 3.34 (1H, m), 3.45 (1H, m), 4.27 (1H, m), 4.35 (1H, m), 4.75 (1H, m), 6.93 (1H, m), 8.07 (1H, s), 8.56, 8.60 (total 1H, s each) MS (TSP): 598 (M$^+$+H)

Example 204

1-(1-Pentyloxycarbonyloxy)ethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate (A Mixture of Diastereomers)

In the same manner as in Example 2, 235 mg of the title compound was obtained from 220 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 300 mg of 1-(1-pentyloxycarbonyloxy)ethyl iodide.

NMR (CDCl$_3$) δ: 0.86–0.92 (3H, m), 1.27, 1.37 (total 3H, d each, J=7.5 Hz), 1.37, 1.38 (total 3H, d each, J=6.5 Hz), 1.60, 1.65 (total 3H, d each, J=5.4 Hz), 1.60–1.80 (2H, m), 2.00 (1H, br.s), 3.22 (3H, s), 3.40–3.50 (1H, q×2), 4.10–4.38 (4H, m), 6.94 (1H, d, J=5.4 Hz), 8.80 (1H, s), 8.57 (1H, s)

Example 205

1-(4-Methyl-1-pentyloxycarbonyloxy)ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (A Mixture of Diastereomers)

In the same manner as in Example 2, the title compound was obtained from 220 mg of sodium(1S,5R,6S)-6-((1R)-1-hydroxyethyl)-2-(7-methane-sulfonylimidazo[5,1-b]thiazol-2-yl)-1-methyl-1-carbapen-2-em-3-carboxylate and 320 mg of 1-(4-methyl-1-pentyloxycarbonyloxy)ethyl iodide.

NMR (CDCl$_3$) δ: 0.86, 0.89 (total 3H, d, J=6.6 Hz), 1.29 (3H, d, J=7.3 Hz), 1.20–1.30 (2H, m), 1.38, 1.39 (total 3H, d, J=6.3 Hz), 1.60, 1.66 (total 3H, d, J=5.4 Hz), 1.50–1.70 (2H, m), 1.95 (1H, dd, J$_1$=8.5 Hz, J$_2$=4.7 Hz), 3.22 (3H, s), 3.34 (1H, dd, J$_1$=6.3 Hz, J$_2$=2.7 Hz), 3.45 (1H, dq, J$_1$=9.3 Hz, J$_2$=7.3 Hz), 4.08–4.40 (4H, m), 6.94 (1H, q, J=5.4 Hz), 8.80 (1H, s), 8.56, 8.57 (1H, s)

Example 206

5-Nonyloxycarbonyloxymethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate In the same manner as in Example 2, 218 mg of the title compound was obtained from 184 mg of sodium(1S,5R,6S)-6-((1R)-1-hydroxyethyl)-2-(7-methane-sulfonylimidazo[5,1-b]thiazol-2-yl)-1-methyl-1-carbapen-2-em-3-carboxylate and 250 mg of 5-nonyloxycarbonyloxymethyl iodide.

NMR (CDCl$_3$) δ: 0.88 (6H, m), 1.28 (3H, d, J=7.2 Hz), 1.33 (8H, m), 1.37 (3H, d, J=6.3 Hz), 1.58 (4H, m), 3.22 (3H, s), 3.35 (1H, dd, J$_1$=6.8 Hz, J$_2$=2.7 Hz), 3.47 (1H, m), 4.28 (1H, m), 4.37 (1H, dd, J$_1$=9.7 Hz, J$_2$=2.7 Hz), 4.73 (1H, m), 5.91, 5.97 (2H, ABq, J=5.8 Hz), 8.09 (1H, s), 8.54 (1H, s) MS (TSP): 612 (M$^+$+H)

Example 207

1-(5-Nonyloxycarbonyloxy)ethyl(1S,5R6S)-6-((1R)-1-hydroxyethyl)-2-(7-methanesulfonyl-imidazo[5,1-b]thiazol-2-yl)-1-methyl-1-carbapen-2-em-3-carboxylate (A Mixture of Diastereomers)

In the same manner as in Example 2, 171 mg of the title compound was obtained from 192 mg of sodium(1S,5R,6S)-6-((1R)-1-hydroxyethyl)-2-(7-methane-sulfonylimidazo[5,1-b]thiazol-2-yl)-1-methyl-1-carbapen-2-em-3-carboxylate and 600 mg of 1-(5-nonyloxycarbonyloxy)ethyl iodide.

NMR (CDCl$_3$) δ: 0.88 (6H, m), 1.26–1.38 (14H, m), 1.58–1.70 (7H, m), 3.21 (3H, s), 3.33 (1H, m), 3.45 (1H, m), 4.25 (1H, m), 4.33 (1H, m), 4.71 (1H, m), 6.93 (1H, m), 8.07 (1H, s), 8.55, 8.58 (total 1H, s each) MS (TSP): 626 (M$^+$+H)

Example 208

1-(2,2-Dimethyl-1-propyloxycarbonyloxy)ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (A Mixture of Diastereomers)

In the same manner as in Example 2, 80.9 mg of the title compound was obtained from sodium(1S,5R,6S)-6-((1R)-1-hydroxyethyl)-2-(7-methane-sulfonylimidazo[5,1-b]thiazol-2-yl)-1-methyl-1-carbapen-2-em-3-carboxylate and 240.8 mg of 1-(2,2-dimethyl-1-propyloxycarbonyloxy)ethyl iodide.

NMR (CDCl$_3$) δ: 0.94, 0.98 (total 9H, s each), 1.27, 1.29 (total 3H, d each, J=3.9 Hz), 1.35, 1.38 (total 3H, d each, J=6.3 Hz), 1.61, 1.67 (total 3H, d each, J=5.6 Hz), 3.22 (3H, s), 3.34 (1H, m), 3.45 (1H, m), 3.88 (2H, m), 4.28 (1H, q, J=6.6 Hz), 4.36 (1H, td, J$_1$=2.5 Hz, J$_2$=10.0 Hz), 6.93, 6.95 (total 1H, q each, J=5.6 Hz), 8.07, 8.07 (total 1H, s each), 8.55, 8.57 (total 1H, s each) MS (TSP): 570 (M$^+$+H)

Example 209

1-(3,3-Dimethyl-2-butyloxycarbonyloxy)ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (A Mixture of Diastereomers)

In the same manner as in Example 2, 124.1 mg of the title compound was obtained from 200.0 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 207.8 mg of 1-(3,3-dimethyl-2-butyloxycarbonyloxy)ethyl iodide.

NMR (CDCl$_3$) δ: 0.88, 0.91, 0.94, 0.96 (total 9H, s each), 1.27, 1.29 (total 3H, d each, J=7.0 Hz), 1.36, 1.38 (total 3H, d each, J=6.3 Hz), 1.60 (3H, d, J=5.4 Hz), 1.66 (3H, d, J=5.3 Hz), 3.22 (3H, s), 3.34 (1H, m), 3.45 (1H, m), 4.28 (1H, m), 4.36 (1H, m), 4.66 (1H, m), 6.94 (1H, m), 8.05, 8.05, 8.06, 8.07 (total 1H, s each), 8.55, 8.57, 8.59, 8.60 (total 1H, s each) MS (TSP): 584 (M$^+$+H)

Example 210

Cyclohexylmethoxycarbonyloxymethyl(1S5R,6S)-6-((1R)-1-hydroxyethyl)-2-(7-methanesulfonylimidazo[5,1-b]thiazol-2-yl)-1-methyl-1-carbapen-2-em-3-carboxylate In the same manner as in Example 2, 283 mg of the title compound was obtained from 218 mg of sodium(1S,5R,6S)-6-((1R)-1-hydroxyethyl)-2-(7-methane-sulfonylimidazo[5,1-b]thiazol-2-yl)-1-methyl-1-carbapen-2-em-3-carboxylate and 225 mg of cyclohexylmethoxycarbonyloxymethyl iodide.

NMR (CDCl$_3$) δ: 0.92–1.30 (6H, m), 1.26 (3H, d, J=7.2 Hz), 1.35 (3H, d, J=6.3 Hz), 1.70–1.80 (5H, m), 3.21 (3H, s), 3.33 (1H, dd, J$_1$=6.7 Hz, J$_2$=2.7 Hz), 3.47 (1H, m), 3.98

(3H, d, J=4.2 Hz), 4.27 (1H, m), 4.35 (1H, dd, $J_1$=9.8 Hz, $J_2$=2.7 Hz), 5.89, 5.94 (2H, ABq, J=5.8 Hz), 8.12 (1H, s), 8.48 (1H, s) MS (TSP): 582 (M$^+$+H)

Example 211

1-(Cyclohexylmethoxycarbonyloxy))-1-propyl(1S, 5R,6S)-6-((1R)-1-hydroxyethyl)-2-(7-methanesulfonylimidazo[5,1-b]thiazol-2-yl)-1-methyl-1-carbapen-2-em-3-carboxylate (A Mixture of Diastereomers)

In the same manner as in Example 2, 225 mg of the title compound was obtained from 414 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 2.07 g of 1-[(cyclohexylmethoxy)carbonyloxy]-1-propyl iodide.

NMR (CDCl$_3$) δ: 1.00, 1.08 (total 3H, t each, J=7.6 Hz), 1.27 (3H, d, J=7.4 Hz), 0.9–2.2 (16H, m), 3.22 (3H, s), 3.34 (1H, dd, $J_1$=6.7 Hz, $J_2$=2.8 Hz), 3.4–3.5 (1H, m), 3.8–4.05 (2H, m), 4.2–4.4 (2H, m), 6.78, 6.80 (total 1H, t each, J=5.5 Hz), 8.08, 8.09 (total 1H, s each), 8.57, 8.59 (total 1H, s each) MS (TSP): 610 (M$^+$+H)

Example 212

1-(Dicyclohexylmethoxycarbonyloxy)ethyl(1S,5R,6S)-6-((1R)-1-hydroxyethyl)-2-(7-methane-sulfonylimidazo[5,1-b]thiazol-2-yl)-1-methyl-1-carbapen-2-em-3-carboxylate (A Mixture of Diastereomers)

In the same manner as in Example 2, 69 mg of the title compound was obtained from 260 mg of sodium(1S,5R,6S)-6-((1R)-1-hydroxyethyl)-2-(7-methane-sulfonylimidazo[5,1-b]thiazol-2-yl)-1-methyl-1-carbapen-2-em-3-carboxylate and 630 mg of 1-(dicyclohexylmethoxycarbonyloxy)ethyl iodide.

NMR (CDCl$_3$) δ: 0.88–1.23 (10H, m), 1.27 (3H, d, J=7.4 Hz), 1.37 (3H, d, J=6.5 Hz), 1.57–1.74 (12H, m), 1.61, 1.66 (total 3H, d each, J=5.3 Hz), 3.21 (3H, s), 3.33 (1H, m), 3.47 (1H, m), 4.25 (1H, m), 4.34 (1H, m), 4.43 (1H, m), 6.91 (1H, m), 8.08 (total 1H, s each), 8.49, 8.56 (total 1H, s each) MS (TSP): 678 (M$^+$+H)

Example 213

Cyclohexyloxycarbonyloxymethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate In the same manner as in Example 2, 191 mg of the title compound was obtained from 188 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 259 mg of cyclohexyloxycarbonyloxymethyl iodide.

NMR (CDCl$_3$) δ: 1.28 (3H, d, J=7.1 Hz), 1.37 (3H, d, J=6.1 Hz), 1.2–2.0 (10H, m), 3.23 (3H, s), 3.35 (1H, dd, $J_1$=6.4 Hz, $J_2$=2.7 Hz), 3.4–3.5 (1H, m), 4.25–4.35 (1H, m), 4.38 (1H, dd, $J_1$=9.9 Hz, $J_2$=2.7 Hz), 4.6–4.7 (1H, m), 5.90 (1H, d, J=5.8 Hz), 5.96 (1H, d, J=5.8 Hz), 8.09 (1H, s), 8.54 (1H, s) MS (TSP): 568 (M$^+$+H)

Example 214

1-(Cyclohexyloxycarbonyloxy)-2-methyl-1-propyl (1S,5R,6S)-6-((1R)-1-hydroxyethyl)-2-(7-methanesulfonylimidazo[5,1-b]thiazol-2-yl)-1-methyl-1-carbapen-2-em-3-carboxylate (A Mixture of Diastereomers)

In the same manner as in Example 2, 151 mg of the title compound was obtained from 268 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 900 mg of 1-(cyclohexyloxycarbonyloxy)-2-methyl-1-propyl iodide.

NMR (CDCl$_3$) δ: 1.02 (6H, m), 1.29 (3H, m), 1.37 (3H, m), 1.31–2.20 (11H, m), 3.22 (3H, s), 3.34 (1H, m), 3.45 (1H, m), 4.28 (1H, m), 4.36 (1H, m), 4.64 (1H, m), 6.63, 6.68 (total 1H, d each, J=5.1 Hz), 8.07, 8.08 (total 1H, s each), 8.59, 8.60 (total 1H, s each) MS (TSP): 610 (M$^+$+H)

Example 215

Cyclohexyl(cyclohexyloxycarbonyloxy)methyl(1S, 5R,6S)-6-((1R)-1-hydroxyethyl)-2-(7-methanesulfonylimidazo[5,1-b]thiazol-2-yl)-1-methyl-1-carbapen-2-em-3-carboxylate (A Mixture of Diastereomers)

In the same manner as in Example 2, 208 mg of the title compound was obtained from 275 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 600 mg of cyclohexyl(cyclohexyloxycarbonyloxy)methyl iodide.

NMR (CDCl$_3$) δ: 1.20–2.05 (21H, m), 1.28 (3H, m), 1.38 (3H, m), 3.22 (3H, s), 3.34 (1H, m), 3.41 (1H, m), 4.29 (1H, m), 4.36 (1H, m), 4.64 (1H, m), 6.63, 6.67 (total 1H, d each, J=5.5 Hz), 8.06 (1H, s), 8.60 (1H, s) MS (TSP): 650 (M$^+$+H)

Example 216

(1R,2S,5R)-(1)-menthyloxycarbonyloxymethy(1S, 5R,6S)-6-((1R)-1-hydroxyethyl)-2-(7-methanesulfonylimidazo[5,1-b]thiazol-2-yl)-1-methyl-1-carbapen-2-em-3-carboxylate In the same manner as in Example 2, 232 mg of the title compound was obtained from 173 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 198 mg of (1R,2S,5R)-(1)-menthyloxycarbonyloxymethyl iodide.

NMR (CDCl$_3$) δ: 0.76 (3H, d, J=6.9 Hz), 0.88 (6H, m), 1.00–1.50 (4H, m), 1.27 (3H, d, J=7.1 Hz), 1.36 (3H, d, J=6.3 Hz), 1.65–2.10 (4H, m), 2.35 (1H, br.s), 3.22 (3H, s), 3.33 (1H, dd, $J_1$=6.9 Hz, $J_2$=2.7 Hz), 3.47 (1H, m), 4.27 (1H, m), 4.34 (1H, dd, $J_1$=9.8 Hz, $J_2$=2.7 Hz), 4.55 (1H, m), 5.91, 5.95 (2H, ABq, J=5.7 Hz), 8.10 (1H, s), 8.52 (1H, s) MS (TSP): 624 (M$^+$+H)

Example 217

1-((1R,2S,5R)-(1)-Menthyloxycarbonyloxy)-ethyl (1S,5R,6S)-6-((1R)-1-hydroxyethyl)-2-(7-methanesulfonylimidazo[5,1-b]thiazol-2-yl)-1-methyl-1-carbapen-2-em-3-carboxylate (A Mixture of Diastereomers)

In the same manner as in Example 2, 215 mg of the title compound was obtained from 187 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 300 mg of 1-((1R,2S,5R)-(1)-menthyloxycarbonyloxy) ethyl iodide.

NMR (CDCl$_3$) δ: 0.79 (3H, m), 0.89 (6H, m), 0.90–1.50 (4H, m), 1.27 (3H, d, J=7.1 Hz), 1.37 (3H, m), 1.60, 1.66 (total 3H, d each, J=5.5 Hz), 1.82–2.20 (4H, m), 3.22 (3H, s), 3.32 (1H, m), 3.45 (1H, m), 4.27 (1H, m), 4.35 (1H, m), 4.53 (1H, m), 6.93 (1H, m), 8.07, 8.08 (total 1H, s each), 8.55, 8.59 (total 1H, s each) MS (TSP): 638 (M$^+$+H)

Example 218

(1S,2R,5S)-(d)-menthyloxycarbonyloxymethyl(1S, 5R,6S)-6-((1R)-1-hydroxyethyl)-2-(7-methanesulfonylimidazo[5,1-b]thiazol-2-yl)-1-methyl-1-carbapen-2-em-3-carboxylate In the same manner as in Example 2, 236 mg of the title compound was obtained from 164 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 333 mg of (1S,2R,5S)-(d)-menthyloxycarbonyloxymethyl iodide.

NMR (CDCl$_3$) δ: 0.74 (3H, d, J=6.9 Hz), 0.89 (6H, m), 1.00–1.10 (2H, m), 1.28 (3H, d, J=7.4 Hz), 1.37 (3H, d, J=6.3 Hz), 1.40–2.14 (6H, m), 3.22 (3H, s), 3.34 (1H, dd, J$_1$=6.9 Hz, J$_2$=2.8 Hz), 3.47 (1H, m), 4.28 (1H, m), 4.36 (1H, dd, J$_1$=9.8 Hz, J$_2$=2.8 Hz), 4.54 (1H, m), 5.88, 5.98 (2H, ABq, J=5.8 Hz), 8.10 (1H, s), 8.54 (1H, s) MS (TSP): 624 (M$^+$+H)

Example 219

(1S,2R,5R)-isomenthyloxycarbonyloxymethyl(1S, 5R,6S)-6-((1R)-1-hydroxyethyl)-2-(7-methanesulfonylimidazo[5,1-b]thiazol-2-yl)-1-methyl-1-carbapen-2-em-3-carboxylate In the same manner as in Example 2, 214 mg of the title compound was obtained from 157 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 291 mg of (1S,2R,5R)-isomenthyloxycarbonyloxymethyl iodide.

NMR (CDCl$_3$) δ: 0.84 (3H, d, J=6.6 Hz), 0.91 (6H, m), 1.15–1.90 (9H, m), 1.26 (3H, d, J=7.4 Hz), 1.36 (3H, d, J=6.3 Hz), 3.22 (3H, s), 3.33 (1H, dd, J$_1$=6.8 Hz, J$_2$=2.8 Hz), 3.47 (1H, m), 4.27 (1H, m), 4.35 (1H, dd, J$_1$=9.8 Hz, J$_2$=2.8 Hz), 4.91 (1H, m), 5.88, 5.97 (2H, ABq, J=5.8 Hz), 8.10 (1H, s), 8.52 (1H, s) MS (TSP): 624 (M$^+$+H)

Example 220

(1S,2S,5R)-Neomenthyloxycarbonyloxymethyl(1S, 5R,6S)-6-((1R)-1-hydroxyethyl)-2-(7-methanesulfonylimidazo[5,1-b]thiazol-2-yl)-1-methyl-1-carbapen-2-em-3-carboxylate In the same manner as in Example 2, 212 mg of the title compound was obtained from 151 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 270 mg of (1S,2S,5R)-neomenthyloxycarbonyloxymethyl iodide.

NMR (CDCl$_3$) δ: 0.82 (3H, d, J=6.7 Hz), 0.87 (6H, m), 0.90–1.12 (3H, m), 1.28 (3H, d, J=7.2 Hz), 1.37 (3H, d, J=6.2 Hz), 1.42–1.80 (6H, m), 2.06 (1H, m), 3.22 (3H, s), 3.34 (1H, dd, J$_1$=6.9 Hz, J$_2$=2.8 Hz), 3.46 (1H, m), 4.28 (1H, m), 4.37 (1H, dd, J$_1$=9.7 Hz, J$_2$=2.8 Hz), 5.09 (1H, m), 5.88, 6.01 (2H, ABq, J=5.9 Hz), 8.10 (1H, s), 8.54 (1H, s) MS (TSP): 624 (M$^+$+H)

Example 221

3,3,5,5-Tetramethylcyclohexyloxycarbonyloxymethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate In the same manner as in Example 2, 202 mg of the title compound was obtained from 158 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 200 mg of 3,3,5,5-tetramethylcyclohexyloxycarbonyloxymethyl iodide.

NMR (CDCl$_3$) δ: 0.94 (6H, s), 1.04 (6H, s), 1.10–1.23 (2H, m), 1.83 (4H, m), 3.22 (3H, s), 3.34 (1H, dd, J$_1$=6.7 Hz, J$_2$=2.8 Hz), 3.47 (1H, m), 4.28 (1H, m), 4.36 (1H, dd, J$_1$=9.8 Hz, J$_2$=2.8 Hz), 4.92 (1H, m), 5.91, 5.94 (2H, ABq, J=5.9 Hz), 8.10 (1H, s), 8.53 (1H, s) MS (TSP): 624 (M$^+$+H)

Example 222

2-Adamantyloxycarbonyloxymethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate In the same manner as in Example 2, 134 mg of the title compound was obtained from 109 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 150 mg of 2-adamantyloxycarbonyloxymethyl iodide.

NMR (CDCl$_3$) δ: 1.28 (3H, d, J=7.1 Hz), 1.37 (3H, d, J=6.3 Hz), 1.52–2.12 (14H, m), 3.23 (3H, s), 3.35 (1H, dd, J$_1$=6.6 Hz, J$_2$=2.8 Hz), 3.46 (1H, m), 4.29 (1H, m), 4.37 (1H, dd, J$_1$=9.8 Hz, J$_2$=2.8 Hz), 4.83 (1H, m), 5.92, 5.97 (2H, ABq, J=5.8 Hz), 8.10 (1H, s), 8.53 (1H, s) MS (TSP): 620 (M$^+$+H)

Example 223

1-((Indan-2-yl)oxycarbonyloxy)ethyl(1S,5R,6S)-6-((1R)-1-hydroxyethyl)-2-(7-methanesulfonylimidazo [5,1-b]thiazol-2-yl)-1-methyl-1-carbapen-2-em-3-carboxylate (A Mixture of Diastereomers)

In the same manner as in Example 2, 137 mg of the title compound was obtained from 180 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 250 mg of 1-((indan-2-yl)oxycarbonyloxy)ethyl iodide.

NMR (CDCl$_3$) δ: 1.28 (3H, m), 1.38 (3H, d, J=6.3 Hz), 1.57, 1.64 (total 3H, d each, J=5.5 Hz), 3.17–3.40 (5H, m), 3.23 (3H, s), 4.29 (1H, m), 4.36 (1H, m), 5.45 (1H, m), 5.51 (1H, m), 6.95 (1H, m), 7.19 (4H, m), 8.08 (1H, s), 8.55 (1H, s) MS (TSP): 616 (M$^+$+H)

Example 224

1-(2-Methylphenoxycarbonyloxy)ethyl(1S,5R,6S)-6-((1R)-1-hydroxyethyl)-1-methyl-2-(7-methanesulfonylimidazo[5,1-b]thiazol-2-yl)-1-carbapen-2-em-3-carboxylate (A Mixture of Diastereomers)

In the same manner as in Example 2, 214.0 mg of the title compound was obtained from 200.0 mg of sodium(1S,5R, 6S)-6-((1R)-1-hydroxyethyl)-1-methyl-2-(7-methanesulfonylimidazo[5,1-b]thiazol-2-yl)-1-carbapen-2-em-3-carboxylate and 500 mg of 1-(2-methylphenoxycarbonyloxy)ethyl iodide.

NMR (CDCl$_3$) δ: 1.28, 1.30 (total 3H, d each, J=7.3 Hz), 1.38, 1.40 (total 3H, d each, J=6.3 Hz), 1.69, 1.74 (total 3H, d each, J=5.4 Hz), 1.80 (1H, m), 2.20, 2.28 (total , 3H, s each), 3.21 (3H, s), 3.33 (1H, m), 3.46 (1H, m), 4.28 (1H, m), 4.35 (1H, m), 7.01 (1H, m), 7.23 (4H, m), 8.05, 8.06 (total 1H, s each), 8.53, 8.56 (total 1H, s each) MS (TSP): 590 (M$^+$+H)

Example 225

1-(2-Ethylphenoxycarbonyloxy)ethyl(1S,5R,6S)-6-((1R)-1-hydroxyethyl)-1-methyl-2-(7-methanesulfonylimidazo[5,1-b]thiazol-2-yl)-1-carbapen-2-em-3-carboxylate (A Mixture of Diastereomers)

In the same manner as in Example 2, 149.0 mg of the title compound was obtained from 200.0 mg of sodium(1S,5R,6S)-6-((1R)-1-hydroxyethyl)-1-methyl-2-(7-methanesulfonylimidazo[5,1-b]thiazol-2-yl)-1-carbapen-2-em-3-carboxylate and 500 mg of 1-(2-ethylphenoxycarbonyloxy)ethyl iodide.

NMR (CDCl$_3$) δ: 1.14, 1.21 (total 3H, t each, J=7.3 Hz), 1.28, 1.30 (total 3H, d each, J=7.3 Hz), 1.38, 1.40 (total 3H, d each, J=6.3 Hz), 1.69, 1.74 (total 3H, d each, J=5.4 Hz), 1.90 (1H, m), 2.56, 2.65 (total 2H, q each, J=7.3 Hz), 3.21 (3H, s), 3.33 (1H, m), 3.46 (1H, m), 4.28 (1H, m), 4.39 (1H, m), 7.01 (1H, m), 7.22 (4H, m), 8.05 (1H, s), 8.52, 8.55 (total 1H, s each) MS (TSP): 604 (M$^+$+H)

Example 226

1-(3-Methylphenoxycarbonyloxy)ethyl(1S,5R,6S)-6-((1R)-1-hydroxyethyl)-1-methyl-2-(7-methanesulfonylimidazo[5,1-b]thiazol-2-yl)-1-carbapen-2-em-3-carboxylate (A Mixture of Diastereomers)

In the same manner as in Example 2, 183.0 mg of the title compound was obtained from 200.0 mg of sodium(1S,5R,6S)-6-((1R)-1-hydroxyethyl)-1-methyl-2-(7-methanesulfonylimidazo[5,1-b]thiazol-2-yl)-1-carbapen-2-em-3-carboxylate and 500 mg of 1-(3-methylphenoxycarbonyloxy)ethyl iodide.

NMR (CDCl$_3$) δ: 1.28, 1.30 (total 3H, d each, J=7.3 Hz), 1.38, 1.40 (total 3H, d each, J=6.3 Hz), 1.69, 1.74 (total 3H, d each, J=5.4 Hz), 1.95 (1H, d, J=4.6 Hz), 2.34, 2.36 (total 1H, s each), 3.21 (3H, s), 3.33 (1H, m), 3.46 (1H, m), 4.28 (1H, m), 4.35 (1H, m), 7.14 (4H, m), 7.25 (1H, m), 8.06 (1H, s), 8.53, 8.56 (total 1H, s each) MS (FAB): 590 (M$^+$+H)

Example 227

1-(4-Methylphenoxycarbonyloxy)ethyl(1S,5R,6S)-6-((1R)-1-hydroxyethyl)-1-methyl-2-(7-methanesulfonylimidazo[5,1-b]thiazol-2-yl)-1-carbapen-2-em-3-carboxylate (A Mixture of Diastereomers)

In the same manner as in Example 2, 158.0 mg of the title compound was obtained from 200.0 mg of sodium(1S,5R,6S)-6-((1R)-1-hydroxyethyl)-1-methyl-2-(7-methanesulfonylimidazo[5,1-b]thiazol-2-yl)-1-carbapen-2-em-3-carboxylate and 500 mg of 1-(4-methylphenoxycarbonyloxy)ethyl iodide.

NMR (CDCl$_3$) δ: 1.28, 1.30 (total 3H, d each, J=7.3 Hz), 1.38, 1.40 (total 3H, d each, J=6.3 Hz), 1.69, 1.74 (total 3H, d each, J=5.4 Hz), 1.79 (1H, m), 2.33, 2.34 (total 3H, s each), 3.21 (3H, s), 3.33 (1H, m), 3.46 (1H, m), 4.28 (1H, m), 4.35 (1H, m), 7.01 (1H, m), 7.04 (1H, m), 7.16 (1H, m), 7.18 (2H, s), 8.05, 8.06 (total 1H, s each), 8.54, 8.56 (total 1H, s each) MS (TSP): 590 (M$^+$+H)

Example 228

1-(2,6-Dimethylphenoxycarbonyloxy)ethyl(1S,5R,6S)-6-((1R)-1-hydroxyethyl)-1-methyl-2-(7-methanesulfonylimidazo[5,1-b]thiazol-2-yl)-1-carbapen-2-em-3-carboxylate (A Mixture of Diastereomers)

In the same manner as in Example 2, 140.0 mg of the title compound was obtained from 200.0 mg of sodium(1S,5R,6S)-6-((1R)-1-hydroxyethyl)-1-methyl-2-(7-methanesulfonylimidazo[5,1-b]thiazol-2-yl)-1-carbapen-2-em-3-carboxylate and 500 mg of 1-(2,6-dimethylphenoxycarbonyloxy)ethyl iodide.

NMR (CDCl$_3$) δ: 1.27 (3H, m), 1.38, 1.40 (total 3H, d each, J=6.3 Hz), 1.69, 1.74 (total 3H, d each, J=5.4 Hz), 2.17 (3H, s), 2.25 (3H, s), 3.21 (3H, s), 3.33 (1H, m), 3.46 (1H, m), 4.28 (1H, m), 4.35 (1H, m), 6.98 (1H, m), 7.04 (3H, m), 8.04, 8.06 (total 1H, s each), 8.46, 8.53 (total 1H, s each) MS (FAB): 604 (M$^+$+H)

Example 229

1-(2,4-Dimethylphenoxycarbonyloxy)ethyl(1S,5R,6S)-6-((1R)-1-hydroxyethyl)-1-methyl-2-(7-methanesulfonylimidazo[5,1-b]thiazol-2-yl)-1-carbapen-2-em-3-carboxylate (A Mixture of Diastereomers)

In the same manner as in Example 2, 133.0 mg of the title compound was obtained from 200.0 mg of sodium(1S,5R,6S)-6-((1R)-1-hydroxyethyl)-1-methyl-2-(7-methanesulfonylimidazo[5,1-b]thiazol-2-yl)-1-carbapen-2-em-3-carboxylate and 500 mg of 1-(2,4-dimethylphenoxycarbonyloxy)ethyl iodide.

NMR (CDCl$_3$) δ: 1.28, 1.30 (total 3H, d each, J=7.3 Hz), 1.38, 1.40 (total 3H, d each, J=6.3 Hz), 1.69, 1.74 (total 3H, d each, J=5.4 Hz), 1.76 (1H, m), 2.15, 2.24 (total 3H, s each), 2.29, 2.30 (total 3H, s each), 3.21, 3.22 (total 3H, s each), 3.33 (1H, m), 3.46 (1H, m), 4.28 (1H, m), 4.38 (1H, m), 7.04 (4H, m), 8.04, 8.05 (total 1H, s each), 8.52, 8.56 (total 1H, s each) MS (TSP): 604 (M$^+$+H)

Example 230

1-(3,5-Dimethylphenoxycarbonyloxy)ethyl(1S,5R,6s)-6-((1R)-1-hydroxyethyl)-1-methyl-2-(7-methanesulfonylimidazo[5,1-b]thiazol-2-yl)-1-carbapen-2-em-3-carboxylate (A Mixture of Diastereomers)

In the same manner as in Example 2, 199.0 mg of the title compound was obtained from 200.0 mg of sodium(1S,5R,6S)-6-((1R)-1-hydroxyethyl)-1-methyl-2-(7-methanesulfonylimidazo[5,1-b]thiazol-2-yl)-1-carbapen-2-em-3-carboxylate and 500 mg of 1-(3,5-dimethylphenoxycarbonyloxy)ethyl iodide.

NMR (CDCl$_3$) δ: 1.28, 1.30 (total 3H, d each, J=7.3 Hz), 1.39 (3H, d, J=6.3 Hz), 1.69, 1.74 (total 3H, d each, J=5.4 Hz), 1.93 (1H, d, J=4.7 Hz), 2.29 (3H, s), 2.32 (3H, s), 3.21 (3H, s), 3.33 (1H, m), 3.46 (1H, m), 4.28 (1H, m), 4.35 (1H, m), 6.78 (1H, s), 6.87 (1H, m), 6.91 (1H, s), 7.01 (1H, m), 8.06 (1H, s), 8.53, 8.57 (total 1H, s each) MS (TSP): 604 (M$^+$+H)

Example 231

1-(2,4,6-Trimethylphenoxycarbonyloxy)ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (A Mixture of Diastereomers)

In the same manner as in Example 2, 200 mg of the title compound was obtained from 191 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 500 mg of 1-(2,4,6-trimethylphenoxycarbonyloxy)ethyl iodide.

NMR (CDCl₃) δ: 1.29 (3H, m), 1.39 (3H, m), 1.69, 1.74 (total 3H, d each, J=5.5 Hz), 2.12, 2.20 (total 3H, s each), 2.26 (3H, s), 3.22 (3H, s), 3.35 (1H, m), 3.44 (1H, m), 4.30 (1H, m), 4.46 (1H, m), 6.85, 6.87 (total 2H, s each), 7.00 (1H, m), 8.05, 8.06 (total 1H, s each), 8.48, 8.56 (total 1H, s each) MS (TSP): 618 (M⁺+H)

Example 232

1-(4-t-Butylphenoxycarbonyloxy)ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (A Mixture of Diastereomers)

In the same manner as in Example 2, 303 mg of the title compound was obtained from 316 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 1.22 g of 1-(4-t-butylphenoxycarbonyloxy)ethyl iodide.

NMR (CDCl₃) δ: 1.27 (3H, d, J=6.1 Hz), 1.29, 1.31 (total 9H, s each), 1.67, 1.73 (total 3H, d each, J=6.1 Hz), 3.21 (3H, s), 3.37 (1H, m), 3.46 (1H, m), 4.31 (1H, m), 4.38 (1H, m), 7.02 (1H, m), 7.09 (1H, d, J=9.8 Hz), 7.22 (1H, d, J=8.8 Hz), 7.37 (1H, d, J=9.7 Hz), 7.40 (1H, d, J=8.8 Hz), 8.05, 8.06 (total 1H, s each), 8.54, 8.56 (total 1H, s each) MS (TSP): 632 (M⁺+H)

Example 233

(Indan-5-yl)oxycarbonyloxymethyl(1S,5R,6S)-6-((1R)-1-hydroxyethyl)-1-methyl-2-(7-methanesulfonylimidazo[5,1-b]thiazol-2-yl)-1-carbapen-2-em-3-carboxylate In the same manner as in Example 2, 213.0 mg of the title compound was obtained from 200.0 mg of sodium(1S,5R,6S)-6-((1R)-1-hydroxyethyl)-1-methyl-2-(7-methanesulfonylimidazo[5,1-b]thiazol-2-yl)-1-carbapen-2-em-3-carboxylate and 500 mg of (indan-5-yl) oxycarbonyloxymethyl iodide.

NMR (CDCl₃) δ: 1.29 (3H, d, J=7.3 Hz), 1.38 (3H, d, J=6.3 Hz), 1.84 (1H, br.d), 2.10 (2H, m), 2.89 (4H, m), 3.21 (3H, s), 3.37 (1H, dd, $J_1$=6.6 Hz, $J_2$=2.8 Hz), 3.44 (1H, m), 4.30 (1H, m), 4.40 (1H, dd, $J_1$=9.6 Hz, $J_2$=2.8 Hz), 6.03 (2H, ABq, J=5.9 Hz), 6.94 (1H, d, J=7.9 Hz), 7.05 (1H, s), 7.19 (1H, d, J=7.9 Hz), 8.06 (1H, s), 8.53 (1H, s) MS (TSP): 602 (M⁺+H)

Example 234

1-((Indan-5-yl)oxycarbonyloxy)ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (A Mixture of Diastereomers)

In the same manner as in Example 2, 115 mg of the title compound was obtained from 198 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 600 mg of 1-((indan-5-yl)oxycarbonyloxy)ethyl iodide.

NMR (CDCl₃) δ: 1.27 (3H, m), 1.38 (3H, m), 1.67, 1.73 (total 3H, d each, J=5.5 Hz), 2.09 (2H, m), 2.88 (4H, m), 3.21 (3H, s), 3.36 (1H, m), 3.45 (1H, m), 4.34 (2H, m), 6.88–7.20 (4H, m), 8.06 (1H, s), 8.51, 8.54 (total 1H, s each) MS (TSP): 616 (M⁺+H)

Example 235

1-((Indan-5-yl)oxycarbonyloxy)-1-propyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate (A Mixture of Diastereomers)

In the same manner as in Example 2, 214 mg of the title compound was obtained from 118 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 700 mg of 1-((indan-5-yl)oxycarbonyloxy)-1-propyl iodide.

NMR (CDCl₃) δ: 1.05, 1.13 (total 3H, t each, J=7.4 Hz), 1.27 (3H, m), 1.39 (3H, m), 1.98–2.10 (5H, m), 2.87 (4H, m), 3.21 (3H, s), 3.35 (1H, m), 3.36 (1H, m), 4.31 (1H, m), 4.38 (1H, m), 6.87 (1H, m), 7.01–7.21 (3H, m), 8.06, 8.07 (total 1H, s each), 8.52, 8.55 (total 1H, s each) MS (TSP): 647 (M⁺+H)

Example 236

Ethyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate The title compound (249 mg) was obtained from 304 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 270 mg of ethyl iodide in the same manner as in Example 2, except that the reaction temperature was room temperature and the reaction time was 6 hr.

NMR (CDCl₃) δ: 1.25 (3H, d, J=7.1 Hz), 1.37 (6H, m), 2.65 (1H, s), 3.20 (3H, s), 3.33 (1H, dd, $J_1$=6.9 Hz, $J_2$=2.8 Hz), 3.46 (1H, m), 4.32 (4H, m), 8.09 (1H, s), 8.41 (1H, s) MS (TSP): 440 (M⁺+H)

Example 237

2-Propyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate The title compound (223 mg) was obtained from 299 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 684 mg of 2-propyl iodide in the same manner as in Example 2, except that the reaction temperature was room temperature and the reaction time was 18 hr.

NMR (CDCl3) δ: 1.27 (3H, d, J=7.2 Hz), 1.32 (3H, d, J=6.3 Hz), 1.37 (6H, m), 3.21 (3H, s), 3.34 (1H, dd, $J_1$=6.8 Hz, $J_2$=2.8 Hz), 3.45 (1H, m), 4.28 (1H, m), 5.29 (2H, s), 4.35 (1H, dd, $J_1$=9.6 Hz, $J_2$=2.8 Hz), 5.16 (1H, m), 8.08 (1H, s), 8.44 (1H, s) MS (TSP): 454 (M⁺+H)

Example 238

1-Decyl(1S,5R,6S)-6-((1R)-1-hydroxyethyl)-2-(7-methanesulfonylimidazo[5,1-b]thiazol-2-yl)-1-methyl-1-carbapen-2-em-3-carboxylate The title compound (177 mg) was obtained from 174 mg of sodium(1S,5R,6S)-6-((1R)-1-hydroxyethyl)-2-(7-methanesulfonylimidazo[5,1-b]thiazol-2-yl)-1-methyl-1-carbapen-2-em-3-carboxylate and 0.43 ml of 1-iododecane in substantially the same manner as in Example 46-c), except that the reaction was initiated under ice cooling and the system was stirred for 18 hr while gradually raising the temperature to room temperature.

NMR (CDCl₃) δ: 0.88 (3H, br.t, J=6.7 Hz), 1.20–1.33 (17H, m), 1.39 (3H, d, J=6.3 Hz), 1.69–1.81 (2H, m), 3.22 (3H, s), 3.35 (1H, dd, $J_1$=6.7 Hz, $J_2$=2.9 Hz), 3.39–3.49 (1H, m), 4.17–4.38 (4H, m), 8.06 (1H, s), 8.49 (1H, s) MS (ESI): 552 (M⁺+H)

Example 239

(Z)-2-(3-Phthalidylidene)ethyl(1S,5R,6S)-6-((1R)-1-hydroxyethyl)-2-(7-methanesulfonyl-imidazo[5,1-b]thiazol-2-yl)-1-methyl-1-carbapen-2-em-3-carboxylate In the same manner as in Example 2, 144 mg of the title compound was obtained from 172 mg of sodium(1S,5R,6S)-

6-((1R)-1-hydroxyethyl)-2-(7-methanesulfonylimidazo[5,1-b]thiazol-2-yl)-1-methyl-1-carbapen-2-em-3-carboxylate and 146 mg of (Z)-2-(3-phthalidylidene)ethyl bromide.

NMR (CDCl$_3$) δ: 1.29 (3H, d, J=7.2 Hz), 1.38 (3H, d, J=6.3 Hz), 3.22 (3H, s), 3.6 (1H, dd, J$_1$=6.6 Hz, J$_2$=2.8 Hz), 3.47 (1H, m), 4.31 (1H, m), 4.39 (1H, dd, J$_1$=9.6 Hz, J$_2$=2.8 Hz), 5.22 (2H, m), 5.83 (1H, t, J=7.0 Hz), 7.60 (1H, m), 7.73 (2H, m), 7.92 (1H, m), 8.11 (1H, s), 8.50 (1H, s) MS (TSP): 570 (M$^+$+H)

Example 240

Acetoxymethyl(1S,5R,6S)-6-((1R)-1-hydroxyethyl)-1-methyl-2-(7-methylthioimidazo-[5,1-b]thiazol-2-yl)-1-carbapen-2-em-3-carboxylate In the same manner as in Example 2, 29 mg of the title compound was obtained from 110 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 0.054 ml of acetoxymethyl bromide.

NMR (CDCl$_3$) δ: 1.29 (3H, d, J=7.4 Hz), 1.38 (3H, d, J=6.3 Hz), 1.91 (1H, br.s), 2.13 (3H, s), 2.45 (3H, s), 3.35 (1H, dd, J$_1$=6.6 Hz, J$_2$=2.6 Hz), 3.45 (1H, m), 4.30 (1H, m), 4.35 (1H, dd, J$_1$=9.7 Hz, J$_2$=2.6 Hz), 5.88, 5.96 (2H, ABq, J=5.7 Hz), 8.04 (1H, s), 8.34 (1H, s) MS (TSP): 452 (M$^+$+H)

Example 241

1-(Acetoxy)ethyl(1S,5R,6S)-6-((1R)-1-hydroxyethyl)-1-methyl-2-(7-methylthioimidazo-[5,1-b]thiazol-2-yl)-1-carbapen-2-em-3-carboxylate (A Mixture of Diastereomers)

In the same manner as in Example 2, 18 mg of the title compound was obtained from 30 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 48 mg of 1-(acetoxy)ethyl iodide.

NMR (CDCl$_3$) δ: 1.29 (3H, d, J=7.4 Hz), 1.38 (3H, m), 1.56, 1.61 (total 3H, d each, J=5.5 Hz), 1.85 (1H, m), 2.07, 2.14 (total 3H, s each), 2.44 (3H, s), 3.33 (1H, m), 3.42 (1H, m), 4.30 (1H, m), 4.34 (1H, m), 7.05 (1H, m), 8.02, 8.03 (total 1H, s each), 8.38 (1H, s) MS (TSP): 466 (M$^+$+H)

Example 242

1-(Isobutyryloxy)ethyl(1S,5R,6S)-6-((1R)-1-hydroxyethyl)-1-methyl-2-(7-methylthioimidazo-[5 1-b]thiazol-2-yl)-1-carbapen-2-em-3-carboxylate (A Mixture of Diastereomers)

In the same manner as in Example 2, 131 mg of the title compound was obtained from 200 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 523 mg of 1-(isobutyryloxy)ethyl iodide.

NMR (CDCl$_3$) δ: 1.15 (3H, m), 1.21 (3H, m), 1.30 (3H, m), 1.38 (3H, m), 1.56, 1.61 (total 3H, d each, J=5.5 Hz), 1.89 (1H, m), 2.44 (3H, s), 2.57 (1H, m), 3.33 (1H, m), 3.43 (1H, m), 4.28 (1H, m), 4.34 (1H, m), 7.06 (1H, m), 8.02 (1H, s), 8.36, 8.39 (total 1H, s each) MS (TSP): 494 (M$^+$+H)

Example 243

Pivaloyloxymethyl(1S,5R,6S)-6-((1R)-1-hydroxyethyl)-1-methyl-2-(7-methylthioimidazo[5,1-b]thiazol-2-yl)-1-carbapen-2-em-3-carboxylate In the same manner as in Example 2, 27 mg of the title compound was obtained from 28 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 0.019 ml of pivaloyloxymethyl iodide.

NMR (CDCl$_3$) δ: 1.19 (9H, s), 1.27 (3H, d, J=7.4 Hz), 1.35 (3H, d, J=6.3 Hz), 2.02 (1H, br.s), 2.42 (3H, s), 3.32 (1H, dd, J$_1$=6.5 Hz, J$_2$=2.8 Hz), 3.44 (1H, m), 4.29 (1H, m), 4.36 (1H, dd, J$_1$=9.6 Hz, J$_2$=2.8 Hz), 5.86, 5.97 (2H, ABq, J=5.5 Hz), 8.04 (1H, s), 8.28 (1H, s) MS (TSP): 494 (M$^+$+H)

Example 244

1-(Pivaloyloxy)ethyl(1S,5R,6S)-6-((1R)-1-hydroxyethyl)-1-methyl-2-(7-methylthioimidazo-[5,1-b]thiazol-2-yl)-1-carbapen-2-em-3-carboxylate (A Mixture of Diastereomers)

In the same manner as in Example 2, 139 mg of the title compound was obtained from 193 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 300 mg of 1-(pivaloyloxy)ethyl iodide.

NMR (CDCl$_3$) δ: 1.17, 1.24 (total 9H, s each), 1.30 (3H, m), 1.38 (3H, m), 1.55, 1.60 (total 3H, d each, J=5.5 Hz), 2.10 (1H, br.s), 2.43 (3H, s), 3.33 (1H, m), 3.43 (1H, m), 4.29 (1H, m), 4.34 (1H, dd, J$_1$=9.6 Hz, J$_2$=2.8 Hz), 7.02 (1H, m), 8.02 (1H, s), 8.34, 8.38 (total 1H, s each) MS (TSP): 508 (M$^+$+H)

Example 245

2-Ethylbutyryloxymethyl(1S,5R,6S)-6-((1R)-1-hydroxyethyl)-1-methyl-2-(7-methylthioimidazo-[5,1-b]thiazol-2-yl)-1-carbapen-2-em-3-carboxylate In the same manner as in Example 2, 217 mg of the title compound was obtained from 253 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 242 mg of 2-ethylbutyryloxymethyl iodide.

NMR (CDCl$_3$) δ: 0.85 (6H, m), 1.28 (3H, d, J=7.4 Hz), 1.37 (3H, d, J=6.3 Hz), 1.68 (4H, m), 2.27 (1H, m), 2.43 (3H, s), 3.33 (1H, dd, J$_1$=6.5 Hz, J$_2$=2.7 Hz), 3.44 (1H, m), 4.29 (1H, m), 4.35 (1H, dd, J$_1$=9.6 Hz, J$_2$=2.7 Hz), 5.94 (2H, s), 8.05 (1H, s), 8.30 (1H, s) MS (TSP): 508 (M$^+$+H)

Example 246

1-(2-Ethylbutyryloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 154 mg of the title compound was obtained from 224 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 500 mg of 1-(2-ethylbutyryloxy)ethyl iodide.

NMR (CDCl$_3$) δ: 0.90 (6H, m), 1.27 (3H, m), 1.38 (3H, m), 1.56, 1.61 (total 3H, d each, J=5.5 Hz), 1.60 (4H, m), 2.05 (1H, br.s), 2.22 (1H, m), 2.43 (3H, s), 3.33 (1H, m), 3.42 (1H, m), 4.29 (1H, m), 4.33 (1H, m), 7.07 (1H, m), 8.02 (1H, s), 8.31, 8.40 (total 1H, s each) MS (TSP): 522 (M$^+$+H)

Example 247

Cyclohexylcarbonyloxymethyl(1S,5R,6S)-6-((1R)-1-hydroxyethyl)-1-methyl-2-(7-methylthioimidazo[5,1-b]thiazol-2-yl)-1-carbapen-2-em-3-carboxylate In the same manner as in Example 2, 284 mg of the title compound was obtained from 255 mg of sodium(1S,5R,6S)-

6-((1R)-1-hydroxyethyl)-1-methyl-2-(7-methylthioimidazo[5,1-b]thiazol-2-yl)-1-carbapen-2-em-3-carboxylate and 267 mg of cyclohexylcarbonyloxymethyl iodide.

NMR (CDCl$_3$) δ: 1.20–1.52 (4H, m), 1.29 (3H, d, J=7.2 Hz), 1.37 (3H, d, J=6.3 Hz), 1.60–1.95 (6H, m), 2.38 (1H, m), 2.44 (3H, s), 3.33 (1H, dd, J$_1$=6.6 Hz, J$_2$=2.8 Hz), 3.44 (1H, m), 4.29 (1H, m), 4.36 (1H, dd, J$_1$=9.8 Hz, J$_2$=2.8 Hz), 5.88, 5.96 (2H, ABq, J=5.6 Hz), 8.04 (1H, s), 8.30 (1H, s) MS (TSP): 520 (M$^+$+H)

Example 248

1-(Cyclohexylcarbonyloxy)ethyl(1S,5R,6S)-6-((1R)-1-hydroxyethyl)-1-methyl-2-(7-methylthio-imidazo[5,1-b]thiazol-2-yl)-1-carbapen-2-em-3-carboxylate (A Mixture of Diastereomers)

In the same manner as in Example 2, 232 mg of the title compound was obtained from 207 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 400 mg of 1-(cyclohexylcarbonyloxy)ethyl iodide.

NMR (CDCl$_3$) δ: 1.20–2.00 (10H, m), 1.28 (3H, m), 1.38 (3H, m), 1.55, 1.59 (total 3H, d each, J=5.5 Hz), 2.10–2.40 (1H, m), 2.43 (3H, s), 3.33 (1H, m), 3.42 (1H, m), 4.29 (1H, m), 4.34 (1H, m), 7.03 (1H, m), 8.02 (1H, s), 8.34, 8.37 (total 1H, s each) MS (TSP): 534 (M$^+$+H)

Example 249

Dicyclohexylacetoxymethyl(1S,5R,6S)-6-((1R)-1-hydroxyethyl)-1-methyl-2-(7-methylthio-imidazo[5,1-b]thiazol-2-yl)-1-carbapen-2-em-3-carboxylate In the same manner as in Example 2, 177 mg of the title compound was obtained from 161 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 219 mg of dicyclohexylacetoxymethyl iodide.

NMR (CDCl$_3$) δ: 0.80–1.21 (10H, m), 1.29 (3H, d, J=7.3 Hz), 1.35 (3H, d, J=6.3 Hz), 1.60 (12H, m), 2.10 (1H, t, J=7.4 Hz), 2.43 (3H, s), 3.34 (1H, dd, J$_1$=6.8 Hz, J$_2$=2.7 Hz), 3.45 (1H, m), 4.28 (1H, m), 4.36 (1H, dd, J$_1$=9.7 Hz, J$_2$=2.8 Hz), 5.89 (1H, d, J=5.6 Hz), 5.95 (1H, d, J=5.6 Hz), 8.07 (1H, s), 8.30 (1H, s) MS (FAB): 616 (M$^+$+H)

Example 250

1-Adamantylcarbonyloxymethyl(1S,5R,6S)-6-((1R)-1-hydroxyethyl)-1-methyl-2-(7-methylthio-imidazo[5,1-b]thiazol-2-yl)-1-carbapen-2-em-3-carboxylate In the same manner as in Example 2, 183 mg of the title compound was obtained from 201 mg of sodium(1S,5R,6S)-6-((1R)-1-hydroxyethyl)-1-methyl-2-(7-5 methylthioimidazo[5,1-b]thiazol-2-yl)-1-carbapen-2-em-3-carboxylate and 264 mg of 1-adamantylcarbonyloxymethyl iodide.

NMR (CDCl$_3$) δ: 1.29 (3H, d, J=7.3 Hz), 1.37 (3H, d, J=6.1 Hz), 1.69 (6H, m), 1.86 (6H, m), 1.99 (3H, m), 2.43(3H, s), 3.35 (1H, dd, J$_1$=6.6 Hz, J$_2$=2.5 Hz), 3.45 (1H, dq, J$_1$=9.6 Hz, J$_2$=7.3 Hz), 4.31 (1H, dq, J=6.3 Hz), 4.35 (1H, dd, J$_1$=9.7 Hz, J$_2$=2.8 Hz), 5.88 (1H, d, J=5.6 Hz), 5.95 (1H, d, J=5.6 Hz), 8.06 (1H, s), 8.27 (1H, s) MS (FAB): 572 (M$^+$+H)

Example 251

1-(1-Adamantylcarbonyloxy)ethyl(1S,5R,6S)-6-((1R)-1-hydroxyethyl)-1-methyl-2-(7-methylthio-imidazo[5,1-b]thiazol-2-yl)-1-carbapen-2-em-3-carboxylate (A Mixture of Diastereomers)

In the same manner as in Example 2, 72 mg of the title compound was obtained from 202 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 500 mg of 1-(1-adamantylcarbonyloxy)ethyl iodide.

NMR (CDCl$_3$) δ: 1.28 (3H, m), 1.38 (3H, m), 1.55, 1.59 (total 3H, d each, J=5.5 Hz), 1.65–2.05 (15H, m), 2.43 (3H, s), 3.33 (1H, m), 3.42 (1H, m), 4.30 (1H, m), 4.34 (1H, m), 7.02 (1H, m), 8.03 (1H, s), 8.31, 8.36 (total 1H, s each) MS (TSP): 586 (M$^+$+H)

Example 252

3-Phthalidyl(1S,5R,6S)-6-((1R)-1-hydroxyethyl)-1-methyl-2-(7-methylthioimidazo-[5,1-b]thiazol-2-yl)-1-carbapen-2-em-3-carboxylate (A Mixture of Diastereomers)

In the same manner as in Example 2, 173 mg of the title compound was obtained from 219 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 230 mg of 3-phthalidyl bromide.

NMR (CDCl$_3$) δ: 1.30 (6H, m), 2.41, 2.43 (total3H, s each), 3.34 (1H, m), 3.48 (1H, m), 4.25 (1H, m), 4.34 (1H, m), 7.45, 7.47 (total 1H, s each), 7.63–7.92 (4H, m), 7.99, 8.03 (total 1H, s each), 8.17, 8.42 (total 1H, s each) MS (TSP): 512 (M$^+$+H)

Example 253

Benzoyloxymethyl(1S,5R,6S)-6-((1R)-1-hydroxyethyl)-1-methyl-2-(7-methylthioimidazo-[5,1-b]thiazol-2-yl)-1-carbapen-2-em-3-carboxylate In the same manner as in Example 2, 192 mg of the title compound was obtained from 201 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 262 mg of benzoyloxymethyl iodide.

NMR (CDCl$_3$) δ: 1.28 (3H, d, J=7.3 Hz), 1.36 (3H, d, J=6.4 Hz), 2.42 (3H, s), 3.33 (1H, dd, J$_1$=6.6 Hz, J$_2$=2.9 Hz), 3.44 (1H, dq, J$_1$=9.5 Hz, J$_2$=7.3 Hz), 4.29 (1H, dq, J=6.3 Hz), 4.36 (1H, dd, J$_1$=9.7 Hz, J$_2$=2.8 Hz), 6.17 (2H, s), 7.44 (2H, t, J=7.8 Hz), 7.58 (1H, m), 8.02 (1H, s), 8.06 (2H, m), 8.30 (1H, s) MS (FAB): 514 (M$^+$+H)

Example 254

1-(Benzoyloxy)ethyl(1S,5R,6S)-6-((1R)-1-hydroxyethyl)-1-methyl-2-(7-methylthioimidazo-[5,1-b]thiazol-2-yl)-1-carbapen-2-em-3-carboxylate (A Mixture of Diastereomers)

In the same manner as in Example 2, 137 mg of the title compound was obtained from 180 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 300 mg of 1-(benzoyloxy)ethyl iodide.

NMR (CDCl$_3$) δ: 1.28 (3H, m), 1.34, 1.38 (total3H, d each, J=6.2 Hz), 1.90 (1H, br.s), 2.42, (3H, s), 3.32 (1H, m), 3.42 (1H, m), 4.29 (1H, m), 4.36 (1H, m), 7.30 (1H, m), 7.45 (2H, m), 7.59 (1H, m), 7.95, 7.96 (total 1H, s each), 8.07 (1H, m), 8.33, 8.38 (total 1H, s each) MS (TSP): 528 (M$^+$+H)

Example 255

2-Methylbenzoyloxymethyl(1S,5R,6S)-6-((1R)-1-hydroxyethyl)-1-methyl-2-(7-methylthioimidazo-[5,1-b]thiazol-2-yl)-1-carbapen-2-em-3-carboxylate In the same manner as in Example 2, 109 mg of the title compound was obtained from 159 mg of sodium(1S,5R,6S)-

6-((1R)-1-hydroxyethyl)-1-methyl-2-(7-methylthioimidazo[5,1-b]thiazol-2-yl)-1-carbapen-2-em-3-carboxylate and 200 mg of 2-methylbenzoyloxymethyl iodide.

NMR (CDCl$_3$) δ: 1.28 (3H, d, J=7.1 Hz), 1.36 (3H, d, J=6.2 Hz), 2.42 (3H, s), 2.52 (1H, br.s), 2.59 (3H, s), 3.23 (1H, dd, J$_1$=6.5 Hz, J$_2$=2.6 Hz), 3.44 (1H, m), 4.29 (1H, m), 4.35 (1H, dd, J$_1$=9.6 Hz, J$_2$=2.6 Hz), 6.13, 6.16 (2H, ABq, J=5.6 Hz), 7.25 (2H, m), 7.42 (1H, m), 7.96 (1H, m), 8.01 (1H, s), 8.31 (1H, s) MS (TSP): 528 (M$^+$+H)

Example 256

1-(2-Methylbenzoyloxy)ethyl(1S,5R,6S)-6-((1R)-1-hydroxyethyl)-1-methyl-2-(7-methylthio-imidazo[5,1-b]thiazol-2-yl)-1-carbapen-2-em-3-carboxylate (A Mixture of Diastereomers)

In the same manner as in Example 2, 120 mg of the title compound was obtained from 159 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 250 mg of 1-(2-methylbenzoyloxy)ethyl iodide.

NMR (CDCl$_3$) δ: 1.28 (3H, m), 1.34, 1.38 (total 3H, d each, J=6.3 Hz), 1.69, 1.74 (total 3H, d each, J=5.5 Hz), 2.42 (3H, s), 2.59, 2.62 (total 3H, s each), 3.33 (1H, m), 3.42 (1H, m), 3.89 (1H, s), 4.28 (1H, m), 4.35 (1H, m), 7.26 (2H, m), 7.40 (1H, m), 7.95 (2H, m), 7.96 (1H, s), 8.34, 8.37 (total 1H, s each) MS (TSP): 542 (M$^+$+H)

Example 257

4-Methylbenzoyloxymethyl(1S,5R,6S)-6-((1R)-1-hydroxyethyl)-1-methyl-2-(7-methylthioimidazo-[5,1-b]thiazol-2-yl)-1-carbapen-2-em-3-carboxylate In the same manner as in Example 2, 105 mg of the title compound was obtained from 127 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 184 mg of 4-methylbenzoyloxymethyl iodide.

NMR (CDCl$_3$) δ: 1.27 (3H, d, J=7.2 Hz), 1.35 (3H, d, J=6.3 Hz), 2.40 (3H, s), 2.42 (3H, s), 2.62 (1H, br.s), 3.32 (1H, dd, J$_1$=6.6 Hz, J$_2$=2.8 Hz), 3.43 (1H, m), 4.28 (1H, m), 4.35 (1H, dd, J$_1$=9.7 Hz, J$_2$=2.8 Hz), 6.15 (2H, s), 7.23 (2H, d, J=8.2 Hz), 7.94 (2H, d, J=8.2 Hz), 7.96 (1H, m), 8.01 (1H, s), 8.30 (1H, s) MS (TSP): 528 (M$^+$+H)

Example 258

4-(2-Propyl)benzoyloxymethyl(1S,5R,6S)-6-((1R)-1-hydroxyethyl)-1-methyl-2-(7-methylthio-imidazo[51,-b]thiazol-2-yl)-1-carbapen-2-em-3-carboxylate In the same manner as in Example 2, 130 mg of the title compound was obtained from 128 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 180 mg of 4-(2-propyl)benzoyloxymethyl iodide.

NMR (CDCl$_3$) δ: 1.24 (3H, s), 1.26 (3H, s), 1.28 (3H, d, J=7.3 Hz), 1.36 (3H, d, J=6.1 Hz), 2.42 (3H, s), 2.95 (1H, m), 3.33 (1H, dd, J$_1$=6.5 Hz, J$_2$=2.3 Hz), 3.43 (1H, m), 4.29 (1H, m), 4.35 (1H, dd, J$_1$=9.8 Hz, J$_2$=2.3 Hz), 6.15 (2H, s), 7.29 (2H, d, J=8.2 Hz), 7.99 (2H, d, J=8.2 Hz), 8.03 (1H, s), 8.31 (1H, s) MS (TSP): 556 (M$^+$+H)

Example 259

2,4-Dimethylbenzoyloxymethyl(1S,5R,6S)-6-((1R)-1-hydroxyethyl)-1-methyl-2-(7-methylthio-imidazo[5,1-b]thiazol-2-yl)-1-carbapen-2-em-3-carboxylate In the same manner as in Example 2, 85 mg of the title compound was obtained from 120 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 150 mg of 2,4-dimethylbenzoyloxymethyl iodide.

NMR (CDCl$_3$) δ: 1.28 (3H, d, J=7.2 Hz), 1.37 (3H, d, J=6.3 Hz), 2.00 (1H, br.s), 2.35 (3H, s), 2.43 (3H, s), 2.57 (3H, s), 3.32 (1H, dd, J$_1$=6.6 Hz, J$_2$=2.7 Hz), 3.44 (1H, m), 4.29 (1H, m), 4.35 (1H, dd, J$_1$=9.6 Hz, J$_2$=2.7 Hz), 6.12, 6.15 (2H, ABq, J=5.7 Hz), 7.05 (2H, m), 7.89 (2H, d, J=7.9 Hz), 8.00 (1H, s), 8.32 (1H, s) MS (TSP): 542 (M$^+$+H)

Example 260

2,4,6-Trimethylbenzoyloxymethyl(1S,5R,6S)-6-((1R)-1-hydroxyethyl)-1-methyl-2-(7-methylthio-imidazo[5,1-b]thiazol-2-yl)-1-carbapen-2-em-3-carboxylate In the same manner as in Example 2, 140 mg of the title compound was obtained from 129 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 198 mg of 2,4,6-trimethylbenzoyloxymethyl iodide.

NMR (CDCl$_3$) δ: 1.27 (3H, d, J=7.1 Hz), 1.37 (3H, d, J=6.3 Hz), 2.26 (3H, s), 2.27 (6H, s), 2.43 (3H, s), 3.33 (1H, dd, J$_1$=6.6 Hz, J$_2$=2.7 Hz), 3.44 (1H, m), 4.29 (1H, m), 4.35 (1H, dd, J$_1$=9.6 Hz, J$_2$=2.7 Hz), 6.10, 6.14 (2H, ABq, J=5.6 Hz), 6.82 (2H, s), 8.03 (1H, s), 8.32 (1H, s) MS (TSP): 542 (M$^+$+H)

Example 261

1-(Benzyloxyacetoxy)ethyl(1S,5R,6S)-6-((1R)-1-hydroxyethyl)-1-methyl-2-(,7-methylthio-imidazo[5,1-b]thiazol-2-yl)-1-carbapen-2-em-3-carboxylate (A Mixture of Diastereomers)

In the same manner as in Example 2, 122 mg of the title compound was obtained from 201 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 400mg of 1-(benzyloxyacetoxy)ethyl iodide.

NMR (CDCl$_3$) δ: 1.27 (3H, d, J=7.3 Hz), 1.36, 1.37 (total 3H, d each, J=6.1 Hz), 1.58, 1.63 (total 3H, d each, J=5.3 Hz), 2.42 (3H, s), 3.33 (1H, m), 3.42 (1H, m), 4.10 (1H, m), 4.21 (1H, m), 4.27 (1H, m), 4.34 (1H, m), 4.60 (1H, s), 4.65 (1H, d, J=11.9 Hz), 4.70 (1H, d, J=11.7 Hz), 7.13 (1H, m), 7.33 (5H, m), 8.04 (1H, s), 8.32, 8.34 (total 1H, s each) MS (TSP): 572 (M$^+$+H)

Example 262

1-(Ethoxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 24 mg of the title compound was obtained from 26 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 31 mg of 1-(ethoxycarbonyloxy)ethyl iodide.

NMR (CDCl$_3$) δ: 1.29–1.40 (9H, m), 1.59, 1.65 (total 3H, d each, J=5.5 Hz), 2.42 (3H, s), 3.32 (1H, m), 3.43 (1H, m), 4.18–4.28 (4H, m), 6.93 (1H, m), 8.03 (1H, s), 8.37, 8.38 (total 1H, s each) MS (TSP): 496 (M$^+$+H)

Example 263

2-Propyloxycarbonyloxymethyl(1S,5R,6S)-6-((1R)-1-hydroxyethyl)-1-methyl-2-(7-methylthio-imidazo[5,1-b]thiazol-2-yl)-1-carbapen-2-em-3-carboxylate In the same manner as in Example 2, 205 mg of the title compound was obtained from 271 mg of sodium(1S,5R,6S)-

6-((1R)-1-hydroxyethyl)-1-methyl-2-(7-methylthioimidazo[5,1-b]thiazol-2-yl)-1-carbapen-2-em-3-carboxylate and 300 mg of 2-propyloxycarbonyloxymethyl iodide.

NMR (CDCl$_3$) δ: 1.29 (9H, m), 1.36 (3H, d, J=6.3 Hz), 2.43 (3H, s), 2.62 (1H, br.s), 3.33 (1H, dd, J$_1$=6.6 Hz, J$_2$=2.9 Hz), 3.44 (1H, m), 4.30 (1H, m), 4.36 (1H, dd, J$_1$=9.6 Hz, J$_2$=2.8 Hz), 5.88, 5.95 (2H, ABq, J=5.9 Hz), 8.04 (1H, s), 8.36 (1H, s) MS (TSP): 496 (M$^+$+H)

Example 264

1-(2-Propyloxycarbonyloxy)ethyl(1S,5R,6S)-6-((1R)-1-hydroxyethyl)-1-methyl-2-(7-methylthio-imidazo[5,1-b]thiazol-2-yl)-1-carbapen-2-em-3-carboxylate (A Mixture of Diastereomers)

In the same manner as in Example 2, 249 mg of the title compound was obtained from 295 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 383 mg of 1-(2-propyloxycarbonyloxy)ethyl iodide.

NMR (CDCl$_3$) δ: 1.28 (6H, m), 1.37 (6H, m), 1.58, 1.64 (total 3H, d each, J=5.3 Hz), 2.43 (3H, s), 3.32 (1H, m), 3.40 (1H, m), 4.30 (1H, m), 4.34 (1H, m), 4.91 (1H, m), 6.93 (1H, m), 8.02 (1H, s), 8.38 (1H, s) MS (TSP): 510 (M$^+$+H)

Example 265

1-(2-Propyloxycarbonyloxy)-1-propyl(1S,5R,6S)-6-((1R)-1-hydroxyethyl)-1-methyl-2-(7-methylthioimidazo[5,1-b]thiazol-2-carbapen-2-em-3-carboxylate (A Mixture of Diastereomers)

In the same manner as in Example 2, 220 mg of the title compound was obtained from 305 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 414 mg of 1-(2-propyloxycarbonyloxy)-1-propyl iodide.

NMR (CDCl$_3$) δ: 1.00, 1.07 (total 3H, d each, J=7.4 Hz), 1.29 (3H, m), 1.36 (3H, m), 1.94 (2H, m), 2.10 (1H, m), 2.43 (3H, s), 3.31 (1H, m), 3.43 (1H, m), 4.28 (1H, m), 4.34 (1H, m), 4.93 (1H, m), 6.80 (1H, m), 8.02 (1H, s), 8.40 (1H, s) MS (TSP): 524 (M$^+$+H)

Example 266

2-Methyl-1-(2-propyloxycarbonyloxy)-1-propyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 169 mg of the title compound was obtained from 170 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 900 mg of 2-methyl-1-(2-propyloxycarbonyloxy)-1-propyl iodide.

NMR (CDCl$_3$) δ: 1.00 (3H, m), 1.07 (3H, m), 1.28 (6H, m), 1.35 (6H, m), 2.12 (1H, m), 2.42 (3H, s), 2.60 (1H, m), 3.32 (1H, m), 3.42 (1H, m), 4.28 (1H, m), 4.35 (1H, m), 4.90 (1H, m), 6.63, 6.68 (total 1H, d each, J=5.6 Hz), 8.01 (1H, s), 8.39, 8.40 (total 1H, s each) MS (TSP): 538 (M$^+$+H)

Example 267

1-(1-Propyloxycarbonyloxy)ethyl(1S,5R,6S)-6-((1R)-1-hydroxyethyl)-1-methyl-2-(7-methylthio-imidazo[5,1-b]thiazol-2-yl)-1-carbapen-2-em-3-carboxylate (A Mixture of Diastereomers)

In the same manner as in Example 2, 147.0 mg of the title compound was obtained from 200.0 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 213.3 mg of 1-(1-propyloxycarbonyloxy)ethyl iodide.

NMR (CDCl$_3$) δ: 0.96 (3H, td, J$_1$=7.3 Hz, J$_2$=15.1 Hz), 1.38 (3H, dd, J$_1$=8.8 Hz, J$_2$=6.3 Hz), 1.60, 1.66 (total 3H, d each, J=5.4 Hz), 1.73 (2H, m), 2.44 (3H, s), 3.32 (1H, d, J=6.3 Hz), 3.43 (1H, m), 4.14 (2H, td, J$_1$=6.8 Hz, J$_2$=21.4 Hz), 4.28 (1H, m), 4.34 (1H, m), 6.94 (1H, m), 8.02, 8.02 (total 1H, s each, J=1.7 Hz), 8.38, 8.39 (total 1H, s each, J=4.6 Hz) MS (TSP): 510 (M$^+$+H)

Example 268

3-Pentyloxycarbonyloxymethyl(1S,5R,6S)-6-((1R)-1-hydroxyethyl)-1-methyl-2-(7-methylthio-imidazo[5,1-b]thiazol-2-yl)-1-carbapen-2-em-3-carboxylate In the same manner as in Example 2, 205 mg of the title compound was obtained from 231 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 310 mg of 3-pentyloxycarbonyloxymethyl iodide.

NMR (CDCl$_3$) δ: 0.89 (6H, q, J=7.1 Hz), 1.28 (3H, d, J=7.1 Hz), 1.37 (3H, d, J=6.1 Hz), 1.62 (4H, m), 2.44 (3H, s), 3.33 (1H, dd, J$_1$=6.5 Hz, J$_2$=2.6 Hz), 3.45 (1H, m), 4.30 (1H, m), 4.35 (1H, dd, J$_1$=9.6 Hz, J$_2$=2.6 Hz), 4.62 (1H, m), 5.91, 5.96 (2H, ABq, J=5.8 Hz), 8.04 (1H, s), 8.36 (1H, s) MS (TSP): 524 (M$^+$+H)

Example 269

1-(3-Pentyloxycarbonyloxy)ethyl(1S,5R,6S)-6-((1R)-1-hydroxyethyl)-1-methyl-2-(7-methylthio-imidazo[5,1-b]thiazol-2-yl)-1-carbapen-2-em-3-carboxylate (A Mixture of Diastereomers)

In the same manner as in Example 2, 210 mg of the title compound was obtained from 297 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 400 mg of 1-(3-pentyloxycarbonyloxy)ethyl iodide.

NMR (CDCl$_3$) δ: 0.90 (6H, m), 1.27 (3H, m), 1.37 (3H, m), 1.62 (7H, m), 2.42 (3H, s), 3.32 (1H, m), 3.43 (1H, m), 4.28 (1H, m), 4.33 (1H, m), 4.62 (1H, m), 6.93 (1H, m), 8.01 (1H, s), 8.35, 8.38 (total 1H, s each) MS (TSP): 538 (M$^+$+H)

Example 270

1-(1-Butyloxycarbonyloxy)ethyl(1S,5R,6S)-6-((1R)-1-hydroxyethyl)-1-methyl-2-(7-methylthio-imidazo[5,1-b]thiazol-2-yl)-1-carbapen-2-em-3-carboxylate (A Mixture of Diastereomers)

In the same manner as in Example 2, 147.3 mg of the title compound was obtained from 200.0 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 258.4 mg of 1-(1-butyloxycarbonyloxy)ethyl iodide.

NMR (CDCl$_3$) δ: 0.93 (3H, td, J$_1$=7.6 Hz, J$_2$=11.9 Hz), 1.28 (3H, dd, J$_1$=7.1 Hz, J$_2$=2.9 Hz), 1.38 (3H, dd, J$_1$=8.5 Hz, J$_2$=6.4 Hz), 1.43 (2H, m), 1.60, 1.65 (total 3H, d each, J=5.3 Hz), 1.68 (2H, m), 2.44 (3H, s), 3.32 (1H, d, J=6.6 Hz), 3.34 (1H, m), 4.16, 4.22 (total 1H, t each, J=6.8 Hz), 4.29 (1H, m), 4.33 (1H, m), 6.94 (1H, m), 8.02, 8.02 (total 1H, s each, J=1.9 Hz), 8.38, 8.39 (total 1H, s each, J=5.1 Hz) MS (TSP): 524 (M$^+$+H)

Example 271

4-Heptyloxycarbonyloxymethyl(1S,5R,6S)-6-((1R)-1-hydroxyethyl)-1-methyl-2-(7-methylthio-imidazo[5,1-b]thiazol-2-yl)-1-carbapen-2-em-3carboxylate In the same manner as in Example 2, 165 mg of the title compound was obtained from 137 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 200 mg of 4-heptyloxycarbonyloxymethyl iodide.

NMR (CDCl$_3$) δ: 0.90 (6H, m), 1.28 (3H, d, J=7.2 Hz), 1.30–1.35 (4H, m), 1.37 (3H, d, J=6.2 Hz), 1.55 (4H, m), 2.43 (3H, s), 3.33 (1H, dd, J$_1$=6.8 Hz, J$_2$=2.8 Hz), 3.44 (1H, m), 4.29 (1H, m), 4.35 (1H, dd, J$_1$=9.6 Hz, J$_2$=2.8 Hz), 4.74 (1H, m), 5.90, 5.95 (2H, ABq, J=5.8 Hz), 8.04 (1H, s), 8.35 (1H, s) MS (TSP): 552 (M$^+$+H)

Example 272

1-(4-Heptyloxycarbonyloxy)ethyl(1S,5R,6S)-6-((1R)-1-hydroxyethyl)-1-methyl-2-(7-methylthio-imidazo[5,1-b]thiazol-2-yl)-1-carbapen-2-em-3-carboxylate (A Mixture of Diastereomers)

In the same manner as in Example 2, 164 mg of the title compound was obtained from 176 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 320 mg of 1-(4-heptyloxycarbonyloxy)ethyl iodide.

NMR (CDCl$_3$) δ: 0.90 (6H, m), 1.29 (3H, m), 1.38 (3H, m), 1.50–1.68 (7H, m), 2.02 (1H, m), 2.43 (3H, s), 3.32 (1H, m), 3.43 (1H, m), 4.28 (1H, m), 4.33 (1H, m), 4.76 (1H, m), 6.93 (1H, m), 8.01 (1H, s), 8.37, 8.40 (total 1H, s each) MS (TSP): 566 (M$^+$+H)

Example 273

1-(3-Methyl-1-butyloxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 57.2 mg of the title compound was obtained from 200.0. mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 232.5 mg of 1-(3-methyl-1-butyloxycarbonyloxy)ethyl iodide.

NMR (CDCl$_3$) δ: 0.90, 0.93 (total 3H, d each, J=6.6Hz), 1.29 (3H, dd, J$_1$=7.3 Hz, J$_2$=2.4 Hz), 1.38 (3H, m), 1.53 (1H, m), 1.60 (3H, m), 1.63 (2H, m), 3.24 (3H, s), 3.32 (1H, m), 3.43 (1H, m), 4.25 (2H, t, J=6.8 Hz), 4.28 (1H, m), 4.33 (1H, m), 6.94 (1H, m), 8.01, 8.03 (total 1H, s each), 8.38, 8.39 (total 1H, s each) MS (TSP): 538 (M$^+$+H)

Example 274

1-(1-Pentyloxycarbonyloxy)ethyl(1S,5R,6S)-6-((1R)-1-hydroxyethyl)-1-methyl-2-(7-methylthio-imidazo[5,1-b]thiazol-2-yl)-1-carbapen-2-em-3-carboxylate (A Mixture of Diastereomers)

In the same manner as in Example 2, 248 mg of the title compound was obtained from 220 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 300 mg of 1-(1-pentyloxycarbonyloxy)ethyl iodide.

NMR (CDCl$_3$) δ: 0.85–0.92 (3H, m), 1.28, 1.29 (total 3H, d, J=7.3 Hz), 1.37, 1.38 (total 3H, d, J=6.4 Hz), 1.25–1.40 (4H, m), 1.60, 1.66 (total 3H, d, J=5.6 Hz), 1.70–1.75 (2H, m), 2.44 (3H, s), 3.33 (total 1H, dd, J=6.6, 2.7 Hz), 3.43 (total 1H, q, J=7.3 Hz), 4.10–4.35 (4H, m), 6.94 (total 1H, q, J=5.6 Hz), 8.01 (total 1H, s), 8.38, 8.40 (total 1H, s)

Example 275

1-(4-Methyl-1-pentyloxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 218 mg of the title compound was obtained from 220 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and of 300 mg of 1-(4-methyl-1-pentyloxycarbonyloxy)ethyl iodide.

NMR (CDCl$_3$) δ: 0.86 (3H, d, J=6.7 Hz), 0.89 (3H, d, J=6.7 Hz), 1.27, 1.29 (total 3H, d, J=7.3 Hz), 1.37, 1.39 (total 3H, d, J=6.3 Hz), 1.20–1.28 (2H, m), 1.60–1.66 (total 3H, d, J=5.5 Hz), 1.50–1.70 (2H, m), 1.92 (1H, dd, J=8.8 Hz, 4.8 Hz), 2.44 (3H, s), 3.33 (total 1H, dd, J=6.8, 2.7 Hz), 3.44 (1H, dq, J=9.3, 7.3 Hz), 4.10–4.35 (4H, m), 6.94 (total 1H, q, J=3.7 Hz), 8.04, 8.05 (total 1H, s), 8.39, 8.40 (total 1H, s)

Example 276

5-Nonyloxycarbonyloxymethyl(1S,5R,6S)-6-((1R)-1-hydroxyethyl)-1-methyl-2-(7-methylthio-imidazo[5,1-b]thiazol-2-yl)-1-carbapen-2-em-3-carboxylate In the same manner as in Example 2, 199 mg of the title compound was obtained from 171 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 250 mg of 5-nonyloxycarbonyloxymethyl iodide.

NMR (CDCl$_3$) δ: 0.85 (6H, m), 1.27 (3H, d, J=7.3 Hz), 1.28 (8H, m), 1.36 (3H, d, J=6.3 Hz), 1.56 (4H, m), 2.42 (3H, s), 2.99 (1H, br.s), 3.32 (1H, dd, J$_1$=6.8 Hz, J$_2$=2.8 Hz), 3.44 (1H, m), 4.28 (1H, m), 4.35 (1H, dd, J$_1$=9.7 Hz, J$_2$=2.8 Hz), 4.71 (1H, m), 5.90, 5.95 (2H, ABq, J=5.8 Hz), 8.03 (1H, s), 8.35 (1H, s) MS (TSP): 580 (M$^+$+H)

Example 277

1-[3-(2,4-Dimethyl)pentoxycarbonyloxy]ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 129 mg of the title compound was obtained from 201 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 346 mg of 1-[3-(2,4-dimethyl)pentoxycarbonyloxy]ethyl iodide.

NMR (CDCl$_3$) δ: 0.89 (12H, m), 1.27, 1.29 (total 3H, d each, J=6.8 Hz), 1.37, 1.39 (total 3H, d each, J=6.2 Hz), 1.61, 1.65 (total 3H, d each, J=5.5 Hz), 2.43 (total 3H, s each), 3.35 (1H, m), 3.43 (1H, m), 4.26–4.44 (3H, m), 6.92 (1H, m), 8.00, 8.01 (total 1H, s each), 8.31, 8.39 (total 1H, s each) MS (TSP): 566 (M$^+$+H)

Example 278

1-(2, 2-Dimethyl-1-propyloxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 175.5 mg of the title compound was obtained from 200.0 mg of sodium(1S,5R, 6S)-6-((1R)-1-hydroxyethyl)-1-methyl-2-(7-methylthioimidazo[5,1-b]thiazol-2-yl)-1-carbapen-2-em-3-carboxylate and 240.8 mg of 1-(2,2-dimethyl-1-propyloxycarbonyloxy)ethyl iodide.

NMR (CDCl$_3$) δ: 0.93, 0.97 (total 9H, s each), 1.27 (3H, m), 1.35 (3H, m), 1.61, 1.65 (total 3H, d each, J=5.4 Hz), 2.43 (3H, s), 3.32 (1H, m), 3.43 (1H, m), 3.89 (2H, m), 4.28 (1H, m), 4.34 (1H, td, J$_1$=3.4 Hz, J$_2$=9.5 Hz), 6.94 (1H, q, J=5.4 Hz), 8.20 (1H, s), 8.37, 8.39 (total 1H, s each) MS (TSP): 538 (M$^+$+H)

Example 279

1-(3,3-Dimethyl-2-butyloxycarbonyloxy)ethyl(1S, 5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 124.8 mg of the title compound was obtained from 200.0 mg of sodium(1S,5R, 6S)-6-((1R)-1-hydroxyethyl)-1-methyl-2-(7-methylthioimidazo[5,1-b]thiazol-2-yl)-1-carbapen-2-em-3-carboxylate and 252.9 mg of 1-(3,3-dimethyl-2-butyloxycarbonyloxy)ethyl iodide.

NMR (CDCl$_3$) δ: 0.88, 0.92, 0.93, 0.95 (total 9H, s each), 1.28 (3H, m), 1.38 (3H, m), 1.63 (3H, m), 1.65 (3H, d, J=5.6 Hz), 2.44 (3H, s), 3.33 (1H, m), 3.43 (1H, m), 4.27 (1H, m), 4.32 (1H, m), 4.58 (1H, m), 6.94 (1H, m), 8.00, 8.01 (total 1H, s each), 8.39, 8.40 (total 1H, s each) MS (TSP): 552 (M$^+$+H)

Example 280

1-(2-Cyclohexyl-1-ethyloxycarbonyloxy)ethyl(1S, 5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

The title compound (102.1 mg) was obtained from 200.0 mg of sodium(1S,5R,6S)-6-((1R)-1-hydroxyethyl)-1-methyl-2-(7-methylthioimidazo-[5,1-b]thiazol-2-yl)-1-carbapen-2-em-3-carboxylate and 344.0 mg of 1-(2-cyclohexyl-1-ethyl oxycarbonyloxy)ethyl iodide in the same manner as in Example 2, except that sodium hydrogencarbonate was not used in the reaction.

NMR (CDCl$_3$) δ: 0.83 (2H, m), 1.10 (4H, m), 1.21 (3H, dd, J$_1$=7.3 Hz, J$_2$=2.0 Hz), 1.28, 1.32 (total 3H, d each, J=6.3 Hz), 1.46 (2H, q, J=6.8 Hz), 1.52, 1.57 (total 3H, d each, J=5.4 Hz), 1.54–1.70 (5H, m), 2.36 (3H, s), 3.25 (1H, m), 3.35, 3.37 (total 1H, t each, J=7.6 Hz), 4.18 (2H, t, J=6.8 Hz), 4.27 (1H, m), 6.86, 6.88 (total 1H, t each, J=5.3 Hz), 7.95, 7.95 (total 1H, s each), 8.31, 8.32 (total 1H, s each) MS (TSP): 578 (M$^+$+H)

Example 281

1-(2-Phenyl-1-ethyloxycarbonyloxy)ethyl(1S,5R, 6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

The title compound (206.4 mg) was obtained from 200.0 mg of sodium(1S,5R,6S)-6-((1R)-1-hydroxyethyl)-1-methyl-2-(7-methylthioimidazo-[5,1-b]thiazol-2-yl)-1-carbapen-2-em-3-carboxylate and 239.2 mg of 1-(2-phenyl-1-ethyl oxycarbonyloxy)ethyl iodide in the same manner as in Example 2, except that sodium hydrogencarbonate was not used in the reaction.

NMR (CDCl$_3$) δ: 1.21 (3H, d, J=7.3 Hz), 1.29, 1.31 (total 3H, d each, J=6.4 Hz), 1.51, 1.57 (total 3H, d each, J=5.6 Hz), 2.36 (3H, s), 2.89, 2.96 (total 2H, t each, J=7.4 Hz), 3.25 (1H, dd, J$_1$=6.6 Hz, J$_2$=2.5 Hz), 3.36 (1H, m), 4.22 (1H, m), 4.27 (1H, m), 4.34 (2H, t, J=7.3 Hz), 6.86 (1H, m), 7.17 (5H, m), 7.94 (1H, s), 8.30 (1H, s) MS (TSP): 572 (M$^+$+H)

Example 282

Cyclohexyloxycarbonyloxymethyl(1S,5R,6S)-6-((1R)-1-hydroxyethyl)-1-methyl-2-(7-methylthioimidazo[5,1-b]thiazol-2-yl)-1-carbapen-2-em-3-carboxylate In the same manner as in Example 2, 27 mg of the title compound was obtained from 24 mg of sodium(1S,5R,6S)-6-((1R)-1-hydroxyethyl)-1-methyl-2-(7-methylthioimidazo [5,1-b]thiazol-2-yl)-1-carbapen-2-em-3-carboxylate and 28 mg of cyclohexyloxycarbonyloxymethyl iodide.

NMR (CDCl$_3$) δ: 1.28 (3H, d, J=7.2 Hz), 1.36 (3H, d, J=6.2 Hz), 1.30–1.67 (4H, m), 1.70–1.95 (6H, m), 2.43 (3H, s), 2.69 (1H, br.s), 3.33 (1H, dd, J$_1$=6.6 Hz, J$_2$=2.7 Hz), 3.44 (1H, m), 4.29 (1H, m), 4.36 (1H, dd, J$_1$=9.6 Hz, J$_2$=2.7 Hz), 4.65 (1H, m), 5.89, 5.95 (2H, ABq, J=5.8 Hz), 8.04 (1H, s), 8.35 (1H, s) MS (TSP): 536 (M$^+$+H)

Example 283

1-(Cyclohexyloxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 261 mg of the title compound was obtained from 314 mg of sodium(1S,5R,6S)-6-((1R)-1-hydroxyethyl)-1-methyl-2-(7-methylthioimidazo [5,1-b]thiazol-2-yl)-1-carbapen-2-em-3-carboxylate and 300 mg of 1-(cyclohexyloxycarbonyloxy)ethyl iodide.

NMR (CDCl$_3$) δ: 1.27 (3H,m), 1.37 (3H, m), 1.20–2.00 (10H, m), 1.59, 1.65 (total 3H, d each, J=5.5 Hz), 2.44 (3H, s), 3.31 (1H, m), 3.42 (1H, m), 4.32 (1H, m), 4.66 (1H, m), 6.94 (1H, m), 8.02 (1H, s), 8.38 (1H, s) MS (TSP): 550 (M$^+$+H)

Example 284

1-(Cyclohexyloxycarbonyloxy)-1-propyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 117 mg of the title compound was obtained from 159 mg of sodium(1S,5R,6S)-6-((1R)-1-hydroxyethyl)-1-methyl-2-(7-methylthioimidazo [5,1-b]thiazol-2-yl)-1-carbapen-2-em-3-carboxylate and 350 mg of 1-(cyclohexyloxycarbonyloxy)-1-propyl iodide.

NMR (CDCl$_3$) δ: 1.00, 1.07 (total 3H, t each, J=7.4 Hz), 1.29 (3H, m), 1.37 (3H, m), 1.30–1.60 (5H, m), 1.77–2.22 (7H, m), 2.43 (3H, s), 3.32 (1H, m), 3.43 (1H, m), 4.27 (1H, m), 4.34 (1H, m), 4.65 (1H, m), 6.80 (1H, m), 8.01 (1H, s), 8.39, 8.40 (total 1H, s each) MS (TSP): 564 (M$^+$+H)

Example 285

1-(Cyclohexyloxycarbonyloxy)-2-methyl-1-propyl (1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 113 mg of the title compound was obtained from 197 mg of sodium(1S,5R,6S)-

6-((1R)-1-hydroxyethyl)-1-methyl-2-(7-methylthioimidazo[5,1-b]thiazol-2-yl)-1-carbapen-2-em-3-carboxylate and 950 mg of 1-(cyclohexyloxycarbonyloxy)-2-methyl-1-propyl iodide.

NMR (CDCl$_3$) δ: 1.04 (6H, m), 1.29 (3H, m), 1.37 (3H, m), 1.30–2.20 (11H, m), 2.43 (3H, s), 3.32 (1H, m), 3.42 (1H, m), 4.39 (1H, m), 4.64 (1H, m), 6.63, 6.68 (total 1H, d each, J=4.7 Hz), 8.01 (1H, s), 8.40, 8.41 (total 1H, s each) MS (TSP): 578 (M$^+$+H)

Example 286

Cyclohexyl(cyclohexyloxycarbonyloxy)methyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 115 mg of the title compound was obtained from 198 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 800 mg of cyclohexyl(cyclohexyloxycarbonyloxy)methyl iodide.

NMR (CDCl$_3$) δ: 1.15–2.02 (21H, m), 1.28 (3H, m), 1.37 (3H, m), 2.35 (1H, br.s), 2.43 (1H, m), 3.32 (1H, m), 3.42 (1H, m), 4.32 (2H, m), 4.63 (1H, m), 6.65 (1H, m), 8.01 (1H, s), 8.39 (1H, s) MS (TSP): 618 (M$^+$+H)

Example 287

2-Adamantyloxycarbonyloxymethyl(1S,5R,6S)-6-((1R)-1-hydroxyethyl)-1-methyl-2-(7-methylthioimidazo[5,1-b]thiazol-2-yl)-1-carbapen-2-em-3-carboxylate In the same manner as in Example 2, 135 mg of the title compound was obtained from 104 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 200 mg of 2-adamantyloxycarbonyloxymethyl iodide.

NMR (CDCl$_3$) δ: 1.28 (3H, d, J=7.2 Hz), 1.37 (3H, d, J=6.3 Hz), 1.50–2.12 (14H, m), 2.43 (3H, s), 3.34 (1H, dd, J$_1$=6.6 Hz, J$_2$=2.8 Hz), 3.44 (1H, m), 4.30 (1H, m), 4.36 (1H, dd, J$_1$=9.6 Hz, J$_2$=2.8 Hz), 4.82 (1H, m), 5.91, 5.96 (2H, ABq, J=5.8 Hz), 8.04 (1H, s), 8.35 (1H, s) MS (TSP): 588 (M$^+$+H)

Example 288

Phenoxycarbonyloxymethyl(1S,5R,6S)-6-((1R)-1-hydroxyethyl)-1-methyl-2-(7-methylthioimidazo-[5,1-b]thiazol-2-yl)-1-carbapen-2-em-3-carboxylate In the same manner as in Example 2, 133 mg of the title compound was obtained from 167 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 170 mg of phenoxycarbonyloxymethyl iodide.

NMR (CDCl$_3$) δ: 1.29 (3H, d, J=7.2 Hz), 1.37 (3H, d, J=6.3 Hz), 2.44 (3H, s), 3.35 (1H, dd, J$_1$=6.3 Hz, J$_2$=2.8 Hz), 3.45 (1H, m), 4.32 (1H, m), 4.38 (1H, dd, J$_1$=9.8 Hz, J$_2$=2.8 Hz), 5.97, 6.11 (2H, ABq, J=5.8 Hz), 7.23 (3H, m), 7.39 (2H, m), 8.02 (1H, s), 8.35 (1H, s) MS (TSP): 530 (M$^+$+H)

Example 289

1-(Phenoxycarbonyloxy)ethyl(1S,5R,6S)-6-((1R)-1-hydroxyethyl)-1-methyl-2-(7-methylthio-imidazo[5,1-b]thiazol-2-yl)-1-carbapen-2-em-3-carboxylate (A Mixture of Diastereomers)

In the same manner as in Example 2, 156 mg of the title compound was obtained from 166 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 300 mg of 1-(phenoxycarbonyloxy)ethyl iodide.

NMR (CDCl$_3$) δ: 1.28 (3H, m), 1.39 (3H, m), 1.67, 1.73 (total 3H, d each, J=5.5 Hz), 2.43 (3H, s), 3.35 (1H, m), 3.44 (1H, m), 4.34 (2H, m), 7.03 (1H, m), 7.18–7.40 (5H, m), 8.01 (1H, s), 8.36 (1H, s) MS (TSP): 544 (M$^+$+H)

Example 290

1-(Phenoxycarbonyloxy)-1-propyl(1S,5R,6S)-6-((1R)-1-hydroxyethyl)-1-methyl-2-(7-methylthio-imidazo[5,1-b]thiaol-2-yl)-1-carbapen-2-em-3-carboxylate (A Mixture of Diastereomers)

In the same manner as in Example 2, 179 mg of the title compound was obtained from 190 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 657 mg of 1-(phenoxycarbonyloxy)-1-propyl iodide.

NMR (CDCl$_3$) δ: 1.05, 1.13 (total 3H, t each, J=7.6 Hz), 1.26 (3H, m), 1.39 (3H, m), 2.01 (2H, m), 2.42 (3H, s), 2.61, 2.71 (total 1H, br.s each), 3.35 (1H, m), 3.43 (1H, m), 4.33 (1H, m), 4.38 (1H, m), 6.87 (1H, m), 7.16–7.40 (5H, m), 8.01 (1H, s), 8.36 (1H, s) MS (TSP): 558 (M$^+$+H)

Example 291

1-(2-Methylphenoxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 200.0 mg of the title compound was obtained from 200.0 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 500 mg of 1-(2-methylphenoxycarbonyloxy)ethyl iodide.

NMR (CDCl$_3$) δ: 1.28, 1.30 (total 3H, d each, J=7.3 Hz), 1.38, 1.40 (total 3H, d each, J=6.3 Hz), 1.69, 1.74 (total 3H, d each, J=5.4 Hz), 1.84 (1H, m), 2.20, 2.28 (total, 3H, s each), 2.43 (3H, s), 3.33 (1H, m), 3.46 (1H, m), 4.28 (1H, m), 4.35 (1H, m), 7.01 (1H, m), 7.20 (4H, m), 8.00, 8.01 (total 1H, s each), 8.35, 8.38 (total 1H, s each) MS (ESI): 558 (M$^+$+H)

Example 292

1-(2-Ethylphenoxycarbonyloxy)ethyl(1S,5R,6s)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 181.0 mg of the title compound was obtained from 200.0 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 500 mg of 1-(2-ethyl phenoxycarbonyloxy)ethyl iodide.

NMR (CDCl$_3$) δ: 1.13, 1.21 (total 3H, t each, J=7.3 Hz), 1.28, 1.30 (total 3H, d each, J=7.3 Hz), 1.38, 1.40 (total 3H, d each, J=6.3 Hz), 1.69, 1.74 (total 3H, d each, J=5.4 Hz), 2.00 (1H, m), 2.43 (3H, s), 2.59, 2.65 (total 2H, q each, J=7.3 Hz), 3.33 (1H, m), 3.46 (1H, m), 4.28 (1H, m), 4.35 (1H, m), 7.01 (1H, m), 7.22 (4H, m), 8.00, 8.01 (total 1H, s each), 8.35, 8.38 (total 1H, s each) MS (TSP): 572 (M$^+$+H)

Example 293

1-(2-Methoxyphenoxycarbonyloxy)ethyl(1S,5g,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 106.0 mg of the title compound was obtained from 200.0 mg of sodium(1S,5R, 6S)-6-((1R)-1-hydroxyethyl)-1-methyl-2-(7-methylthioimidazo[5,1-b]thiazol-2-yl)-1-carbapen-2-em-3-carboxylate and 500 mg of 1-(2-methoxyphenoxycarbonyloxy)ethyl iodide.

NMR (CDCl₃) δ: 1.28, 1.30 (total 3H, d each, J=7.3 Hz), 1.39 (3H, d, J=6.3 Hz), 1.69, 1.74 (total 3H, d each, J=5.4 Hz), 1.92 (1H, m), 2.43 (3H, s), 3.33 (1H, m), 3.46 (1H, m), 3.81, 3.86 (total 3H, s each), 4.28 (1H, m), 4.35 (1H, m), 6.98 (3H, m),, 7.21 (2H, m), 7.99, 8.00 (total 1H, s each), 8.34, 8.37 (total 1H, s each). MS (TSP): 574 (M⁺+H)

Example 294

1-(3-Methylphenoxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 171.0 mg of the title compound was obtained from 200.0 mg of sodium(1S,5R, 6S)-6-((1R)-1-hydroxyethyl)-1-methyl-2-(7-methylthioimidazo[5,1-b]thiazol-2-yl)-1-carbapen-2-em-3-carboxylate and 500 mg of 1-(3-methylphenoxycarbonyloxy)ethyl iodide.

NMR (CDCl₃) δ: 1.28, 1.30 (total 3H, d each, J=7.3 Hz), 1.38, 1.40 (total 3H, d each, J=6.3 Hz), 1.69, 1.74 (total 3H, d each, J=5.4 Hz), 2.11, 2.17 (total 1H, d each, J=5.4 Hz), 2.34, 2.36 (total, 3H, s each), 2.43 (3H, s), 3.33 (1H, m), 3.46 (1H, m), 4.28 (1H, m), 4.35 (1H, m), 7.03 (4H, m), 7.25 (1H, m), 8.01, 8.02 (total 1H, s each), 8.35, 8.37 (total 1H, s each) MS (TSP): 558 (M⁺+H)

Example 295

1-(3-Methoxyphenoxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 189.0 mg of the title compound was obtained from 200.0 mg of sodium(1S,5R, 6S)-6-((1R)-1-hydroxyethyl)-1-methyl-2-(7-methylthioimidazo[5,1-b]thiazol-2-yl)-1-carbapen-2-em-3-carboxylate and 500 mg of 1-(3-methoxyphenoxycarbonyloxy)ethyl iodide.

NMR (CDCl₃) δ: 1.28, 1.30 (total 3H, d each, J=7.3 Hz), 1.38, 1.40 (total 3H, d each, J=6.3 Hz), 1.69, 1.74 (total 3H, d each, J=5.4 Hz), 1.88 (1H, m), 2.43 (3H, s), 3.33 (1H, m), 3.46 (1H, m), 3.78, 3.80 (total 3H, s each), 4.28 (1H, m), 4.35 (1H, m), 6.77 (1H, m), 6.91 (1H, m), 7.02 (1H, m), 7.27 (1H, m), 8.01, 8.02 (total 1H, s each), 8.37, 8.39 (total 1H, s each) MS (TSP): 574 (M⁺+H)

Example 296

1-(4-Methylphenoxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 148.0 mg of the title compound was obtained from 200.0 mg of sodium(1S,5R, 6S)-6-((1R)-1-hydroxyethyl)-1-methyl-2-(7-methylthioimidazo[5,1-b]thiazol-2-yl)-1-carbapen-2-em-3-carboxylate and 500 mg of 1-(4-methylphenoxycarbonyloxy)ethyl iodide.

NMR (CDCl₃) δ: 1.29 (3H, m), 1.39 (3H, m), 1.70 (3H, m), 1.83 (1H, m), 2.34 (3H, s), 2.43 (3H, s), 3.33 (1H, m), 3.46 (1H, m), 4.28 (1H, m), 4.35 (1H, m), 7.03 (2H, m), 7.17 (3H, m), 8.01 (1H, m), 8.38 (1H, m) MS (TSP): 558 (M⁺+H)

Example 297

1-(4-Ethylphenoxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 182.0 mg of the title compound was obtained from 200.0 mg of sodium(1S,5R, 6S)-6-((1R)-1-hydroxyethyl)-1-methyl-2-(7-methylthioimidazo[5,1-b]thiazol-2-yl)-1-carbapen-2-em-3-carboxylate and 500 mg of 1-(4-ethyl phenoxycarbonyloxy)ethyl iodide.

NMR (CDCl₃) δ: 1.21, 1.22 (total 3H, t each, J=7.3 Hz), 1.28, 1.30 (total 3H, d each, J=7.3 Hz), 1.38, 1.40 (total 3H, d each, J=6.3 Hz), 1.69, 1.74 (total 3H, d each, J=5.4 Hz), 1.89 (1H, m), 2.43 (3H, s), 2.63, 2.64 (total 2H, q each, J=7.3 Hz), 3.34 (1H, m), 3.46 (1H, m), 4.28 (1H, m), 4.35 (1H, m), 7.04 (2H, m), 7.19 (3H, m), 8.00, 8.01 (total 1H, s each), 8.36, 8.38 (total 1H, s each) MS (TSP): 572 (M⁺+H)

Example 298

1-(4-Methoxyphenoxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 158.0 mg of the title compound was obtained from 200.0 mg of sodium(1S,5R, 6S)-6-((1R)-1-hydroxyethyl)-1-methyl-2-(7-methylthioimidazo[5,1-b]thiazol-2-yl)-1-carbapen-2-em-3-carboxylate and 500 mg of 1-(4-methoxyphenoxycarbonyloxy)ethyl iodide.

NMR (CDCl₃) δ: 1.28, 1.30 (total 3H, d each, J=7.3 Hz), 1.38, 1.40 (total 3H, d each, J=6.3 Hz), 1.69, 1.74 (total 3H, d each, J=5.4 Hz), 1.94 (1H, m), 2.43 (3H, s), 3.33 (1H, m), 3.46 (1H, m), 3.78, 3.79 (total 3H, s each), 4.28 (1H, m), 4.35 (1H, m), 6.87 (2H, m), 7.01 (1H, m), 7.09 (1H, m), 7.22 (1H, m), 8.01, 8.02 (total 1H, s each), 8.37, 8.38 (total 1H, s each) MS (TSP): 574 (M⁺+H)

Example 299

1-(2,6-Dimethylphenoxycarbonyloxy)ethyl(1S,5R, 6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 110.0 mg of the title compound was obtained from 200.0 mg of sodium(1S,5R, 6S)-6-((1R)-1-hydroxyethyl)-1-methyl-2-(7-methylthioimidazo[5,1-b]thiazol-2-yl)-1-carbapen-2-em-3-carboxylate and 500 mg of 1-(2,6-dimethylphenoxycarbonyloxy)ethyl iodide.

NMR (CDCl₃) δ: 1.28, 1.30 (total 3H, d each, J=7.3 Hz), 1.38, 1.40 (total 3H, d each, J=6.3 Hz), 1.68 (1H, m), 1.69, 1.74 (total 3H, d each, J=5.4 Hz), 2.17 (3H, s), 2.25 (3H, s), 2.43 (3H, s), 3.33 (1H, m), 3.46 (1H, m), 4.28 (1H, m), 4.35 (1H, m), 6.99 (1H, m), 7.04 (3H, m), 8.01, 8.02 (total 1H, s each), 8.31, 8.38 (total 1H, s each) MS (APCI): 572 (M⁺+H)

Example 300

1-(2,4-Dimethylphenoxycarbonyloxy)ethyl(1S,5R, 6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 150.0 mg of the title compound was obtained from 200.0 mg of sodium(1S,5R, 6S)-6-((1R)-1-hydroxyethyl)-1-methyl-2-(7-methylthioimidazo[5,1-b]thiazol-2-yl)-1-carbapen-2-em-3-carboxylate and 500 mg of 1-(2,4-dimethylphenoxycarbonyloxy)ethyl iodide.

NMR (CDCl$_3$) δ: 1.28, 1.30 (total 3H, d each, J=7.3 Hz), 1.38, 1.40 (total 3H, d each, J=6.3 Hz), 1.69, 1.74 (total 3H, d each, J=5.4 Hz), 1.89 (1H, m), 2.15, 2.23 (total 3H, s each), 2.29, 2.30 (total 3H, s each), 2.43, 2.44 (total 3H, s each), 3.33 (1H, m), 3.46 (1H, m), 4.28 (1H, m), 4.35 (1H, m), 7.02 (4H, m), 8.00, 8.01 (total 1H, s each), 8.34, 8.38 (total 1H, s each), MS (TSP): 572 (M$^+$+H)

Example 301

1-(2,5-Dimethylphenoxycarbonyloxy)ethyl(1S,5R, 6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 174.0 mg of the title compound was obtained from 200.0 mg of sodium(1S,5R, 6S)-6-((1R)-1-hydroxyethyl)-1-methyl-2-(7-methylthioimidazo[5,1-b]thiazol-2-yl)-1-carbapen-2-em-3-carboxylate and 500 mg of 1-(2,5-dimethylphenoxycarbonyloxy)ethyl iodide.

NMR (CDCl$_3$) δ: 1.28, 1.30 (total 3H, d each, J=7.3 Hz), 1.38, 1.40 (total 3H, d each, J=6.3 Hz), 1.69, 1.74 (total 3H, d each, J=5.4 Hz), 2.00 (1H, m), 2.14, 2.22 (total 3H, s each), 2.29, 2.31 (total 3H, s each), 2.43 (3H, s), 3.33 (1H, m), 3.46 (1H, m), 4.28 (1H, m), 4.35 (1H, m), 7.00 (4H, m), 8.00, 8.01 (total 1H, s each), 8.34, 8.38 (total 1H, s each) MS (TSP): 572 (M$^+$+H)

Example 302

1-[2-Methyl-5-(2-propyl)phenoxycarbonyloxy]-ethyl (1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 172.0 mg of the title compound was obtained from 200.0 mg of sodium(1S,5R, 6S)-6-((1R)-1-hydroxyethyl)-1-methyl-2-(7-methylthioimidazo[5,1-b]thiazol-2-yl)-1-carbapen-2-em-3-carboxylate and 500 mg of 1-[2-methyl-5-(2-propyl)phenoxycarbonyloxy]ethyl iodide.

NMR (CDCl$_3$) δ: 1.22 (6H, t, J=7.3 Hz), 1.29 (3H, d, J=7.3 Hz), 1.39 (3H, d, J=6.3 Hz), 1.69, 1.74 (total 3H, d each, J=5.4 Hz), 2.00 (1H, m), 2.15, 2.23 (total 3H, s each), 2.43 (3H, s), 2.87 (1H, m), 3.33 (1H, m), 3.46 (1H, m), 4.28 (1H, m), 4.35 (1H, m), 7.04 (4H, m), 8.00, 8.01 (total 1H, s each), 8.35, 8.39 (total 1H, s each) MS (TSP): 600 (M$^+$+H)

Example 303

1-(3,5-Dimethylphenoxycarbonyloxy)ethyl(1S,5R, 6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 167.0 mg of the title compound was obtained from 200.0 mg of sodium(1S,5R, 6S)-6-((1R)-1-hydroxyethyl)-1-methyl-2-(7-methylthioimidazo[5,1-b]thiazol-2-yl)-1-carbapen-2-em-3-carboxylate and 500 mg of 1-(3,5-dimethylphenoxycarbonyloxy)ethyl iodide.

NMR (CDCl$_3$) δ: 1.28, 1.30 (total 3H, d each, J=7.3 Hz), 1.38, 1.40 (total 3H, d each, J=6.3 Hz), 1.69, 1.74 (total 3H, d each, J=5.4 Hz), 2.05 (1H, m), 2.29 (3H, s), 2.31 (3H, s), 2.43 (3H, s), 3.33 (1H, m), 3.46 (1H, m), 4.28 (1H, m), 4.35 (1H, m), 6.78 (1H, s), 6.89 (2H, m), 7.01 (1H, m), 7.25 (1H, m), 8.00, 8.01 (total 1H, s each), 8.35, 8.38 (total 1H, s each) MS (TSP): 572 (M$^+$+H)

Example 304

1-(2,4,6-Trimethylphenoxycarbonyloxy)ethyl(1S,5R, 6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 163 mg of the title compound was obtained from 168 mg of sodium(1S,5R,6S)-6-((1R)-1-hydroxyethyl)-1-methyl-2-(7-methylthioimidazo [5,1-b]thiazol-2-yl)-1-carbapen-2-em-3-carboxylate and 200 mg of 1-(2,4,6-trimethylphenoxycarbonyloxy)ethyl iodide.

NMR (CDCl$_3$) δ: 1.28 (3H, m), 1.38 (3H, m), 1.67, 1.72 (total 3H, d each, J=5.5 Hz), 2.12, 2, 20 (total 6H, s each), 2.24, 2.25 (total 3H, s each), 2.43 (3H, s), 3.33 (1H, m), 3.43 (1H, m), 4.29 (1H, m), 4.34 (1H, m), 6.84, 6.86 (total 2H, s each), 7.69 (1H, m), 8.00, 8.01 (total 1H, s each), 8.28, 8.35 (total 1H, s each) MS (TSP): 586 (M$^+$+H)

Example 305

1-((Indan-5-yl)oxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 157 mg of the title compound was obtained from 156 mg of sodium(1S,5R,6S)-6-((1R)-1-hydroxyethyl)-1-methyl-2-(7-methylthioimidazo [5,1-b]thiazol-2-yl)-1-carbapen-2-em-3-carboxylate and 527 mg of 1-((indan-5-yl)oxycarbonyloxy)ethyl iodide.

NMR (CDCl$_3$) δ: 1.27 (3H, m), 1.39 (3H, m), 1.66, 1.72 (total 3H, d each, J=5.3 Hz), 2.08 (2H, m), 2.42 (3H, s), 2.87 (4H, m), 3.33 (1H, m), 3.42 (1H, m), 4.33 (2H, m), 6.88–7.20 (4H, m), 8.01 (1H, s), 8.33, 8.35 (total 1H, s each) MS (TSP): 584 (M$^+$+H)

Example 306

1-((Indan-5-yl)oxycarbonyloxy)-1-propyl(1S,5R, 6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 189 mg of the title compound was obtained from 182 mg of sodium(1S,5R,6S)-6-((1R)-1-hydroxyethyl)-1-methyl-2-(7-methylthioimidazo [5,1-b]thiazol-2-yl)-1-carbapen-2-em-3-carboxylate and 700 mg of 1-((indan-5-yl)oxycarbonyloxy)-1-propyl iodide.

NMR (CDCl$_3$) δ: 1.05, 1.29 (total 3H, t each, J=7.6 Hz), 1.29 (3H, m), 1.40 (3H, m), 2.06 (4H, m), 2.21 (1H, m), 2.43 (3H, s), 2.88 (4H, m), 3.14 (1H, m), 3.43 (1H, m), 4.33 (2H, m), 6.87 (1H, m), 7.02–7.20 (3H, m), 8.00, 8.01 (total 1H, s each), 8.36, 8.39 (total 1H, s each) MS (TSP): 598 (M$^+$+H)

Example 307

1-Heptyl(1S,5R,6S)-6-((1R)-1-hydroxyethyl)-1-methyl-2-(7-methylthioimidazo[5,1-b]thiazol-2-yl)-1-carbapen-2-em-3-carboxylate The title compound (128 mg) was obtained from 161 mg of sodium(1S,5R,6S)-6-((1R)-1-hydroxyethyl)-1-methyl-2-

(7-methylthioimidazo[5,1-b]thiazol-2-yl)-1-carbapen-2-em-3-carboxylate and 0.33 ml of 1-iodoheptane in substantially the same manner as in Example 46-c), except that the reaction was initiated under ice cooling and the system was stirred for 18 hr while gradually raising the temperature to room temperature.

NMR (CDCl$_3$) δ: 0.88 (3H, br.t, J=6.7 Hz), 1.25–1.33 (11H, m), 1.39 (3H, d, J=6.3 Hz), 1.69–1.81 (2H, m), 2.43 (3H, s), 3.33 (1H, dd, J$_1$=6.7 Hz, J$_2$=2.9 Hz), 3.37–3.48 (1H, m), 4.17–4.38 (4H, m), 8.01 (1H, s), 8.27 (1H, s) MS (TSP): 478 (M$^+$+H)

Example 308

5-Methyl-2-oxo-1,3-dioxolen-4-ylmethyl(1S,5R,6S)-6-((1R)-1-hydroxyethyl)-1-methyl-2-(7-methylthioimidazo[5,1-b]thiazol-2-yl)-1-carbapen-2-em-3-carboxylate In the same manner as in Example 2, 205 mg of the title compound was obtained from 231 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 240 mg of 5-methyl-2-oxo-1,3-dioxolen-4-ylmethyl bromide.

NMR (CDCl$_3$) δ: 1.29 (3H, d, J=7.1 Hz), 1.37 (3H, d, J=6.0 Hz), 2.22 (3H, s), 2.44 (3H, s), 3.34 (1H, dd, J$_1$=6.3 Hz, J$_2$=2.7 Hz), 3.47 (1H, m), 4.30 (1H, m), 4.36 (1H, dd, J$_1$=9.8 Hz, J$_2$=2.7 Hz), 5.00, 5.08 (2H, ABq, J=14.0 Hz), 8.06 (1H, s), 8.22 (1H, s) MS (TSP): 492 (M$^+$+H)

Example 309

(Z)-2-(3-Phthalidylidene)ethyl(1S,5R,6S)-6-((1R)-1-hydroxyethyl)-1-methyl-2-(7-methylthio-imidazo[5,1-b]thiazol-2-yl)-1-carbapen-2-em-3-carboxylate In the same manner as in Example 2, 169 mg of the title compound was obtained from 170 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 130 mg of (Z)-2-(3-phthalidylidene)ethyl bromide.

NMR (CDCl$_3$) δ: 1.28 (3H, d, J=7.4 Hz), 1.37 (3H, d, J=6.2 Hz), 2.41 (3H, s), 2.70 (1H, br.s), 3.34 (1H, dd, J$_1$=6.5 Hz, J$_2$=2.7 Hz), 3.44 (1H, m), 4.31 (1H, m), 4.36 (1H, dd, J$_1$=9.6 Hz, J$_2$=2.7 Hz), 5.20 (2H, s), 5.82 (1H, t, J=7.1 Hz), 7.58 (1H, m), 7.69 (2H, m), 7.89 (1H, m), 8.03 (1H, s), 8.31 (1H, s) MS (TSP): 538 (M$^+$+H)

Example 310

1-(1,1-Dimethyl-1-butyloxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

A solution of 156.6 mg of 1-(1,1-dimethyl-1-butyloxycarbonyloxy)ethyl chloride in 2.0 ml of DMF was added to a suspension of 176.1 mg of silver iodide in 2.0 ml of DMF. The mixture was stirred in an argon atmosphere at room temperature for one hr. A solution of 200.0 mg of sodium(1S,5R,6S)-6-((1R)-1-hydroxyethyl)-1-methyl-2-(7-methylthio-imidazo[5,1-b]thiazol-2-yl)-1-carbapen-2-em-3-carboxylate in 1.0 ml of DMF was added thereto, followed by stirring for 3 hr. Water (10 ml) was added to the reaction solution to terminate the reaction. The system was extracted three times with 10 ml of ethyl acetate, followed by washing three times with 30 ml of semisaturated brine. The organic layer was dried over anhydrous magnesium sulfate and filtered. The residue was purified by chromatography on silica gel (chloroform:methanol=20:1) to give 82.3 mg of the title compound.

NMR (CDCl$_3$) δ: 0.82, 0.85 (total 3H, t each, J=7.3 Hz), 1.20 (3H, m), 1.25 (2H, m), 1.30 (3H, m), 1.37, 1.42 (total 6H, s each), 1.49 (3H, m), 1.61 (2H, m), 2.37 (3H, s), 3.23, 3.25 (total 1H, t each, J=2.9 Hz), 3.35 (1H, m), 4.21 (1H, m), 4.26 (1H, m), 6.83 (1H, t, J=5.4 Hz), 7.94 (1H, s), 8.32, 8.34 (total 1H, s each) MS (TSP): 552 (M$^+$+H)

Example 311

1-(3,3-Dimethyl-1-butyloxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

The title compound (38.9 mg) was obtained from 200.0 mg of sodium(1S,5R,6S)-6-((1R)-1-hydroxyethyl)-1-methyl-2-(7-methylthioimidazo-[5,1-b]thiazol-2-yl)-1-carbapen-2-em-3-carboxylate and 453.0 mg of 1-(3,3-dimethyl-1-butyloxycarbonyloxy)ethyl iodide in the same manner as in Example 2, except that sodium hydrogencarbonate was not used in the reaction.

NMR (CDCl$_3$) δ: 0.84, 0.88 (total 9H, s each), 1.20 (3H, dd, J$_1$=7.3 Hz, J$_2$=1.7 Hz), 1.30, 1.33 (total 3H, d each, J=6.3 Hz), 1.49 (2H, m), 1.52, 1.58 (total 3H, d each, J=5.4 Hz), 3.25 (1H, dd, J$_1$=6.6 Hz, J$_2$=2.7 Hz), 3.35, 3.37 (total 1H, d each, J=7.3 Hz), 4.14 (2H, m), 4.20 (1H, m), 4.26 (1H, td, J$_1$=3.2 Hz, J$_2$=9.5 Hz), 6.87 (1H, m), 7.95, 7.96 (total 1H, s each), 8.31, 8.33 (total 1H, s each) MS (TSP): 552 (M$^+$+H)

Example 312

1-(2-Methoxybenzoyloxy)ethyl(1S,5R,6S)-6-((1R)-1-hydroxyethyl)-1-methyl-2-(7-methylthio-imidazo[5,1-b]thiazol-2-yl)-1-carbapen-2-em-3-carboxylate (A Mixture of Diastereomers)

Sodium(1S,5R,6S)-6-((1R)-1-hydroxyethyl)-1-methyl-2-(7-methylthioimidazo[5,1-b]thiazol-2-yl)-1-carbapen-2-em-3-carboxylate (170 mg) was dissolved in 2 ml of DMF. Triethylbenzylammonium chloride (193 mg) and 182 mg of 2-methoxybenzoyloxymethyl chloride were added to the solution in an argon atmosphere. The mixture was stirred under ice cooling for 2 hr and then stirred at room temperature for 5 hr. Ethyl acetate (30 ml) was added to the reaction solution. The mixture was washed twice with 20 ml of semisaturated brine. The organic layer was dried over anhydrous magnesium sulfate, filtered, and then concentrated to a volume of 5 ml under the reduced pressure. The residue was purified by column chromatography on silica gel (dichloromethane:methanol=40:1) to give 131 mg of the title compound.

NMR (CDCl$_3$) δ: 1.27 (3H, m), 1.37 (3H, m), 1.68, 1.72 (total 3H, d each, J=5.4 Hz), 2.42 (3H, s), 3.32 (1H, m), 3.40 (1H, m), 3.87, 3.90 (total 3H, s each), 4.30 (2H, m), 6.97 (2H, m), 7.27 (1H, m), 7.50 (1H, m), 7.88 (1H, m), 7.94 (1H, s), 8.30, 8.36 (total 1H, s each) MS (TSP): 558 (M$^+$+H)

Example 313

3,5-Dimethylbenzoyloxymethyl(1S,5R,6S)-6-((1R)-1-hydroxyethyl)-1-methyl-2-(7-methylthio-imidazo[5,1-b]thiazol-2-yl)-1-carbapen-2-em-3-carboxylate In the same manner as in Example 2, 130 mg of the title compound was obtained from 180 mg of sodium(1S,5R,6S)-6-((1R)-1-hydroxyethyl)-1-methyl-2-(7-methylthioimidazo

[5,1-b]thiazol-2-yl)-1-carbapen-2-em-3-carboxylate and 200 mg of 3,5-dimethylbenzoyloxymethyl iodide.

NMR (CDCl$_3$) δ: 1.28 (3H, d, J=7.4 Hz), 1.37 (3H, d, J=6.3 Hz), 2.04 (1H, m), 2.35 (6H, s), 2.43 (3H, s), 3.33 (1H, dd, J$_1$=6.6 Hz, J$_2$=2.9 Hz), 3.43 (1H, m), 4.29 (1H, m), 4.35 (1H, dd, J$_1$=9.8 Hz, J$_2$=2.9 Hz), 6.14, 6.18 (2H, ABq, J=5.6 Hz), 7.22 (1H, s), 7.68 (2H, s), 8.01 (1H, s), 8.30 (1H, S) MS (TSP): 542 (M$^4$+H)

Example 314

1-[2-(2-Propyl)phenoxycarbonyloxy]ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 150.0 mg of the title compound was obtained from 200.0 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 500 mg of 1-[2-(2-propyl)phenoxycarbonyloxy]ethyl iodide.

NMR (CDCl$_3$) δ: 1.17 (3H, d, J=6.9Hz), 1.22, 1.24 (total, 3H, d each, J=6.9 Hz), 1.28, 1.30 (total, 3H, d each, J=7.3 Hz), 1.38, 1.40 (total, 3H, d each, J=6.3 Hz), 1.69, 1.74 (total 3H, d each, J=5.4 Hz), 2.00 (1H, m), 2.43 (3H, s), 3.14 (1H, m), 3.33 (1H, m), 3.46 (1H, m), 4.28 (1H, m), 4.35 (1H, m), 7.01 (1H, m), 7.20 (4H, m), 8.00, 8.01 (total 1H, s each), 8.35, 8.37 (total 1H, s each) MS (FAB): 586 (M$^+$+H)

Example 315

(2,2-Dimethyl-1-propyloxycarbonyloxy)methyl(1S,5R,6S)-6-((1R)-1-hydroxyethyl)-1-methyl-2-(7-methylthioimidazo[5,1-b]thiazol-2-yl)-1-carbapen-2-em-3-carboxylate In the same manner as in Example 2, 161.6 mg of the title compound was obtained from 200.0 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 204.1 mg of (2,2-dimethyl-1-propyloxycarbonyloxy)methyl iodide.

NMR (CDCl$_3$) δ: 0.92 (9H, s), 1.27 (3H, d, J=7.3 Hz), 1.35 (3H, d, J=6.1 Hz), 2.42 (3H, s), 3.31 (1H, dd, J$_1$=6.9 Hz, J$_2$=2.6 Hz), 3.42 (1H, m), 3.86 (2H, s), 4.26 (1H, m), 4.33 (1H, dd, J$_1$=9.8 Hz, J$_2$=2.6 Hz), 5.89, 5.94 (2H, ABq, J=5.6 Hz), 8.01 (1H, s), 8.33 (1H, s) MS (TSP): 524 (M$^+$+H)

Example 316

1-(2-Ethyl-1-butyloxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

(1S,5R,6S)-6-((1R)-1-Hydroxyethyl)-1-methyl-2-(7-methylthioimidazo[5,1-b]thiazol-2-yl)-1-carbapen-2-em-3-carboxylic acid was prepared from sodium(1S,5R,6S)-6-((1R)-1-hydroxyethyl)-1-methyl-2-(7-methylthioimidazo[5,1-b]thiazol-2-yl)-1-carbapen-2-em-3-carboxylate and a 1.0 N aqueous hydrochloric acid solution. The title compound (33.5 mg) was obtained using this compound (103.0 mg), 123.7 mg of benzyltriethylammonium chloride, 113.3 mg of 1-(2-ethyl-1-butyloxycarbonyloxy)ethyl chloride, 54.9 mg of triethylamine, and 24 ml of DMF according to the method described in Publication No. 504039/1999 of the Translation of International Patent Application.

NMR (CDCl$_3$) δ: 0.80, 0.83 (total 6H, t each, J=7.3 Hz), 1.21 (3H, dd, J$_1$=7.3 Hz, J$_2$=3.0 Hz), 1.28 (1H, m), 1.32 (3H, m), 1.46 (4H, m), 1.52, 1.58 (total 3H, d each, J=5.6 Hz), 2.37 (3H, s), 3.25 (1H, m), 3.35, 3.37 (total 1H, t each, J=7.1 Hz), 4.01 (2H, m), 4.21 (1H, m), 4.26 (1H, td, J$_1$=2.7 Hz, J$_2$=9.7 Hz), 6.87 (1H, m), 7.95, 7.95 (total 1H, s each), 8.31, 8.33 (total 1H, s each) MS (TSP): 552 (M$^+$+H)

Example 317

1-(3-Methyl-1-butyloxycarbonyloxy)-1-propyl(1S,5R,6S)-6-((1R)-1-hydroxyethyl)-1-methyl-2-(7-methylthioimidazo[5,1-b]thiazol-2-yl,)-1-carbapen-2-em-3-carboxylate (A Mixture of Diastereomers)

In the same manner as in Example 310, 38.5 mg of the title compound was obtained from 200.0 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 307.2 mg of 1-(3-methyl-1-butyloxycarbonyloxy)-1-propyl chloride.

NMR (CDCl$_3$) δ: 0.82, 0.86 (total 6H, dd each, J$_1$=6.6 Hz, J$_2$=1.3 Hz), 0.93, 1.00 (total 3H, t each, J=7.5 Hz), 1.22 (3H, dd, J$_1$=7.3 Hz, J$_2$=2.9 Hz), 1.26, 1.29 (total 3H, d each, J=6.3 Hz), 1.47, 1.53 (total 2H, q each, J=6.8 Hz), 1.68 (1H, m), 1.91 (2H, m), 2.36 (3H, s), 3.25 (1H, m), 3.36 (1H, m), 4.14 (2H, m), 4.21 (1H, m), 4.26 (1H, m), 6.72, 6.74 (total 1H, t each, J=5.6 Hz), 7.95, 7.95 (total 1H, s each), 8.32, 8.34 (total 1H, s each) MS (TSP): 552 (M$^+$+H)

Example 318

1-(2,6-Dimethylphenoxycarbonyloxy)methyl(1S,5R,6S)-6-((1R)-1-hydroxyethyl)-1-methyl-2-(7-methylthioimidazo[5,1-b]thiazol-2-yl)-1-carbapen-2-em-3-carboxylate In the same manner as in Example 2, 223.0 mg of the title compound was obtained from 200.0 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 500 mg of 1-(2,6-dimethylphenoxycarbonyloxy)methyl iodide.

NMR (CDCl$_3$) δ: 1.29 (3H, d, J=7.3 Hz), 1.38 (3H, d, J=6.3 Hz), 2.15 (1H, br d), 2.19 (6H, s), 2.44 (3H, s), 3.33 (1H, dd, J$_1$=6.6 Hz, J$_2$=2.8 Hz), 3.44 (1H, m), 4.30 (1H, m), 4.36 (1H, dd, J$_1$=9.6 Hz, J$_2$=2.8 Hz), 6.04 (2H, ABq, J=5.9 Hz), 7.05 (3H, m), 8.00, 8.00 (1H, s), 8.34 (1H, s) MS (TSP): 558 (M$^+$+H)

Example 319

1-(2,3,5-Trimethylphenoxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 156.0 mg of the title compound was obtained from 200.0 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 500 mg of 1-(2,3,5-trimethylphenoxycarbonyloxy)ethyl iodide.

NMR (CDCl$_3$) δ: 1.28, 1.30 (total, 3H, d each, J=7.3 Hz), 1.38, 1.40 (total, 3H, d each, J=6.3 Hz), 1.69, 1.74 (total 3H, d each, J=5.4 Hz), 1.99 (1H, m), 2.03, 2.11 (total 3H, s each), 2.25 (6H, m), 2.43 (3H, s), 3.33 (1H, m), 3.46 (1H, m), 4.28 (1H, m), 4.35 (1H, m), 6.77, 6.95 (total 1H, s each), 6.88 (1H, s), 7.01 (1H, m), 8.00, 8.01 (total 1H, s each), 8.33, 8.37 (total 1H, s each) MS (TSP): 586 (M$^+$+H)

Example 320

2-Naphthylcarbonyloxymethyl(1S,5R,6S)-6-((1R)-1-hydroxyethyl)-1-methyl-2-(7-methylthio-imidazo[5,1-b]thiazol-2-yl)-1-carbapen-2-em-3-carboxylate In the same manner as in Example 2, 95 mg of the title compound was obtained from 201 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 201 mg of 2-naphthylcarbonyloxymethyl iodide.

NMR (CDCl$_3$) δ: 1.28 (3H, d, J=7.2 Hz), 1.36 (3H, d, J=6.2 Hz), 2.41 (3H, s), 3.34 (1H, dd, J$_1$=6.6 Hz, J$_2$=2.7 Hz), 3.42 (1H, m), 4.30 (1H, m), 4.35 (1H, dd, J$_1$=9.7 Hz, J$_2$=2.7 Hz), 6.24 (2H, s), 7.57 (2H, m), 7.87–8.08 (5H, m), 8.32 (1H, s), 8.66 (1H, s) MS (TSP): 564 (M$^+$+H)

Example 321

2,5-Dimethylbenzoyloxymethyl(1S,5R,6S)-6-((1R)-1-hydroxyethyl)-1-methyl-2-(7-methylthio-imidazo[5,1-b]thiazol-2-yl)-1-carbapen-2-em-3-carboxylate In the same manner as in Example 2, 155 mg of the title compound was obtained from 182 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 263 mg of 2,5-dimethylbenzoyloxymethyl iodide.

NMR (CDCl$_3$) δ: 1.28 (3H, d, J=7.1 Hz), 1.37 (3H, d, J=6.2 Hz), 2.12 (1H, m), 2.33 (3H, s), 2.43 (3H, s), 2.55 (3H, s), 3.33 (1H, dd, J$_1$=6.6 Hz, J$_2$=2.8 Hz), 3.45 (1H, m), 4.29 (1H, m), 4.34 (1H, dd, J$_1$=9.6 Hz, J$_2$=2.8 Hz), 6.15 (2H, s), 7.13 (2H, d, J=7.7 Hz), 7.23 (2H, d, J=7.7 Hz), 7.79 (1H, s), 8.00 (1H, s), 8.31 (1H, s) MS (TSP): 542 (M$^+$+H)

Example 322

Cyclohexyloxycarbonyloxymethyl(1S,5R,6S)-2-[7-(N,N-dimethylaminosulfonyl)imidazo[5,1-b]thiazol-2-yl]-6-((1R)-1-hydroxyethyl)-1-methyl-1-carbapen-2-em-3-carboxylate In the same manner as in Example 2, 322 mg of the title compound was obtained from 255 mg of sodium(1S,5R,6S)-2-[7-(N,N-dimethylaminosulfonyl)-imidazo[5,1-b]thiazol-2-yl]-6-((1R)-1-hydroxyethyl)-1-methyl-1-carbapen-2-em-3-carboxylate and 316 mg of cyclohexyloxycarbonyloxymethyl iodide.

NMR (CDCl$_3$) δ: 1.26 (3H, d, J=7.4 Hz), 1.26–1.96 (10H, m), 1.35 (3H, d, J=6.2 Hz), 2.59 (1H, br.s), 2.86 (6H, s), 3.33 (1H, dd, J$_1$=6.6 Hz, J$_2$=2.7 Hz), 3.47 (1H, m), 4.27 (1H, m), 4.35 (1H, dd, J$_1$=9.8 Hz, J$_2$=2.7 Hz), 4.65 (1H, m), 5.89, 5.94 (2H, ABq, J=5.8 Hz), 8.08 (1H, s), 8.48 (1H, s) MS (TSP): 597 (M$^+$+H)

Example 323

2-Methyl-1-(phenoxycarbonyloxy)-1-propyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 16.0 mg of the title compound was obtained from 200.0 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 500 mg of 2-methyl-1-(phenoxycarbonyloxy)-1-propyl iodide.

NMR (CDCl$_3$) δ: 1.04, 1.08 (total, 3H, d each, J=6.9 Hz), 1.14 (1H, d, J=6.9 Hz), 1.28, 1.30 (total, 3H, d each, J=7.3 Hz), 1.38, 1.40 (total, 3H, d each, J=6.3 Hz), 2.22 (2H, m), 2.43 (3H, s), 3.33 (1H, m), 3.46 (1H, m), 4.28 (1H, m), 4.35 (1H, m), 6.71, 6.76 (total 1H, d each, J=5.4 Hz), 7.28 (5H, m), 8.00 (1H, s), 8.38, 8.39 (total 1H, s each) MS (TSP): 572 (M$^+$+H)

Example 324

1-(1-Naphthoxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 171.0 mg of the title compound was obtained from 200.0 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 500 mg of 1-(1-naphthoxycarbonyloxy)ethyl iodide.

NMR (CDCl$_3$) δ: 1.28, 1.30 (total 3H, d each, J=7.3 Hz), 1.38, 1.40 (total 3H, d each, J=6.3 Hz), 1.69, 1.74 (total 3H, d each, J=5.4 Hz), 2.12, 2.18 (total 1H, d each, J=4.8 Hz), 2.43 (3H, s), 3.33 (1H, m), 3.46 (1H, m), 4.28 (1H, m), 4.35 (1H, m), 7.06 (1H, m), 7.46 (4H, m), 7.90 (3H, m), 7.98, 7.99 (total 1H, s each), 8.32, 8.33 (total 1H, s each) MS (TSP): 594 (M$^+$+H)

Example 325

1-[2-(1-Propyl)phenoxycarbonyloxyl]ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 177.0 mg of the title compound was obtained from 200.0 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 500 mg of 1-[2-(1-propyl)phenoxycarbonyloxy]ethyl iodide.

NMR (CDCl$_3$) δ: 0.85, 0.95 (total 3H, d each, J=7.3 Hz), 1.28, 1.30 (total 3H, d each, J=7.3 Hz), 1.38, 1.40 (total 3H, d each, J=6.3 Hz), 1.57 (2H, m), 1.69, 1.74 (total 3H, d each, J=5.4 Hz), 1.93 (1H, m), 2.43 (3H, s), 3.33 (1H, m), 3.46 (1H, m), 4.28 (1H, m), 4.35 (1H, m) 7.02 (1H, m), 7.20 (4H, m), 8.00, 8.01 (total 1H, s each), 8.36, 8.38 (total 1H, s each) MS (TSP): 586 (M$^+$+H)

Example 326

(2-Ethylphenoxycarbonyloxy)ethyl(1S,5R, 6S)-2-(7-acetylimidazo[5,1-b]thiazol-2-yl)-6-((1R)-1-hydroxyethyl)-1-methyl-1-carbapen-2-em-3-carboxylate (A Mixture of Diastereomers)

In the same manner as in Example 2, 196.0 mg of the title compound was obtained from 200.0 mg of sodium(1S,5R,6S)-2-(7-acetylimidazo[5,1-b]thiazol-2-yl)-6-((1R)-1-hydroxyethyl)-1-methyl-1-carbapen-2-em-3-carboxylate and 500 mg of 1-(2-ethyl-phenoxycarbonyloxy)ethyl iodide.

NMR (CDCl₃) δ: 1.12, 1.21 (total 3H, d each, J=7.3 Hz), 1.28, 1.30 (total 3H, d each, J=7.3 Hz), 1.38, 1.40 (total 3H, d each, J=6.3 Hz), 1.69, 1.74 (total 3H, d each, J=5.4 Hz), 1.93 (1H, m), 2.55, 2.66 (total 3H, q each, J=7.3 Hz), 2.62 (3H, s), 3.33 (1H, m), 3.46 (1H, m), 4.28 (1H, m), 4.35 (1H, m), 7.02 (1H, m), 7.20 (4H, m), 7.99, 8.00 (total 1H, s each), 8.58, 8.62 (total 1H, s each) MS (TSP): 568 (M⁺+H)

Example 327

(2-Ethylphenoxycarbonyloxy)ethyl(1S,5R,6S)-2-[7-(N,N-dimethylaminosulfonyl)imidazo[5,1-b]thiazol-2-yl]6-((1R)-1-hydroxyethyl)-1-methyl-1-carbapen-2-em-3-carboxylate (A Mixture of Diastereomers)

In the same manner as in Example 2, 147.0 mg of the title compound was obtained from 200.0 mg of sodium(1S,5R,6S)-2-[7-(N,N-dimethylaminosulfonyl)-imidazo[5,1-b]thiazol-2-yl]-6-((1R)-1-hydroxyethyl)-1-methyl-1-carbapen-2-em-3-carboxylate and 500 mg of 1-(2-ethyl-phenoxycarbonyloxy)ethyl iodide.

NMR (CDCl₃) δ: 1.12, 1.21 (total 3H, d each, J=7.3 Hz), 1.28, 1.30 (total 3H, d each, J=7.3 Hz), 1.38, 1.40 (total 3H, d each, J=6.3 Hz), 1.69, 1.74 (total 3H, d each, J=5.4 Hz), 2.02 (1H, m), 2.55, 2.66 (total 3H, q each, J=7.3 Hz), 2.86 (6H, s), 3.33 (1H, m), 3.46 (1H, m), 4.28 (1H, m), 4.35 (1H, m), 7.02 (1H, m), 7.20 (4H, m), 8.03, 8.04 (total 1H, s each), 8.49, 8.53 (total 1H, s each) MS (TSP): 633 (M⁺+H)

Example 328

Pivaloyloxymethyl(1S,5R,6S)-6-((1R)-1-hydroxyethyl)-1-methyl-2-(7-methylsulfinyl-imidazo[5,1-b]thiazol-2-yl)-1-carbapen-2-em-3-carboxylate (A Mixture of Diastereomers)

In the same manner as in Example 2, 120.0 mg of the title compound was obtained from 200.0 mg of sodium(1S,5R,6S)-6-((1R)-1-hydroxyethyl)-1-methyl-2-(7-methylsulfinylimidazo[5,1-b]thiazol-2-yl)-1-carbapen-2-em-3-carboxylate (A Mixture of Diastereomers) and 173 mg of pivaloyloxymethyl iodide.

NMR (CDCl₃) δ: 1.20, 1.21 (total 9H, s each), 1.24 (3H, m), 1.35, 1.38 (total 3H, d each, J=6.3 Hz), 2.95, 2.97 (total 3H, s each), 3.33 (1H, m), 3.46 (1H, m), 4.28 (1H, m), 4.35 (1H, m), 5.88, 5.87, 5.99 (total 2H, ABq each, J=5.6 Hz), 8.11 (1H, s), 8.47, 8.48 (total 1H, s each) MS (TSP): 510 (M⁺+H)

Example 329

1-(2-Benzyloxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 310, 22.8 mg of the title compound was obtained from 200.0 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 160.1 mg of 1-(2-benzyloxycarbonyloxy)ethyl chloride.

NMR (CDCl₃) δ: 1.21 (3H, d, J=7.3 Hz), 1.30, 1.31 (total 3H, d each, J=6.1 Hz), 1.52, 1.57 (total 3H, d each, J=5.6 Hz), 2.37 (total 3H, s each), 3.26 (1H, m), 3.36 (1H, m), 4.22 (1H, m), 4.26 (1H, dt, J₁=9.5 Hz, J₂=2.7 Hz), 6.88 (1H, m), 7.24–7.36 (5H, m), 7.94, 7.95 (total 1H, s each), 8.29, 8.29 (total 1H, s each) MS (TSP): 558 (M⁺+H)

Example 330

1-(2-Methyl-1-propyloxycarbonyloxy)ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 310, 24.9 mg of the title compound was obtained from 200.0 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 1-(2-methyl-1-propyloxycarbonyloxy)ethyl chloride.

NMR (CDCl₃) δ: 0.85, 0.89 (total 6H, d each, J=6.6 Hz), 1.20, 1.22 (total 3H, dd each, J₁=3.7 Hz, J₂=7.3 Hz), 1.29, 1.32 (total 3H, d each, J=6.3 Hz), 1.53, 1.68 (total 3H, d each, J=5.6 Hz), 1.91 (1H, m), 2.36 (3H, s), 3.26 (1H, m), 3.36 (1H, qd, J₁=7.3 Hz, J₂=9.5 Hz), 3.86, 3.92 (total 2H, brd each, J=6.6 Hz), 4.22 (1H, m), 4.27 (1H, m), 6.87 (1H, m), 7.65, 7.65 (total 1H, s each), 8.31, 8.32 (total 1H, s each) MS (TSP): 524 (M⁺+H)

Example 331

4-(N,N-di-n-propylaminosulfonyl)benzoyl-oxymethyl(1S,5R,6S)-6-((1R)-1-hydroxyethyl)-1-methyl-2-(7-methylthioimidazo[5,1-b]thiazol-2-yl)-1-carbapen-2-em-3-carboxylate In the same manner as in Example 2, 298 mg of the title compound was obtained from 201 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 365 mg of 4-(N,N-di-n-propylaminosulfonyl)benzoyloxymethyl iodide.

NMR (CDCl₃) δ: 0.86 (6H, t, J=7.4 Hz), 1.29 (3H, d, J=7.4 Hz), 1.36 (3H, d, J=6.2 Hz), 1.54 (4H, m), 2.19 (1H, br.s), 2.44 (3H, s), 3.09 (6H, t, J=7.6 Hz), 3.33 (1H, dd, J₁=6.7 Hz, J₂=2.8 Hz), 3.46 (1H, m), 4.29 (1H, m), 4.36 (1H, dd, J₁=9.7 Hz, J₂=2.8 Hz), 6.16, 6.22 (2H, ABq, J=5.6 Hz), 7.88 (2H, d, J=7.9 Hz), 8.05 (1H, s), 8.19 (2H, d, J=7.9 Hz), 8.32 (1H, s) MS (TSP): 677 (M⁺+H)

Example 332

1-[4-(N,N-Di-n-propylaminosulfonyl)benzoyl-oxy]ethyl(1S,5R,6S)-6-((1R)-1-hydroxyethyl)-1-methyl-2-(7-methylthioimidazo[5,1-b]thiazol-2-yl)-1-carbapen-2-em-3-carboxylate (A Mixture of Diastereomers)

In the same manner as in Example 2, 187 mg of the title compound was obtained from 228 mg of sodium(1S,5R,6S)-6-((1R)-1-hydroxyethyl)-1-methyl-2-(7-methylthioimidazo[5,1-b]thiazol-2-yl)-1-carbapen-2-em-3-carboxylate and 625 mg of 1-[4-(N,N-di-n-propylaminosulfonyl)benzoyloxy]ethyl iodide.

NMR (CDCl₃) δ: 0.86 (6H, m), 1.26, 1.28 (total 3H, d each, J=7.3 Hz), 1.33, 1.37 (total 3H, d each, J=6.2 Hz), 1.53 (4H, m), 1.71, 1.76 (total 3H, d each, J=5.5 Hz), 2.40, 2.41 (total 3H, s each), 3.08 (4H, m), 3.33 (1H, m), 3.44 (1H, m), 4.27 (1H, m), 4.35 (1H, m), 7.29 (1H, m), 7.86 (2H, m), 8.01 (1H, s), 8.14, 8.21 (total 2H, d each, J=8.8 Hz), 8.32, 8.35 (total 1H, s each) MS (TSP): 691 (M⁺+H)

The compounds prepared in the above examples had the following structures.

In the following table, * represents bonding to the 2-position of the carbapenem ring. POM represents pivaloyloxymethyl.

| EXAMPLE | $R^1$ | $R^2$ | $R^3$ | $R^4$ | $R^5$ | R |
|---|---|---|---|---|---|---|
| 1 | $CH_3$ | * | H | H | $C(O)CH_2CH_3$ | Na |
| 2 | $CH_3$ | * | H | H | $C(O)CH_2CH_3$ | $CH_2CH_3$-$OC(O)C(CH_3)_2CH_3$ |
| 3 | $CH_3$ | * | H | H | CH=NOH (Derived from low-polarity side chain component) | Na |
| 4 | H | H | * | H | CH=NOCH$_3$ (Derived from low-polarity side chain component) | Na |
| 5 | H | H | * | H | CH=NOCH$_3$ (Derived from low-polarity side chain component) | $CH_2CH_3$-$OC(O)C(CH_3)_2CH_3$ |
| 6 | $CH_3$ | * | H | H | $C(O)C(CH_3)_3$ | Na |
| 7 | $CH_3$ | * | H | H | $C(O)C(CH_3)_3$ | $CH_2CH_3$-$OC(O)C(CH_3)_2CH_3$ |
| 8 | H | * | $CH_3$ | H | $C(O)CH_3$ | Na |
| 9 | H | * | $CH_3$ | H | $C(O)CH_3$ | $CH_2CH_3$-$OC(O)C(CH_3)_2CH_3$ |
| 10 | $CH_3$ | * | H | H | $C(O)CH(CH_3)NHCHO$ (High polarity component) | Na |
| 11 | $CH_3$ | * | H | H | $C(O)CH(CH_3)NHCHO$ (Low polarity component) | Na |
| 12 | $CH_3$ | * | H | H | $C(O)CH(CH_3)_2$ | Na |
| 13 | $CH_3$ | * | H | H | $C(O)CH(CH_3)_2$ | $CH_2CH_3$-$OC(O)C(CH_3)_2CH_3$ |
| 14 | H | H | * | H | $C(O)CH_2CH_3$ | Na |
| 15 | H | * | H | H | $C(O)CH_3$ | Na |
| 16 | H | * | H | H | $C(O)CH_3$ | $CH_2CH_3$-$OC(O)C(CH_3)_2CH_3$ |
| 17 | H | * | H | H | $C(O)CH(CH_3)_2$ | Na |
| 18 | H | * | H | H | $C(O)CH(CH_3)_2$ | $CH_2CH_3$-$OC(O)C(CH_3)_2CH_3$ |
| 19 | $CH_3$ | * | H | $CH_3$ | $C(O)CH_3$ | Na |

-continued

| EXAMPLE | R¹ | R² | R³ | R⁴ | R⁵ | R |
|---|---|---|---|---|---|---|
| 20 | CH₃ | * | H | CH₃ | C(O)CH₃ | 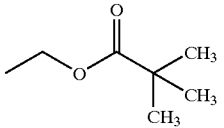 |
| 21 | CH₃ | * | CH₃ | H | C(O)CH₃ | Na |
| 22 | CH₃ | * | CH₃ | H | C(O)CH₃ | 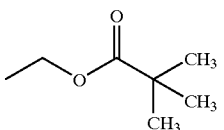 |
| 23 | H | * | H | H | SO₂CH₃ | Na |
| 24 | H | H | * | H | SO₂CH₃ | Na |
| 25 | CH₃ | H | * | H | SO₂CH₃ | Na |
| 26 | CH₃ | * | H | H | S(O)CH₃ | Na |
| 27 | H | * | H | H | C(O)CH₂CH₃ | Na |
| 28 | H | * | H | H | C(O)CH₂CH₃ | 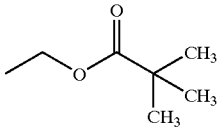 |
| 29 | H | H | * | H | C(O)CH₃ | 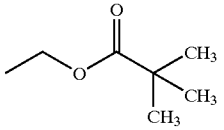 |
| 30 | CH₃ | * | H | H | SO₂CH₂CH₃ | Na |
| 31 | CH₃ | * | H | H | SO₂NHCH₃ | Na |
| 32 | H | * | H | H | SO₂NHCH₃ | Na |
| 33 | H | * | H | CH₃ | C(O)CH₃ | Na |
| 34 | H | * | H | H | SO₂CH₂CH₃ | Na |
| 35 | CH₃ | * | H | H | 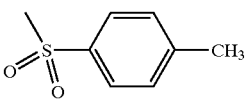 | Na |
| 36 | H | * | H | H | C(O)CH₂OH | Na |
| 37 | CH₃ | * | H | H | C(O)Ph | Na |
| 38 | H | H | * | H | C(O)CH₂OH | Na |
| 39 | H | * | H | H | C(O)Ph | Na |
| 40 | CH₃ | * | H | H | 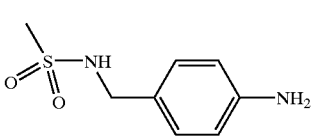 | Na |
| 41 | CH₃ | * | H | H | F | Na |
| 42 | CH₃ | * | H | H | SO₂N(CH₃)CH₂CH₂OH | Na |
| 43 | CH₃ | * | H | H | C(O)CH₂NHC(O)CH₃ | Na |
| 44 | CH₃ | * | H | CH₃ | SO₂CH₃ | Na |
| 45 | CH₃ | * | H | CH₃ | S(O)CH₃ | Na |
| 46 | CH₃ | * | H | H | C(O)CH₃ | 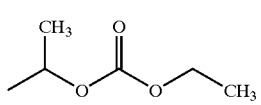 |
| 47 | CH₃ | * | H | H | C(O)CH₃ | 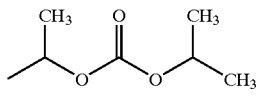 |

-continued
| EXAMPLE | R¹ | R² | R³ | R⁴ | R⁵ | R |
|---|---|---|---|---|---|---|
| 48 | CH₃ | * | H | H | C(O)CH₃ | 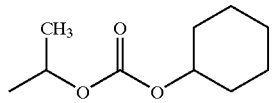 |
| 49 | CH₃ | * | H | H | C(O)CH₃ | 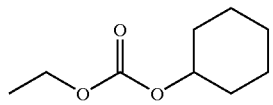 |
| 50 | CH₃ | * | H | H | C(O)CH₃ | 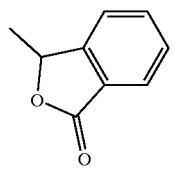 |
| 51 | CH₃ | * | H | H | C(O)CH₃ | 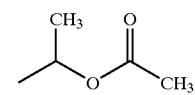 |
| 52 | CH₃ | * | H | H | C(O)CH₃ | 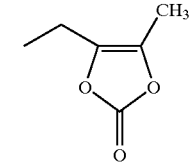 |
| 53 | CH₃ | * | H | H | CH₂NHC(O)CH₃ | Na |
| 54 | CH₃ | * | H | H | CH₂NHC(O)CH₃ | 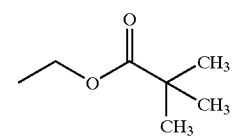 |
| 55 | CH₃ | * | H | H | CH₂NHC(O)CH₃ | 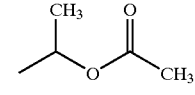 |
| 56 | CH₃ | * | H | H | CH₂NHC(O)CH₃ | 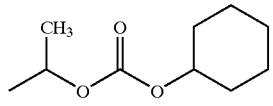 |
| 57 | CH₃ | * | H | H | CH₂NHC(O)CH₃ | 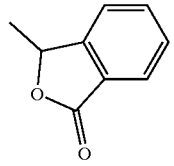 |
| 58 | CH₃ | * | H | H | CH₂NHC(O)CH₃ | 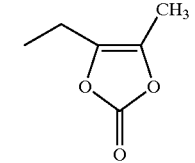 |

-continued

| EXAMPLE | R¹ | R² | R³ | R⁴ | R⁵ | R |
|---|---|---|---|---|---|---|
| 59 | CH₃ | * | H | H | CH₂NHC(O)CH₃ | isopropyl (cyclohexylmethyl) carbonate |
| 60 | CH₃ | * | H | H | CH₂NHC(O)CH₃ | ethyl menthyl carbonate |
| 61 | CH₃ | * | H | H | CH₂NHC(O)CH₃ | sec-butyl cyclohexyl carbonate |
| 62 | CH₃ | * | H | H | SO₂CH₃ | Na |
| 63 | CH₃ | * | H | H | SO₂CH₃ | ethyl pivalate |
| 64 | CH₃ | * | H | H | SO₂CH₃ | isopropyl acetate |
| 65 | CH₃ | * | H | H | SO₂CH₃ | isopropyl cyclohexyl carbonate |
| 66 | CH₃ | * | H | H | SO₂CH₃ | 3-methylphthalide |
| 67 | CH₃ | * | H | H | SO₂CH₃ | 4-ethyl-5-methyl-1,3-dioxol-2-one |
| 68 | CH₃ | * | H | H | SO₂CH₃ | isopropyl (cyclohexylmethyl) carbonate |
| 69 | CH₃ | * | H | H | SO₂CH₃ | ethyl 1-methylcyclohexanecarboxylate |

-continued
| EXAMPLE | R¹ | R² | R³ | R⁴ | R⁵ | R |
|---|---|---|---|---|---|---|
| 70 | CH₃ | * | H | H | SO₂CH₃ | 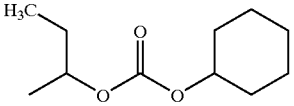 |
| 71 | CH₃ | * | H | H | C(O)CH₂OH | Na |
| 72 | CH₃ | * | H | H | C(O)CH₂OH | 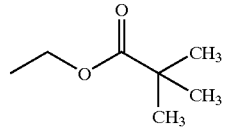 |
| 73 | CH₃ | * | H | H | C(O)CH₂OH | 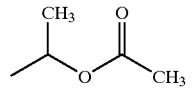 |
| 74 | CH₃ | * | H | H | C(O)CH₂OH | 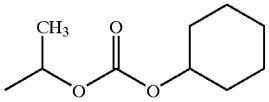 |
| 75 | CH₃ | * | H | H | C(O)CH₂OH | 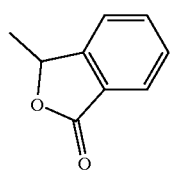 |
| 76 | CH₃ | * | H | H | C(O)CH₂OH | 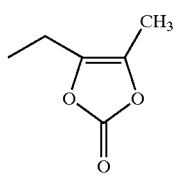 |
| 77 | CH₃ | * | H | H | C(O)CH₂OH | 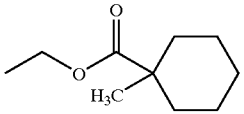 |
| 78 | CH₃ | * | H | H | C(O)CH₂OH | 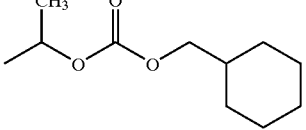 |
| 79 | CH₃ | * | H | H | C(O)CH₂OH | 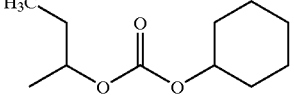 |
| 80 | CH₃ | * | H | H | C(O)CH₂C(O)N(CH₃)₂ | Na |
| 81 | CH₃ | * | H | H | C(O)CH₂C(O)N(CH₃)₂ | 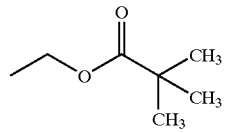 |

-continued
| EXAMPLE | R¹ | R² | R³ | R⁴ | R⁵ | R |
|---|---|---|---|---|---|---|
| 82 | CH₃ | * | H | H | C(O)CH₂C(O)N(CH₃)₂ | 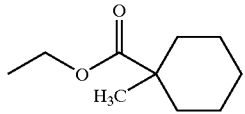 |
| 83 | CH₃ | * | H | H | C(O)CH₂C(O)N(CH₃)₂ | 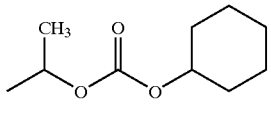 |
| 84 | CH₃ | * | H | H | C(O)CH₂C(O)N(CH₃)₂ | 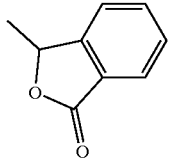 |
| 85 | CH₃ | * | H | H | C(O)CH₂C(O)N(CH₃)₂ | 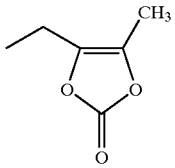 |
| 86 | CH₃ | * | H | H | C(O)CH₂C(O)N(CH₃)₂ | 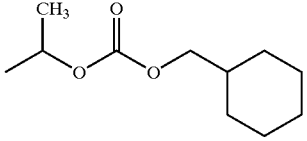 |
| 87 | CH₃ | * | H | H | C(O)CH₂C(O)N(CH₃)₂ | 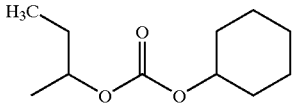 |
| 88 | CH₃ | * | H | H | SO₂N(CH₃)₂ | Na |
| 89 | CH₃ | * | H | H | SO₂N(CH₃)₂ | 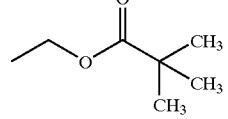 |
| 90 | CH₃ | * | H | H | SO₂N(CH₃)₂ | 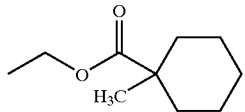 |
| 91 | CH₃ | * | H | H | SO₂N(CH₃)₂ | 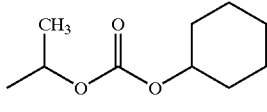 |
| 92 | CH₃ | * | H | H | SO₂N(CH₃)₂ | 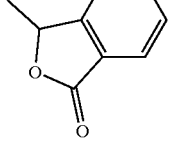 |

-continued

| EXAMPLE | R¹ | R² | R³ | R⁴ | R⁵ | R |
|---|---|---|---|---|---|---|
| 93 | $CH_3$ | * | H | H | $SO_2N(CH_3)_2$ | 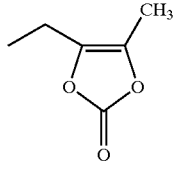 |
| 94 | $CH_3$ | * | H | H | $SO_2N(CH_3)_2$ | 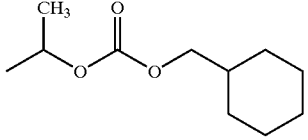 |
| 95 | $CH_3$ | * | H | H | $SO_2N(CH_3)_2$ | 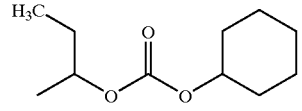 |
| 96 | $CH_3$ | * | H | H | $CO_2CH_3$ | Na |
| 97 | $CH_3$ | * | H | H | $SO_2NCH_3(OCH_3)$ | Na |
| 98 | $CH_3$ | * | H | H | $C(O)CF_3$ | Na |
| 99 | $CH_3$ | * | H | H | $SO_2NH_2$ | Na |
| 100 | $CH_3$ | * | H | H | 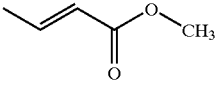 | Na |
| 101 | $CH_3$ | * | H | H | 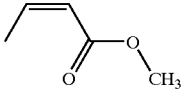 | Na |
| 102 | $CH_3$ | * | H | H | 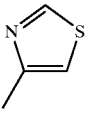 | Na |
| 103 | $CH_3$ | * | H | $CH_3$ | $C(O)CH_2OH$ | Na |
| 104 | H | * | H | $CH_3$ | $SO_2CH_3$ | Na |
| 105 | H | * | H | $CH_3$ | $S(O)CH_3$ | Na |
| 106 | H | * | H | $CH_3$ | $C(O)CH_2OH$ | Na |
| 107 | $CH_3$ | * | H | $CH_3$ | $SO_2CH_3$ | 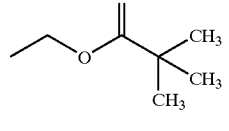 |
| 108 | $CH_3$ | * | H | H | $C(O)CH_2NHSO_2CH_3$ | Na |
| 109 | $CH_3$ | * | H | $CH_3$ | $SCH_3$ | Na |
| 110 | $CH_3$ | * | H | H | $CH_2NHSO_2CH_3$ | Na |
| 111 | $CH_3$ | * | H | H | $SCH_3$ | Na |
| 112 | H | * | H | H | $SO_2N(CH_3)_2$ | Na |
| 113 | H | * | H | H | $SO_2NH_2$ | Na |
| 114 | $CH_3$ | * | H | H | (E)-CH=CHC(O)$CH_3$ | Na |
| 115 | $CH_3$ | * | H | $CH_3$ | CHO | Na |
| 116 | H | * | H | H | $SCH_3$ | Na |
| 117 | H | * | H | H | $S(O)CH_3$ | Na |
| 118 | H | * | H | H | $C(O)CH_2NHSO_2N(CH_3)_2$ | Na |
| 119 | $CH_3$ | * | H | H | $C(O)CH_2NHSO_2N(CH_3)_2$ | Na |
| 120 | H | * | H | $CH_3$ | $SCH_3$ | Na |
| 121 | $CH_3$ | * | H | H | $C(O)CH_2NH_2$ | Na |
| 122 | $CH_3$ | * | H | H | $CH_2NH_2$ | Na |
| 123 | $CH_3$ | * | H | H | $C(O)CH_2NHSO_2CH_2CH_2NH_2$ | Na |
| 124 | H | * | H | H | $C(O)CH_2NHSO_2CH_2CH_2NH_2$ | Na |
| 125 | $CH_3$ | * | H | $SO_2CH_3$ | H | Na |
| 126 | $CH_3$ | * | H | $SCH_3$ | H | Na |
| 127 | $CH_3$ | * | H | $SCH_3$ | $SCH_3$ | Na |

-continued

| EXAMPLE | R¹ | R² | R³ | R⁴ | R⁵ | R |
|---|---|---|---|---|---|---|
| 128 | CH₃ | * | H | H | SPh | Na |
| 129 | H | H | * | H | SCH₃ | Na |
| 130 | H | * | H | H | SPh | Na |
| 131 | CH₃ | * | SCH₃ | H | H | Na |
| 132 | CH₃ | * | H | H | SCH₂CH₃ | Na |
| 133 | H | * | SCH₃ | H | H | Na |
| 134 | H | * | H | H | SCH₂CH₃ | Na |
| 135 | H | * | CH₃ | H | SCH₃ | Na |
| 136 | CH₃ | * | H | SCH₃ | S(O)CH₃ | Na |
| 137 | H | * | CH₂OH | H | SCH₃ | Na |
| 138 | H | * | Ph | H | H | Na |
| 139 | H | * | H | H | C(O)CH₂NH₂ | Na |
| 140 | CH₃ | * | H | S(O)CH₃ | H | Na |
| 141 | CH₃ | * | H | S(O)CH₃ | S(O)CH₃ | Na |
| 142 | CH₃ | * | H | S(O)CH₃ | SO₂CH₃ | Na |
| 143 | CH₃ | * | H | SO₂CH₃ | SO₂CH₃ | Na |
| 144 | H | * | CH₂NH₂ | H | H | Na |
| 145 | H | * | CH₂OH | H | H | Na |
| 146 | H | * | H | SCH₃ | SCH₃ | Na |
| 147 | CH₃ | * | H | C(O)CH₃ | SCH₃ | Na |
| 148 | CH₃ | * | SCH₃ | H | SCH₃ | Na |
| 149 | CH₃ | * | H | C(O)CH₃ | SO₂CH₃ | Na |
| 150 | CH₃ | * | H | Br | SCH₃ | Na |
| 151 | H | * | H | C(O)CH₃ | SCH₃ | Na |
| 152 | CH₃ | * | H | CN | SCH₃ | Na |
| 153 | H | * | SCH₃ | H | SCH₃ | Na |
| 154 | CH₃ | * | H | Cl | SCH₃ | Na |
| 155 | H | * | H | CN | SCH₃ | Na |
| 156 | CH₃ | * | H | H | SCH₂CH₂CH₃ | Na |
| 157 | H | * | H | H | SCH₂CH₂CH₃ | Na |
| 158 | CH₃ | * | H | H | SCH(CH₃)₂ | Na |
| 159 | H | * | H | H | SCH(CH₃)₂ | Na |
| 160 | CH₃ | * | H | CH₃ | SO₂CH₃ | 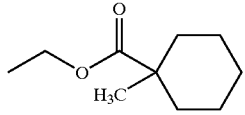 |
| 161 | CH₃ | * | H | CH₃ | SO₂CH₃ | 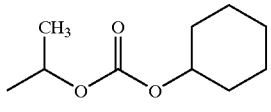 |
| 162 | CH₃ | * | H | CH₃ | SO₂CH₃ | 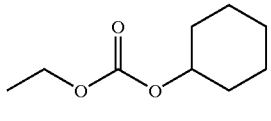 |
| 163 | CH₃ | * | H | CH₃ | SO₂CH₃ | 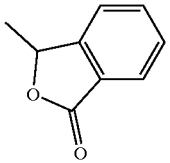 |
| 164 | CH₃ | * | H | CH₃ | SO₂CH₃ | 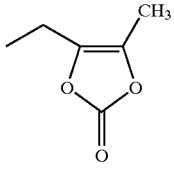 |
| 165 | CH₃ | * | H | CH₃ | SO₂CH₃ | 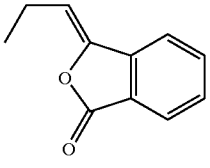 |

-continued
| EXAMPLE | R$^1$ | R$^2$ | R$^3$ | R$^4$ | R$^5$ | R |
| --- | --- | --- | --- | --- | --- | --- |
| 166 | CH$_3$ | * | H | CH$_3$ | C(O)CH$_3$ | 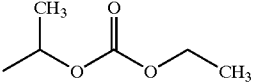 |
| 167 | CH$_3$ | * | H | CH$_3$ | C(O)CH$_3$ | 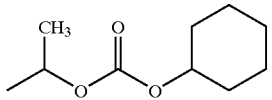 |
| 168 | CH$_3$ | * | H | CH$_3$ | C(O)CH$_3$ | 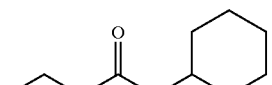 |
| 169 | CH$_3$ | * | H | CH$_3$ | C(O)CH$_3$ | 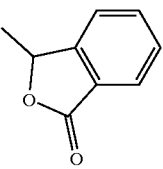 |
| 170 | CH$_3$ | * | H | CH$_3$ | C(O)CH$_3$ | 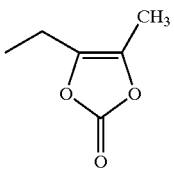 |
| 171 | CH$_3$ | * | H | CH$_3$ | C(O)CH$_3$ | 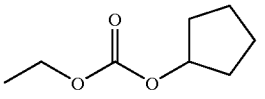 |
| 172 | CH$_3$ | * | H | H | C(O)CH$_3$ | 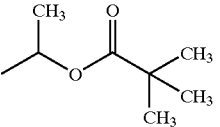 |
| 173 | CH$_3$ | * | H | H | C(O)CH$_3$ | 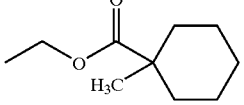 |
| 174 | CH$_3$ | * | H | H | C(O)CH$_3$ | 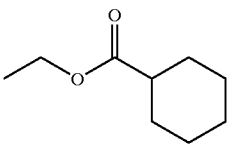 |
| 175 | CH$_3$ | * | H | H | C(O)CH$_3$ | 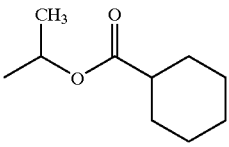 |
| 176 | CH$_3$ | * | H | H | C(O)CH$_3$ | 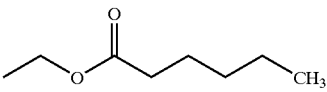 |

-continued
| EXAMPLE | R¹ | R² | R³ | R⁴ | R⁵ | R |
|---|---|---|---|---|---|---|
| 177 | CH₃ | * | H | H | C(O)CH₃ | 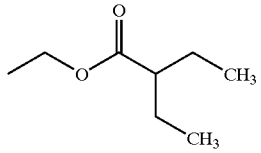 |
| 178 | CH₃ | * | H | H | C(O)CH₃ | 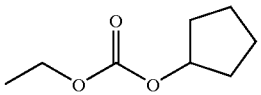 |
| 179 | CH₃ | * | H | H | C(O)CH₃ | 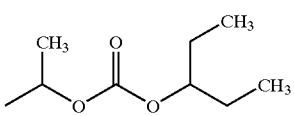 |
| 180 | CH₃ | * | H | H | C(O)CH₃ | 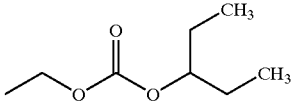 |
| 181 | CH₃ | * | H | H | C(O)CH₃ | 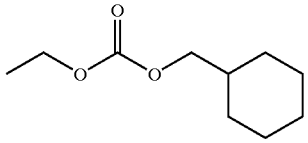 |
| 182 | CH₃ | * | H | H | SO₂CH₃ | 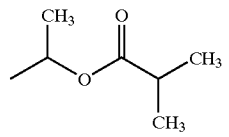 |
| 183 | CH₃ | * | H | H | SO₂CH₃ | 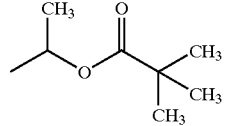 |
| 184 | CH₃ | * | H | H | SO₂CH₃ | 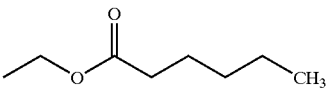 |
| 185 | CH₃ | * | H | H | SO₂CH₃ | 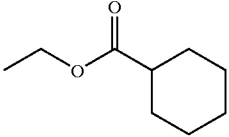 |
| 186 | CH₃ | * | H | H | SO₂CH₃ | 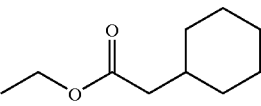 |

-continued

| EXAMPLE | R¹ | R² | R³ | R⁴ | R⁵ | R |
|---|---|---|---|---|---|---|
| 187 | CH₃ | * | H | H | SO₂CH₃ | ethyl 2,2-dicyclohexylacetate |
| 188 | CH₃ | * | H | H | SO₂CH₃ | isopropyl 1-methylcyclohexane-1-carboxylate |
| 189 | CH₃ | * | H | H | SO₂CH₃ | ethyl adamantane-1-carboxylate |
| 190 | CH₃ | * | H | H | SO₂CH₃ | isopropyl adamantane-1-carboxylate |
| 191 | CH₃ | * | H | H | SO₂CH₃ | isopropyl benzoate |
| 192 | CH₃ | * | H | H | SO₂CH₃ | ethyl 4-isopropylbenzoate |
| 193 | CH₃ | * | H | H | SO₂CH₃ | ethyl 4-butylbenzoate |
| 194 | CH₃ | * | H | H | SO₂CH₃ | ethyl 4-phenylbenzoate |

-continued

| EXAMPLE | R¹ | R² | R³ | R⁴ | R⁵ | R |
|---|---|---|---|---|---|---|
| 195 | $CH_3$ | * | H | H | $SO_2CH_3$ | ethyl 4-tert-butylbenzoate |
| 196 | $CH_3$ | * | H | H | $SO_2CH_3$ | isopropyl 4-tert-butylbenzoate |
| 197 | $CH_3$ | * | H | H | $SO_2CH_3$ | ethyl 2,4,6-trimethylbenzoate |
| 198 | $CH_3$ | * | H | H | $SO_2CH_3$ | diisopropyl carbonate |
| 199 | $CH_3$ | * | H | H | $SO_2CH_3$ | isopropyl sec-butyl carbonate |
| 200 | $CH_3$ | * | H | H | $SO_2CH_3$ | isopropyl 3-pentyl carbonate |
| 201 | $CH_3$ | * | H | H | $SO_2CH_3$ | isopropyl butyl carbonate |
| 202 | $CH_3$ | * | H | H | $SO_2CH_3$ | ethyl 4-heptyl carbonate |
| 203 | $CH_3$ | * | H | H | $SO_2CH_3$ | isopropyl 4-heptyl carbonate |
| 204 | $CH_3$ | * | H | H | $SO_2CH_3$ | isopropyl pentyl carbonate |
| 205 | $CH_3$ | * | H | H | $SO_2CH_3$ | isopropyl 4-methylpentyl carbonate |

-continued

| EXAMPLE | R¹ | R² | R³ | R⁴ | R⁵ | R |
|---|---|---|---|---|---|---|
| 206 | CH₃ | * | H | H | SO₂CH₃ | ethyl (heptan-4-yl) carbonate |
| 207 | CH₃ | * | H | H | SO₂CH₃ | isopropyl (heptan-4-yl) carbonate |
| 208 | CH₃ | * | H | H | SO₂CH₃ | isopropyl neopentyl carbonate |
| 209 | CH₃ | * | H | H | SO₂CH₃ | isopropyl (3,3-dimethylbutan-2-yl) carbonate |
| 210 | CH₃ | * | H | H | SO₂CH₃ | ethyl (cyclohexylmethyl) carbonate |
| 211 | CH₃ | * | H | H | SO₂CH₃ | sec-butyl (cyclohexylmethyl) carbonate |
| 212 | CH₃ | * | H | H | SO₂CH₃ | isopropyl (cyclohexyl(cyclohexyl)methyl) carbonate |
| 213 | CH₃ | * | H | H | SO₂CH₃ | ethyl cyclohexyl carbonate |
| 214 | CH₃ | * | H | H | SO₂CH₃ | (3-methylbutan-2-yl) cyclohexyl carbonate |
| 215 | CH₃ | * | H | H | SO₂CH₃ | (1-cyclohexylethyl) cyclohexyl carbonate |

-continued

| EXAMPLE | R¹ | R² | R³ | R⁴ | R⁵ | R |
|---|---|---|---|---|---|---|
| 216 | CH₃ | * | H | H | SO₂CH₃ | ethyl (1R,2S,5R)-menthyl carbonate |
| 217 | CH₃ | * | H | H | SO₂CH₃ | isopropyl (1R,2S,5R)-menthyl carbonate |
| 218 | CH₃ | * | H | H | SO₂CH₃ | ethyl menthyl carbonate (stereoisomer) |
| 219 | CH₃ | * | H | H | SO₂CH₃ | ethyl menthyl carbonate (stereoisomer) |
| 220 | CH₃ | * | H | H | SO₂CH₃ | ethyl menthyl carbonate (stereoisomer) |
| 221 | CH₃ | * | H | H | SO₂CH₃ | ethyl 3,3,5-trimethylcyclohexyl carbonate |
| 222 | CH₃ | * | H | H | SO₂CH₃ | ethyl 2-adamantyl carbonate |

-continued
| EXAMPLE | R¹ | R² | R³ | R⁴ | R⁵ | R |
|---|---|---|---|---|---|---|
| 223 | CH₃ | * | H | H | SO₂CH₃ | 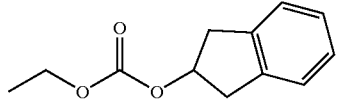 |
| 224 | CH₃ | * | H | H | SO₂CH₃ | 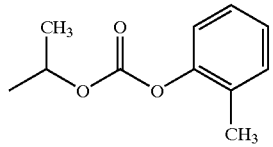 |
| 225 | CH₃ | * | H | H | SO₂CH₃ | 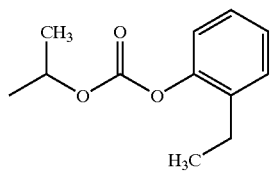 |
| 226 | CH₃ | * | H | H | SO₂CH₃ | 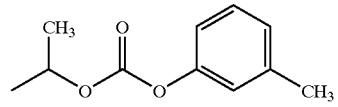 |
| 227 | CH₃ | * | H | H | SO₂CH₃ | 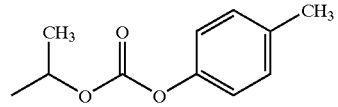 |
| 228 | CH₃ | * | H | H | SO₂CH₃ | 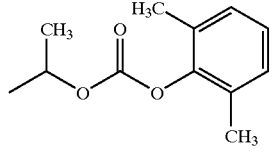 |
| 229 | CH₃ | * | H | H | SO₂CH₃ | 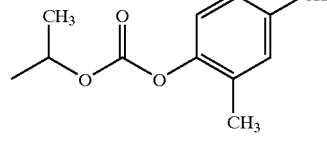 |
| 230 | CH₃ | * | H | H | SO₂CH₃ | 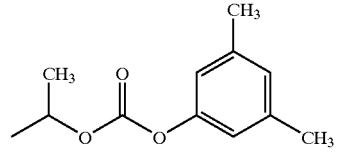 |
| 231 | CH₃ | * | H | H | SO₂CH₃ | 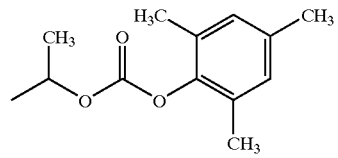 |
| 232 | CH₃ | * | H | H | SO₂CH₃ | 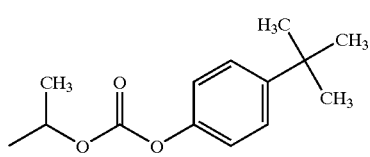 |

-continued
| EXAMPLE | R¹ | R² | R³ | R⁴ | R⁵ | R |
|---|---|---|---|---|---|---|
| 233 | CH₃ | * | H | H | SO₂CH₃ | 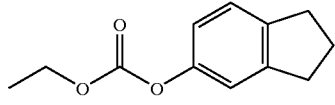 |
| 234 | CH₃ | * | H | H | SO₂CH₃ | 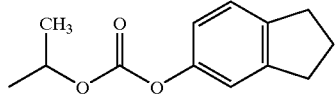 |
| 235 | CH₃ | * | H | H | SO₂CH₃ | 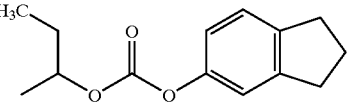 |
| 236 | CH₃ | * | H | H | SO₂CH₃ | CH₂CH₃ |
| 237 | CH₃ | * | H | H | SO₂CH₃ | CH(CH₃)₂ |
| 238 | CH₃ | * | H | H | SO₂CH₃ | (CH₂)₉CH₃ |
| 239 | CH₃ | * | H | H | SO₂CH₃ | 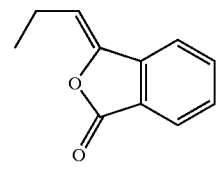 |
| 240 | CH₃ | * | H | H | SCH₃ | 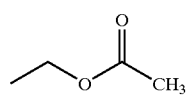 |
| 241 | CH₃ | * | H | H | SCH₃ | 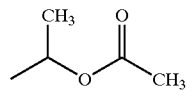 |
| 242 | CH₃ | * | H | H | SCH₃ | 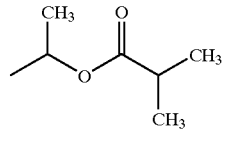 |
| 243 | CH₃ | * | H | H | SCH₃ | 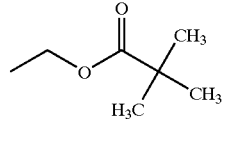 |
| 244 | CH₃ | * | H | H | SCH₃ | 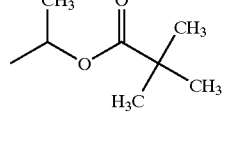 |
| 245 | CH₃ | * | H | H | SCH₃ | 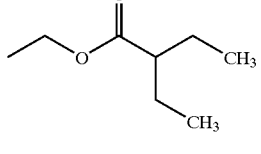 |

-continued

| EXAMPLE | R¹ | R² | R³ | R⁴ | R⁵ | R |
|---|---|---|---|---|---|---|
| 246 | CH₃ | * | H | H | SCH₃ | isopropyl 2-ethylbutanoate |
| 247 | CH₃ | * | H | H | SCH₃ | ethyl cyclohexanecarboxylate |
| 248 | CH₃ | * | H | H | SCH₃ | isopropyl cyclohexanecarboxylate |
| 249 | CH₃ | * | H | H | SCH₃ | ethyl 2,2-dicyclohexylacetate |
| 250 | CH₃ | * | H | H | SCH₃ | ethyl adamantane-1-carboxylate |
| 251 | CH₃ | * | H | H | SCH₃ | isopropyl adamantane-1-carboxylate |
| 252 | CH₃ | * | H | H | SCH₃ | 3-methylphthalide |
| 253 | CH₃ | * | H | H | SCH₃ | ethyl benzoate |
| 254 | CH₃ | * | H | H | SCH₃ | isopropyl benzoate |

-continued
| EXAMPLE | R¹ | R² | R³ | R⁴ | R⁵ | R |
|---|---|---|---|---|---|---|
| 255 | CH₃ | * | H | H | SCH₃ | 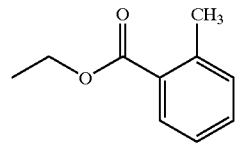 |
| 256 | CH₃ | * | H | H | SCH₃ | 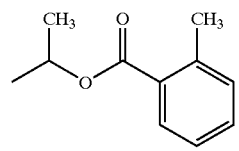 |
| 257 | CH₃ | * | H | H | SCH₃ | 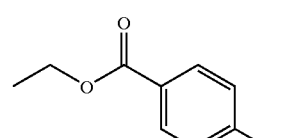 |
| 258 | CH₃ | * | H | H | SCH₃ | 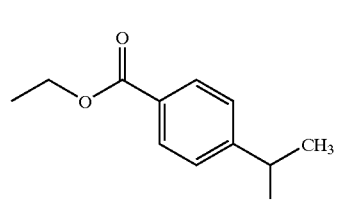 |
| 259 | CH₃ | * | H | H | SCH₃ | 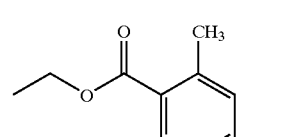 |
| 260 | CH₃ | * | H | H | SCH₃ | 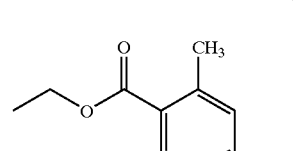 |
| 261 | CH₃ | * | H | H | SCH₃ | 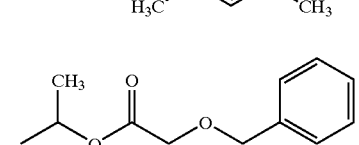 |
| 262 | CH₃ | * | H | H | SCH₃ | 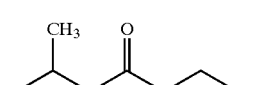 |
| 263 | CH₃ | * | H | H | SCH₃ | 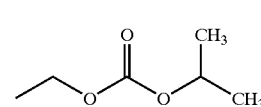 |
| 264 | CH₃ | * | H | H | SCH₃ | 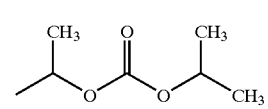 |

-continued
| EXAMPLE | R¹ | R² | R³ | R⁴ | R⁵ | R |
|---|---|---|---|---|---|---|
| 265 | CH₃ | * | H | H | SCH₃ | 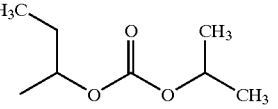 |
| 266 | CH₃ | * | H | H | SCH₃ | 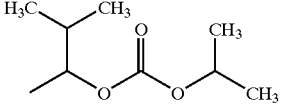 |
| 267 | CH₃ | * | H | H | SCH₃ | 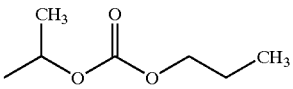 |
| 268 | CH₃ | * | H | H | SCH₃ | 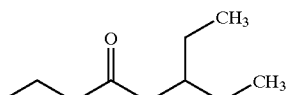 |
| 269 | CH₃ | * | H | H | SCH₃ | 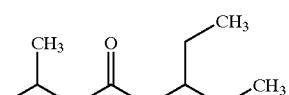 |
| 270 | CH₃ | * | H | H | SCH₃ | 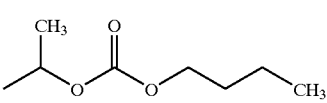 |
| 271 | CH₃ | * | H | H | SCH₃ | 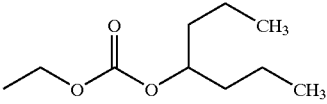 |
| 272 | CH₃ | * | H | H | SCH₃ | 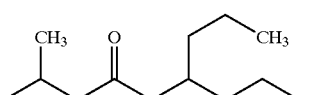 |
| 273 | CH₃ | * | H | H | SCH₃ | 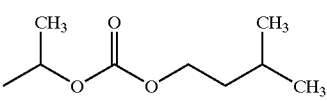 |
| 274 | CH₃ | * | H | H | SCH₃ | 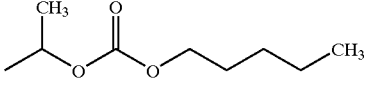 |
| 275 | CH₃ | * | H | H | SCH₃ | 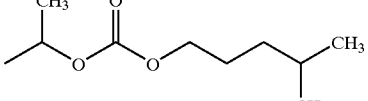 |
| 276 | CH₃ | * | H | H | SCH₃ | 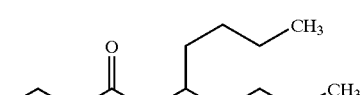 |

-continued

| EXAMPLE | R¹ | R² | R³ | R⁴ | R⁵ | R |
|---|---|---|---|---|---|---|
| 277 | CH₃ | * | H | H | SCH₃ | isopropyl (1-isopropyl-2-methylpropyl) carbonate |
| 278 | CH₃ | * | H | H | SCH₃ | isopropyl neopentyl carbonate |
| 279 | CH₃ | * | H | H | SCH₃ | isopropyl (3,3-dimethylbutan-2-yl) carbonate |
| 280 | CH₃ | * | H | H | SCH₃ | isopropyl (2-cyclohexylethyl) carbonate |
| 281 | CH₃ | * | H | H | SCH₃ | isopropyl (2-phenylethyl) carbonate |
| 282 | CH₃ | * | H | H | SCH₃ | ethyl cyclohexyl carbonate |
| 283 | CH₃ | * | H | H | SCH₃ | isopropyl cyclohexyl carbonate |
| 284 | CH₃ | * | H | H | SCH₃ | sec-butyl cyclohexyl carbonate |
| 285 | CH₃ | * | H | H | SCH₃ | (3-methylbutan-2-yl) cyclohexyl carbonate |
| 286 | CH₃ | * | H | H | SCH₃ | (1-cyclohexylethyl) cyclohexyl carbonate |
| 287 | CH₃ | * | H | H | SCH₃ | ethyl 2-adamantyl carbonate |

-continued
| EXAMPLE | R¹ | R² | R³ | R⁴ | R⁵ | R |
|---|---|---|---|---|---|---|
| 288 | CH₃ | * | H | H | SCH₃ | 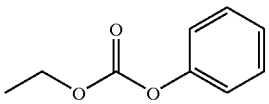 |
| 289 | CH₃ | * | H | H | SCH₃ | 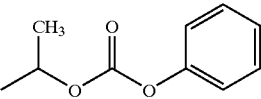 |
| 290 | CH₃ | * | H | H | SCH₃ | 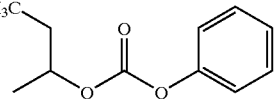 |
| 291 | CH₃ | * | H | H | SCH₃ | 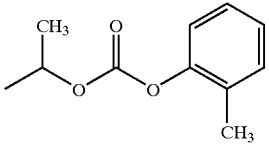 |
| 292 | CH₃ | * | H | H | SCH₃ | 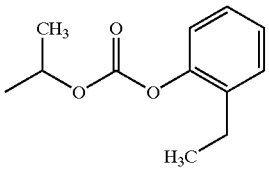 |
| 293 | CH₃ | * | H | H | SCH₃ | 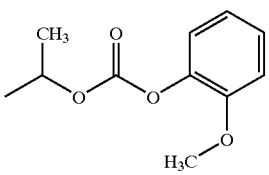 |
| 294 | CH₃ | * | H | H | SCH₃ | 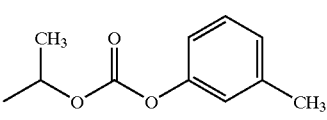 |
| 295 | CH₃ | * | H | H | SCH₃ | 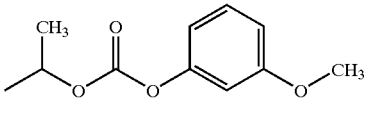 |
| 296 | CH₃ | * | H | H | SCH₃ | 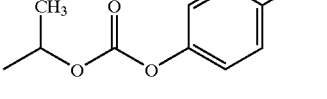 |
| 297 | CH₃ | * | H | H | SCH₃ | 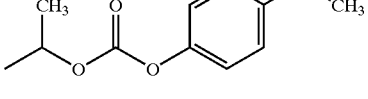 |
| 298 | CH₃ | * | H | H | SCH₃ | 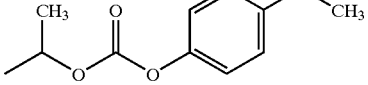 |

-continued

| EXAMPLE | R¹ | R² | R³ | R⁴ | R⁵ | R |
|---|---|---|---|---|---|---|
| 299 | $CH_3$ | * | H | H | $SCH_3$ | 2,6-dimethylphenyl isopropyl carbonate |
| 300 | $CH_3$ | * | H | H | $SCH_3$ | 2,4-dimethylphenyl isopropyl carbonate |
| 301 | $CH_3$ | * | H | H | $SCH_3$ | 2,5-dimethylphenyl isopropyl carbonate |
| 302 | $CH_3$ | * | H | H | $SCH_3$ | 5-isopropyl-2-methylphenyl isopropyl carbonate |
| 303 | $CH_3$ | * | H | H | $SCH_3$ | 3,5-dimethylphenyl isopropyl carbonate |
| 304 | $CH_3$ | * | H | H | $SCH_3$ | 2,4,6-trimethylphenyl isopropyl carbonate |
| 305 | $CH_3$ | * | H | H | $SCH_3$ | indan-5-yl isopropyl carbonate |
| 306 | $CH_3$ | * | H | H | $SCH_3$ | indan-5-yl sec-butyl carbonate |
| 307 | $CH_3$ | * | H | H | $SCH_3$ | $(CH_2)_6CH_3$ |
| 308 | $CH_3$ | * | H | H | $SCH_3$ | 4-ethyl-5-methyl-1,3-dioxol-2-one |

-continued

| EXAMPLE | R¹ | R² | R³ | R⁴ | R⁵ | R |
|---|---|---|---|---|---|---|
| 309 | $CH_3$ | * | H | H | $SCH_3$ | (propylidene phthalide structure) |
| 310 | $CH_3$ | * | H | H | $SCH_3$ | (isopropyl 2-methyl-2-butyl carbonate) |
| 311 | $CH_3$ | * | H | H | $SCH_3$ | (isopropyl 3,3-dimethylbutyl carbonate) |
| 312 | $CH_3$ | * | H | H | $SCH_3$ | (isopropyl 2-methoxybenzoate) |
| 313 | $CH_3$ | * | H | H | $SCH_3$ | (ethyl 3,5-dimethylbenzoate) |
| 314 | $CH_3$ | * | H | H | $SCH_3$ | (isopropyl 2-isopropylphenyl carbonate) |
| 315 | $CH_3$ | * | H | H | $SCH_3$ | (ethyl neopentyl carbonate) |
| 316 | $CH_3$ | * | H | H | $SCH_3$ | (isopropyl 2-ethylbutyl carbonate) |
| 317 | $CH_3$ | * | H | H | $SCH_3$ | (sec-butyl isopentyl carbonate) |

-continued
| EXAMPLE | R¹ | R² | R³ | R⁴ | R⁵ | R |
|---|---|---|---|---|---|---|
| 318 | CH₃ | * | H | H | SCH₃ | 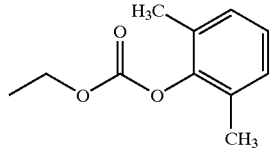 |
| 319 | CH₃ | * | H | H | SCH₃ | 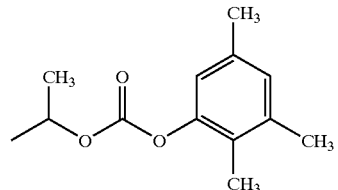 |
| 320 | CH₃ | * | H | H | SCH₃ | 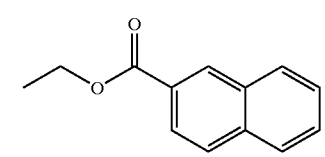 |
| 321 | CH₃ | * | H | H | SCH₃ | 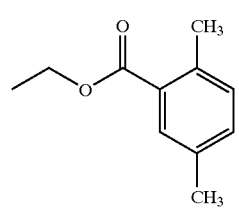 |
| 322 | CH₃ | * | H | H | SO₂N(CH₃)₂ | 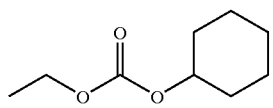 |
| 323 | CH₃ | * | H | H | SCH₃ | 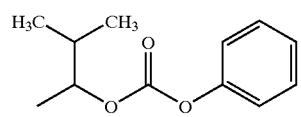 |
| 324 | CH₃ | * | H | H | SCH₃ | 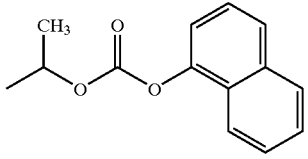 |
| 325 | CH₃ | * | H | H | SCH₃ | 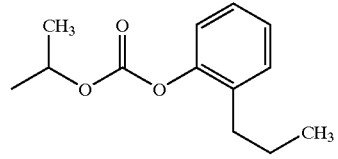 |
| 326 | CH₃ | * | H | H | C(O)CH₃ | 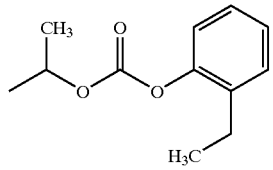 |

-continued

| EXAMPLE | R¹ | R² | R³ | R⁴ | R⁵ | R |
|---|---|---|---|---|---|---|
| 327 | CH₃ | * | H | H | SO₂N(CH₃)₂ | 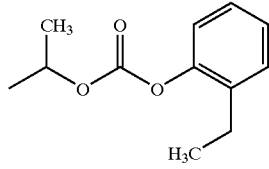 |
| 328 | CH₃ | * | H | H | S(O)CH₃ | 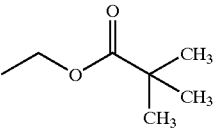 |
| 329 | CH₃ | * | H | H | SCH₃ | 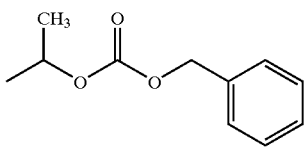 |
| 330 | CH₃ | * | H | H | SCH₃ | 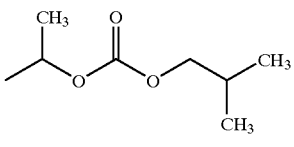 |
| 331 | CH₃ | * | H | H | SCH₃ | 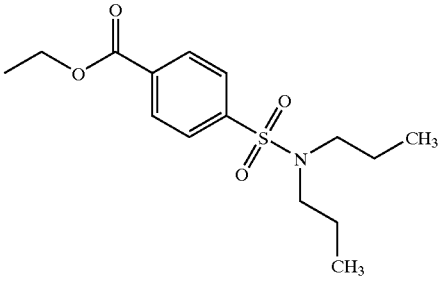 |
| 332 | CH₃ | * | H | H | SCH₃ | 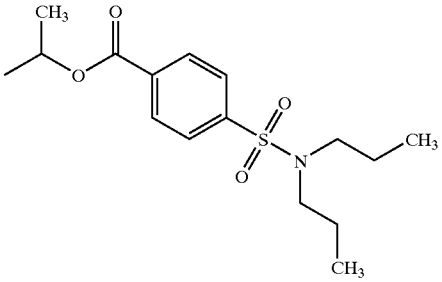 |

Injections

Aseptical charging into vials was carried out so that each vial contained 1000 mg (potency) of the compound prepared in Example 62.

Capsules
Compound prepared in Example 63 250 parts (potency)
Milk sugar 60 parts (potency)
Magnesium stearate 5 parts (potency)

These ingredients were homogeneously mixed together. The mixture was filled into capsules so as to provide 250 mg (potency) per capsule.

Soft Capsules for Rectal Administration

Olive oil 160 parts (potency)
Polyoxyethylene lauryl ether 10 parts (potency)
Sodium hexametaphosphate 5 parts (potency)

The compound (250 parts (potency)) prepared in Example 63 was added to and homogeneously mixed with a homogeneous base comprising the abvoe ingredients. The mixture was filled into soft capsules for rectal administration to provide 250 mg (potency) per capsule.

Test 1: Anti-microbial Activities

The minimum inhibiting concentrations (MIC, µg/ml) of the compounds according to the present invention to various pathogenic bacteria was measured in accordance with the method described in CHEMOTHERAPY, vol. 16, No. 1, 99, 1968. The culture medium for measurement was Sensitivity Disk agar-N+5% Horse blood, and the amount of inoculants was $10^6$ CFU/ml.

The results are shown in the following table.

having a titer of 2000 μg/ml was added to the partly purified DHP-I's of the above described animals so as to have a final concentration of 100 μg (titer)/ml. As a blank, 50 mM Tris

| Test Organisms | Example No. | | | | | | | Compound | |
|---|---|---|---|---|---|---|---|---|---|
| | 26 | 27 | 44 | 62 | | 88 | 111 | A | B |
| S. aureus 209P JC-1 | <0.025 | 0.05 | 0.05 | <0.025 | <0 | <0.025 | <0.025 | <0.025 | <0.025 |
| S. aureus M126* | 6.25 | 0.78 | 3.13 | 1.56 | 3. | 1.56 | 1.56 | 25 | 6.25 |
| S. epidermidis ATCC14990 | <0.025 | 0.05 | 0.05 | <0.025 | <0. | <0.025 | <0.025 | <0.025 | 0.05 |
| E. hirae ATCC8043 | 0.78 | 0.39 | 0.78 | 0.39 | 0. | 0.39 | 0.39 | 0.78 | 1.56 |
| E. faecalis W-73 | 0.39 | 0.10 | 0.78 | 0.20 | 0. | 0.39 | 0.20 | 0.78 | 3.13 |
| S. pneumoniae PRC9** | 0.10 | 0.05 | 0.10 | 0.05 | 0. | 0.05 | 0.05 | 0.20 | 0.39 |
| M. catarrhalis W-0500 | 0.05 | <0.025 | <0.025 | <0.025 | <0. | <0.025 | <0.025 | 0.05 | <0.025 |
| H. influenzae PRC2 | <0.025 | <0.025 | <0.025 | <0.025 | <0. | <0.025 | <0.025 | 0.78 | 0.10 |
| H. influenzae PRC44 | 0.05 | 0.05 | 0.10 | 0.05 | 0. | 0.10 | 0.05 | 12.5 | 0.78 |
| E. coli NIHJ JC-2 | 0.05 | 0.20 | 0.78 | 0.05 | <0. | 0.39 | 0.78 | 0.10 | 0.05 |
| K. pneumoniae PCI602 | 0.10 | 0.10 | 1.56 | 0.05 | <0. | 0.39 | 0.78 | 0.20 | 0.10 |
| P. vulgaris GN7919 | 0.20 | 0.20 | 0.78 | 0.10 | <0. | 0.78 | 0.39 | 0.10 | 0.10 |
| C. freundii GN346 | 1.56 | 0.39 | 12.5 | 1.56 | 0. | 3.13 | 1.56 | 0.20 | 0.10 |

In the table,
*methicillin hyperresistant strain (MRSA);
**penicillin-hyperresistant strain (PRSP);
Compound A: imipenem;
Compound B: (1R, 5S, 6S)-6-((1R)-1-hydroxyethyl)-1-methyl-2-[(3S, 5S)-5-(6-methylimidazo[5,1-b]thiazolium-2-yl) methylpyrrolidin-3-yl]thiocarbapen-2-em-3-carboxylic acid iodide.

As is apparent from the above described test results, the compounds according to the present invention have strong anti-microbial activities against MRSA, PRSP, enterococci, influenza as well as various pathogenic bacteria including β-lactamase producing bacteria.

Test 2: Stability Against DHP-I

The stabilities of the compounds according to the present invention against porcine and mouse renal dehydropeptidases were measured by the following method.

(1) Preparation of DHP-1 from Kidney Acetone Powders of Various Animals

Kidney acetone powder, Porcine Type II(Sigma; Lot. 33H7225; 1.5 g) was suspended in a 50 mM Tris.HCl buffer (pH 7.0) containing 20% butanol, and the mixture was stirred at 5° C. for 48 hours. Dialysis (Cellulose tube 30/32; Viskase Sales Corp) was conducted with a 50 mM Tris.HCl buffer (pH 7.0) in order to remove butanol to a level of no smell of butanol. The dialysate was centrifuged at 10000×g (KUBOTA 6800) for 20 minutes to give a supernatant as a partly purified DHP-I, which was divided into portions and stored at −80° C. Also, a partly purified DHP-I was prepared from 1.5 g of Mouse (Lot. 23F8105), and stored in the same manner as above.

(2) Measurement of Stabilities to Various DHP-I's

The compounds according to the present invention as a basic pharmaceutical was diluted with sterile purified water to prepare a solution having a titer of 2000 μg/ml. The solution of the compound according to the present invention HCl buffer (pH 7.0) was used in place of the partly purified DHP-I's of the animals. After reaction at 370° C. for 3 hours, a portion of the reaction mixture was taken out, diluted with the same amount of methanol to stop the reaction by cooling in ice. The reaction mixture was filtered through SUNPLEP LCR13-LH, MILLIPORE), and subjected to HPLC (column: CAPCELL PACK C18 SG120, SHISEIDO; UV detector; mobile phase: acetonitrile—10 mM aqueous acetic acid solution) to measure the residual amount (%) of the partly purified DHP-I according to the following equation.

$$\text{Residual amount (\%)} = \frac{\text{Sample peak area}}{\text{Blank peak area}} \times 100$$

The residual amounts (%) of the compounds according to the present invention after 3 hours are shown below.

| DHP-I | Example 19 | Example 26 | Example 27 | Example 44 | Example 62 | Example 71 | Example 88 | Compound A | Compound C |
|---|---|---|---|---|---|---|---|---|---|
| Porcine | 77 | 44 | 38 | 100 | 64 | 33 | 73 | <0.3 | 41 |
| Mouse | 45 | 11 | 1.2 | nt | 1.5 | <0.1 | <0.1 | 14 | 8.5 |

In the table,
nt: not tested
Compound A: imipenem;
Compound B: meropenem.

In the table, nt: not tested

Compound A: imipenem;

Compound C: meropenem.

It is understood from the above table that the compounds according to the present invention have high stabilities to the porcine renal DHP-I.

Test 3: Oral Absorption Ability Test (1)

The compounds of Examples 62, 63 and 69 were orally administered to mice (ICR, male, n=3) in an amount of 0.5 mg (based on the weight of the compound of Example 62 from which the compounds of Examples 63 and 69 were derived)/0.2 ml/mouse as a 0.5% methylcellulose suspension, and then cilastatin was immediately administered subcutaneously in the same amount (because of the instability of the compound of Example 62 to mouse DHP-I, cilastatin as an inhibitor of DHP-I was used in combination). As a result, the compound of Example 62 was excreted in urine in 6%, 18% and 35% of bio-availability (BA) by 24 hours after the compounds of Examples 62, 63 and 69 were administered. The "BA" is a ratio of the recovery of a mother compound in urine when a test compound, i.e., a pro-drug of the mother compound, is orally administered to the recovery of the mother compound when the mother compound is administered intravenously.

The compounds of Examples 111, 243 and 282 were tested. As a result, the compound of Example 111 from which the compounds of Examples 243 and 282 were derived was excreted in urine in 4%, 16% and 26% of BA by 24 hours after the compounds of Examples 111, 243 and 282 were administered, respectively.

The compound of Example 49 was tested. As a result, the compound of Example 46-b) from which the compounds of Example 49 was derived was excreted in urine in 37% of BA by 24 hours after the compound of Example 49 was administered.

The compound of Example 77 was tested. As a result, the compound of Example 71 from which the compounds of Example 77 was derived was excreted in urine in 22% of BA by 24 hours after the compound of Example 77 was administered.

The compound of Example 89 was tested. As a result, the compound of Example 88 from which the compounds of Example 89 was derived was excreted in urine in 18% of BA by 24 hours after the compound of Example 89 was administered.

The compound of Example 107 was tested. As a result, the compound of Example 44 from which the compounds of Example 107 was derived was excreted in urine in 21% of BA by 24 hours after the compound of Example 107 was administered.

The compound of Example 168 was tested. As a result, the compound of Example 19 from which the compounds of Example 168 was derived was excreted in urine in 29% of BA by 24 hours after the compound of Example 168 was administered.

It is understood from the above results that the compounds of formula (I') which is a ester at the 3-position on the carbapenem ring of the compound of the present invention can be absorbed orally and metabolically hydrolyzed in organisms to give as a mother compound, a compound of formula (I) having antibacterial activity.

Test 4: Oral Absorption Ability Test (2)

Some compounds were tested in the same manner as in Test 3 provided that 5%HCO60 was used instead of 0.5% methylcellulose suspension.

The compounds of Examples 63, 189, 195 and 218 were tested. As a result, the compound of Example 62 from which the compounds of Examples 189, 195 and 218 were derived was excreted in urine in 29%, 44%, 24% and 26% of BA by 24 hours after the compounds of Examples 63, 189, 195 and 218 were administered, respectively.

The compounds of Examples 243, 250, 253, 273, 287, 292, 301 and 319 were tested. As a result, the compound of Example 111 from which these compounds were derived was excreted in urine in 25%, 39%, 37%, 36%, 24%, 53%, 50%, and 51% of BA by 24 hours after the compounds of Examples 243, 250, 253, 273, 287, 292, 301 and 319 were administered, respectively.

It is understood from the above results that the compounds of formula (I') which is a ester at the 3-position on the carbapenem ring of the compound of the present invention can be absorbed orally and metabolically hydrolyzed in organisms to give as a mother compound, a compound of formula (I) having antibacterial activity.

Test 5: Acute Toxicity (i.v.)

The compound of Example 44, 62, 88 and 111 were administered to mice (ICR, male, n=3), respectively, at a dose of 2,000 mg/kg i.v. provided that in case of Example 111 the dose was 1,500 mg/kg because of its limited solubility. All of the animal survived.

The compounds of Examples 44, 62, 88, and 111 were tested again in the same manner as the above provided that cilastatin sodium was co-administered. All of the animal survived.

It is understood from these results that the compounds of the present invention have more than 2,000 mg/kg (or 1,500 mg/kg) of $LD_{50}$ and low toxicity.

Test 6: Acute Toxicity (oral)

The compounds of Examples 63, 243, and 283 as a 0.5% methylcellulose suspension and the compounds of Examples 218 and 292 as a 5%HCO60 suspension were orally administered to mice (SD, male, n=4) at a dose of 2,000 mg/kg. As a result, all of the animal survived.

It is understood from the results of the test that the compounds of the formula (I'), which are carbonates at 3-position of carbapenem derivatives according to the present invention have more than 2,000 mg/kg (or 1,500 mg/kg) of $LD_{50}$ and low toxicity.

What is claimed is:

1. A compound represented by the formula (I), or a pharmaceutically acceptable salt thereof:

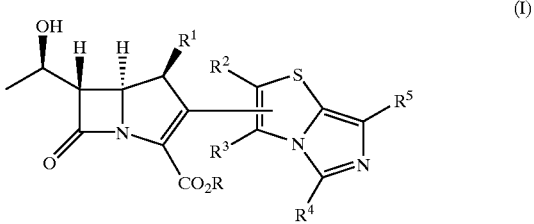

(I)

wherein
$R^1$ represents a methyl group,
$R^2$ represents the bonding to the 2-position on the carbapenem ring,
$R^3$ and $R^4$ represent hydrogen,
$R^5$ represents the aminoacetyl group, and
R represents a hydrogen atom or a group which may be hydrolyzed in organisms.

2. A process for treating infectious bacterial diseases, comprising administering the compound according to claim 1 to animals including humans.

* * * * *